US012787643B2

(12) United States Patent
Moon et al.

(10) Patent No.: US 12,787,643 B2
(45) Date of Patent: Nov. 3, 2026

(54) PLURALITY OF HOST MATERIALS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Doo-Hyeon Moon, Gyeonggi-do (KR); Sung-Woo Jang, Gyeonggi-do (KR); Mi-Ja Lee, Gyeonggi-do (KR); Kyoung-Jin Park, Gyeonggi-do (KR); Du-Yong Park, Gyeonggi-do (KR); Hyo-Soon Park, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 1002 days.

(21) Appl. No.: 18/075,632

(22) Filed: Dec. 6, 2022

(65) Prior Publication Data

US 2023/0217820 A1 Jul. 6, 2023

(30) Foreign Application Priority Data

Jan. 6, 2022 (KR) ........................ 10-2022-0002049

(51) Int. Cl.

| | |
|---|---|
| ***H10K 85/60*** | (2023.01) |
| ***C07D 471/04*** | (2006.01) |
| ***C09K 11/06*** | (2006.01) |
| ***H10K 50/11*** | (2023.01) |
| ***H10K 101/00*** | (2023.01) |
| ***H10K 101/10*** | (2023.01) |

(52) U.S. Cl.

CPC ....... *H10K 85/6572* (2023.02); *C07D 471/04* (2013.01); *C09K 11/06* (2013.01); *H10K 85/654* (2023.02); *C09K 2211/1018* (2013.01); *H10K 50/11* (2023.02); *H10K 2101/10* (2023.02); *H10K 2101/90* (2023.02)

(58) Field of Classification Search

CPC ...................................................... C09K 11/06

See application file for complete search history.

(56) References Cited

U.S. PATENT DOCUMENTS

2013/0299794 A1* 11/2013 Jung ...................... H05B 33/10 544/333

FOREIGN PATENT DOCUMENTS

| | | | | | |
|---|---|---|---|---|---|
| CN | 110804053 | A | * | 2/2020 | C07D 471/04 |
| KR | 20120078326 | A | * | 7/2012 | H10K 50/00 |

OTHER PUBLICATIONS

Request for the Submission of an Opinion from Korea Intellectual Property Office, Application No. 10-2022-0002049, Filing Date: Jan. 6, 2022.

* cited by examiner

*Primary Examiner* — Chanceity N Robinson

(74) *Attorney, Agent, or Firm* — G. Creston Campbell

(57) ABSTRACT

A plurality of host materials containing at least one first host compound and at least one second host compound provides an organic electroluminescent device having high luminous efficiency and/or long lifespan characteristics.

9 Claims, No Drawings

PLURALITY OF HOST MATERIALS AND ORGANIC ELECTROLUMINESCENT DEVICE COMPRISING THE SAME

TECHNICAL FIELD

The present disclosure relates to a plurality of host materials and an organic electroluminescent device comprising the same.

BACKGROUND ART

The TPD/$Alq_3$ bilayer small molecule organic electroluminescent device (OLED) with green-emission, which is constituted with a light-emitting layer and a charge transport layer, was first developed by Tang, et al., of Eastman Kodak in 1987. Thereafter, the studies on an organic electroluminescent device have been rapidly commercialized. At present, an organic electroluminescent device mainly includes phosphorescent materials having excellent luminous efficiency in panel realization. In many applications such as TVs and lightings, OLED lifetime is insufficient, and high efficiency of OLEDs is still required. Typically, the higher the luminance of an OLED corresponds to a shorter lifetime of the OLED. Accordingly, for prolonged use and high resolution of the display, an OLED having high luminous efficiency and/or long lifespan is necessary.

Various materials or concepts have been proposed for the organic layer of an organic electroluminescent device in order to improve luminous efficiency, driving voltage and/or lifespan, but they have not been satisfactory for practical use.

Korean Patent Application Laid-Open No. 2012-0078326 discloses a compound for organic photoelectric device having H-imidazo[1,2-a]pyridine as a core. However, said reference does not specifically disclose an organic electroluminescent device using the specific combination of a plurality of host materials as described in the present disclosure. In addition, there is still a need to develop a host material for improving OLED performance.

DISCLOSURE OF THE INVENTION

Technical Problem

The object of the present disclosure is firstly, to provide a plurality of host materials which is able to produce an organic electroluminescent device having high luminous efficiency and long lifespan characteristics, and secondly, to provide an organic electroluminescent device with high luminous efficiency and long lifespan characteristics by comprising a specific combination of compounds according to the present disclosure as a plurality of host materials.

Solution to Problems

As a result of intensive studies to solve the technical problem above, the present inventors found that the aforementioned objective can be achieved by a plurality of host materials comprising at least one first host compound represented by the following formula 1 and at least one second host compound represented by the following formula 2, so that the present invention was completed.

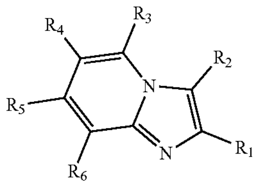

(1)

in formula 1, $R_1$ to $R_6$ each independently represent hydrogen, deuterium, halogen, cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, —$SiR'_1R'_2R'_3$, or —$NR'_4R'_5$; or may be linked to the adjacent substituents to form a ring(s);

provided that at least one of $R_1$ to $R_6$ is (are) -$(L_1)_n$-HAr;

$L_1$ represents a single bond, a substituted or unsubstituted (C6-C30)arylene, or a substituted or unsubstituted (3- to 30-membered)heteroarylene;

HAr represents a substituted or unsubstituted nitrogen-containing (3- to 30-membered)heteroaryl;

n represents an integer of 1 to 3, when n is an integer of 2 or more, each of $L_1$ may be the same or different; and $R'_1$ to $R'_5$ each independently represent a substituted or unsubstituted (C1-C30)alkyl, a substituted or unsubstituted (C2-C30)alkenyl, a substituted or unsubstituted (C6-C30) aryl, or a substituted or unsubstituted (3- to 30-membered) heteroaryl;

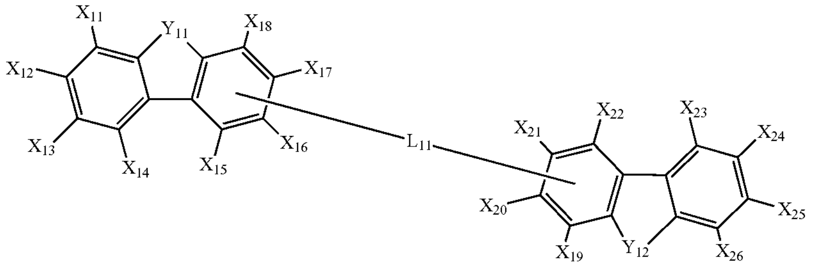

(2)

in formula 2, $Y_{11}$ represents —N-$A_1$, O, S or $CR_{21}R_{22}$;

$Y_{12}$ represents —N-$A_2$, O, S or $CR_{21}R_{22}$;

$A_1$ and $A_2$ each independently represent a substituted or unsubstituted (C6-C30)aryl, a substituted or unsubstituted dibenzofuranyl, a substituted or unsubstituted dibenzothiophenyl, or a substituted or unsubstituted carbazolyl;

$L_{11}$ represents a single bond, or (C6-C30)arylene unsubstituted or substituted by deuterium;

$X_{11}$ to $X_{26}$ each independently represent hydrogen, deuterium, a substituted or unsubstituted (C6-C30)aryl, or a substituted or unsubstituted (3- to 30-membered)heteroaryl; or may be linked to the adjacent substituents to form a ring(s); and $R_{21}$ and $R_{22}$ each independently represent a substituted or unsubstituted (C1-C3)alkyl or a substituted or unsubstituted (C6-C12)aryl; or may be linked to the adjacent substituents to form a ring(s).

Advantageous Effects of Invention

By comprising the specific combination of the compound according to the present disclosure as host materials, an organic electroluminescent device having excellent luminous characteristics and significantly improved long lifespan characteristics can be provided.

EMBODIMENTS OF THE INVENTION

Hereinafter, the present disclosure will be described in detail. However, the following description is intended to explain the invention, and is not meant in any way to restrict the scope of the invention.

The present disclosure relates to a plurality of host materials comprising a first host compound including at least one compound represented by formula 1 and a second host compound including at least one compound represented by formula 2, and an organic electroluminescent device comprising the host materials.

The present disclosure relates to an organic electroluminescent compound represented by formula 1A, and an organic electroluminescent device comprising the same.

The term "organic electroluminescent compound" in the present disclosure means a compound that may be used in an organic electroluminescent device, and may be comprised in any material layer constituting an organic electroluminescent device, as necessary.

Herein, the term "organic electroluminescent material" means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material (containing host and dopant materials), an electron buffer material, a hole blocking material, an electron transport material, or an electron injection material, etc.

The term "a plurality of organic electroluminescent materials" in the present disclosure means an organic electroluminescent material comprising a combination of at least two compounds, which may be comprised in any layer constituting an organic electroluminescent device. It may mean both a material before being comprised in an organic electroluminescent device (for example, before vapor deposition) and a material after being comprised in an organic electroluminescent device (for example, after vapor deposition). For example, a plurality of organic electroluminescent materials may be a combination of at least two compounds, which may be comprised in at least one layer of a hole injection layer, a hole transport layer, a hole auxiliary layer, a light-emitting auxiliary layer, an electron blocking layer, a light-emitting layer, an electron buffer layer, a hole blocking layer, an electron transport layer, and an electron injection layer. Such at least two compounds may be comprised in the same layer or in different layers, and may be mixture-evaporated or co-evaporated, or may be individually evaporated.

Herein, the term "a plurality of host materials" means an organic electroluminescent material comprising a combination of at least two host materials. It may mean both a material before being comprised in an organic electroluminescent device (e.g., before vapor deposition) and a material after being comprised in an organic electroluminescent device (e.g., after vapor deposition). A plurality of host materials of the present disclosure may be comprised in any light-emitting layer constituting an organic electroluminescent device. The at least two compounds comprised in a plurality of host materials may be comprised together in one light-emitting layer, or may each be comprised in separate light-emitting layers. When at least two compounds are comprised in one light-emitting layer, the at least two compounds may be mixture-evaporated to form a layer or may be individually and simultaneously co-evaporated to form a layer.

Herein, "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tent-butyl, sec-butyl, etc. Herein, the term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. Herein, "(3- to 7-membered) heterocycloalkyl" is meant to be a cycloalkyl having 3 to 7 ring backbone atoms and including at least one heteroatoms selected from the group consisting of B, N, O, S, Si, and P, preferably the group consisting of O, S and N, in which the number of the ring backbone carbon atoms is preferably 5 to 7, for example, tetrahydrofuran, pyrrolidine, thiolane, tetrahydropyran, etc. Herein, "(C6-C30)aryl(ene)" is a monocyclic or fused ring radical derived from an aromatic hydrocarbon having 6 to 30 ring backbone carbon atoms, in which the number of the ring backbone carbon atoms is preferably 6 to 20, more preferably 6 to 15, may be partially saturated, and may include a spiro structure. Examples of the aryl specifically may be phenyl, biphenyl, terphenyl, quaterphenyl, naphthyl, binaphthyl, phenylnaphthyl, naphthylphenyl, fluorenyl, phenylfluorenyl, dimethylfluorenyl, diphenylfluorenyl, benzofluorenyl, diphenylbenzofluorenyl, dibenzofluorenyl, phenanthrenyl, benzophenanthrenyl, phenylphenanthrenyl, anthracenyl, benzanthracenyl, indenyl, triphenylenyl, pyrenyl, tetracenyl, perylenyl, chrysenyl, benzochrysenyl, naphthacenyl, fluoranthenyl, benzofluoranthenyl, tolyl, xylyl, mesityl, cumenyl, spiro[fluoren-fluoren]yl, spiro[fluoren-benzofluoren]yl, azulenyl, tetramethyldihydrophenanthrenyl, etc. More specifically, the aryl may be o-tolyl, m-tolyl, p-tolyl, 2,3-xylyl, 3,4-xylyl, 2,5-xylyl, mesityl, o-cumenyl, m-cumenyl, p-cumenyl, p-t-butylphenyl, p-(2-phenylpropyl)phenyl, 4'-methylbiphenyl, 4"-t-butyl-p-terphenyl-4-yl, o-biphenyl, m-biphenyl, p-biphenyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 1-naphthyl, 2-naphthyl, 1-fluorenyl, 2-fluorenyl, 3-fluorenyl, 4-fluorenyl, 9-fluorenyl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 1-anthryl, 2-anthryl, 9-anthryl, 1-phenanthryl, 2-phenanthryl, 3-phenanthryl, 4-phenanthryl, 9-phenanthryl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 3-fluoranthenyl, 4-fluoranthenyl, 8-fluoranthenyl, 9-fluoranthenyl, benzofluoranthenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc. Herein, "(3- to 30-membered)heteroaryl(ene)" is an aryl having 3 to 30 ring backbone atoms and including at least one, preferably 1 to 4 heteroatoms selected from the group consisting of B, N, O, S, Si, P, Se, and Ge, in which the number of the ring backbone carbon atoms is preferably 3 to 30, and more preferably 5 to 20. The above heteroaryl(ene) may be a monocyclic ring, or a fused ring condensed with at least one benzene ring; and may be partially saturated. Also, the above heteroaryl or heteroarylene herein may be one formed by linking at least one heteroaryl or aryl group to a heteroaryl group via a single bond(s), and may comprise a spiro structure. Examples of the heteroaryl specifically may be a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, dibenzoselenophenyl, benzofuroquinolinyl, benzofuroquinazolinyl, benzofuronaphthiridinyl, benzofuropyrimidinyl, naphthofuropyrimidinyl, benzothienoquinolinyl, benzothienoquinazolinyl, benzothienonaphthiridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzoimidazolyl, benzothiazolyl, benzoisothiazolyl, benzoisoxazolyl, benzoxazolyl, imidazopyridinyl, isoindolyl, indolyl, benzoindolyl, indazolyl, benzothiadiazolyl, quinolyl, isoquinolyl, cinnolinyl, quinazolinyl, quinoxalinyl, carbazolyl, azacarbazolyl, benzocarbazolyl, dibenzocarbazolyl, phenoxazinyl, phenanthridinyl, benzodioxolyl, indolizidinyl, acridinyl, silafluorenyl, germafluorenyl, benzotriazolyl, phenazinyl, imidazopyridinyl, chromenoquinazolinyl, thiochromenoquinazolinyl, dimethylbenzopyrimidinyl, indolocarbazolyl, indenocarbazolyl, etc. More specifically, the heteroaryl may be 1-pyrrolyl, 2-pyrrolyl, 3-pyrrolyl, 2-pyridinyl, 3-pyridinyl, 4-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolizidinyl, 2-indolizidinyl, 3-indolizidinyl, 5-indolizidinyl, 6-indolizidinyl, 7-indolizidinyl, 8-indolizidinyl, 2-imidazopyridinyl, 3-imidazopyridinyl, 5-imidazopyridinyl, 6-imidazopyridinyl, 7-imidazopyridinyl, 8-imidazopyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazol-1-yl, azacarbazol-2-yl, azacarbazol-3-yl, azacarbazol-4-yl, azacarbazol-5-yl, azacarbazol-6-yl, azacarbazol-7-yl, azacarbazol-8-yl, azacarbazol-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. Herein, the term "a fused ring of (C3-C30) aliphatic ring and (C6-C30) aromatic ring" means a ring formed by fusing at least one aliphatic ring having 3 to 30 ring backbone carbon atoms in which the carbon atoms number is preferably 3 to 25, more preferably 3 to 18, and at least one aromatic ring haying 6 to 30 ring backbone carbon atoms in which the carbon atoms number is preferably 6 to 25, more preferably 6 to 18. For example, the fused ring may be a fused ring of at least one benzene and at least one cyclohexane, or a fused ring of at least one naphthalene and at least one cyclopentane, etc. Herein, the carbon atoms in the fused ring of (C3-C30) aliphatic ring and (C6-C30) aromatic ring may be replaced with at least one heteroatom selected from B, N, O, S, Si and P, preferably at least one heteroatom selected from N, O and S. The term "Halogen" in the present disclosure includes F, Cl, Br, and I.

In addition, "ortho (o)," "meta (m)," and "para (p)" are meant to signify the substitution position of all substituents. Ortho position is a compound with substituents, which are adjacent to each other, e.g., at the 1 and 2 positions on benzene. Meta position is the next substitution position of the immediately adjacent substitution position, e.g., a compound with substituents at the 1 and 3 positions on benzene. Para position is the next substitution position of the meta position, e.g., a compound with substituents at the 1 and 4 positions on benzene.

Herein, the term "a ring formed in linking to an adjacent substituent" means a substituted or unsubstituted (3- to 30-membered) mono- or polycyclic, alicyclic, aromatic ring, or a combination thereof, formed by linking or fusing two or more adjacent substituents, preferably a substituted or unsubstituted (5- to 25-membered) mono- or polycyclic, alicyclic, aromatic ring, or a combination thereof. Further, the formed ring may include at least one heteroatom selected from the group consisting of B, N, O, S, Si and P, preferably, N, O and S. According to one embodiment of the present disclosure, the number of atoms in the ring skeleton is 5 to 20; according to another embodiment of the present disclosure, the number of atoms in the ring skeleton is 5 to 15. In one embodiment, the fused ring may be, for example, a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzofluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring, etc.

In addition, "substituted" in the expression "substituted or unsubstituted" means that a hydrogen atom in a certain functional group is replaced with another atom or functional group, i.e., a substituent, and substituted with a group to which two or more substituents are connected among the substituents. For example, "a substituent to which two or more substituents are connected" may be pyridine-triazine. That is, pyridine-triazine may be heteroaryl or may be interpreted as one substituent in which two heteroaryls are connected. The substituents of the substituted alkyl, the substituted alkenyl, the substituted cycloalkyl, the substituted cycloalkenyl, the substituted heterocycloalkyl, the substituted aryl(ene), and the substituted heteroaryl(ene) in the formulas of the present disclosure, each independently represent at least one selected from the group consisting of deuterium; halogen; cyano; carboxyl; nitro; hydroxyl; (C1-C30)alkyl; halo(C1-C30)alkyl; (C2-C30)alkenyl; (C2-C30)alkynyl; (C1-C30)alkoxy; (C1-C30)alkylthio; (C3-C30)cycloalkyl; (C3-C30)cycloalkenyl; (3- to 7-membered) heterocycloalkyl; (C6-C30)aryloxy; (C6-C30)arylthio; (3- to 50-membered)heteroaryl unsubstituted or substituted by at least one of (C1-C30)alkyl, (C6-C30)aryl and di(C6-C30)arylamino; (C6-C30)aryl unsubstituted or substituted by at least one of deuterium, cyano, (C1-C30)alkyl, (3- to 50-membered)heteroaryl, di(C6-C30)arylamino and tri(C6-C30)arylsilyl; tri(C1-C30)alkylsilyl; tri(C6-C30)arylsilyl; di(C1-C30)alkyl(C6-C30)arylsilyl; (C1-C30)alkyldi(C6-C30)arylsilyl; tri(C6-C30)arylgermanyl; amino; mono- or di-(C1-C30)alkylamino; mono- or di-(C6-C30)arylamino; (C1-C30)alkyl(C6-C30)arylamino; (C1-C30)alkylcarbonyl; (C1-C30)alkoxycarbonyl; (C6-C30)arylcarbonyl; di(C6-C30)arylboronyl; di(C1-C30)alkylboronyl; (C1-C30)alkyl(C6-C30)arylboronyl; (C6-C30)ar(C1-C30)alkyl; and (C1-C30)alkyl(C6-C30)aryl. For example, the substituents of the substituted groups may be deuterium, methyl, phenyl, biphenyl, naphthyl, triphenylsilanyl, triphenylgermanyl, carbazolyl, dibenzofuranyl, or dibenzothiophenyl, etc.

Hereinafter, the plurality of host materials according to one embodiment will be described.

The plurality of host materials according to one embodiment comprise at least one first host compound comprising a compound represented by formula 1 and at least one second host compound comprising a compound represented by formula 2; and the plurality of host materials may be comprised in the light-emitting layer of an organic electroluminescent device according to one embodiment.

The first host compound as the host materials according to one embodiment is represented by the following formula 1.

(1)

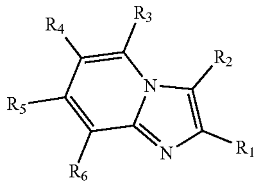

in formula 1, $R_1$ to $R_6$ each independently represent hydrogen, deuterium, halogen, cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $—SiR'_1R'_2R'_3$, or $—NR'_4R'_5$; or may be linked to the adjacent substituents to form a ring(s);

provided that at least one of $R_1$ to $R_6$ is (are) $-(L_1)_n$-HAr;

$L_1$ represents a single bond, a substituted or unsubstituted (C6-C30)arylene, or a substituted or unsubstituted (3- to 30-membered)heteroarylene;

HAr represents a substituted or unsubstituted nitrogen-containing (3- to 30-membered)heteroaryl;

n is an integer of 1 to 3, when n is an integer of 2 or more, each of $L_1$ may be the same or different; and $R'_1$ to $R'_5$ each independently represent a substituted or unsubstituted (C1-C30)alkyl, a substituted or unsubstituted (C2-C30)alkenyl, a substituted or unsubstituted (C6-C30) aryl, or a substituted or unsubstituted (3- to 30-membered) heteroaryl.

In one embodiment, $R_1$ to $R_6$ each independently may be hydrogen, deuterium, cyano, a substituted or unsubstituted (C6-C30)aryl, a substituted or unsubstituted (3- to 30-membered)heteroaryl, or $—SiR'_1R'_2R'_3$, preferably hydrogen, deuterium, cyano, a substituted or unsubstituted (C6-C25) aryl, a substituted or unsubstituted (5- to 25-membered) heteroaryl, or $—SiR'_1R'_2R'_3$, more preferably hydrogen, deuterium, cyano, a substituted or unsubstituted (C6-C25) aryl, a substituted or unsubstituted (5- to 18-membered) heteroaryl, or $—SiR'_1R'_2R'_3$. Wherein, $R'_1$ to $R'_3$ each independently may be a substituted or unsubstituted (C6-C30) aryl. For example, $R_1$ to $R_6$ each independently may be hydrogen, deuterium, cyano, a substituted or unsubstituted phenyl, a substituted or unsubstituted biphenyl, a substituted or unsubstituted naphthalenyl, a substituted or unsubstituted o-terphenyl, a substituted or unsubstituted phenanthrenyl, a substituted or unsubstituted fluorenyl, a substituted or unsubstituted spirobifluorenyl, a substituted or unsubstituted carbazolyl, a substituted or unsubstituted dibenzofuranyl, a substituted or unsubstituted dibenzothiophenyl, a substituted or unsubstituted dibenzoselenophenyl, or a substituted or unsubstituted triphenylsilyl. For example, the substituents of the substituted groups may be deuterium, methyl, phenyl, triphenylsilanyl, or triphenylgermanyl.

Provided that at least one of $R_1$ to $R_6$ may be $-(L_1)_n$-HAr, preferably $R_1$ or $R_2$ may be $-(L_1)_n$-HAr. For example, the compound represented by formula 1 may be represented by the following formula 1-1 or 1-2.

(1-1)

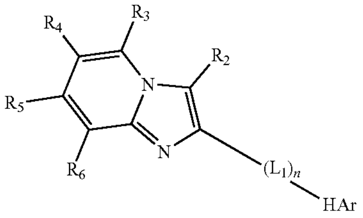

(1-2)

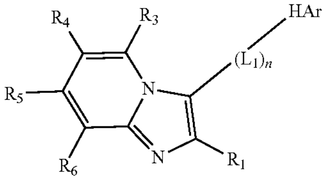

in formulas 1-1 and 1-2, $R_1$ to $R_6$, $L_1$, HAr, and n are as defined in formula 1.

In one embodiment, $L_1$ may be a substituted or unsubstituted (C6-C30)arylene or a substituted or unsubstituted (5- to 30-membered)heteroarylene, preferably a substituted or unsubstituted (C6-C25)arylene or a substituted or unsubstituted (5- to 25-membered)heteroarylene, more preferably a substituted or unsubstituted (C6-C25)arylene or a substituted or unsubstituted (5- to 18-membered)heteroarylene. For example, $L_1$ may be a substituted or unsubstituted phenylene, a substituted or unsubstituted naphthalenylene, a substituted or unsubstituted p-biphenylene, a substituted or unsubstituted m-biphenylene, a substituted or unsubstituted o-biphenylene, a substituted or unsubstituted m-terphenylene, a substituted or unsubstituted o-terphenylene, a substituted or unsubstituted phenanthrenylene, a substituted or unsubstituted fluorenylene, a substituted or unsubstituted spirobifluorenylene, a substituted or unsubstituted carbazolylene, a substituted or unsubstituted dibenzofuranylene, or a substituted or unsubstituted dibenzothiophenylene. For example, the substituents of the substituted groups may be methyl, phenyl, or biphenyl.

In one embodiment, HAr may be a substituted or unsubstituted nitrogen-containing (5- to 30-membered)heteroaryl, preferably a substituted or unsubstituted (5- to 25-membered)heteroaryl containing at least two nitrogens, more preferably a substituted or unsubstituted (5- to 18-membered)heteroaryl containing at least three nitrogens. For example, HAr may be a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, or a substituted or unsubstituted benzothienopyrimidinyl. For example, the substituents of the substituted groups may be (C6-C30)aryl or (5- to 30-membered)heteroaryl. For example, HAr may be triazinyl substituted by at least one selected from the group consisting of phenyl, p-biphenyl, m-biphenyl, o-biphenyl, naphthyl, m-terphenyl, o-terphenyl, phenanthrenyl, triphenylenyl, dimethylfluorenyl, diphenylfluorenyl, spirobifluorenyl, dibenzofuranyl, dibenzothiophenyl, and carbazolyl unsubstituted or substituted by phenyl.

According to one embodiment, the first host compound represented by the formula 1 may be more specifically illustrated by the following compounds, but is not limited thereto.

C-1

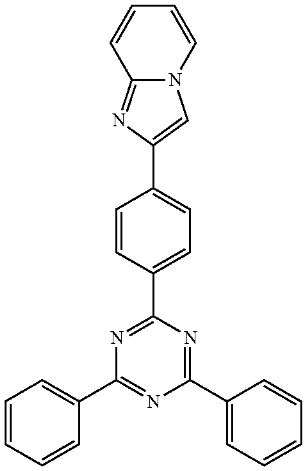

C-2

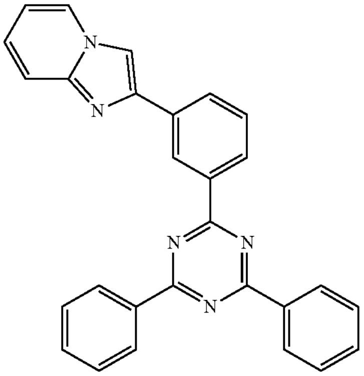

C-3

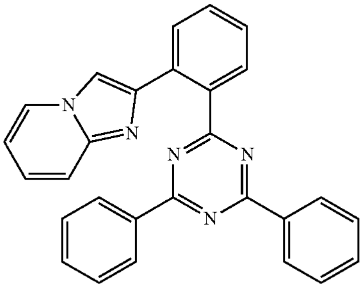

-continued

C-4

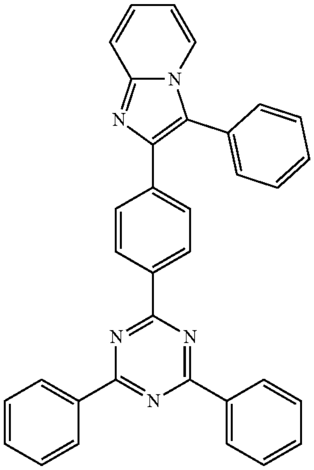

C-5

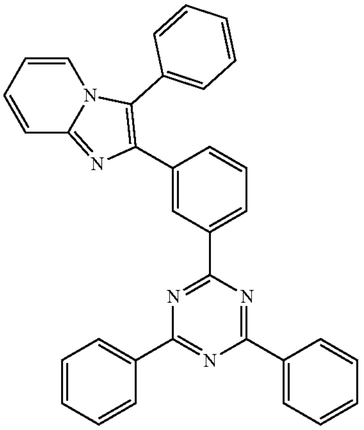

C-6

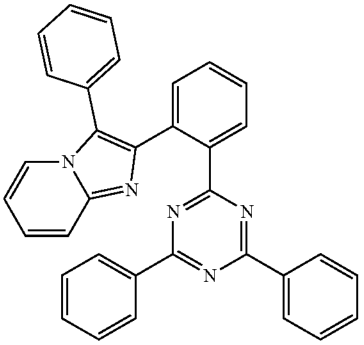

-continued
C-7
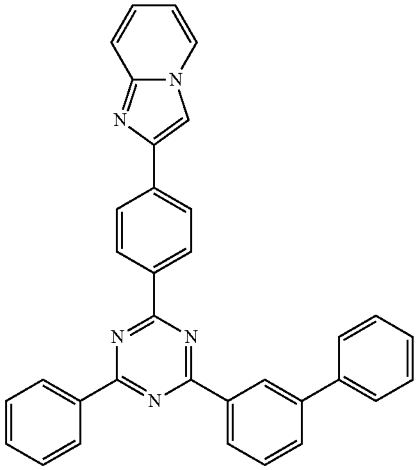
C-8
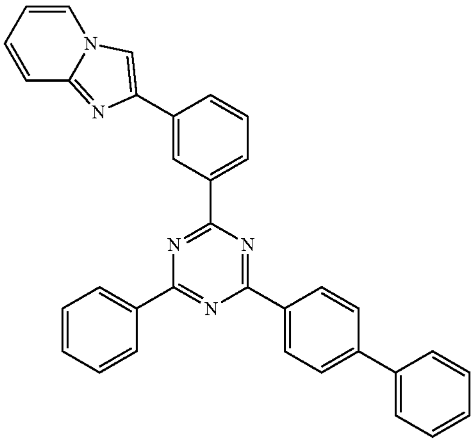
C-9
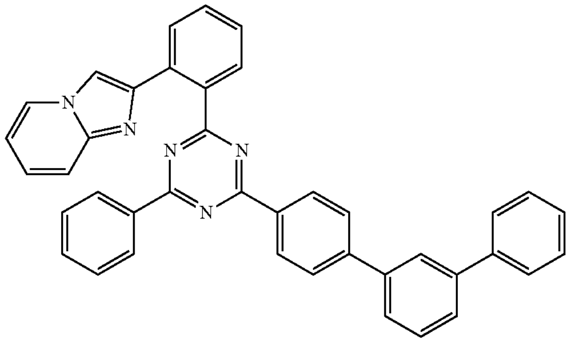
-continued
C-10
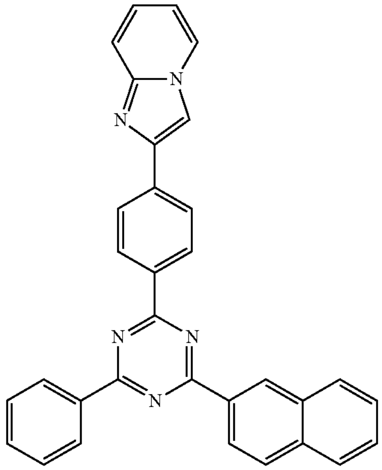
C-11
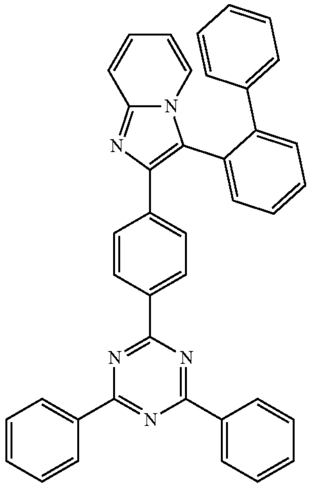
C-12
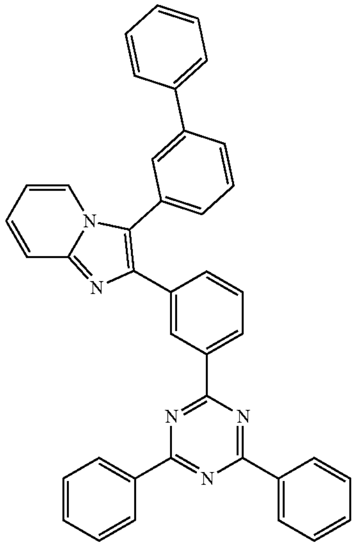

-continued
C-13
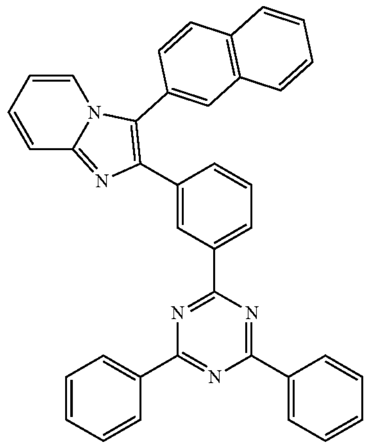
C-14
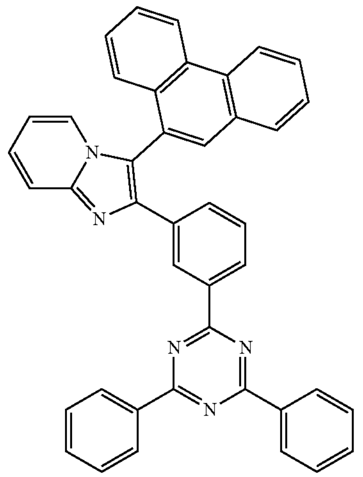
C-15
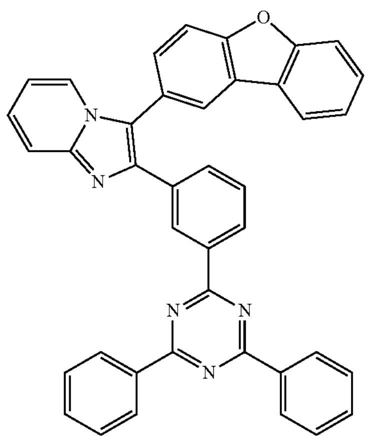
-continued
C-16
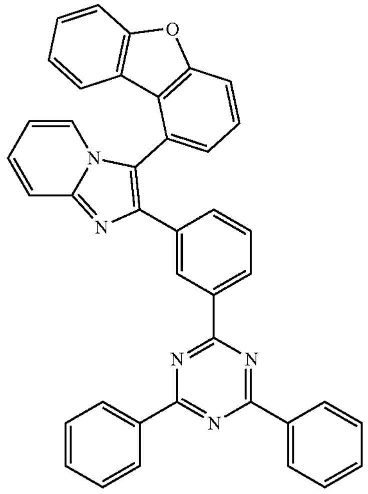
C-17
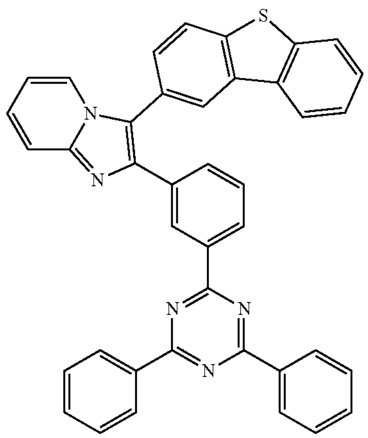
C-18
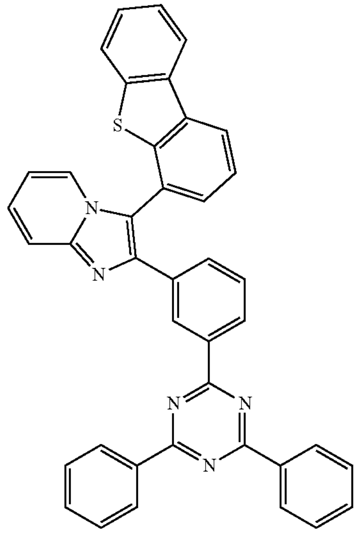

-continued
C-19
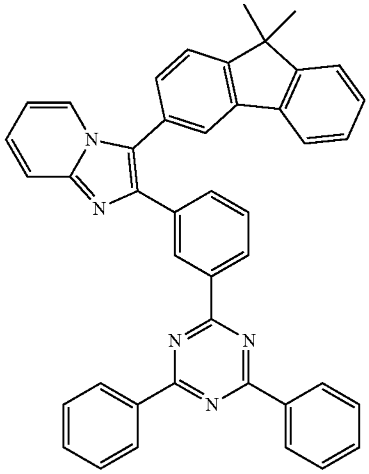
C-20
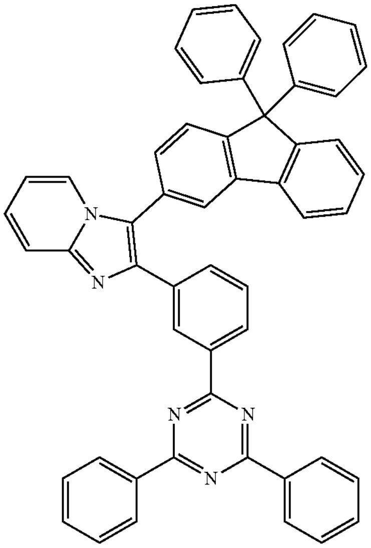
C-21
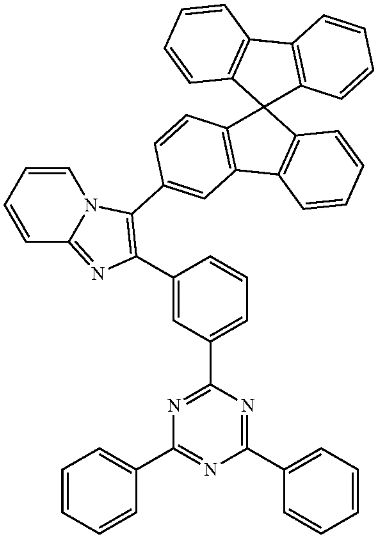
-continued
C-22
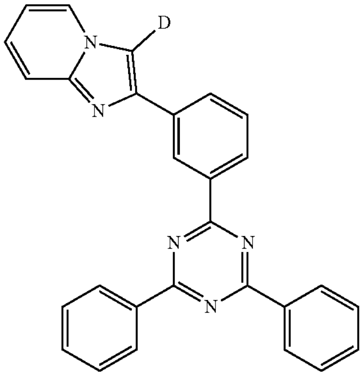
C-23
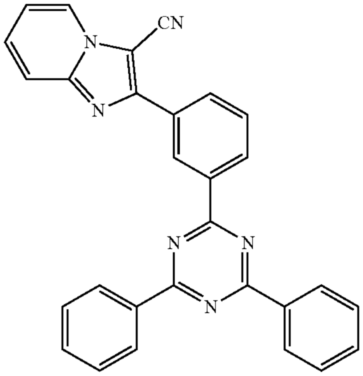
C-24
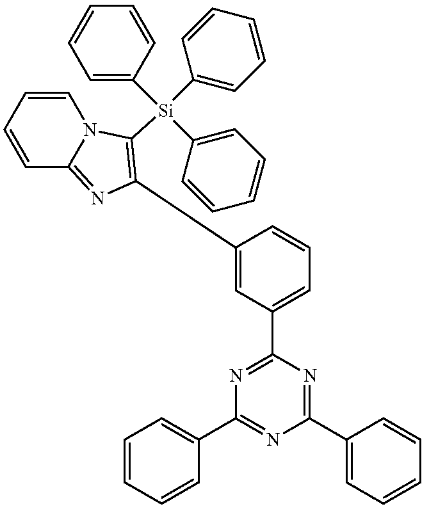

-continued
C-25
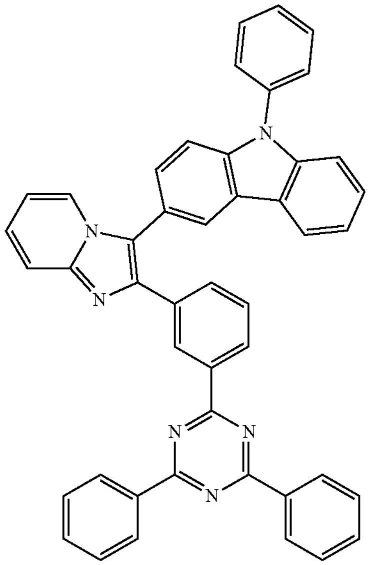
C-26
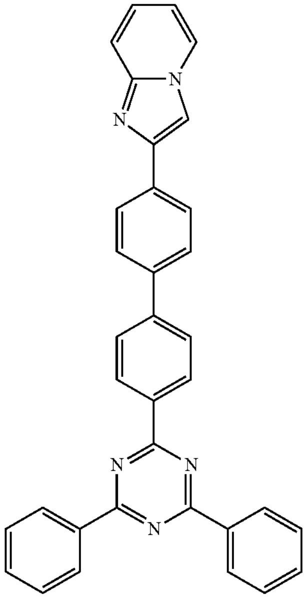
-continued
C-27
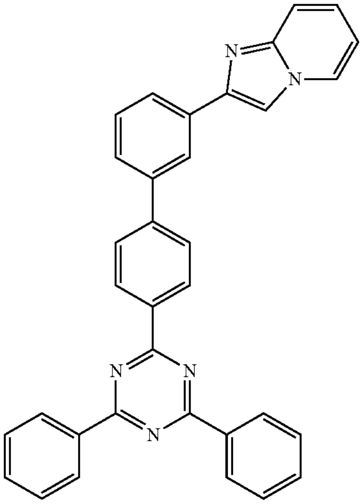
C-28
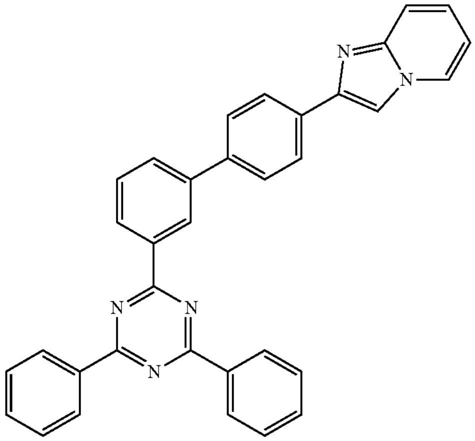
C-29
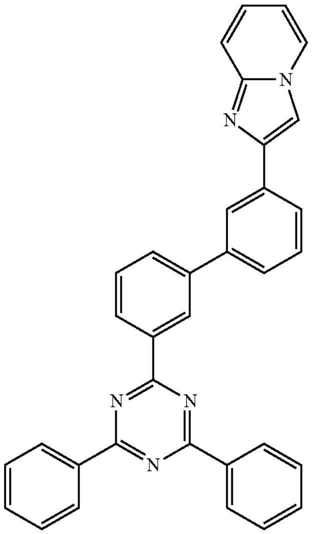

-continued
C-30
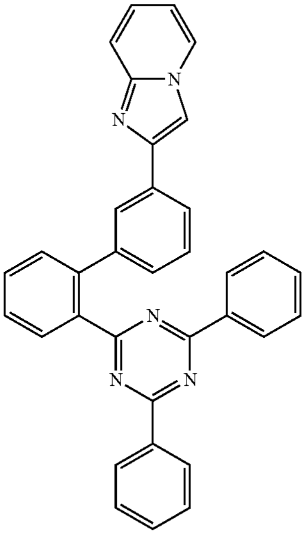
C-31
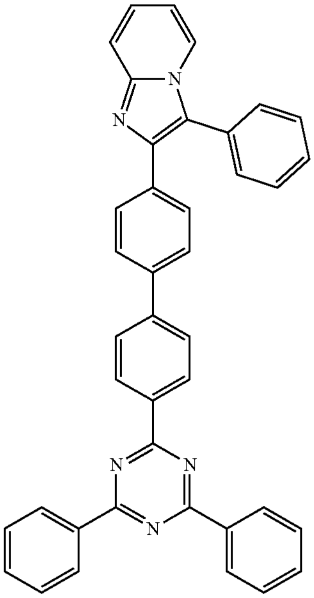
C-32
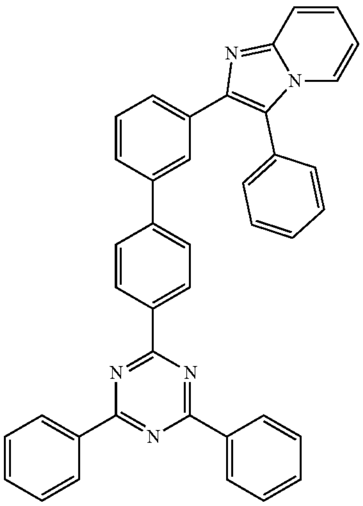
-continued
C-33
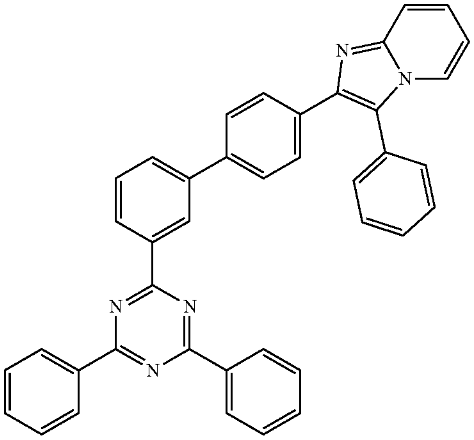
C-34
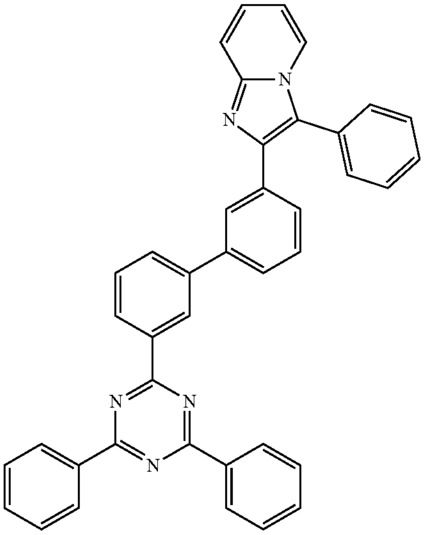
C-35
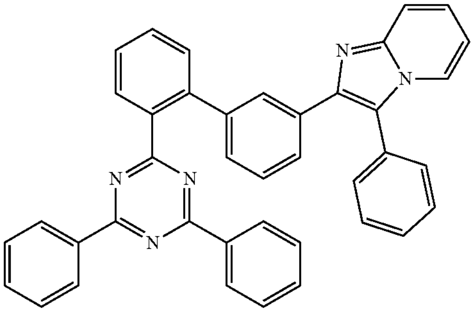

-continued
C-36
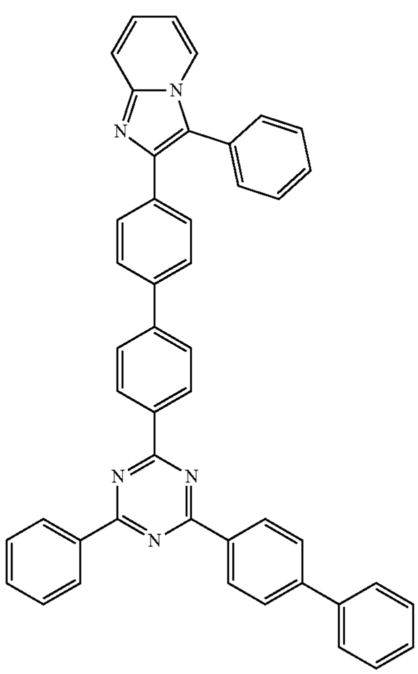
C-37
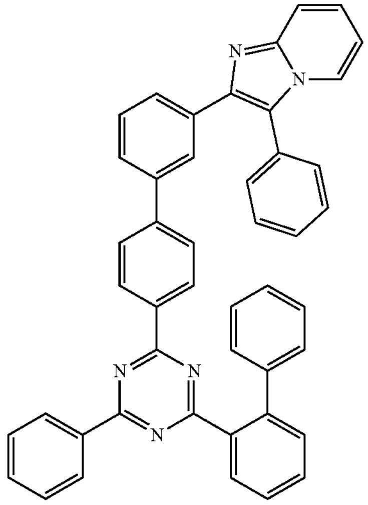
C-38
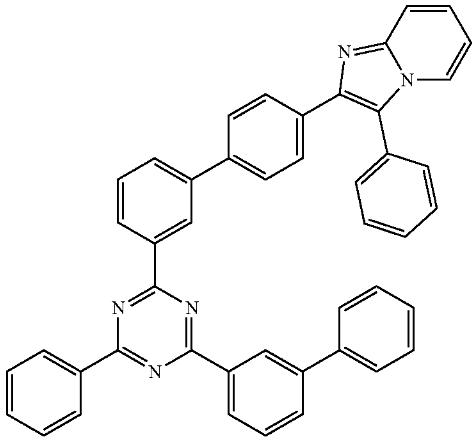
-continued
C-39
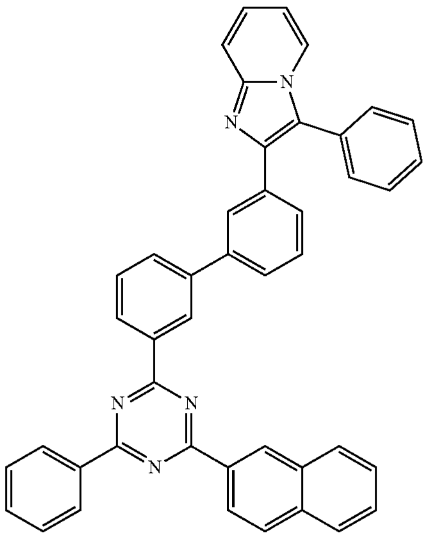
C-40
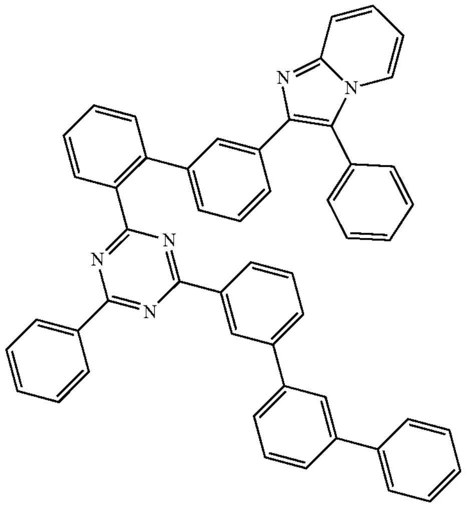
C-41
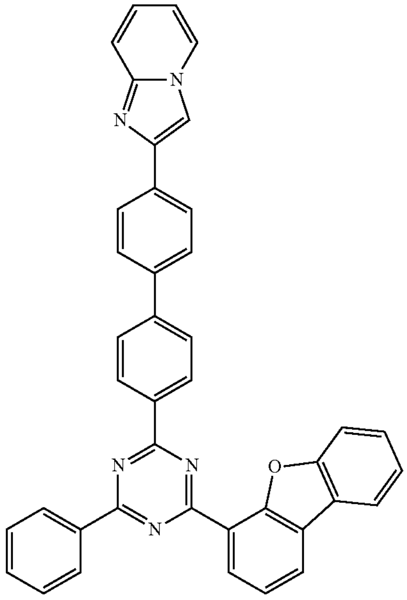

-continued
C-42
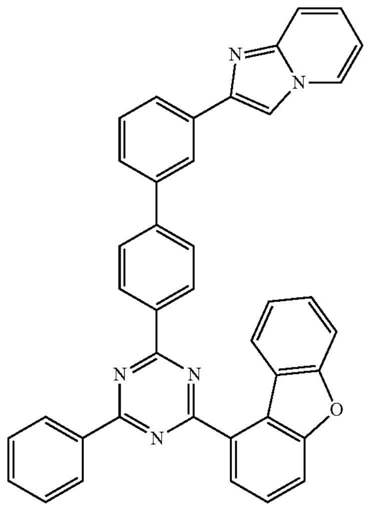
C-43
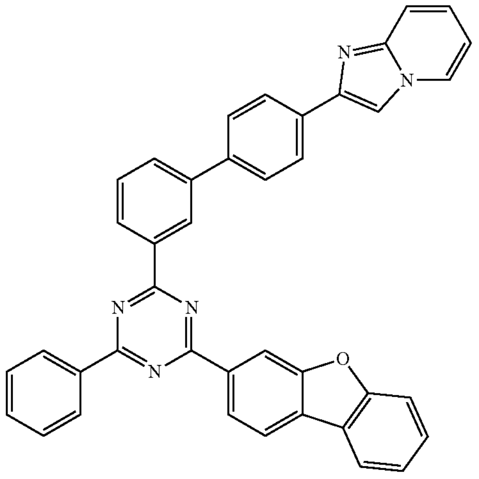
C-44
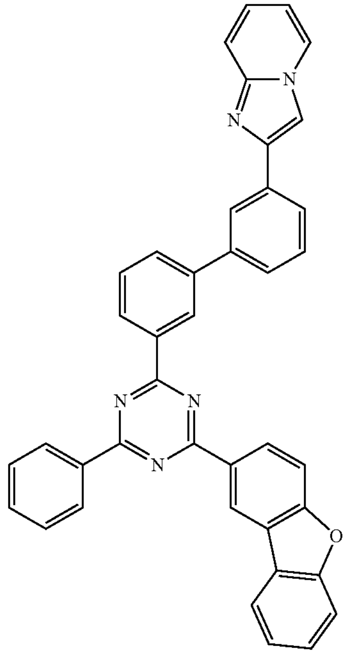
-continued
C-45
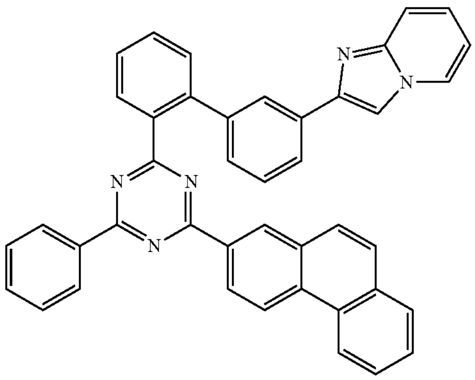
C-46
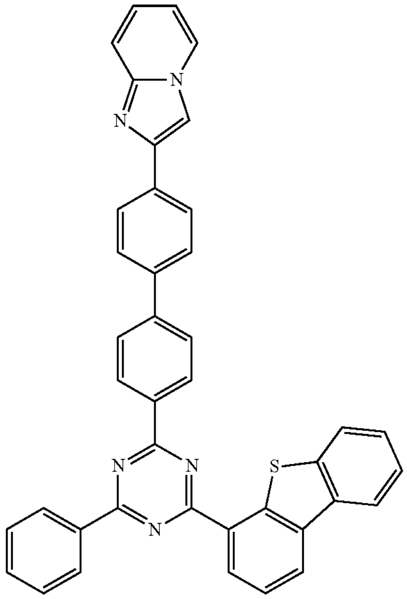
C-47
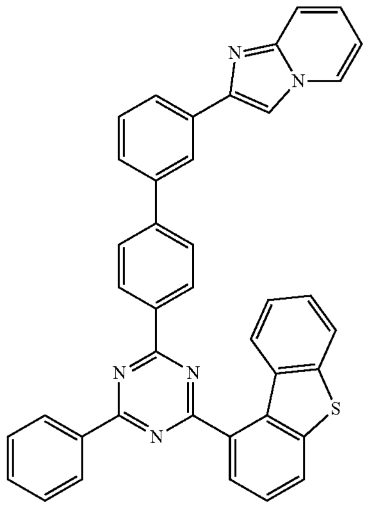

-continued
C-48
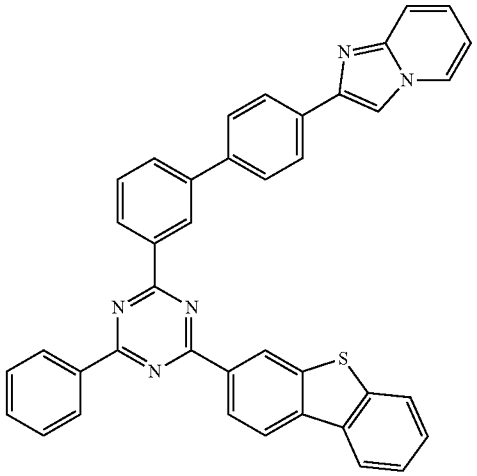
C-49
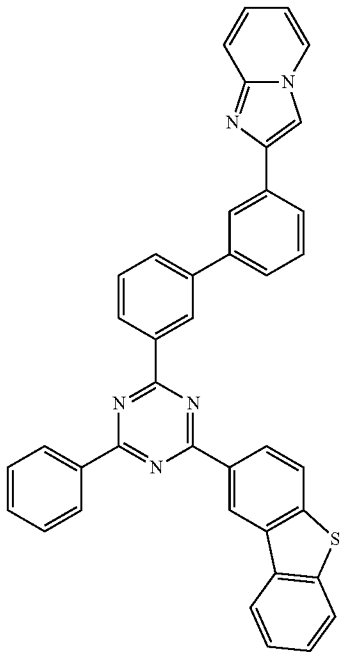
C-50
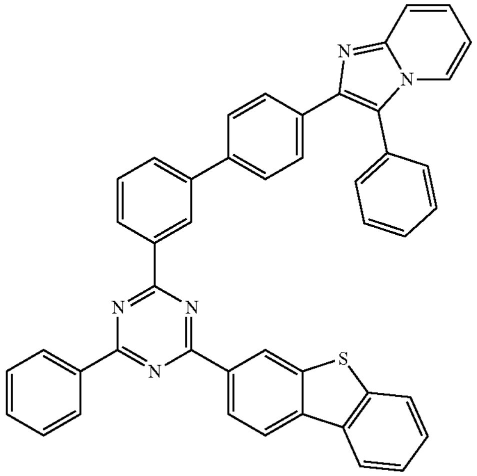
-continued
C-51
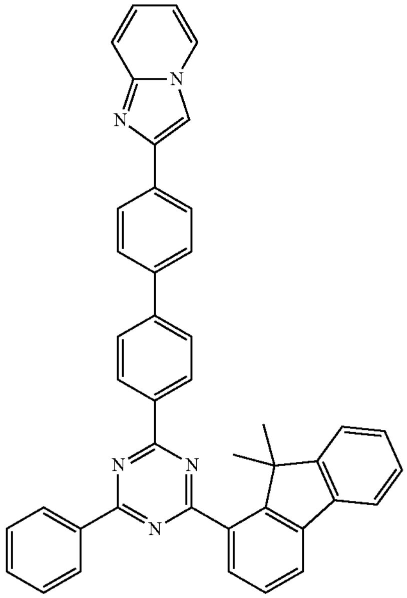
C-52
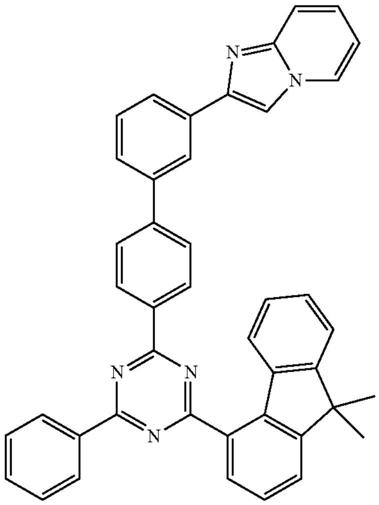
C-53
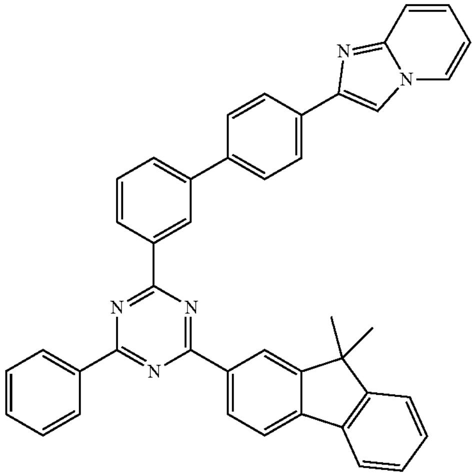

-continued
C-54
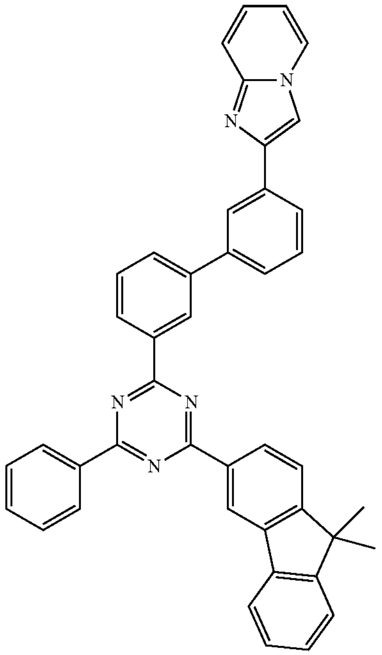
C-55
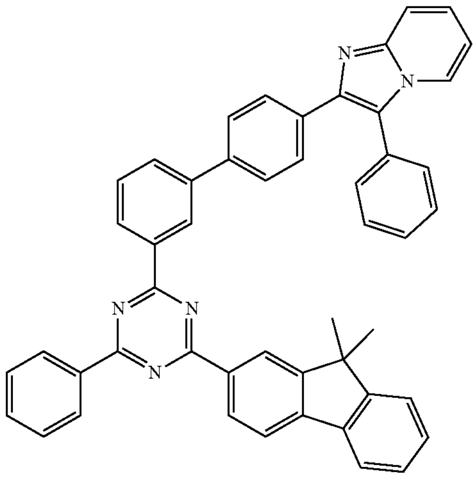
-continued
C-56
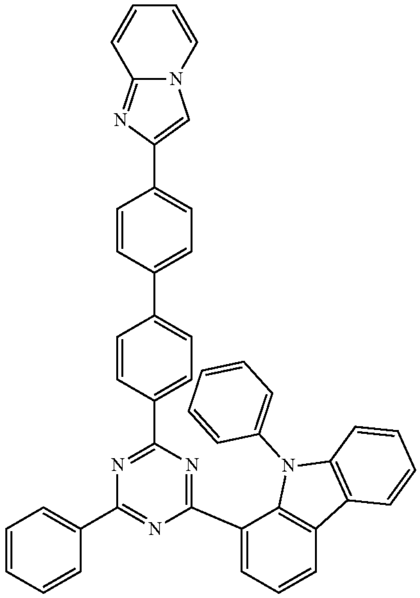
C-57
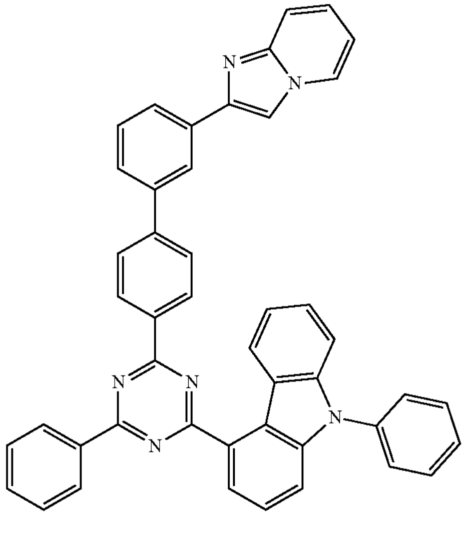
C-58
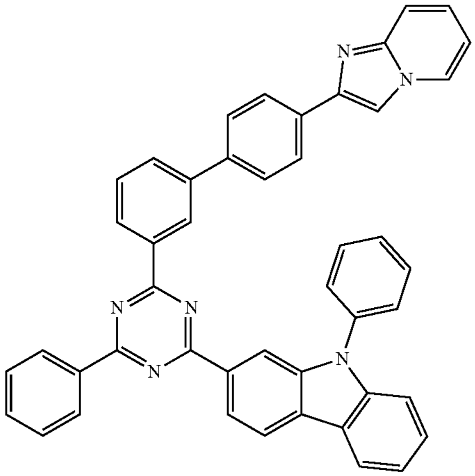

-continued
C-59
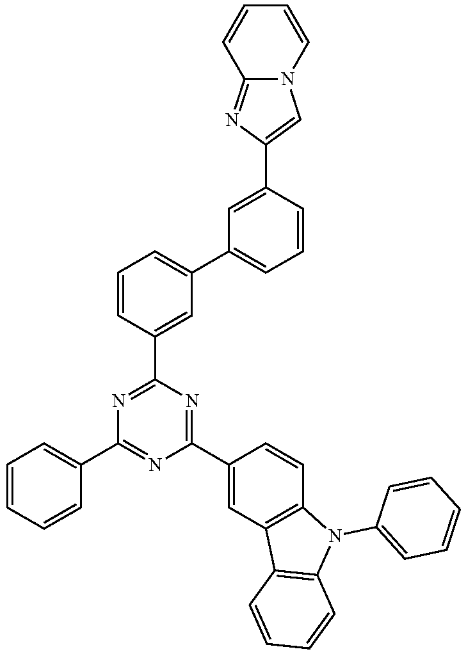
C-60
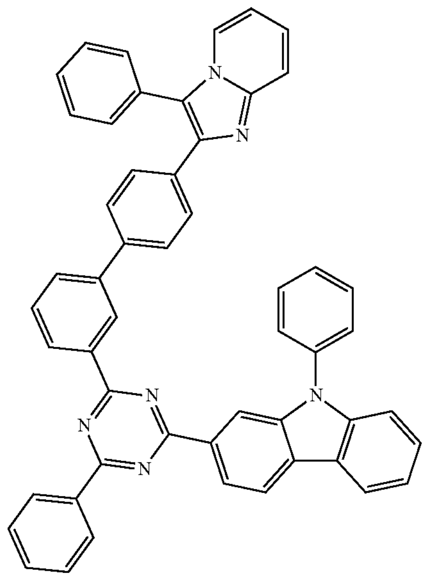
-continued
C-61
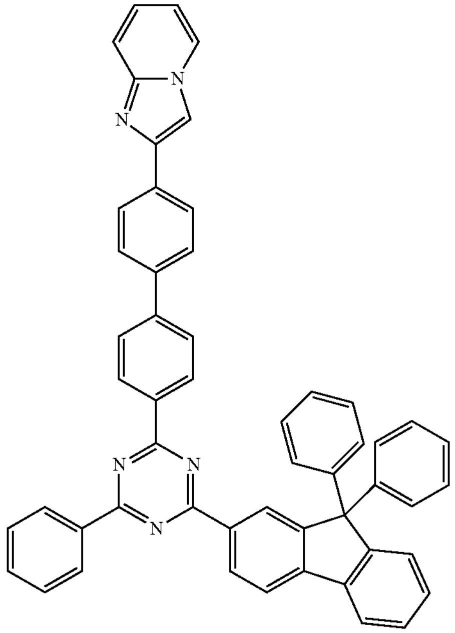
C-62
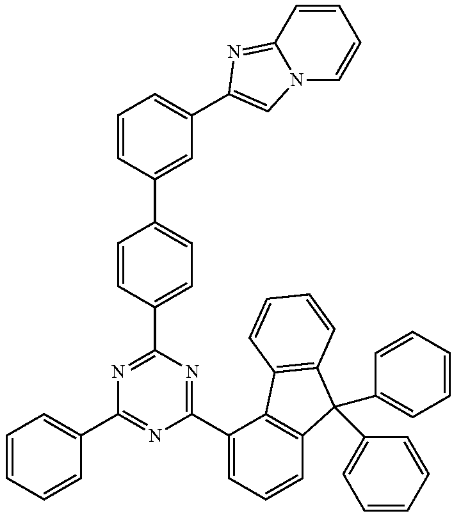
C-63
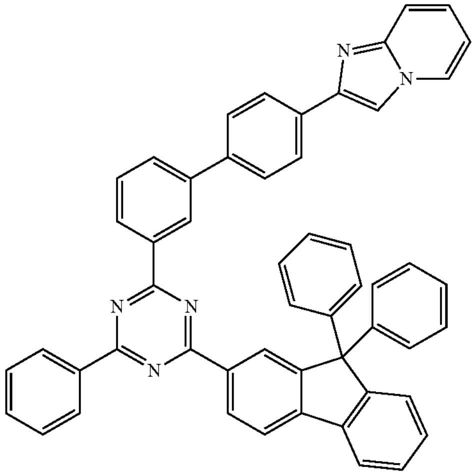

-continued
C-64
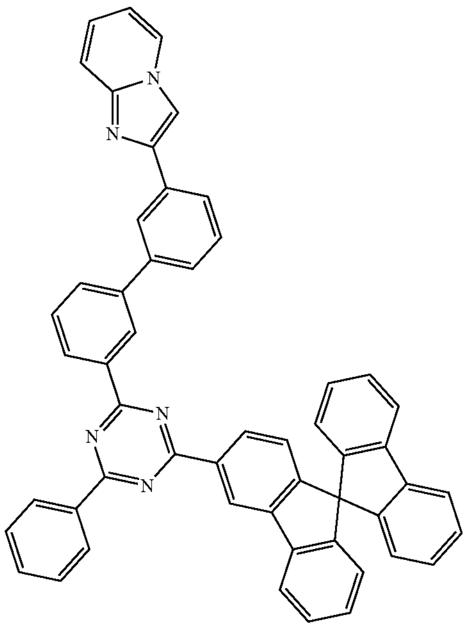
C-65
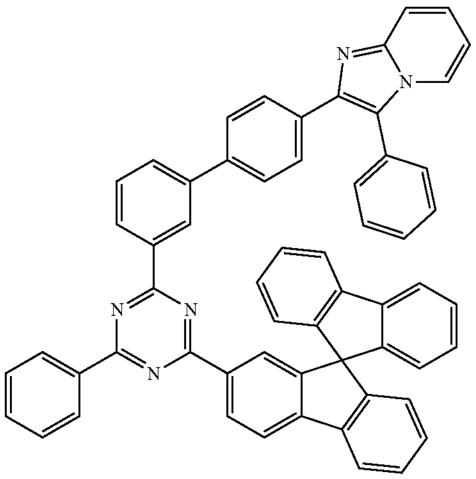
-continued
C-66
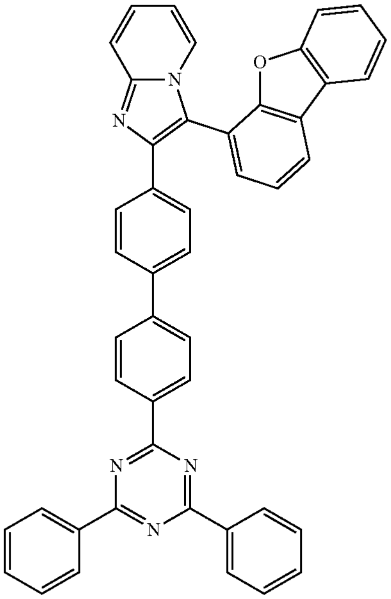
C-67
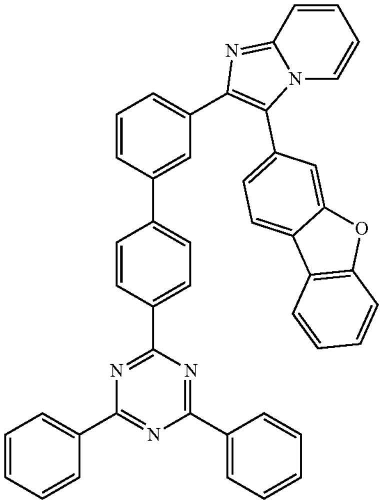
C-68
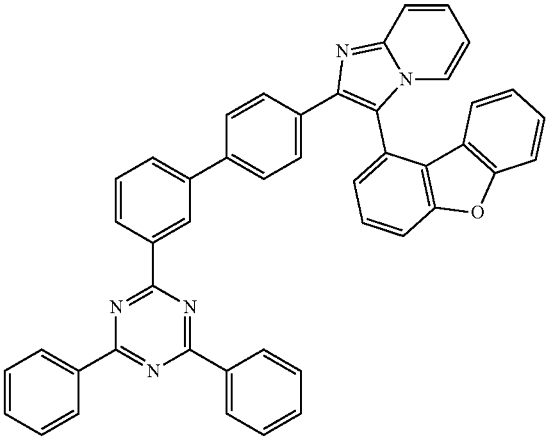

-continued
C-69
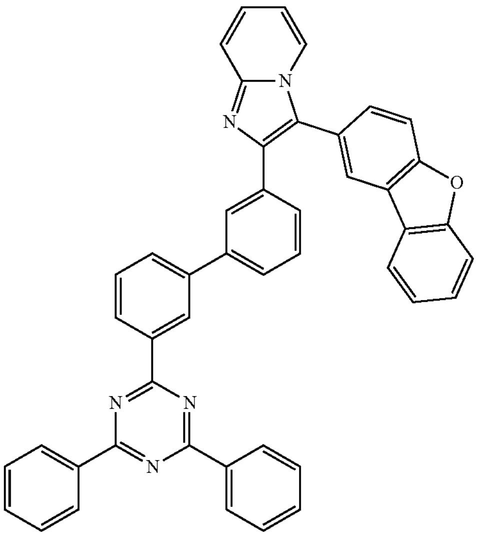
C-70
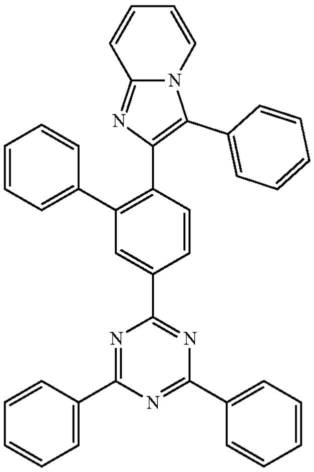
C-71
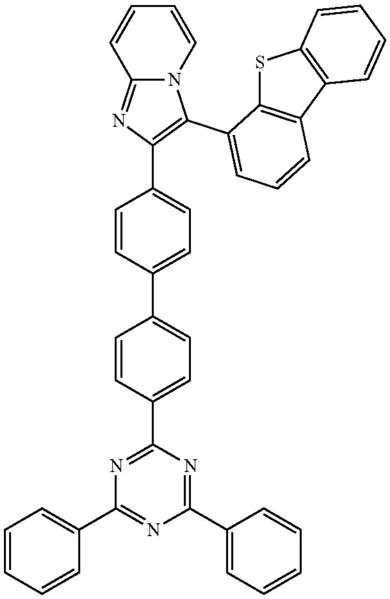
-continued
C-72
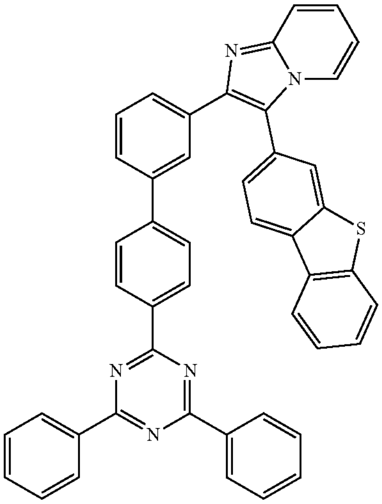
C-73
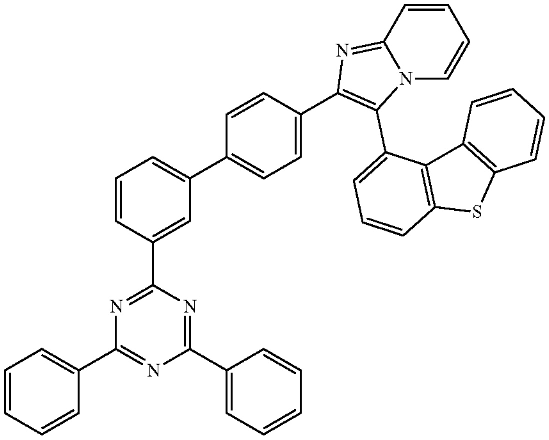
C-74
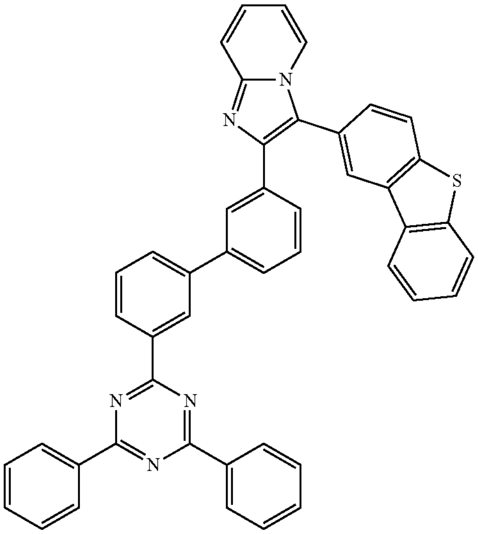

-continued
C-75
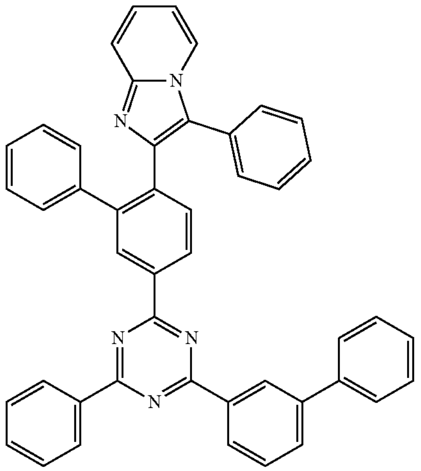
C-76
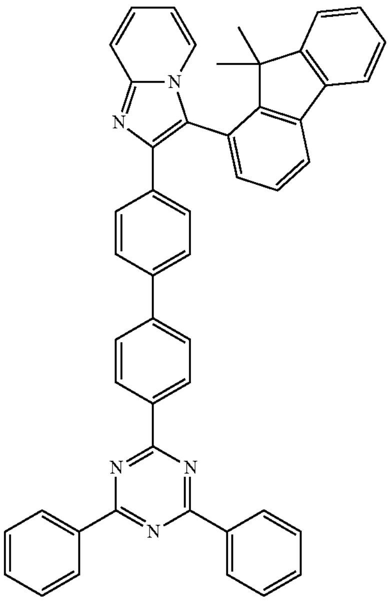
C-77
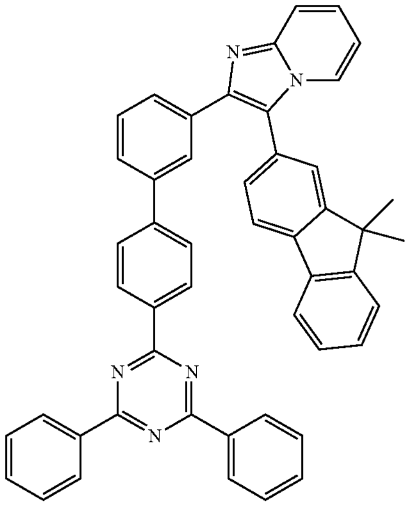
-continued
C-78
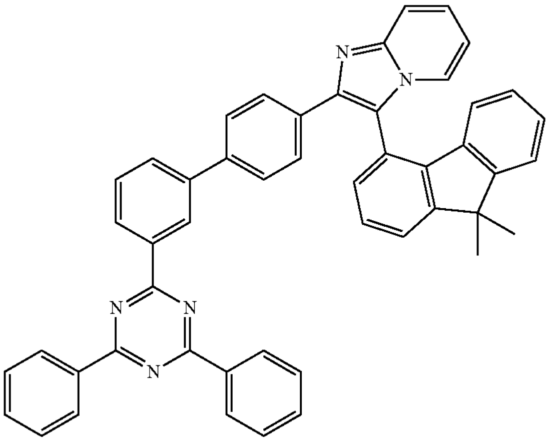
C-79
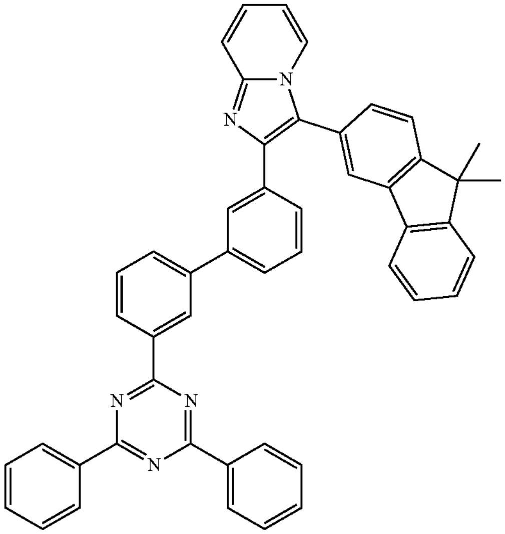
C-80
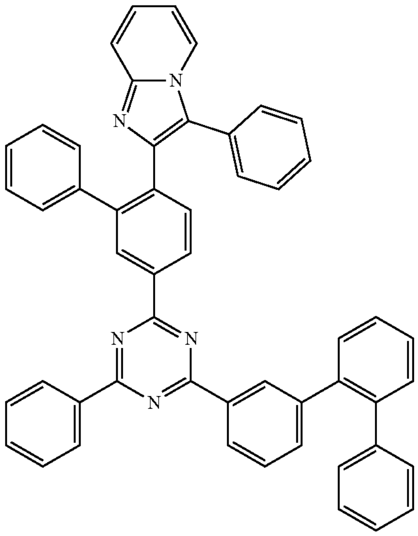

-continued
C-81
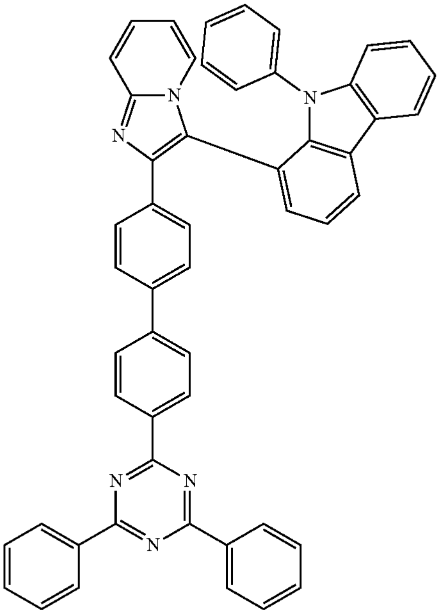
C-82
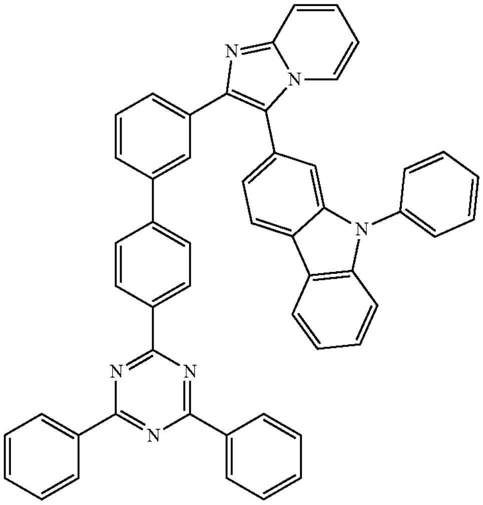
C-83
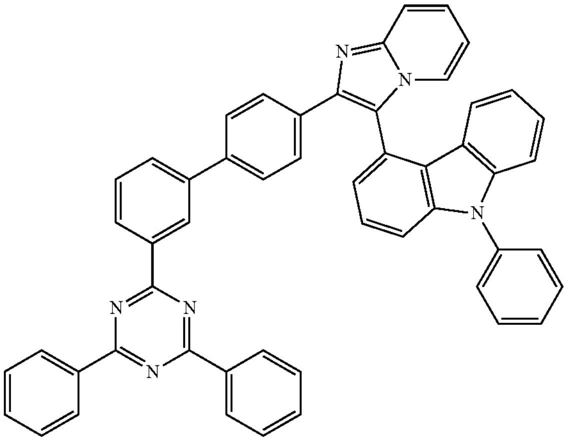
-continued
C-84
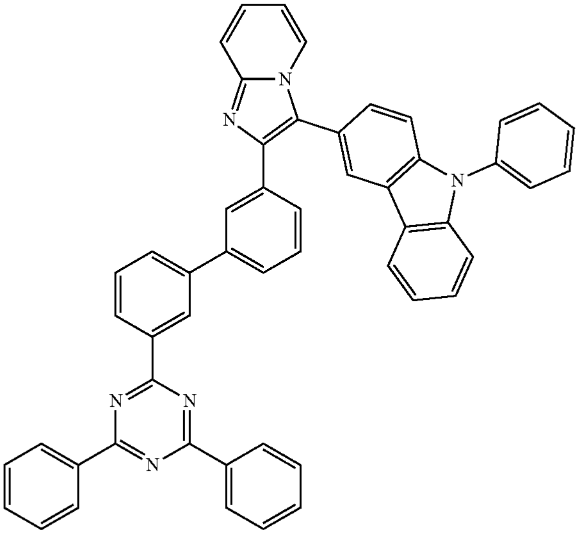
C-85
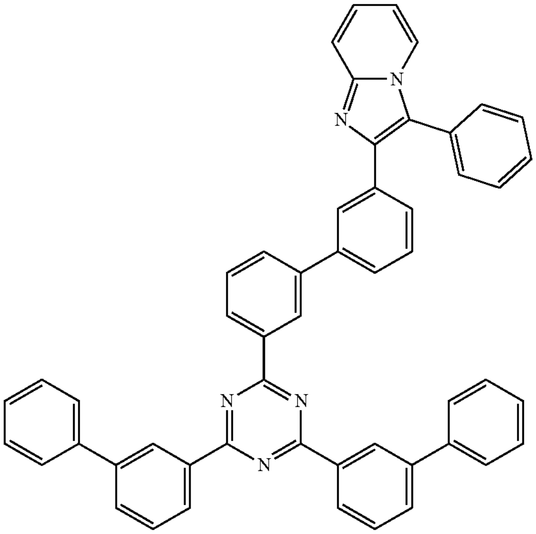

-continued
C-86
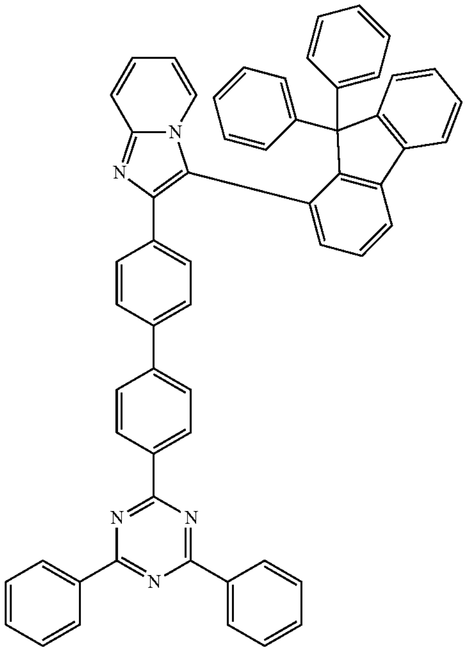
C-87
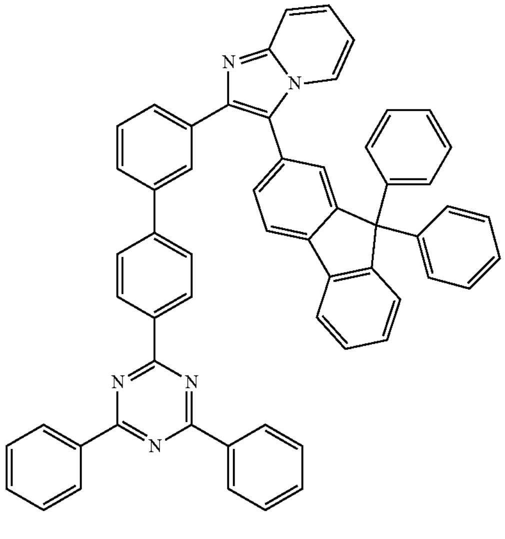
C-88
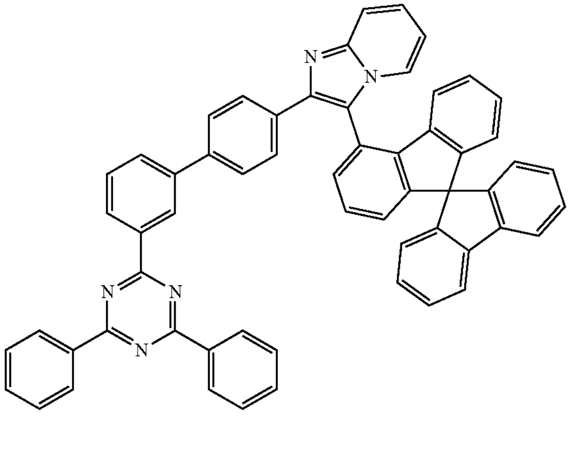
-continued
C-89
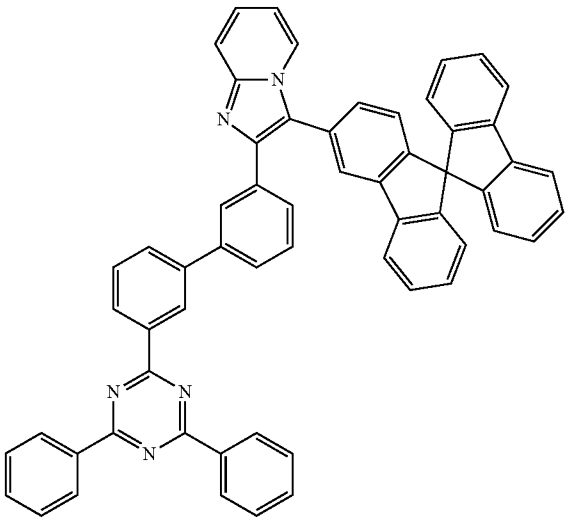
C-90
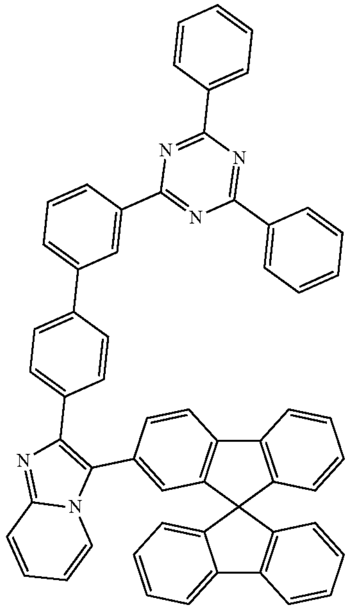
C-91
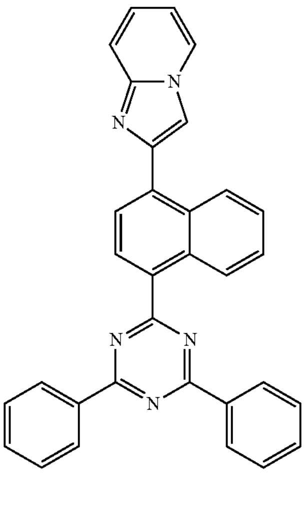

-continued
C-92
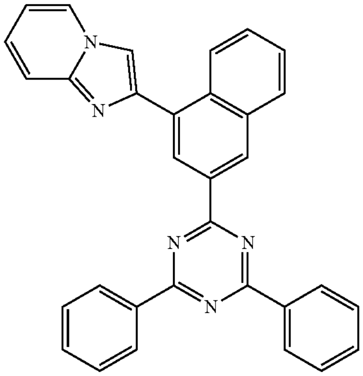
C-93
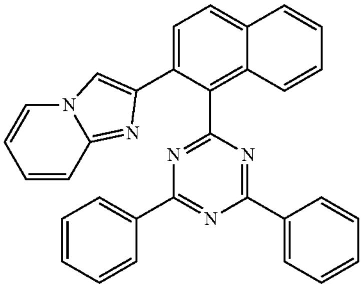
C-94
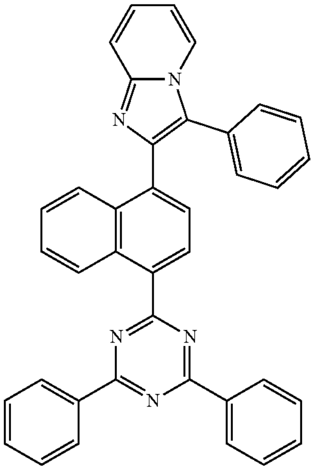
C-95
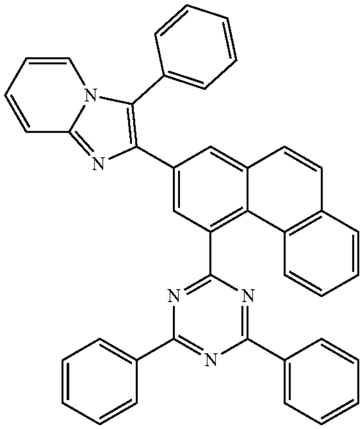
-continued
C-96
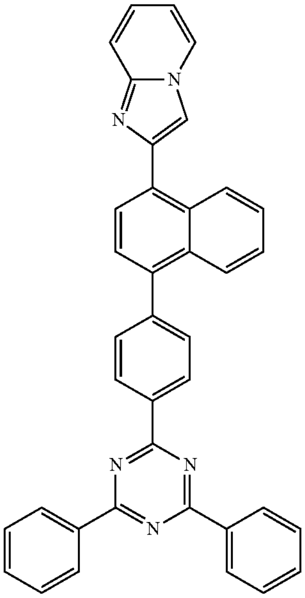
C-97
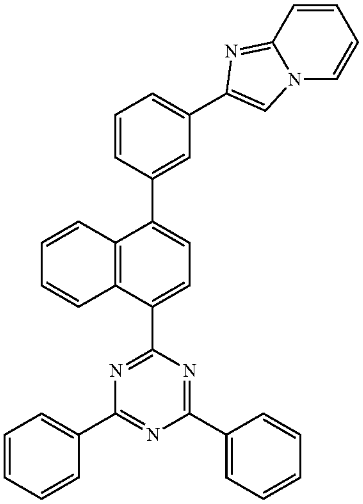
C-98
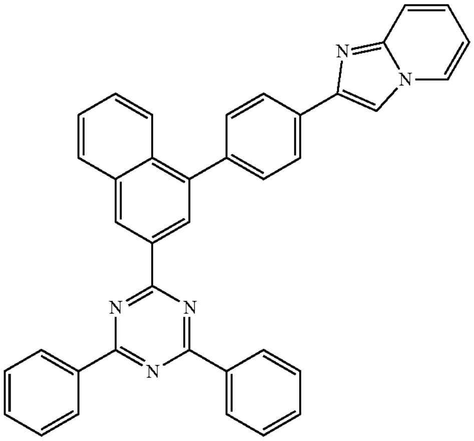

-continued
C-99
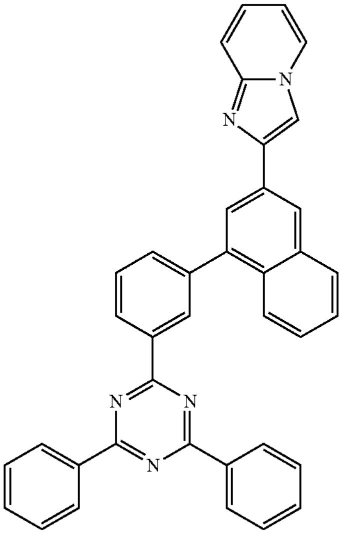
C-100
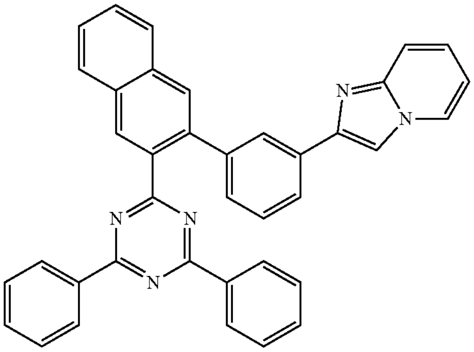
C-101
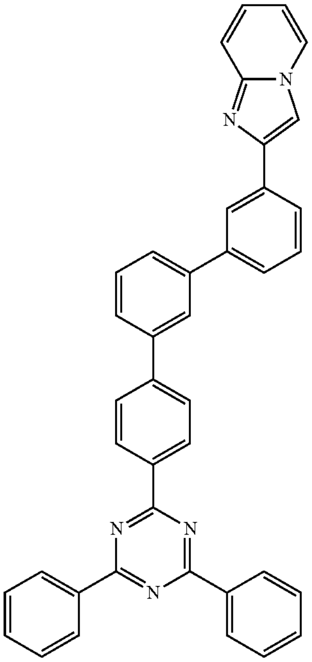
-continued
C-102
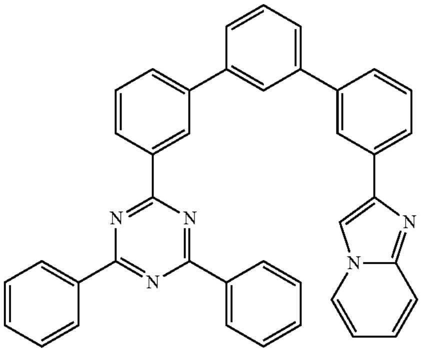
C-103
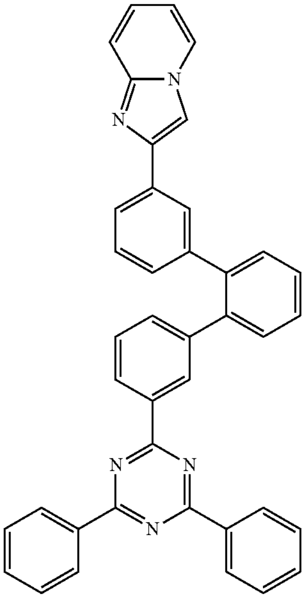
C-104
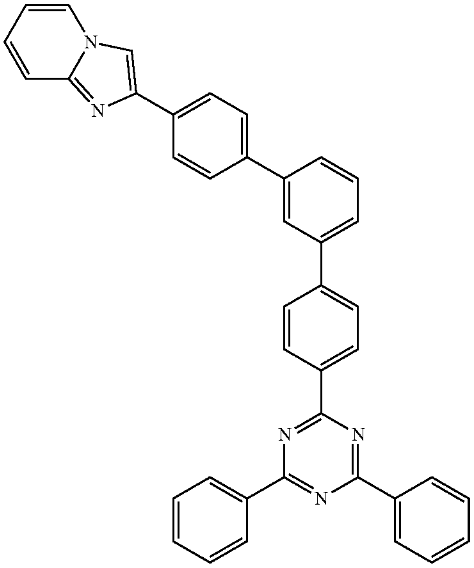

-continued
C-105
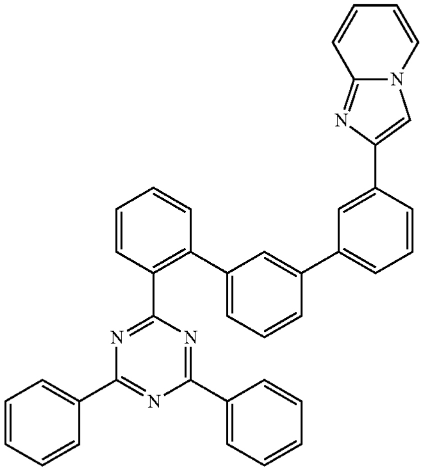
C-106
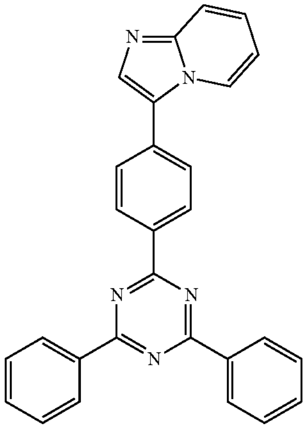
C-107
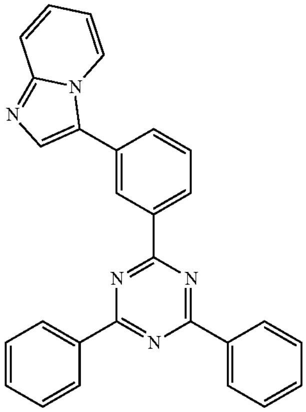
C-108
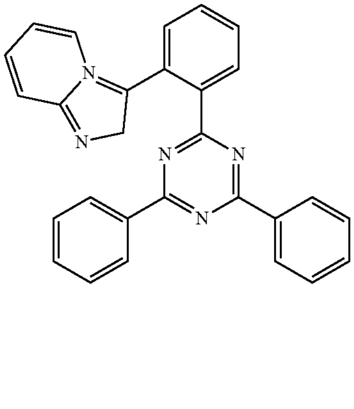
-continued
C-109
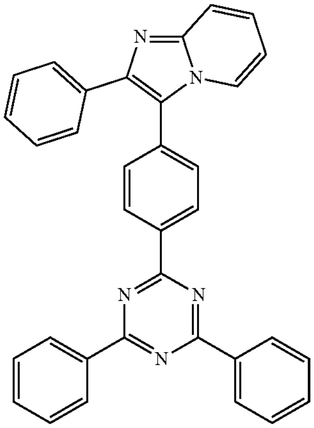
C-110
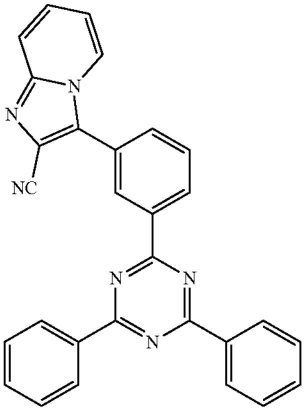
C-111
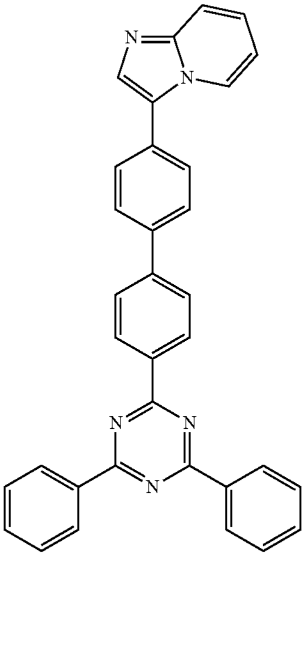

-continued
C-112
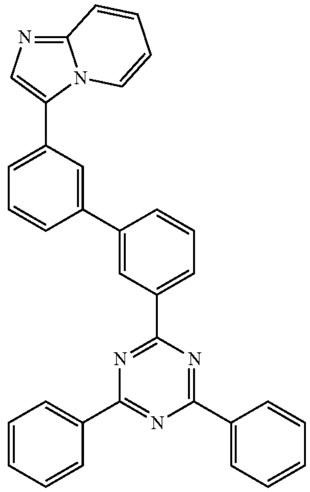
C-113
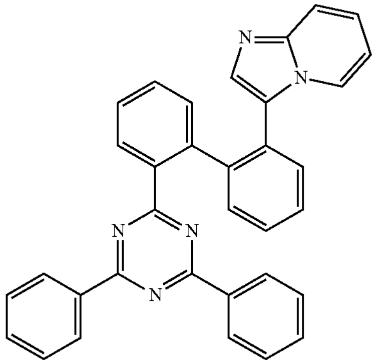
C-114
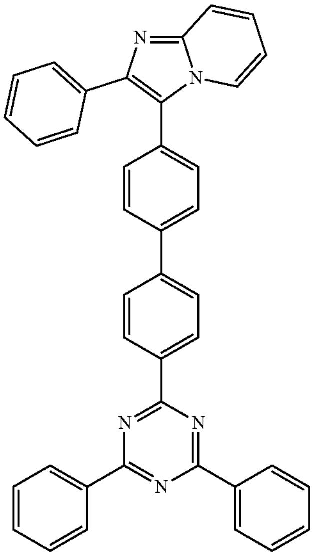
-continued
C-115
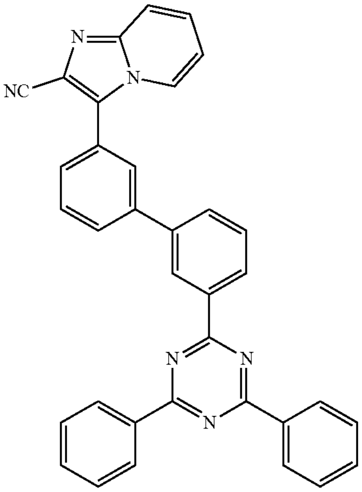
C-116
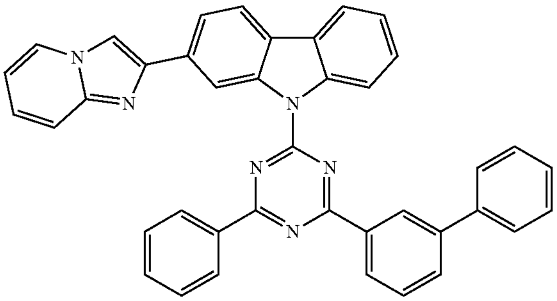
C-117
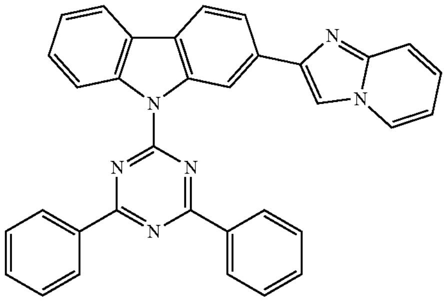
C-118
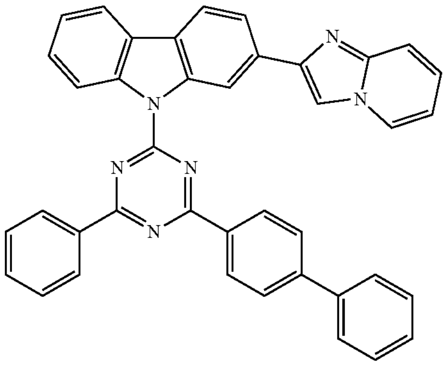

C-119
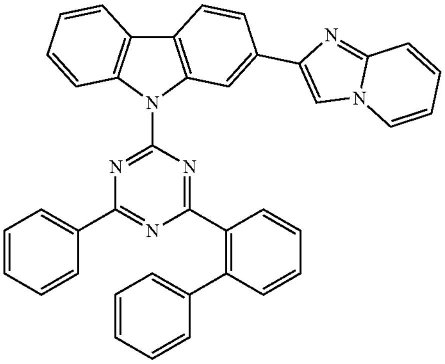
C-120
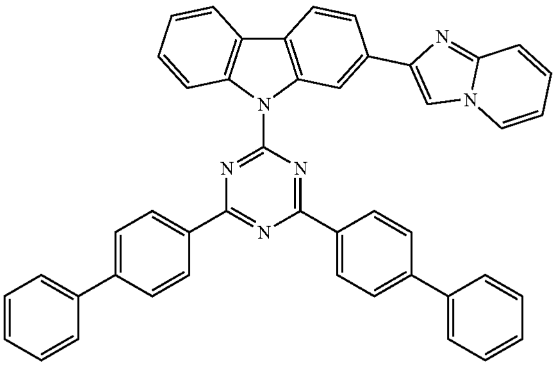
C-121
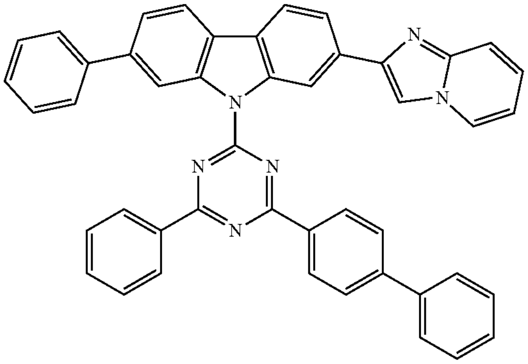
C-122
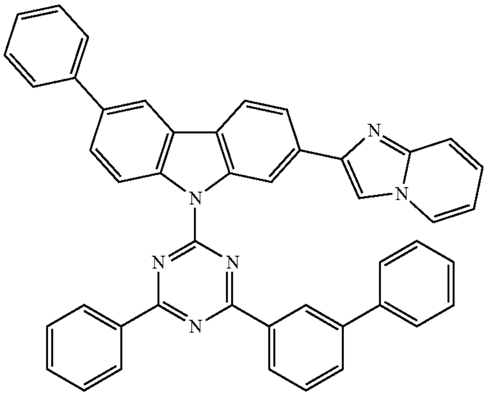
C-123
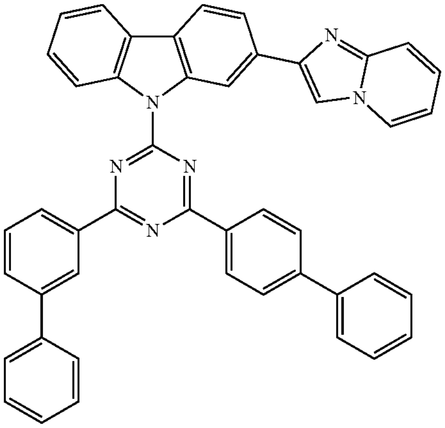
C-124
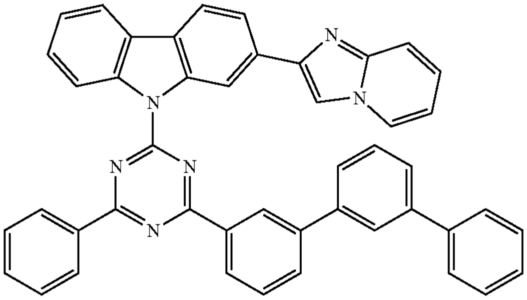
C-125
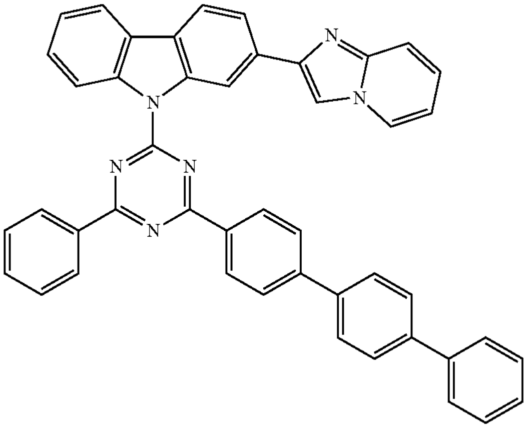
C-126
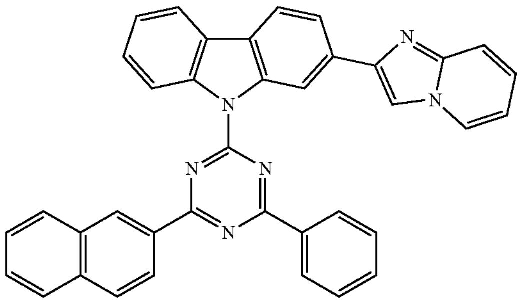

-continued
C-127
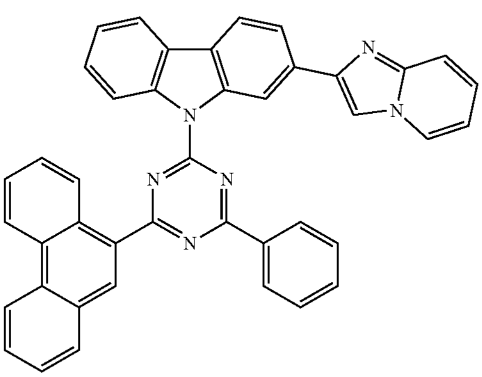
C-128
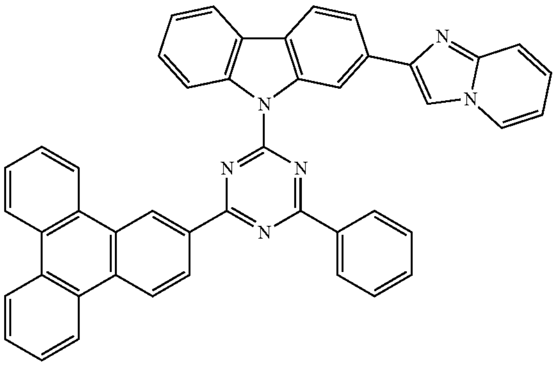
C-129
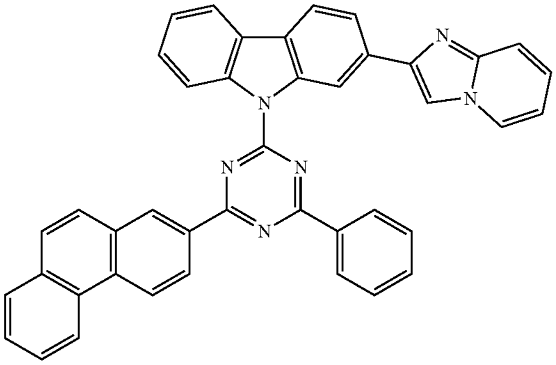
C-130
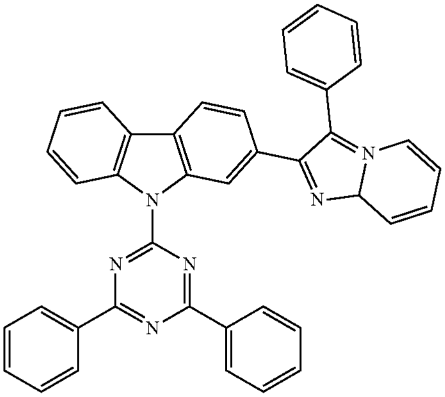
-continued
C-131
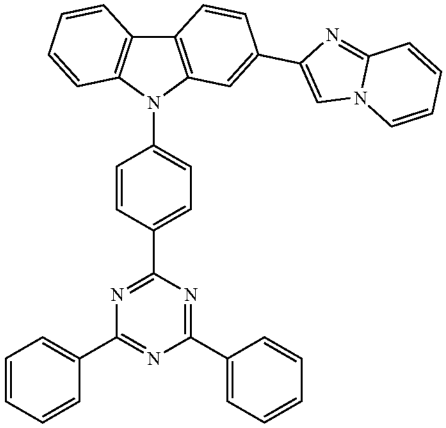
C-132
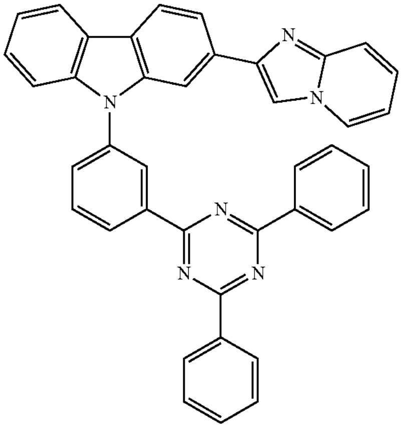
C-133
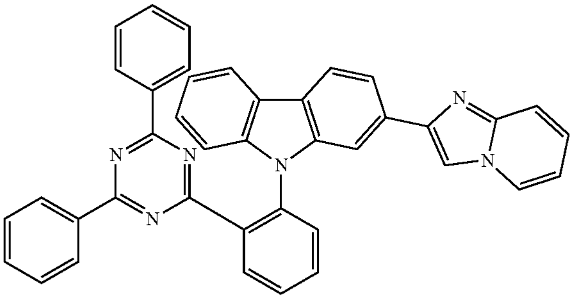

-continued
C-134
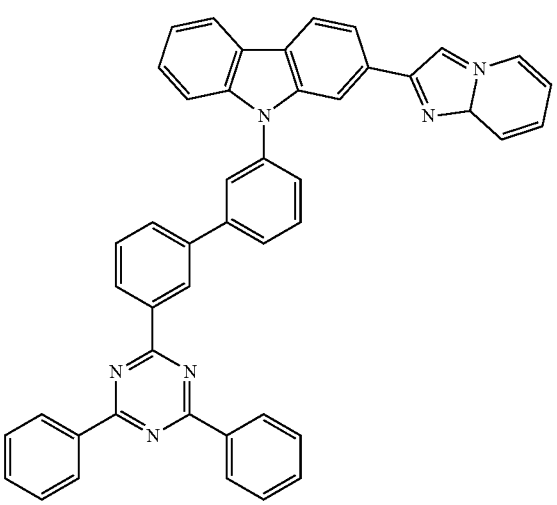
C-135
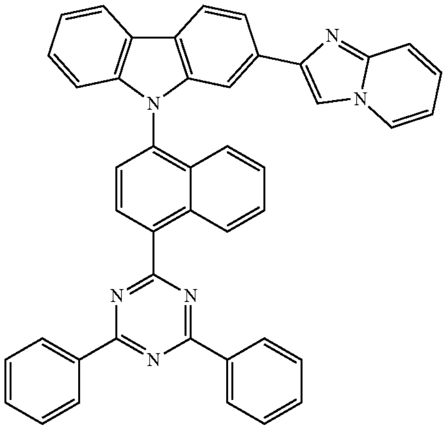
C-136
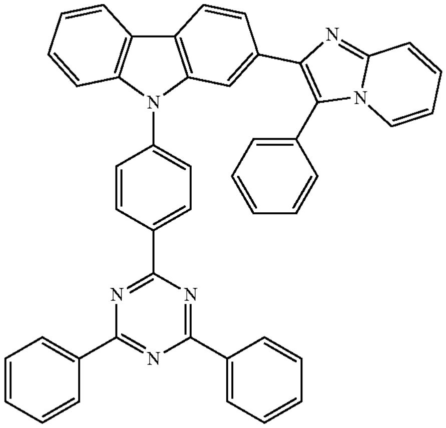
-continued
C-137
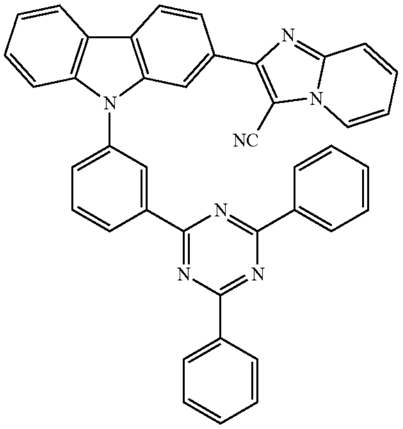
C-138
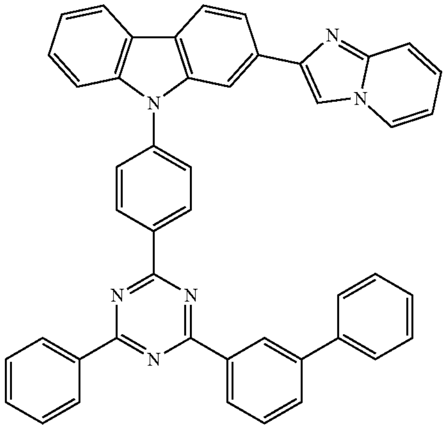
C-139
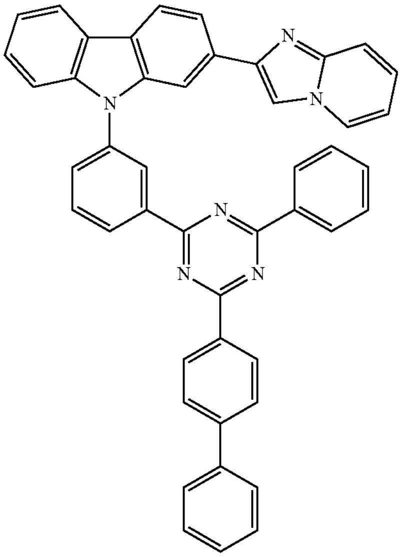

-continued
C-140
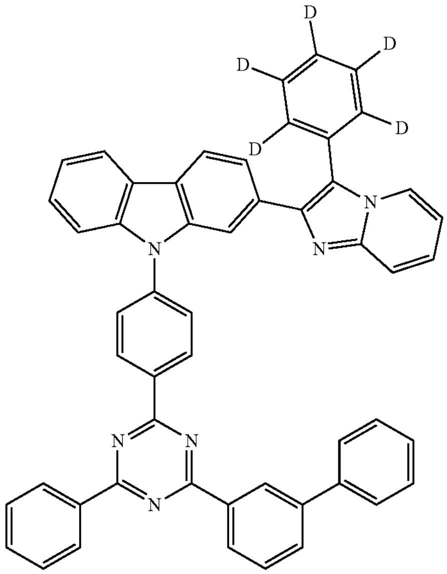
C-141
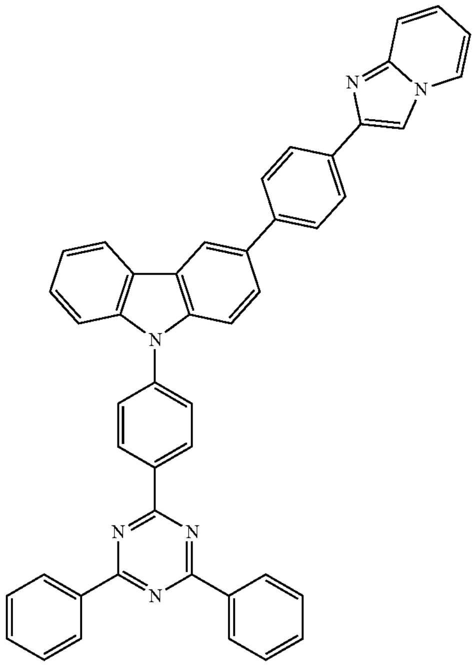
-continued
C-142
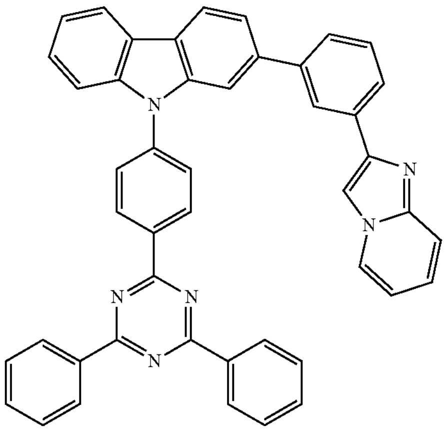
C-143
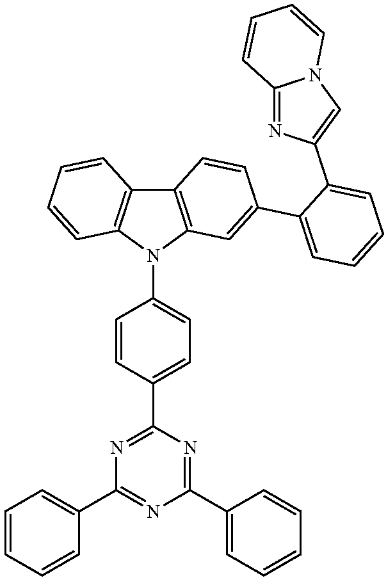
C-144
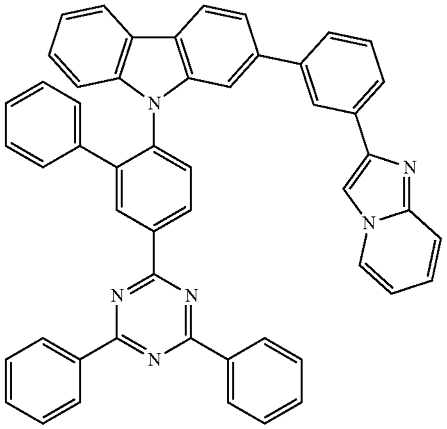

C-145
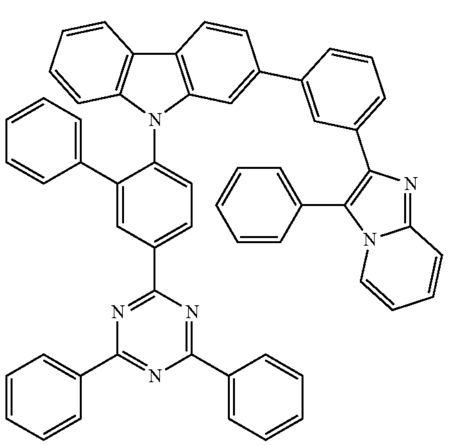
C-146
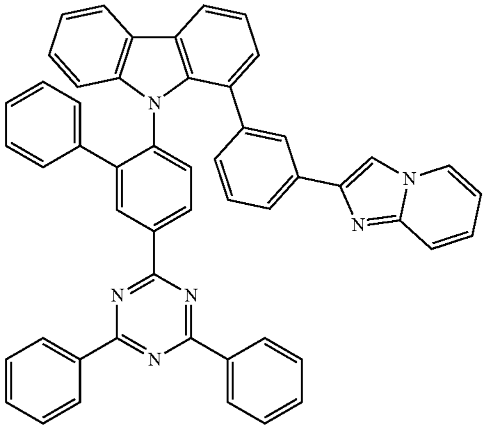
C-147
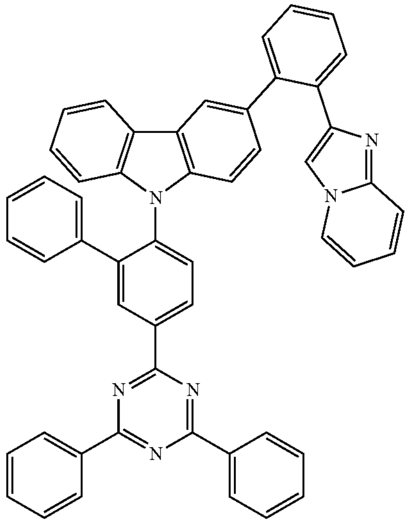
C-148
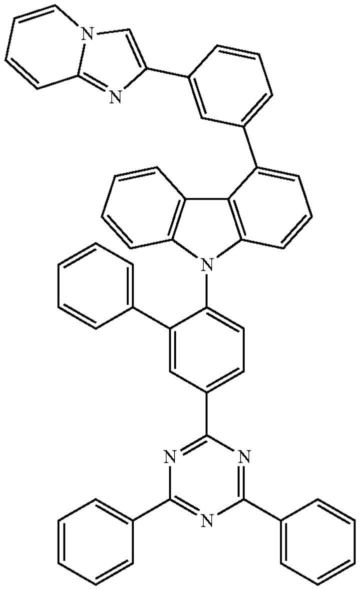
C-149
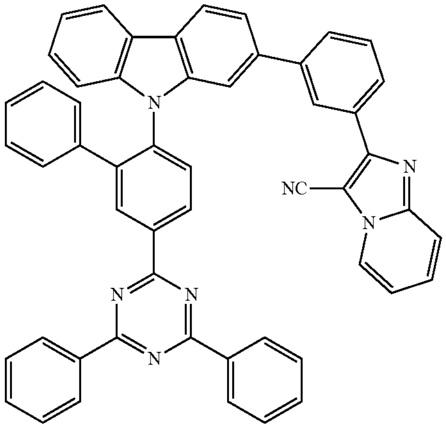
C-150
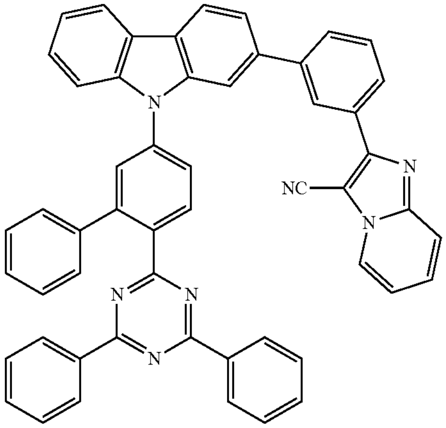

-continued
C-151
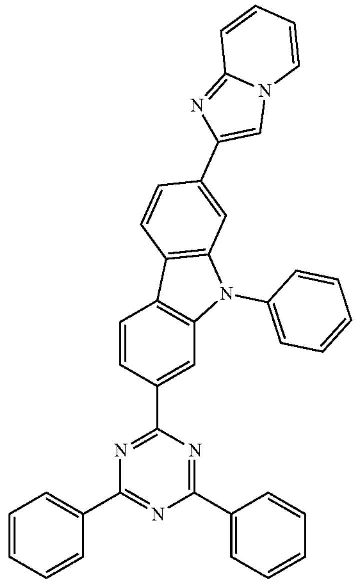
C-152
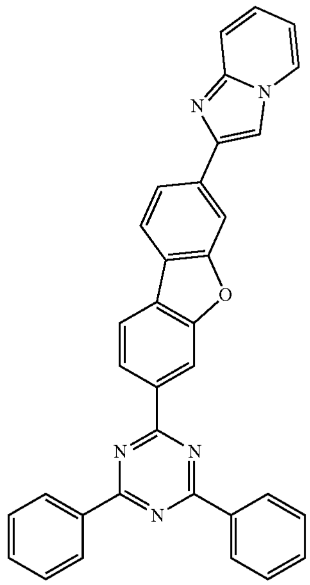
-continued
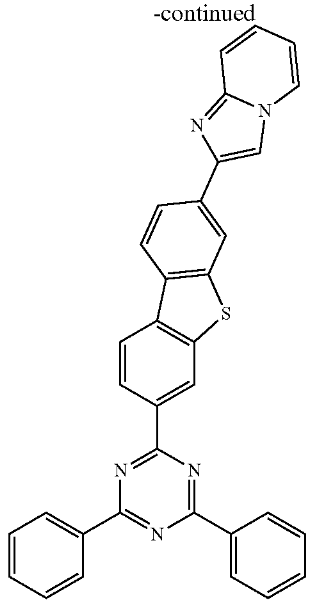
C-154
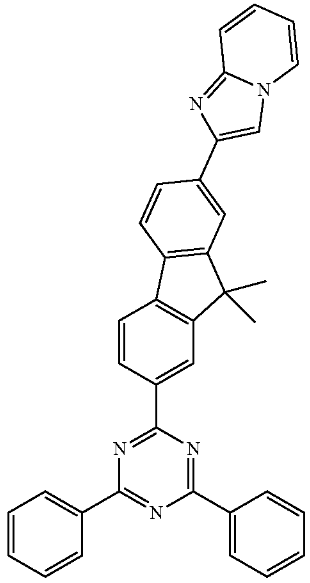

-continued
C-155
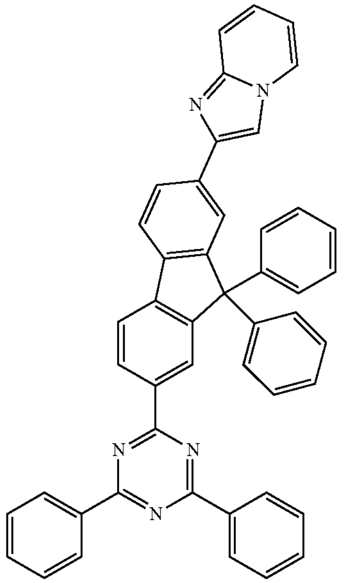
C-156
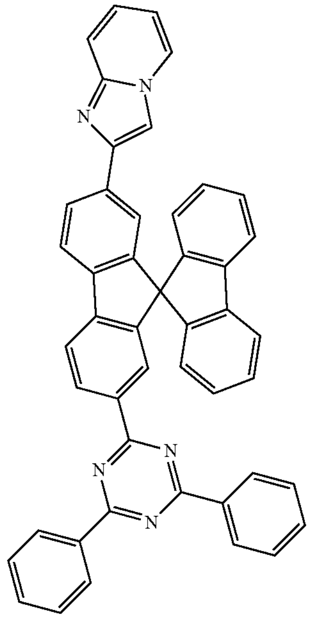
-continued
C-157
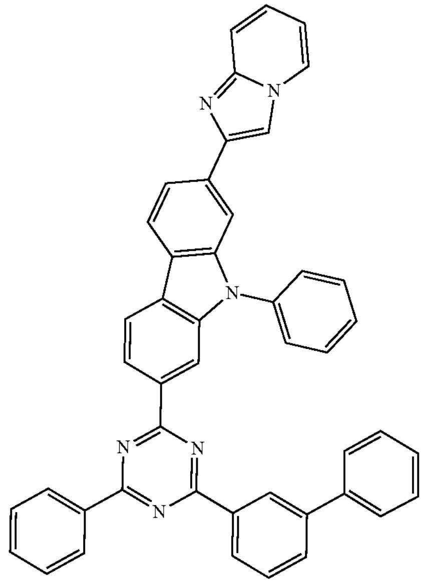
C-158
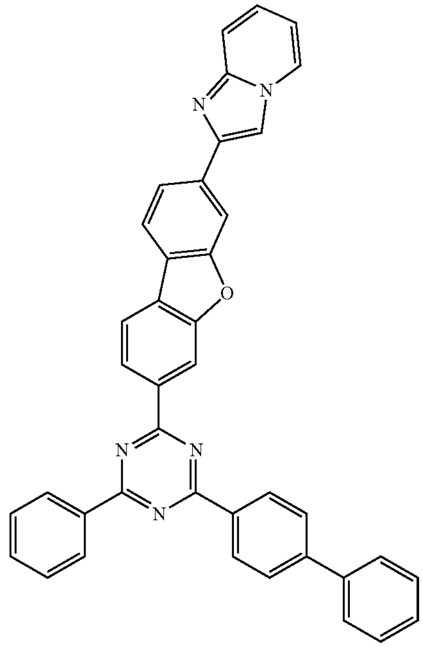

-continued
C-159
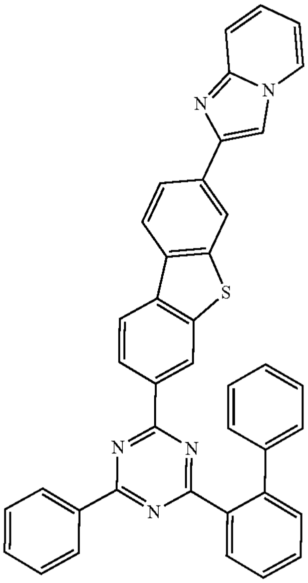
C-160
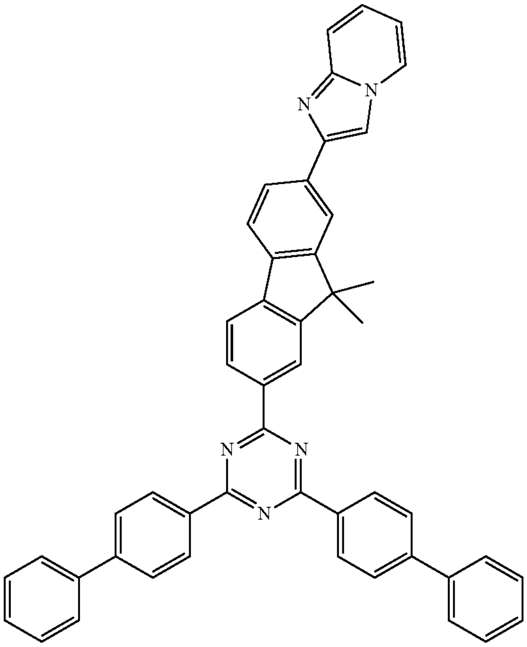
-continued
C-161
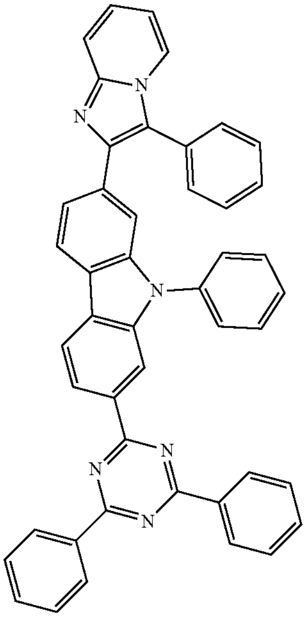
C-162
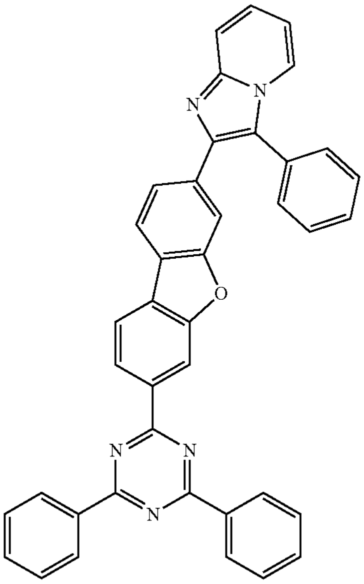

-continued
C-163
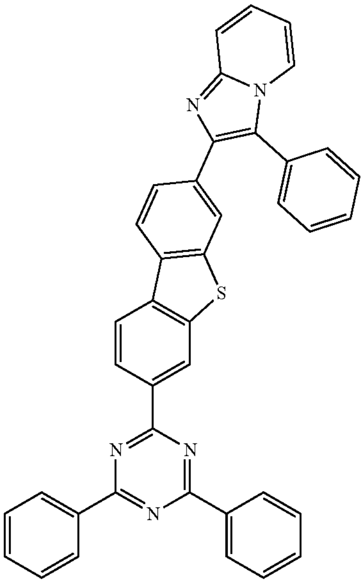
C-164
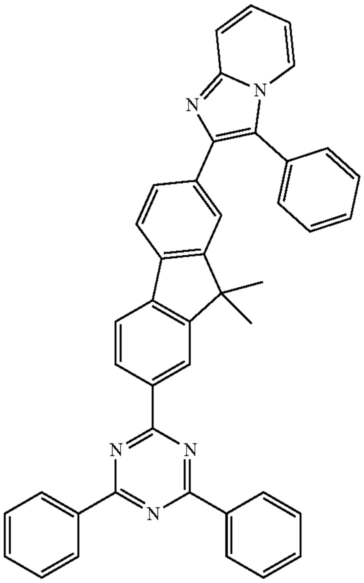
-continued
C-165
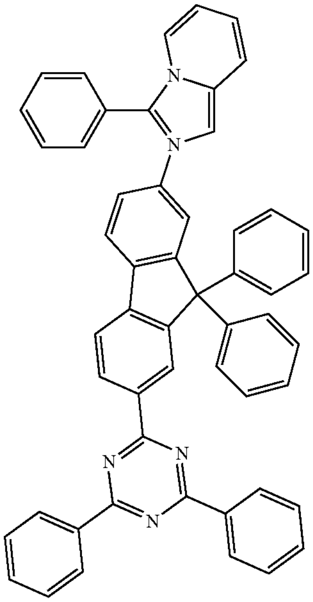
C-166
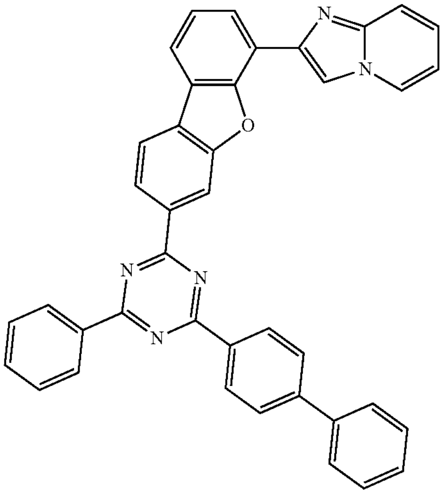

-continued
C-167
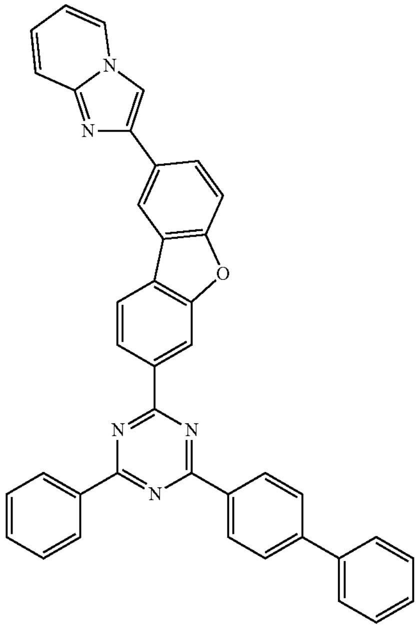
C-168
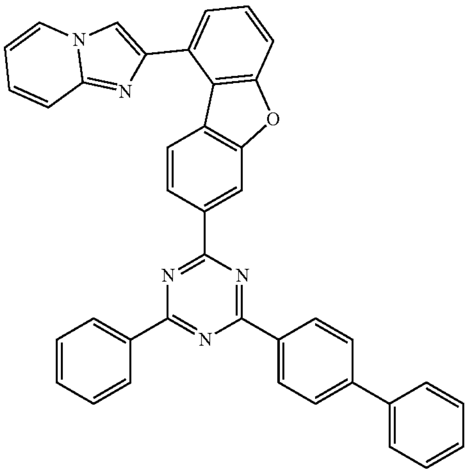
-continued
C-169
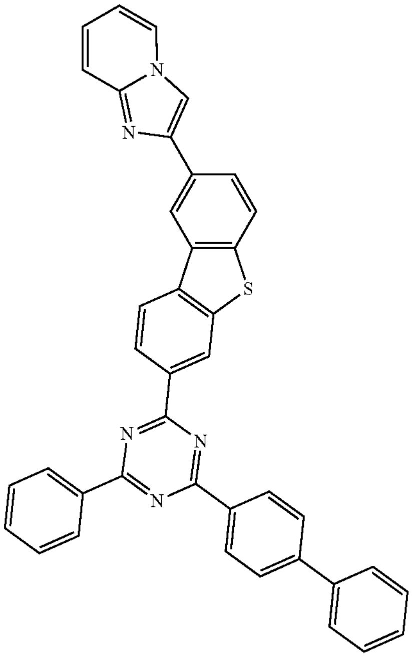
C-170
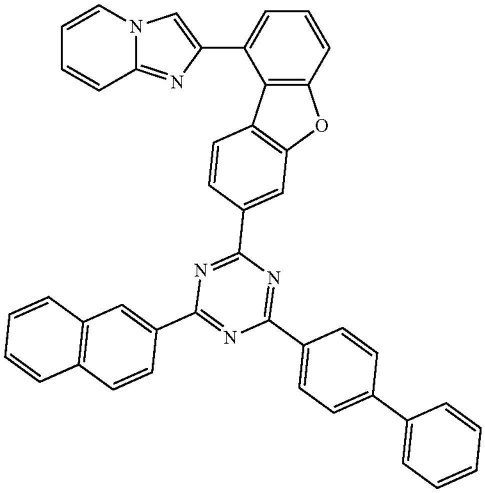
C-171
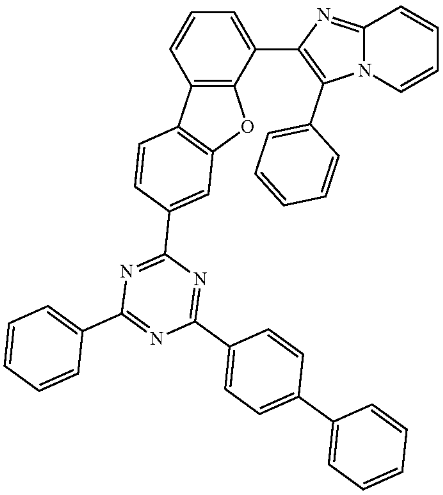

-continued
C-172
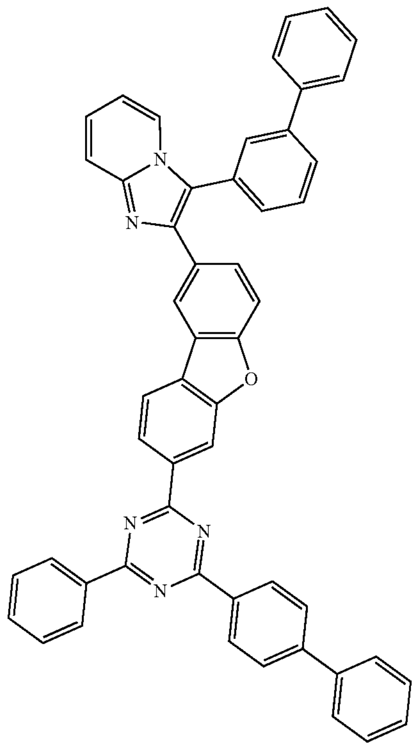
C-173
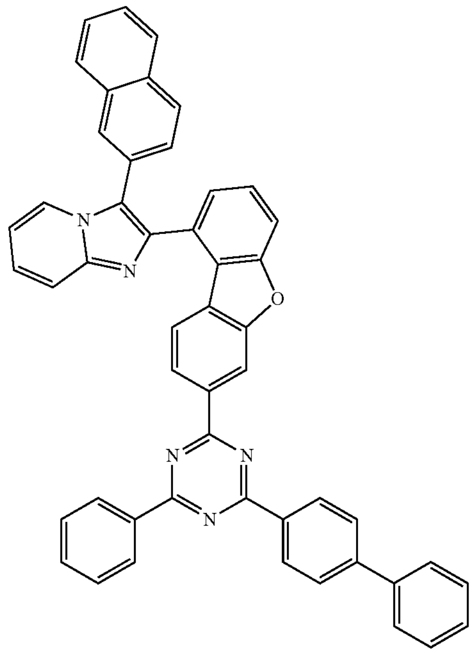
-continued
C-174
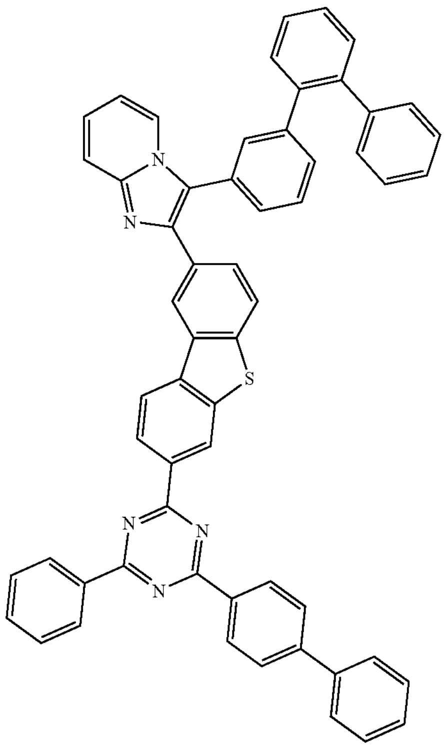
C-175
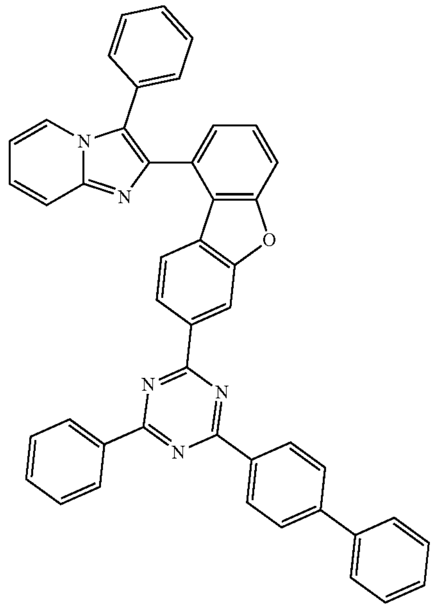

C-176
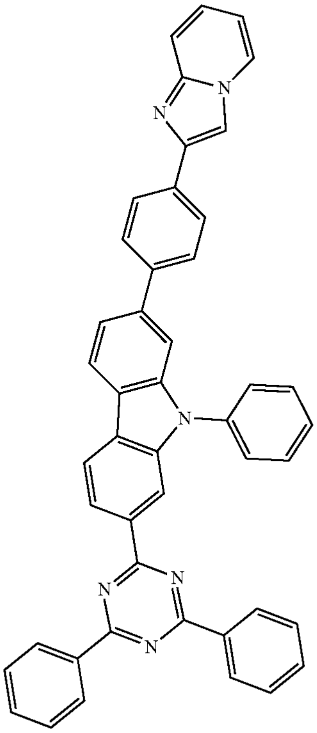
C-177
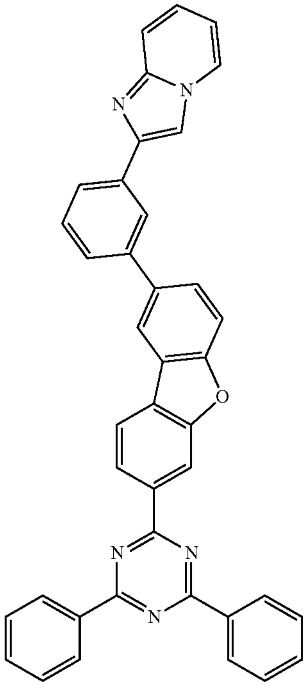
C-178
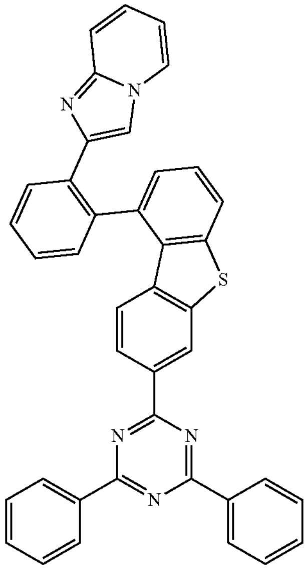
C-179
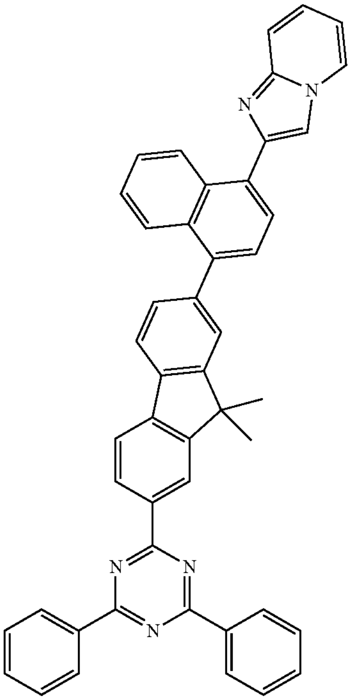

-continued
C-180
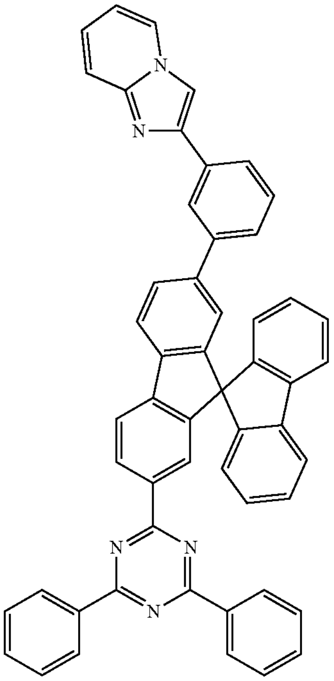
C-181
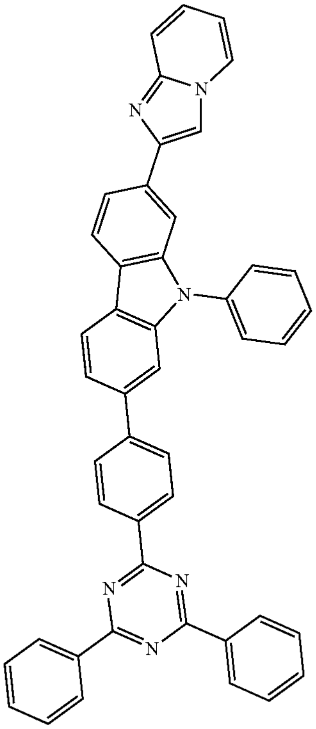
-continued
C-182
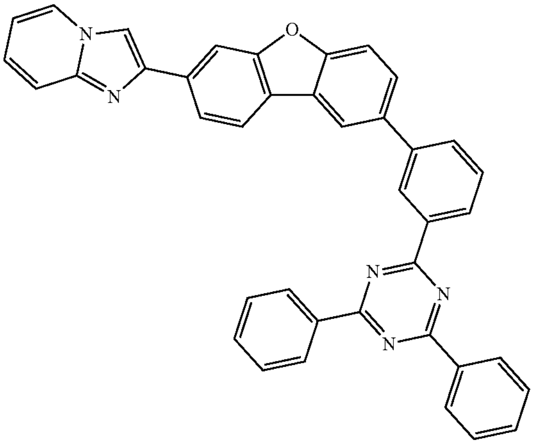
C-183
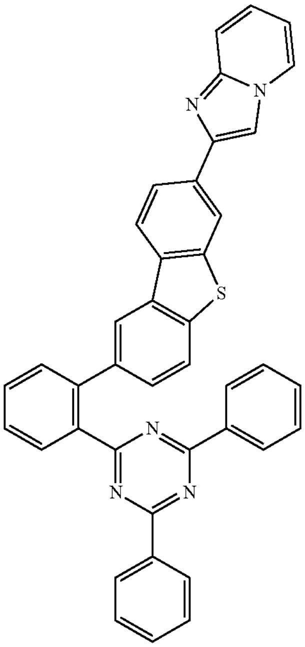

-continued
C-184
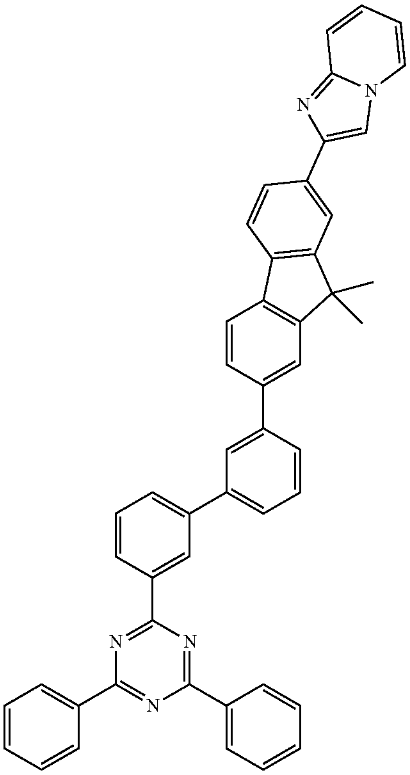
C-185
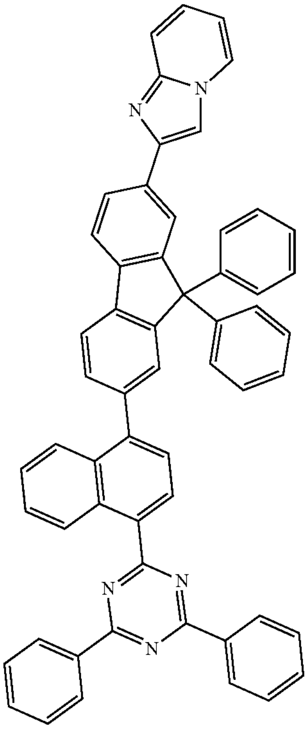
-continued
C-186
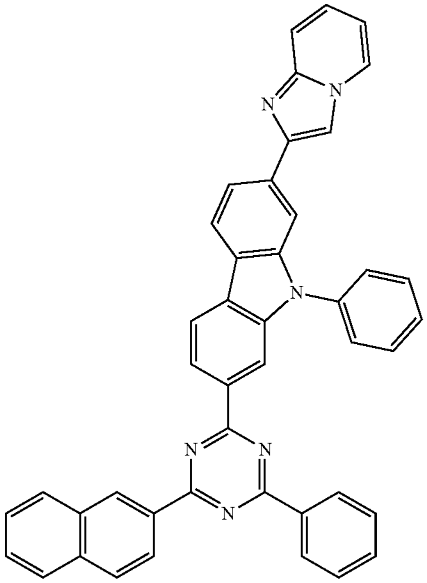
C-187
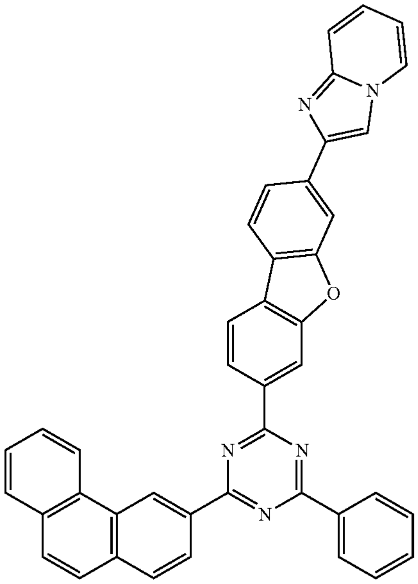

-continued
C-188
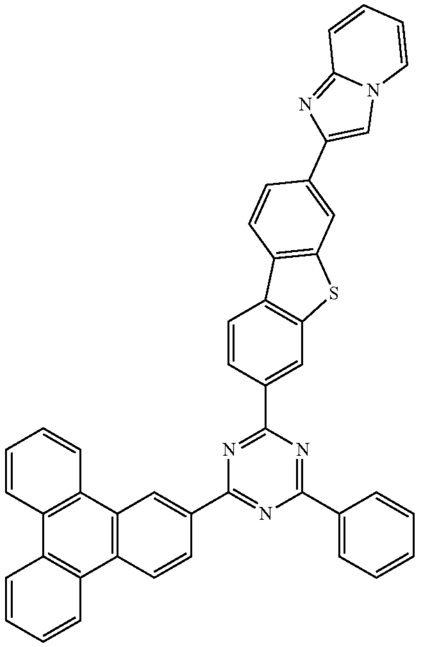
C-189
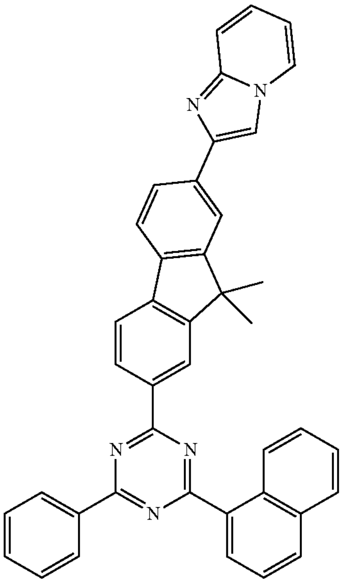
-continued
C-190
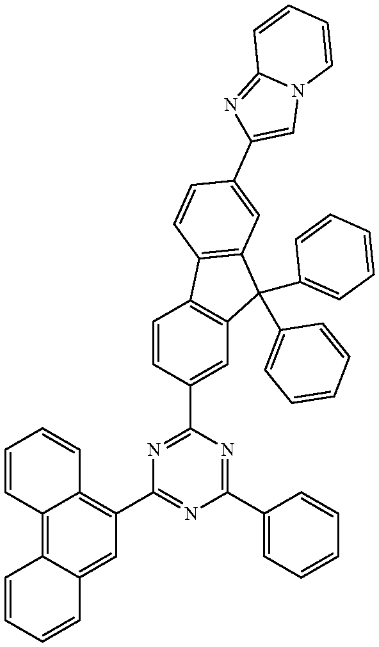
C-191
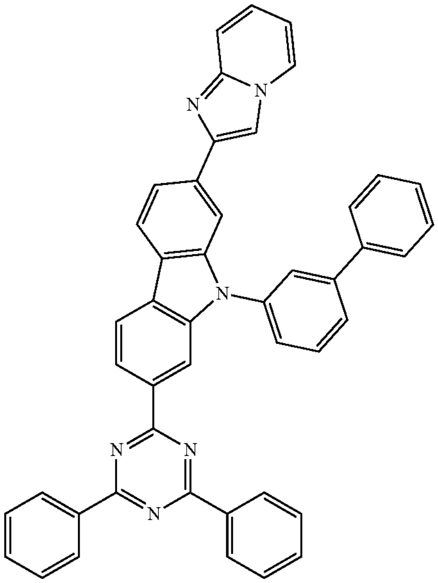

C-192
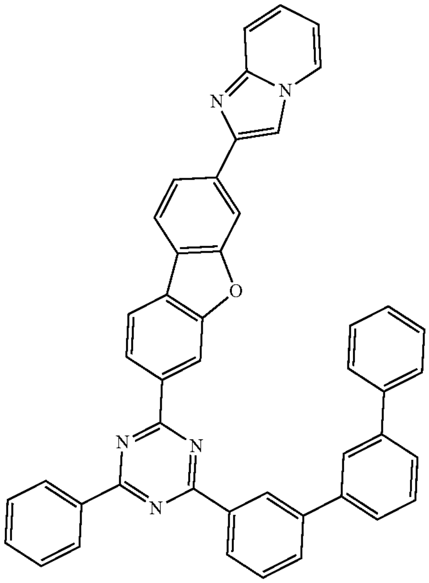
C-193
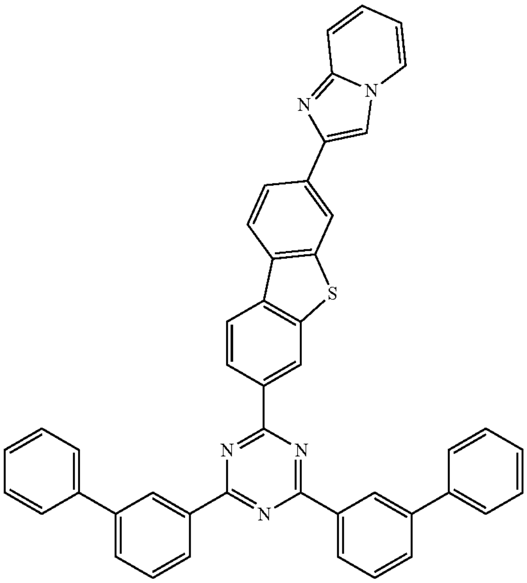
C-194
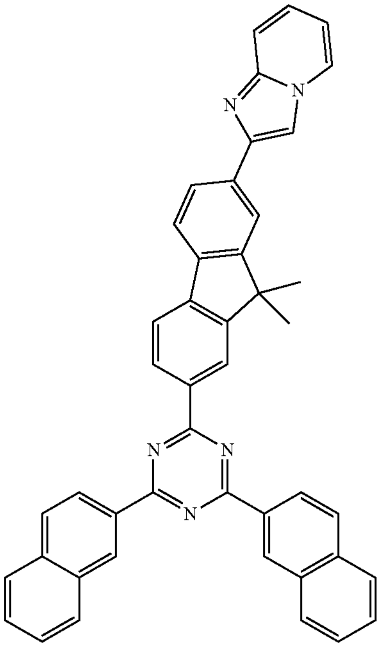
C-195
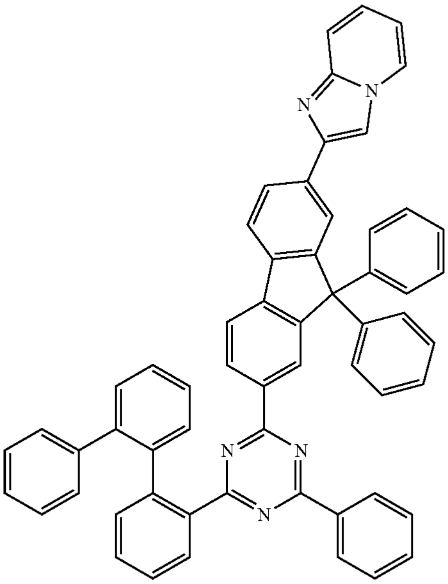

-continued
C-196
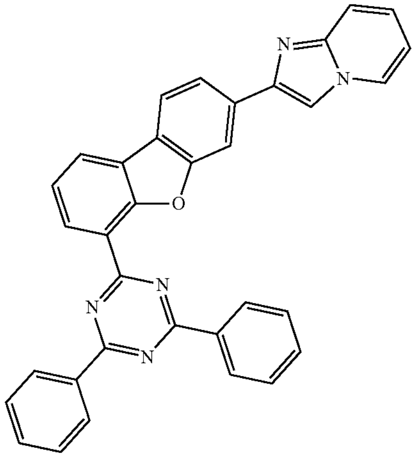
C-197
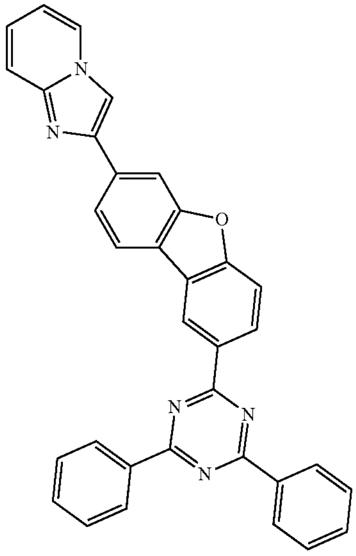
C-198
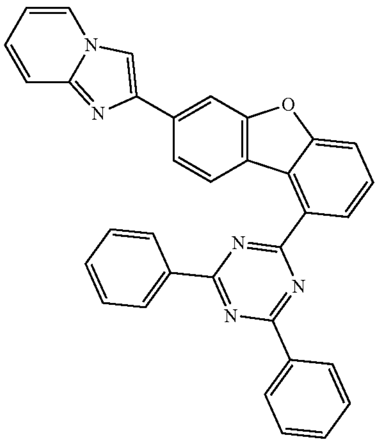
-continued
C-199
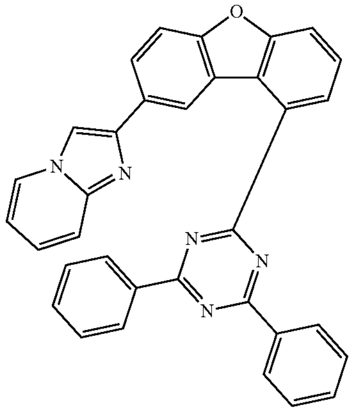
C-200
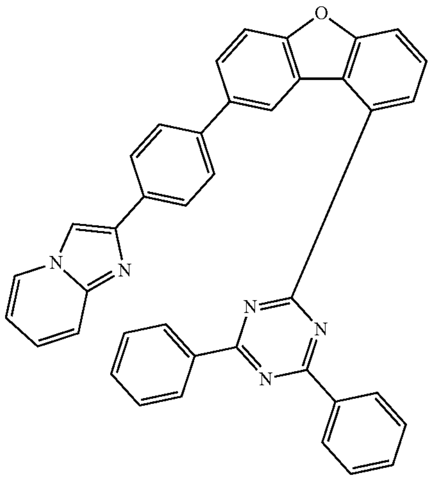
C-201
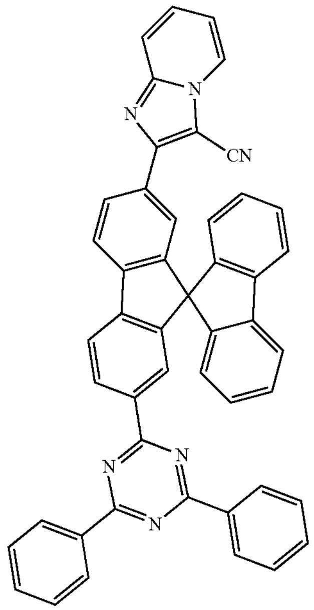

-continued
C-202
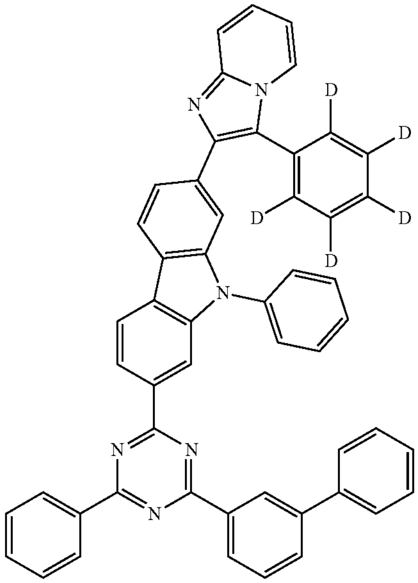
C-203
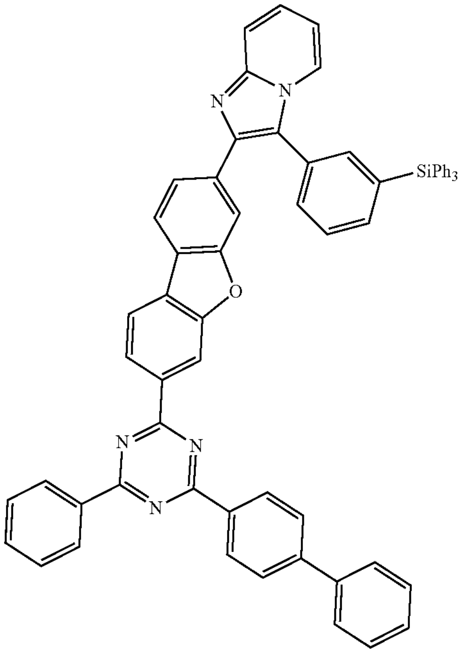
-continued
C-204
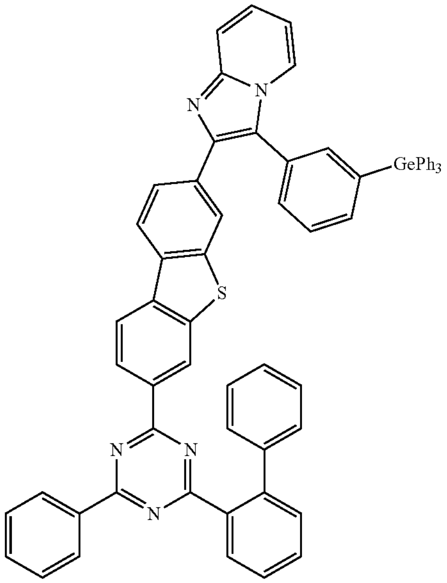
C-205
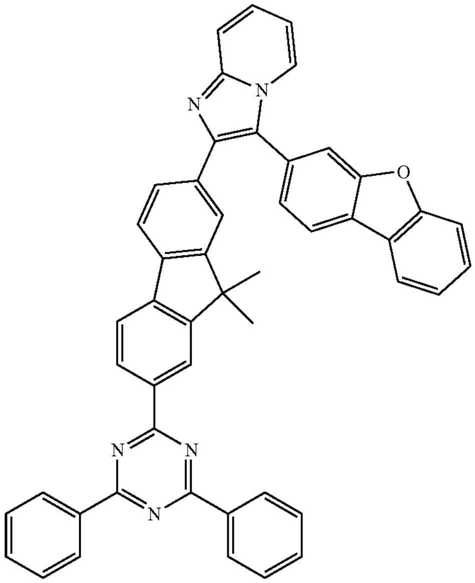

-continued
C-206
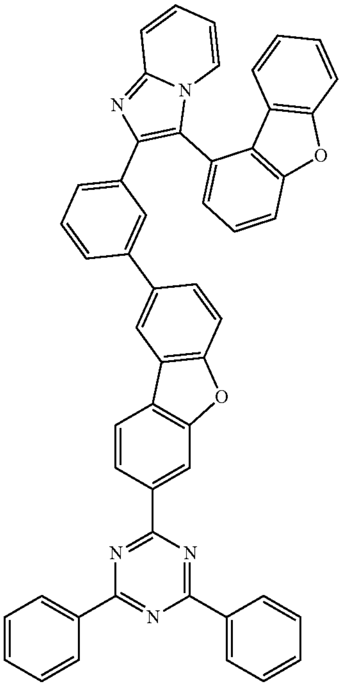
C-207
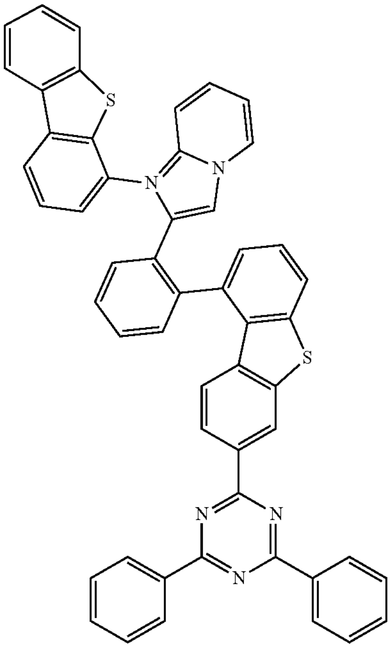
-continued
C-208
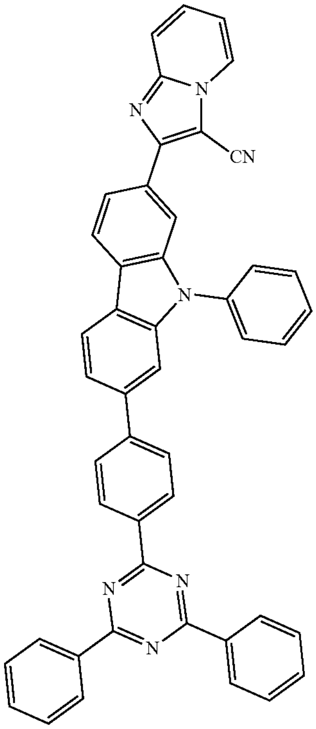
C-209
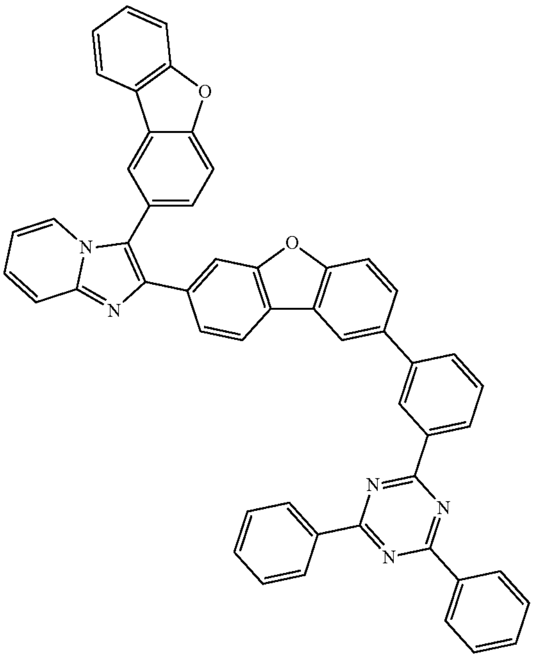

-continued
C-210
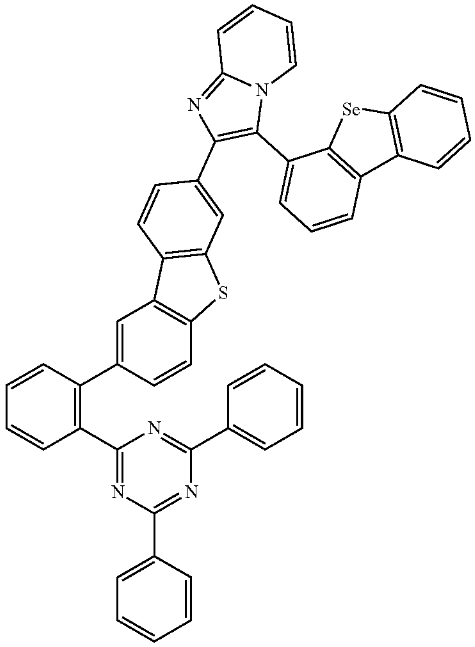
C-211
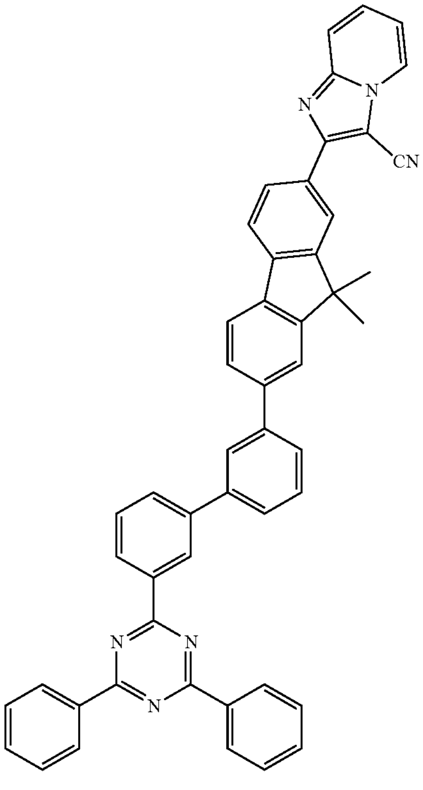
-continued
C-212
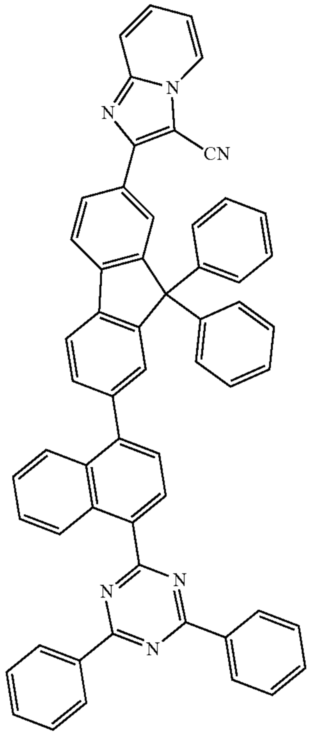
C-213
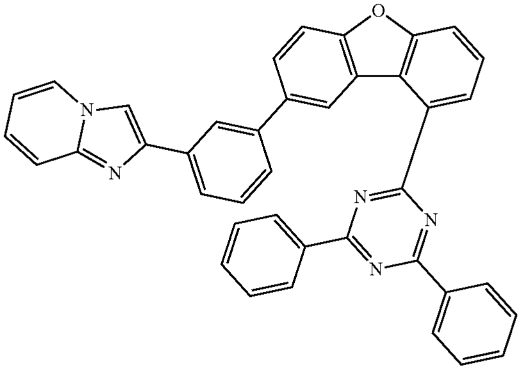
C-214
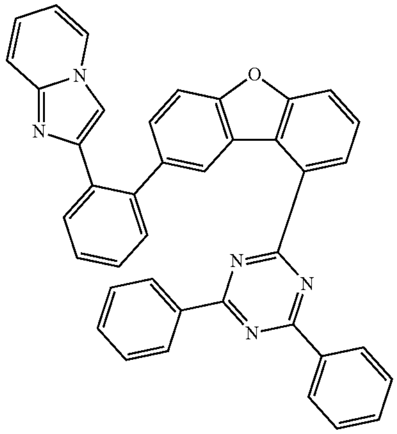

-continued
C-215
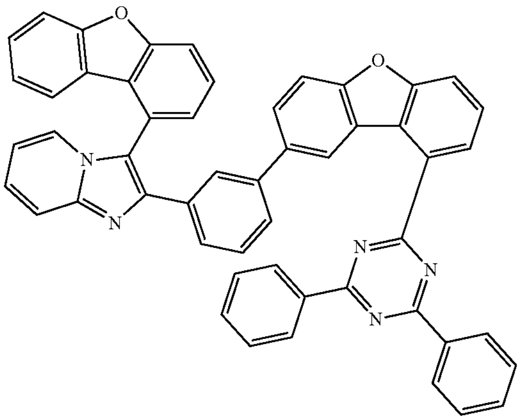
C-216
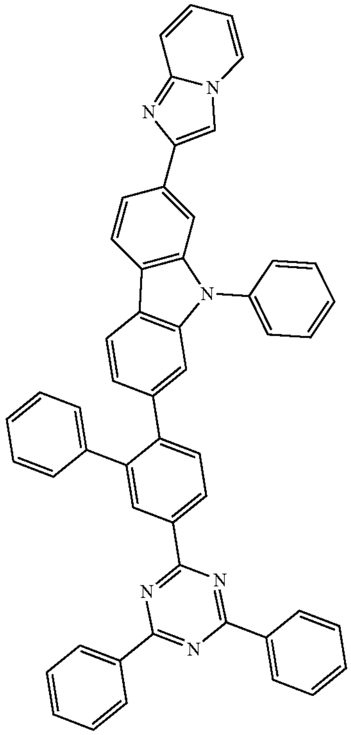
-continued
C-217
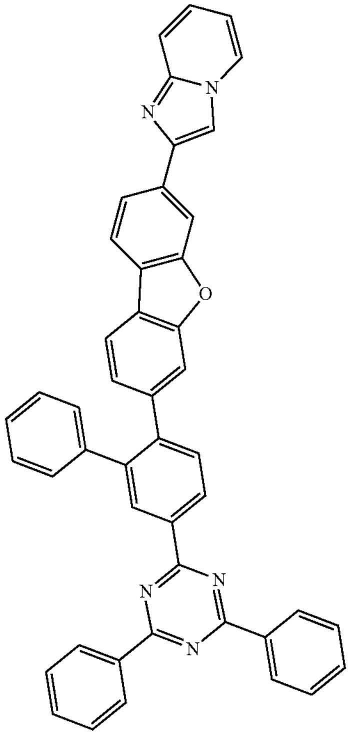
C-218
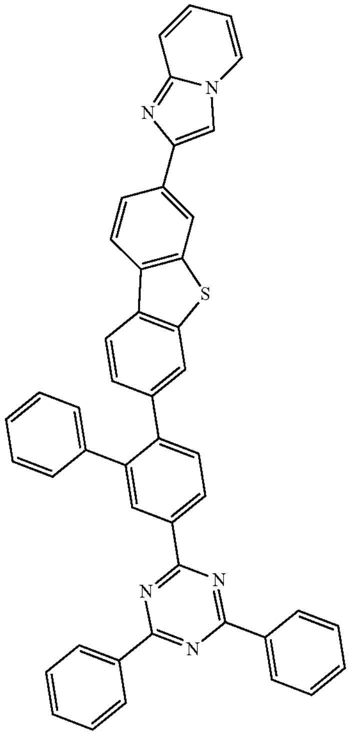

-continued

C-219

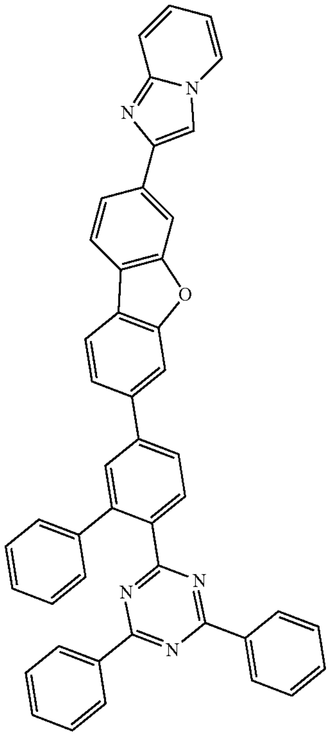

C-220

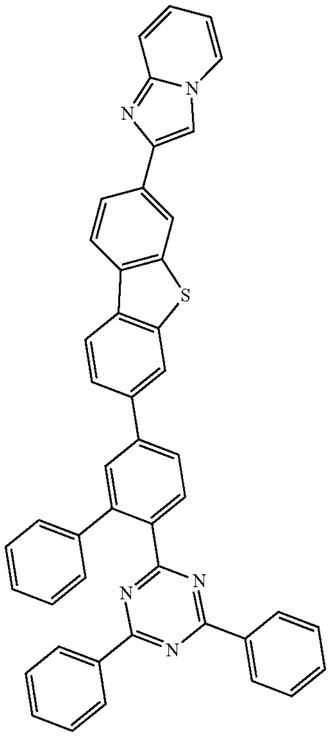

The compound of formula 1 according to the present disclosure may be prepared as represented by the following reaction scheme 1 or 2, but is not limited thereto; they may further be produced by a synthetic method known to a person skilled in the art.

[Reaction Scheme 1]

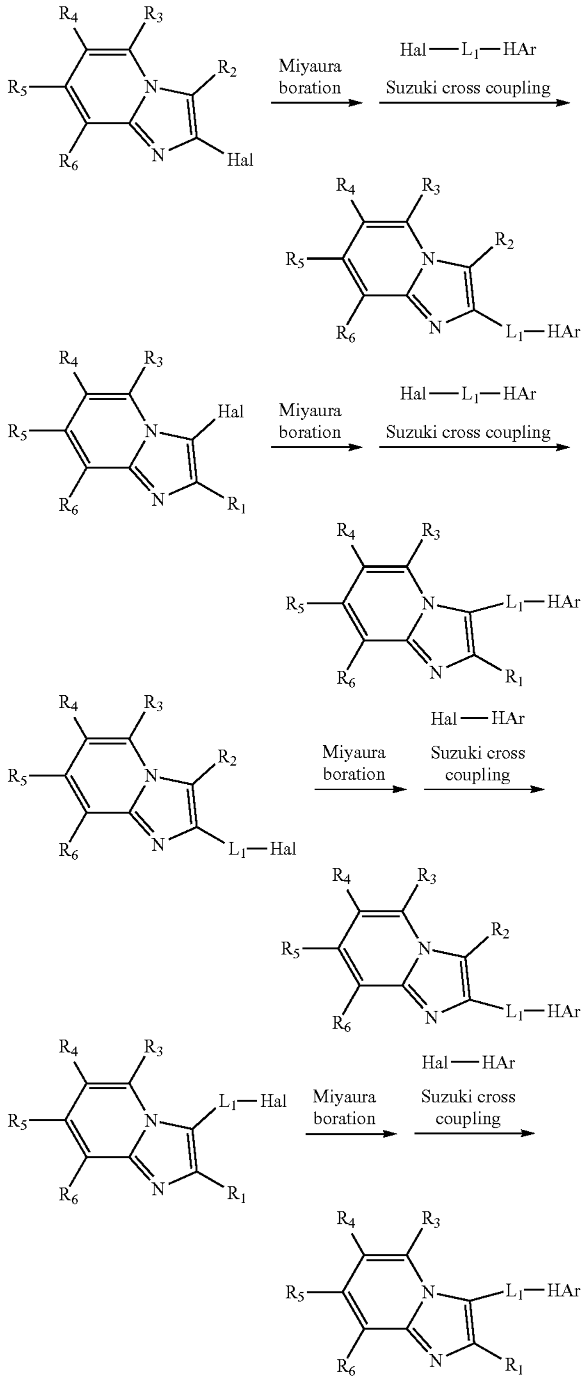

$L_1 \neq$ single bond
Hal: halogen atom

In reaction schemes 1 and 2, the definition of each of the substituents is as defined in formula 1.

As described above, exemplary synthesis examples of the compounds represented by formula 1 according to the present disclosure are described, but they are based on Miyaura borylation reaction, Suzuki cross-coupling reaction, Buchwald-Hartwig cross coupling reaction, N-arylation reaction, H-mont-mediated etherification reaction, Intramolecular acid-induced cyclization reaction, Pd(II)- catalyzed oxidative cyclization reaction, Grignard reaction, Heck reaction, Cyclic Dehydration reaction, $SN_1$ substitution reaction, $SN_2$ substitution reaction, and Phosphine-mediated reductive cyclization reaction, etc. It will be understood by one skilled in the art that the above reaction proceeds even if other substituents defined in the formula 1 other than the substituents described in the specific synthesis examples are bonded.

The second host compound as another host material according to one embodiment is represented by the following formula 2.

substituted or unsubstituted phenanthrenyl, a substituted or unsubstituted dibenzofuranyl, a substituted or unsubstituted carbazolyl, or a substituted or unsubstituted dibenzothiophenyl. For example, $A_1$ and $A_2$ each independently may be phenyl, naphthyl, biphenyl, terphenyl, triphenylenyl, naphthylphenyl, phenylnaphthyl, phenyl substituted by triphenylenyl, phenyl substituted by methyl, phenyl substituted by pyridyl, phenyl substituted by phenylpyridyl, phenyl substituted by dibenzofuranyl, phenyl substituted by diben- (2)

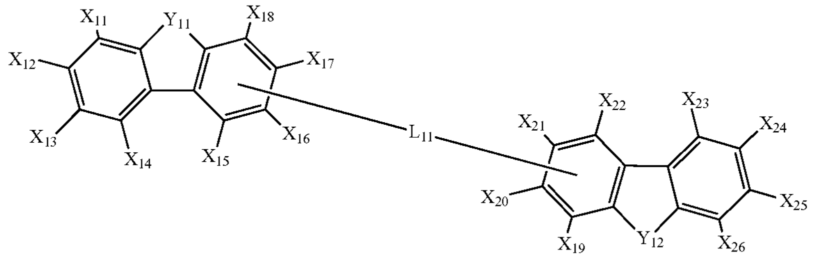

zothiophenyl, phenyl substituted by triphenylsilyl, diphenylfluorenyl, dimethylfluorenyl, dimethylbenzofluorenyl, dibenzofuranyl, dibenzothiophenyl, dibenzofuranyl substituted by phenyl, dibenzothiophenyl substituted by phenyl, carbazolyl substituted by phenyl, carbazolyl substituted by naphthyl, etc.

in formula 2, $Y_{11}$ represents —N-$A_1$, O, S or $CR_{21}R_{22}$;

$Y_{12}$ represents —N-$A_2$, O, S or $CR_{21}R_{22}$;

$A_1$ and $A_2$ each independently represent a substituted or unsubstituted (C6-C30)aryl, a substituted or unsubstituted dibenzofuranyl, a substituted or unsubstituted dibenzothiophenyl, or a substituted or unsubstituted carbazolyl;

$L_{11}$ represents a single bond or a substituted or unsubstituted (C6-C30)arylene;

$X_{11}$ to $X_{26}$ each independently represent hydrogen, deuterium, a substituted or unsubstituted (C6-C30)aryl, or a substituted or unsubstituted (3- to 30-membered)heteroaryl; or may be linked to the adjacent substituents to form a ring(s); and $R_{21}$ and $R_{22}$ each independently represent a substituted or unsubstituted (C1-C3)alkyl or a substituted or unsubstituted (C6-C12)aryl; or may be linked to the adjacent substituents to form a ring(s).

In one embodiment, $A_1$ and $A_2$ each independently may be a substituted or unsubstituted (C6-C30)aryl, a substituted or unsubstituted dibenzofuranyl, a substituted or unsubstituted dibenzothiophenyl, or a substituted or unsubstituted carbazolyl, preferably a substituted or unsubstituted (C6-C25) aryl, a substituted or unsubstituted dibenzofuranyl, a substituted or unsubstituted dibenzothiophenyl, or a substituted or unsubstituted carbazolyl, the substituents of (C6-C25)aryl may be at least one of (C1-C6)alkyl; (C6-C20)aryl; (5- to 15-membered)heteroaryl unsubstituted or substituted by (C6-C20)aryl; tri(C6-C12)arylsilyl, and the substituents of dibenzofuranyl, dibenzothiophenyl and carbazolyl may be at least one (C6-C12)aryl. For example, $A_1$ and $A_2$ each independently may be a substituted or unsubstituted phenyl, a substituted or unsubstituted biphenyl, a substituted or unsubstituted terphenyl, a substituted or unsubstituted naphthyl, a substituted or unsubstituted fluorenyl, a substituted or unsubstituted benzofluorenyl, a substituted or unsubstituted triphenylenyl, a substituted or unsubstituted fluoranthenyl, a In one embodiment, $X_{11}$ to $X_{26}$ each independently may be hydrogen, deuterium, a substituted or unsubstituted (C6-C30)aryl, or a substituted or unsubstituted (5- to 30-membered)heteroaryl; or may be linked to the adjacent substituents to form a ring(s), preferably hydrogen, deuterium, a substituted or unsubstituted (C6-C12)aryl, or a substituted or unsubstituted (5- to 15-membered)heteroaryl; or may be linked to the adjacent substituents to form a substituted or unsubstituted (3- to 30-membered) monocyclic or polycyclic aromatic ring(s), more preferably hydrogen, deuterium, unsubstituted (C6-C12)aryl, or unsubstituted (5- to 15-membered)heteroaryl; or may be linked to the adjacent substituents to form a substituted or unsubstituted (5- to 18-membered) monocyclic or polycyclic aromatic ring(s). For example, $X_{11}$ to $X_{26}$ each independently may be hydrogen, deuterium, phenyl, dibenzofuranyl, or dibenzothiophenyl, or may be linked to the adjacent substituents to form a benzene ring(s).

In one embodiment, $L_{11}$ may be a single bond or a substituted or unsubstituted (C6-C25)arylene, preferably a single bond or a substituted or unsubstituted (C6-C18) arylene, more preferably a single bond or (C6-C18)arylene unsubstituted or substituted by deuterium or (C1-C6)alkyl. For example, $L_{11}$ may be a single bond or a substituted or unsubstituted phenylene, a substituted or unsubstituted naphthylene, a substituted or unsubstituted p-biphenylene, a substituted or unsubstituted m-biphenylene, or a substituted or unsubstituted o-biphenylene. For example, the substituent of the substituted groups may be deuterium or methyl.

The compound represented by formula 2 according to one embodiment may be represented by any one of the following formulas 2-1 to 2-8.

(2-1)
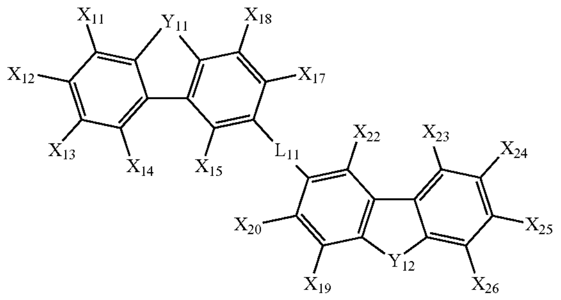
(2-2)
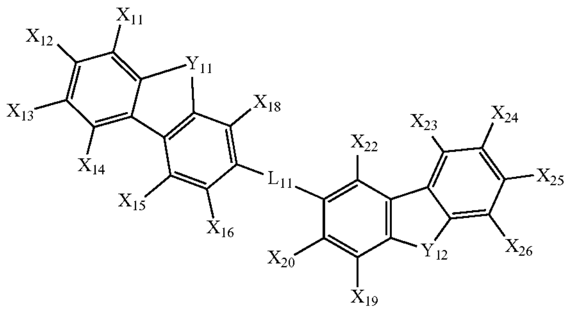
(2-3)
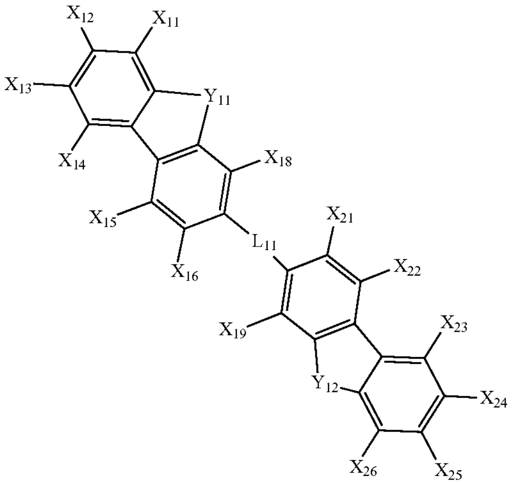
(2-4)
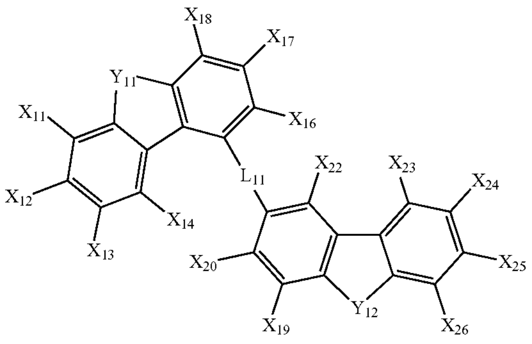
-continued
(2-5)
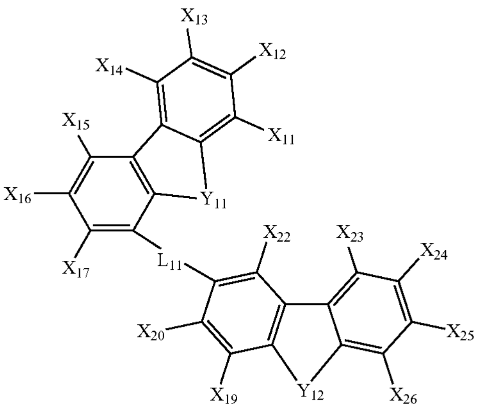
(2-6)
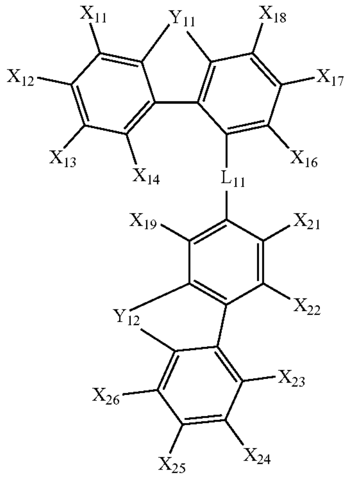
(2-7)
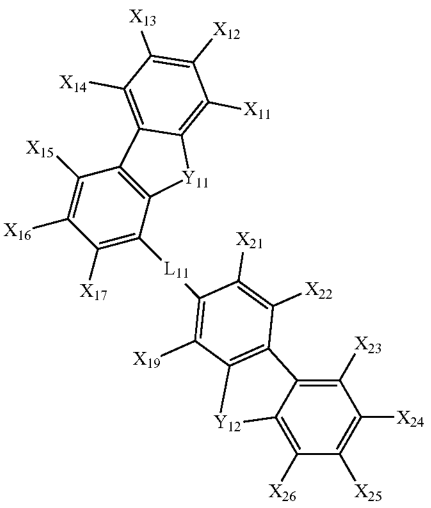

-continued
(2-8)
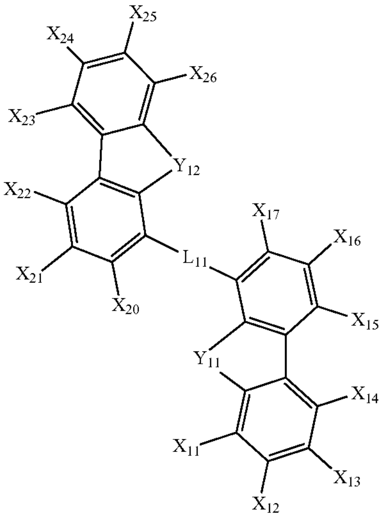
in formulas 2-1 to 2-8,
$Y_{11}$, $Y_{12}$, $L_{11}$, and $X_{11}$ to $X_{26}$ are as defined in formula 2.
According to one embodiment, the second host compound represented by formula 2 may be more specifically illustrated by the following compounds, but is not limited thereto.
H2-1
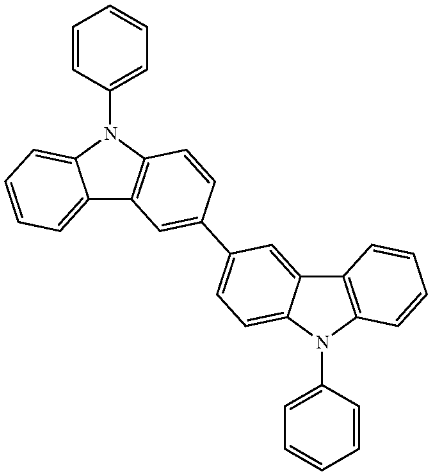
H2-2
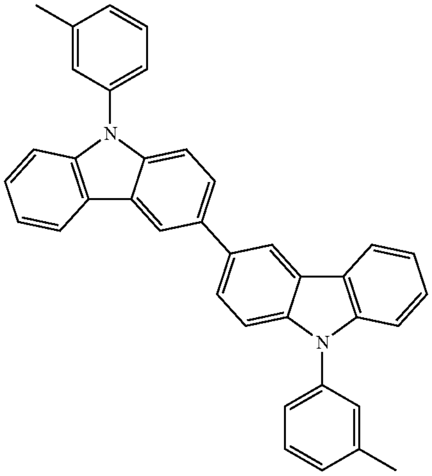
-continued
H2-3
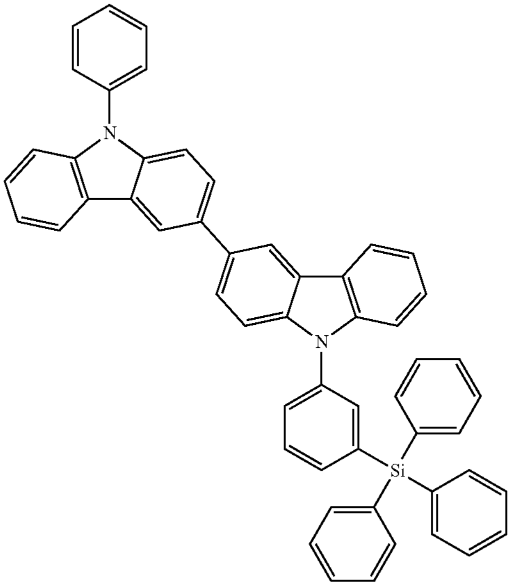
H2-4
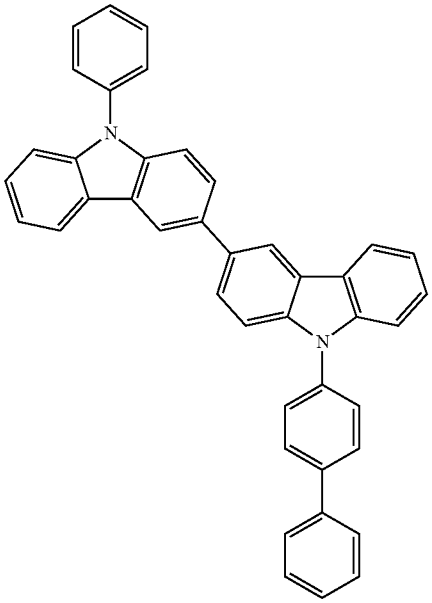

-continued
H2-5
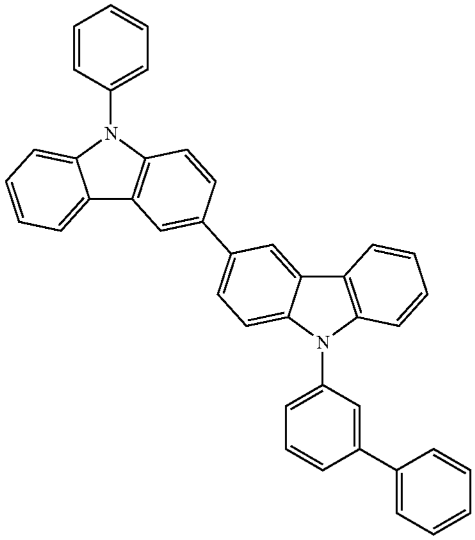
H2-6
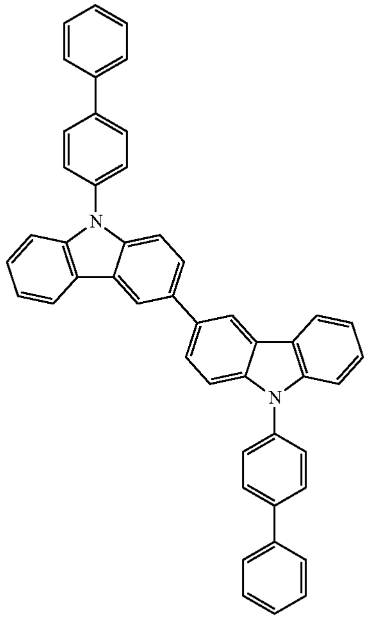
-continued
H2-7
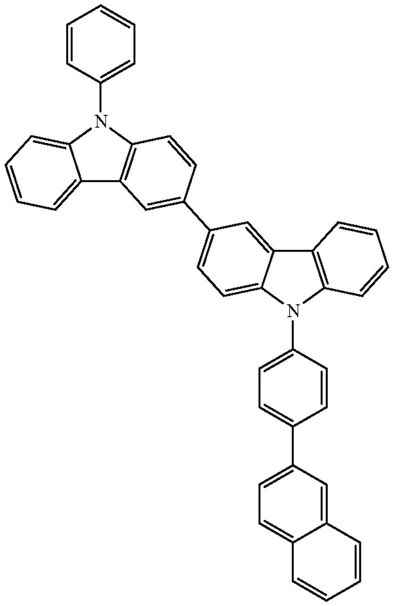
H2-8
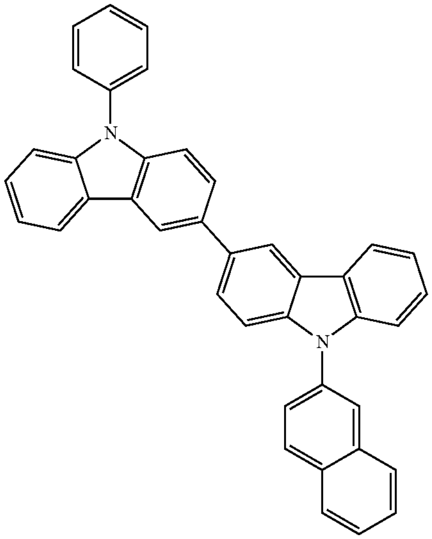

-continued
H2-9
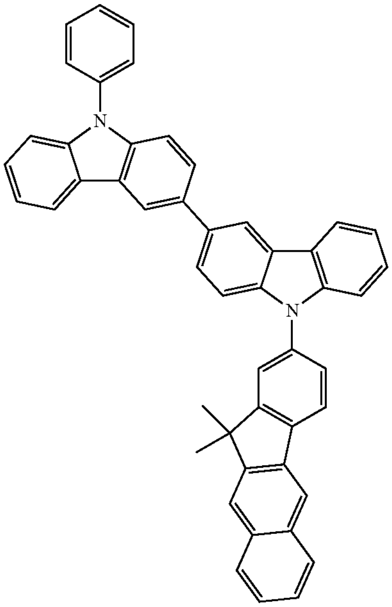
H2-10
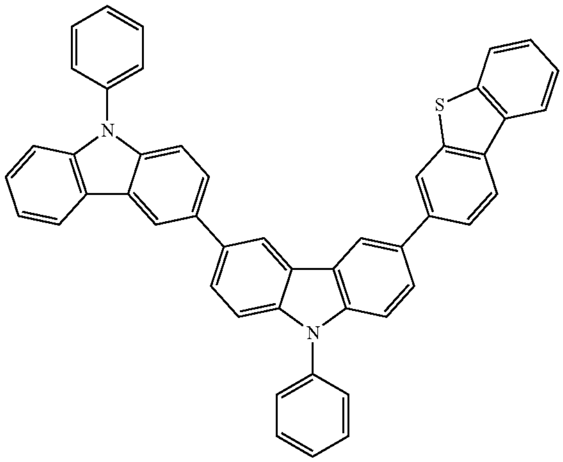
H2-11
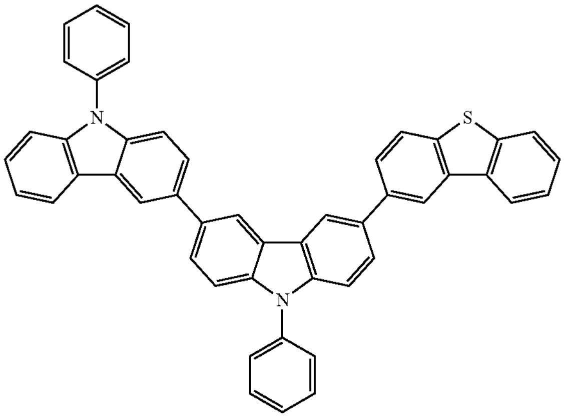
-continued
H2-12
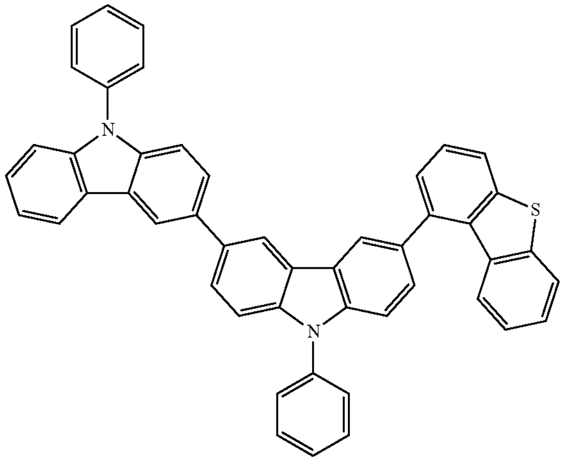
H2-13
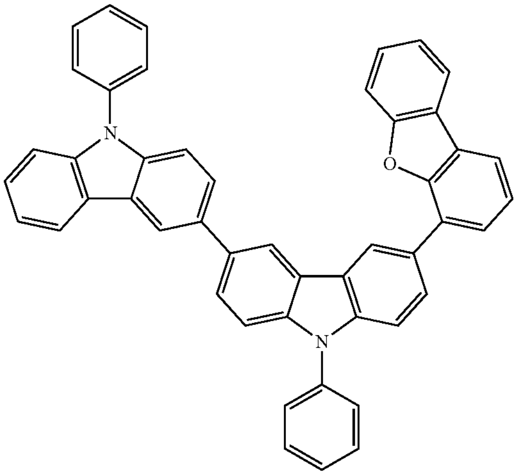
H2-14
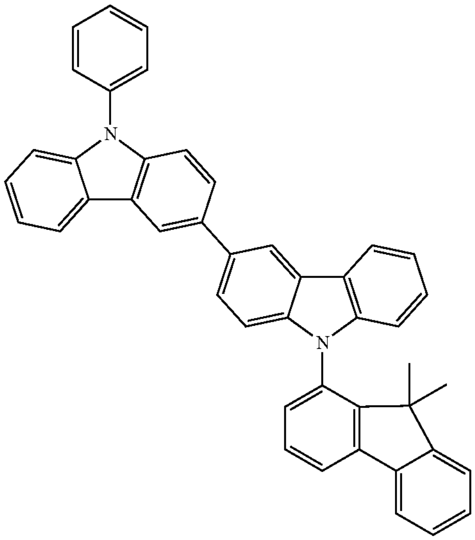

-continued
H2-15
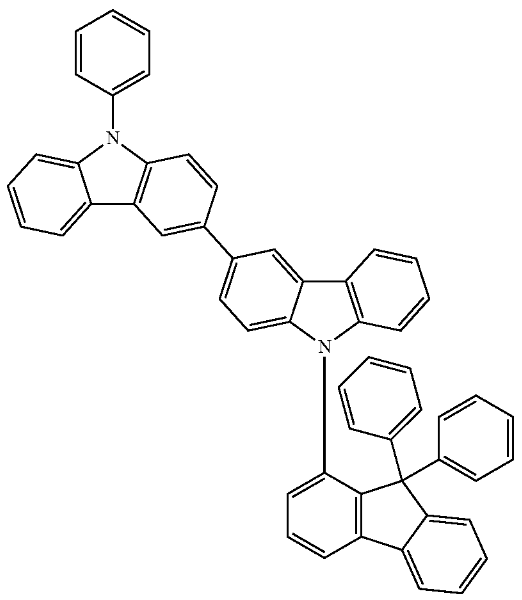
H2-16
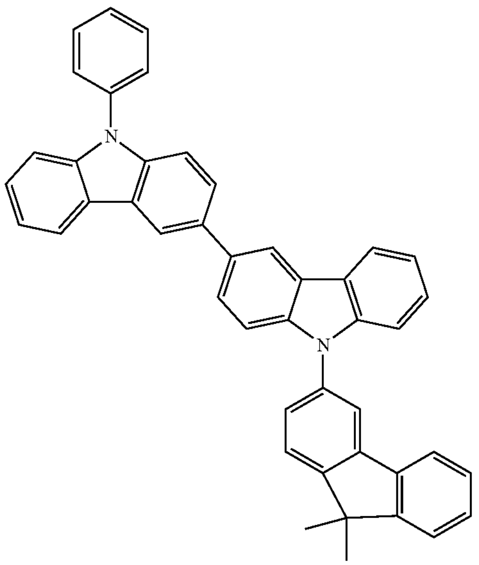
-continued
H2-17
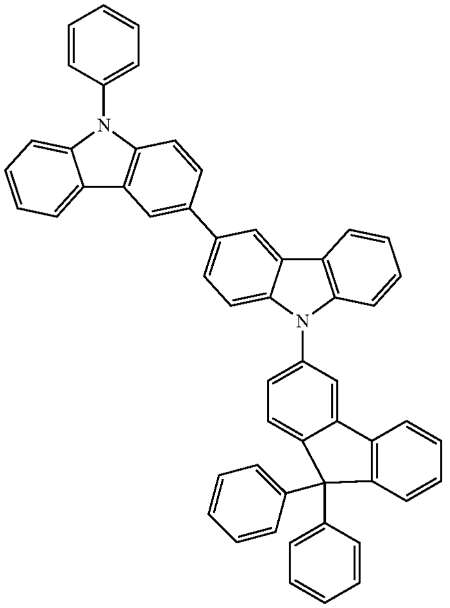
H2-18
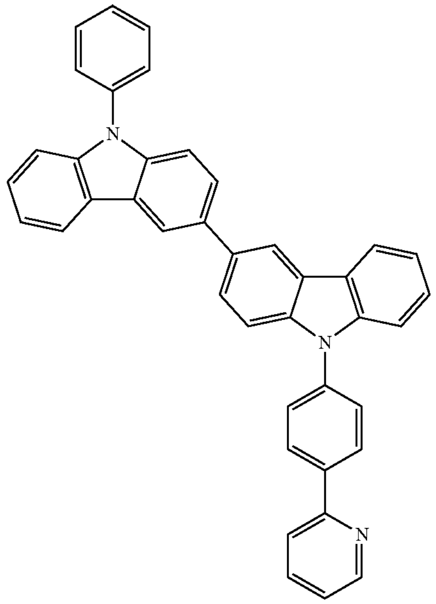

-continued
H2-19
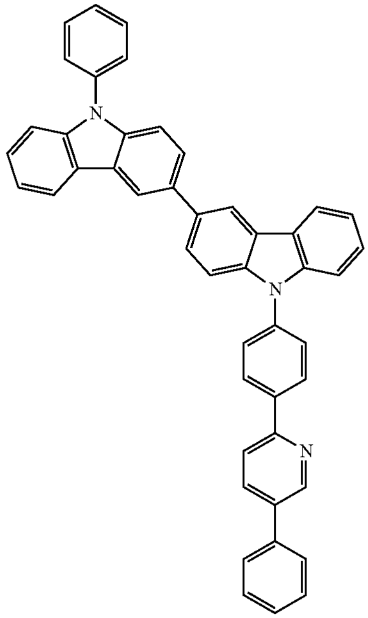
H2-20
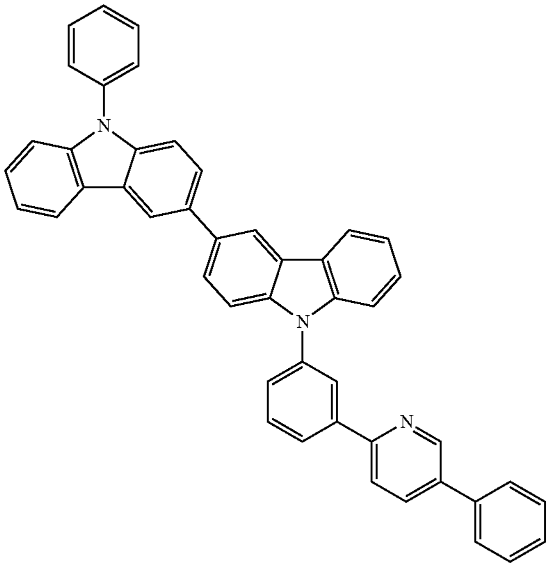
-continued
H2-21
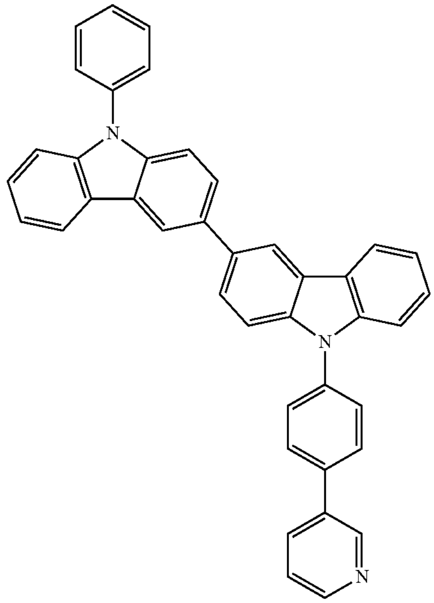
H2-22
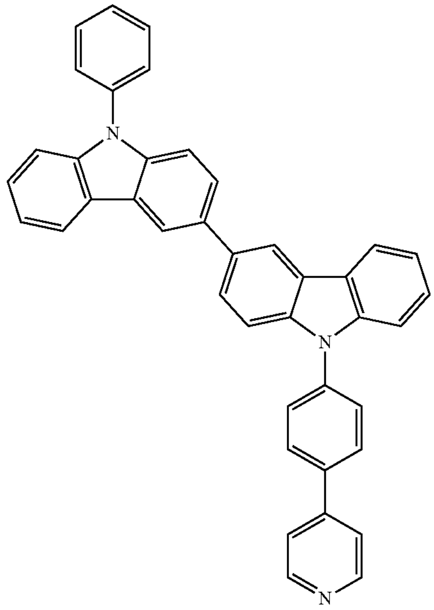

-continued
H2-23
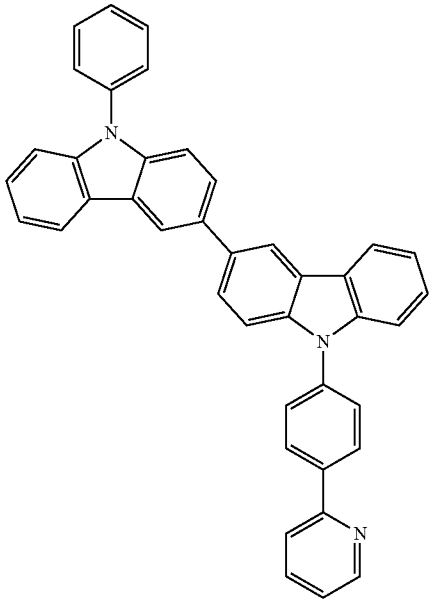
H2-24
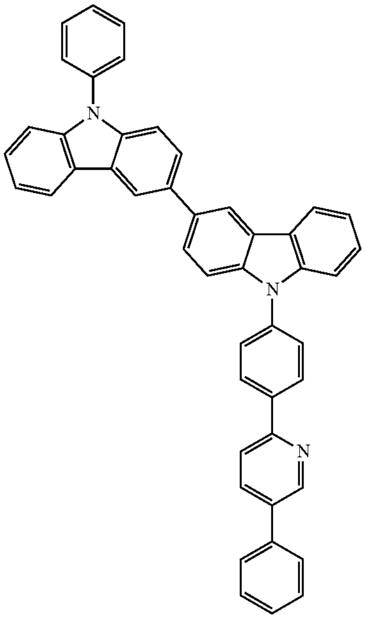
-continued
H2-25
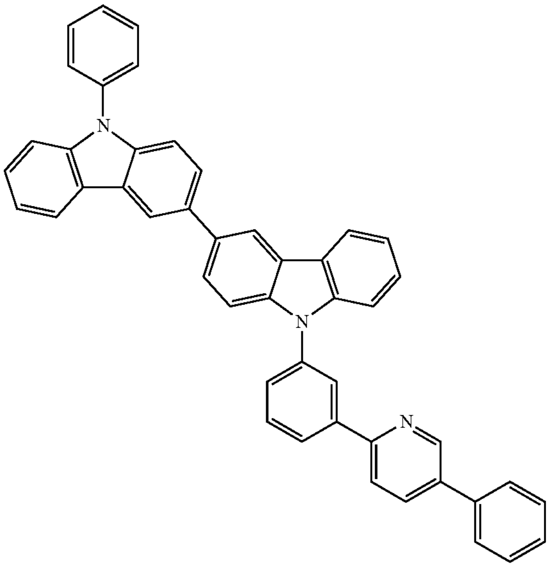
H2-26
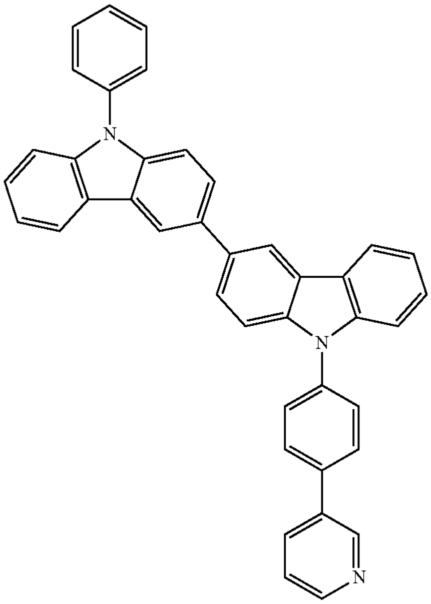

-continued
H2-27
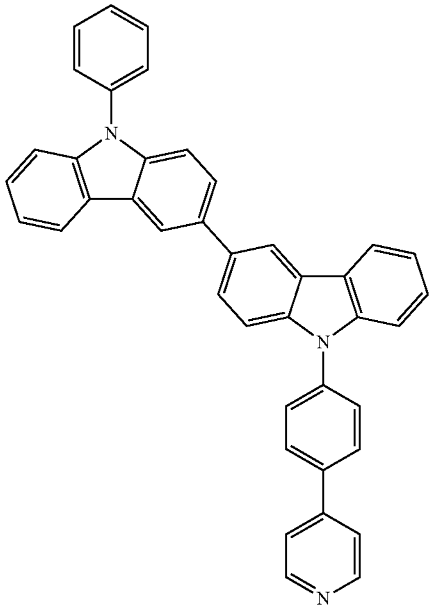
H2-28
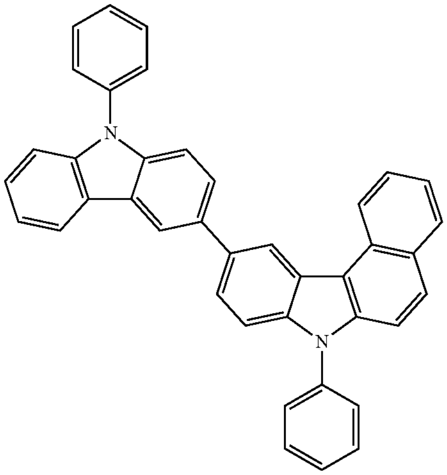
H2-29
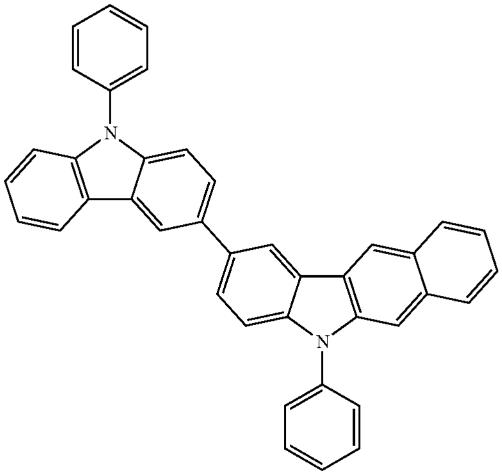
-continued
H2-30
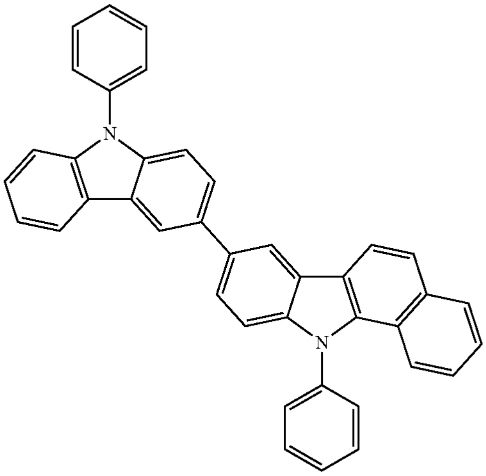
H2-31
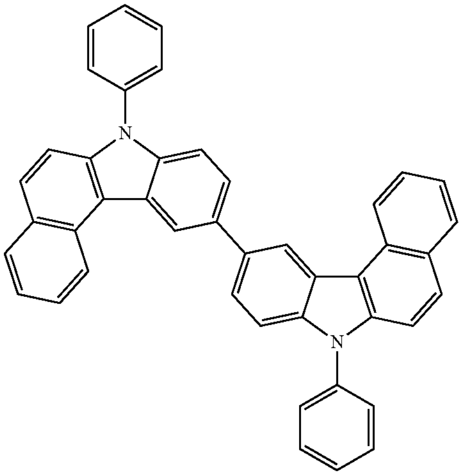
H2-32
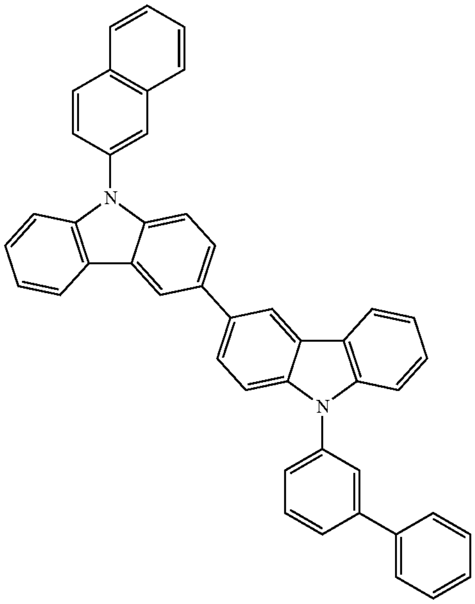

-continued
H2-33
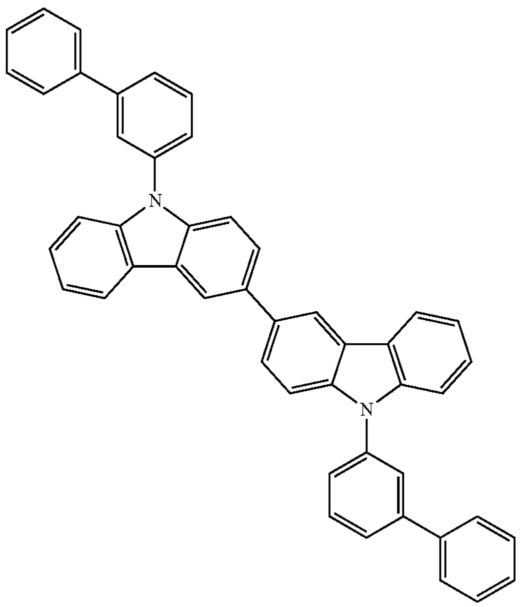
H2-34
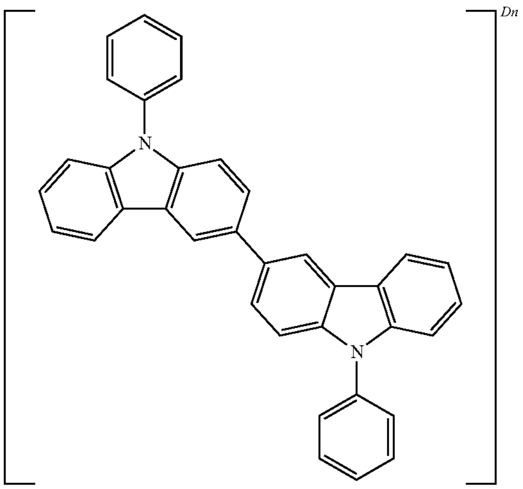
-continued
H2-35
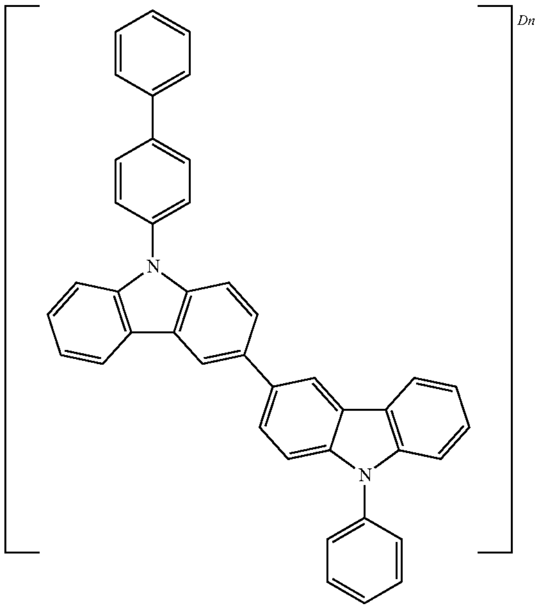
H2-36
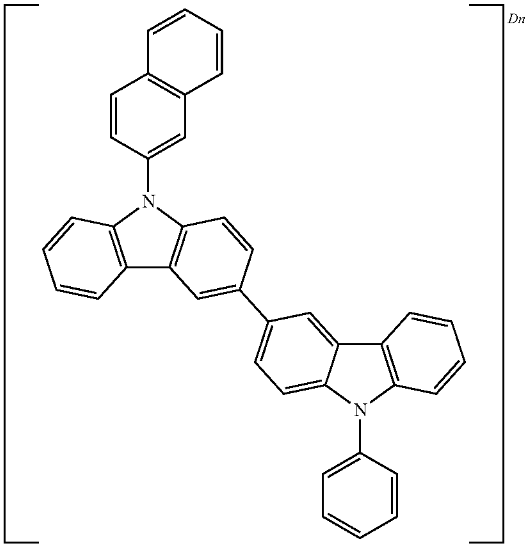

-continued
H2-37
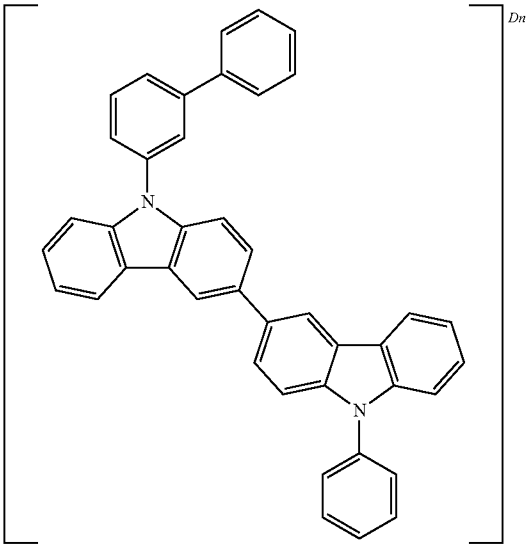
H2-38
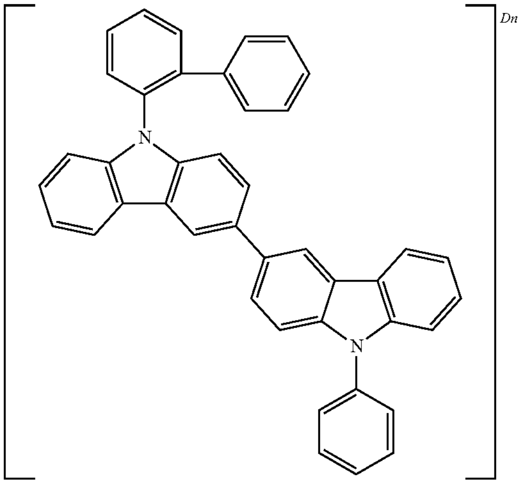
H2-39
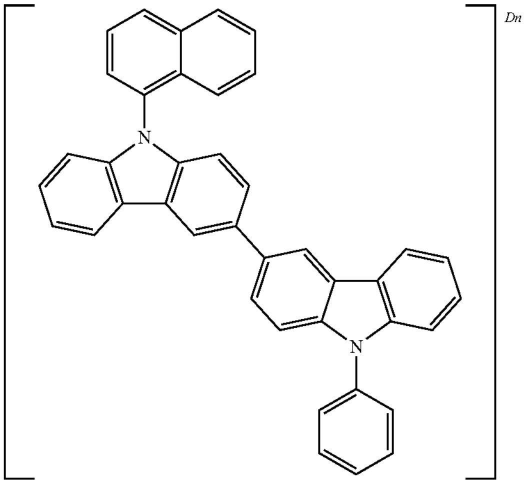
-continued
H2-40
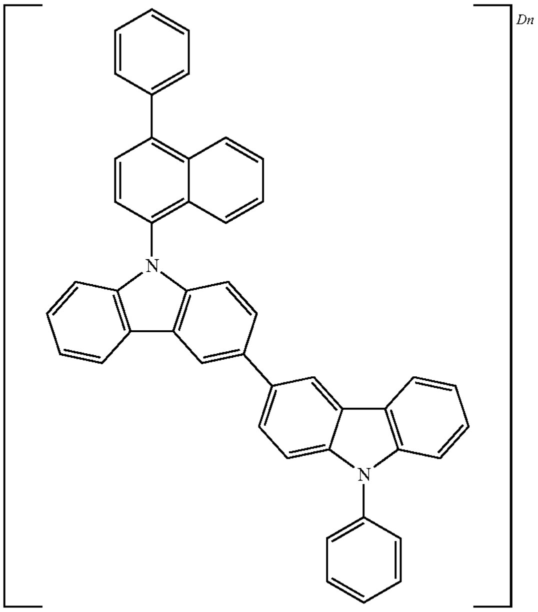
H2-41
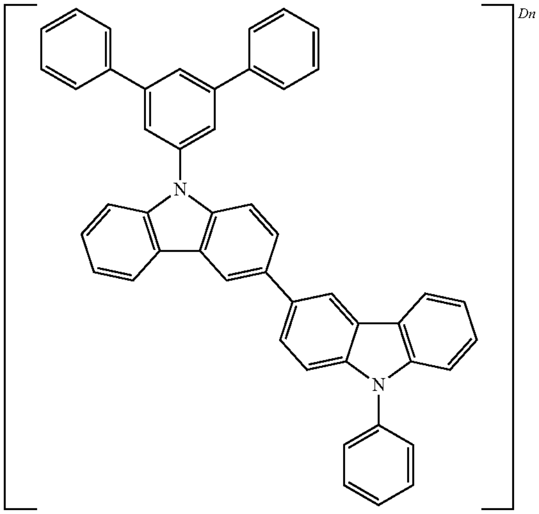

-continued
H2-42
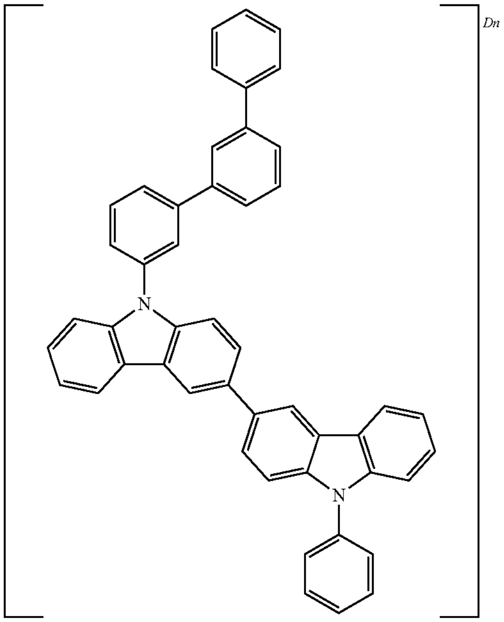
H2-43
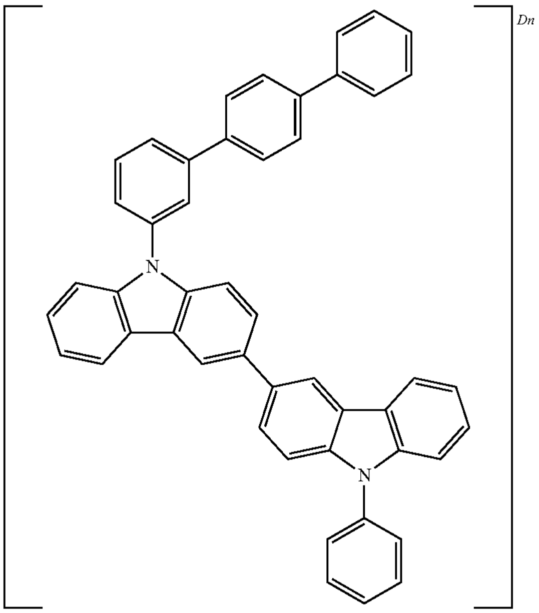
-continued
H2-44
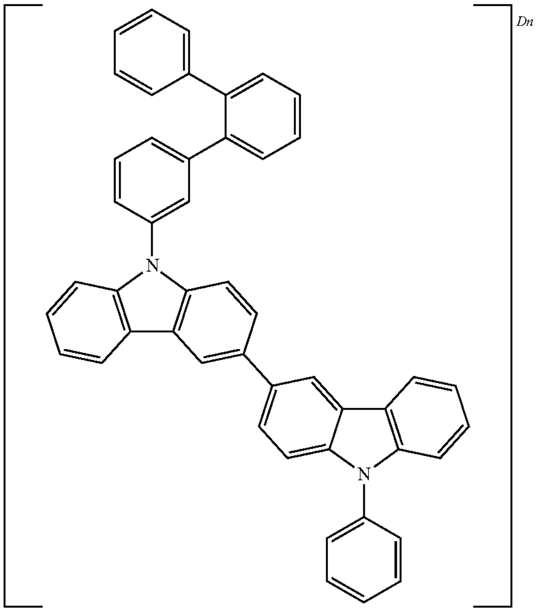
H2-45
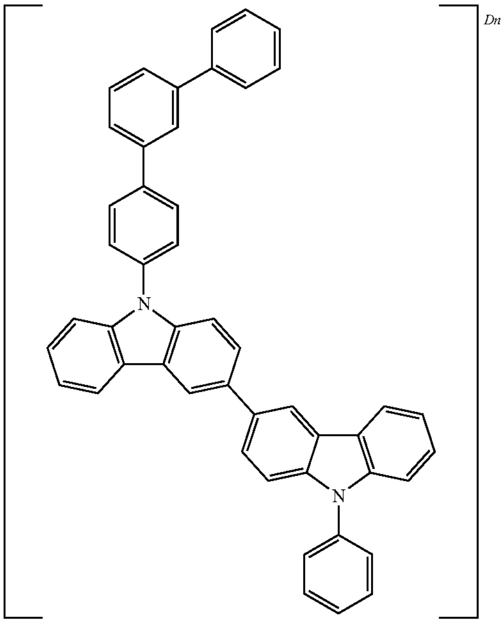

-continued
H2-46
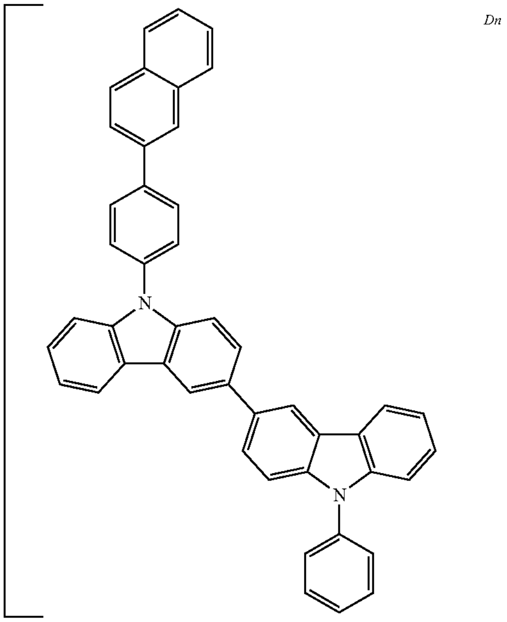
-continued
H2-48
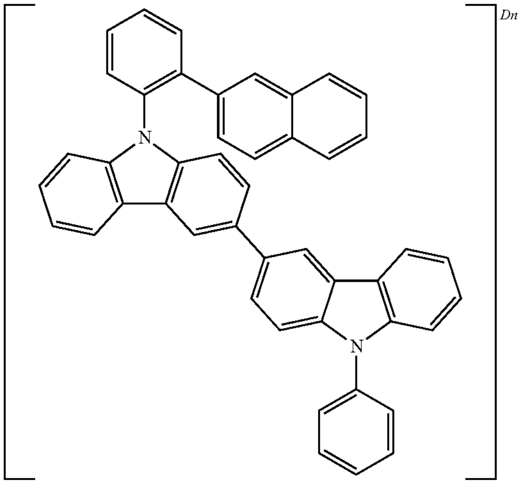
H2-47
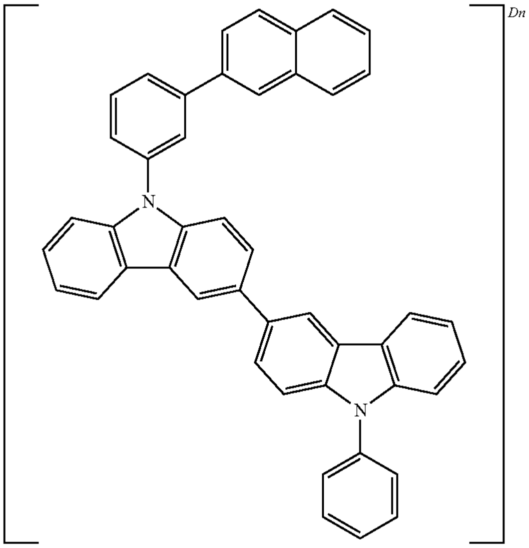
H2-49
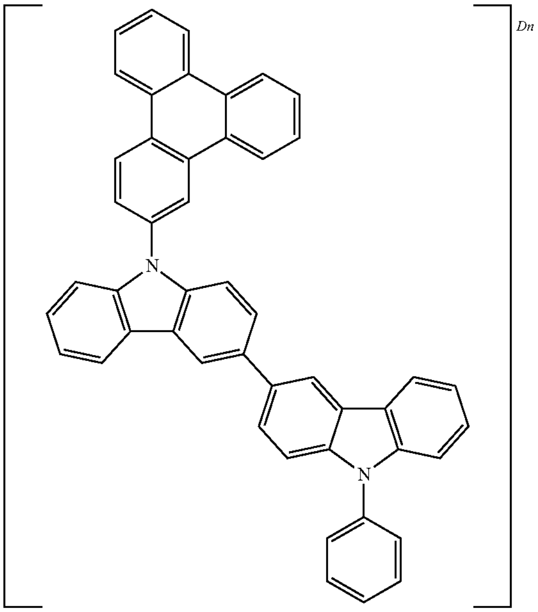

H2-50
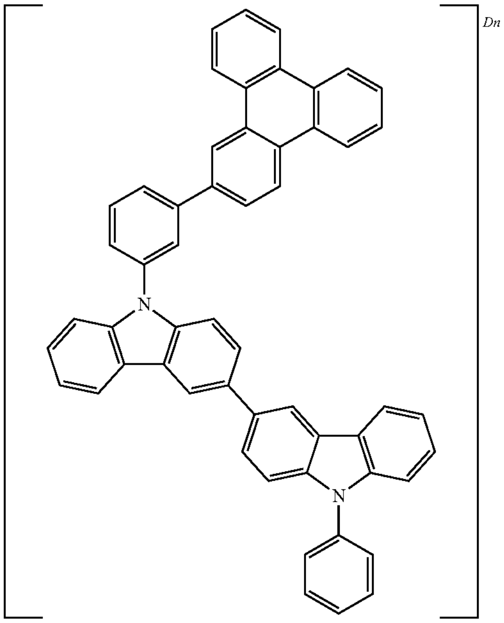
H2-52
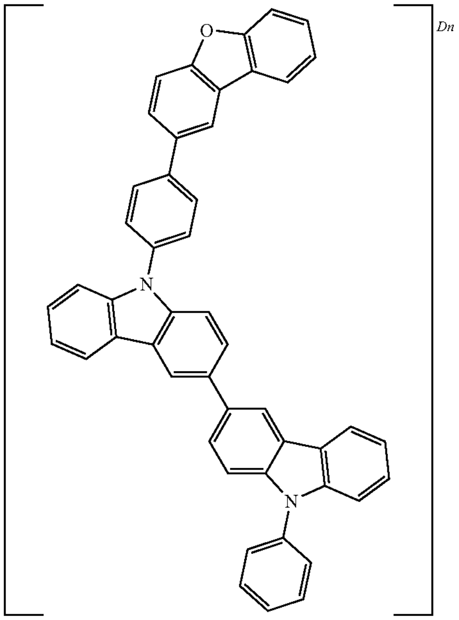
H2-51
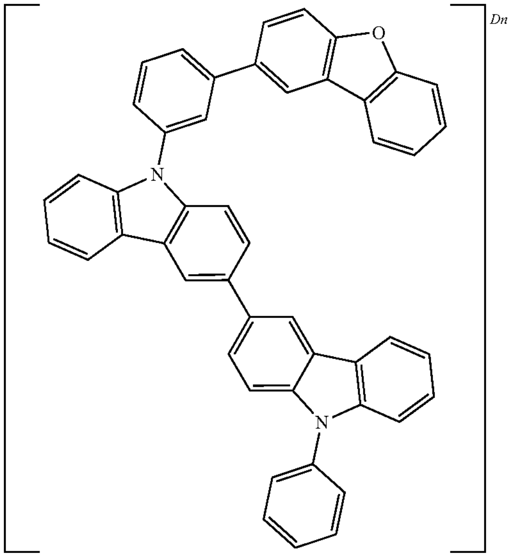
H2-53
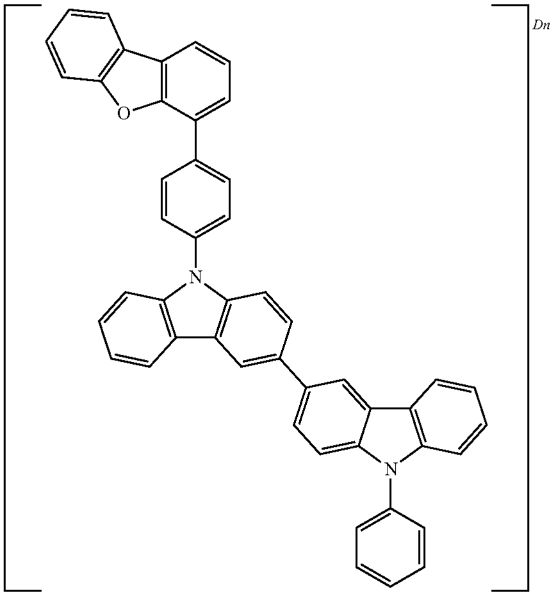

-continued
H2-54
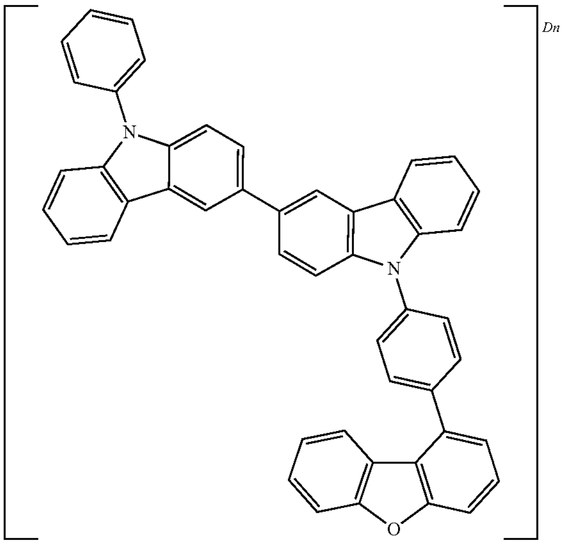
H2-55
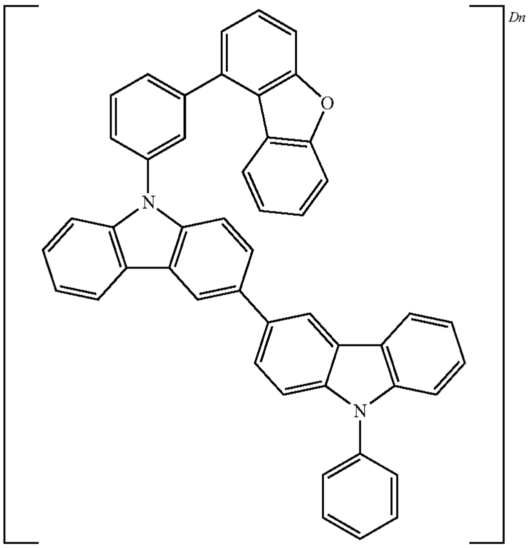
-continued
H2-56
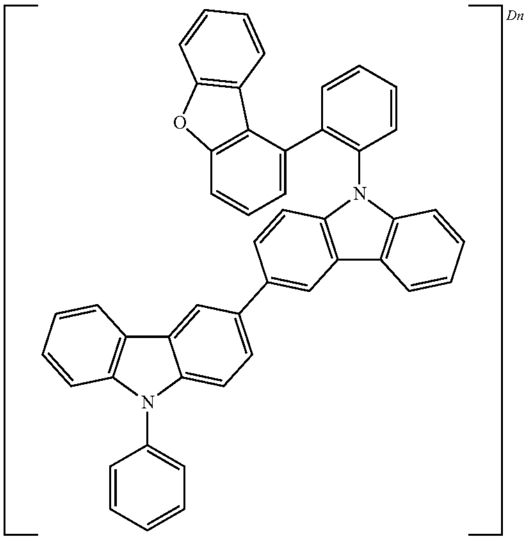
H2-57
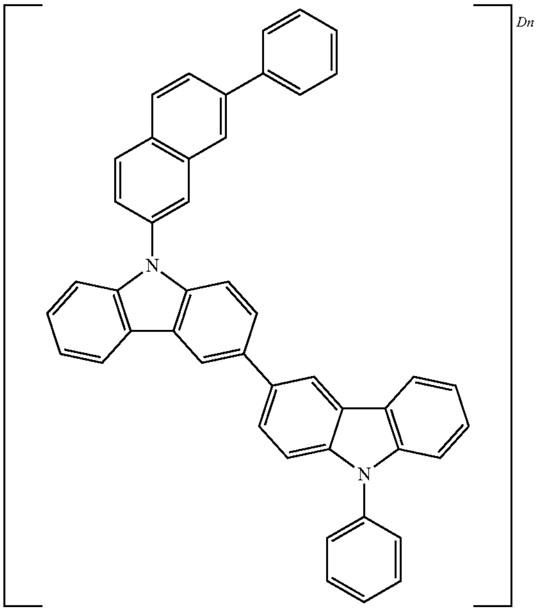

-continued
H2-58
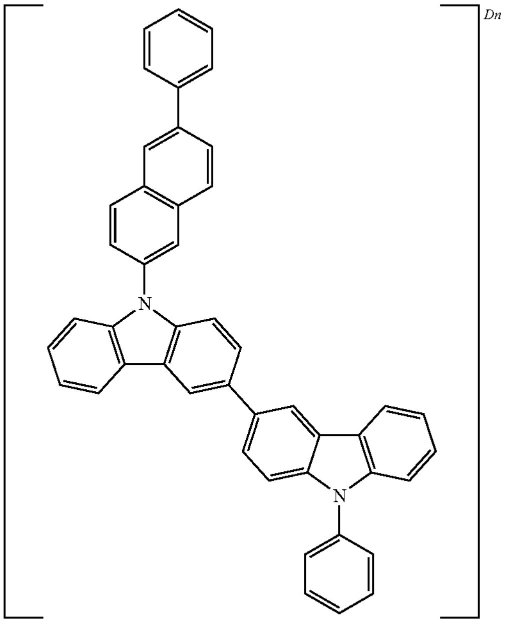
H2-59
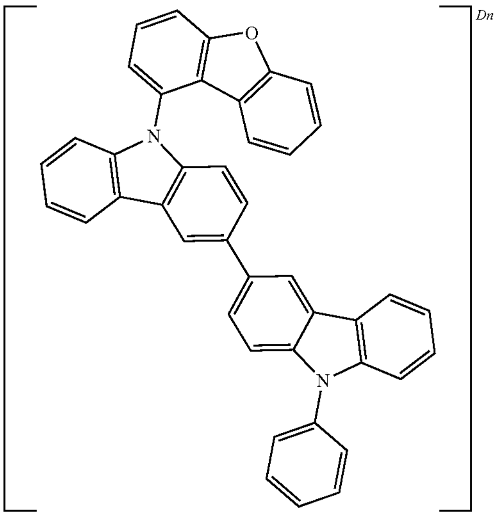
-continued
H2-60
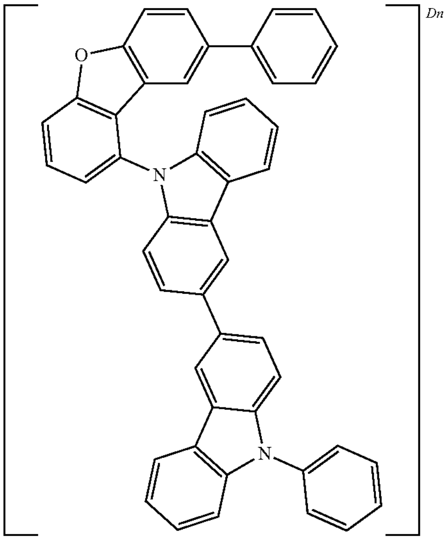
H2-61
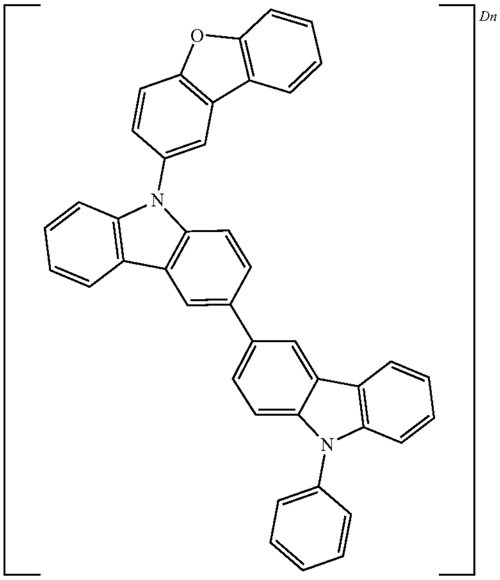

-continued
H2-62
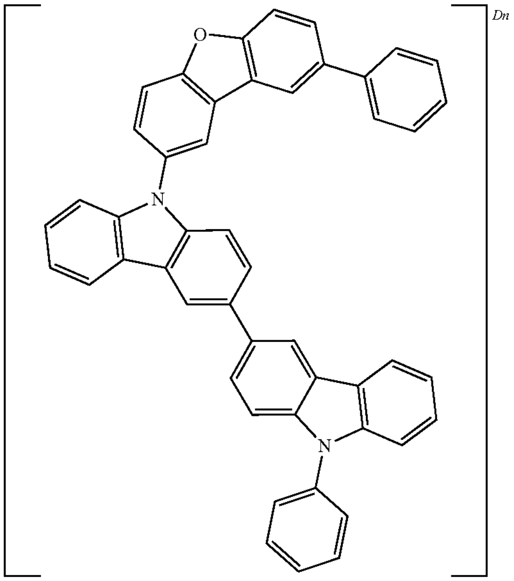
H2-63
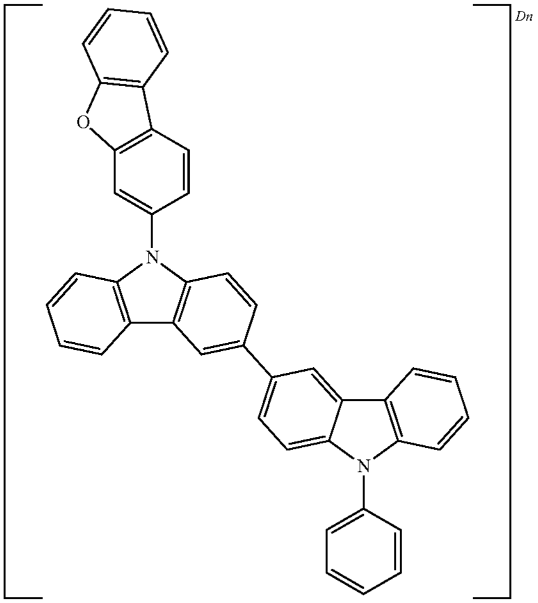
-continued
H2-64
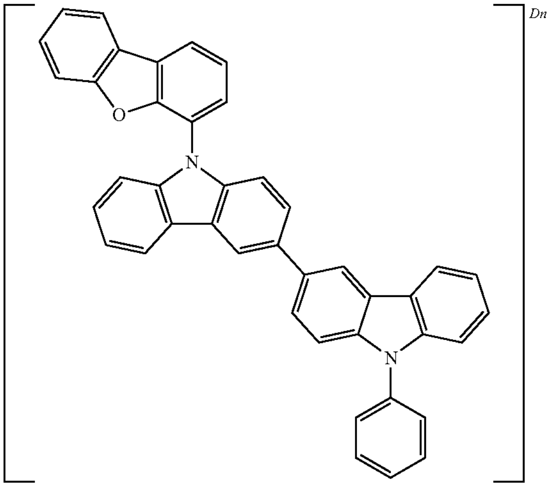
H2-65
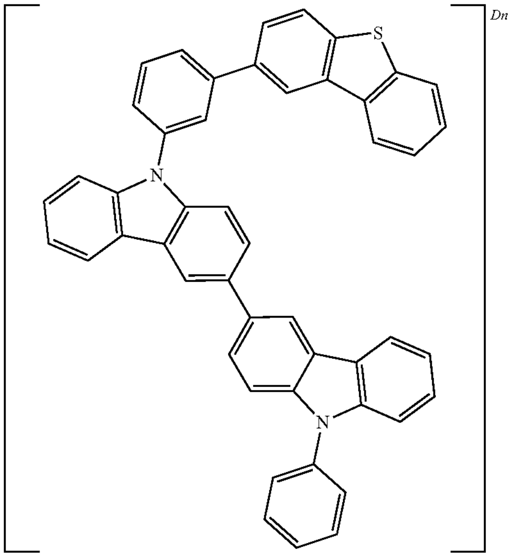

-continued
H2-66
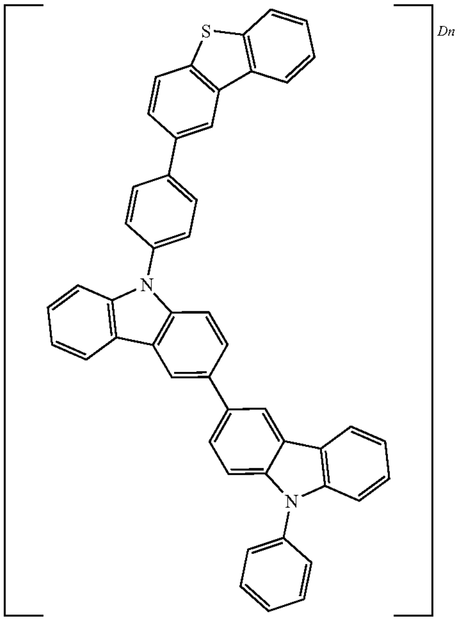
H2-67
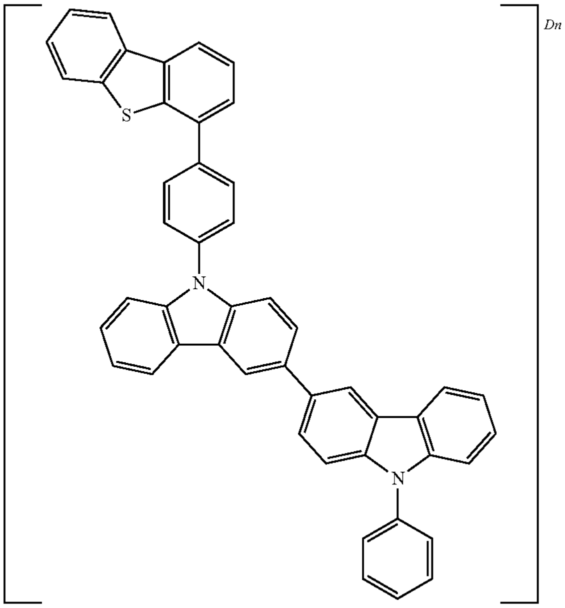
-continued
H2-68
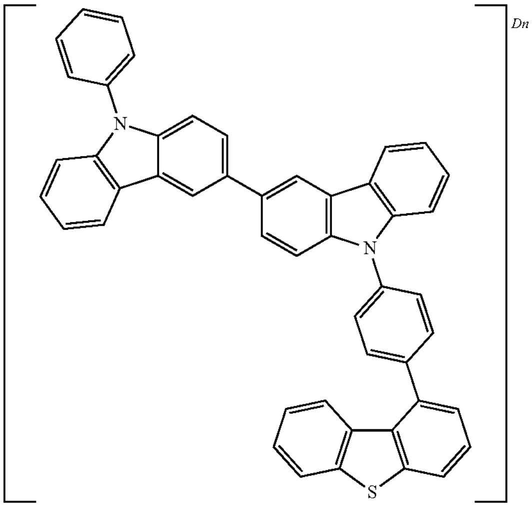
H2-69
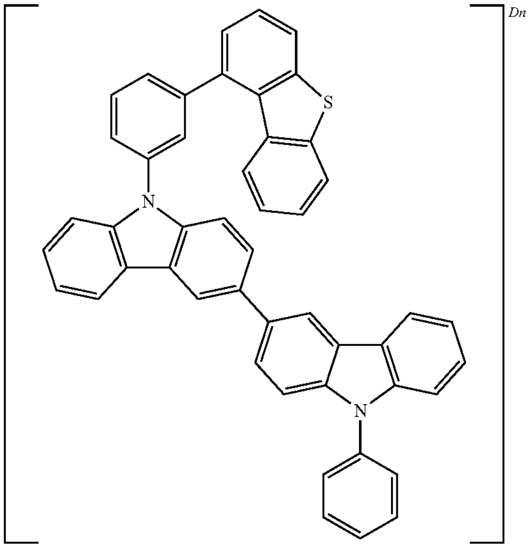
H2-70
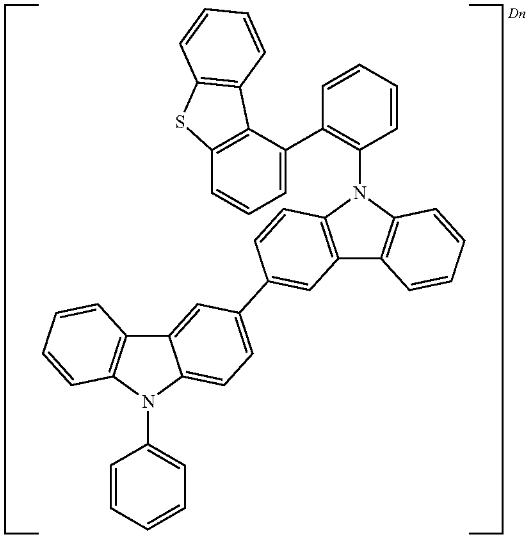

-continued
H2-71
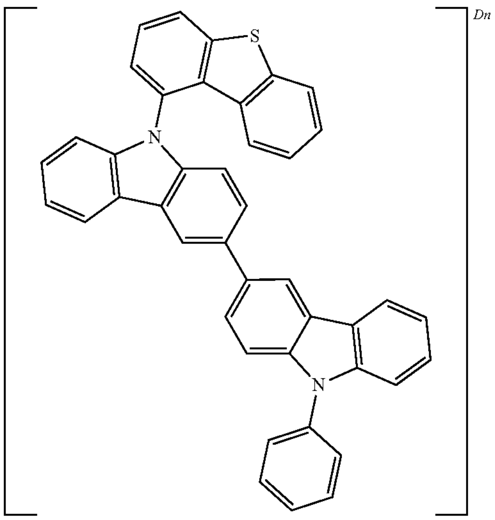
H2-72
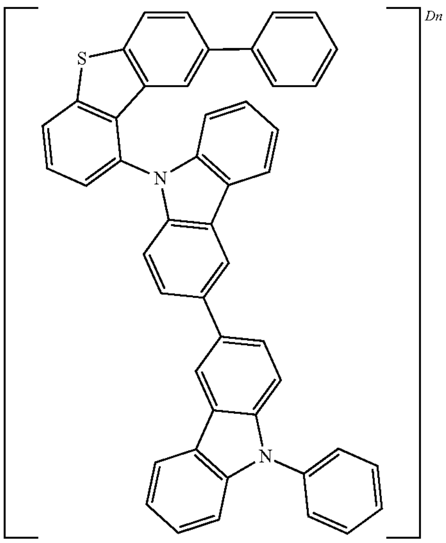
-continued
H2-73
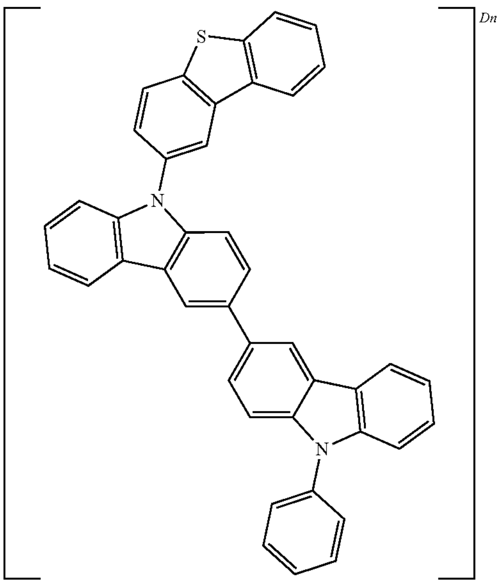
H2-74
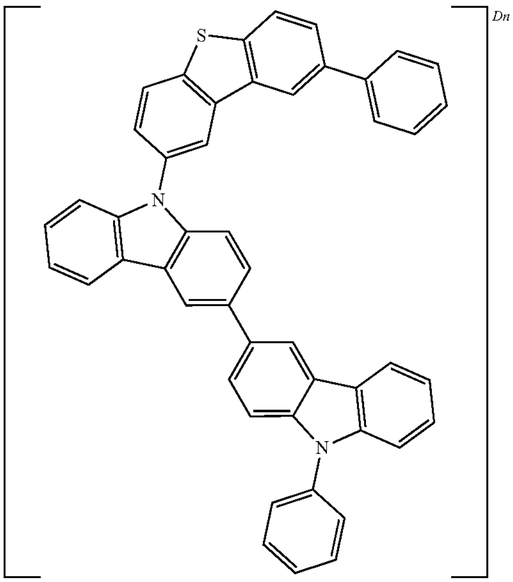

-continued
H2-75
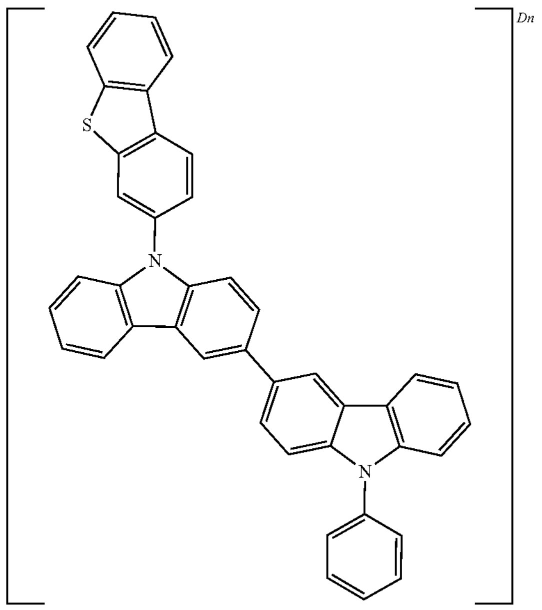
-continued
H2-77
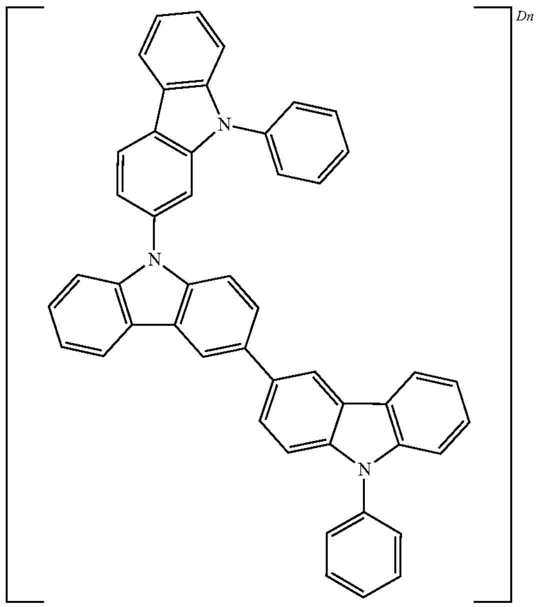
H2-76
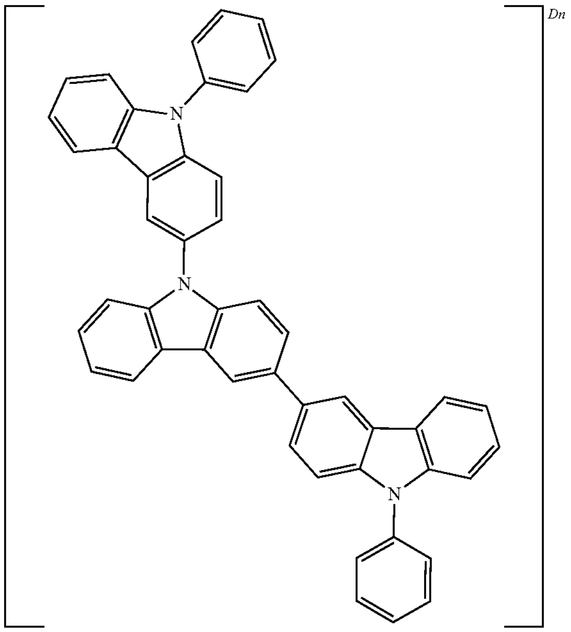
H2-78
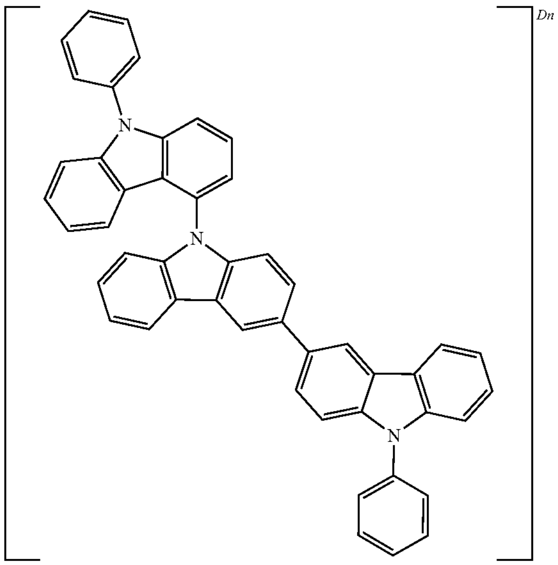

-continued
H2-79
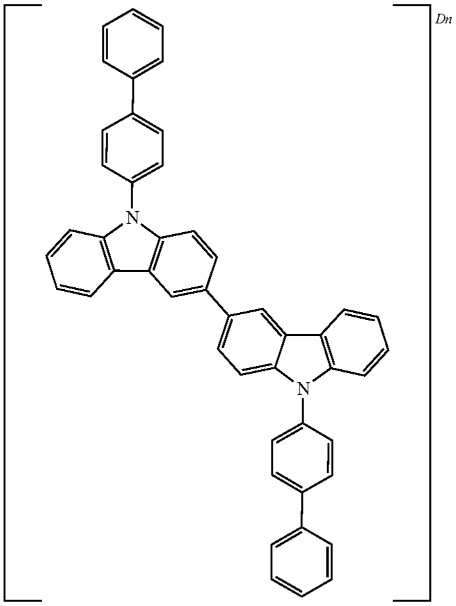
H2-80
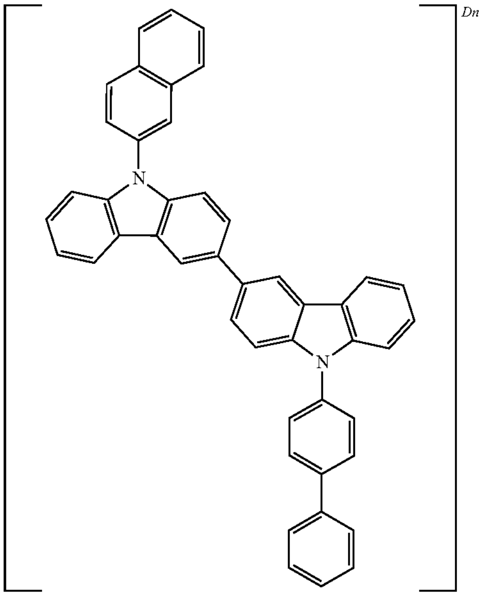
-continued
H2-81
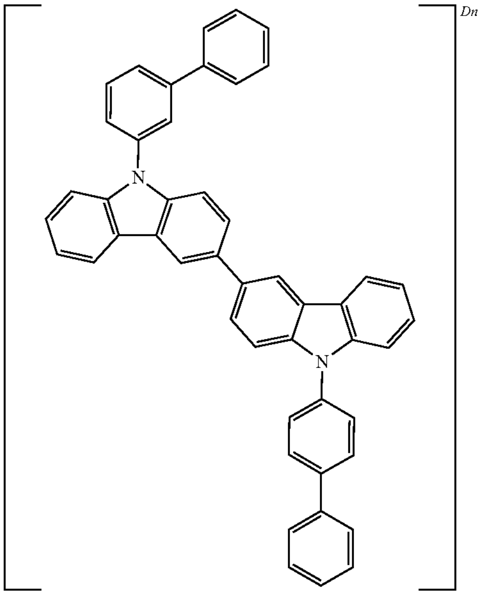
H2-82
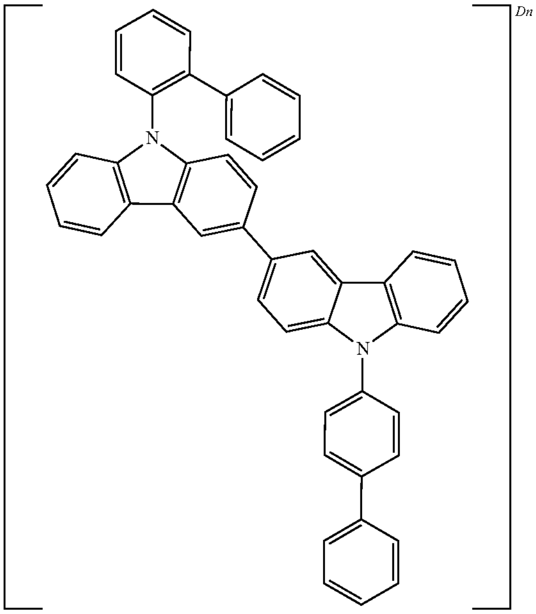

-continued
H2-83
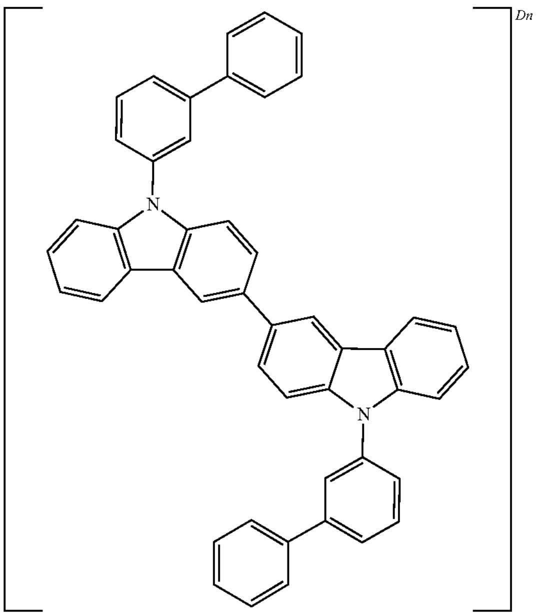
H2-84
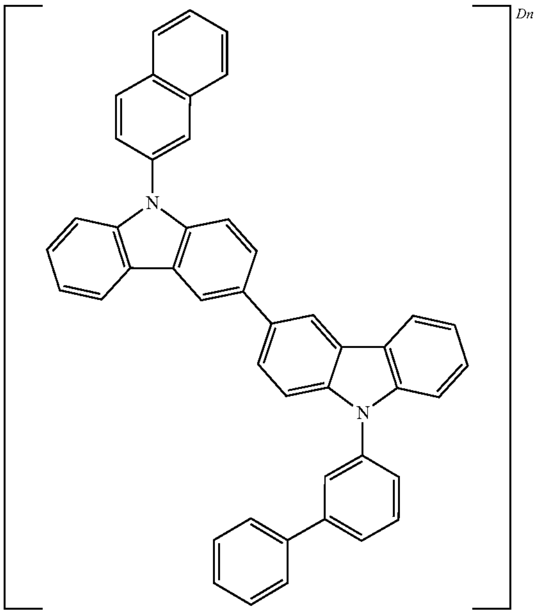
-continued
H2-85
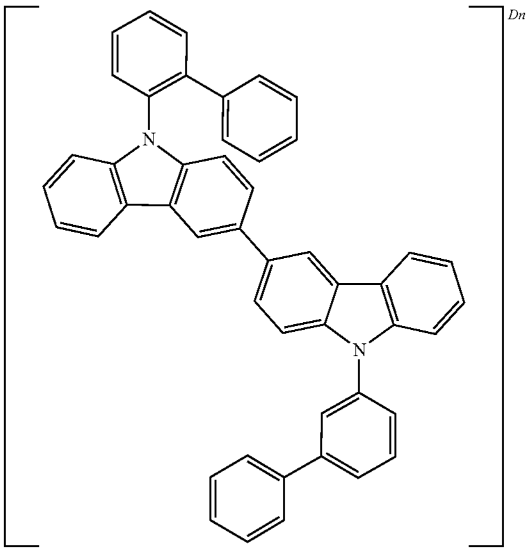
H2-86
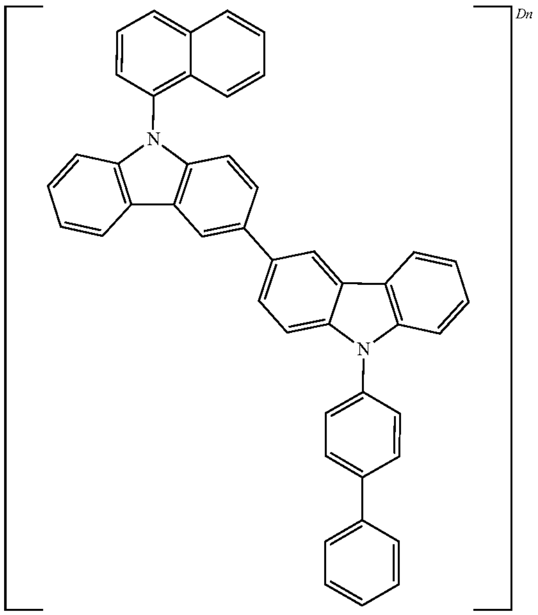

-continued
H2-87
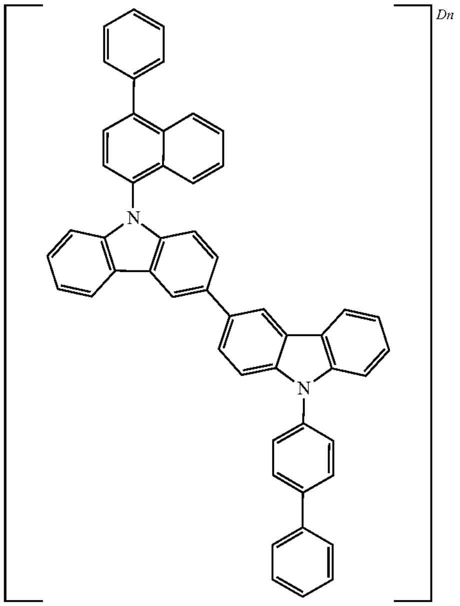
H2-88
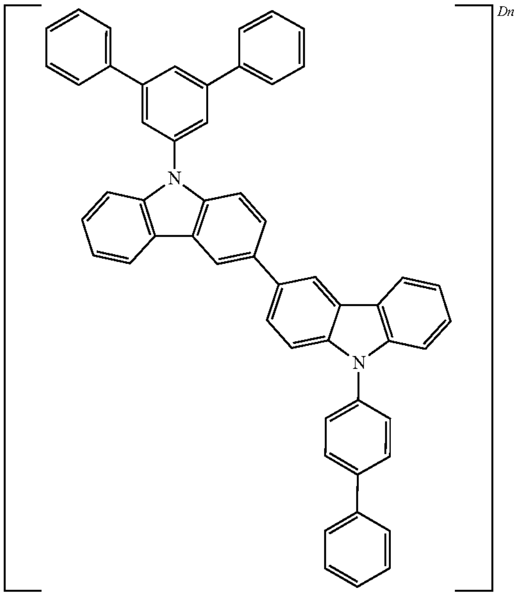
-continued
H2-89
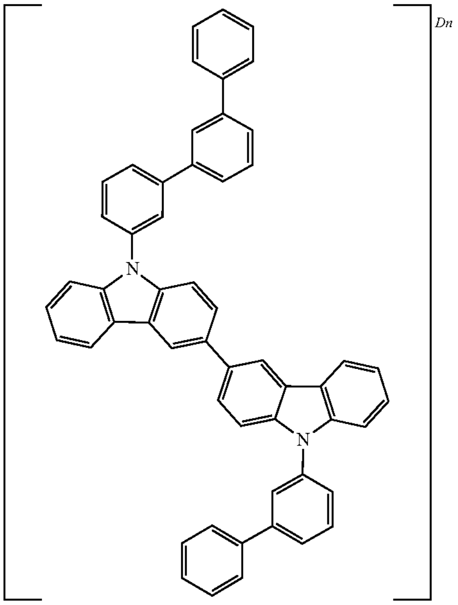
H2-90
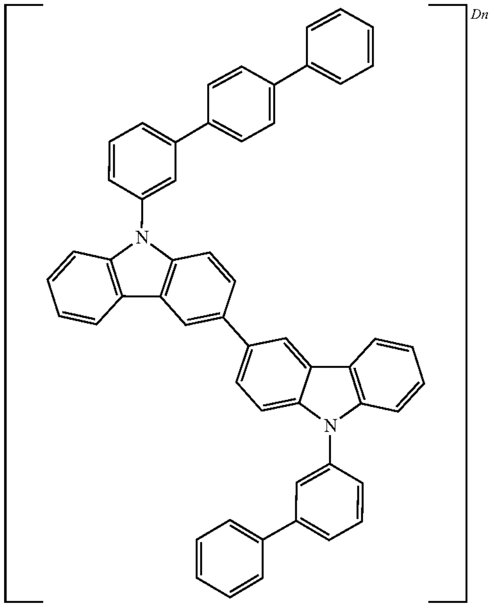

-continued
H2-91
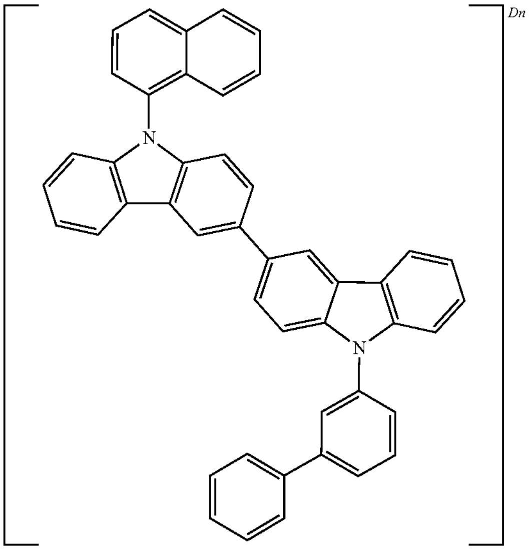
H2-92
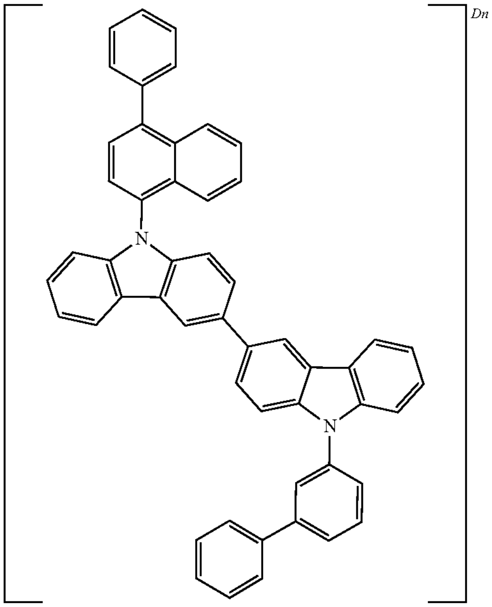
-continued
H2-93
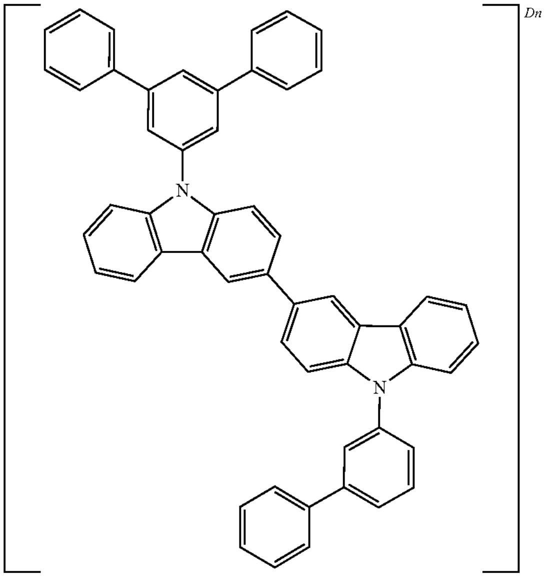
H2-94
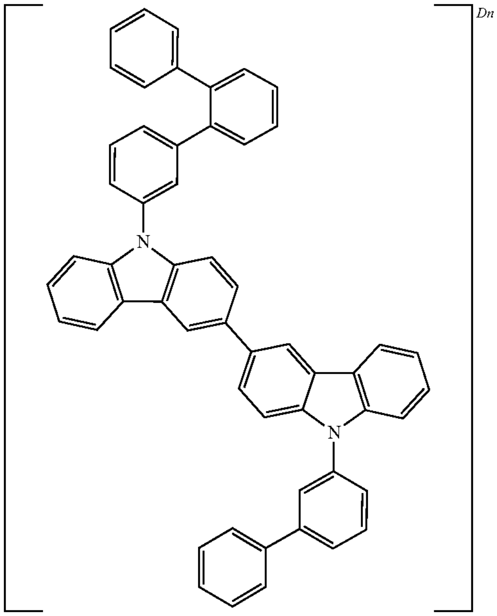

-continued
H2-95
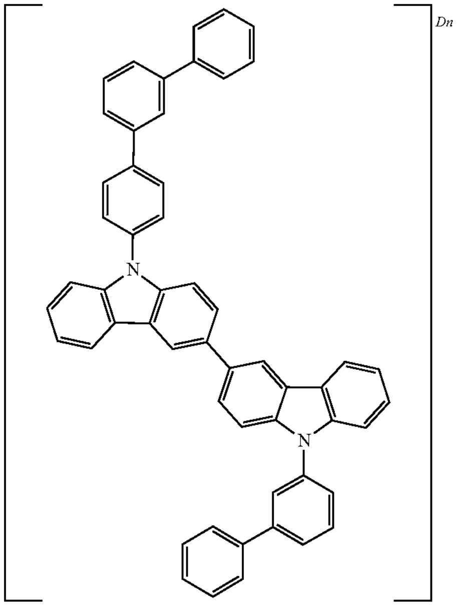
H2-96
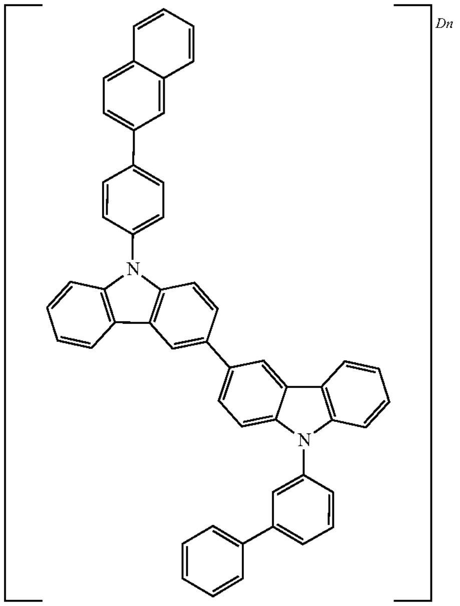
-continued
H2-97
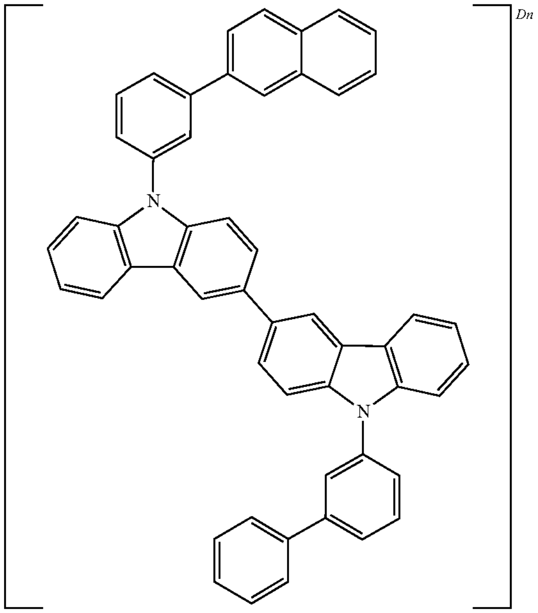
H2-98
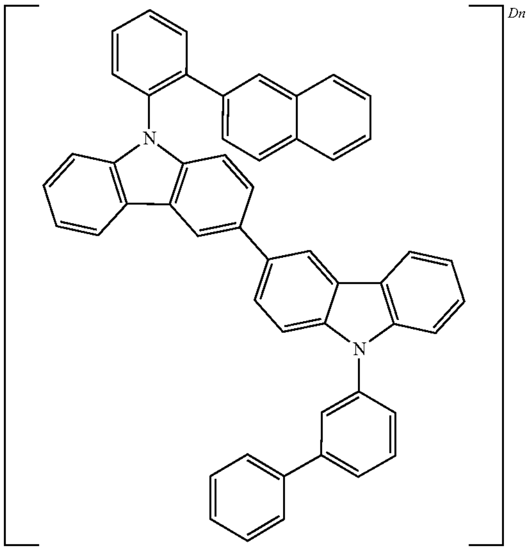

-continued
H2-99
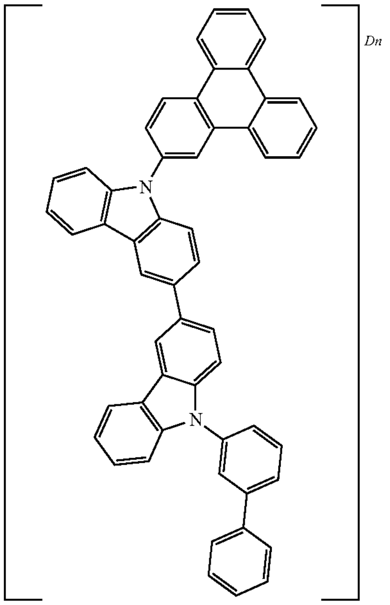
H2-100
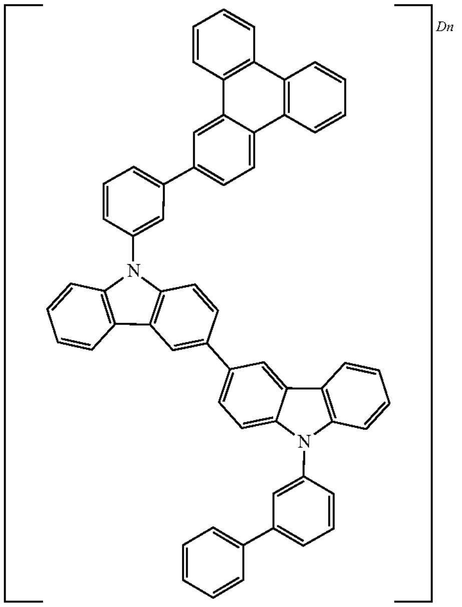
-continued
H2-101
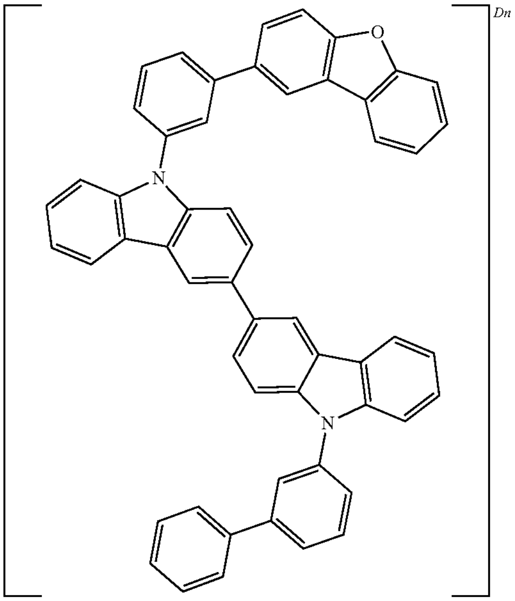
H2-102
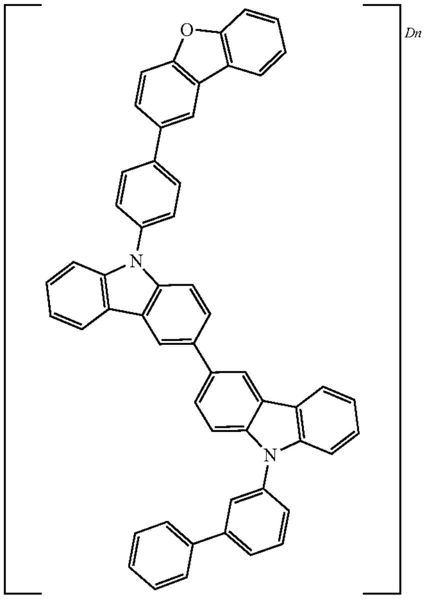

-continued
H2-103
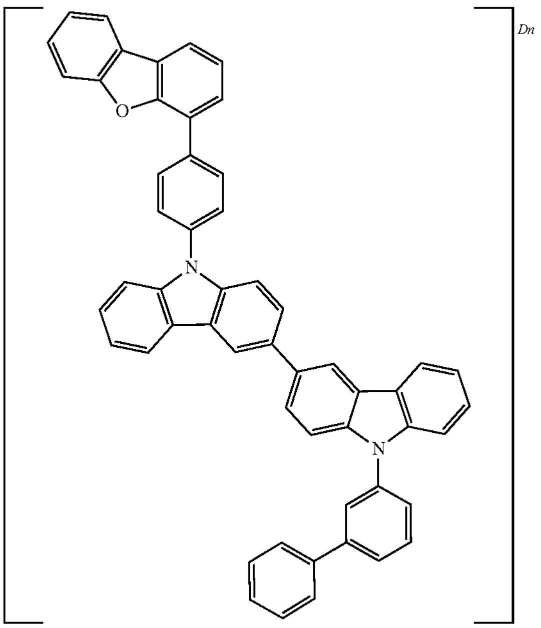
-continued
H2-105
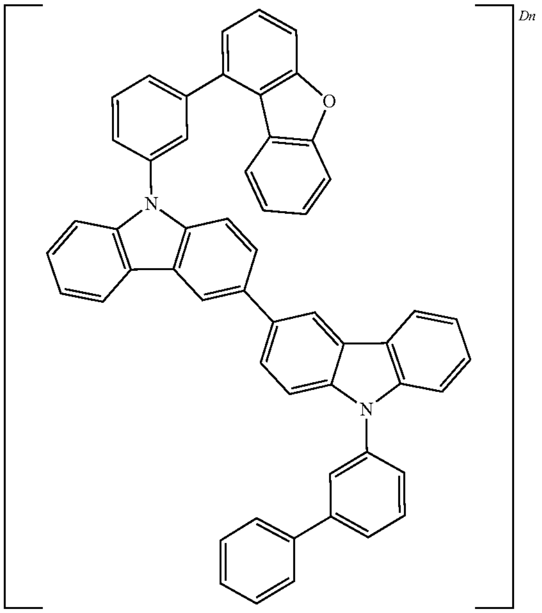
H2-104
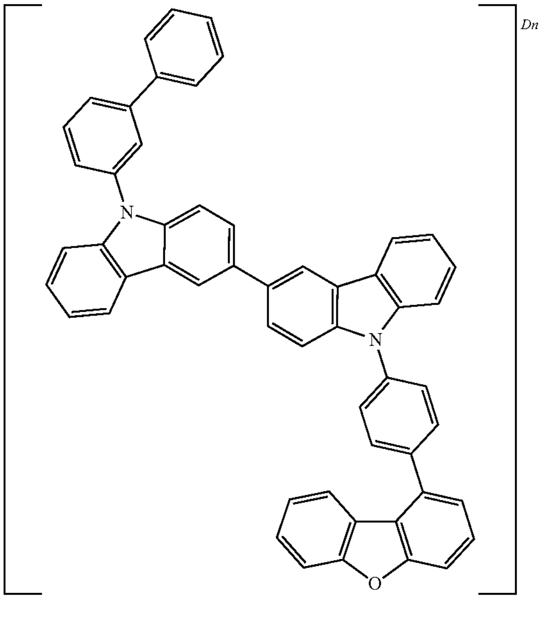
H2-106
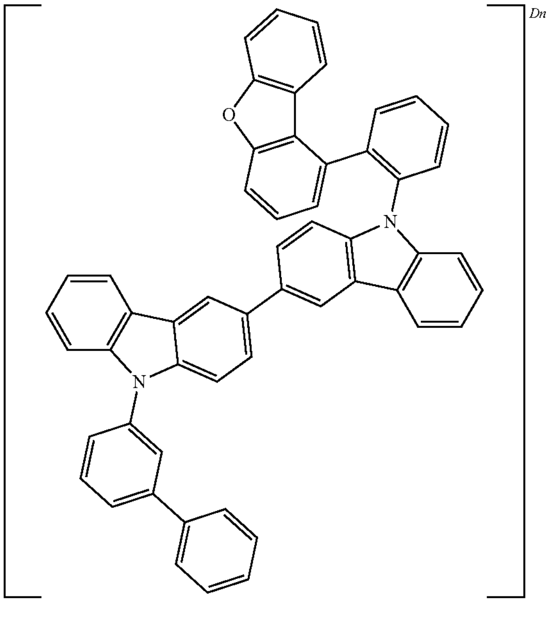

-continued
H2-107
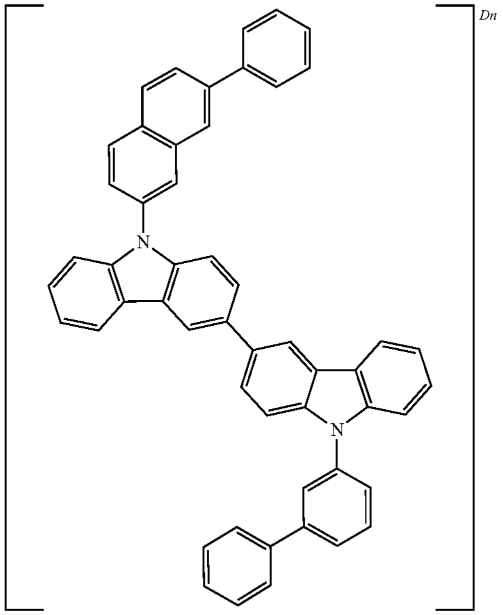
H2-108
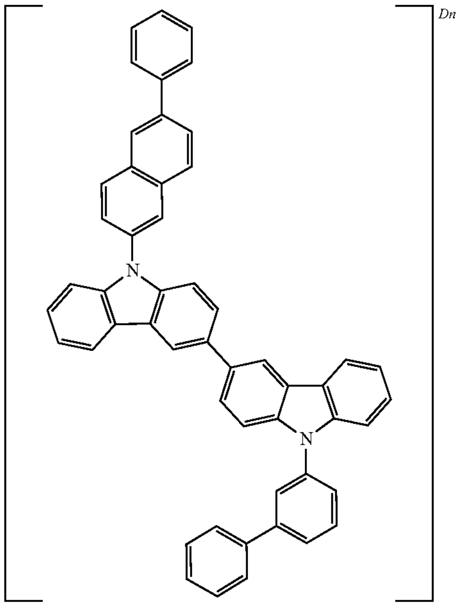
-continued
H2-109
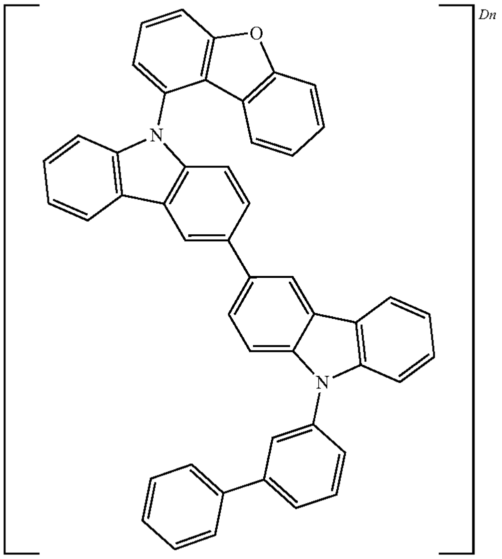
H2-110
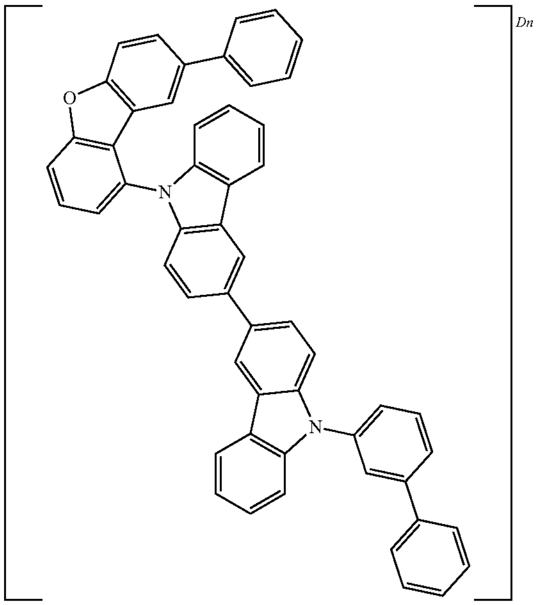

-continued
H2-111
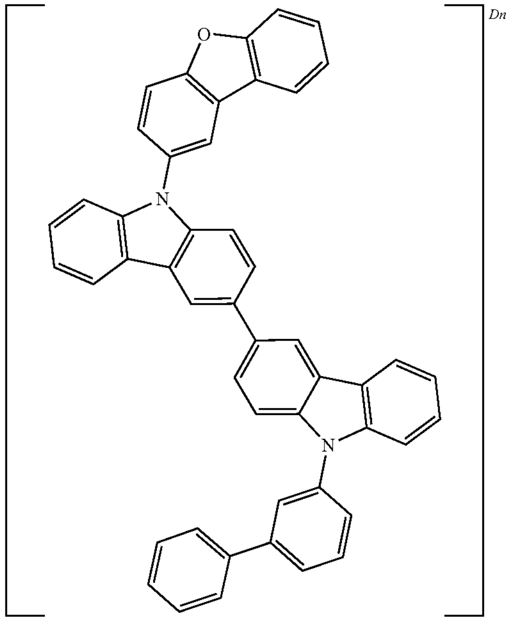
H2-112
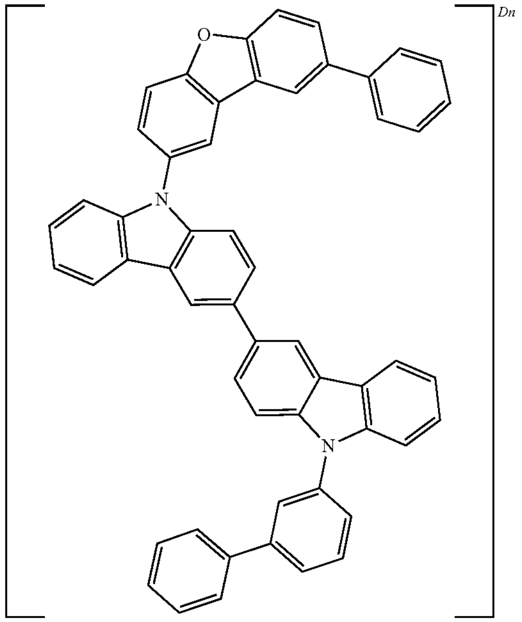
-continued
H2-113
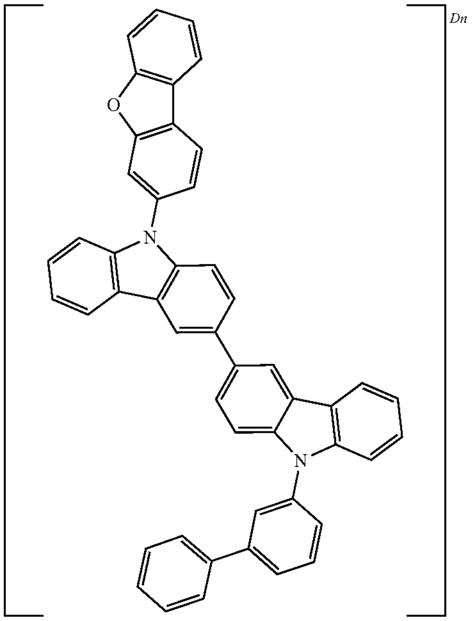
H2-114
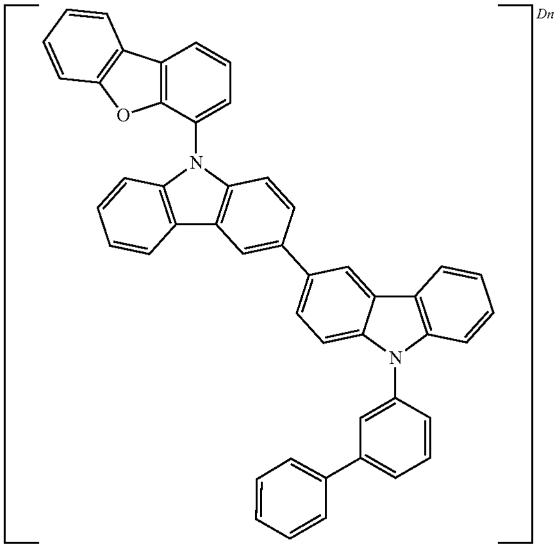

-continued
H2-115
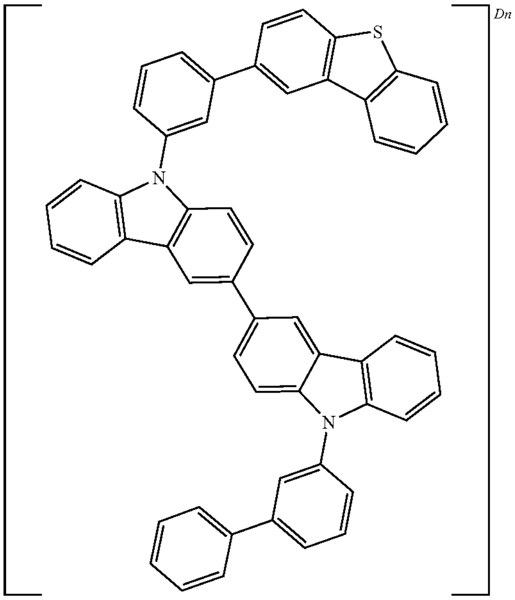
H2-117
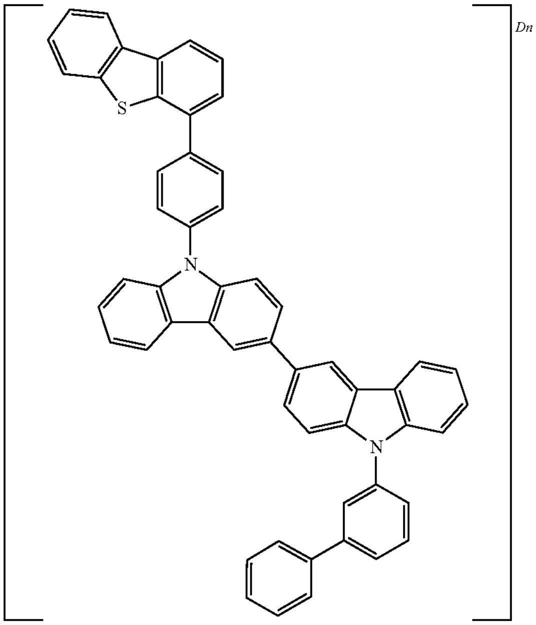
H2-116
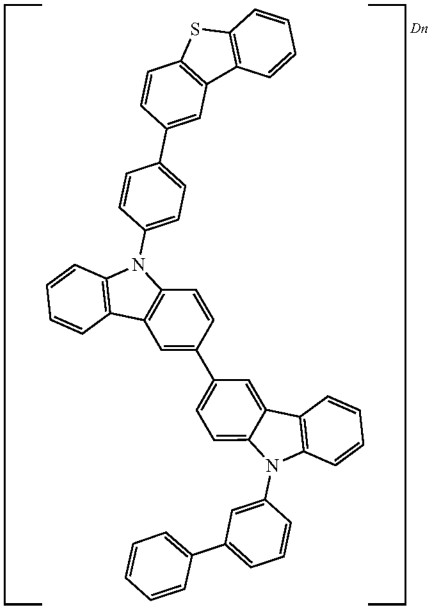
H2-118
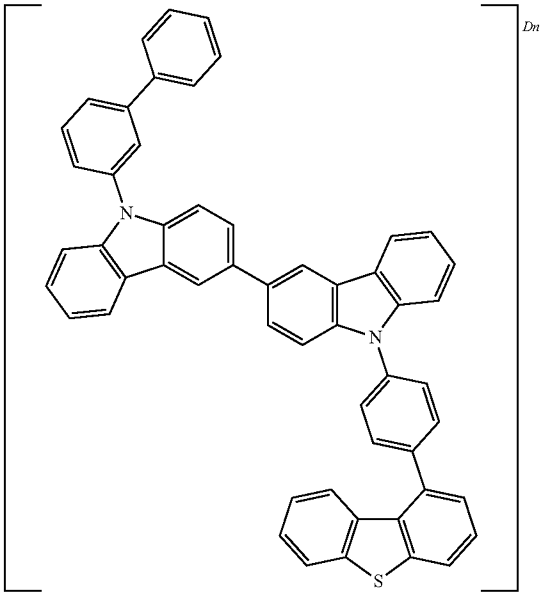

-continued
H2-119
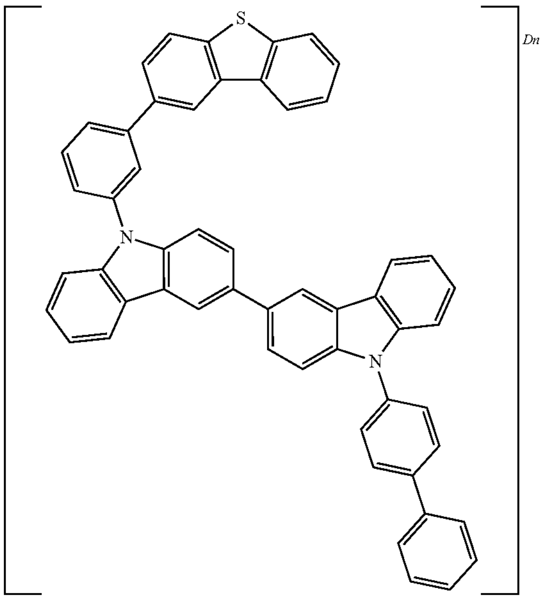
H2-120
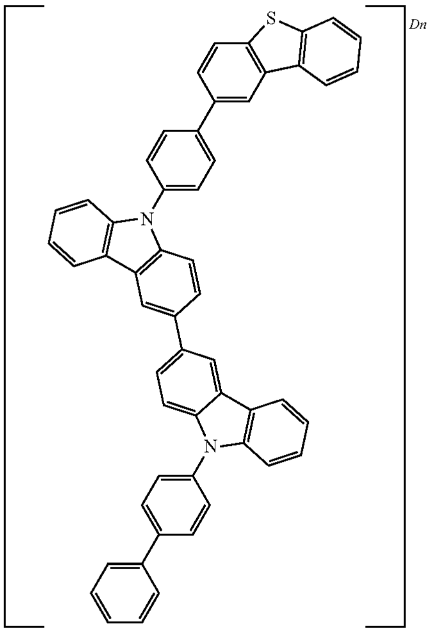
-continued
H2-121
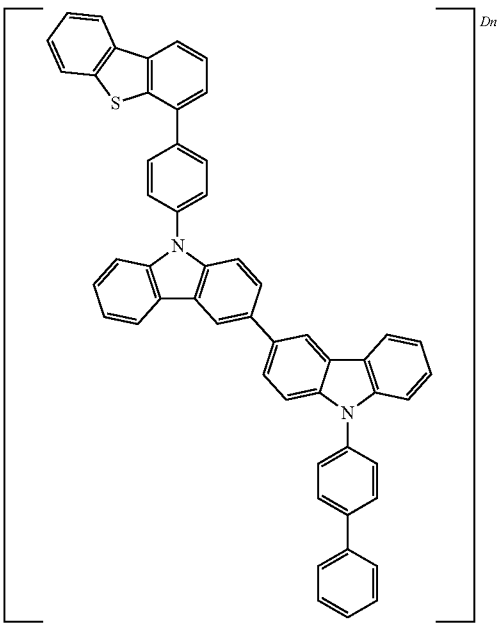
H2-122
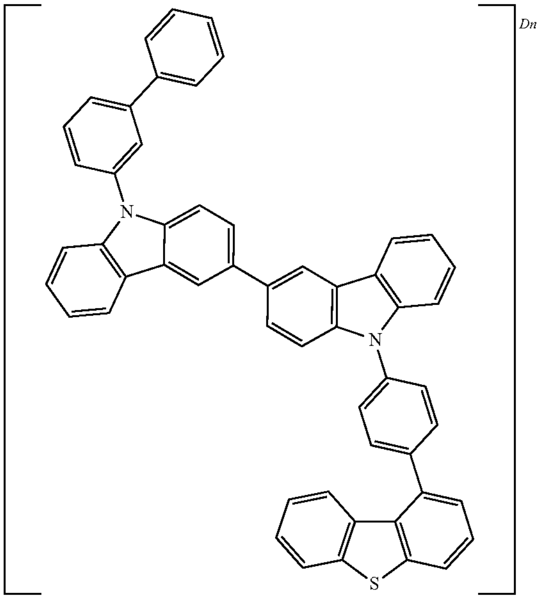

-continued
H2-123
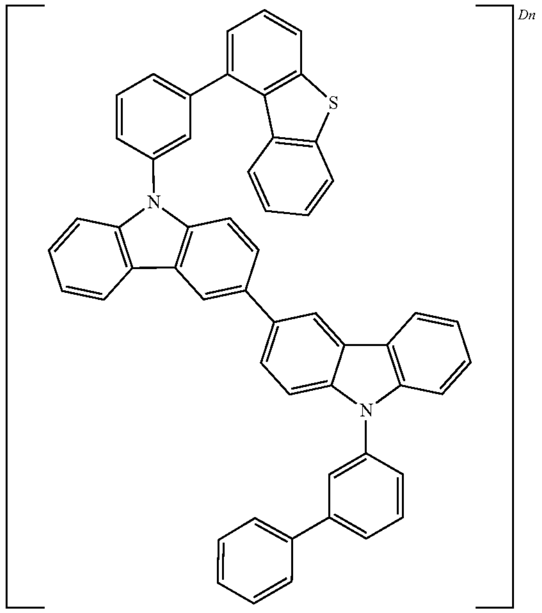
H2-125
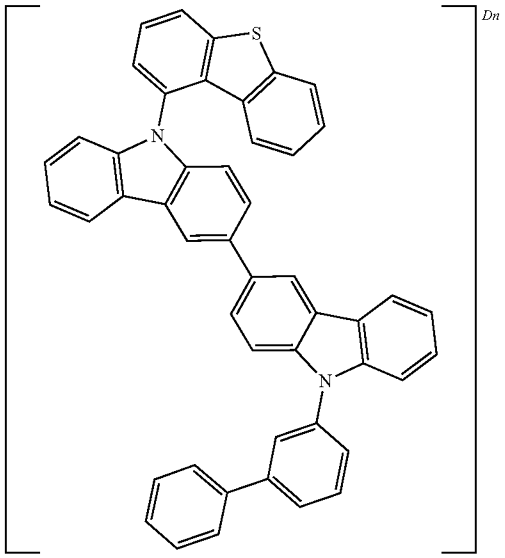
H2-124
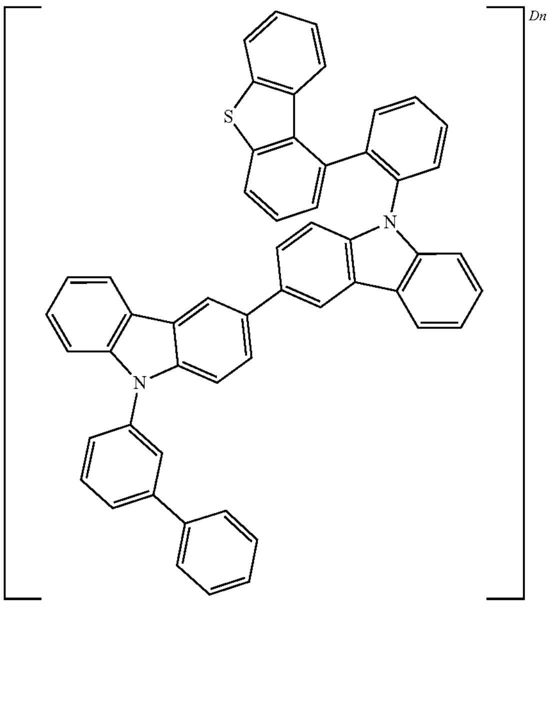
H2-126
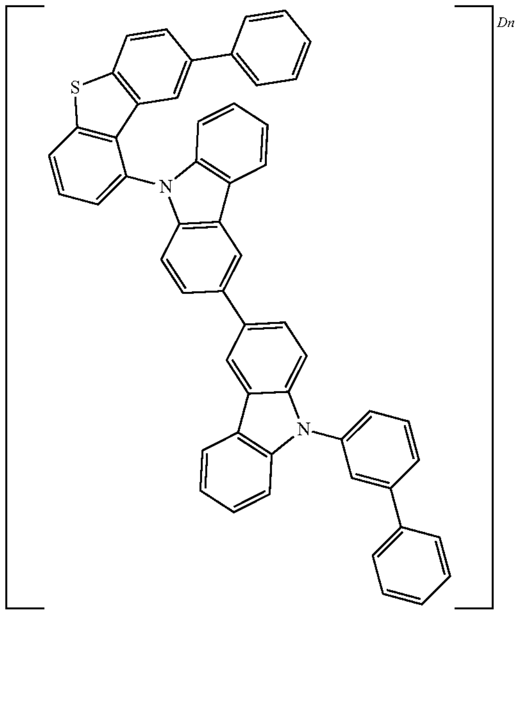

-continued
H2-127
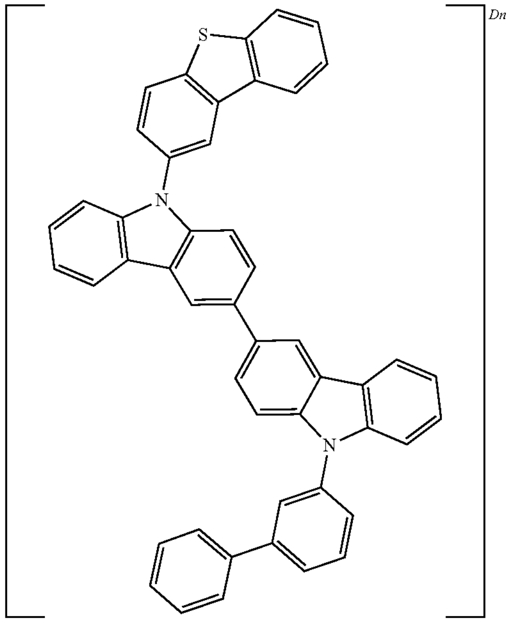
-continued
H2-129
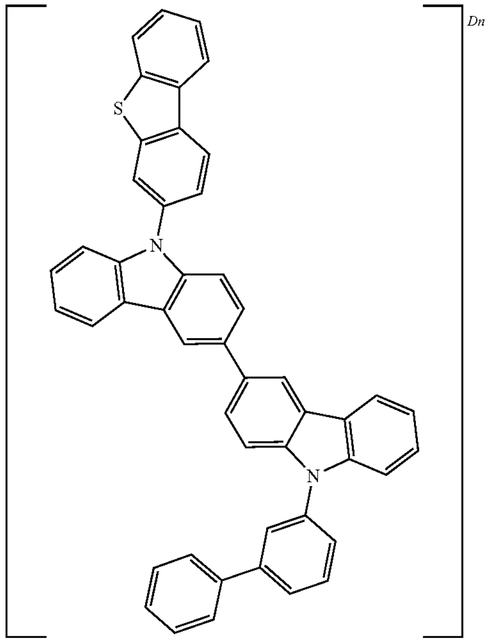
H2-128
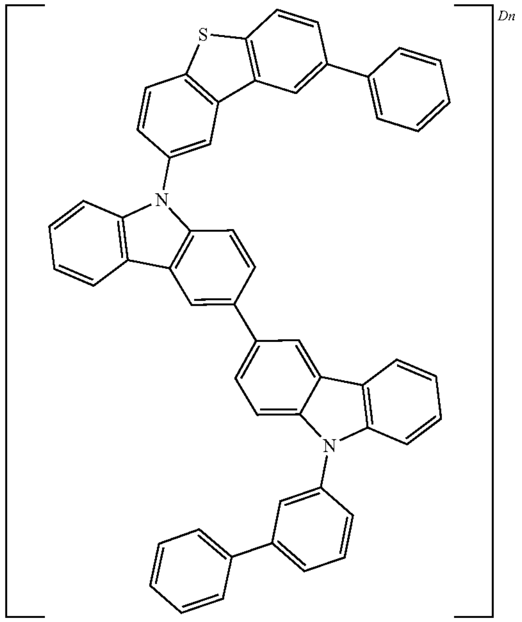
H2-130
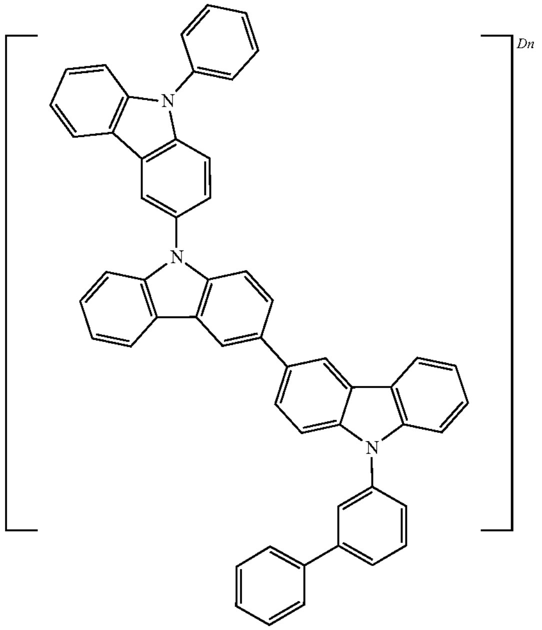

-continued
H2-131
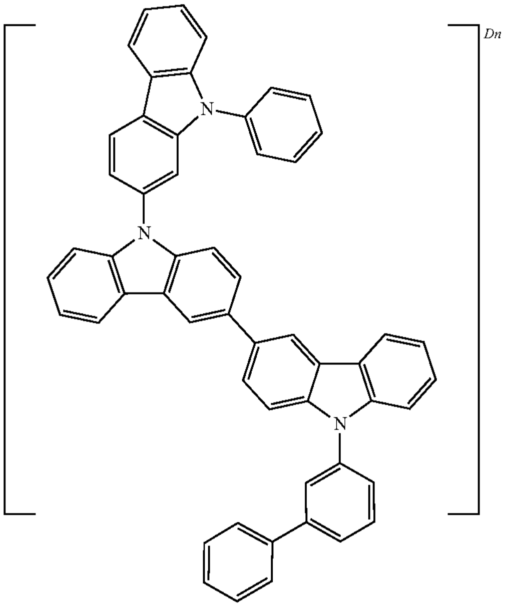
H2-132
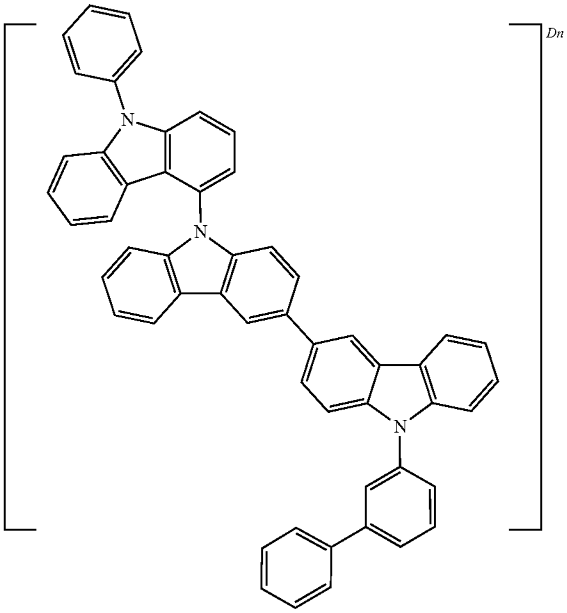
-continued
H2-133
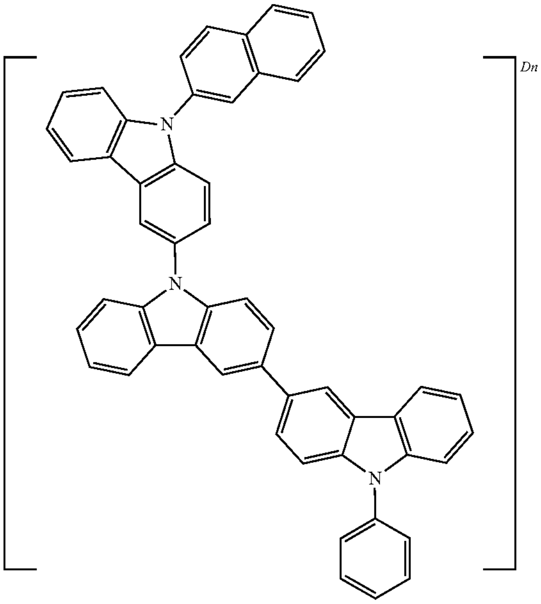
H2-134
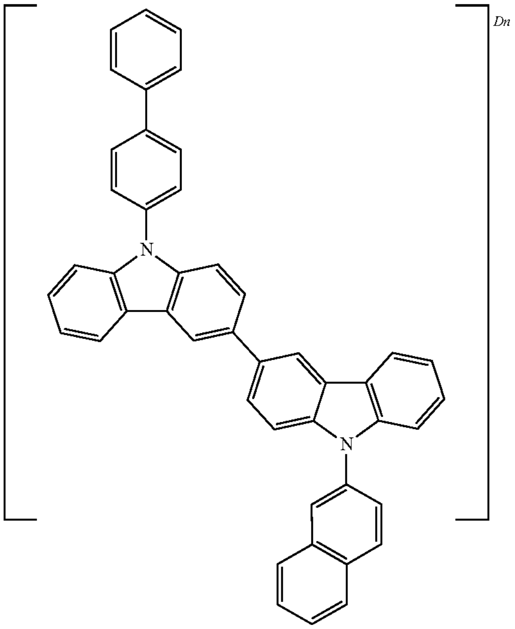

-continued
H2-135
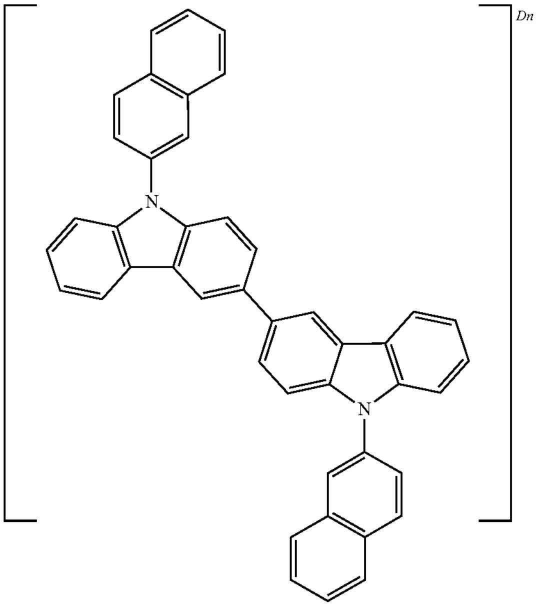
H2-136
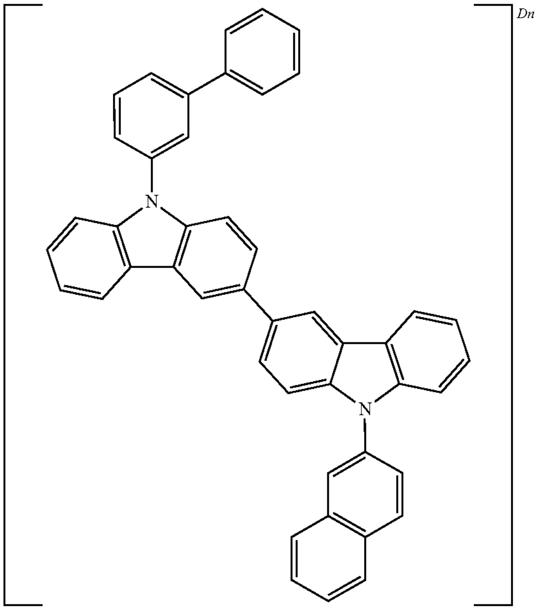
-continued
H2-137
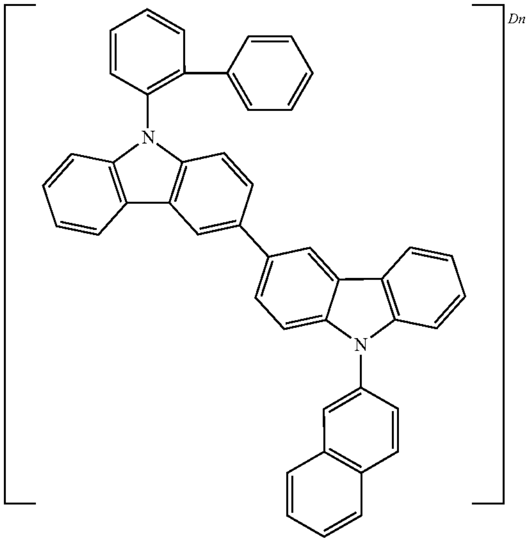
H2-138
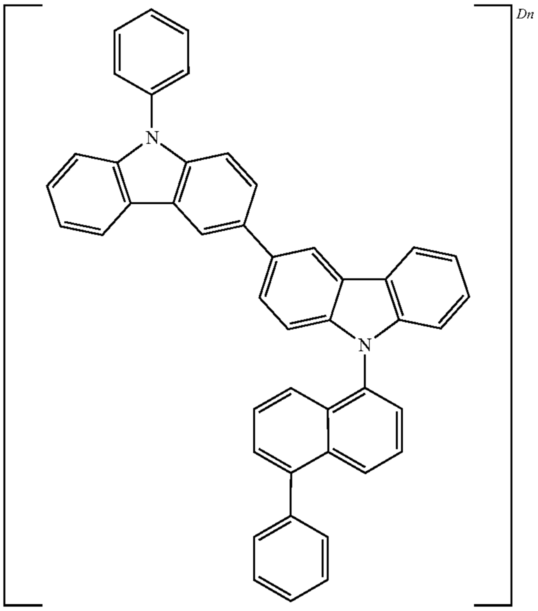

-continued
H2-139
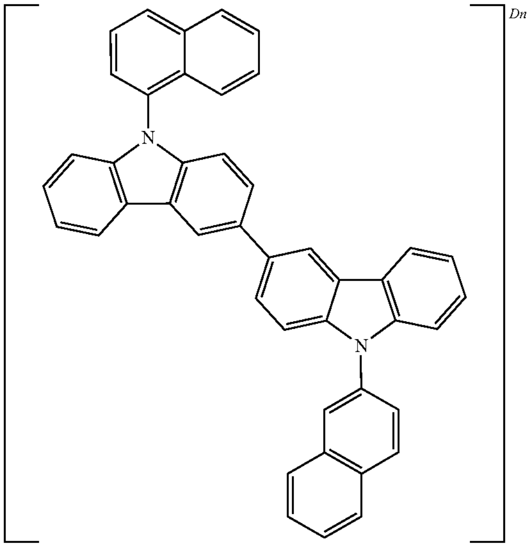
H2-140
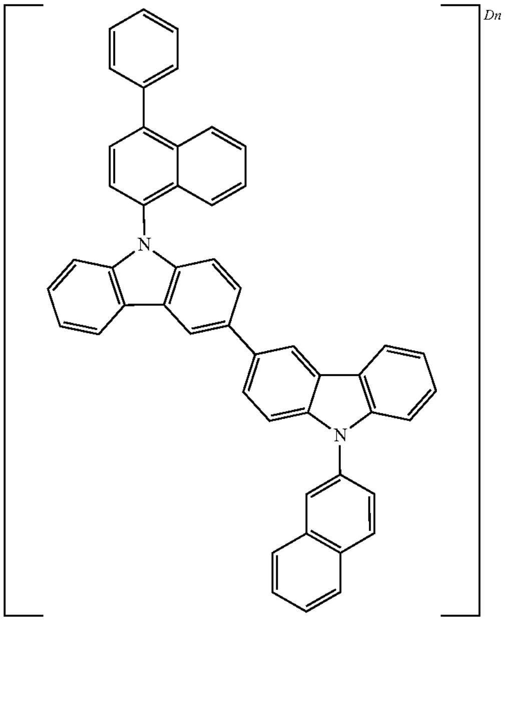
-continued
H2-141
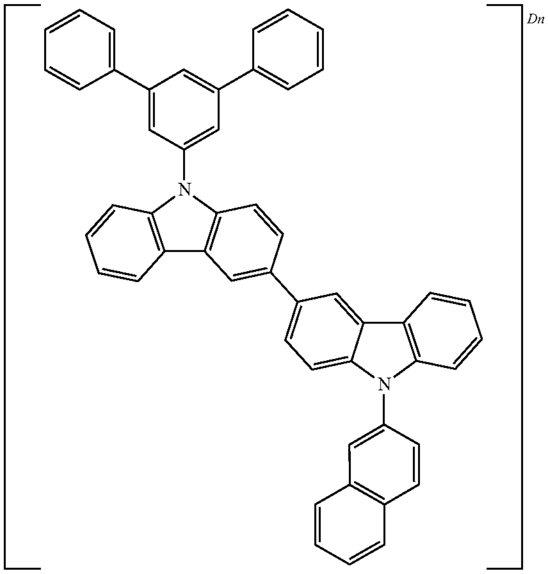
H2-142
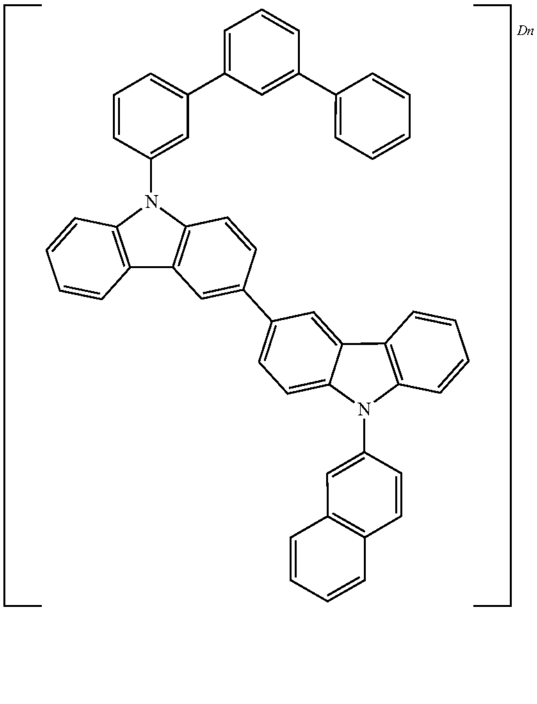

-continued
H2-143
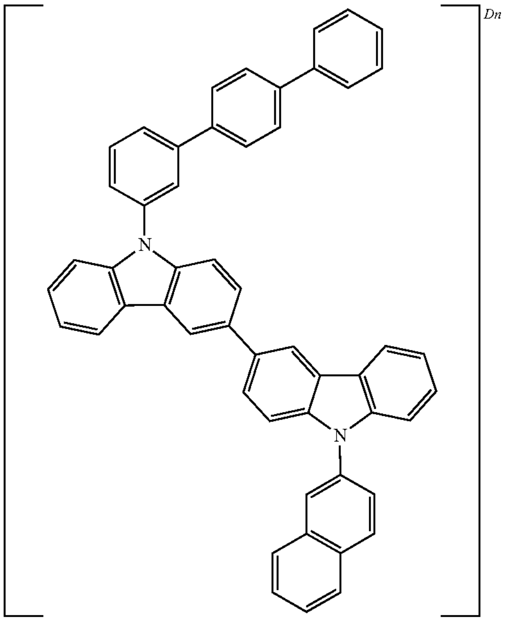
H2-144
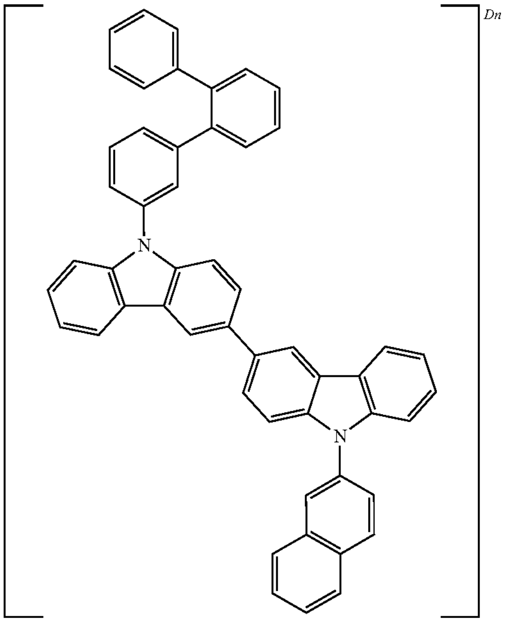
-continued
H2-145
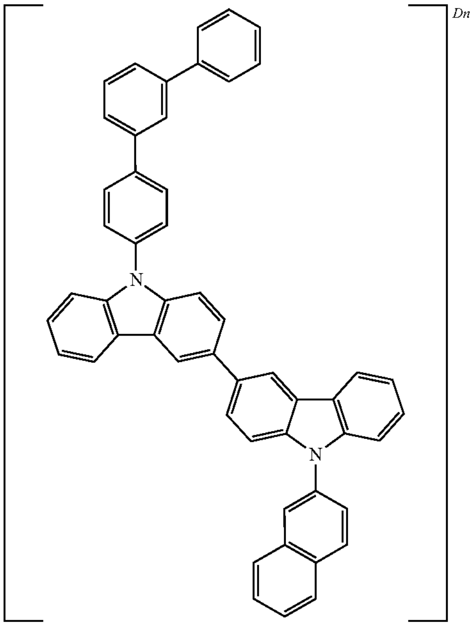
H2-146
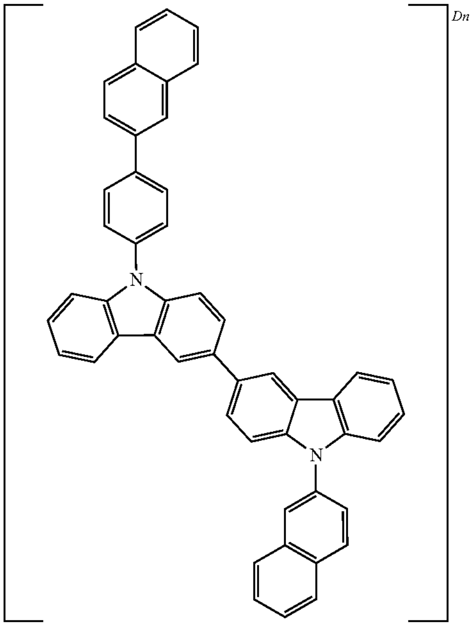

-continued
H2-147
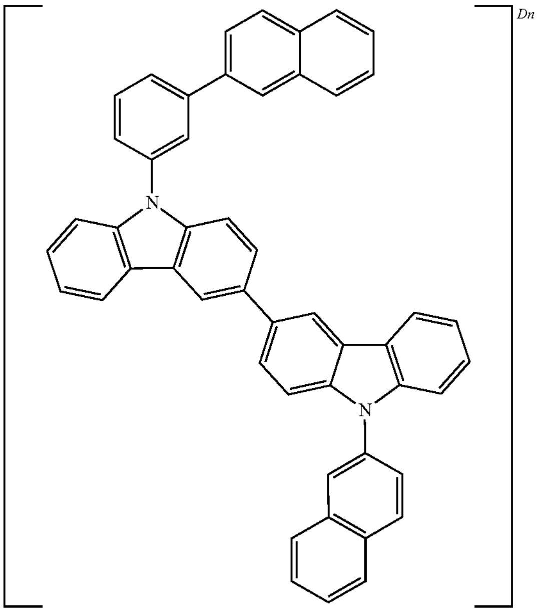
H2-148
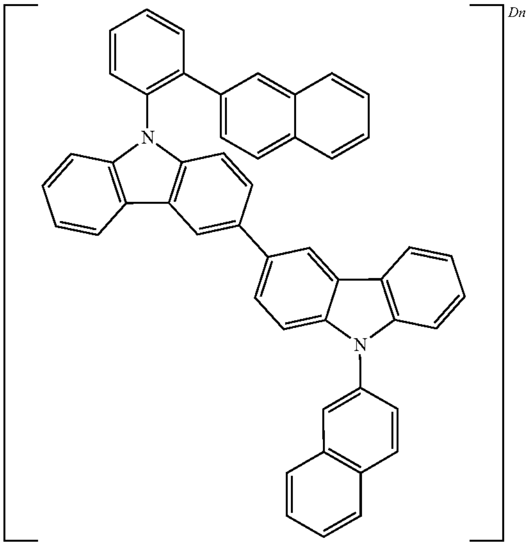
-continued
H2-149
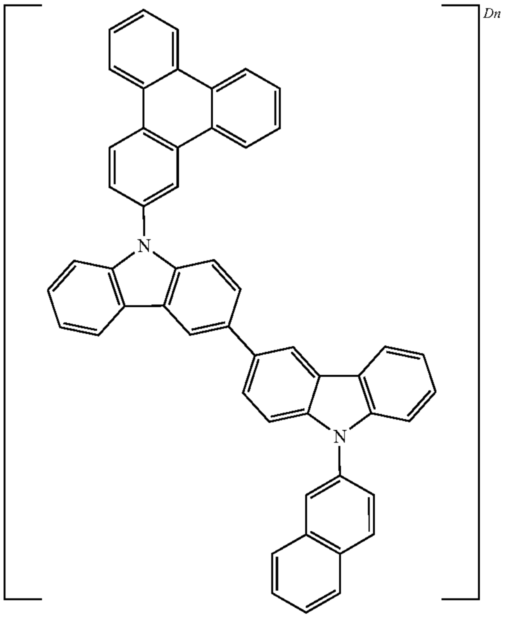
H2-150
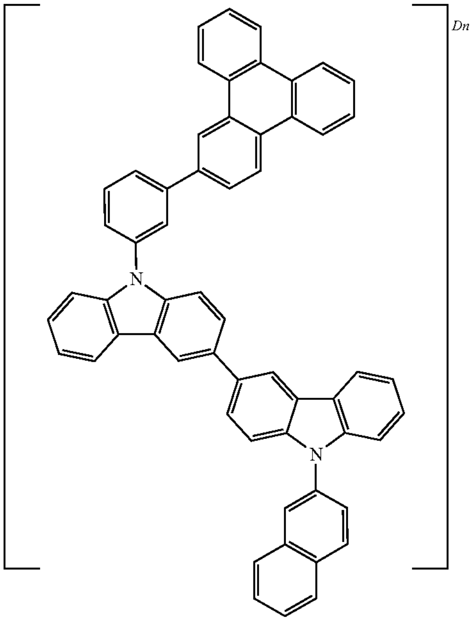

-continued
H2-151
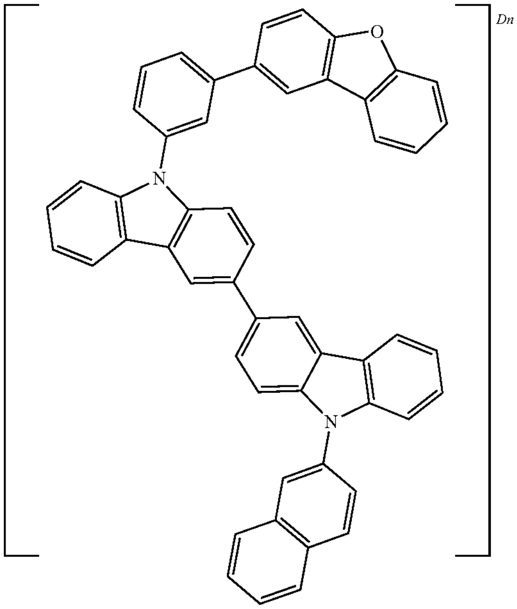
H2-152
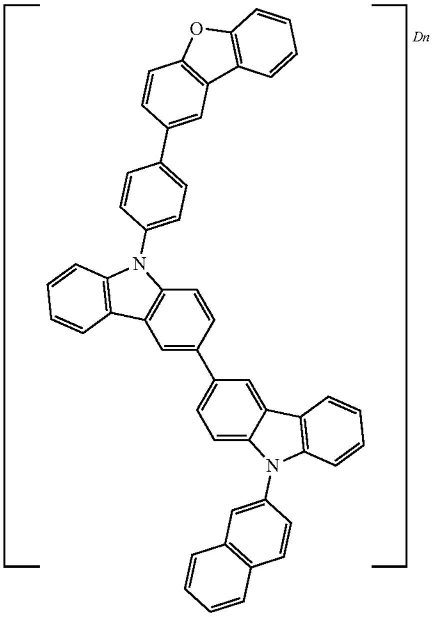
-continued
H2-153
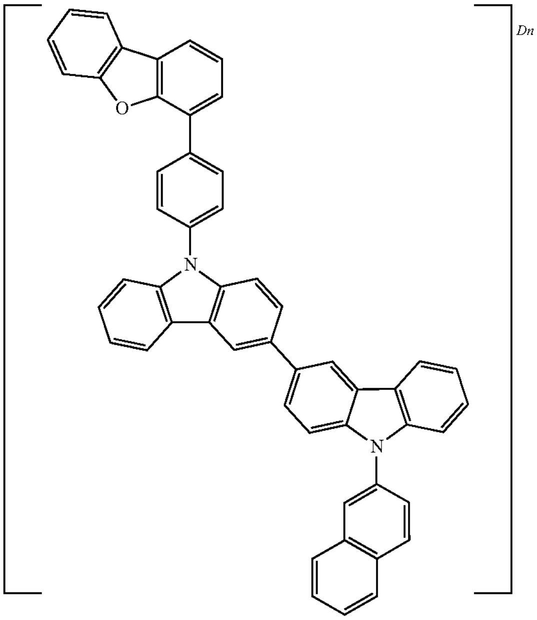
H2-154
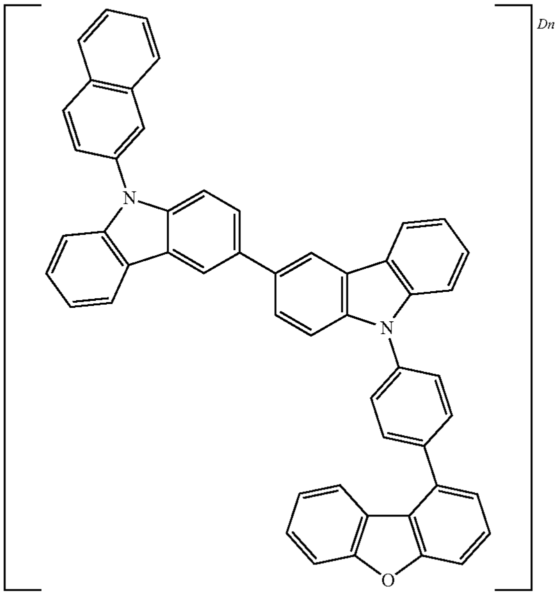

-continued
H2-155
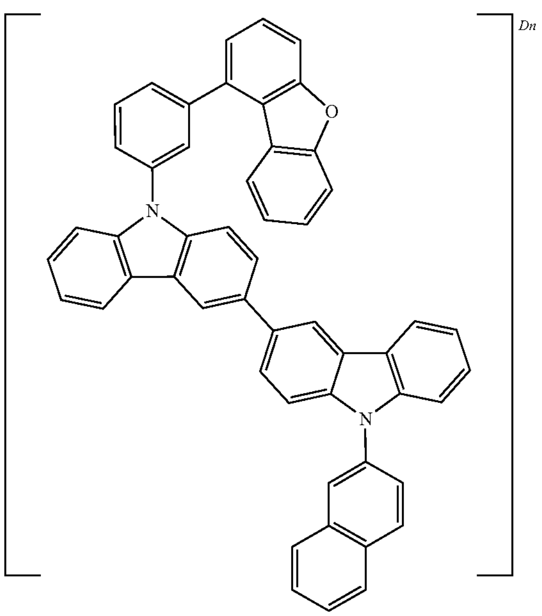
-continued
H2-157
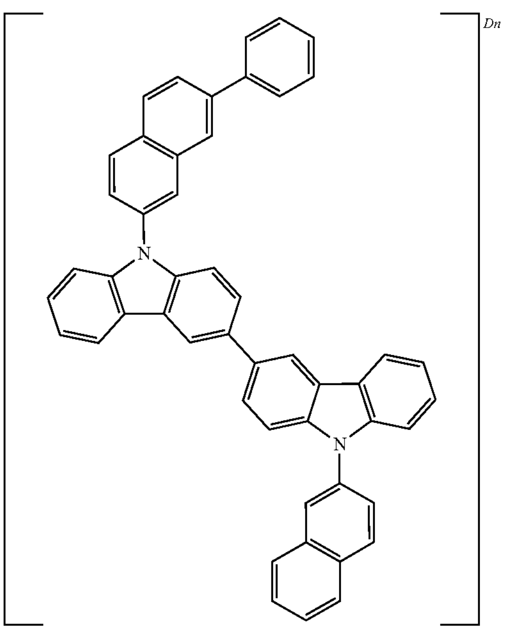
H2-156
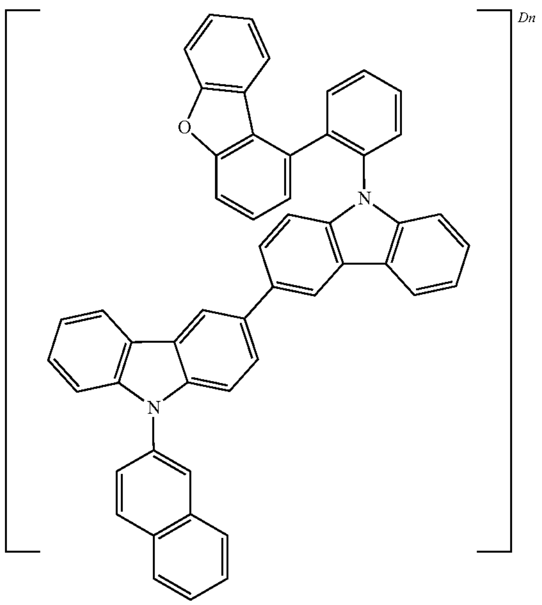
H2-158
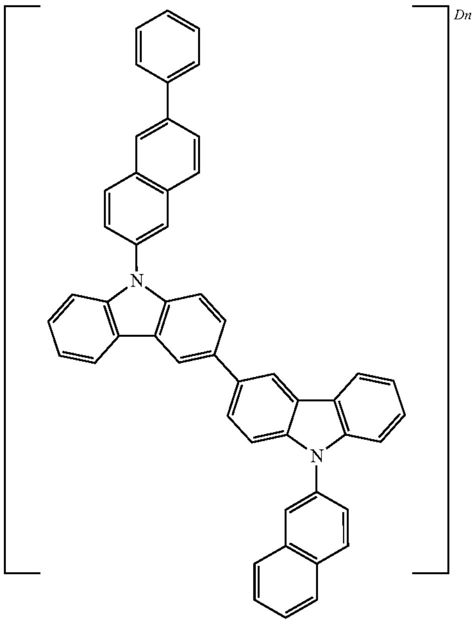

-continued
H2-159
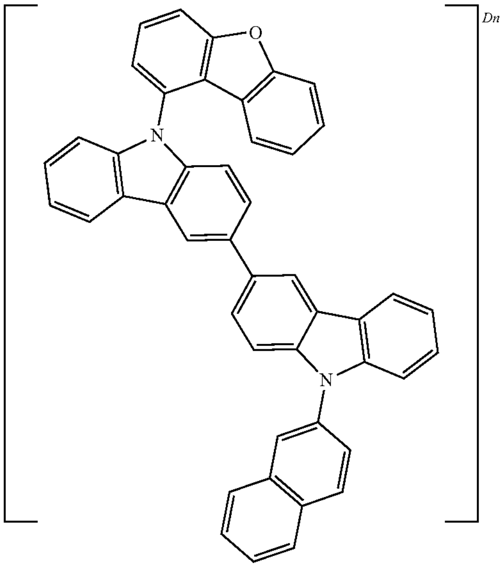
H2-160
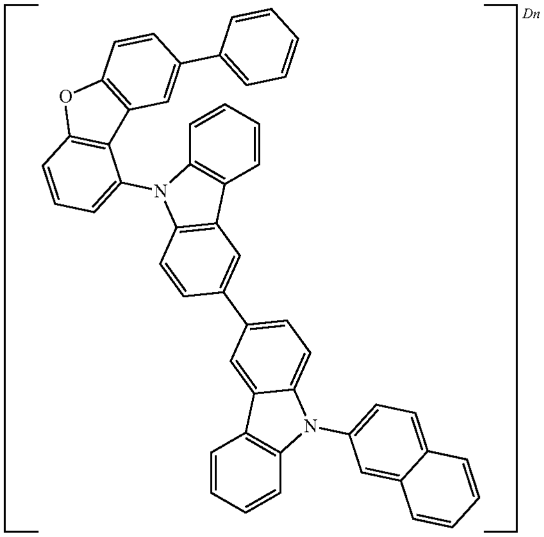
-continued
H2-161
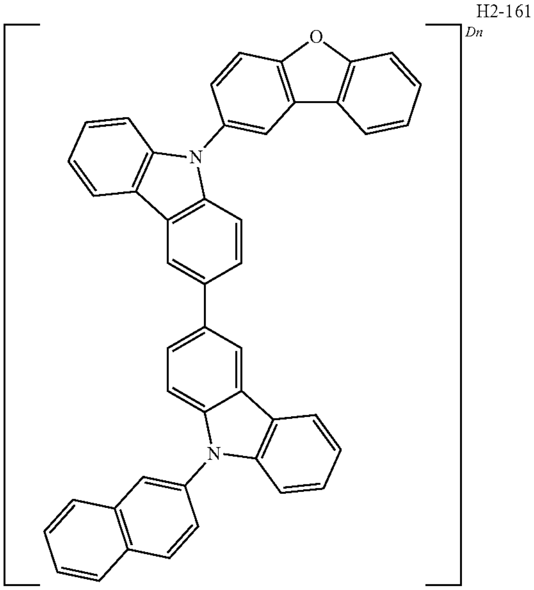
H2-162
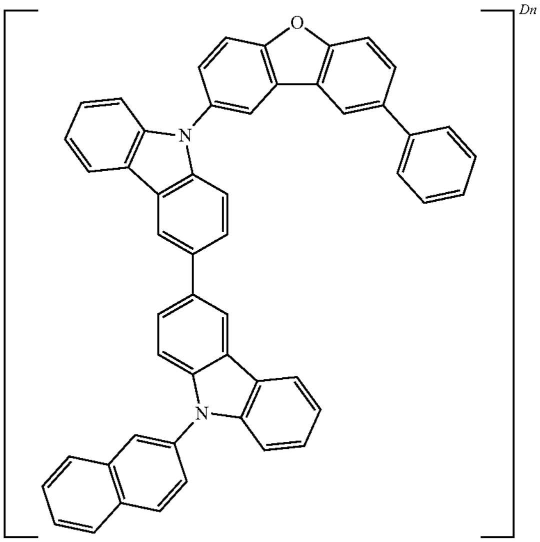

-continued
H2-163
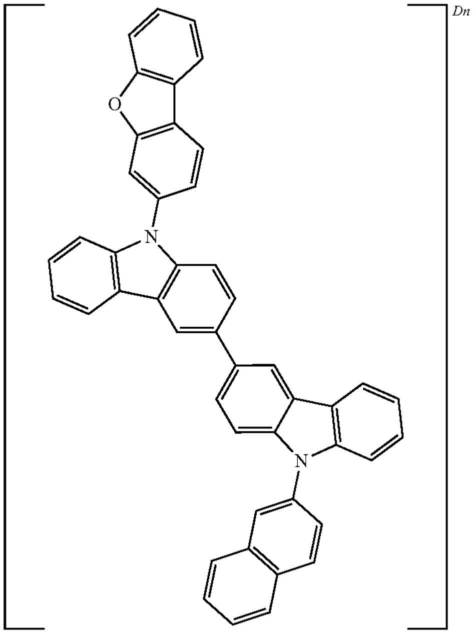
H2-164
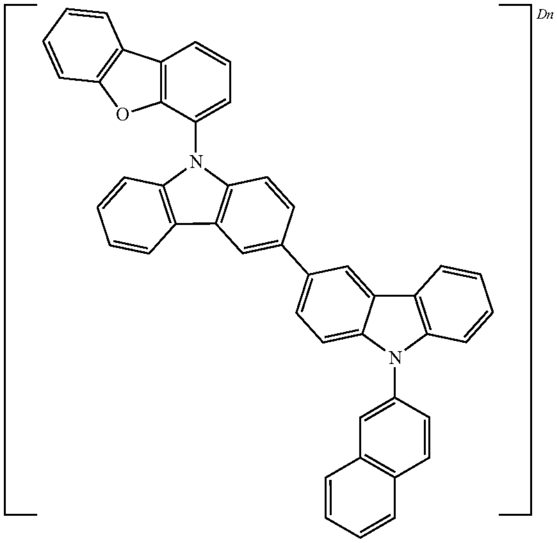
-continued
H2-165
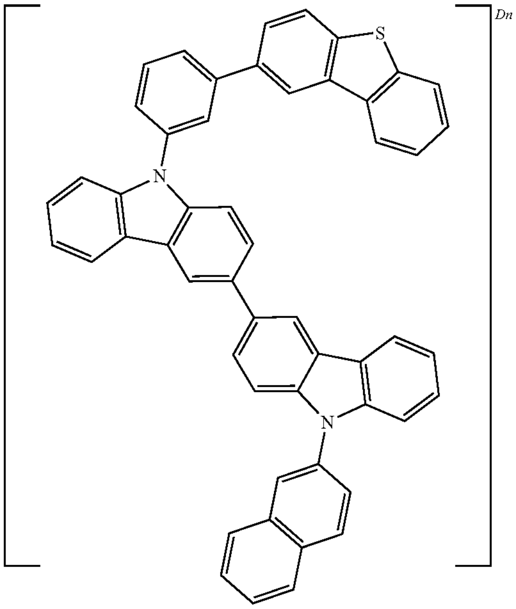
H2-166
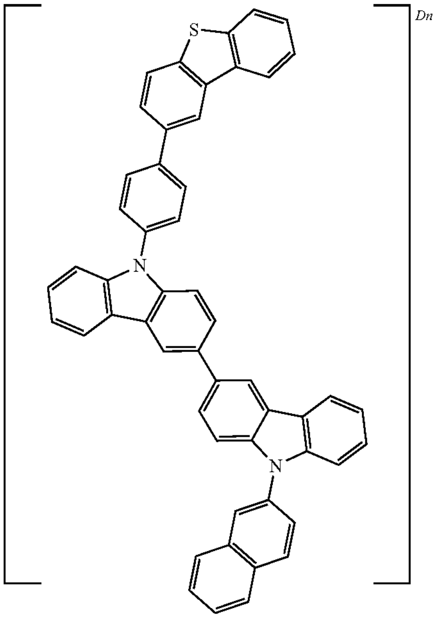

-continued
H2-167
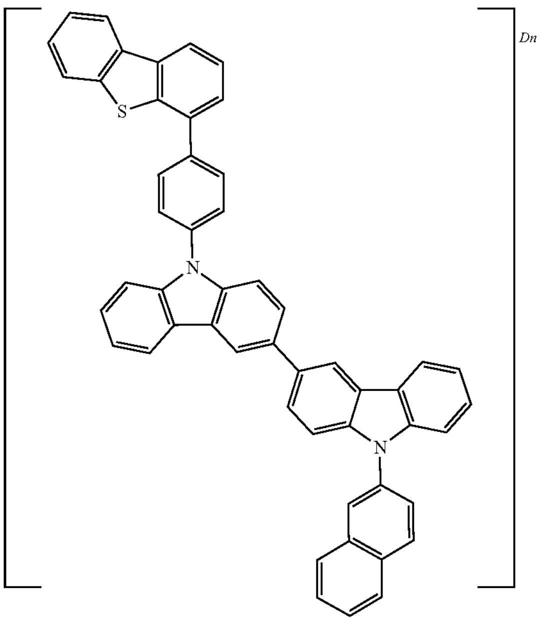
H2-169
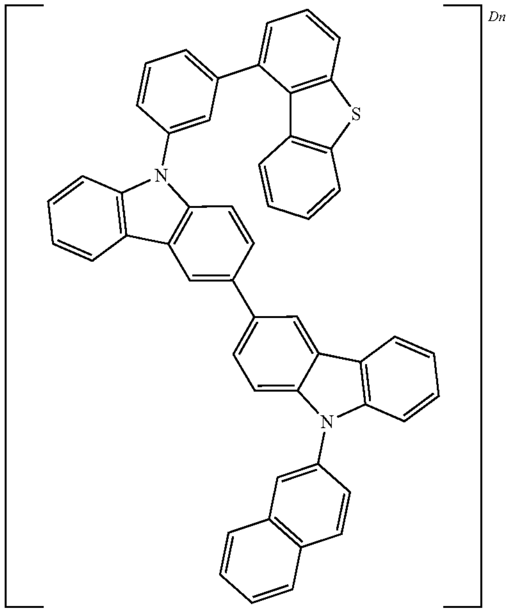
H2-168
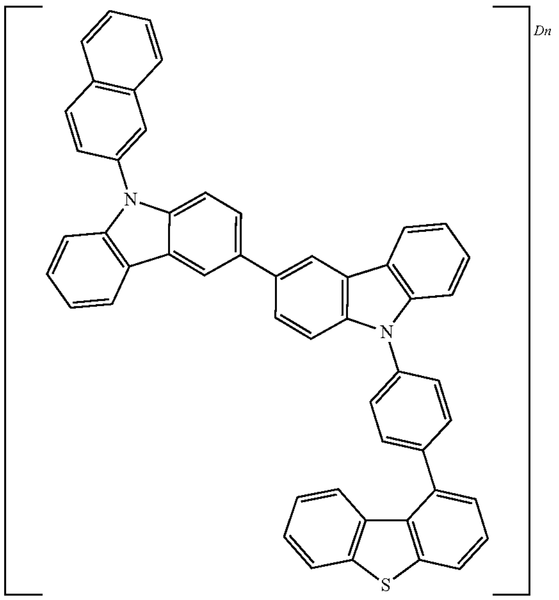
H2-170
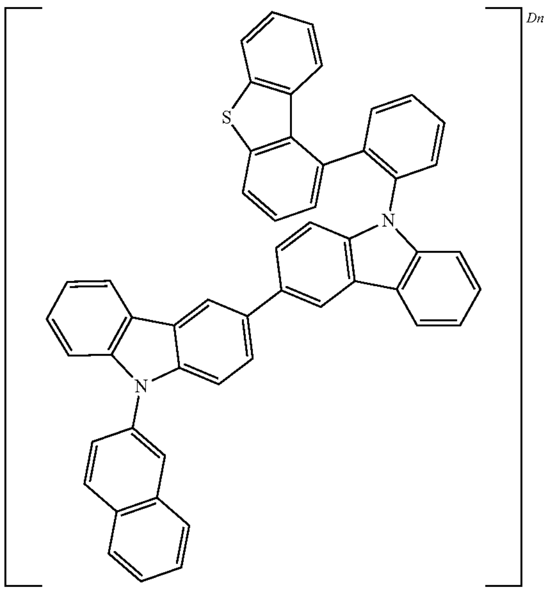

-continued
H2-171
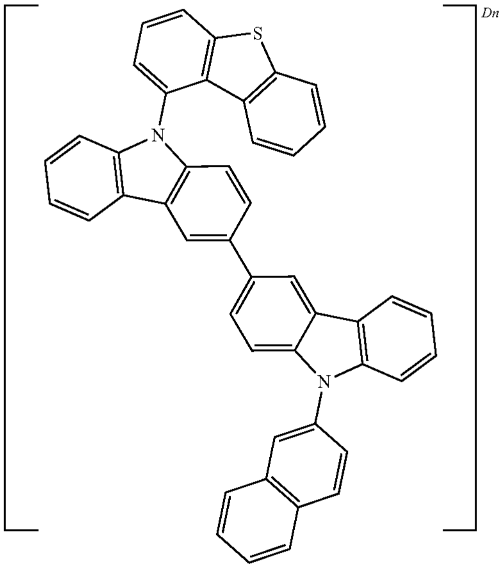
H2-172
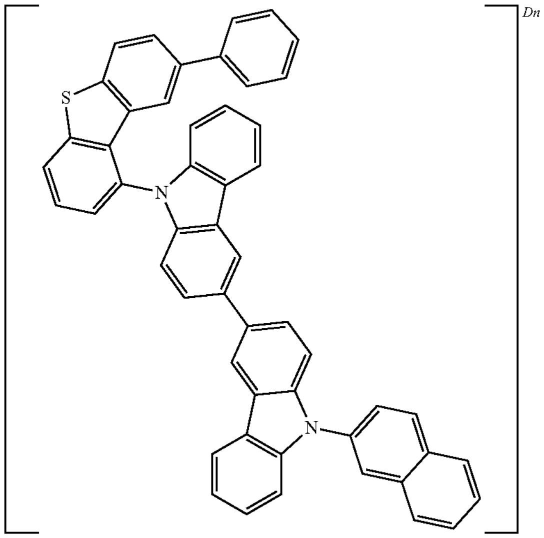
-continued
H2-173
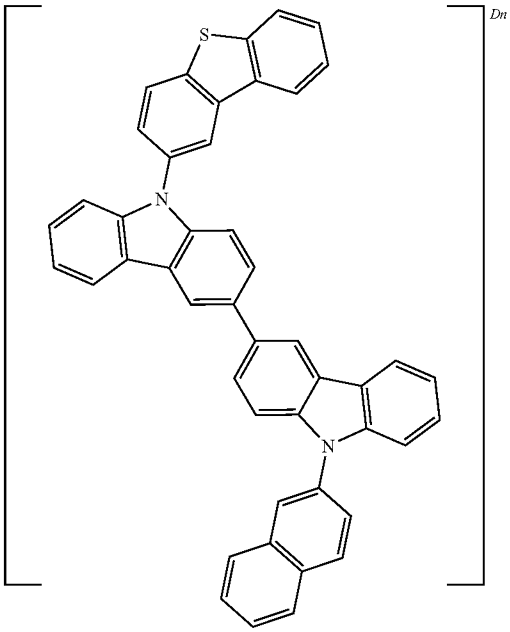
H2-174
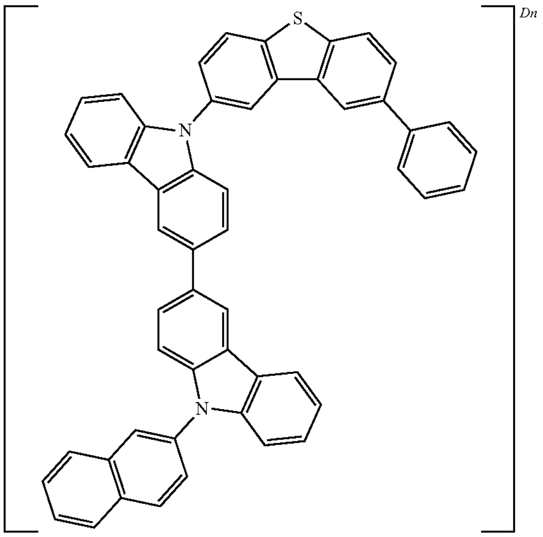

-continued
H2-175
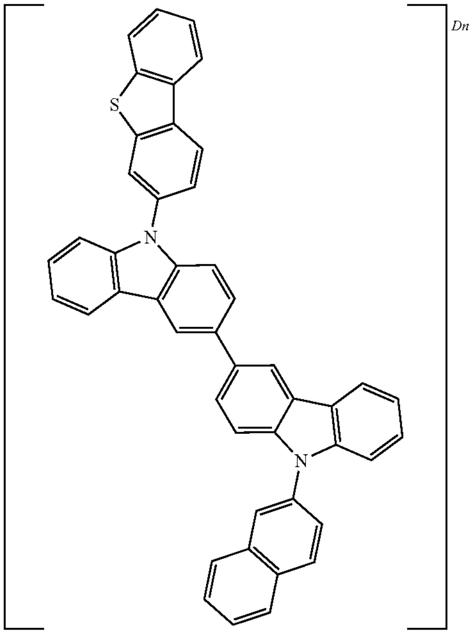
H2-176
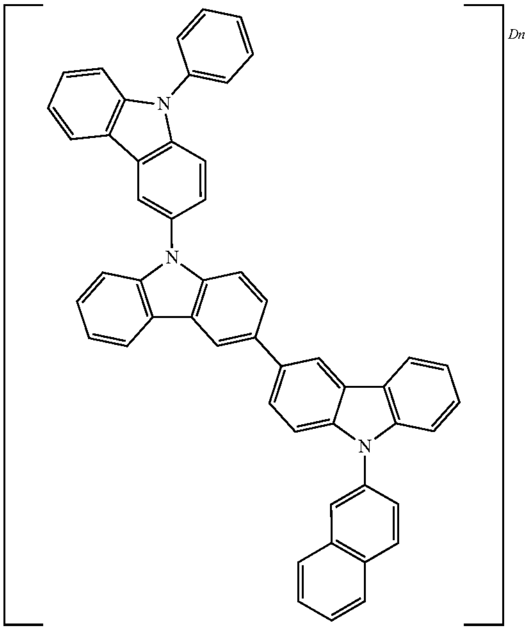
-continued
H2-177
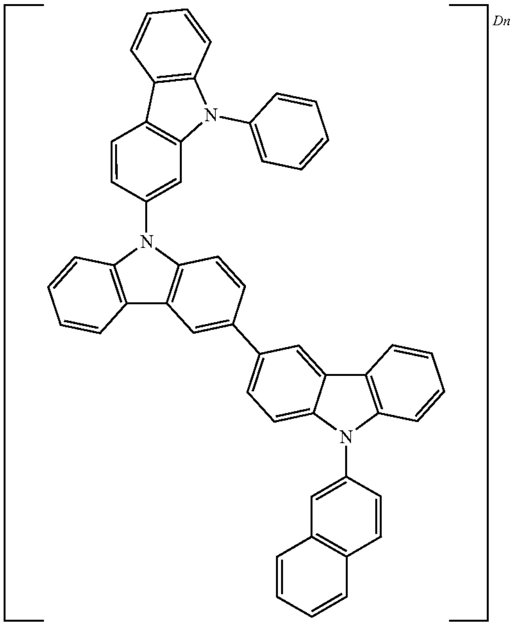
H2-178
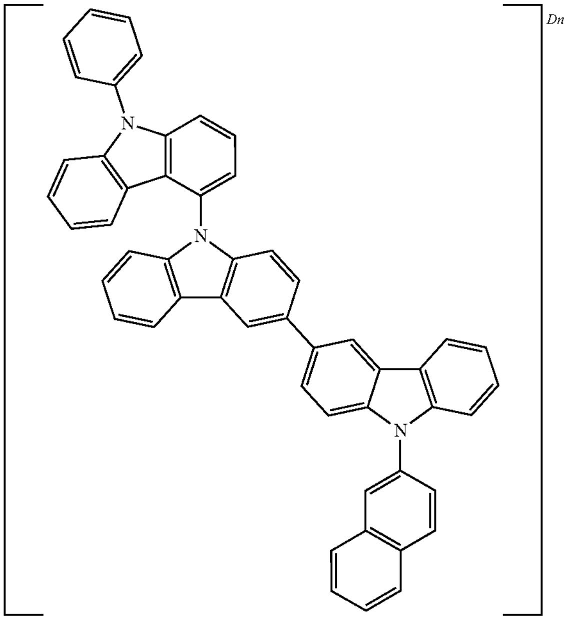

-continued
H2-179
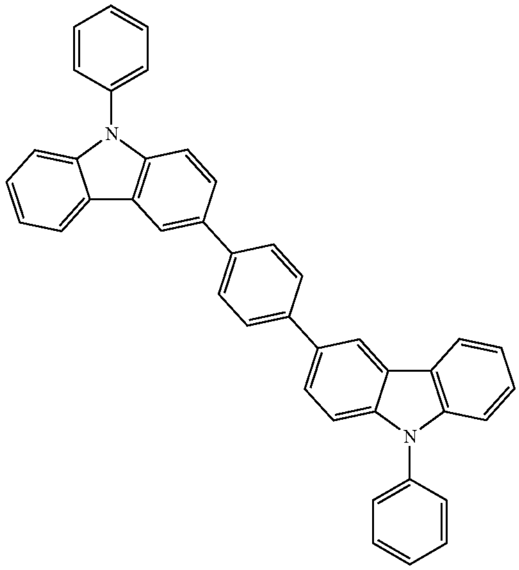
H2-180
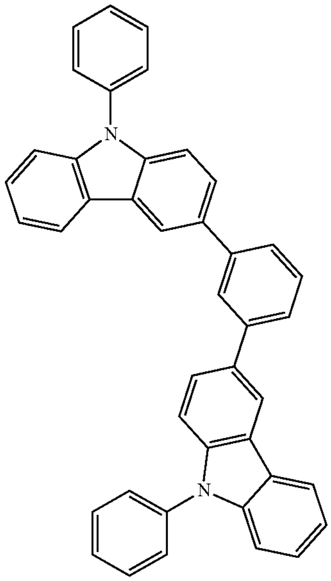
H2-181
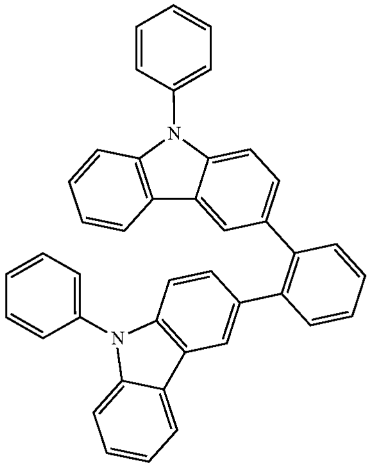
-continued
H2-182
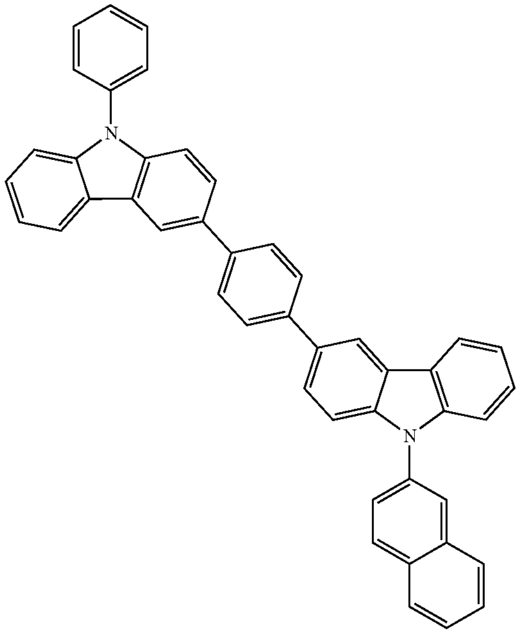
H2-183
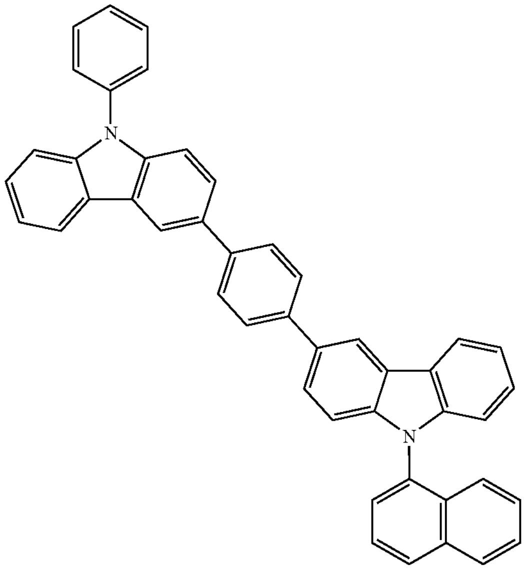

-continued
H2-184
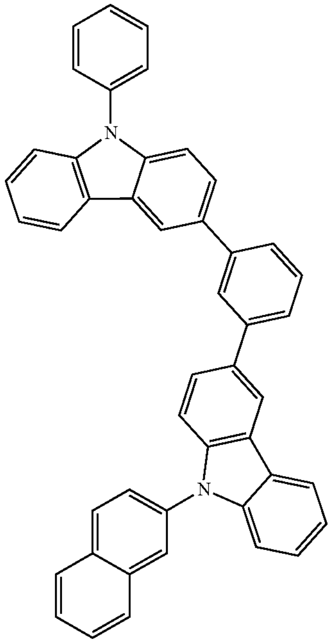
H2-185
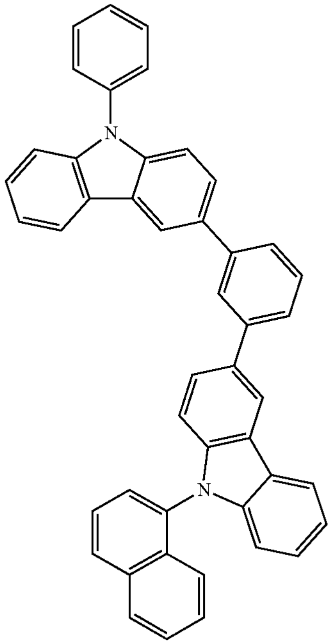
-continued
H2-186
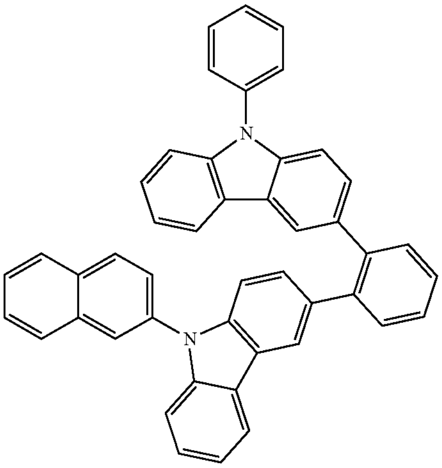
H2-187
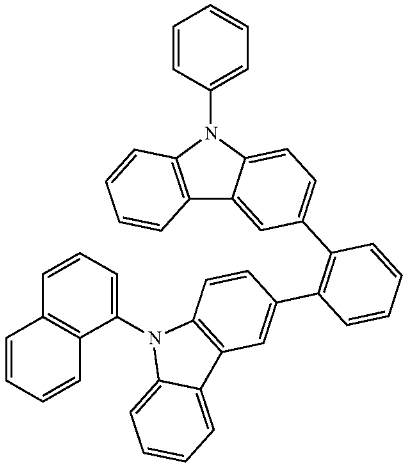
H2-188
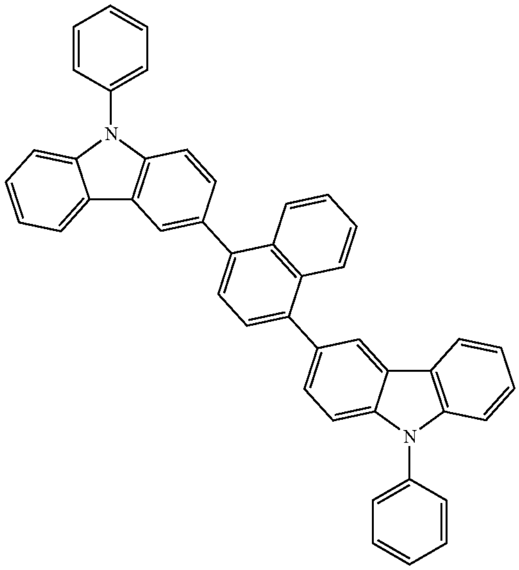

-continued
H2-189
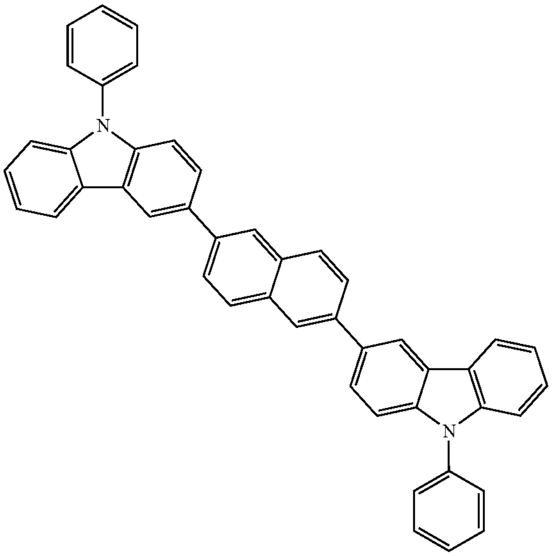
H2-190
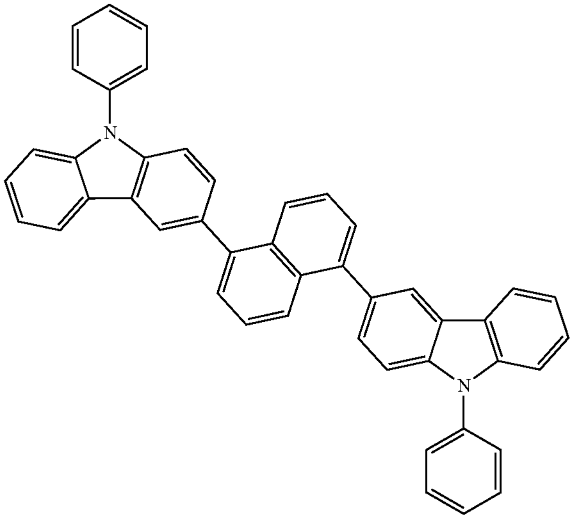
-continued
H2-191
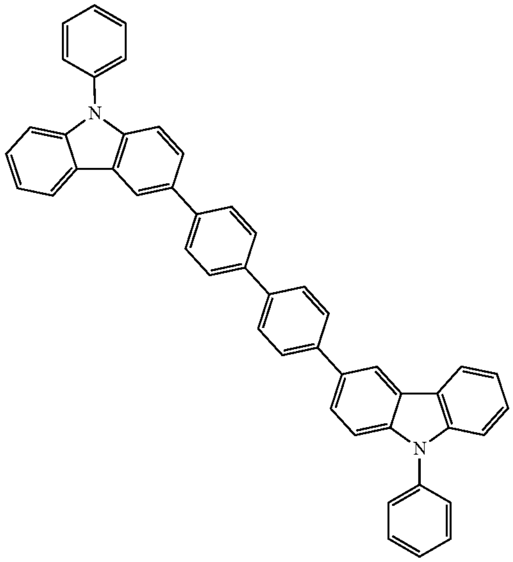
H2-192
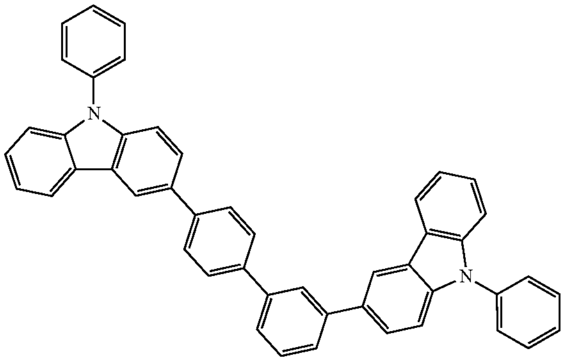
H2-193
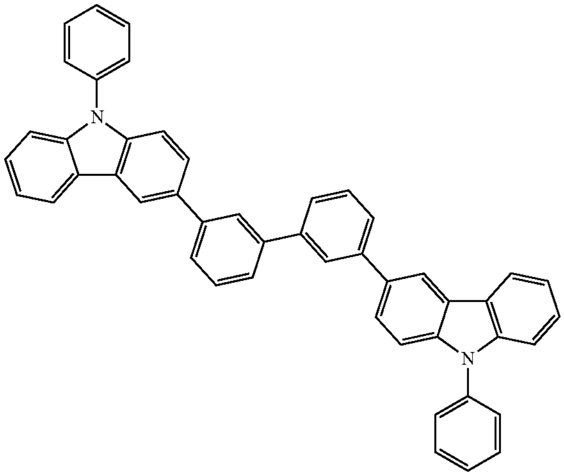

-continued
H2-194
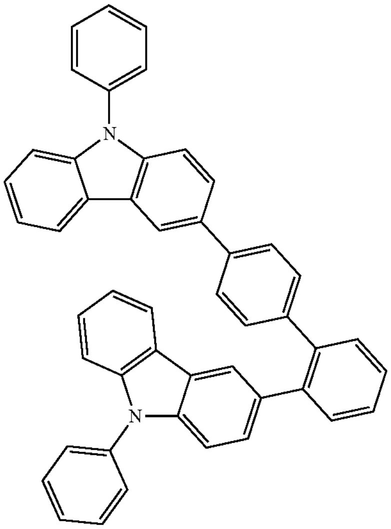
H2-195
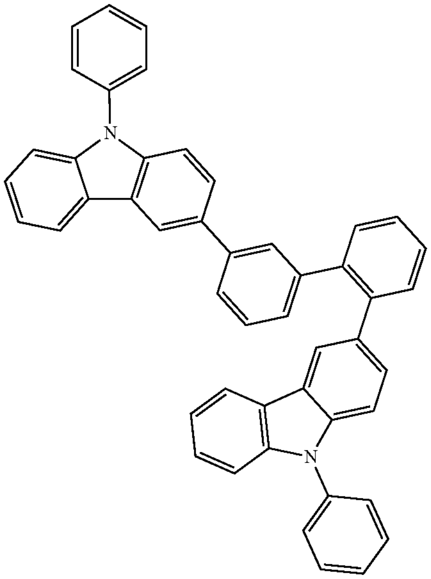
-continued
H2-196
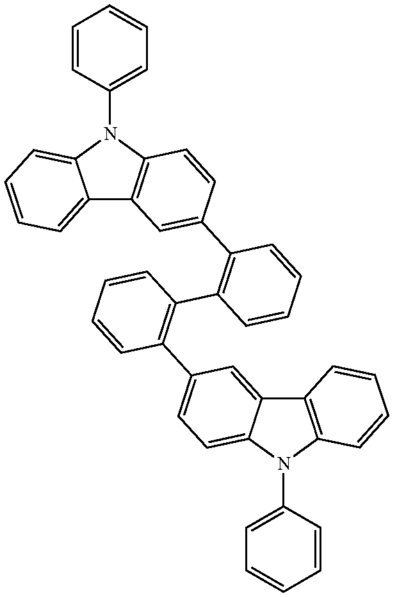
H2-197
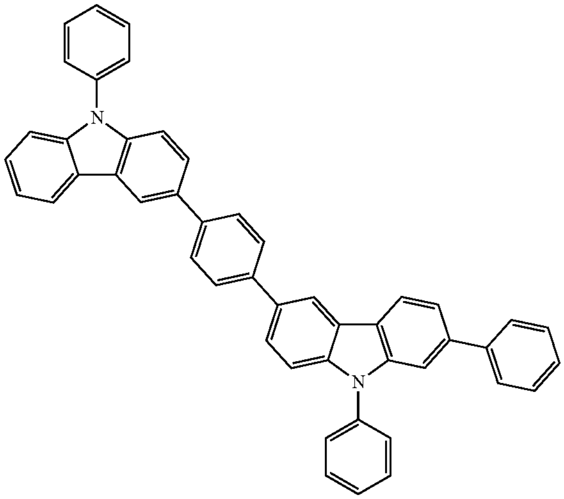

-continued
H2-198
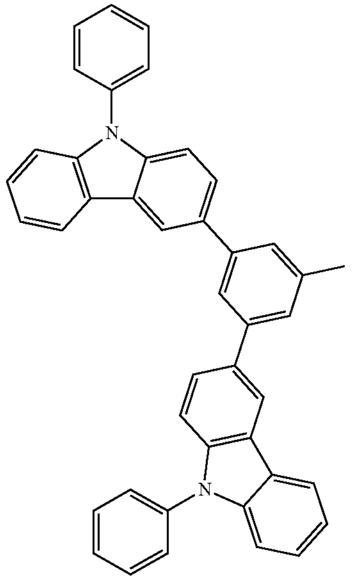
H2-199
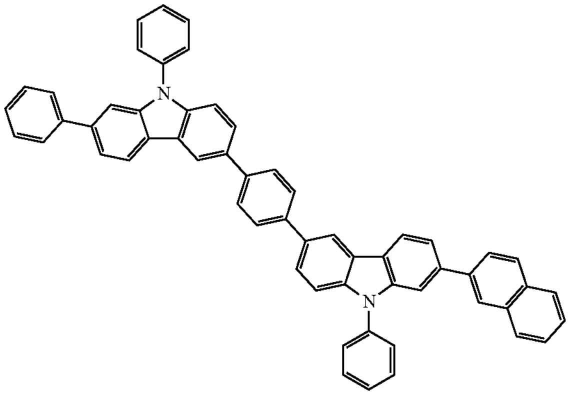
H2-200
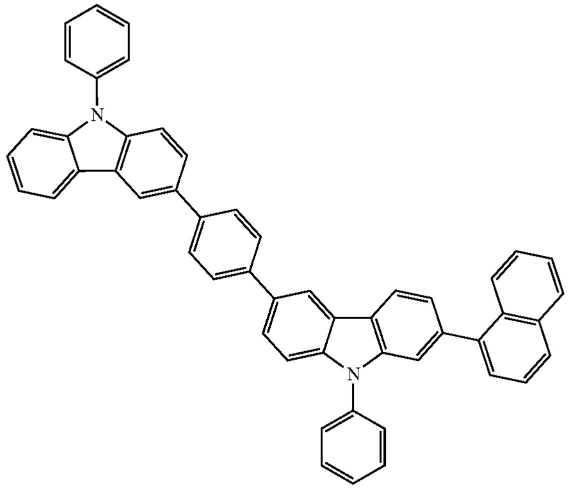
-continued
H2-201
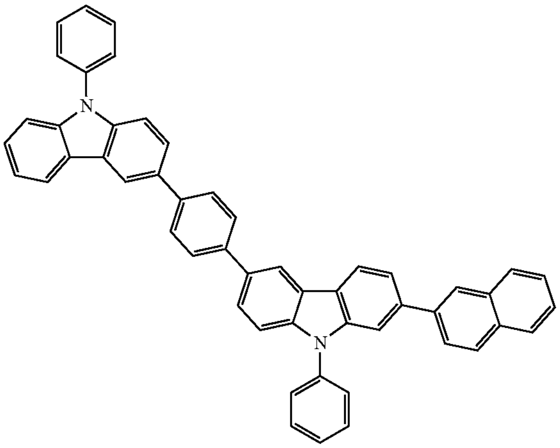
H2-202
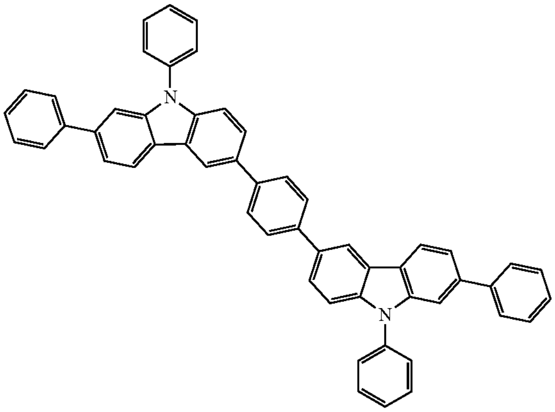
H2-203
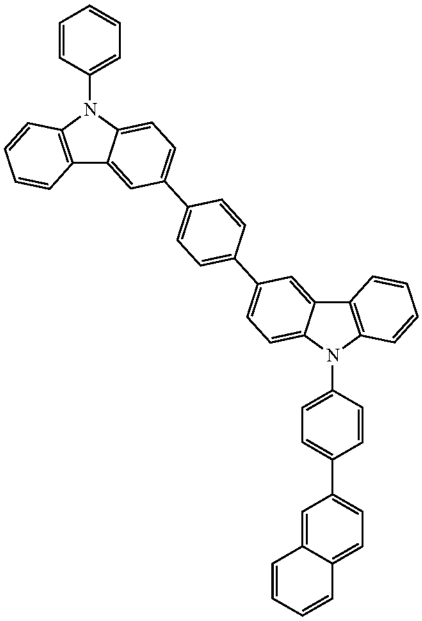

-continued
H2-204
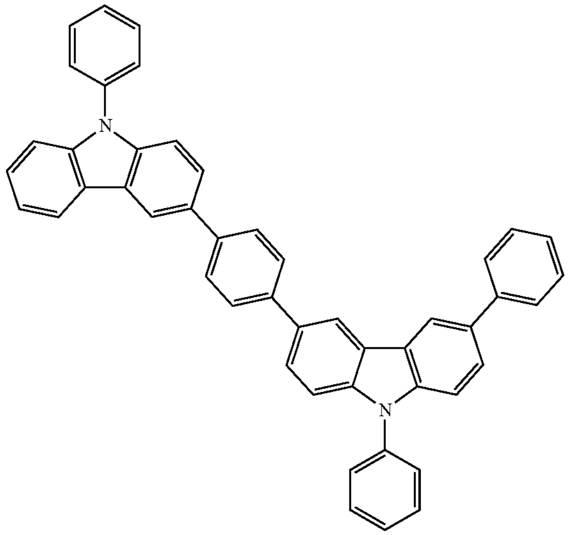
H2-205
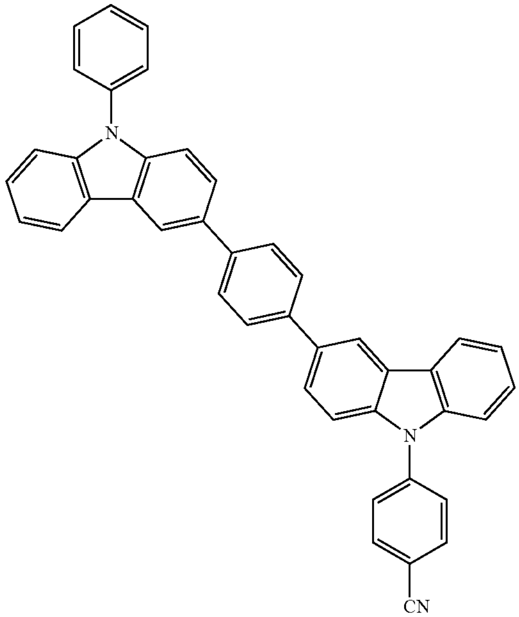
-continued
H2-206
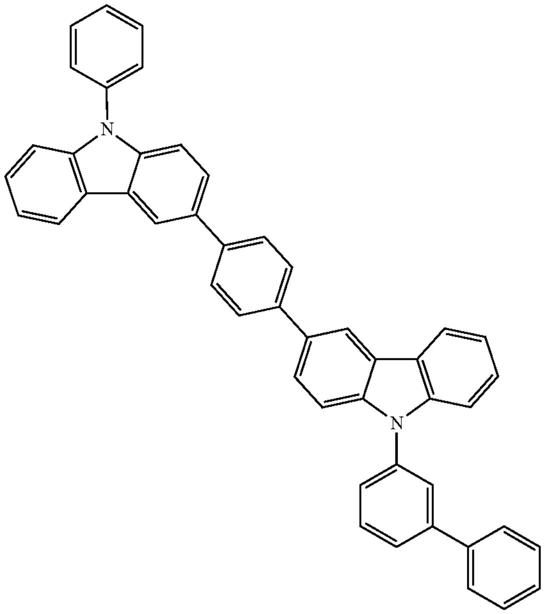
H2-207
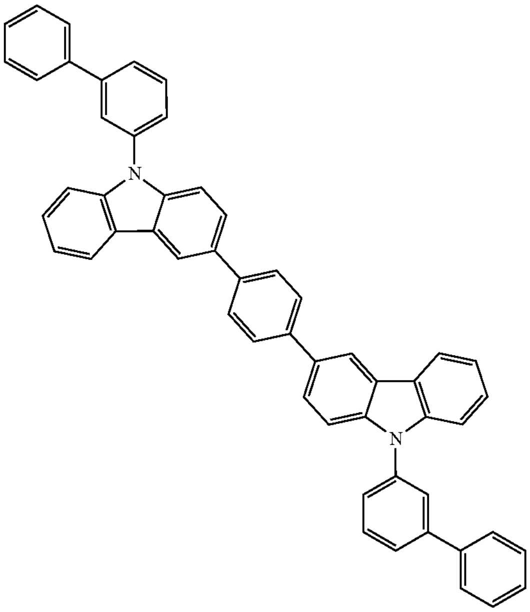

-continued
H2-208
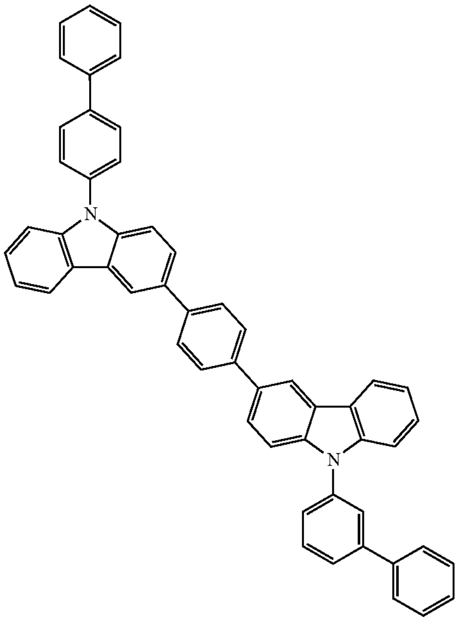
H2-209
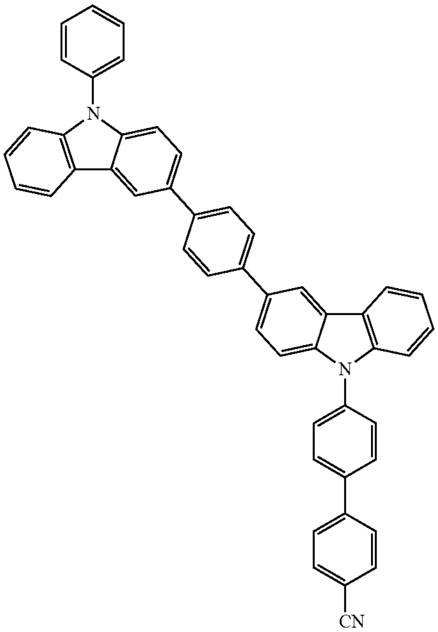
-continued
H2-210
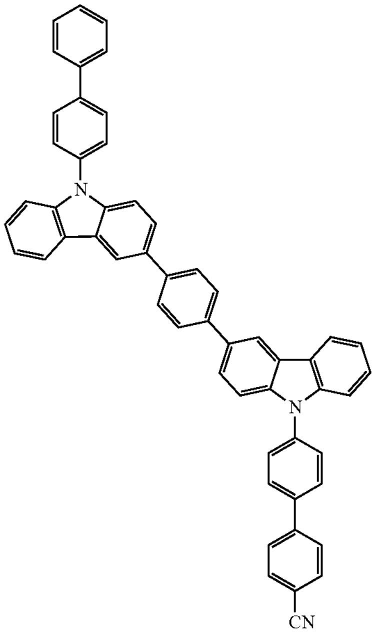
H2-211
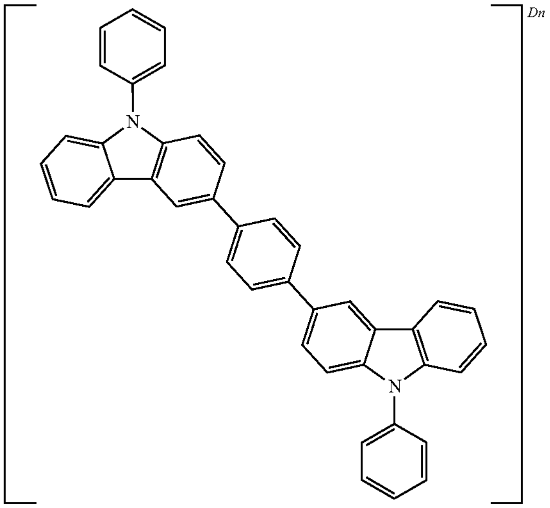

-continued
H2-212
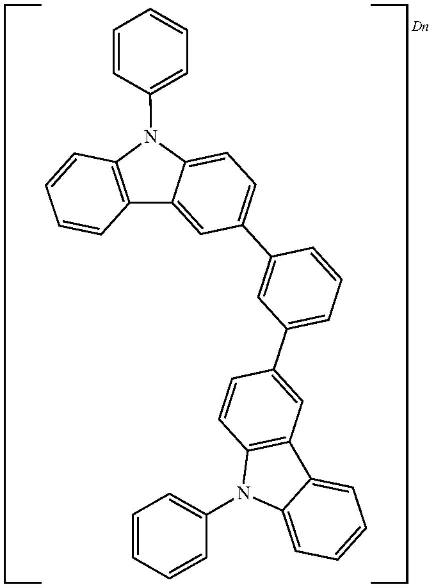
H2-213
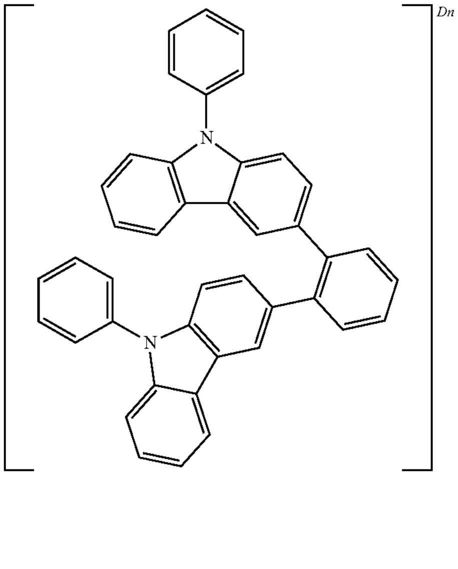
-continued
H2-214
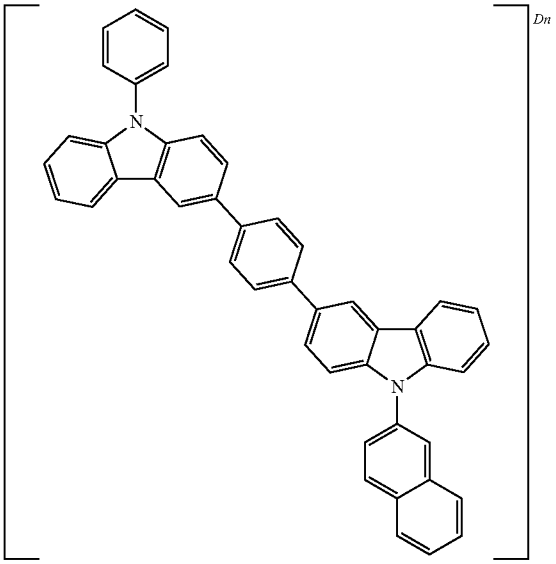
H2-215
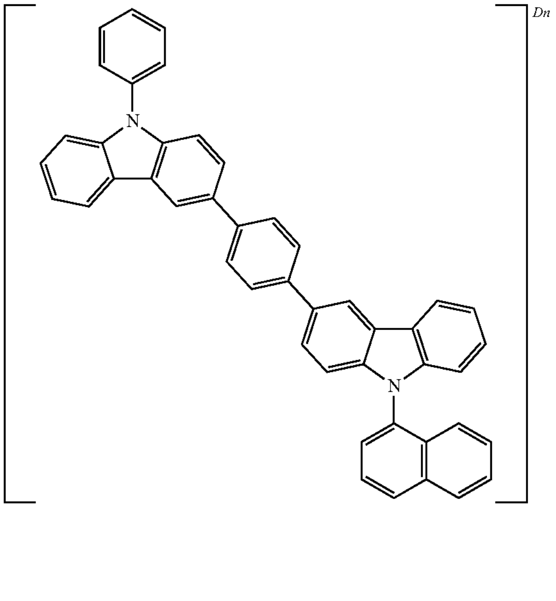

-continued
H2-216
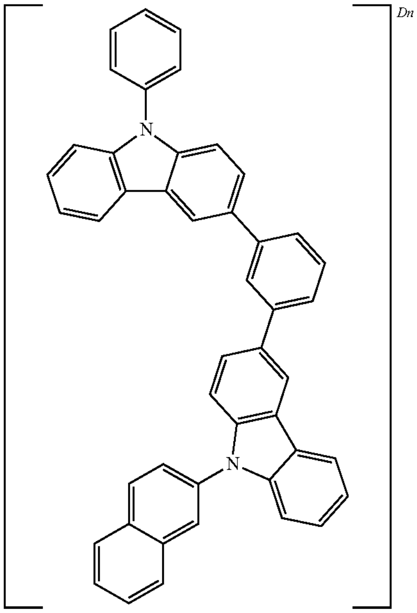
H2-217
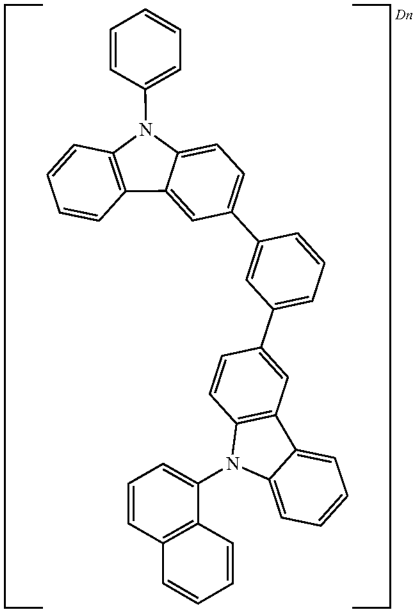
-continued
H2-218
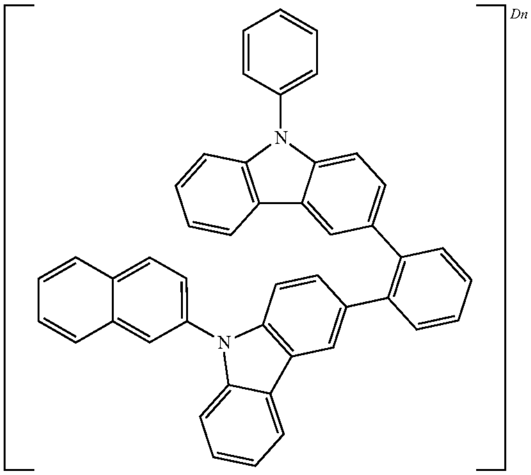
H2-219
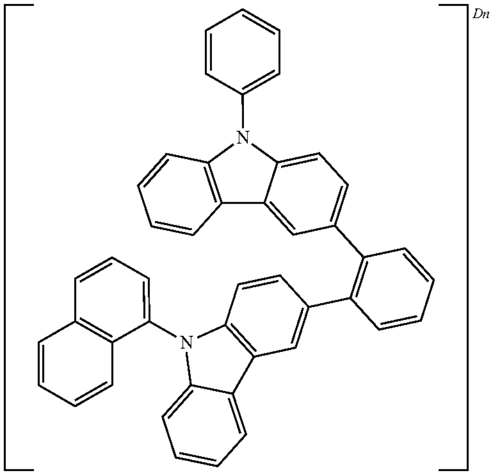
H2-220
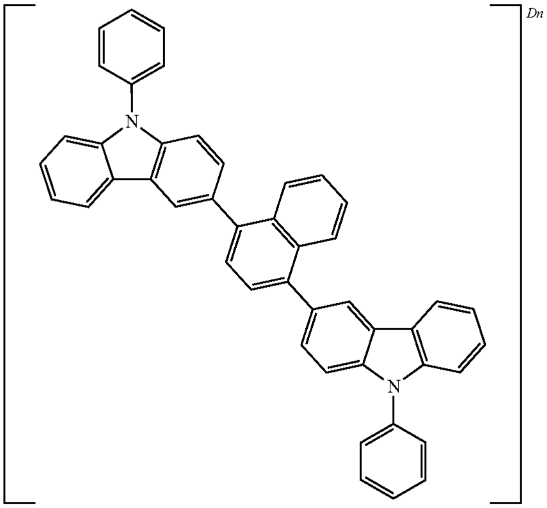

-continued
H2-221
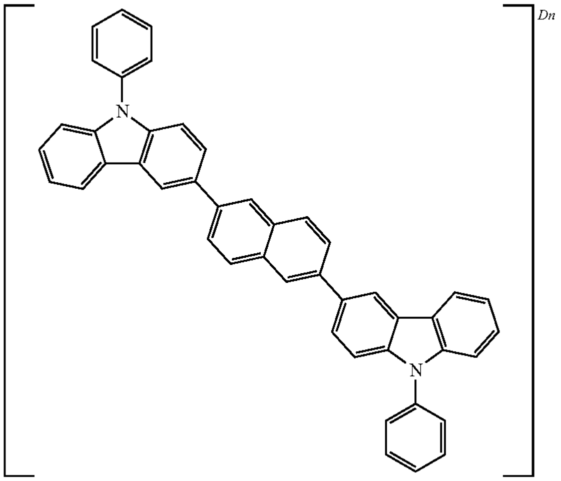
H2-222
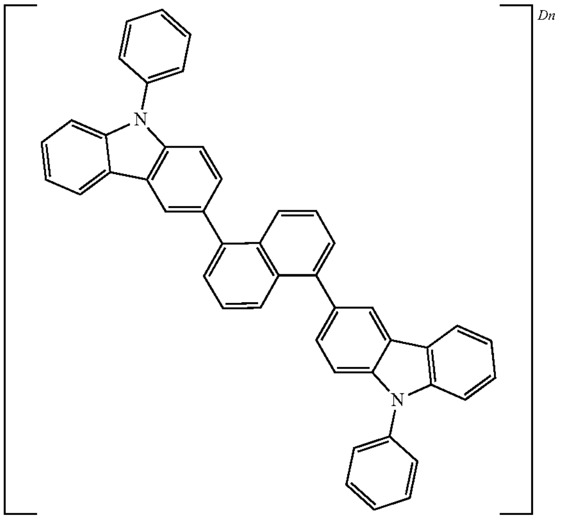
H2-223
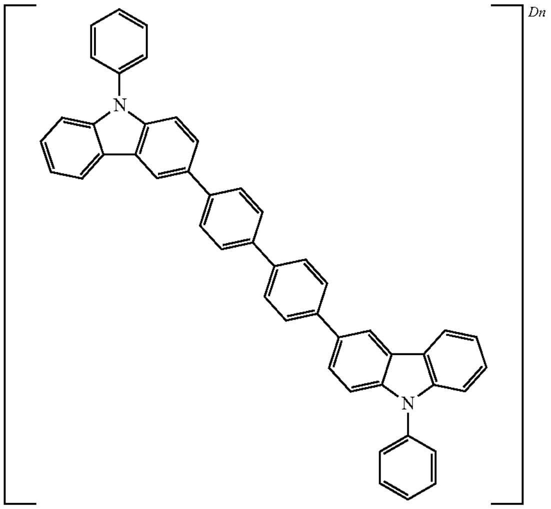
-continued
H2-224
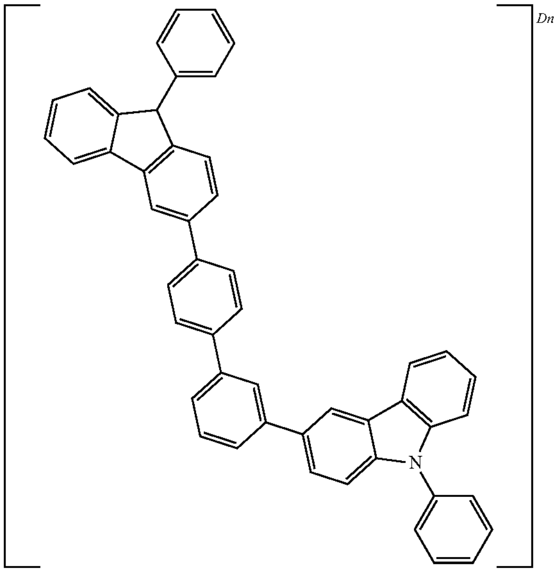
H2-225
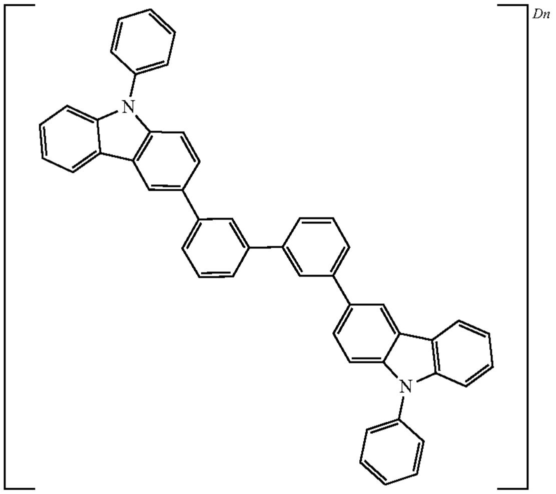
H2-226
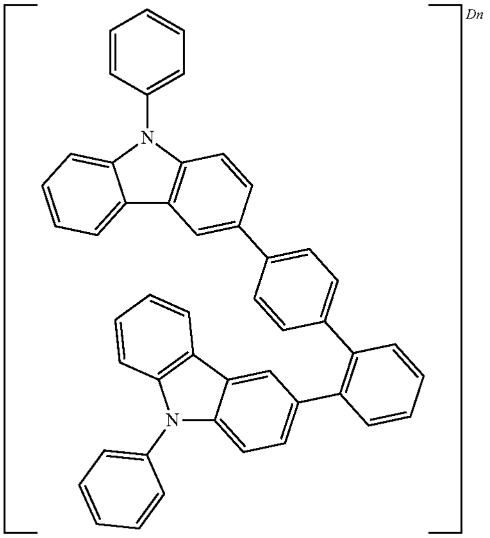

-continued

H2-227

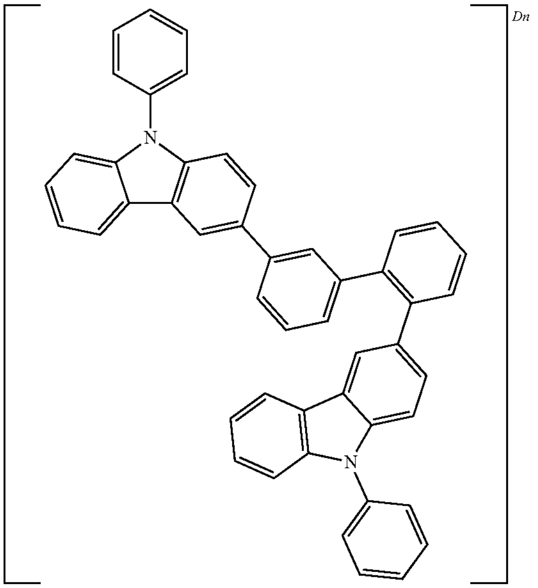

H2-228

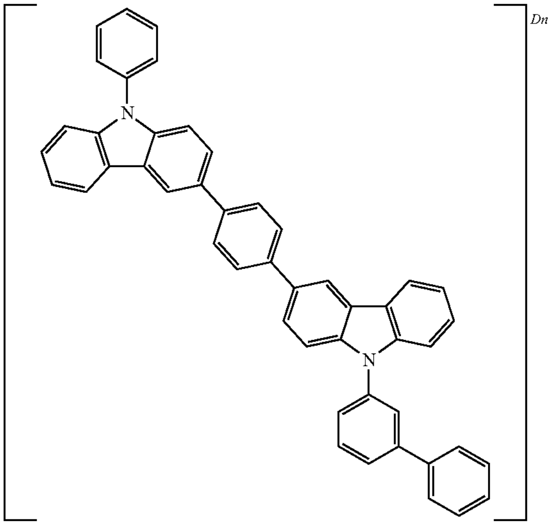

-continued

H2-229

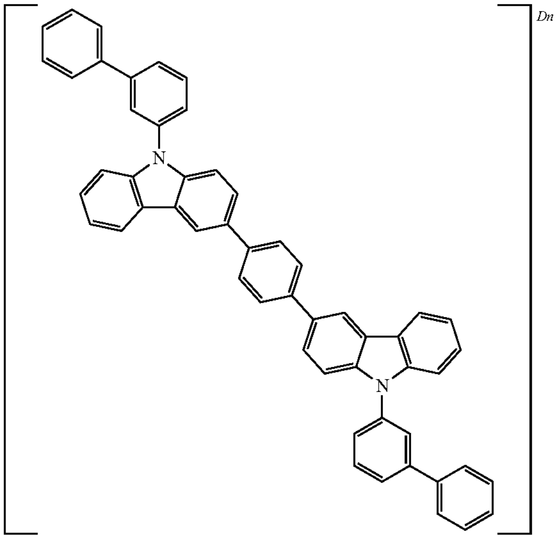

H2-230

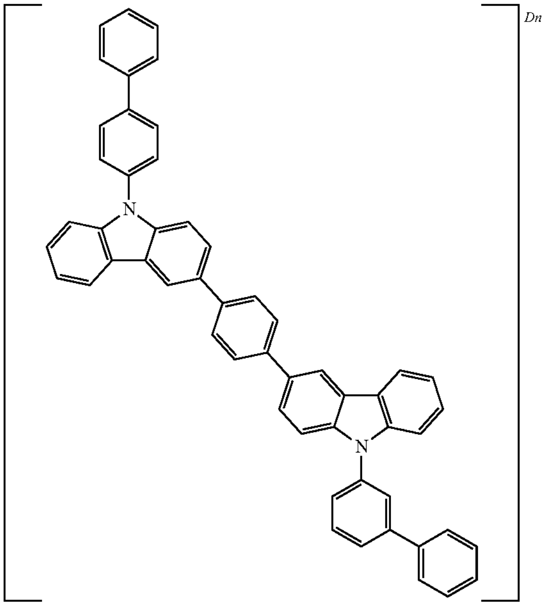

In the compounds above, Dn means that n number of hydrogens is replaced with deuterium, wherein the upper limit of n is determined according to the number of hydrogens that may be substituted for each compound. For example, n may be an integer of 1 to 50. According to one embodiment, n may be an integer of 4 or more, preferably an integer of 6 or more, more preferably an integer of 8 or more, even more preferably an integer of 10 or more, and more preferably an integer of 14 or more. When deuterated with a number equal to or higher than the lower limit, the bond dissociation energy according to deuteration increases, thereby increasing the stability of the compound. When such a compound is used in an organic electroluminescent device, improved lifespan property may be exhibited.

The compound represented by formula 2 according to one embodiment can be prepared by a synthetic method known to one skilled in the art. In addition, the deuteriumated compound of formula 2 can be prepared using a deuteriumized precursor material in a similar manner, or more generally can be prepared by treating a non-deuteriumized compound with a deuteriumized solvent, D6-benzene in the presence of a Lewis acid H/D exchange catalyst such as aluminum trichloride or ethyl aluminum chloride. In addition, the degree of deuteriumization can be controlled by varying reaction conditions such as reaction temperature. For example, the number of deuterium in formula 2 can be adjusted by controlling the reaction temperature and time, the equivalent of acid, etc.

According to another embodiment of the present disclosure, the present disclosure provides an organic electroluminescent compound represented by the following formula 1A.

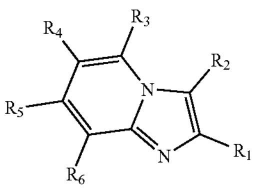

(1A)

in formula 1A, $R_1$ to $R_6$ each independently represent hydrogen, deuterium, halogen, cyano, a substituted or unsubstituted (C1-C30)alkyl, a substituted or unsubstituted (C3-C30)cycloalkyl, a substituted or unsubstituted (C3-C30)cycloalkenyl, a substituted or unsubstituted (3- to 7-membered)heterocycloalkyl, a substituted or unsubstituted (C6-C30)aryl, a substituted or unsubstituted (3- to 30-membered)heteroaryl, $-SiR'_1R'_2R'_3$, or $-NR'_4R'_5$; or may be linked to the adjacent substituents to form a ring(s);

provided that at least one of $R_1$ to $R_6$ is (are) $-(L_1)_n$-HAr;

$L_1$ represents a substituted or unsubstituted (C6-C30) arylene or a substituted or unsubstituted (10- to 30-membered)heteroarylene;

HAr represents a substituted or unsubstituted nitrogen-containing (3- to 30-membered)heteroaryl;

n represents an integer of 1 to 3, when n is 1, $L_1$ represents a substituted or unsubstituted (10- to 30-membered)heteroarylene or a substituted or unsubstituted fluorenylene, and when n is an integer of 2 or more, at least one of $L_1$ is (are) a substituted or unsubstituted (10- to 30-membered) heteroarylene or a substituted or unsubstituted fluorenylene; and $R'_1$ to $R'_5$ each independently represent a substituted or unsubstituted (C1-C30)alkyl, a substituted or unsubstituted (C2-C30)alkenyl, a substituted or unsubstituted (C6-C30) aryl, or a substituted or unsubstituted (3- to 30-membered) heteroaryl.

In one embodiment, $L_1$ may be a substituted or unsubstituted (C6-C25)arylene or a substituted or unsubstituted (10- to 30-membered)heteroarylene, preferably (C6-C25)arylene unsubstituted or substituted by (C1-C10)alkyl or (C6-C30) aryl or (10- to 30-membered)heteroarylene unsubstituted or substituted by (C6-C30)aryl. For example, when n is 1, $L_1$ may be a substituted or unsubstituted dibenzofuranylene, a substituted or unsubstituted dibenzothiophenylene, a substituted or unsubstituted carbazolylene, a substituted or unsubstituted fluorenylene, or a substituted or unsubstituted spirobifluorenylene, and when n is an integer of 2 or more, at least one of $L_1$ may be a substituted or unsubstituted dibenzofuranylene, a substituted or unsubstituted dibenzothiophenylene, a substituted or unsubstituted carbazolylene, a substituted or unsubstituted fluorenylene, or a substituted or unsubstituted spirobifluorenylene.

According to one embodiment, the organic electroluminescent compound represented by formula 1A may be more specifically illustrated by the following compounds, but is not limited thereto.

C-116

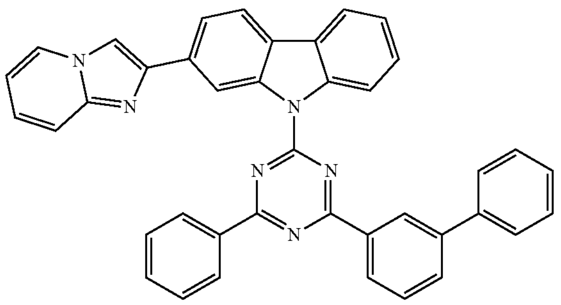

C-117

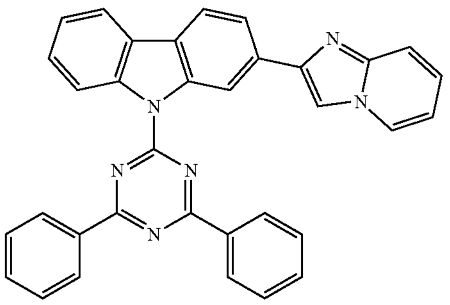

C-118

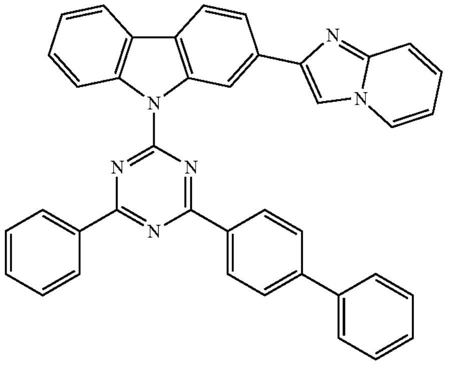

C-119

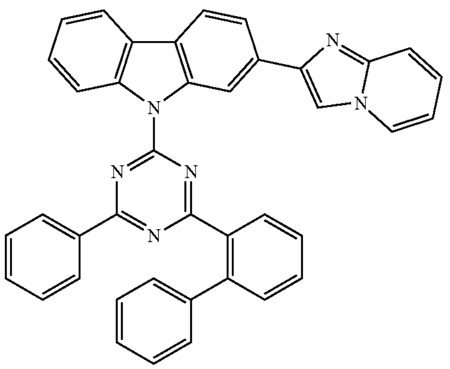

-continued
C-120
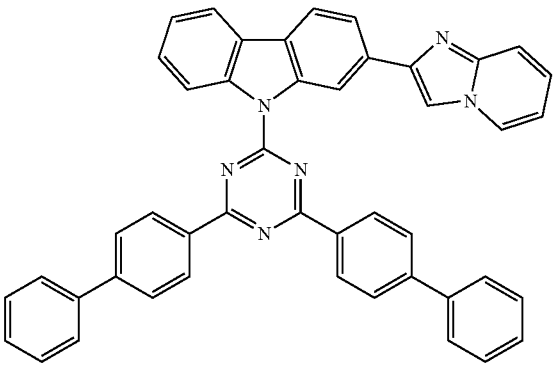
C-121
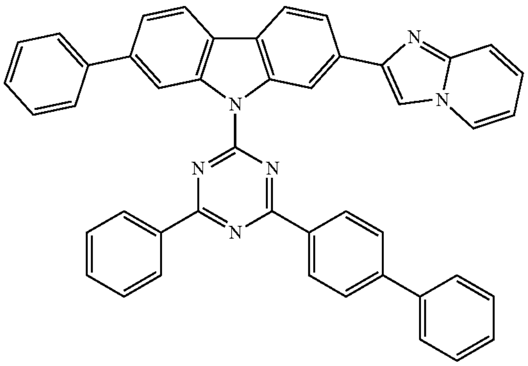
C-122
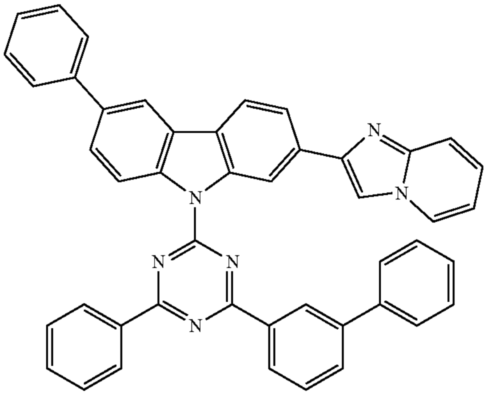
C-123
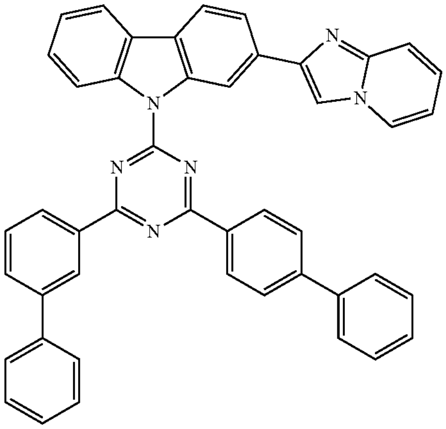
-continued
C-124
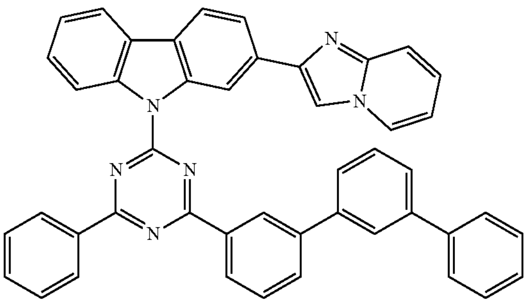
C-125
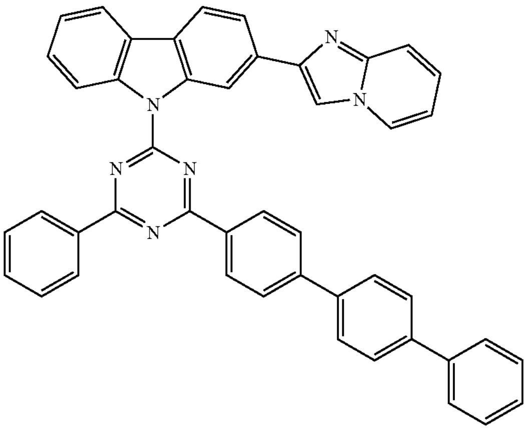
C-126
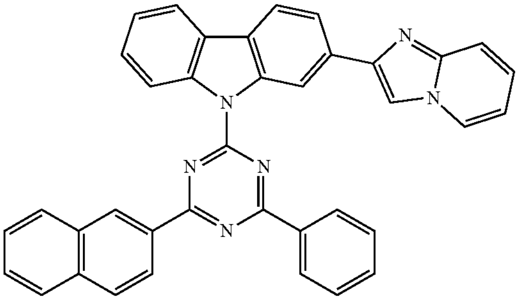
C-127
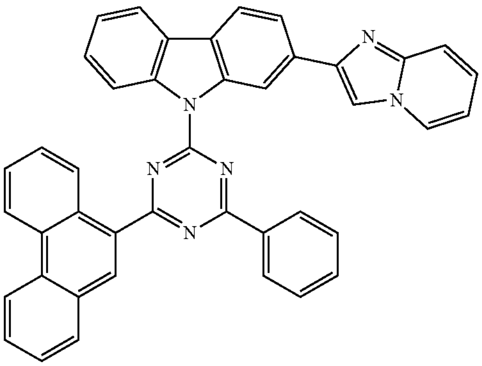

-continued
C-128
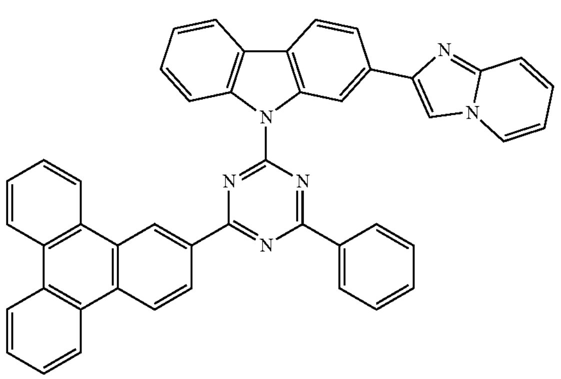
C-129
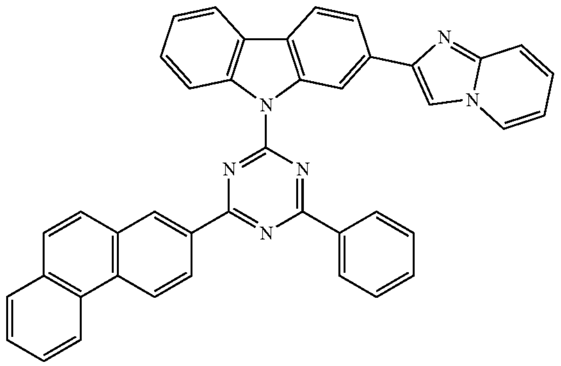
C-130
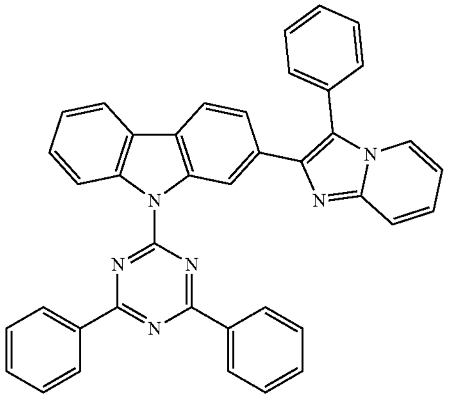
C-131
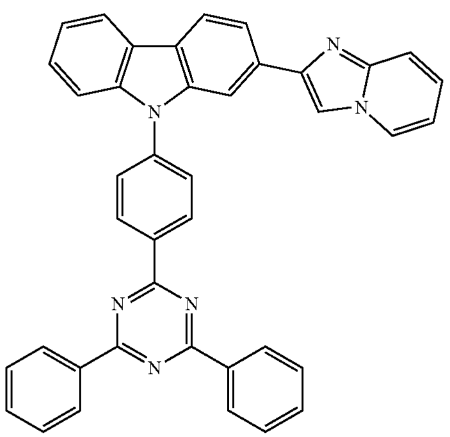
-continued
C-132
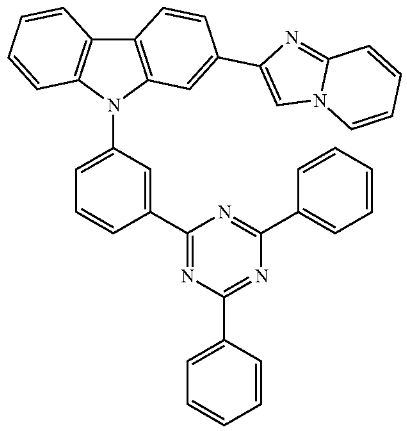
C-133
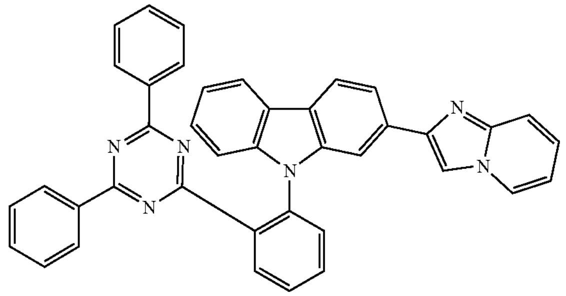
C-134
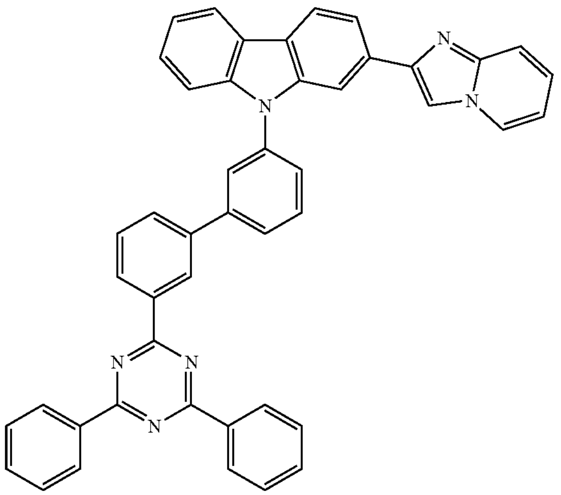

-continued
C-135
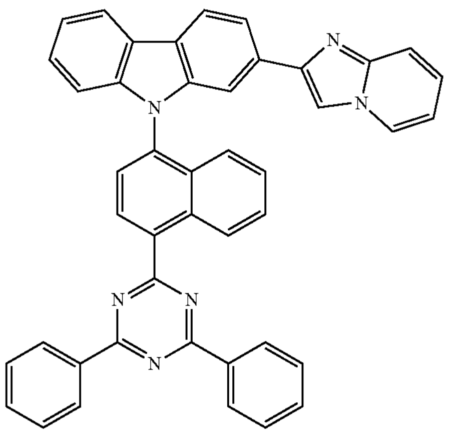
C-136
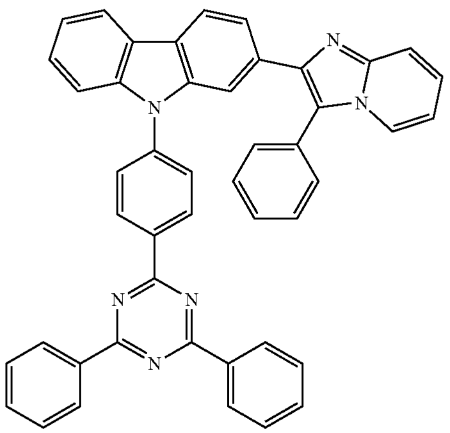
C-137
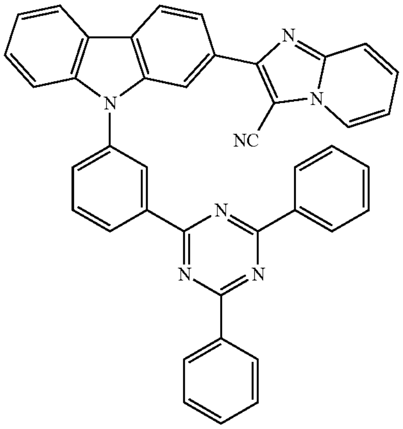
-continued
C-138
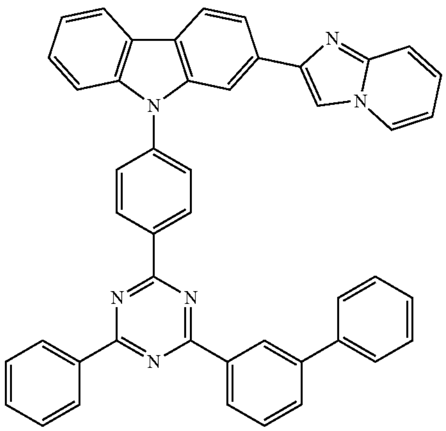
C-139
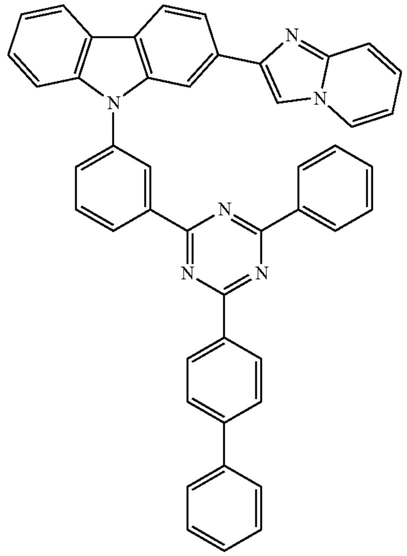
C-140
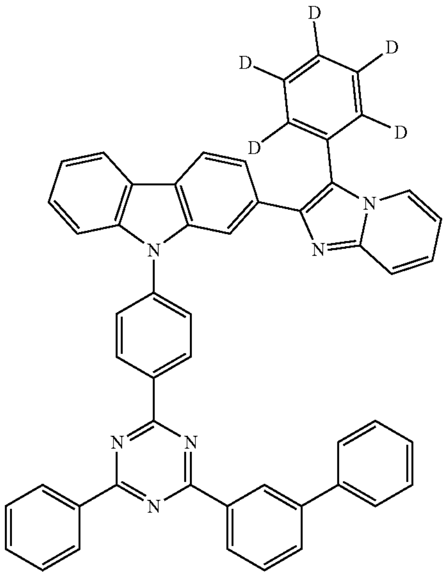

-continued
C-141
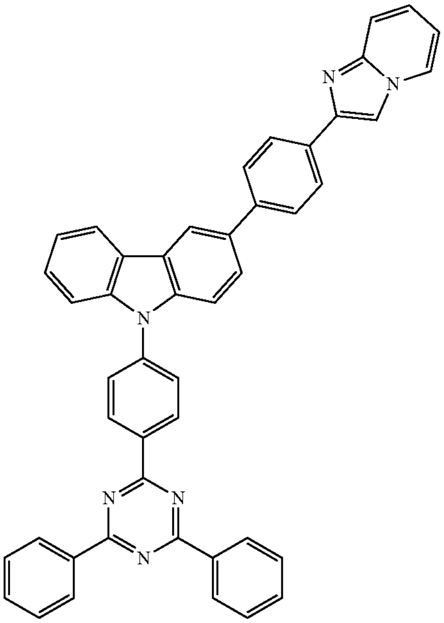
C-142
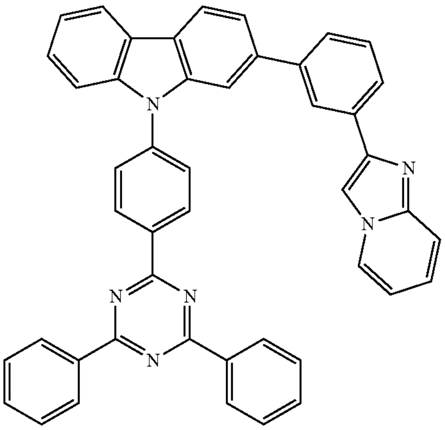
C-143
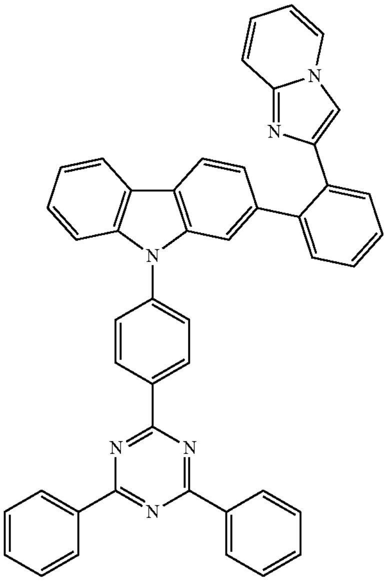
-continued
C-144
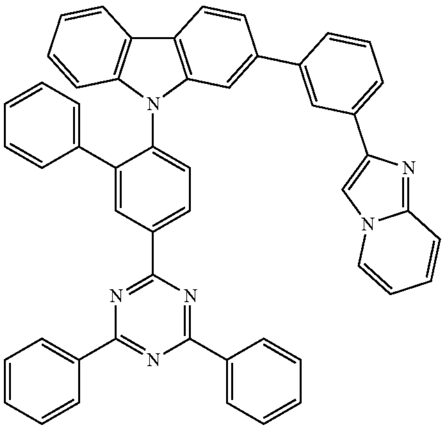
C-145
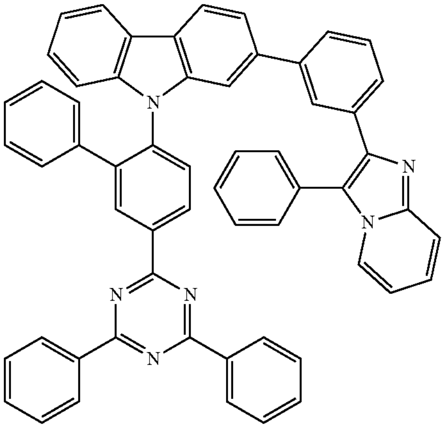
C-146
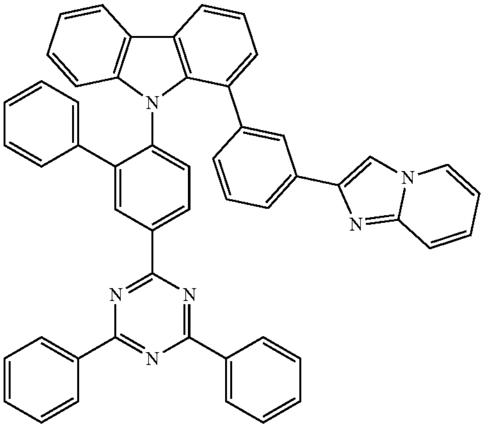

-continued
C-147
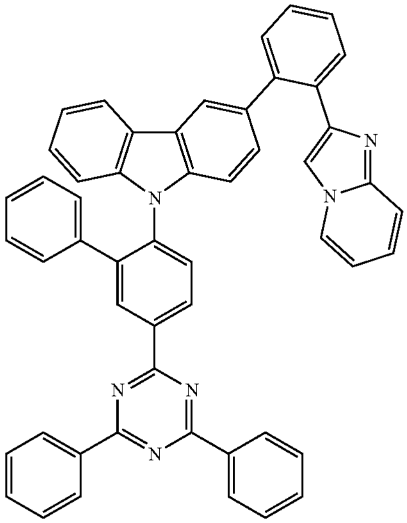
C-148
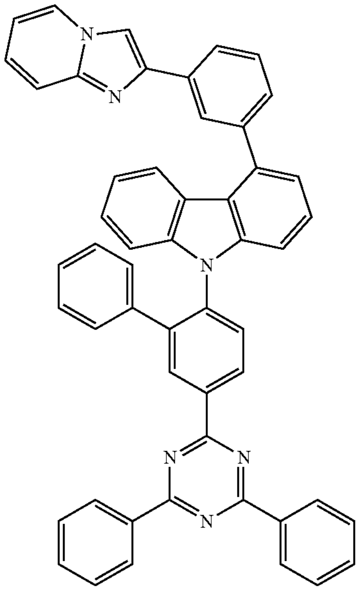
C-149
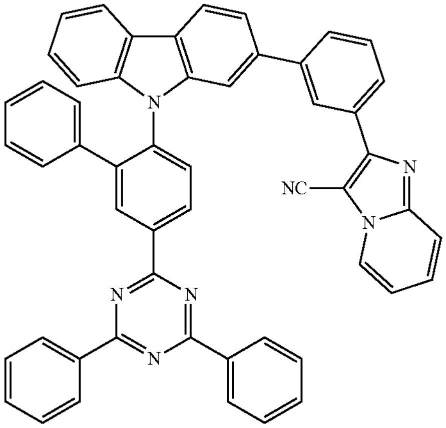
-continued
C-150
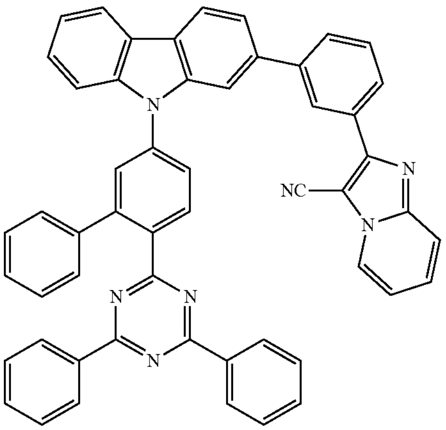
C-151
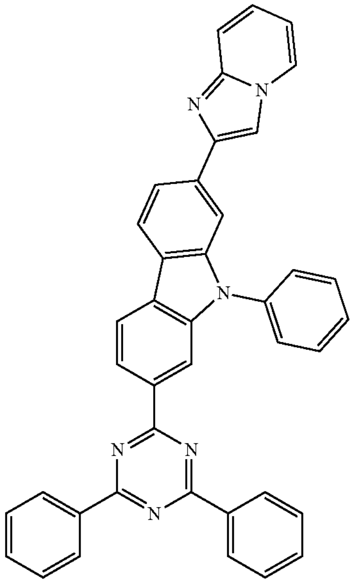
C-152
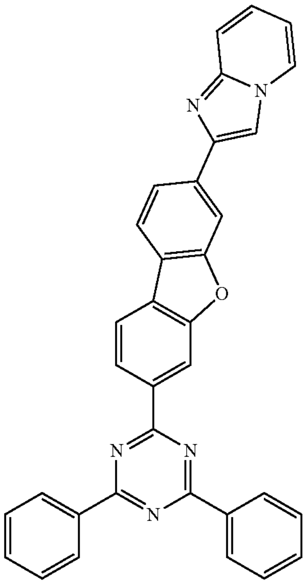

-continued
C-153
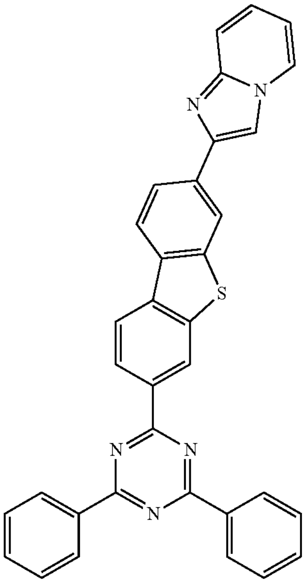
C-154
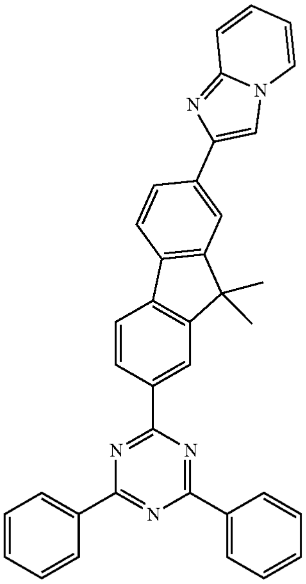
-continued
C-155
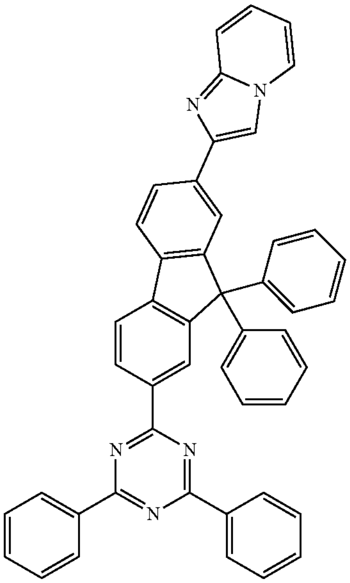
C-156
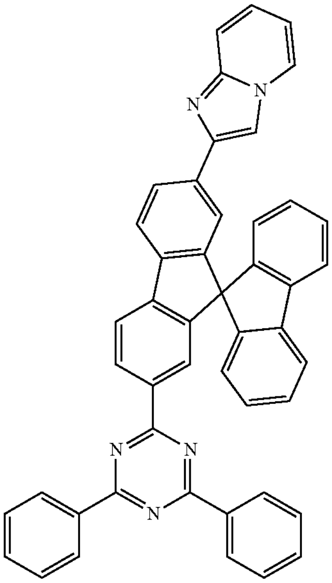

-continued
C-157
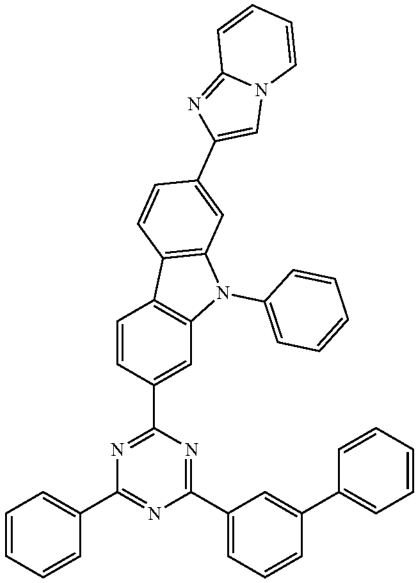
C-158
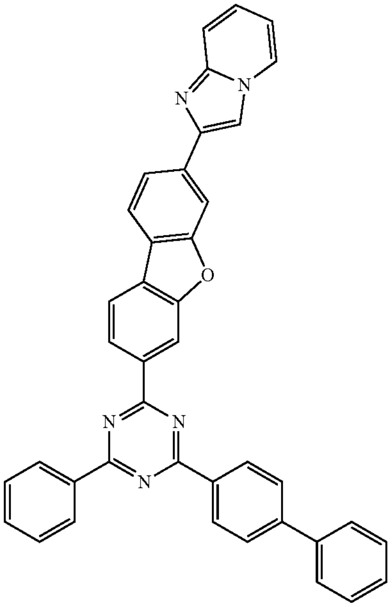
-continued
C-159
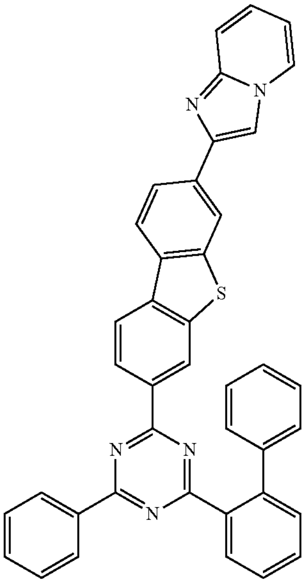
C-160
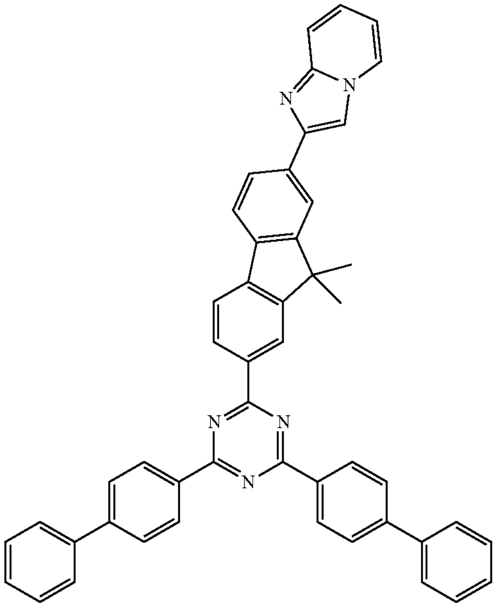

C-161
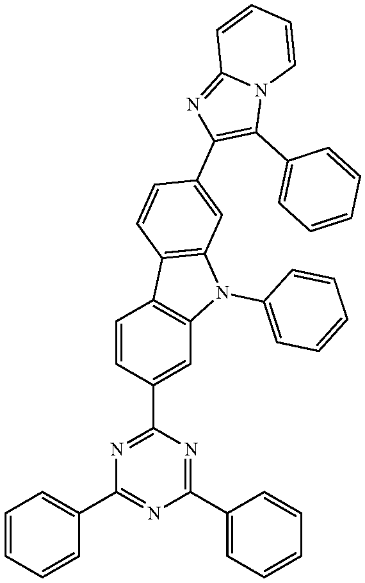
C-162
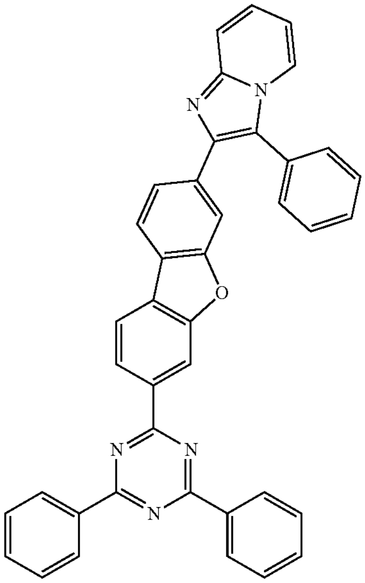
C-163
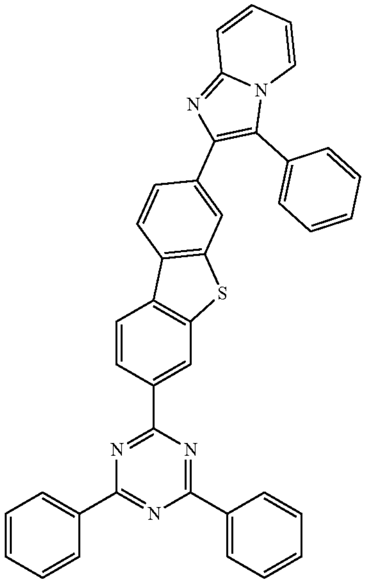
C-164
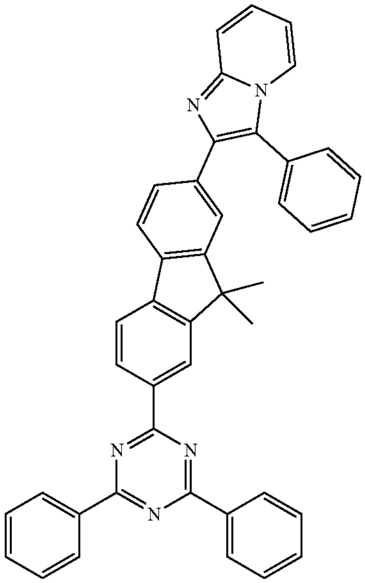

-continued
C-165
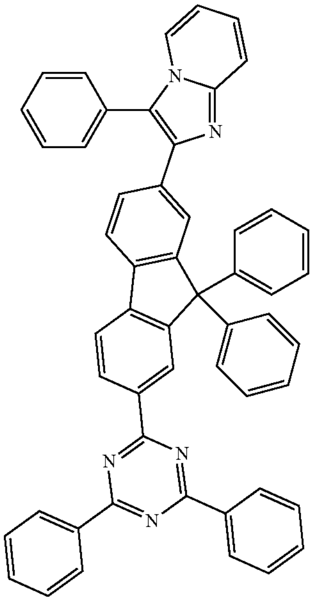
C-166
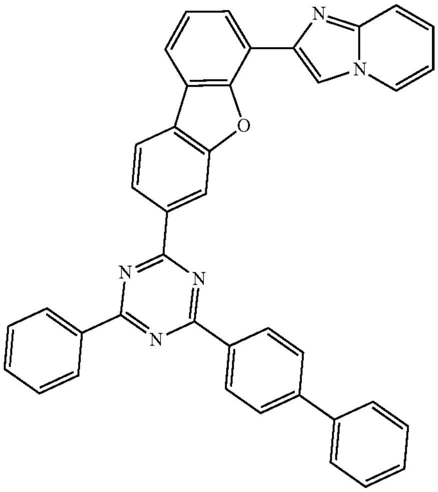
-continued
C-167
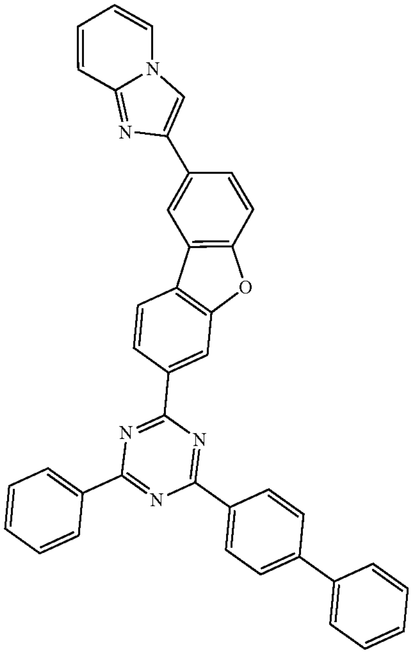
C-168
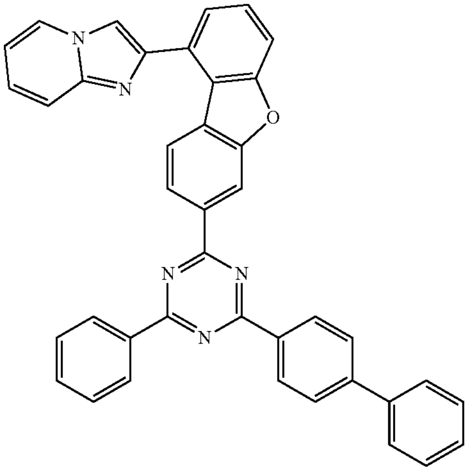

-continued
C-169
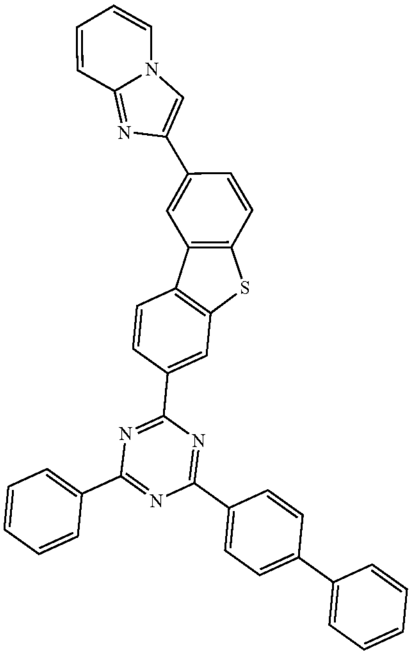
C-170
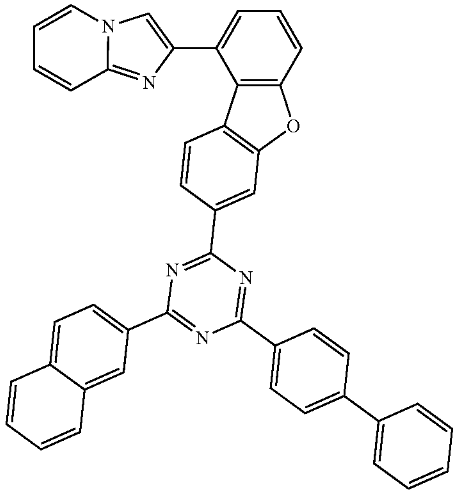
C-171
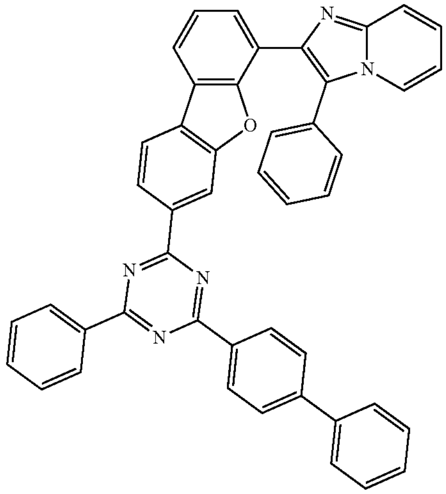
-continued
C-172
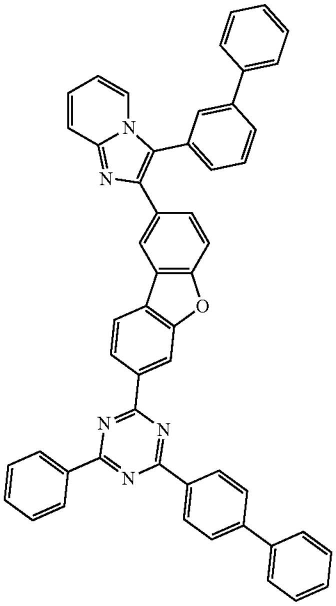
C-173
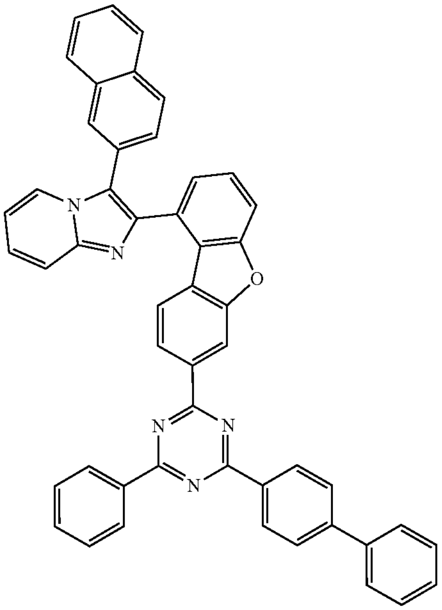

-continued
C-174
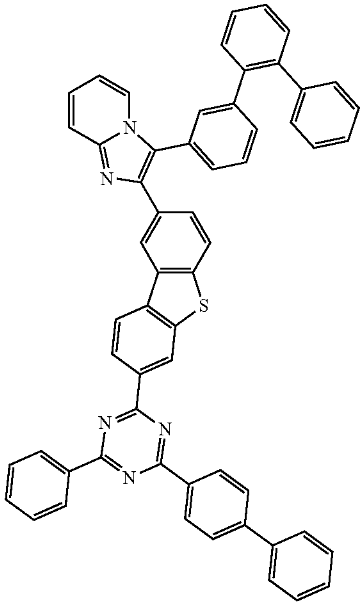
C-175
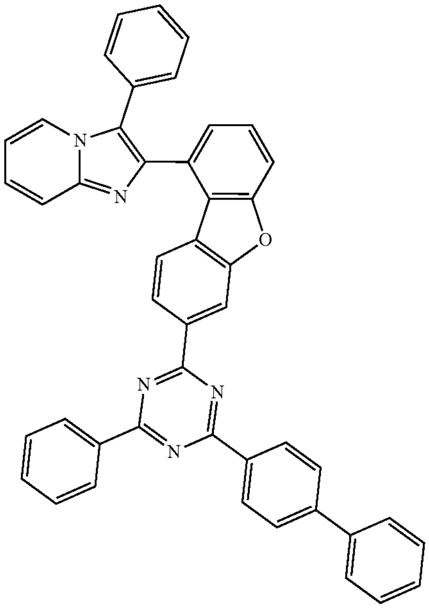
-continued
C-176
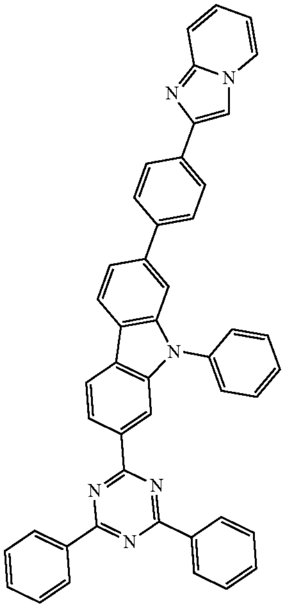
C-177
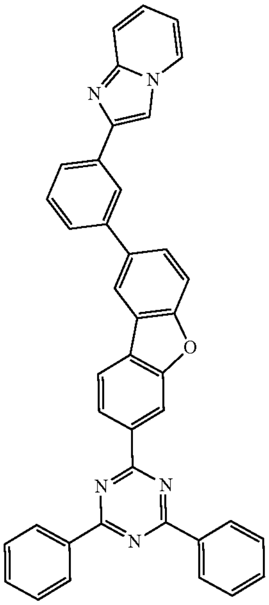

-continued
C-178
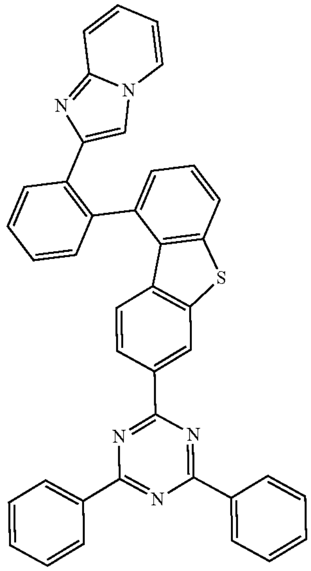
C-180
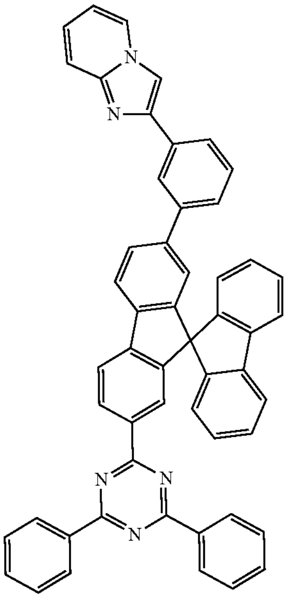
C-179
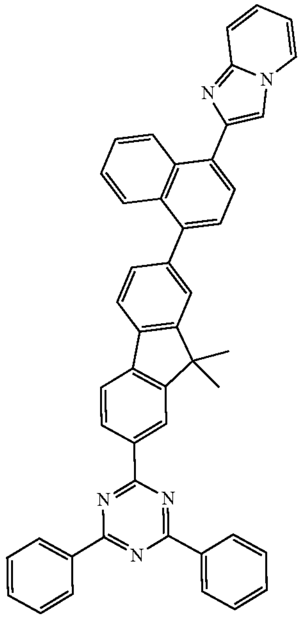
C-181
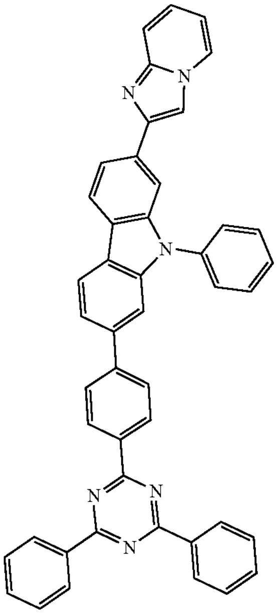

-continued
C-182
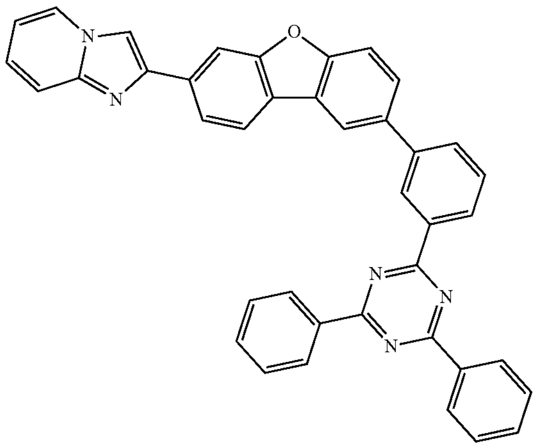
C-183
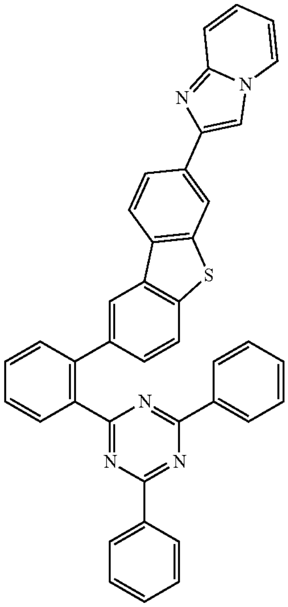
-continued
C-184
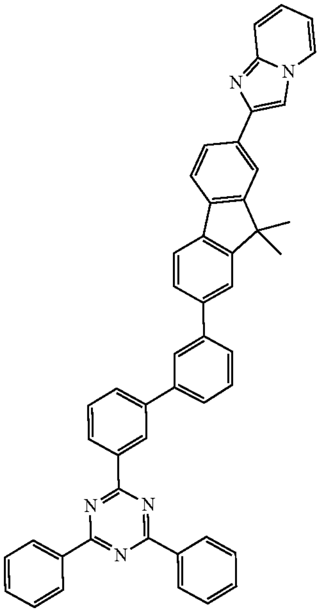
C-185
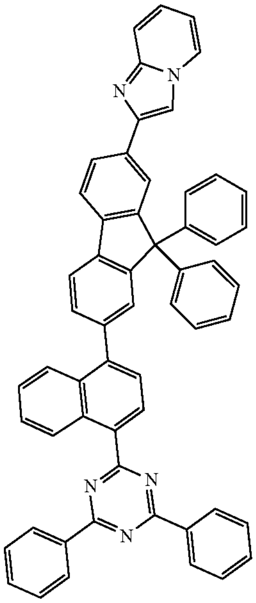

-continued
C-186
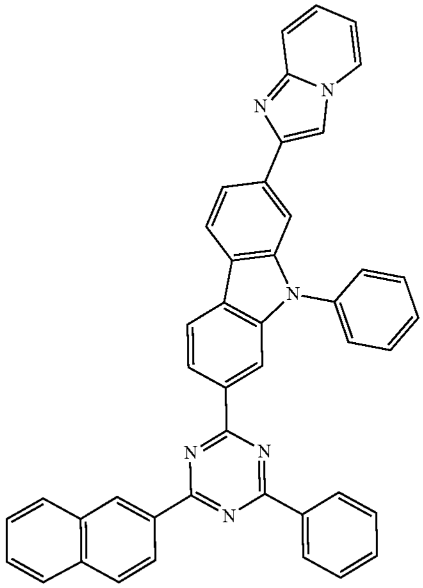
C-187
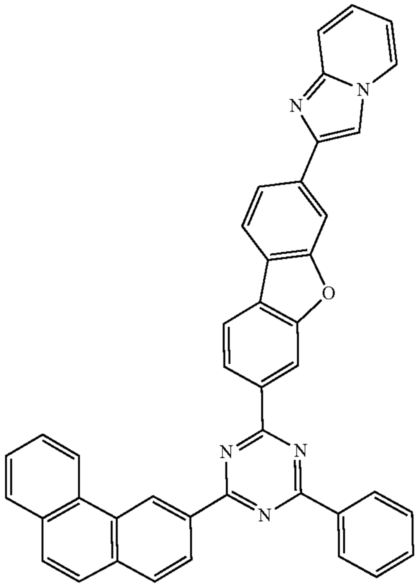
-continued
C-188
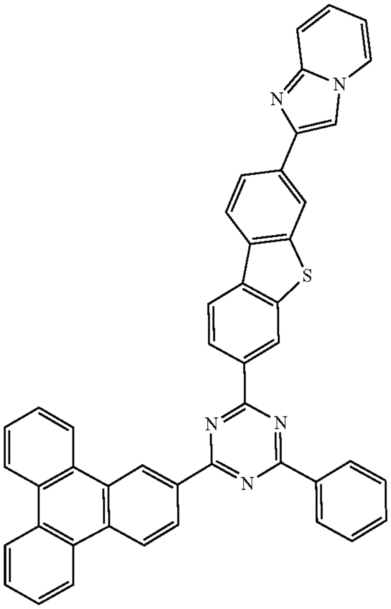
C-189
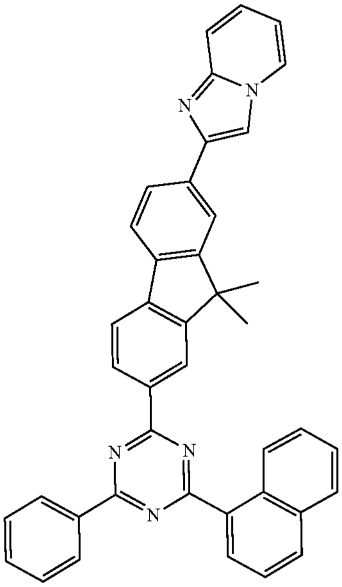

-continued
C-190
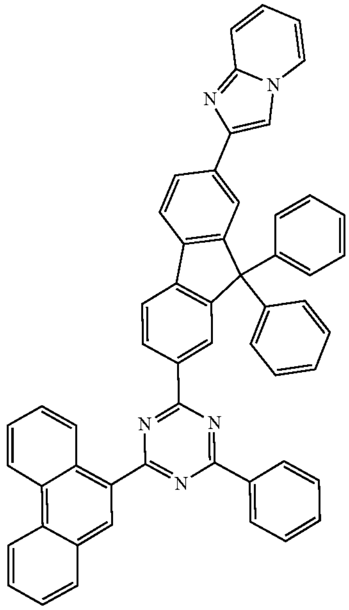
C-191
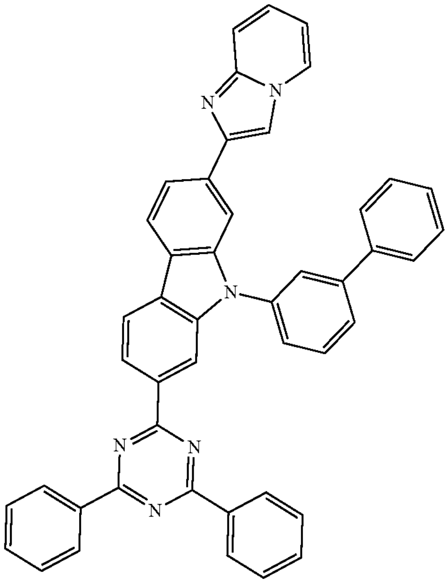
-continued
C-192
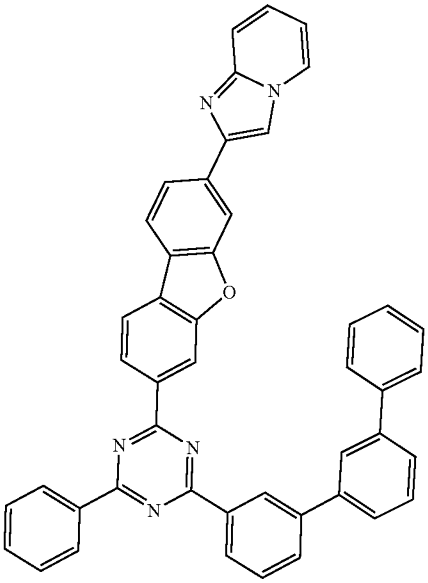
C-193
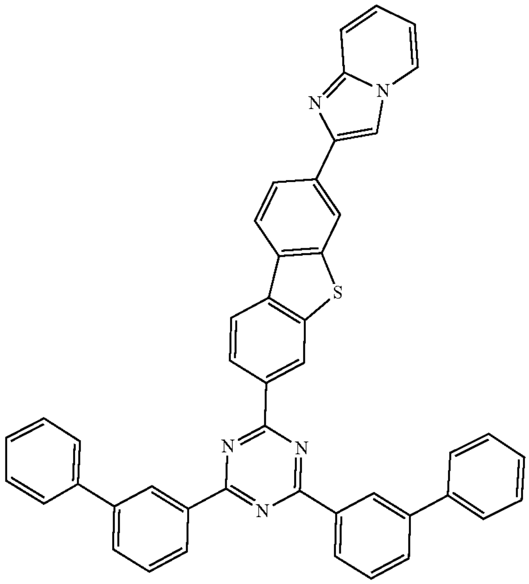

-continued
C-194
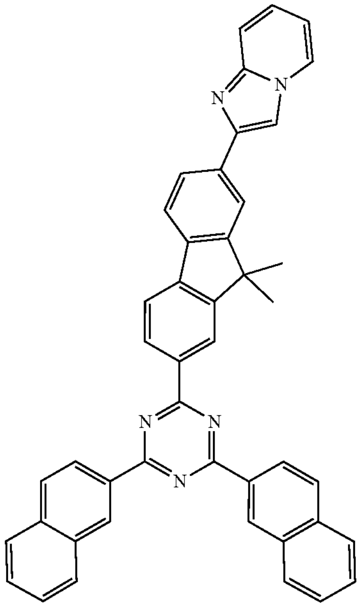
C-195
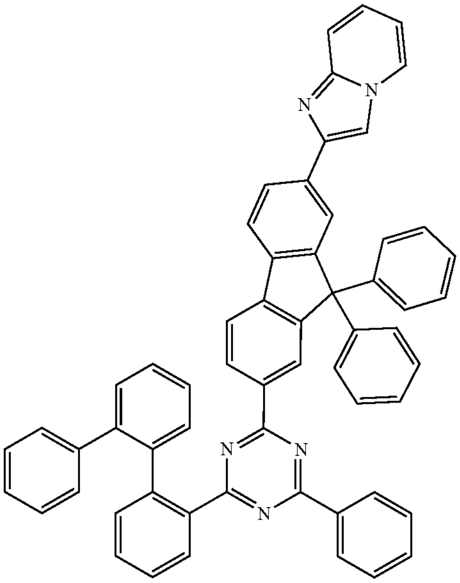
C-196
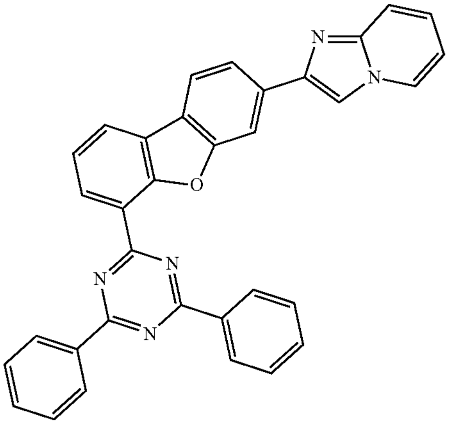
-continued
C-197
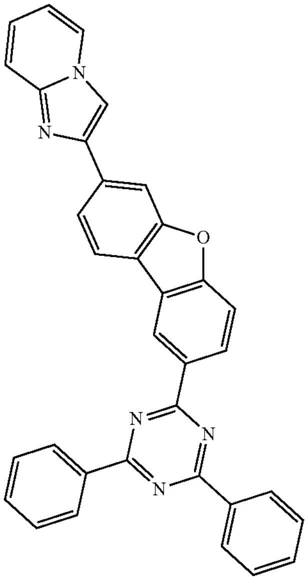
C-198
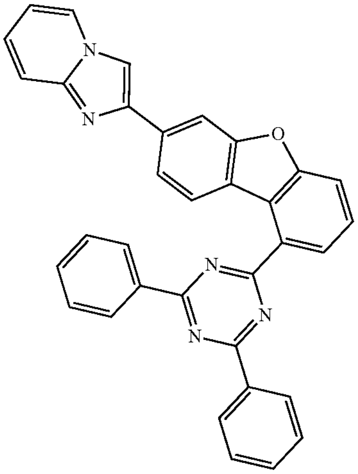
C-199
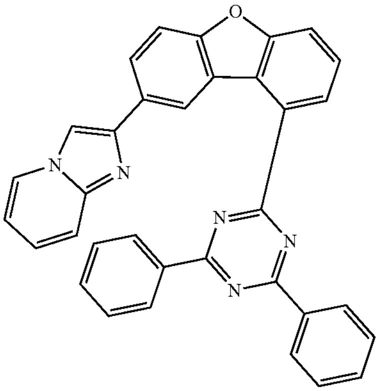

-continued
C-200
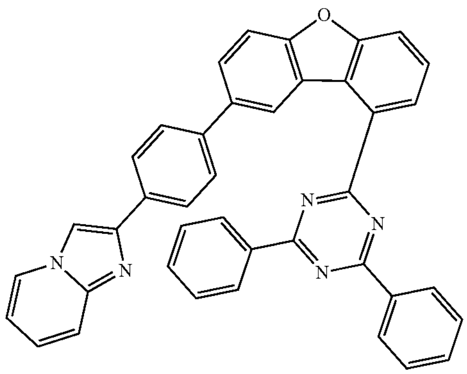
C-201
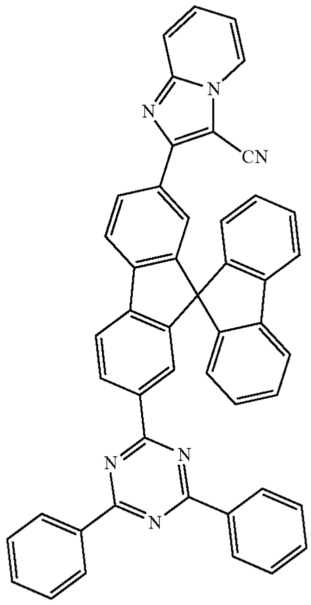
C-202
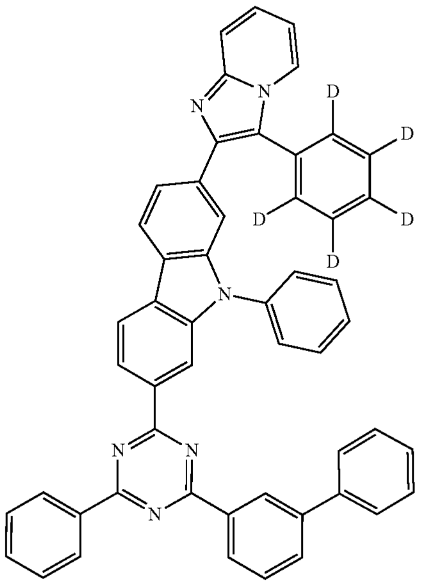
-continued
C-203
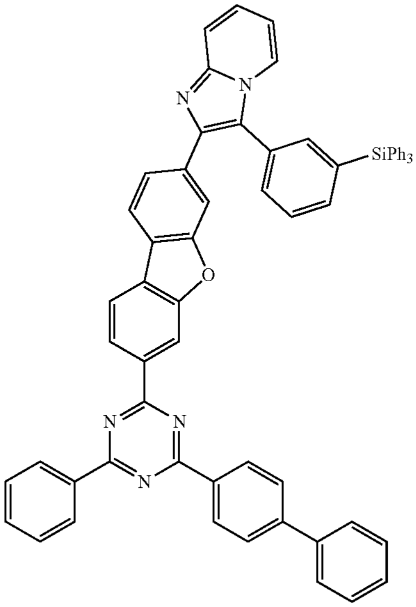
C-204
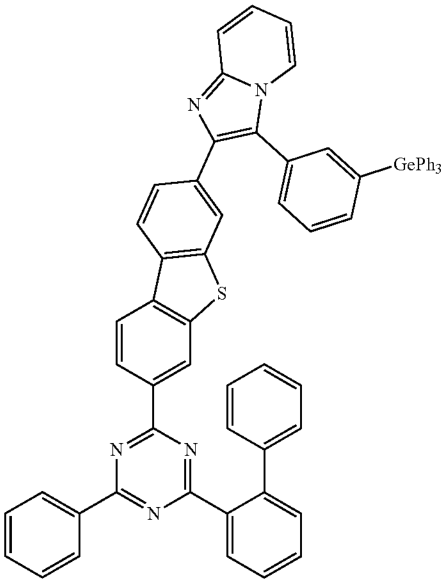

-continued
C-205
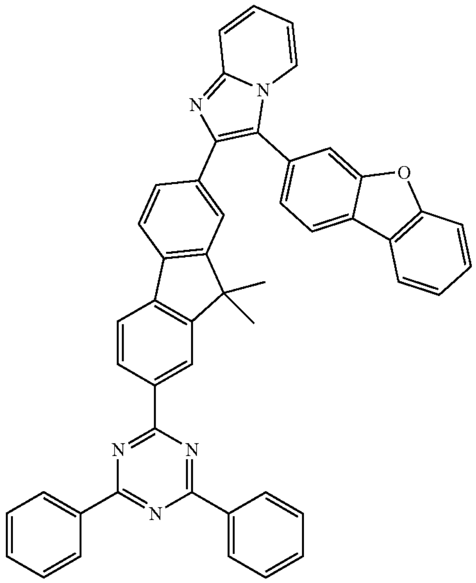
C-206
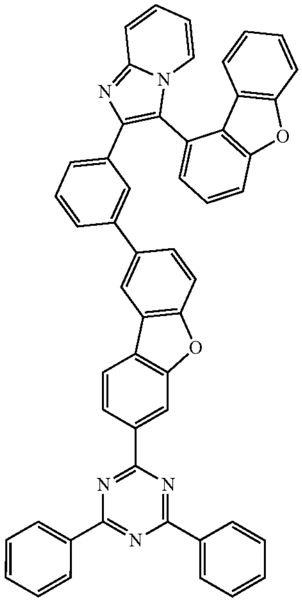
-continued
C-207
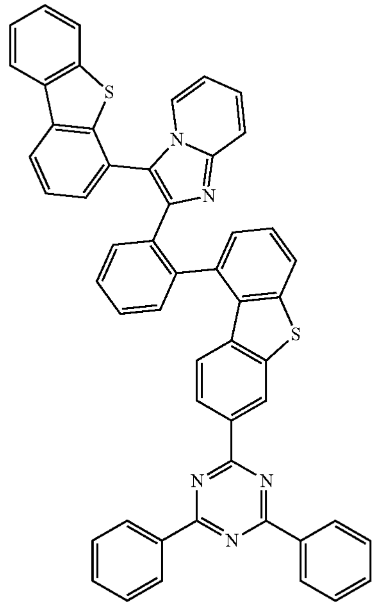
C-208
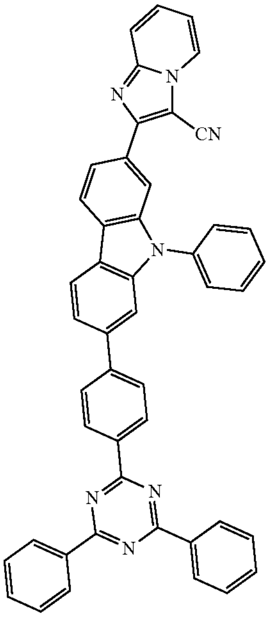

-continued
C-209
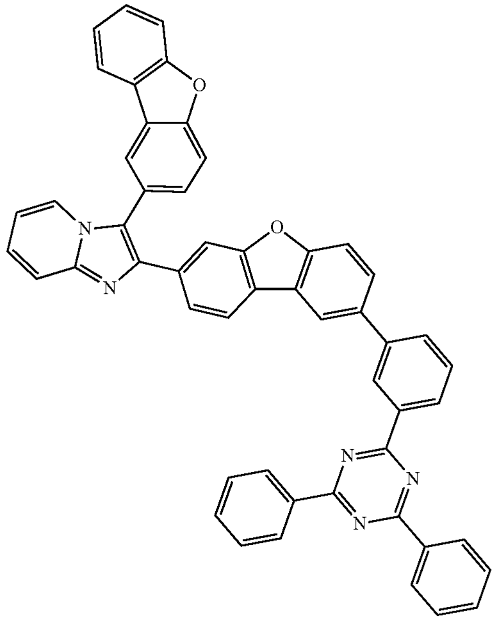
C-210
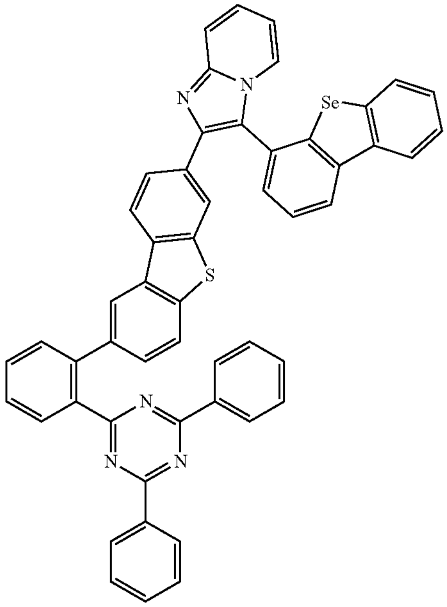
-continued
C-211
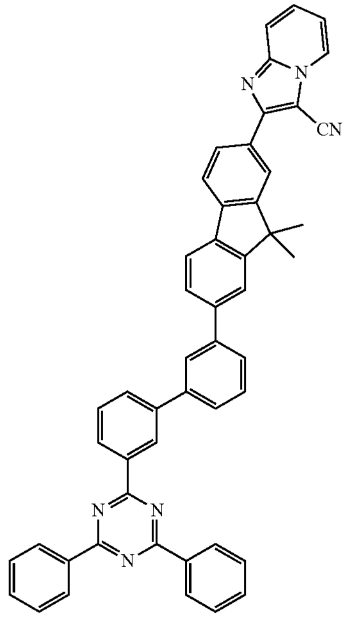
C-212
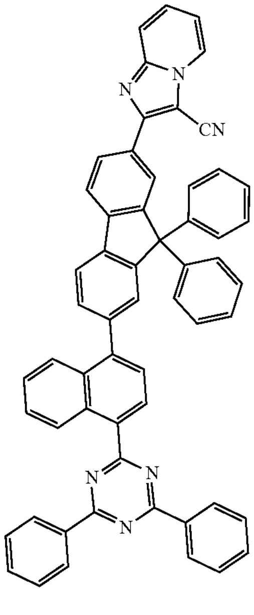
C-213
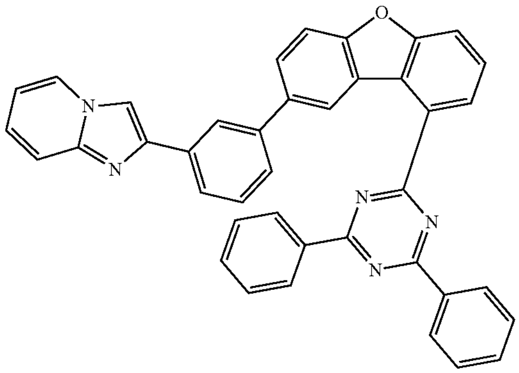

-continued
C-214
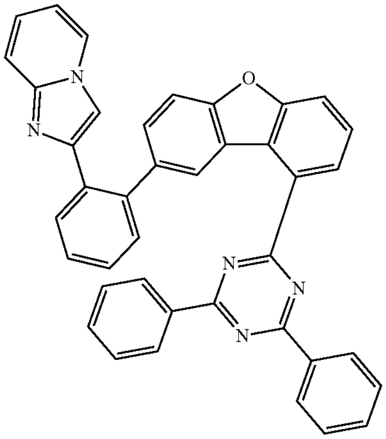
C-215
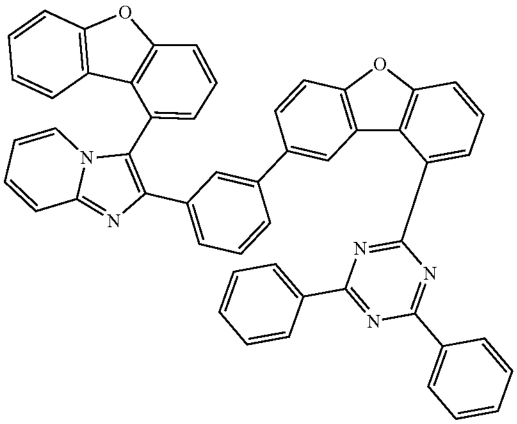
C-216
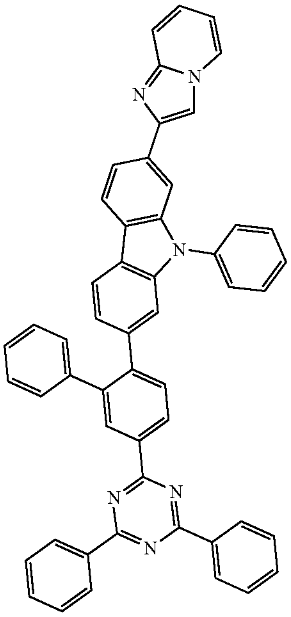
-continued
C-217
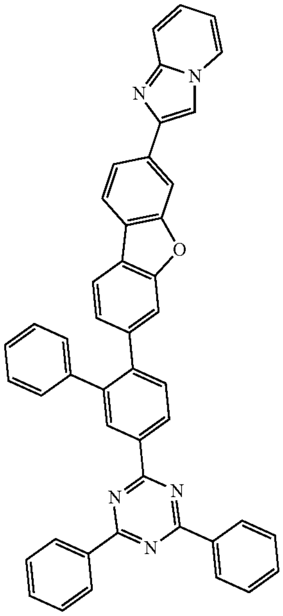
C-218
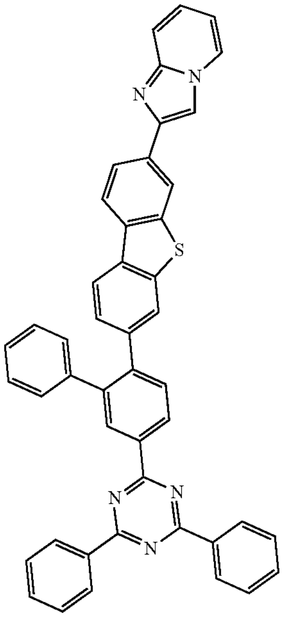

-continued

C-219

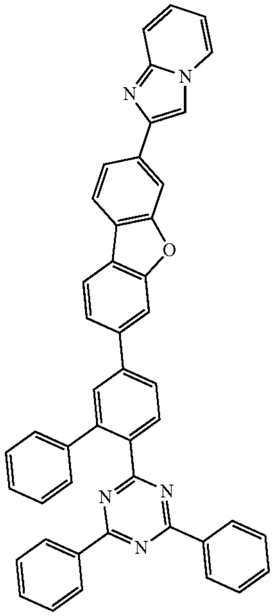

C-220

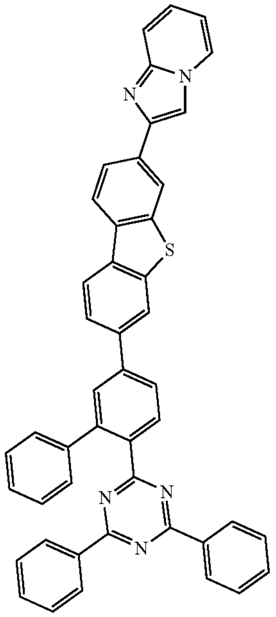

Hereinafter, an organic electroluminescent device to which the aforementioned plurality of host materials and/or organic electroluminescent compound is (are) applied, will be described.

The organic electroluminescent device according to one embodiment includes a first electrode; a second electrode; and at least one organic layer(s) interposed between the first electrode and the second electrode. The organic layer may include a light-emitting layer, and the light-emitting layer may comprise a plurality of host materials comprising at least one first host material represented by formula 1 and at least one second host material represented by formula 2.

According to another embodiment, the organic layer may include a light-emitting layer, an electron transport layer, and a hole blocking layer, and the light-emitting layer, the electron transport layer, and the hole blocking layer may comprise an organic electroluminescent compound represented by formula 1A.

According to one embodiment, the organic electroluminescent material of the present disclosure comprises at least one compound(s) of compounds C-1 to C-220, which is a first host material, and at least one compound(s) of compounds H2-1 to H2-230, which is a second host material. The plurality of host materials may be included in the same organic layer, for example the same light-emitting layer, or may be included in different light-emitting layers, respectively.

The organic layer may further comprise at least one layer selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer in addition to the light-emitting layer. The organic layer may further comprise an amine-based compound and/or an azine-based compound other than the light-emitting material according to the present disclosure. Specifically, the hole injection layer, the hole transport layer, the hole auxiliary layer, the light-emitting layer, the light-emitting auxiliary layer, or the electron blocking layer may contain the amine-based compound, e.g., an arylamine-based compound and a styrylarylamine-based compound, etc., as a hole injection material, a hole transport material, a hole auxiliary material, a light-emitting material, a light-emitting auxiliary material, or an electron blocking material. In addition, the electron transport layer, the electron injection layer, the electron buffer layer, or the hole blocking layer may contain the azine-based compound as an electron transport material, an electron injection material, an electron buffer material, or a hole blocking material. Further, the organic layer may further comprise at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising such a metal.

The plurality of host materials according to one embodiment may be used as light-emitting materials for a white organic light-emitting device. The white organic light-emitting device has suggested various structures such as a parallel side-by-side arrangement method, a stacking arrangement method, or CCM (color conversion material) method, etc., according to the arrangement of R (Red), G (Green), YG (yellowish green), or B (blue) light-emitting units. In addition, the plurality of host materials according to one embodiment may also be applied to the organic electroluminescent device comprising a QD (quantum dot).

One of the first electrode and the second electrode may be an anode and the other may be a cathode. Wherein, the first electrode and the second electrode may each be formed as a transmissive conductive material, a transflective conductive material, or a reflective conductive material. The organic electroluminescent device may be a top emission type, a bottom emission type, or a both-sides emission type according to the kinds of the material forming the first electrode and the second electrode.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. Also, the hole injection layer may be doped as a p-dopant. Also, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. The hole transport layer or the electron blocking layer may be multi-layers, and wherein each layer may use a plurality of compounds.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer may be placed between the electron transport layer (or electron injection layer) and the light-emitting layer, and blocks the arrival of holes to the cathode, thereby improving the probability of recombination of electrons and holes in the light-emitting layer. The hole blocking layer or the electron transport layer may also be multi-layers, wherein each layer may use a plurality of compounds. In addition, the electron injection layer may be doped as an n-dopant.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. When an organic electroluminescent device includes two or more hole transport layers, the hole transport layer, which is further included, may be used as the hole auxiliary layer or the electron blocking layer. The light-emitting auxiliary layer, the hole auxiliary layer, or the electron blocking layer may have an effect of improving the efficiency and/or the lifespan of the organic electroluminescent device.

In the organic electroluminescent device of the present disclosure, preferably, at least one layer (hereinafter, "a surface layer") selected from a chalcogenide layer, a halogenated metal layer, and a metal oxide layer may be placed on an inner surface(s) of one or both of a pair of electrodes. Specifically, a chalcogenide (including oxides) layer of silicon and aluminum is preferably, placed on an anode surface of an electroluminescent medium layer, and a halogenated metal layer or a metal oxide layer is preferably placed on a cathode surface of an electroluminescent medium layer. The operation stability for the organic electroluminescent device may be obtained by the surface layer. Preferably, the chalcogenide includes $SiO_X(1 \leq X \leq 2)$, $AlO_X$ $(1 \leq X \leq 1.5)$, SiON, SiAlON, etc.; the halogenated metal includes LiF, $MgF_2$, $CaF_2$, a rare earth metal fluoride, etc.; and the metal oxide includes $Cs_2O$, $Li_2O$, MgO, SrO, BaO, CaO, etc.

In addition, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. Additionally, a reductive dopant layer may be employed as a charge generating layer to prepare an organic electroluminescent device having two or more light-emitting layers and emitting white light.

An organic electroluminescent device according to one embodiment may further comprise at least one dopant in the light-emitting layer.

The dopant comprised in the organic electroluminescent device of the present disclosure may be at least one phosphorescent or fluorescent dopant, preferably, a phosphorescent dopant. The phosphorescent dopant material applied to the organic electroluminescent device of the present disclosure is not particularly limited, but may be preferably, a metallated complex compounds) of a metal atom(s) selected from iridium (Ir), osmium (Os), copper (Cu), and platinum (Pt), more preferably, an ortho-metallated complex compound(s) of a metal atom(s) selected from iridium (Ir), osmium (Os), copper (Cu), and platinum (Pt), and even more preferably, ortho-metallated iridium complex compound(s).

The dopant comprised in the organic electroluminescent device of the present disclosure may use the compound represented by the following formula 101, but is not limited thereto.

(101)

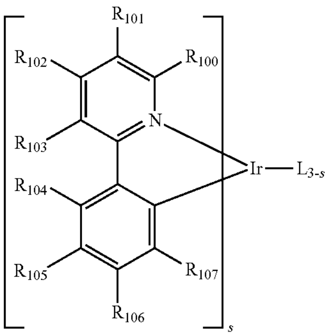

in formula 101,

L is selected from the following structures 1 to 3;

structure (1)

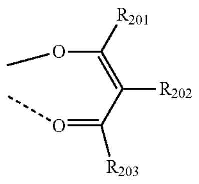

-continued structure (2)

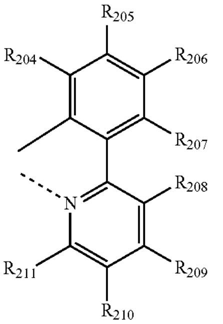

structure (3)

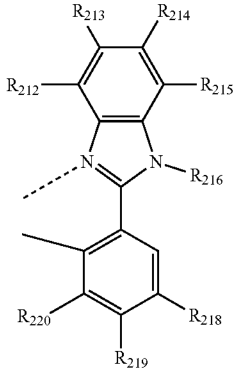

$R_{100}$ to $R_{103}$ each independently represent hydrogen, deuterium, halogen, (C1-C30)alkyl unsubstituted or substituted by deuterium and/or halogen, a substituted or unsubstituted (C3-C30)cycloalkyl, a substituted or unsubstituted (C6-C30)aryl, cyano, a substituted or unsubstituted (3- to 30-membered)heteroaryl, or a substituted or unsubstituted (C1-C30)alkoxy; or may be linked to the adjacent substituents to form a ring(s), for example, to form a ring(s) with a pyridine, e.g., a substituted or unsubstituted quinoline, a substituted or unsubstituted benzofuropyridine, a substituted or unsubstituted benzothienopyridine, a substituted or unsubstituted indenopyridine, a substituted or unsubstituted benzofuroquinoline, a substituted or unsubstituted benzothienoquinoline, or a substituted or unsubstituted indenoquinoline;

$R_{104}$ to $R_{107}$ each independently represent hydrogen, deuterium, halogen, (C1-C30)alkyl unsubstituted or substituted by deuterium and/or halogen, a substituted or unsubstituted (C3-C30)cycloalkyl, a substituted or unsubstituted (C6-C30)aryl, a substituted or unsubstituted (3- to 30-membered) heteroaryl, cyano, or a substituted or unsubstituted (C1-C30) alkoxy; or may be linked to an adjacent substituent(s) to form a substituted or unsubstituted ring(s), for example, to form a ring(s) with a benzene, e.g., a substituted or unsubstituted naphthalene, a substituted or unsubstituted fluorene, a substituted or unsubstituted dibenzothiophene, a substituted or unsubstituted dibenzofuran, a substituted or unsubstituted indenopyridine, a substituted or unsubstituted benzofuropyridine, or a substituted or unsubstituted benzothienopyridine;

$R_{201}$ to $R_{220}$ each independently represent hydrogen, deuterium, halogen, (C1-C30)alkyl unsubstituted or substituted by deuterium and/or halogen, a substituted or unsubstituted (C3-C30)cycloalkyl, or a substituted or unsubstituted (C6-C30)aryl; or may be linked to an adjacent substituent(s) to form a substituted or unsubstituted ring(s); and s represents an integer of 1 to 3.

Specifically, the specific examples of the dopant compound include the following, but are not limited thereto.

D-1

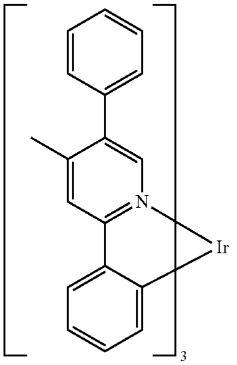

D-2

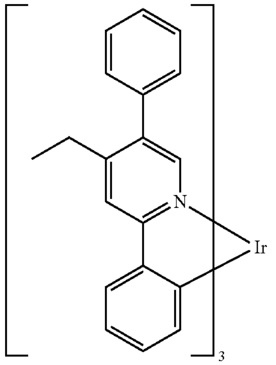

D-3

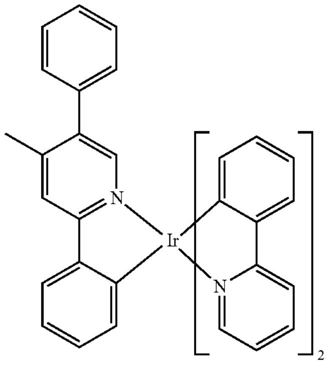

D-4

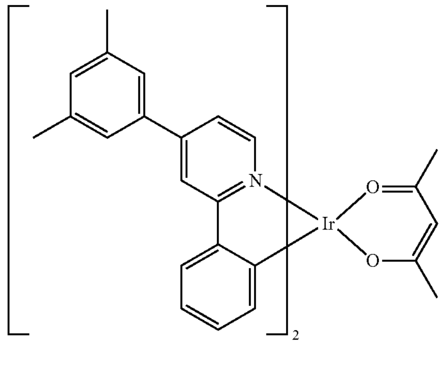

-continued
D-5
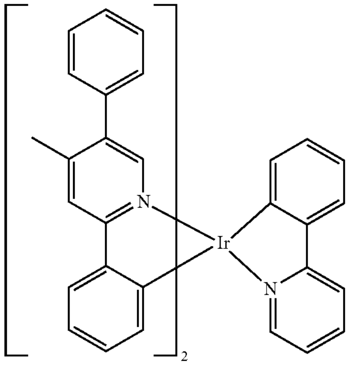
D-6
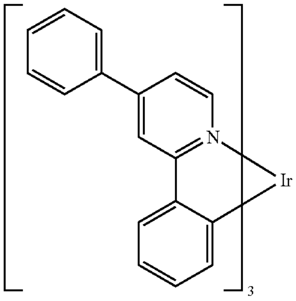
D-7
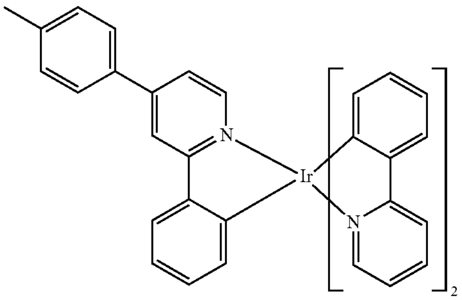
D-8
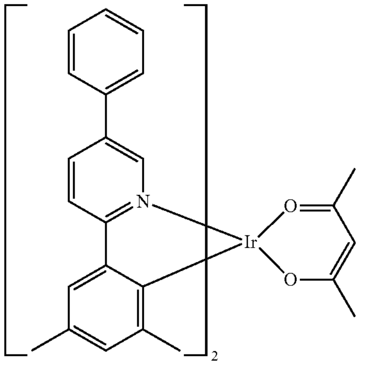
-continued
D-9
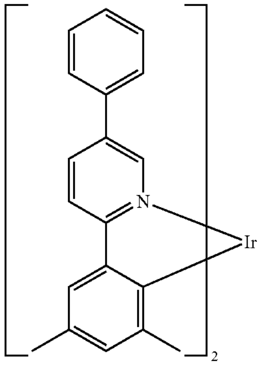
D-10
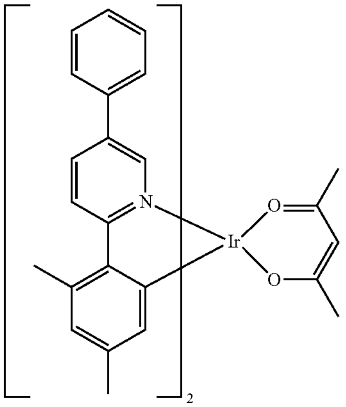
D-11
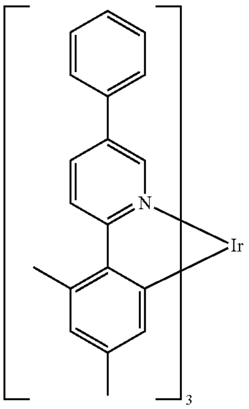
D-12
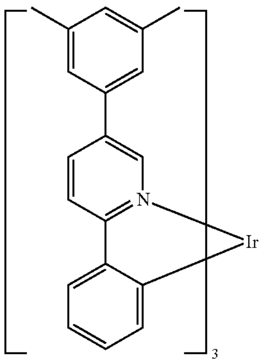

-continued
D-13
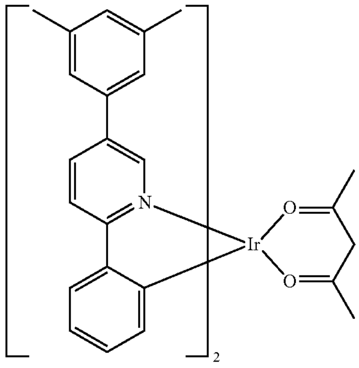
D-14
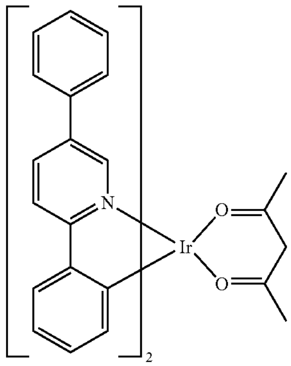
D-15
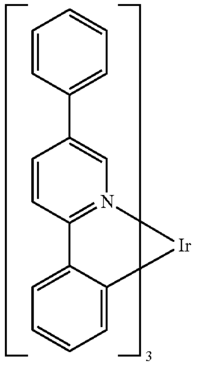
D-16
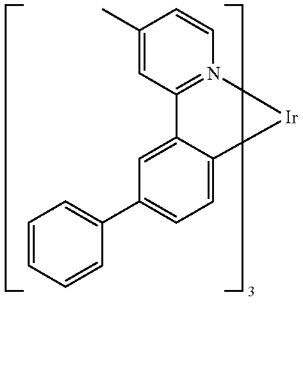
-continued
D-17
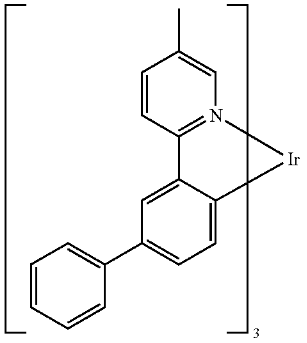
D-18
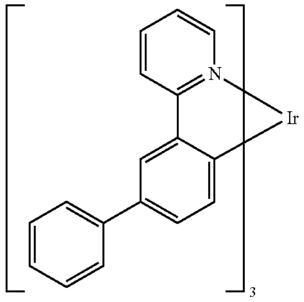
D-19
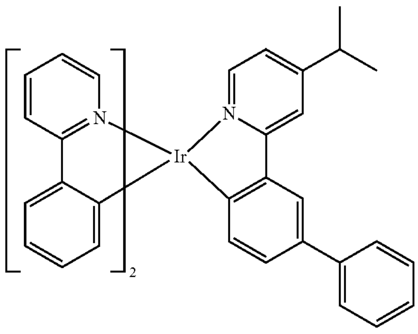
D-20
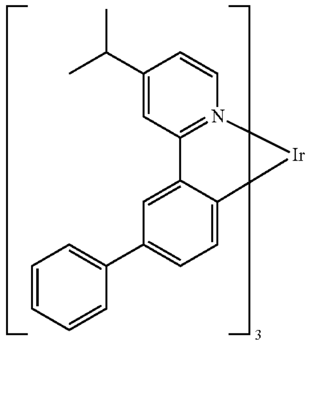

-continued
D-21
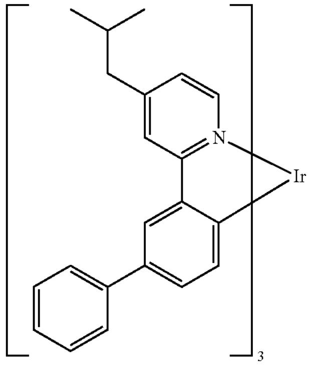
D-22
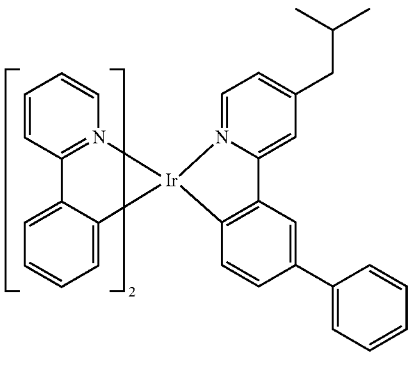
D-23
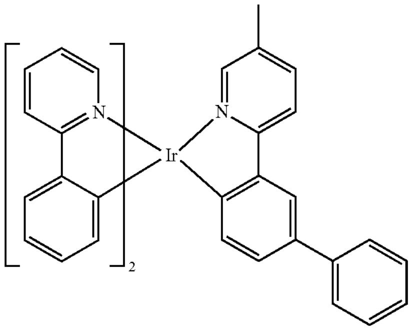
D-24
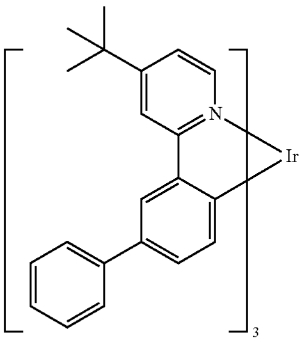
-continued
D-25
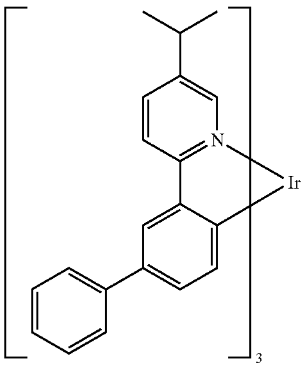
D-26
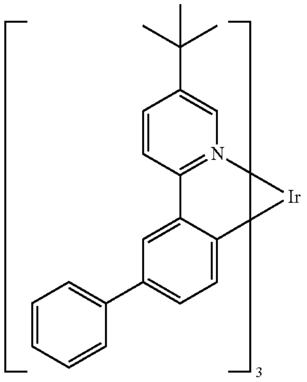
D-27
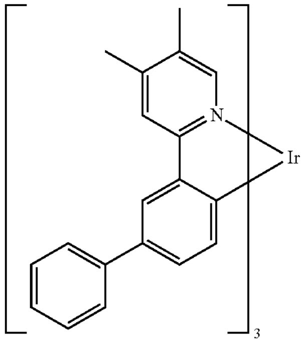
D-28
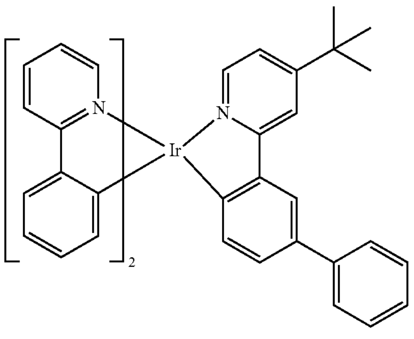

-continued
D-29
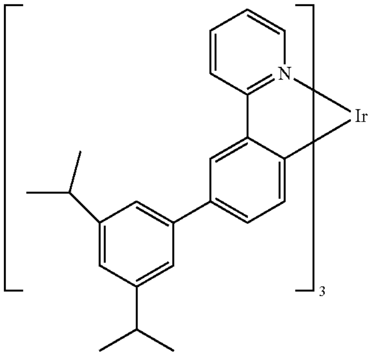
D-30
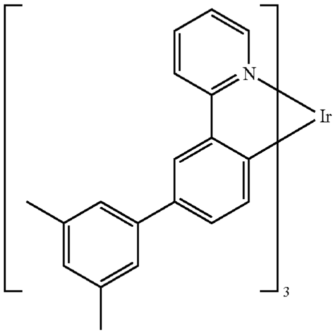
D-31
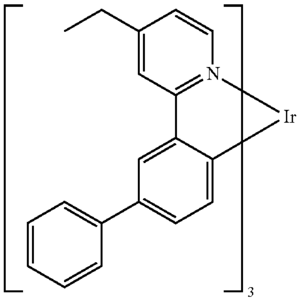
D-32
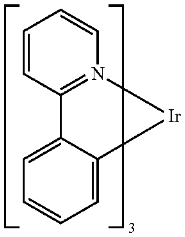
D-33
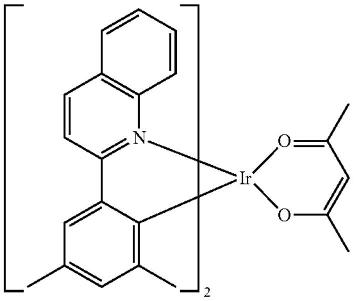
-continued
D-34
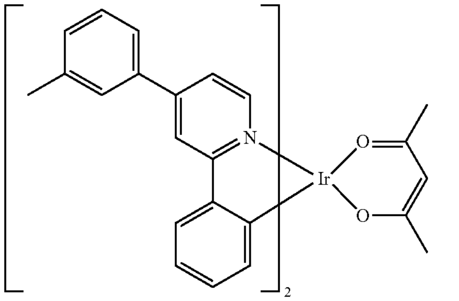
D-35
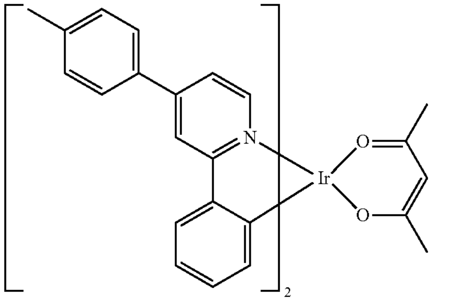
D-36
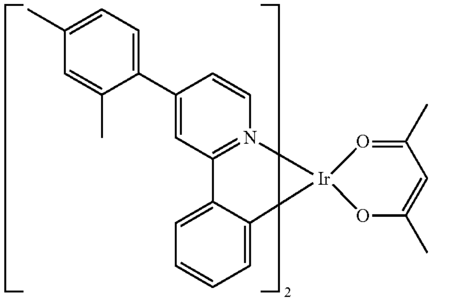
D-37
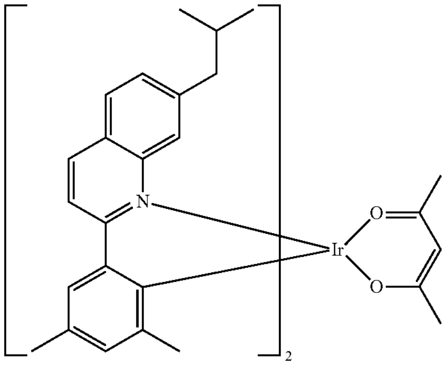
D-38
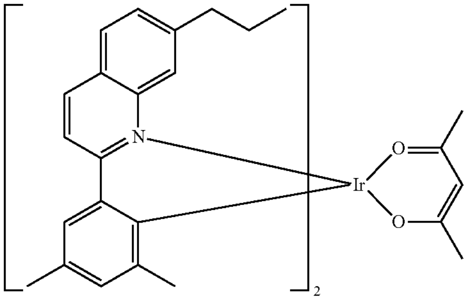

-continued
D-39
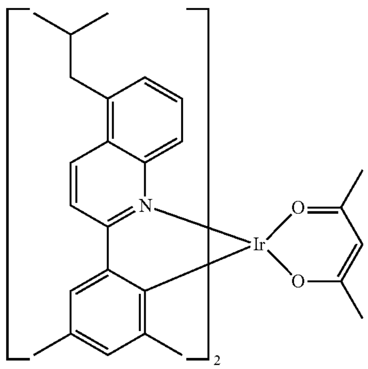
D-40
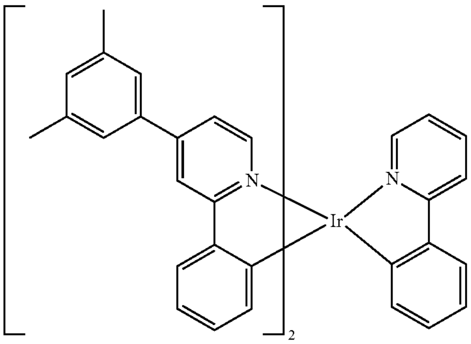
D-41
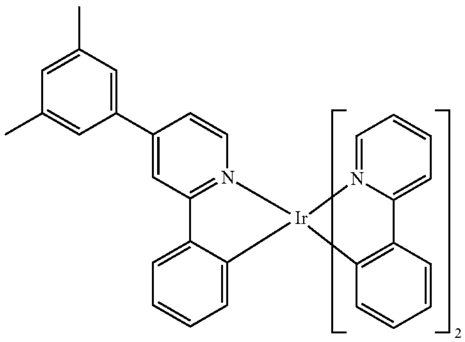
D-42
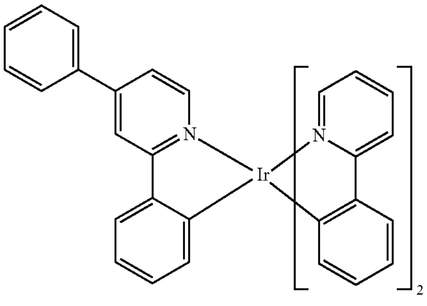
-continued
D-43
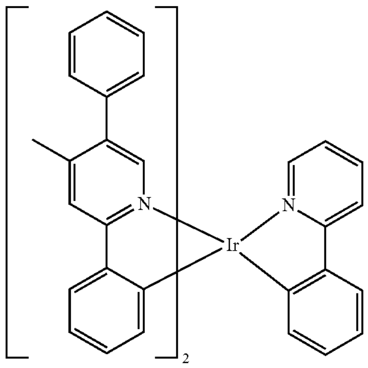
D-44
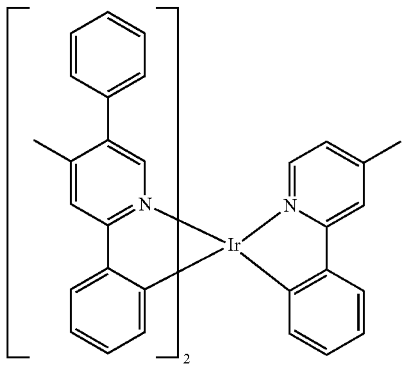
D-45
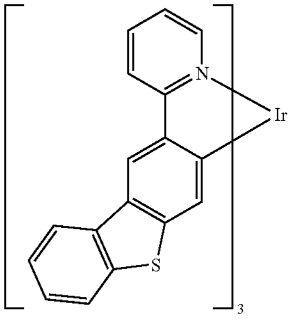
D-46
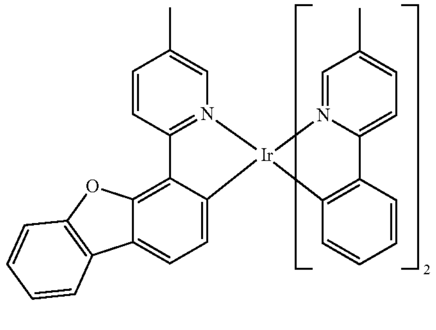

-continued
D-47
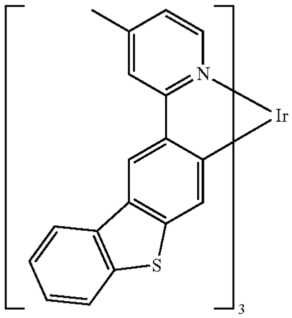
D-48
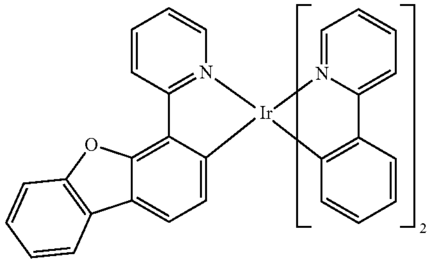
D-49
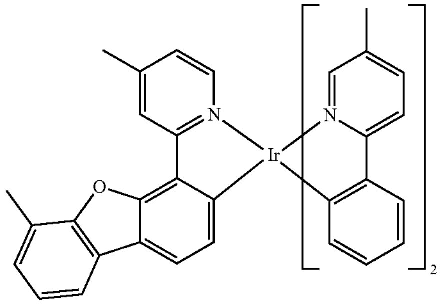
D-50
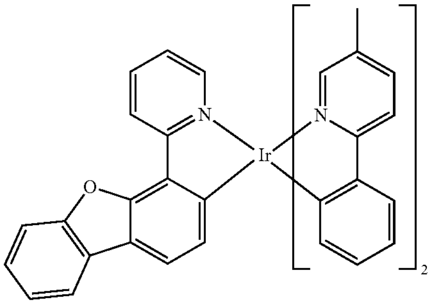
D-51
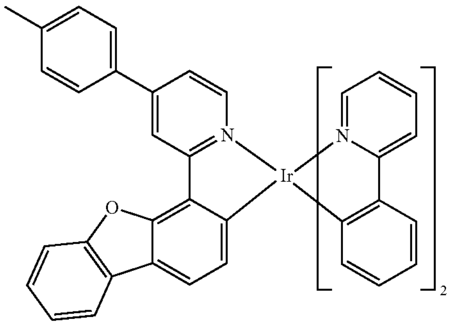
-continued
D-52
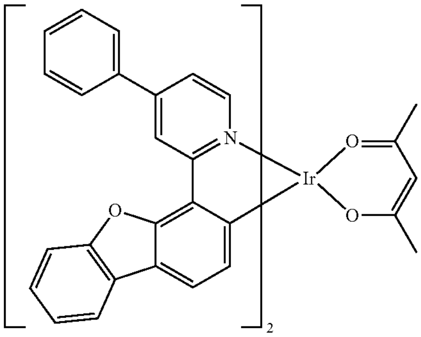
D-53
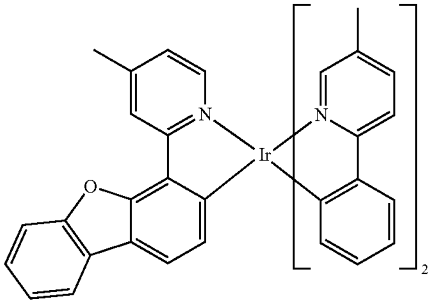
D-54
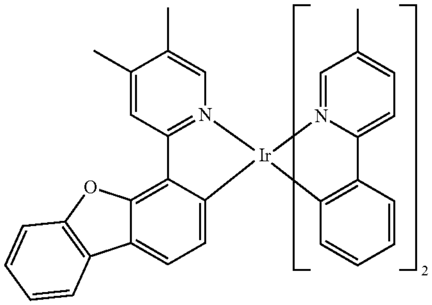
D-55
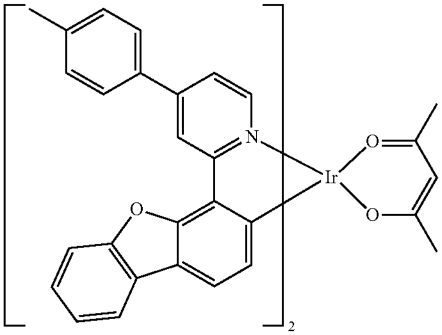
D-56
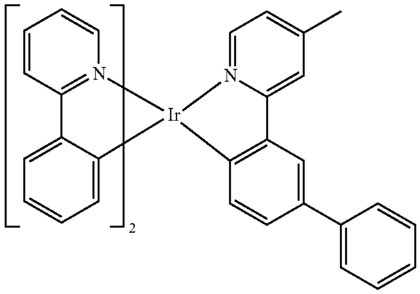

-continued
D-57
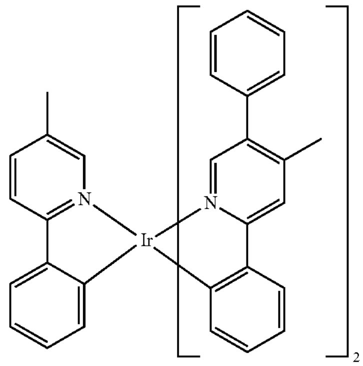
D-58
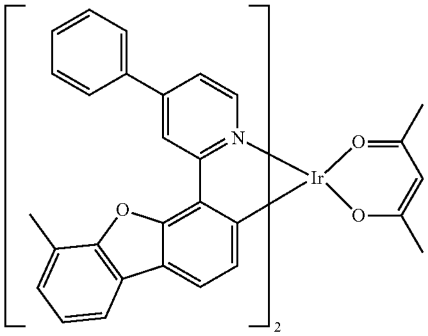
D-59
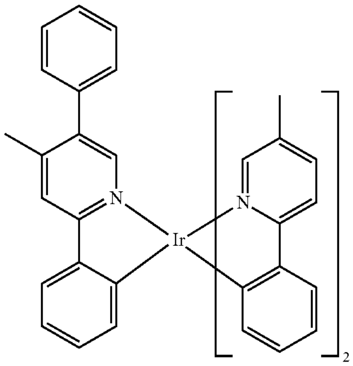
D-60
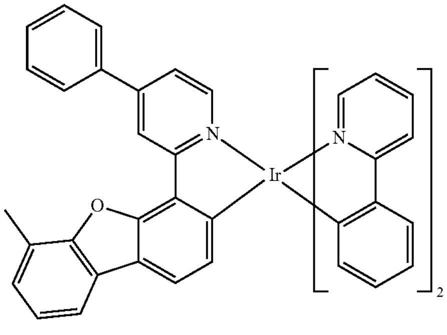
-continued
D-61
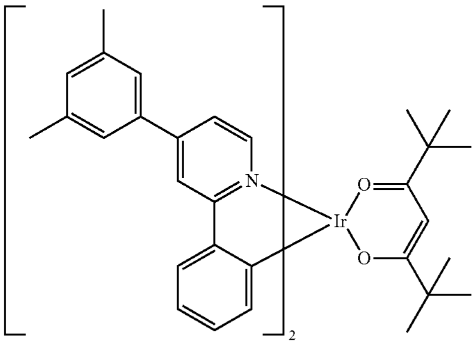
D-62
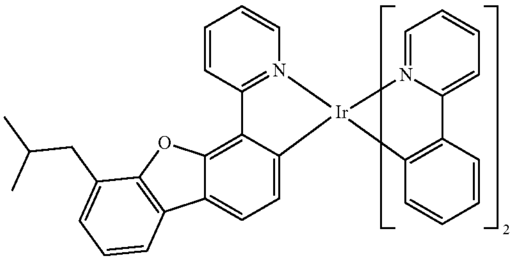
D-63
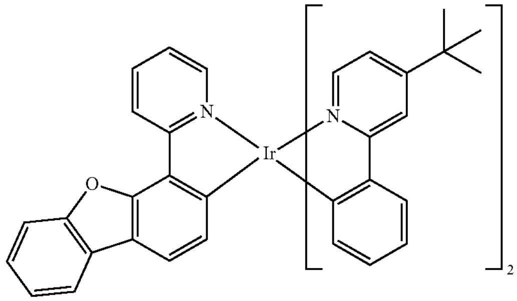
D-64
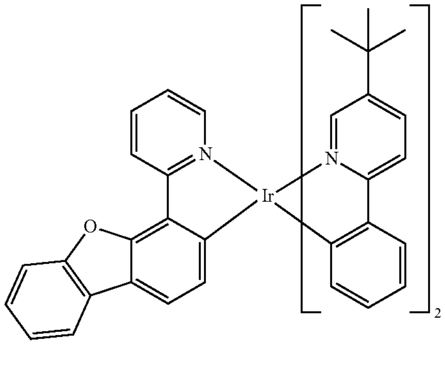

-continued
D-65
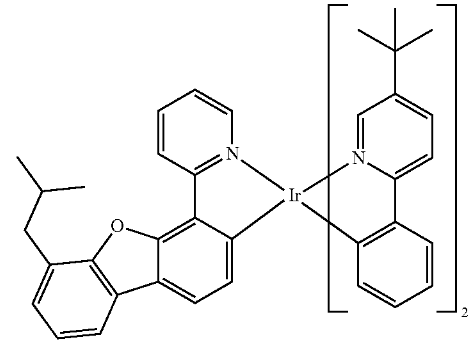
D-66
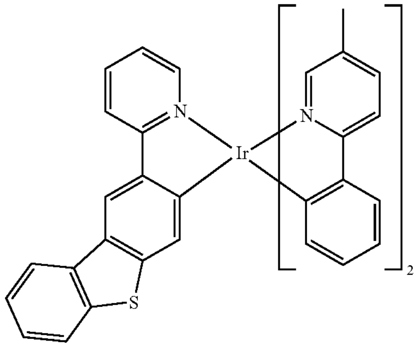
D-67
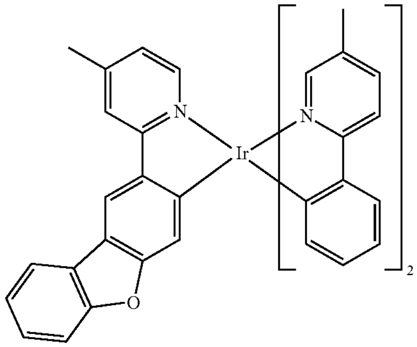
D-68
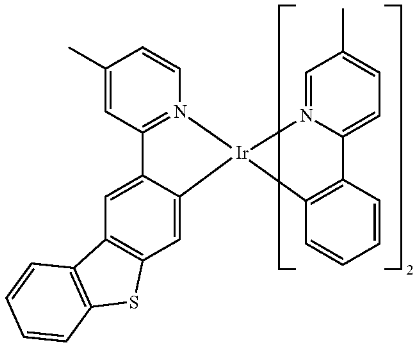
-continued
D-69
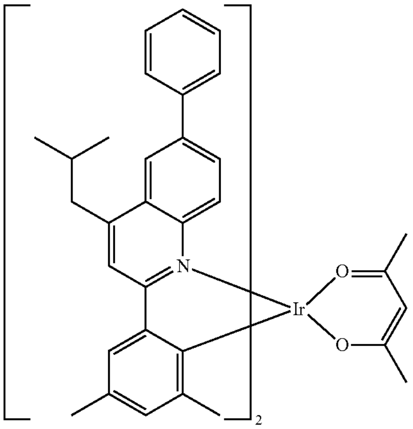
D-70
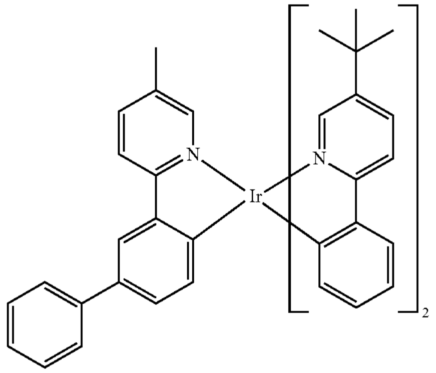
D-71
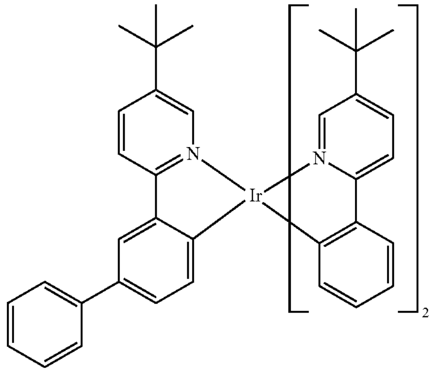
D-72
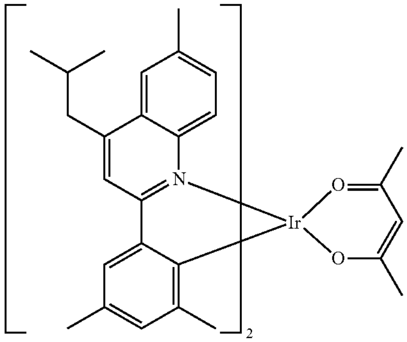

D-73
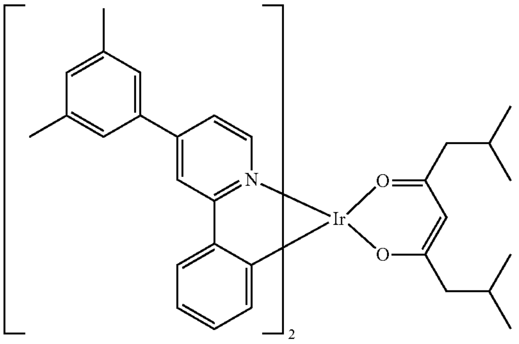
D-74
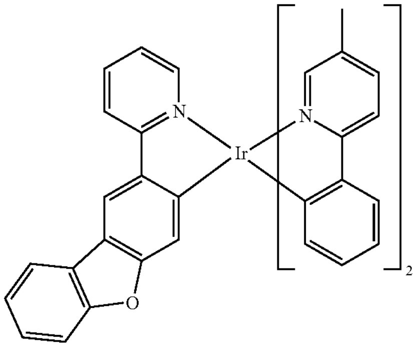
D-75
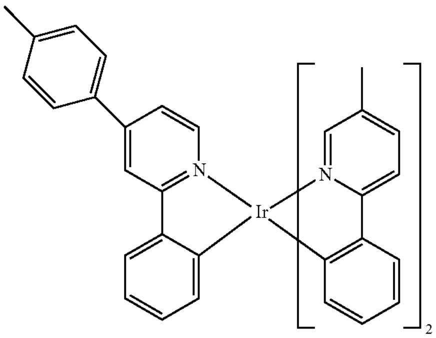
D-76
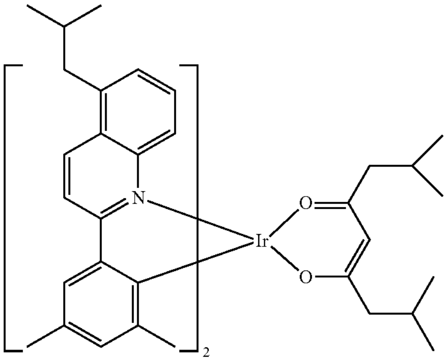
D-77
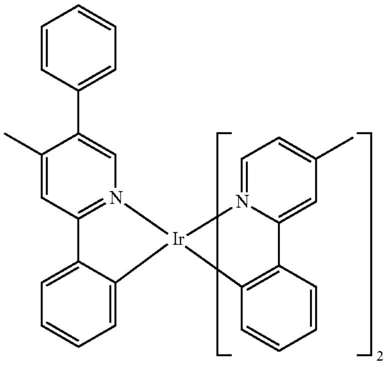
D-78
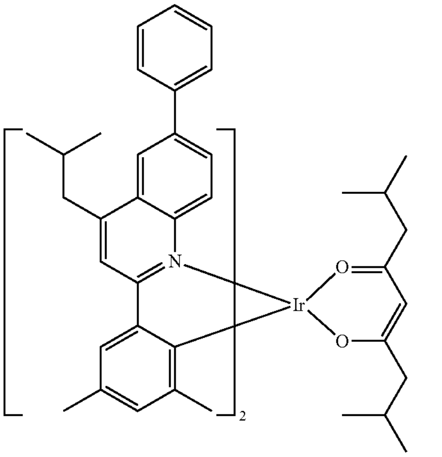
D-79
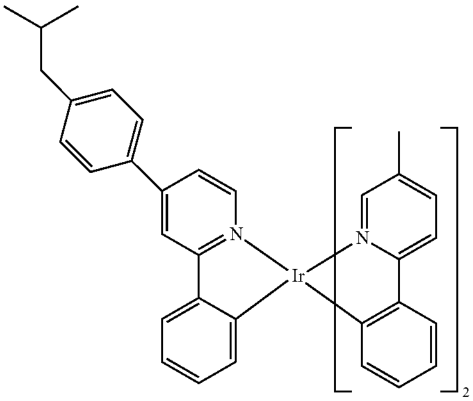
D-80
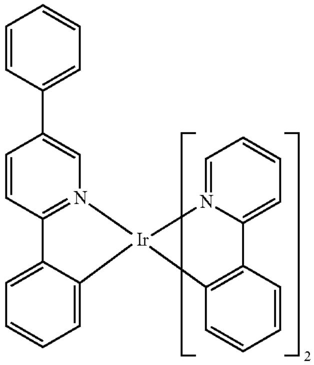

-continued
D-81
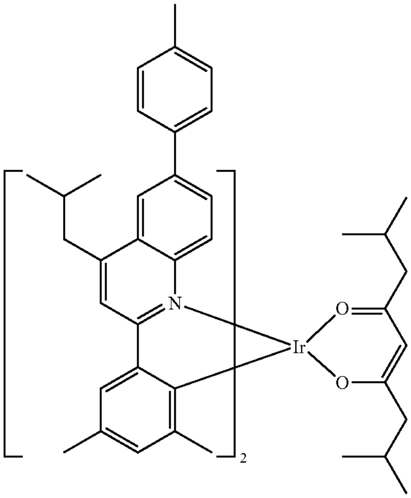
D-82
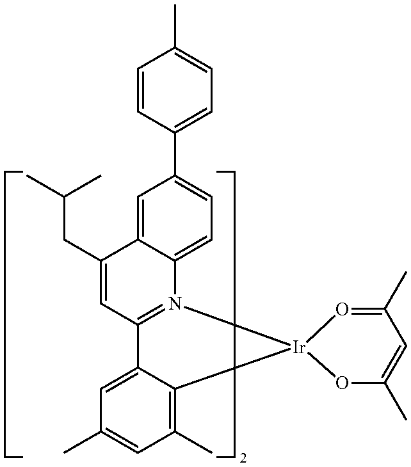
D-83
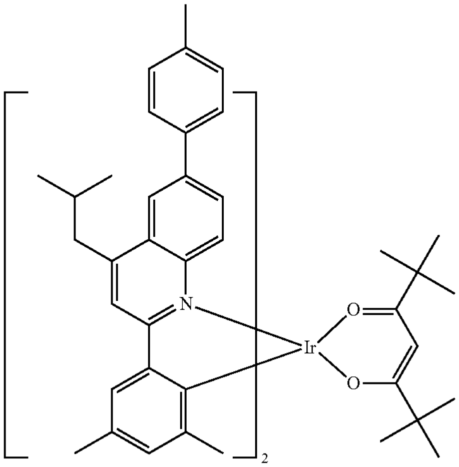
-continued
D-84
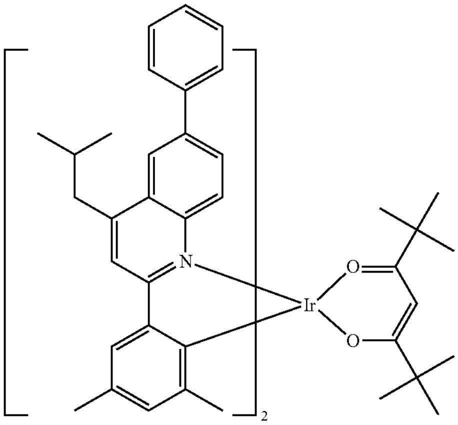
D-85
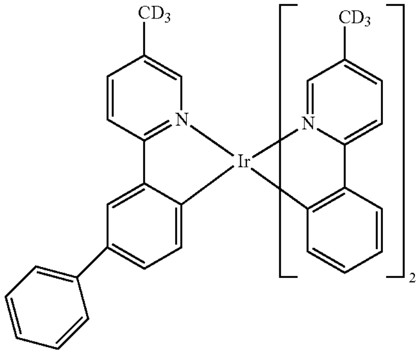
D-86
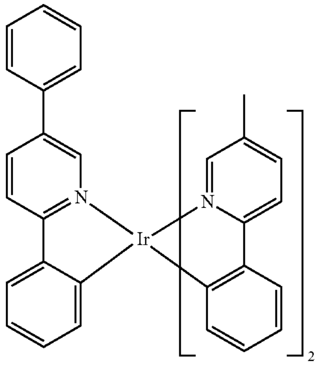
D-87
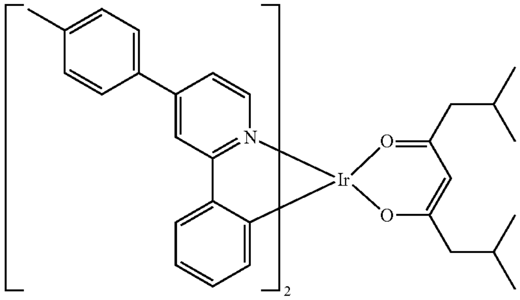

-continued
D-88
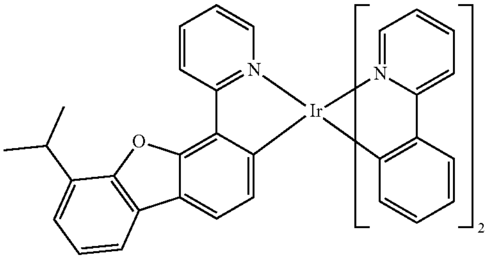
D-89
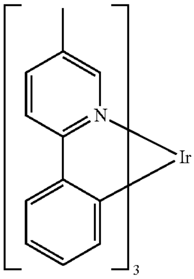
D-90
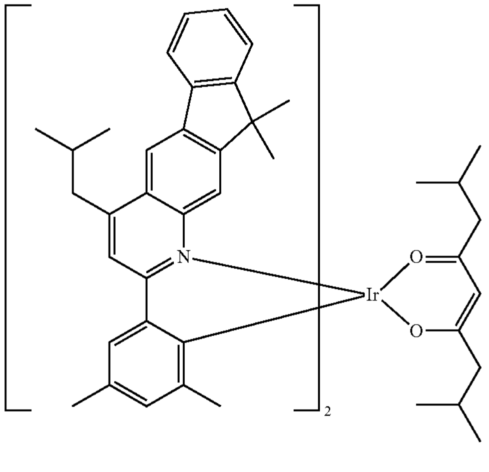
D-91
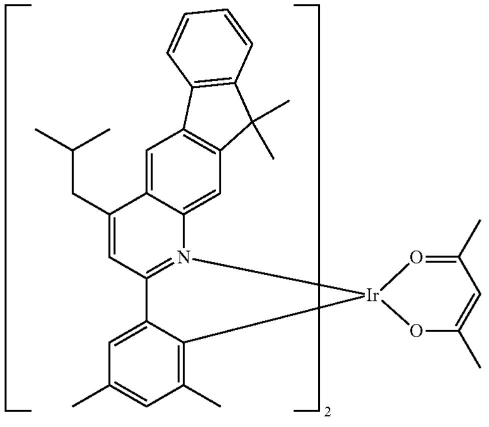
-continued
D-92
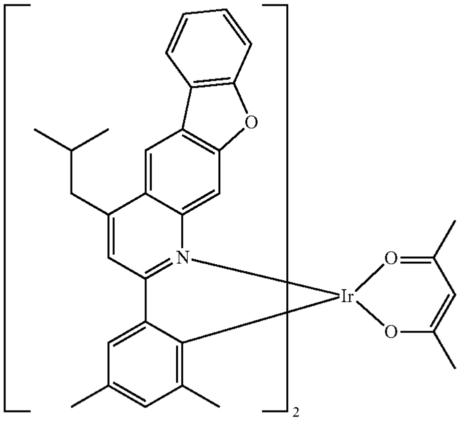
D-93
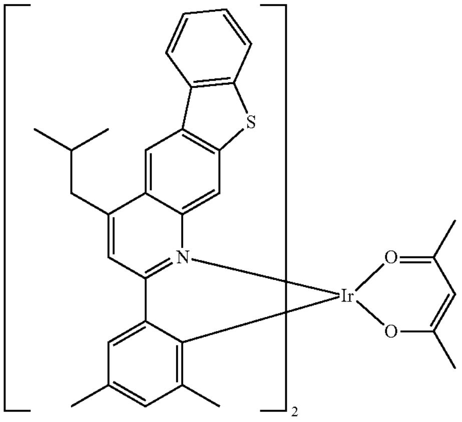
D-94
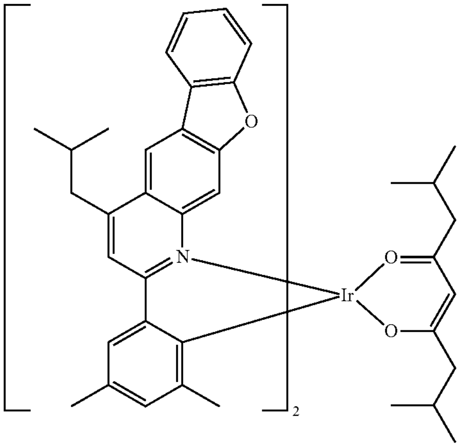

-continued
D-95
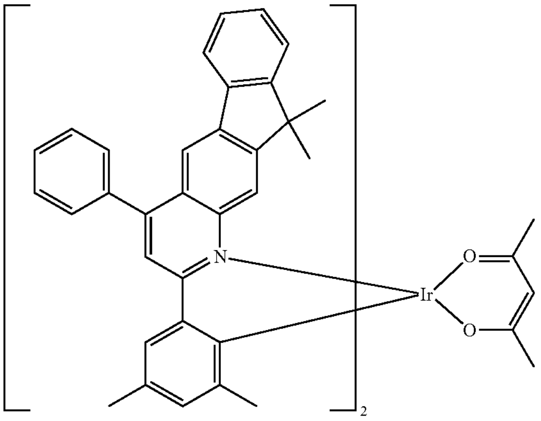
D-96
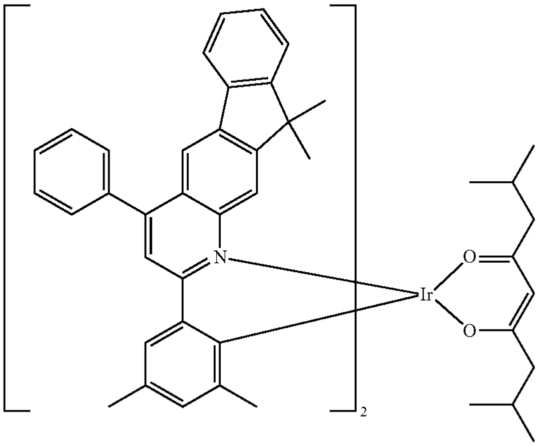
D-97
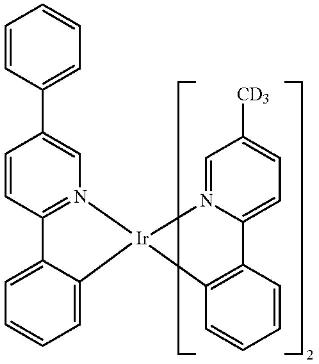
D-98
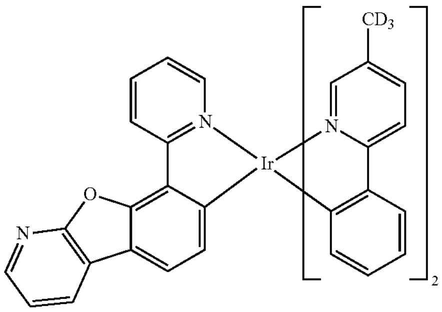
-continued
D-99
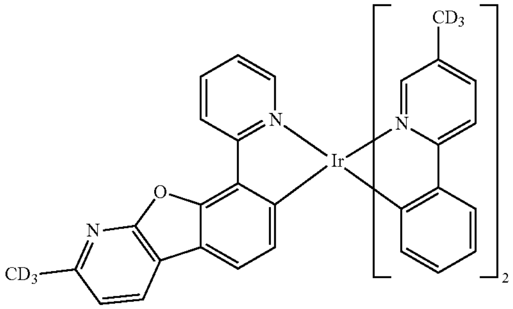
D-100
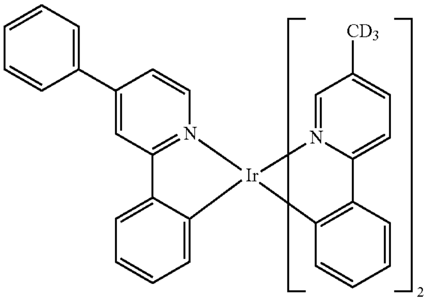
D-101
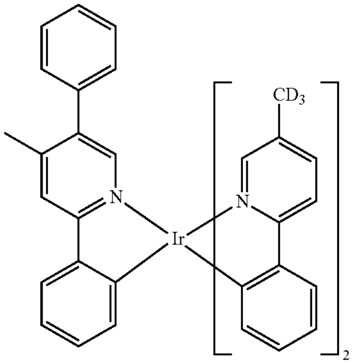
D-102
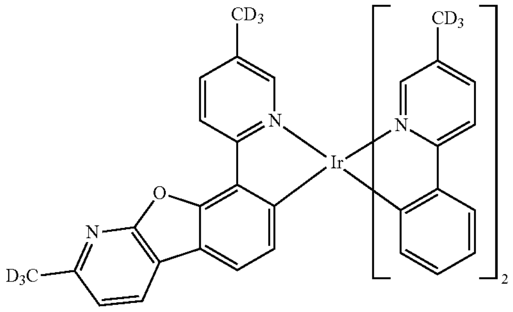

-continued
D-103
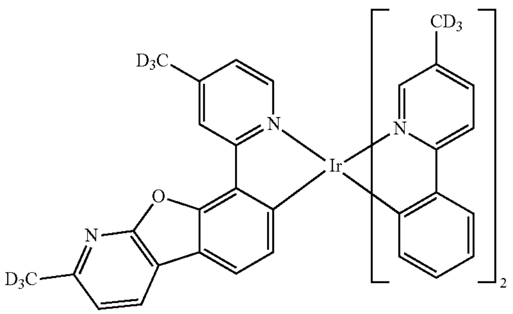
D-104
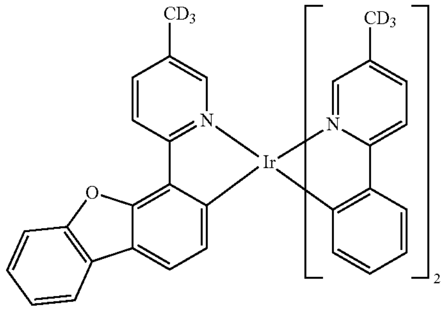
D-105
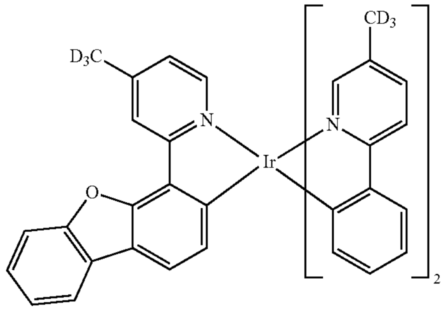
D-106
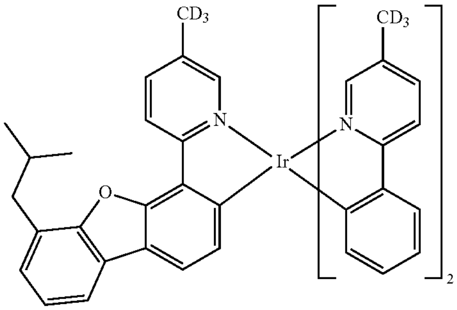
D-107
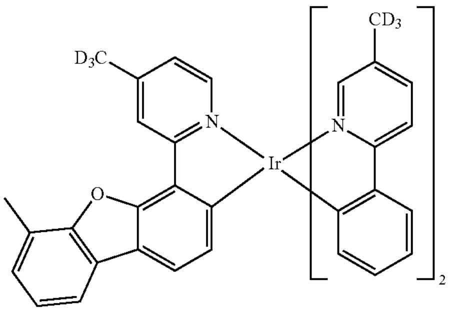
-continued
D-108
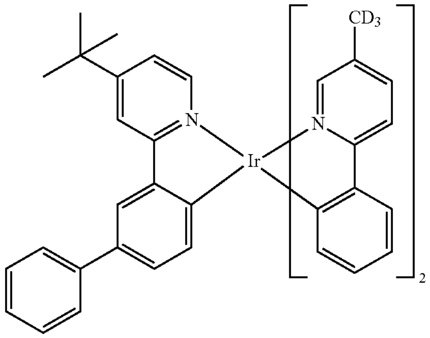
D-109
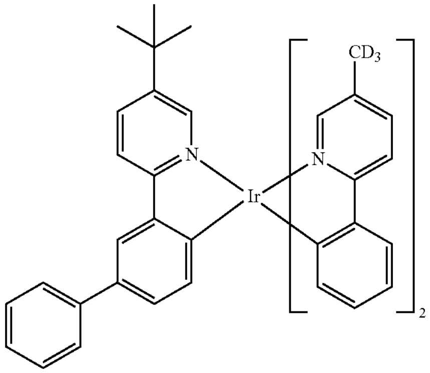
D-110
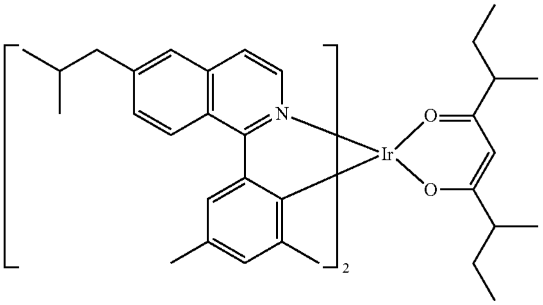
D-111
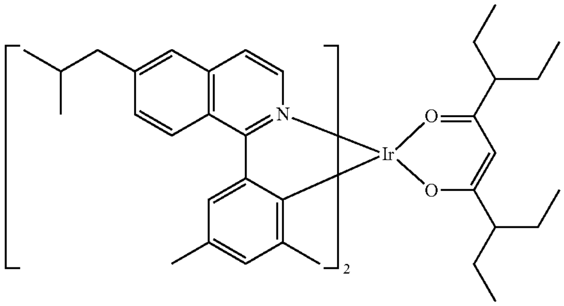

-continued
D-112
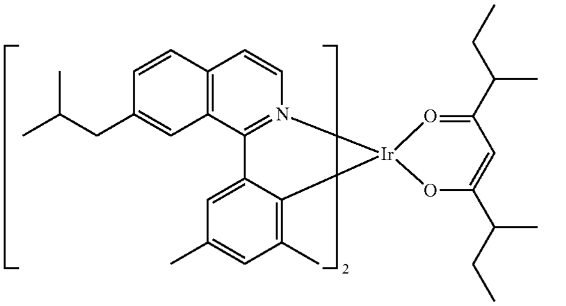
D-113
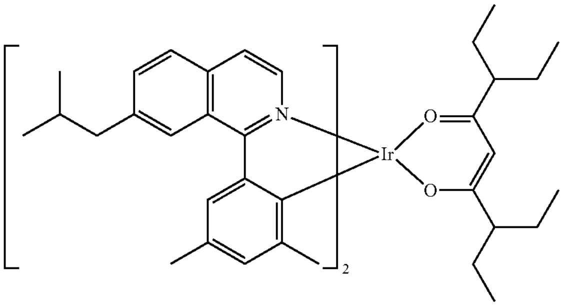
D-114
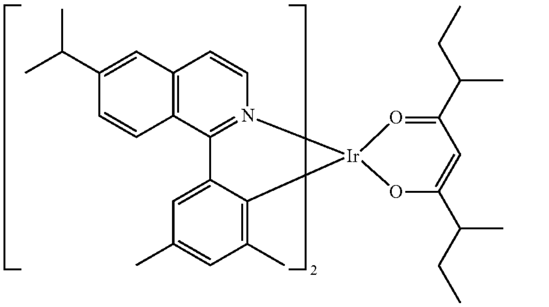
D-115
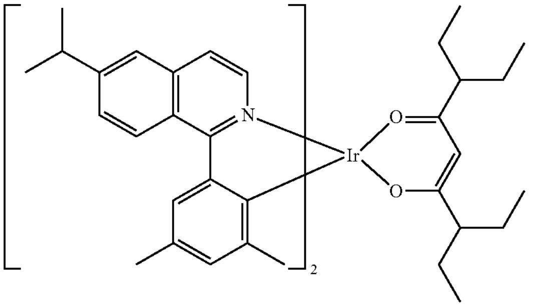
D-116
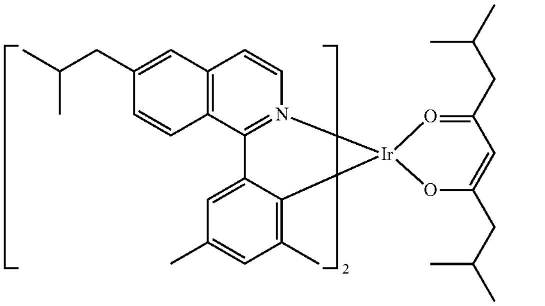
-continued
D-117
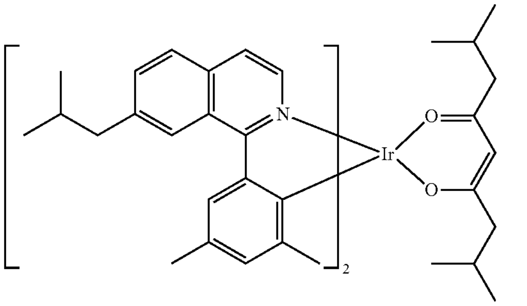
D-118
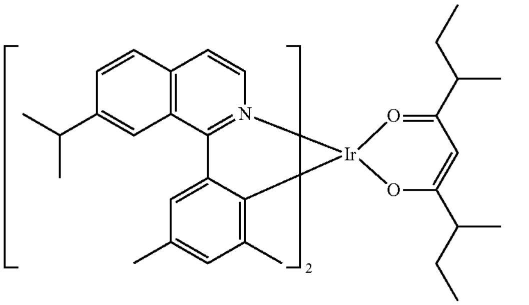
D-119
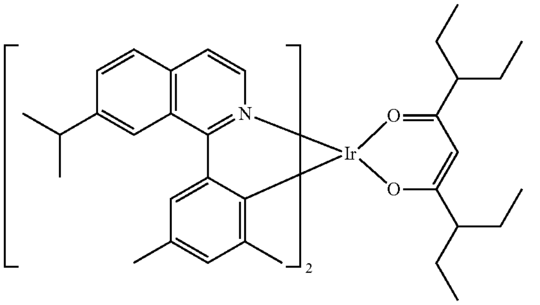
D-120
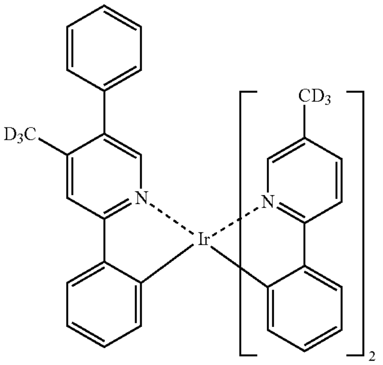

-continued
D-121
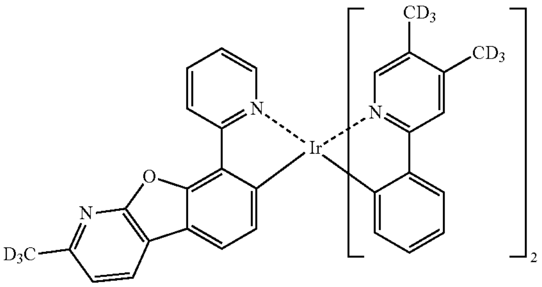
D-122
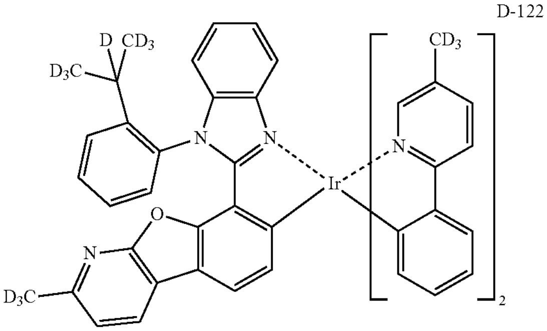
D-123
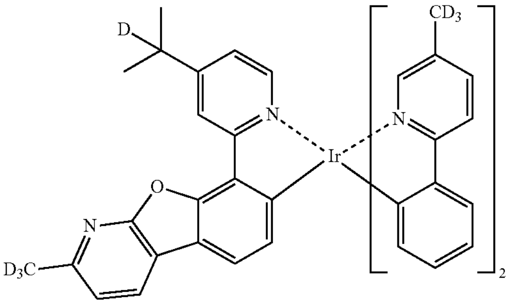
D-124
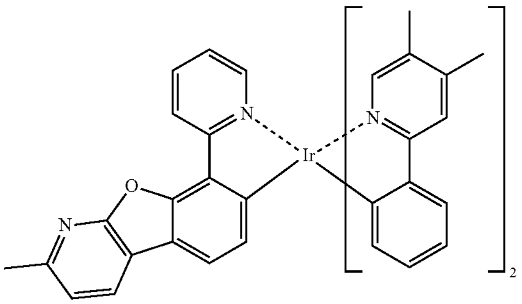
D-125
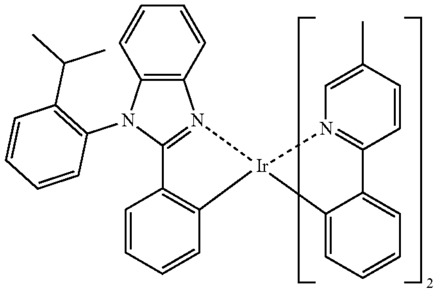
-continued
D-126
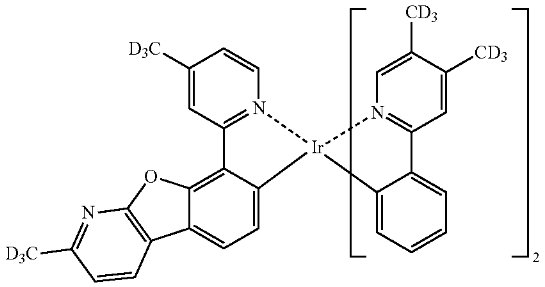
D-127
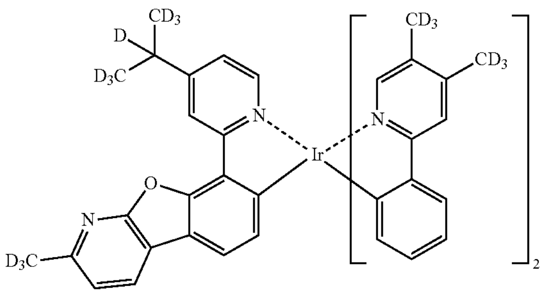
D-128
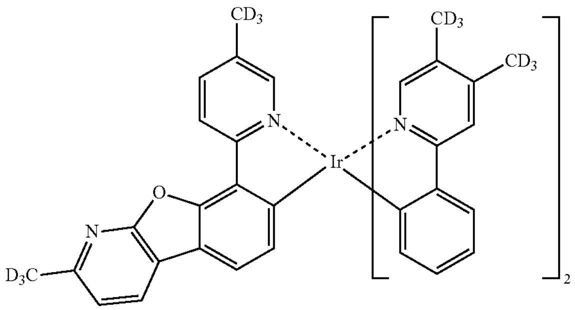
D-129
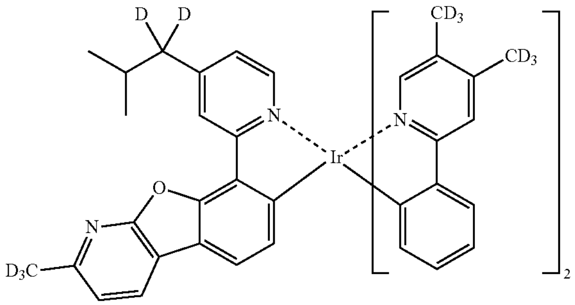
D-130
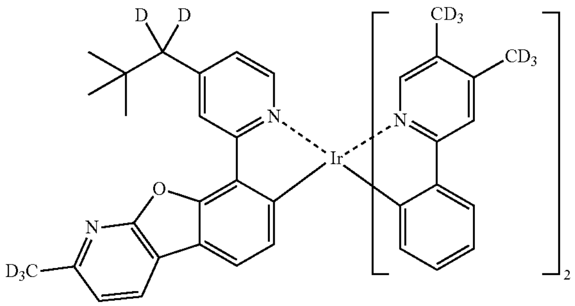

-continued
D-131
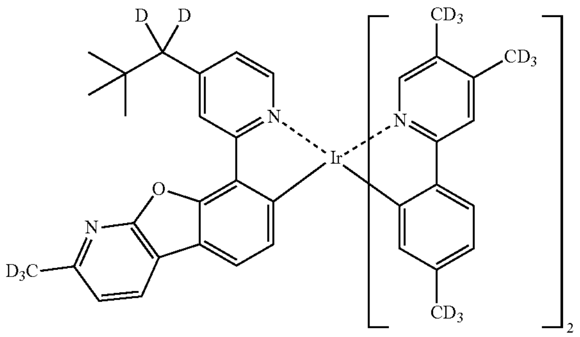
D-132
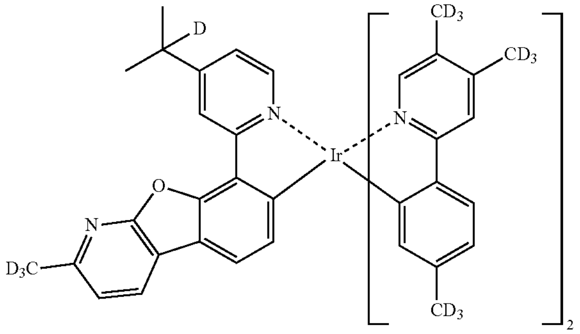
D-133
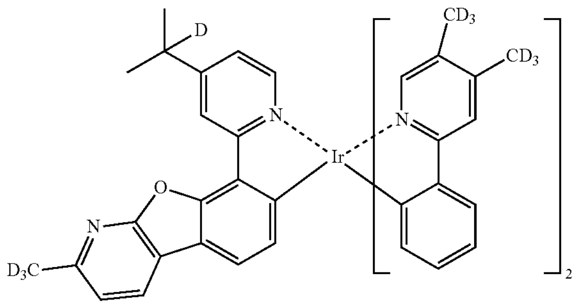
D-134
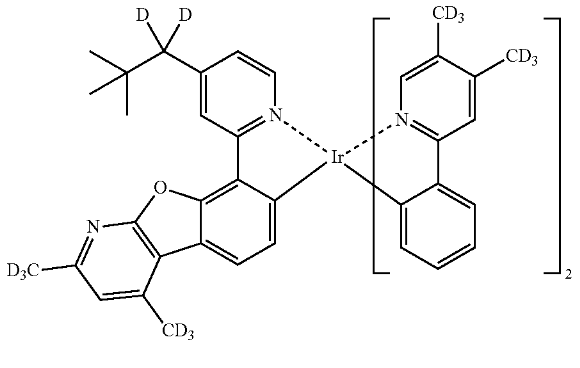
-continued
D-135
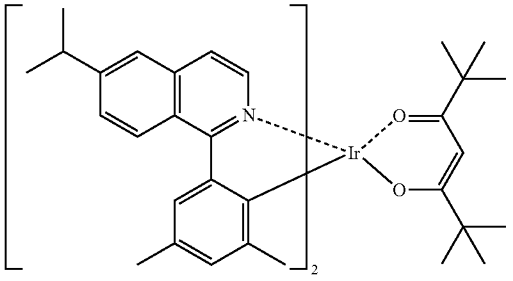
D-136
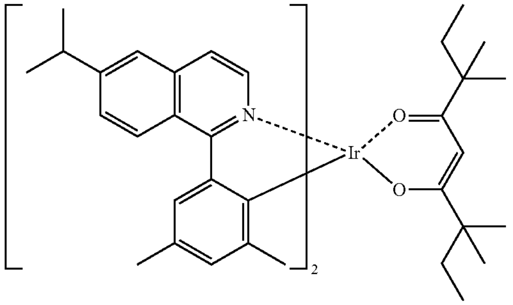
D-137
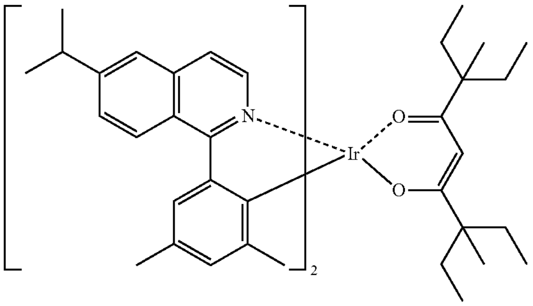
D-138
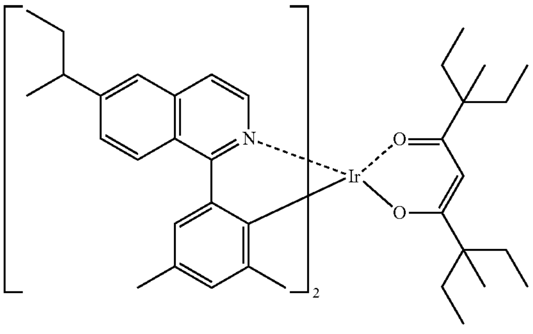
D-139
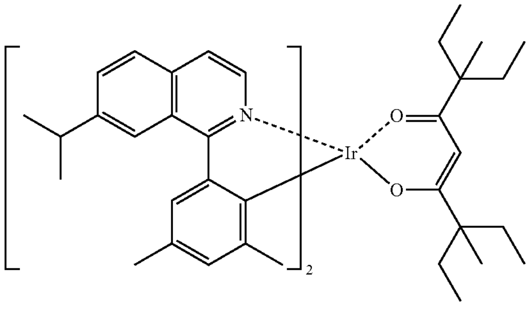

-continued
D-140
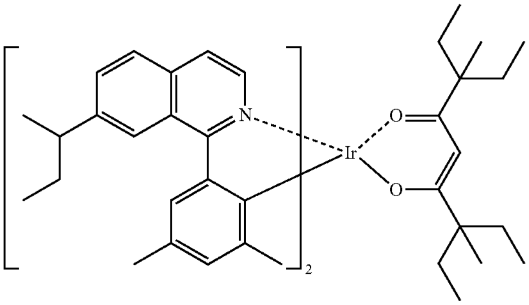
D-141
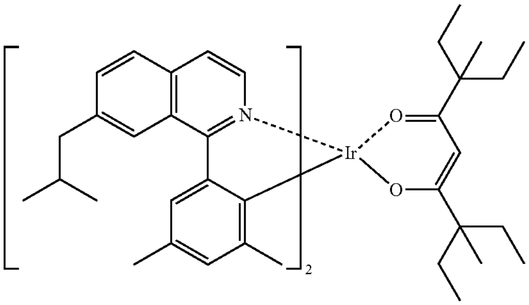
D-142
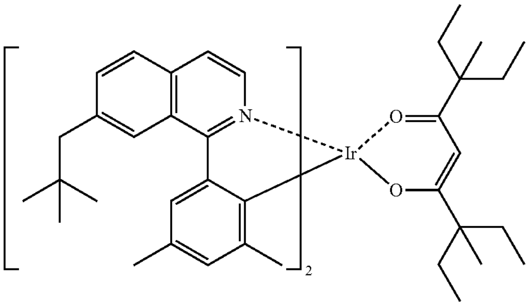
D-143
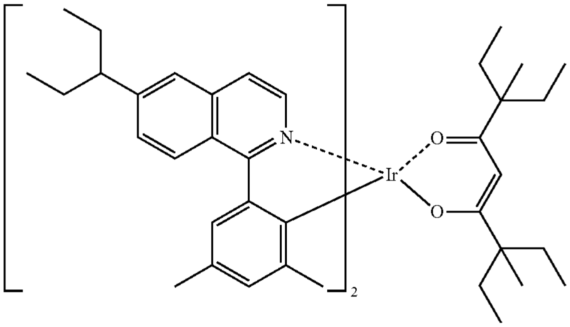
-continued
D-144
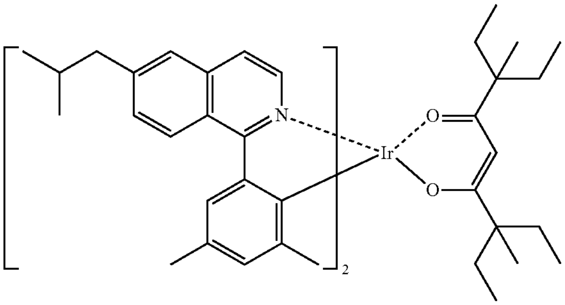
D-145
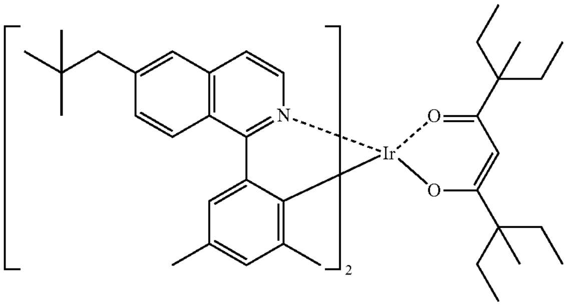
D-146
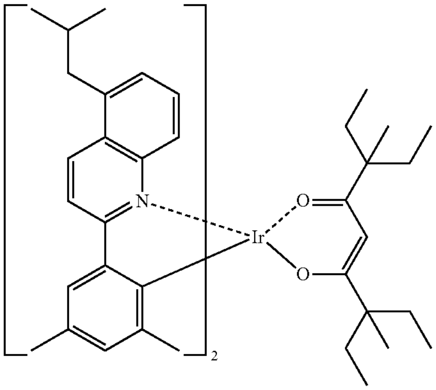
D-147
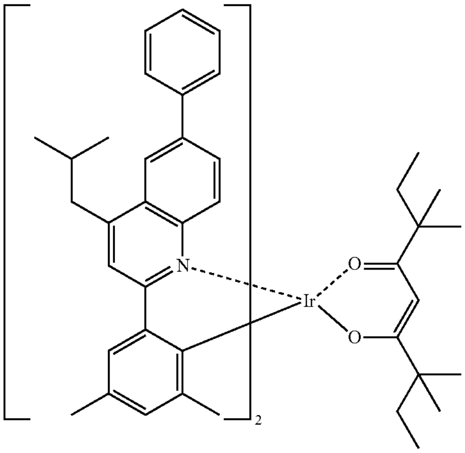

-continued

D-148

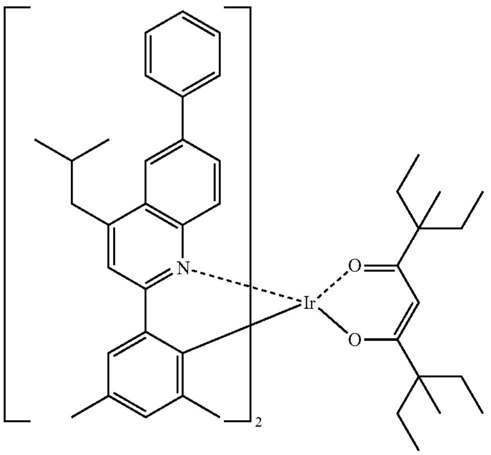

D-149

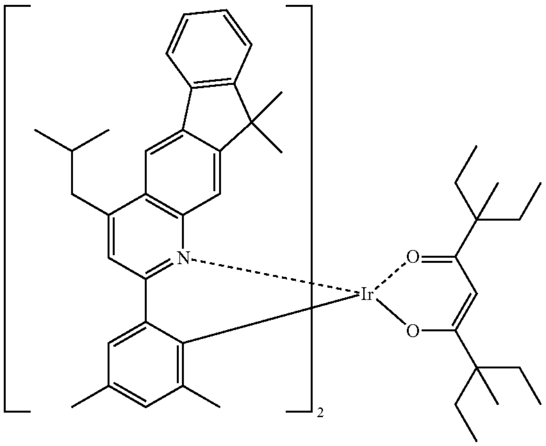

In order to form each layer of the organic electroluminescent device of the present disclosure, dry film-forming methods such as vacuum evaporation, sputtering, plasma, ion plating methods, etc., or wet film-forming methods such as spin coating, dip coating, flow coating methods, etc., can be used. When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

When forming a layer by the first host compound and the second host compound according to one embodiment, the layer can be formed by the above-listed methods, and can often be formed by co-deposition or mixture-deposition. The co-deposition is a mixed deposition method in which two or more materials are put into respective individual crucible sources and a current is applied to both cells simultaneously to evaporate the materials and to perform mixed deposition; and the mixed deposition is a mixed deposition method in which two or more materials are mixed in one crucible source before deposition, and then a current is applied to one cell to evaporate the materials.

According to one embodiment, when the first host compound and the second host compound exist in the same layer or different layers in the organic electroluminescent device, the layers by the two host compounds may be separately formed. For example, after depositing the first host compound, a second host compound may be deposited.

According to one embodiment, the present disclosure can provide display devices comprising a plurality of host materials comprising a first host compound represented by formula 1 and a second host compound represented by formula 2. In addition, the organic electroluminescent device of the present disclosure can be used for the manufacture of display devices such as smartphones, tablets, notebooks, PCs, TVs, or display devices for vehicles, or lighting devices such as outdoor or indoor lighting.

Hereinafter, the preparation method of host compounds according to the present disclosure will be explained with reference to the synthesis method of a representative compound or intermediate compound in order to understand the present disclosure in detail.

EXAMPLE 1

Synthesis of of Compound C-28

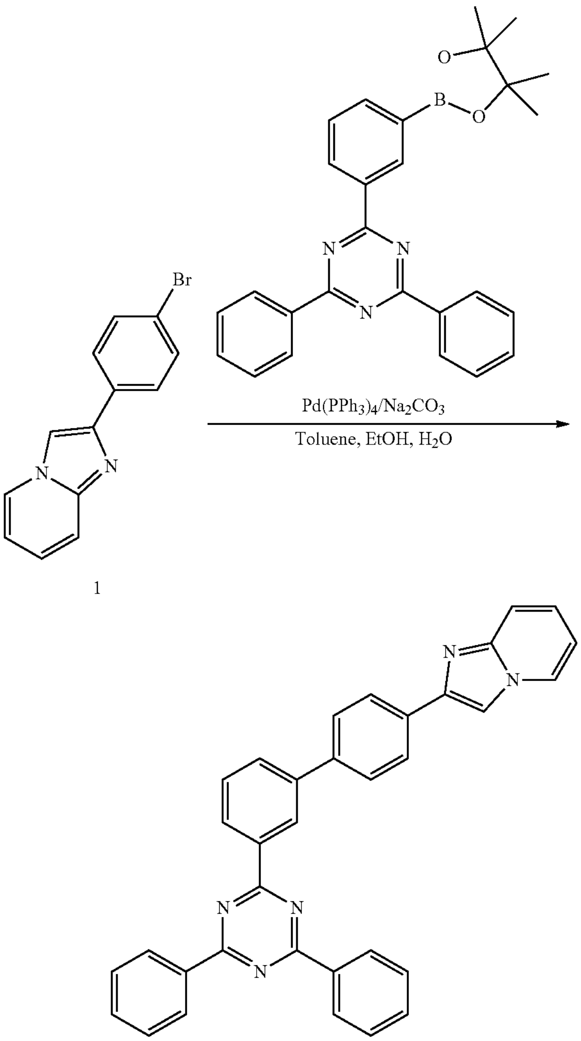

1

C-28

Compound 1 (5.0 g, 18.31 mmol), 2,4-diphenyl-6-(3-(4,4,5,5-tetermethyl-1,3,2-dioxaboran-2-yl)phenyl)-1,3,5-triazine (7.2 g, 16.64 mmol), tetrakis(triphenylphosphine) palladium ($Pd(PPh_3)_4$) (0.6 g, 0.50 mmol), sodium carbonate ($Na_2CO_3$) (4.4 g, 41.60 mmol), 83 mL of toluene, 21 mL of ethanol, and 21 mL of $H_2O$ were added to the reaction vessel, and then stirred at 120° C. for 4 hours. After completion of the reaction, the mixture was washed with distilled water, the organic layer was extracted with ethyl acetate, followed by drying with magnesium sulfate, and the solvent was removed with rotary evaporator. Next it was separated by column chromatography to obtain compound C-28 (5.9 g, yield: 71%).

| | MW | M.P |
|---|---|---|
| C-28 | 501.59 | 275° C. |

EXAMPLE 2

Synthesis of of Compound C-31

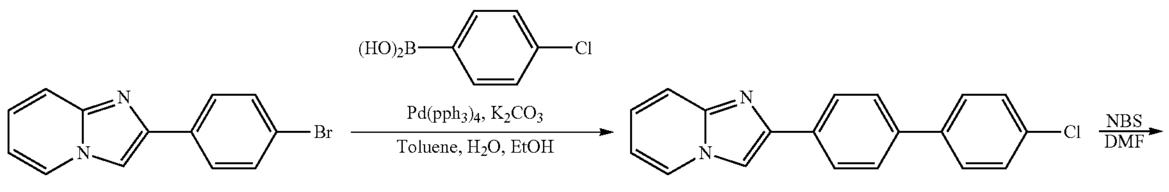

1

2-1

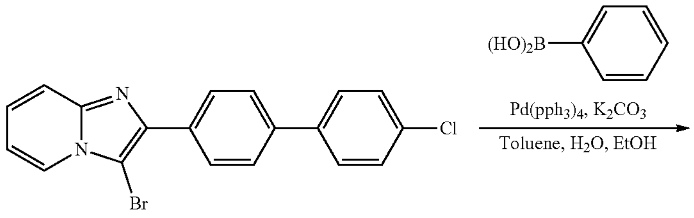

2-2

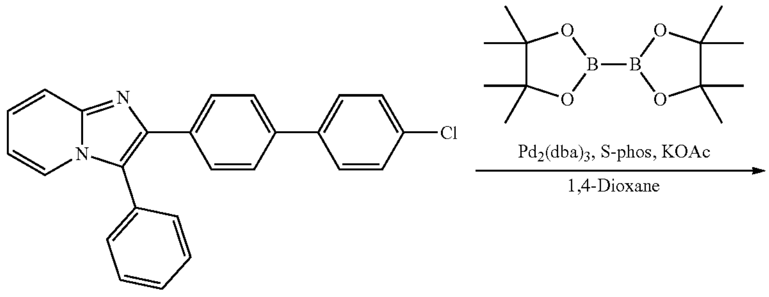

2-3

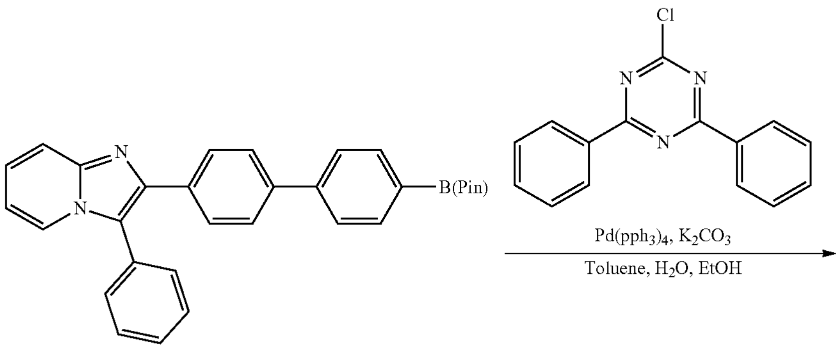

2-4

-continued

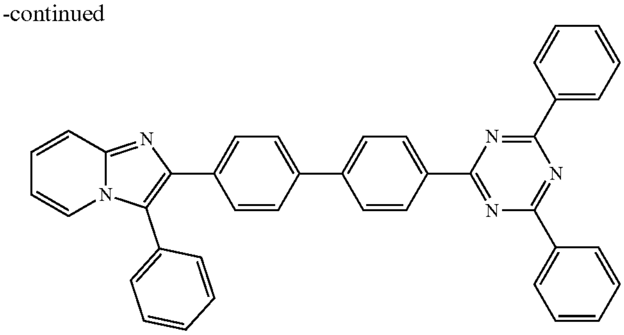

C-31

1) Synthesis of of Compound 2-1

Compound 1 (20 g, 73.23 mmol), (4-chlorophenyl)boronic acid (12.6 g, 80.55 mmol), $Pd(PPh_3)_4$ (2.54 g, 2.2 mmol), $K_2CO_3$ (25.3 g, 183.1 mmol), 366 mL of toluene, 92 mL of ethanol and 92 mL of water were dissolved in a flask, and then stirred under reflux at 120° C. for 4 hours. After completion of the reaction, the organic layer was extracted with ethyl acetate, followed by drying with magnesium sulfate. Next, it was distilled under reducted pressure, and separated by column chromatography to obtain compound 2-1 (10.9 g, yield: 49%).

2) Synthesis of of Compound 2-2

Compound 2-1 (10.3 g, 33.80 mmol) and 170 mL of dimethylformamide (DMF) were dissolved in a flask, and then stirred under reflux at 0° C. for 10 minutes. Next, N-bromosuccinimide (NBS) (7.82 g, 43.93 mmol) was added to the mixture, and then stirred under reflux for 1 hour. After completion of the reaction, the solid was extracted with $H_2O$, and washed with methanol. Next it was separated by column chromatography to obtain compound 2-2 (11.0 g, yield: 85%).

3) Synthesis of of Compound 2-3

Compound 2-2 (10.6 g, 27.63 mmol), phenylboronic acid (3.7 g, 30.38 mmol), $Pd(PPh_3)_4$ (0.96 g, 0.83 mmol), $K_2CO_3$ (9.5 g, 69.1 mmol), 140 mL of toluene, 35 mL of ethanol, and 35 mL of $H_2O$ were dissolved in a flask, and then stirred under reflux at 120° C. for 4 hours. After completion of the reaction, the organic layer was extracted with ethyl acetate, followed by drying with magnesium sulfate. Next, it was distilled under reducted pressure, and separated by column chromatography to obtain compound 2-3 (9.4 g, yield: 81%).

4) Synthesis of of Compound 2-4

Compound 2-3 (9.4 g, 24.68 mmol), bis(pinacolato)diboron (7.52 g, 29.61 mmol), tris(dibenzylideneacetone)dipalladium (0)($Pd_2(dba)_3$) (0.9 g, 0.99 mmol), S-Phos, (0.8 g, 1.97 mmol), potassium acetate (KOAc) (7.3 g, 74.0 mmol), and 50 mL of 1,4-dioxane were added to a flask, and then stirred under reflux. After completion of the reaction, the organic layer was extracted with ethyl acetate, followed by drying with magnesium sulfate. Next, it was distilled under reducted pressure, and separated by column chromatography to obtain compound 2-4 (11.5 g, yield: 99%).

5) Synthesis of of Compound C-31

Compound 2-4 (5.0 g, 10.58 mmol), 2-chloro-4,6-diphenyl-1,3,5-triazine (3.55 g, 10.58 mmol), $Pd(PPh_3)_4$ (0.37 g, 0.32 mmol), $K_2CO_3$ (3.7 g, 26.37 mmol), 50 mL of toluene, 12.5 mL of ethanol, and 12.5 mL of $H_2O$ were dissolved in a flask, and then stirred under reflux at 120° C. for 4 hours. After completion of the reaction, the organic layer was extracted with ethyl acetate, followed by drying with magnesium sulfate. Next, it was distilled under reducted pressure, and separated by column chromatography to obtain compound C-31 (2.7 g, yield: 44%).

| | MW | M.P |
|---|---|---|
| C-31 | 577.7 | 217.0° C. |

EXAMPLE 3

Synthesis of of Compound C-38

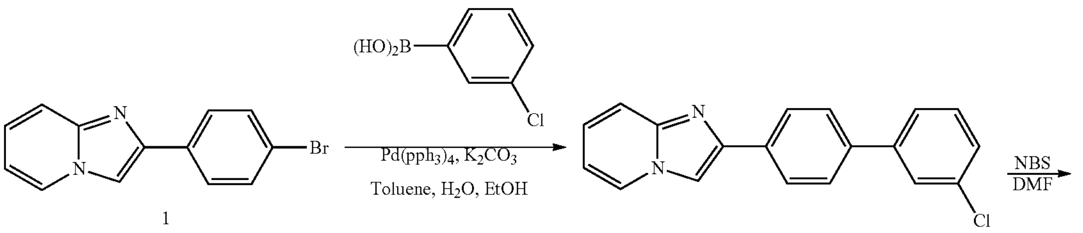

1

3-1

-continued

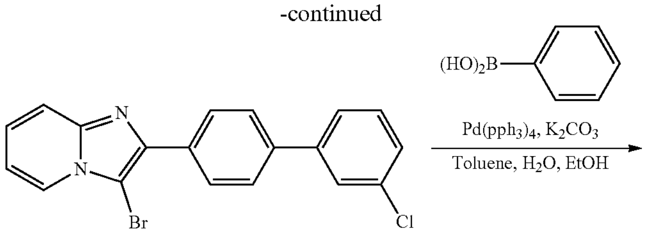

3-2

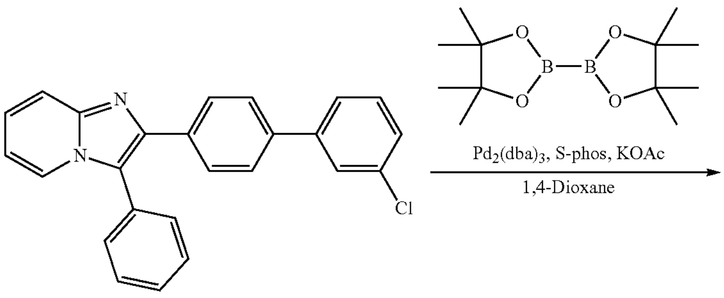

3-3

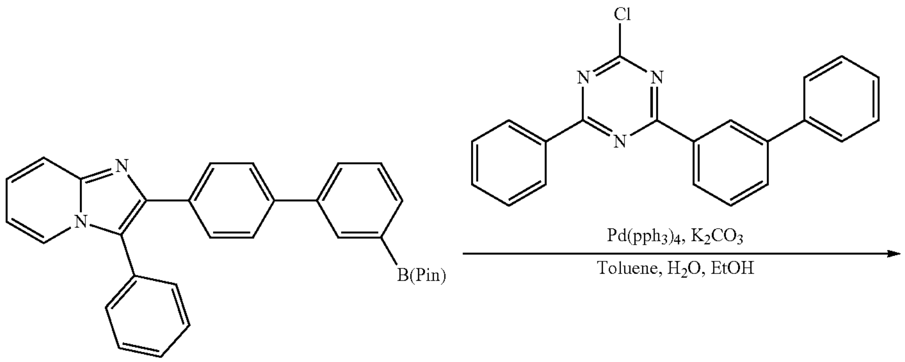

3-4

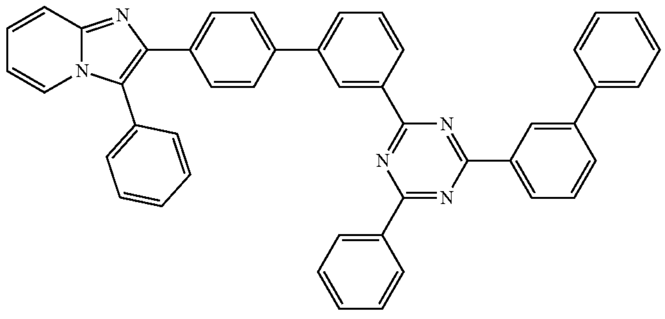

C-38

1) Synthesis of of Compound 3-1

Compound 1 (20 g, 73.23 mmol), (3-chlorophenyl)boronic acid (12.6 g, 80.55 mmol), $Pd(PPh_3)_4$ (2.54 g, 2.2 mmol), $K_2CO_3$ (25.3 g, 183.1 mmol), 366 mL of toluene, 92 mL of ethanol, and 92 mL of $H_2O$ were dissolved in a flask, and then stirred under reflux at 120° C. for 4 hours. After completion of the reaction, the organic layer was extracted with ethyl acetate, followed by drying with magnesium sulfate. Next, it was distilled under reducted pressure, and separated by column chromatography to obtain compound 3-1 (18.0 g, yield: 81%).

2) Synthesis of of Compound 3-2

Compound 3-1 (18.0 g, 59.06 mmol) amd 300 mL of DMF were dissolved in a flask, and then stirred under reflux at 0° C. for 10 minutes. Next, NBS (13.7 g, 76.78 mmol) was added to the mixture, and stirred under reflux for 1 hour. After completion of the reaction, the solid was extracted with $H_2O$, and washed with methanol. Next, it was separated by column chromatography to obtain compound 3-2 (19.0 g, yield: 83%).

3) Synthesis of of Compound 3-3

Compound 3-2 (19.0 g, 49.52 mmol), phenylboronic acid (6.6 g, 54.47 mmol), $Pd(PPh_3)_4$ (1.72 g, 1.49 mmol), $K_2CO_3$ (17.1 g, 123.8 mmol), 250 mL of toluene, 62 mL of ethanol, and 62 mL of $H_2O$ were dissolved in a flask, and then stirred under reflux at 120° C. for 4 hours. After completion of the reaction, the organic layer was extracted with ethyl acetate, followed by drying with magnesium sulfate. Next, it was distilled under reducted pressure, and separated by column chromatography to obtain compound 3-3 (11.0 g, yield: 58%).

4) Synthesis of of Compound 3-4

Compound 3-3 (11.0 g, 28.88 mmol), bis(pinacolato) diboron (8.8 g, 34.65 mmol), $Pd_2(dba)_3$ (1.1 g, 1.15 mmol), S-phos, (0.95 g, 2.31 mmol), KOAc (8.5 g, 86.6 mmol), and 145 mL of 1,4-dioxane were added to a flask, and then stirred under reflux. After completion of the reaction, the organic layer was extracted with ethyl acetate, followed by drying with magnesium sulfate. Next, it was distilled under reducted pressure, and separated by column chromatography to obtain compound 3-4 (8.1 g, yield: 59%).

5) Synthesis of of Compound C-38

Compound 3-4 (5.0 g, 10.58 mmol), 2-([1,1'-dibiphenyl] 3-yl)-4-chloro-6-phenyl-1,3,5-triazine (3.55 g, 10.58 mmol), tetrakis(triphenylphosphine) palladium (O) (0.37 g, 0.32 mmol), potassium carbonate ($K_2CO_3$) (3.7 g, 26.37 mmol), 50 mL of toluene, 12.5 mL of ethanol and 12.5 mL of $H_2O$ were dissolved in a flask, and then stirred under reflux at 120° C. for 4 hours. After completion of the reaction, the organic layer was extracted with ethyl acetate, followed by drying with magnesium sulfate. Next, it was distilled under reducted pressure, and separated by column chromatography to obtain compound C-38 (1.7 g, yield: 28%).

| | MW | M.P |
|---|---|---|
| C-38 | 577.7 | 204.0° C. |

EXAMPLE 4

Preparation of Compound C-116

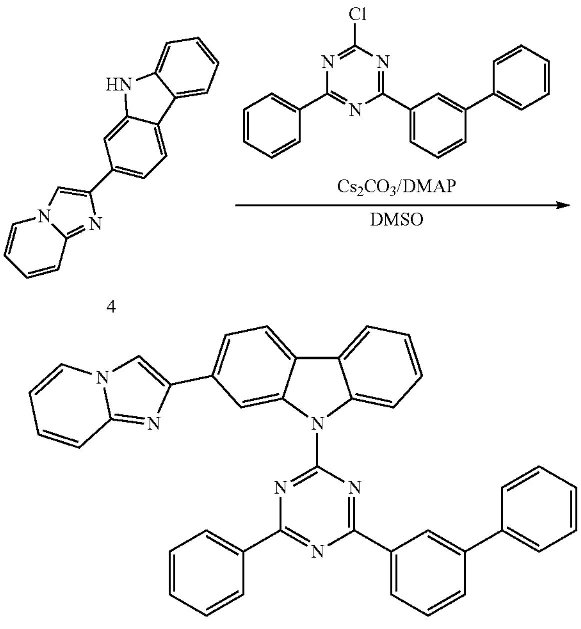

4

C-116

Compound 4 (2.6 g, 9.18 mmol), 2-([1,1'-diphenyl]-3-yl)-4-chloro-6-phenyl-1,3,5-triazine (3.8 g, 11.01 mmol), cesium carbonate ($Cs_2CO_3$) (3.0 g, 9.18 mmol), 4-dimethylaminopyridine (DMAP) (0.6 g, 4.59 mmol), and 46 mL of dimethylsulfoxide (DMSO) were added to the reaction vessel, and then stirred at 100° C. for 3 hours. After completion of the reaction, the mixture was washed with distilled water, and the organic layer was extracted with ethyl acetate, followed by drying with magnesium sulfate. Thereafter, the solvent was removed with a rotary evaporator. Next, it was separated by column chromatography to obtain compound C-116 (3.3 g, yield: 61%).

| | MW | M.P |
|---|---|---|
| C-116 | 590.87 | 324° C. |

Hereinafter, the preparation method of an organic electroluminescent device comprising the plurality of host materials and/or the organic electroluminescent compound according to the present disclosure, and the device property thereof will be explained in order to understand the present disclosure in detail.

DEVICE EXAMPLES 1 TO 3

Preparation of OLEDs Comprising a Plurality of Host Materials According to the Present Disclosure OLEDs according to the present disclosure were produced. First, a transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and thereafter was stored in isopropyl alcohol and then used. Thereafter, the ITO substrate was mounted on a substrate holder of a vacuum vapor deposition apparatus. Then, compound HI-1 was introduced into a cell of the vacuum vapor deposition apparatus, and compound HT-1 was introduced into another cell. The two materials were evaporated at different rates and compound HI-1 was deposited in a doping amount of 3 wt % based on the total amount of the two compounds to form a hole injection layer having a thickness of 10 nm. Next, compound HT-1 was deposited as a first hole transport layer having a thickness of 80 nm on the hole injection layer. Compound HT-2 was then introduced into another cell of the vacuum vapor deposition apparatus and was evaporated by applying an electric current to the cell, thereby forming a second hole transport layer having a thickness of 30 nm on the first hole transport layer. After forming the hole injection layer and the hole transport layers, a light-emitting layer was formed thereon as follows: each of the first host and the second host described in the following Tables 1 to 3 were introduced into two cells of the vacuum vapor deposition apparatus as hosts, respectively, and compound D-130 was introduced into another cell as a dopant. The two host materials were evaporated at a different rate of 2:1 and the dopant material was evaporated at a different rate, simultaneously, and was deposited in a doping amount of 10 wt % based on the total amount of the hosts and dopant to form a light-emitting layer having a thickness of 40 nm on the second hole transport layer. Next, compounds ETL-1 and EIL-1 as electron transport materials were deposited at a weight ratio of 40:60 to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, OLEDs were produced. Each compound used for all the materials was purified by vacuum sublimation under $10^{-6}$ torr.

COMPARATIVE EXAMPLES 1 TO 3

Preparation of OLEDs Comprising a Single Host Compound

OLEDs were manufactured in the same manner as in Device Example 1, except that the compound of the following Tables 1 to 3 was used as the host of the light-emitting layer alone.

The driving voltage, luminous efficiency, and the luminous color at a luminance of 1,000 nits and the time taken for luminance to decrease from 100% to 80% at a luminance of 20,000 nits (lifespan: T80) of the OLEDs of Device Examples 1 to 3 and Comparative Examples 1 to 3 produced as described above, are measured, and the results thereof are shown in the following Tables 1 to 3.

TABLE 1

| | First Host | Second Host | Driving Voltage (V) | Luminous Efficiency (cd/A) | Luminous Color | Lifespan (T80, hr) |
|---|---|---|---|---|---|---|
| Device Example 1 | C-28 | H2-4 | 3.2 | 107.4 | Green | 67.7 |
| Comparative Example 1 | C-28 | — | 3.5 | 91.6 | Green | 1.2 |

TABLE 2

| | First Host | Second Host | Driving Voltage (V) | Luminous Efficiency (cd/A) | Luminous Color | Lifespan (T80, hr) |
|---|---|---|---|---|---|---|
| Device Example 2 | C-31 | H2-4 | 2.9 | 90.3 | Green | 9.4 |
| Comparative Example 2 | C-31 | — | 3.3 | 35.6 | Green | 1.4 |

TABLE 3

| | First Host | Second Host | Driving Voltage (V) | Luminous Efficiency (cd/A) | Luminous Color | Lifespan (T80, hr) |
|---|---|---|---|---|---|---|
| Device Example 3 | C-38 | H2-4 | 3.1 | 103.6 | Green | 15.0 |
| Comparative Example 3 | C-38 | — | 2.8 | 70.2 | Green | 0.7 |

From Tables 1 to 3 above, it can be seen that an organic electroluminescent device comprising a specific combination of compounds according to the present disclosure as host materials has excellent light-emitting characteristics, and significantly improved lifespan characteristics.

DEVICE EXAMPLE 4

Preparation of an OLED Comprising a Single Host Compound

An OLED was manufactured in the same manner as in Device Example 1, except that Compound C-116 was used as the host of the light-emitting layer alone.

The luminous color at a luminance of 1,000 nits and the time taken for luminance to decrease from 100% to 80% at a luminance of 20,000 nits (lifespan: T80) of the OLED of Device Example 4 produced as described above, are measured, and the results thereof are compared with Comparative Examples 1 to 3 above and are shown in the following Table 4.

TABLE 4

| | Host Material | Luminous Color | Lifespan (T80, hr) |
|---|---|---|---|
| Device Example 4 | C-116 | Green | 3.2 |
| Comparative Example 1 | C-28 | Green | 1.2 |
| Comparative Example 2 | C-31 | Green | 1.4 |
| Comparative Example 3 | C-38 | Green | 0.7 |

From Table 4 above, it can be confirmed that the organic electroluminescent device comprising the organic electroluminescent compound represented by formula 1A as a host material exhibits improved lifespan characteristics.

The compounds used in Device Examples and Comparative Examples are specifically shown in the following Table 5.

TABLE 5

| | |
|---|---|
| Hole Injection Layer/ Hole Transport Layer | 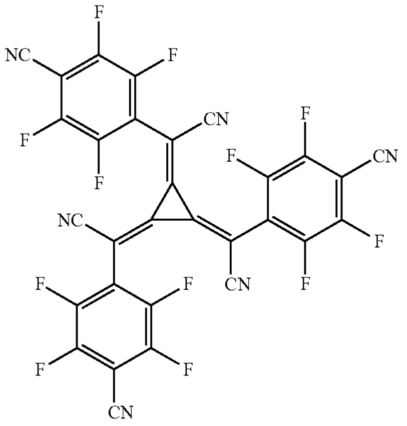 HI-1 |

TABLE 5-continued
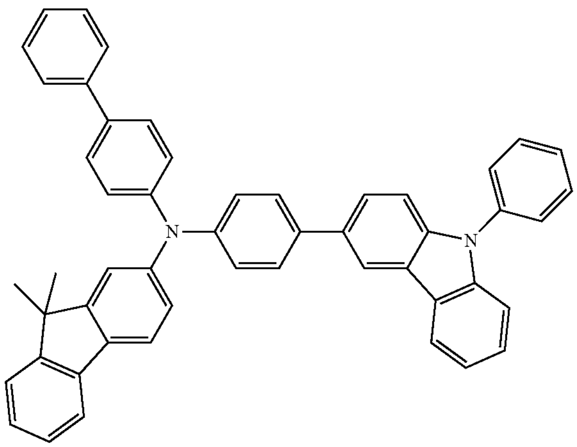
HT-1
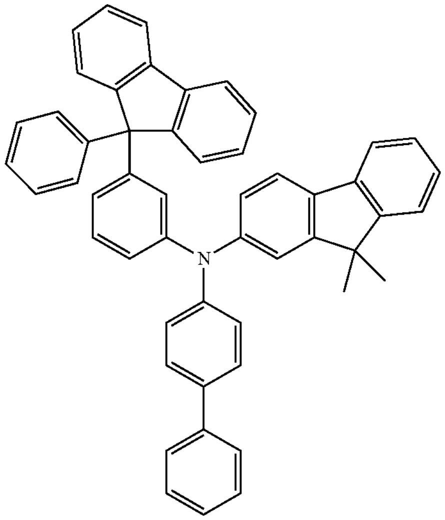
HT-2
Light-Emitting Layer
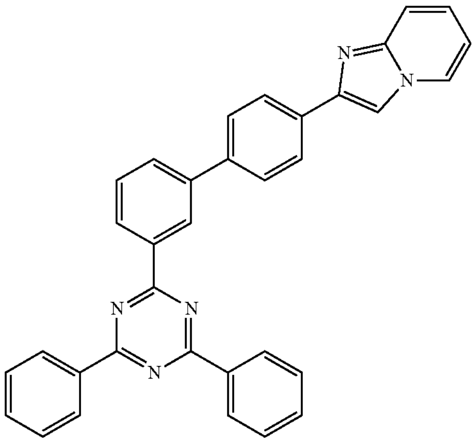
C-28

TABLE 5-continued
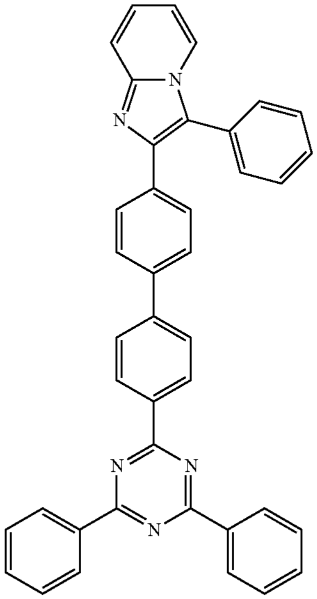
C-31
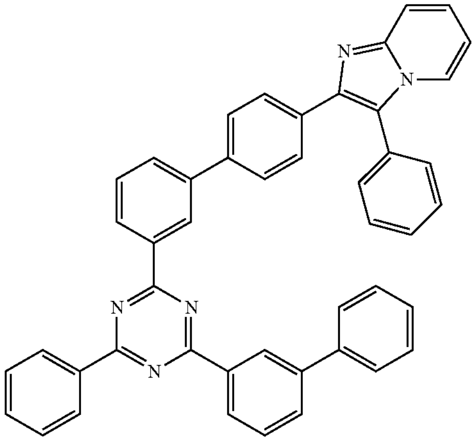
C-38
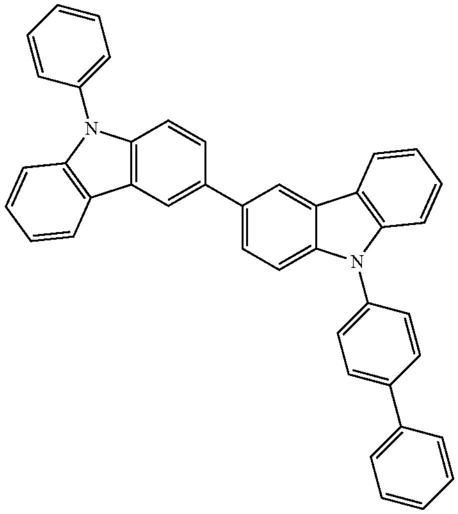
H2-4

TABLE 5-continued
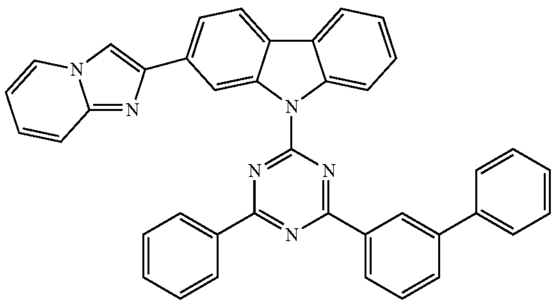
C-116
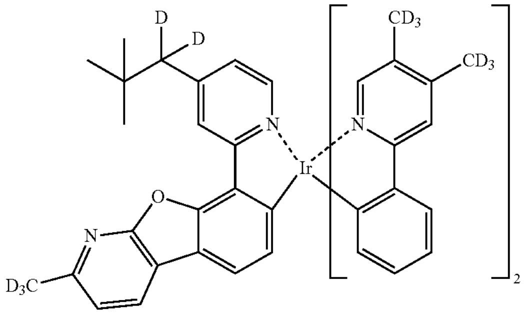
D-130
Electron Transport Layer/
Electron Injection Layer
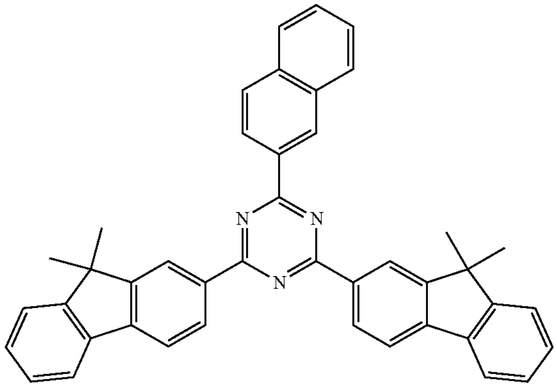
ETL-1
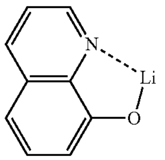
EIL-1

The invention claimed is:

1. A plurality of host materials comprising at least one first host compound and at least one second host compound, wherein the at least one first host compound is represented by the following formula 1 and the at least one second host compound is represented by the following formula 2:

(1)

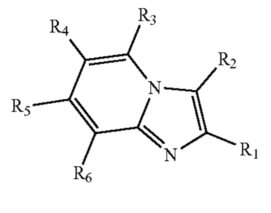

wherein, $R_1$ to $R_6$ each independently represent hydrogen, deuterium, halogen, cyano, a substituted or unsubstituted (C1-C30)alkyl, a substituted or unsubstituted (C3-C30) cycloalkyl, a substituted or unsubstituted (C3-C30) cycloalkenyl, a substituted or unsubstituted (3-to 7-membered)heterocycloalkyl, a substituted or unsubstituted (C6-C30)aryl, a substituted or unsubstituted (3-to 30-membered)heteroaryl, —$SiR'_1R'_2R'_3$, or —$NR'_4R'_5$; or may be linked to the adjacent substituents to form a ring(s);

provided that at least one of $R_1$ to $R_6$ is (are) $-(L_1)_n$-HAr;

$L_1$ represents a single bond, a substituted or unsubstituted (C6-C30) arylene, or a substituted or unsubstituted (3-to 30-membered)heteroarylene;

HAr represents a substituted or unsubstituted nitrogen-containing (3-to 30-membered)heteroaryl;

n represents an integer of 1 to 3, when n is an integer of 2 or more, each of $L_1$ may be the same or different; and $R'_1$ to $R'_5$ each independently represent a substituted or unsubstituted (C1-C30)alkyl, a substituted or unsubstituted (C2-C30)alkenyl, a substituted or unsubstituted (C6-C30)aryl, or a substituted or unsubstituted (3-to 30-membered)heteroaryl;

(2)

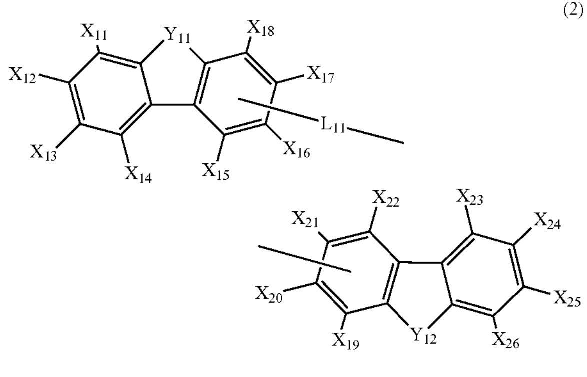

wherein, $Y_{11}$ represents —N-$A_1$, O, S or $CR_{21}R_{22}$;

$Y_{12}$ represents —N-$A_2$, O, S or $CR_{21}R_{22}$;

$A_1$ and $A_2$ each independently represent a substituted or unsubstituted (C6-C30)aryl, a substituted or unsubstituted dibenzofuranyl, a substituted or unsubstituted dibenzothiophenyl, or a substituted or unsubstituted carbazolyl;

$L_{11}$ represents a single bond or a substituted or unsubstituted (C6-C30)arylene;

$X_{11}$ to $X_{26}$ each independently represent hydrogen, deuterium, a substituted or unsubstituted (C6-C30)aryl, or a substituted or unsubstituted (3- to 30-membered) heteroaryl; or may be linked to the adjacent substituents to form a ring(s); and $R_{21}$ and $R_{22}$ each independently represent a substituted or unsubstituted (C1-C3)alkyl or a substituted or unsubstituted (C6-C12)aryl; or may be linked to the adjacent substituents to form a ring(s).

2. The plurality of host materials according to claim 1, wherein the substituents of the substituted alkyl, the substituted alkenyl, the substituted cycloalkyl, the substituted cycloalkenyl, the substituted heterocycloalkyl, the substituted aryl(ene), and the substituted heteroaryl(ene) each independently represent at least one selected from the group consisting of deuterium; halogen; cyano; carboxyl; nitro; hydroxyl; (C1-C30)alkyl; halo(C1-C30)alkyl; (C2-C30)alkenyl; (C2-C30)alkynyl; (C1-C30)alkoxy; (C1-C30)alkylthio; (C3-C30)cycloalkyl; (C3-C30)cycloalkenyl; (3- to 7-membered)heterocycloalkyl; (C6-C30)aryloxy; (C6-C30) arylthio; (3- to 50-membered)heteroaryl unsubstituted or substituted by at least one of (C1-C30)alkyl, (C6-C30)aryl and di(C6-C30)arylamino; (C6-C30)aryl unsubstituted or substituted by at least one of deuterium, cyano, (C1-C30) alkyl, (3-to 50-membered)heteroaryl, di(C6-C30)arylamino and tri(C6-C30)arylsilyl; tri(C1-C30)alkylsilyl; tri(C6-C30) arylsilyl; di(C1-C30)alkyl(C6-C30)arylsilyl; (C1-C30)alkyldi(C6-C30)arylsilyl; tri(C6-C30)arylgermanyl; amino; mono- or di-(C1-C30)alkylamino; mono- or di-(C6-C30) arylamino; (C1-C30)alkyl(C6-C30)arylamino; (C1-C30)alkylcarbonyl; (C1-C30)alkoxycarbonyl; (C6-C30)arylcarbonyl; di(C6-C30)arylboronyl; di(C1-C30)alkylboronyl; (C1-C30)alkyl(C6-C30)arylboronyl; (C6-C30)ar(C1-C30)alkyl; and (C1-C30)alkyl(C6-C30)aryl.

3. The plurality of host materials according to claim 1, wherein the at least one first host compound represented by formula 1 is represented by the following formula 1-1 to 1-2:

(1-1)

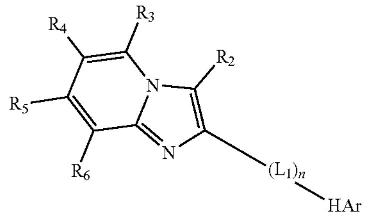

(1-2)

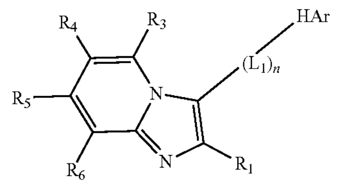

wherein, $R_1$ to $R_6$, $L_1$, HAr, and n are as defined in claim 1.

4. The plurality of host materials according to claim 1, wherein HAr is a substituted or unsubstituted triazinyl, a substituted or unsubstituted pyridyl, a substituted or unsubstituted pyrimidinyl, a substituted or unsubstituted quinazolinyl, a substituted or unsubstituted benzoquinazolinyl, a substituted or unsubstituted quinoxalinyl, a substituted or unsubstituted benzoquinoxalinyl, a substituted or unsubstituted quinolyl, a substituted or unsubstituted benzoquinolyl, a substituted or unsubstituted isoquinolyl, a substituted or unsubstituted benzoisoquinolyl, a substituted or unsubstituted triazolyl, a substituted or unsubstituted pyrazolyl, a substituted or unsubstituted naphthyridinyl, or a substituted or unsubstituted benzothienopyrimidinyl.

5. The plurality of host materials according to claim 1, wherein the at least one second host compound represented by formula 2 is represented by any one of the following formulas 2-1 to 2-8:

(2-1)

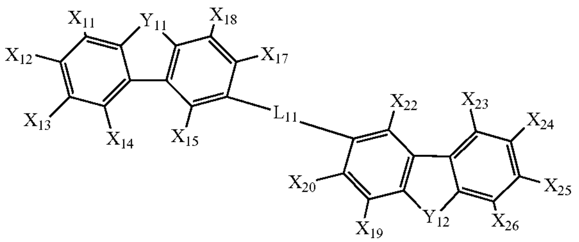

(2-2)

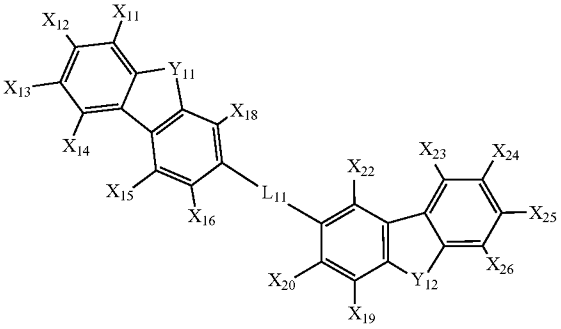

(2-3)

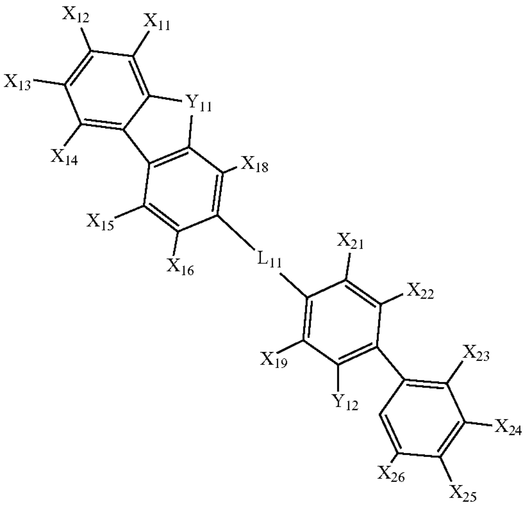

-continued (2-4)

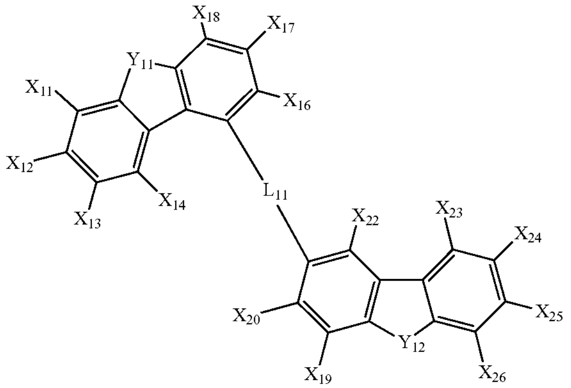

(2-5)

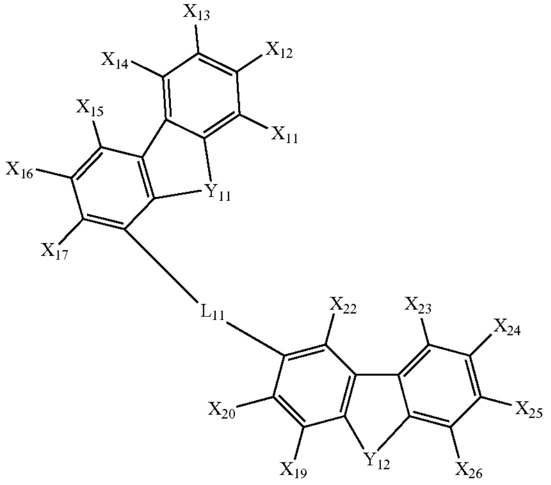

(2-6)

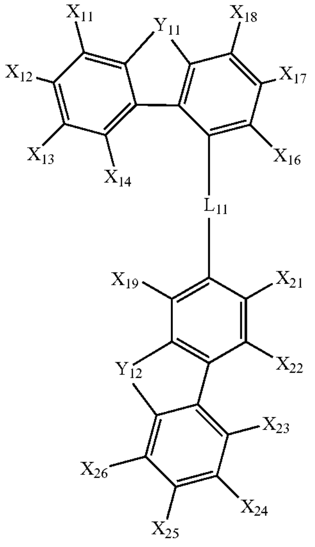

-continued (2-7)

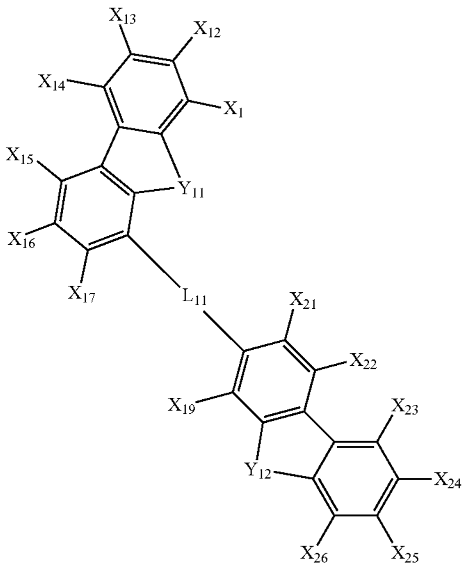

(2-8)

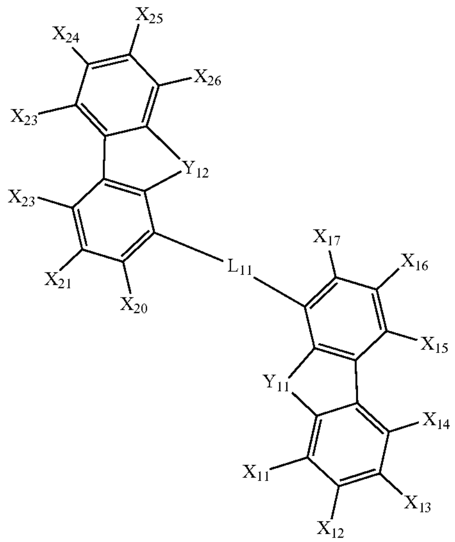

wherein, $Y_{11}$, $Y_{12}$, $L_{11}$, and $X_{11}$ to $X_{26}$ are as defined in claim 1.

6. The plurality of host materials according to claim 1, wherein $A_1$ and $A_2$ each independently represent a substituted or unsubstituted phenyl, a substituted or unsubstituted biphenyl, a substituted or unsubstituted terphenyl, a substituted or unsubstituted naphthyl, a substituted or unsubstituted fluorenyl, a substituted or unsubstituted benzofluorenyl, a substituted or unsubstituted triphenylenyl, a substituted or unsubstituted fluoranthenyl, a substituted or unsubstituted phenanthrenyl, a substituted or unsubstituted dibenzofuranyl, a substituted or unsubstituted carbazolyl, or a substituted or unsubstituted dibenzothiophenyl.

7. The plurality of host materials according to claim 1, wherein the compound represented by formula 1 is selected from the following compounds:

C-1

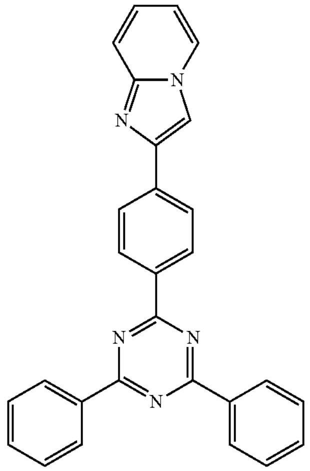

C-2

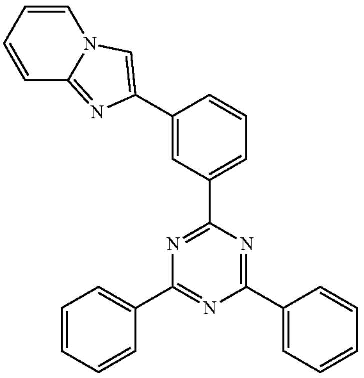

C-3

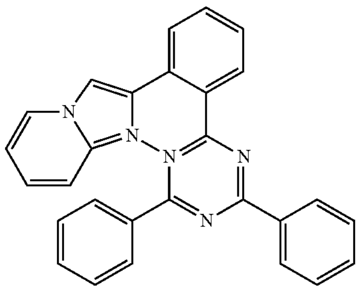

C-4

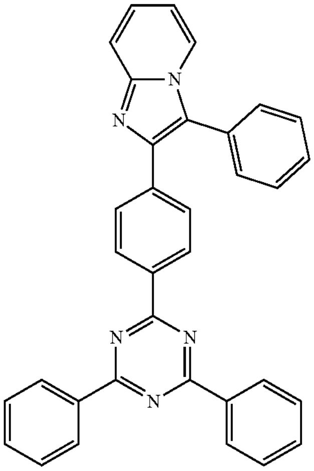

-continued
C-5
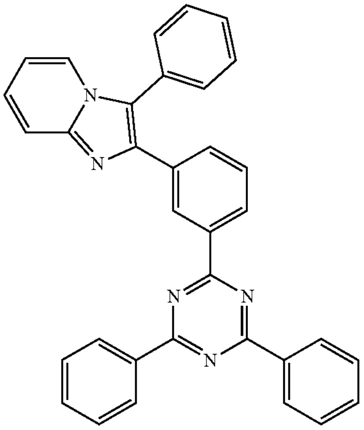
C-6
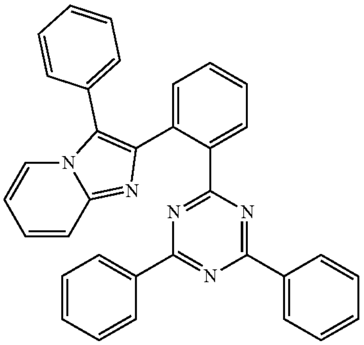
C-7
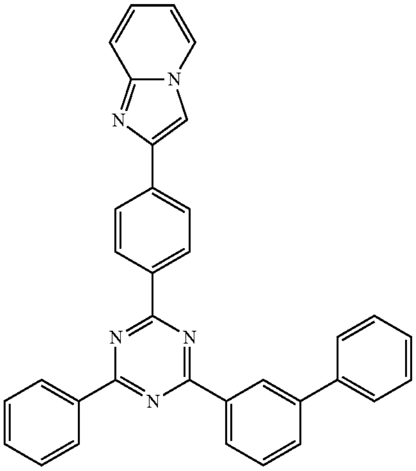
-continued
C-8
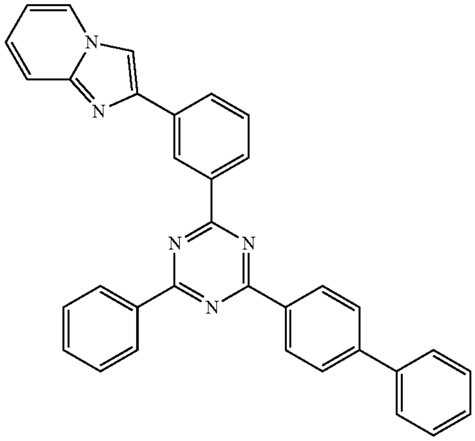
C-9
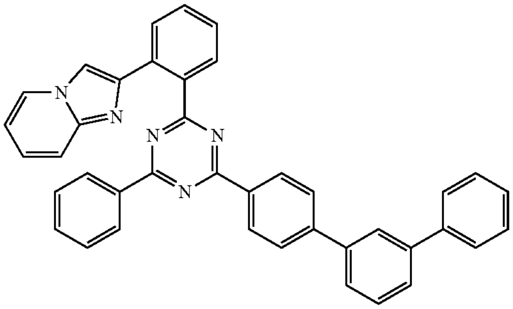
C-10
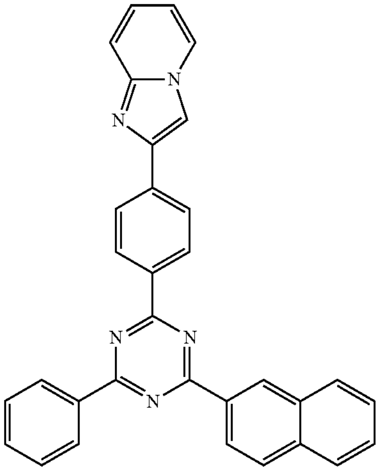

-continued
C-11
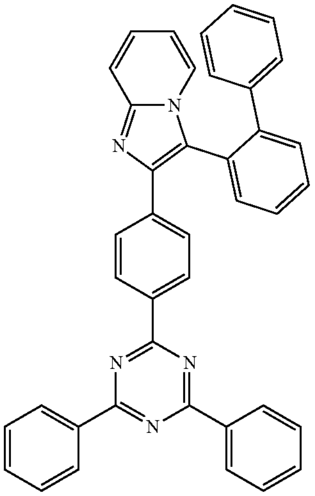
C-12
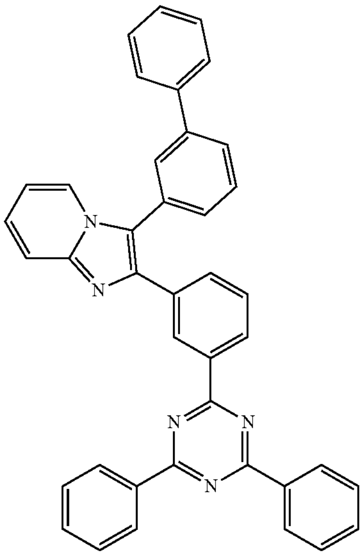
C-13
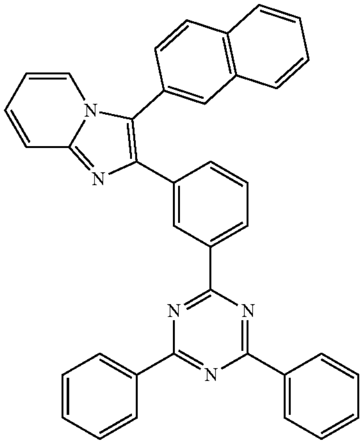
-continued
C-14
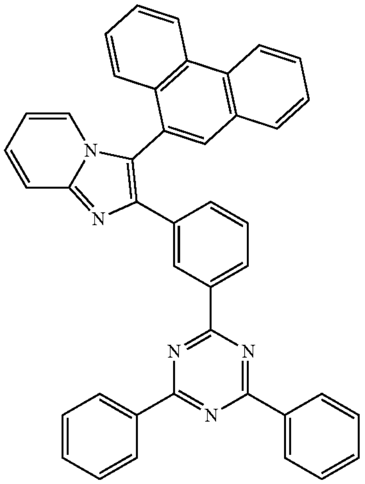
C-15
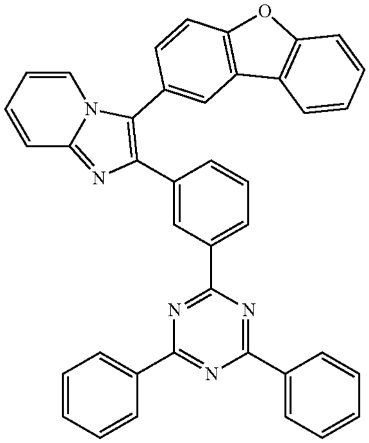
C-16
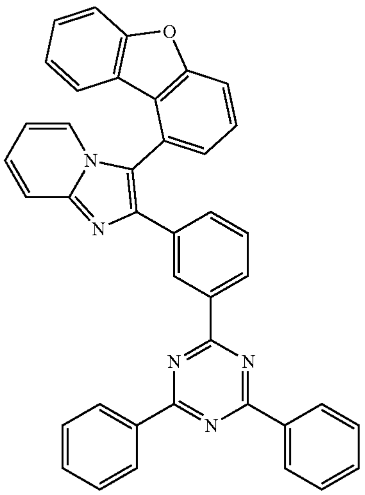

-continued
C-17
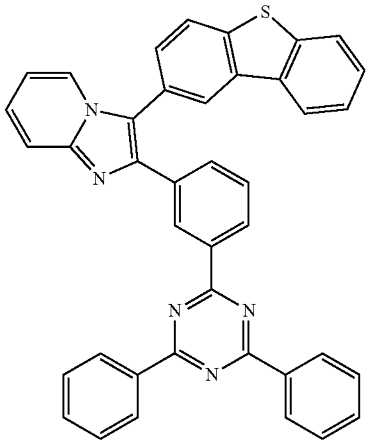
C-18
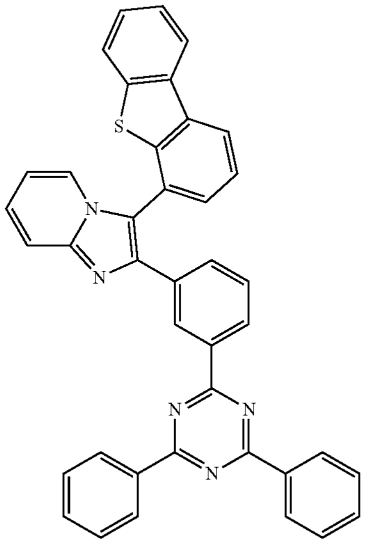
C-19
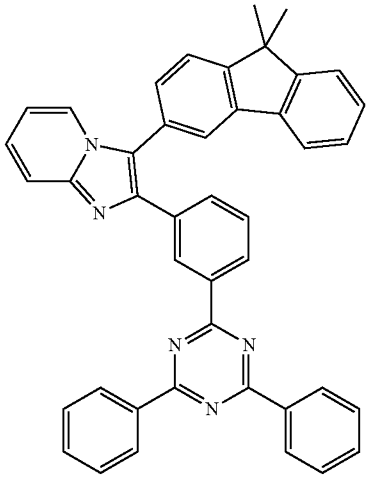
-continued
C-20
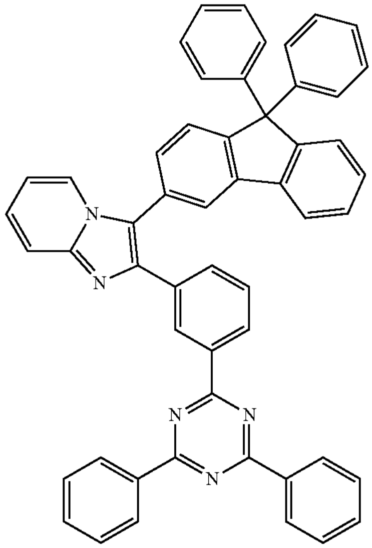
C-21
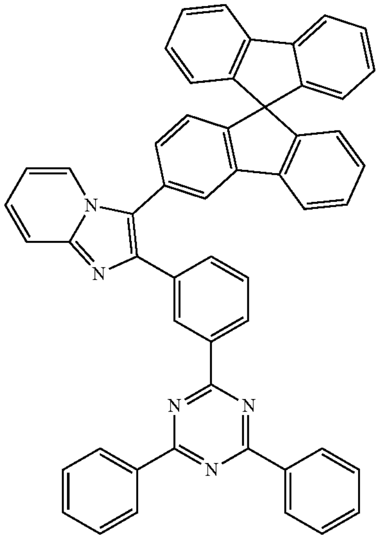
C-22
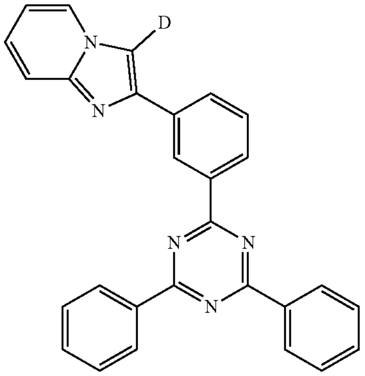

-continued
C-23
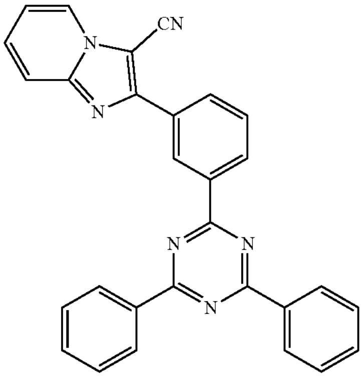
C-24
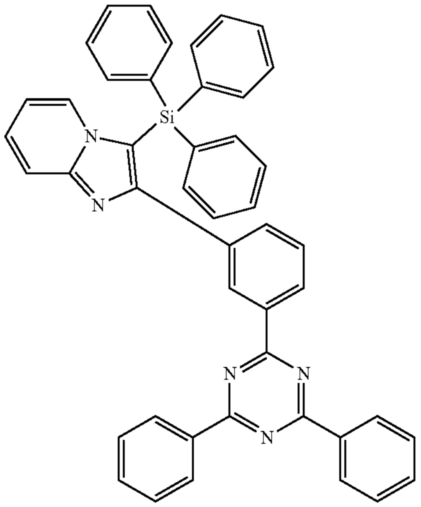
C-25
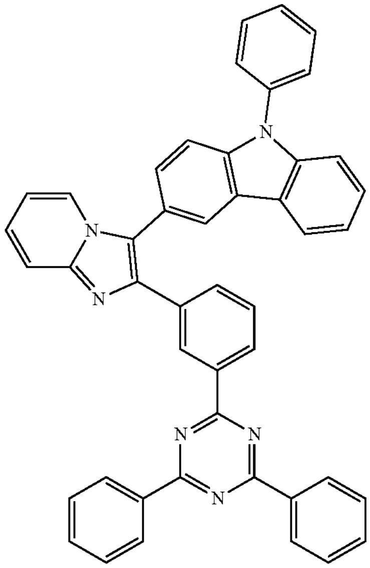
-continued
C-26
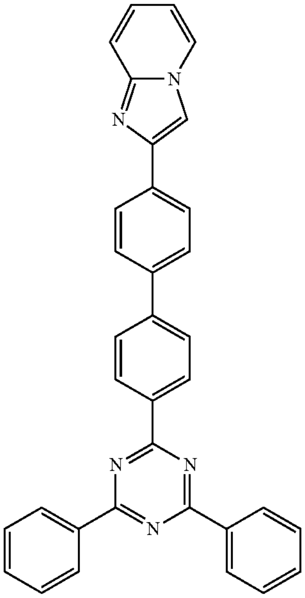
C-27
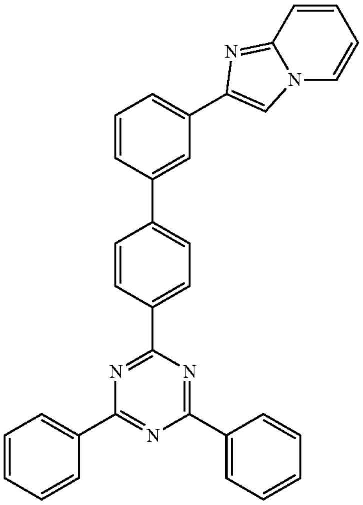
C-28
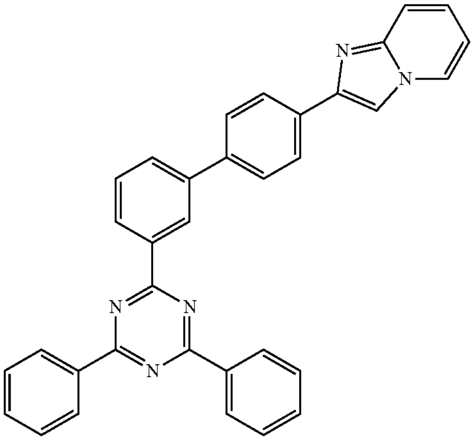

-continued
C-29
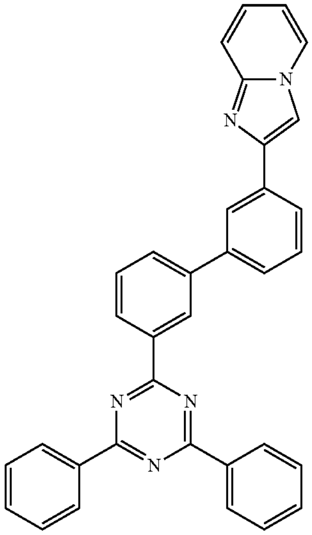
C-30
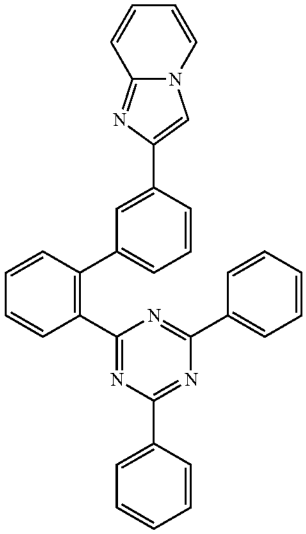
C-31
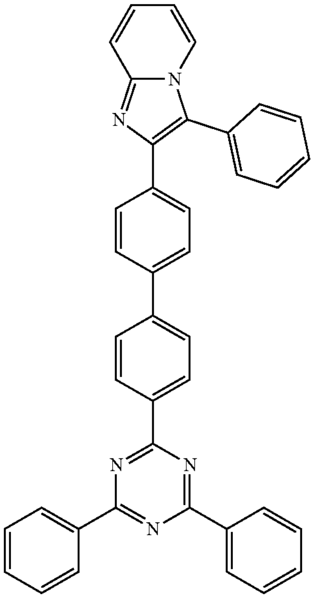
-continued
C-32
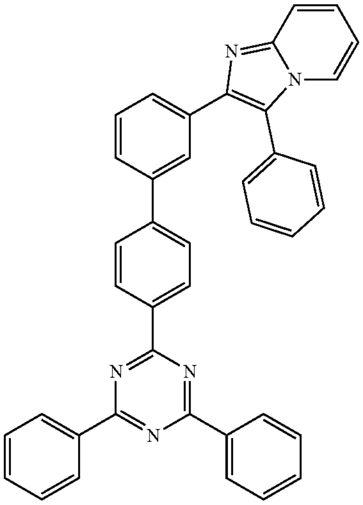
C-33
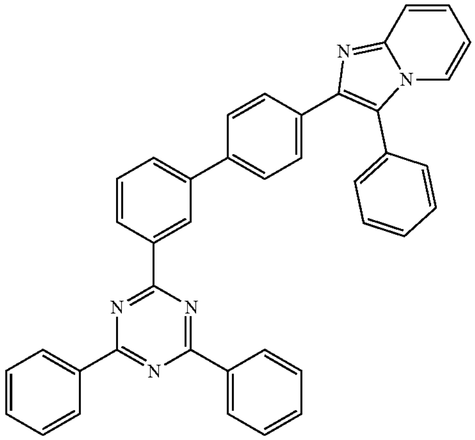
C-34
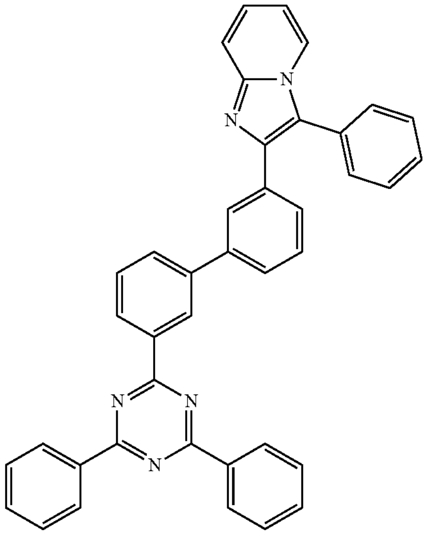

-continued
C-35
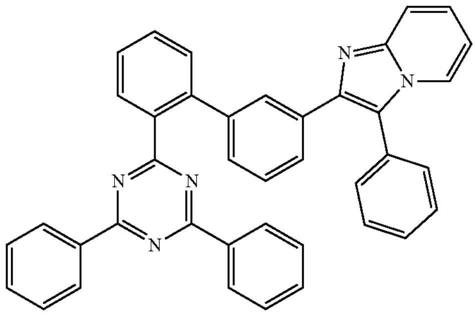
C-36
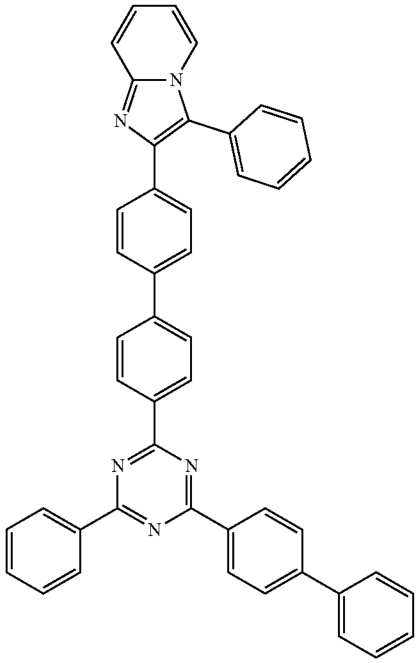
C-37
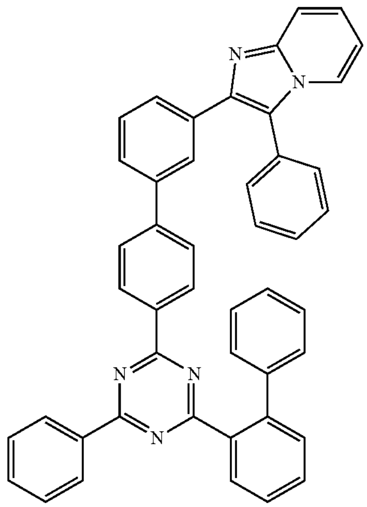
-continued
C-38
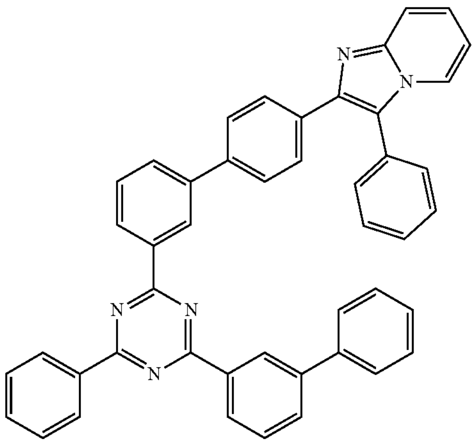
C-39
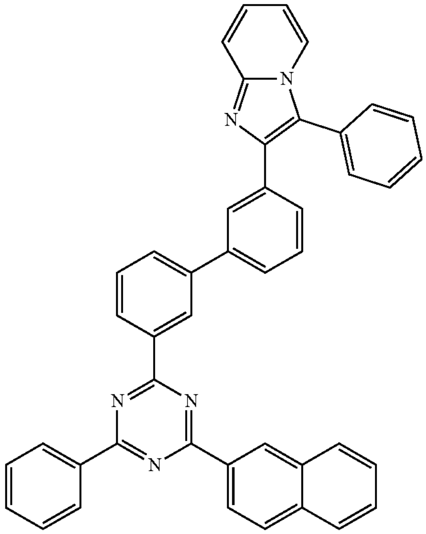
C-40
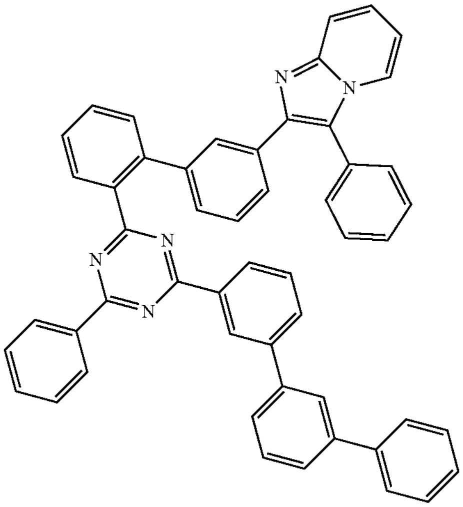

-continued
C-41
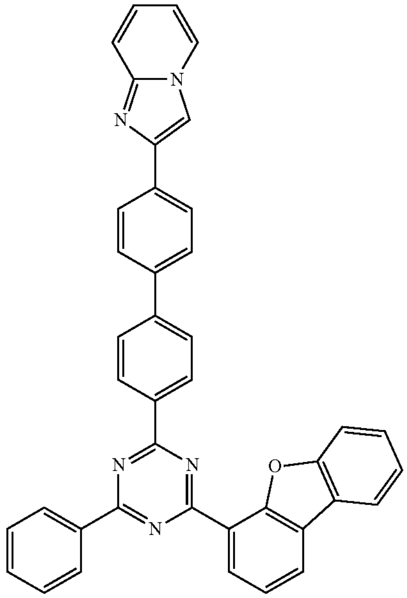
C-42
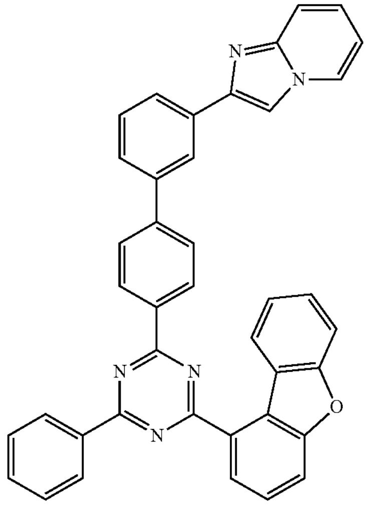
C-43
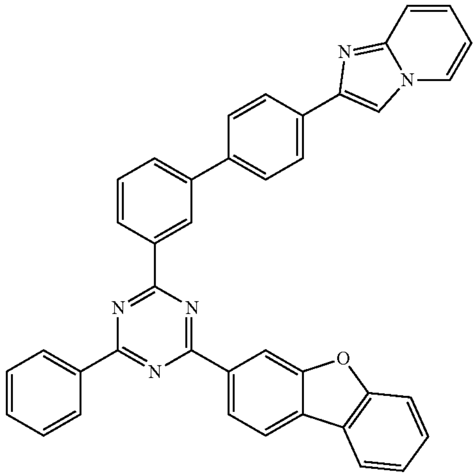
-continued
C-44
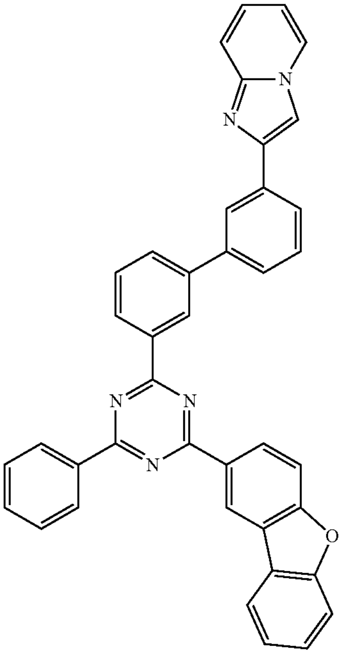
C-45
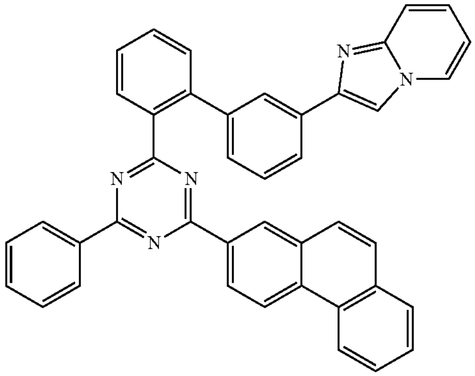
C-46
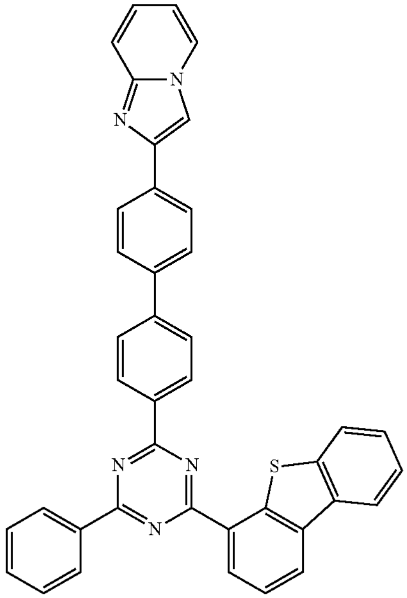

-continued
C-47
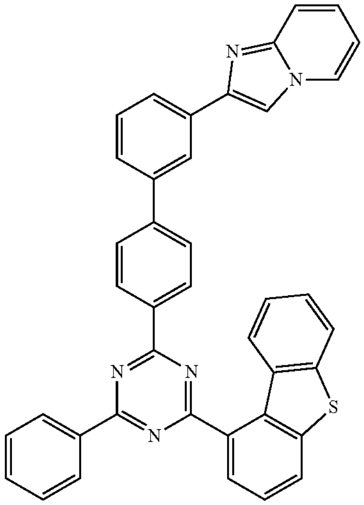
C-48
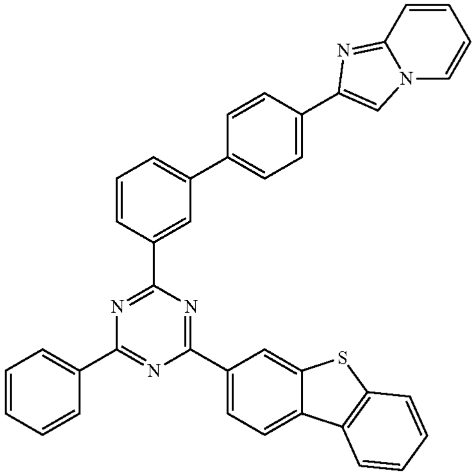
C-49
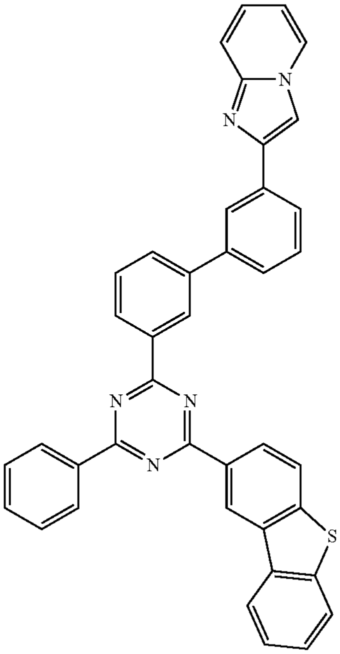
-continued
C-50
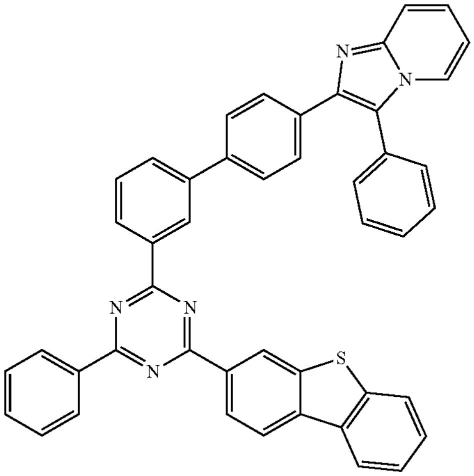
C-51
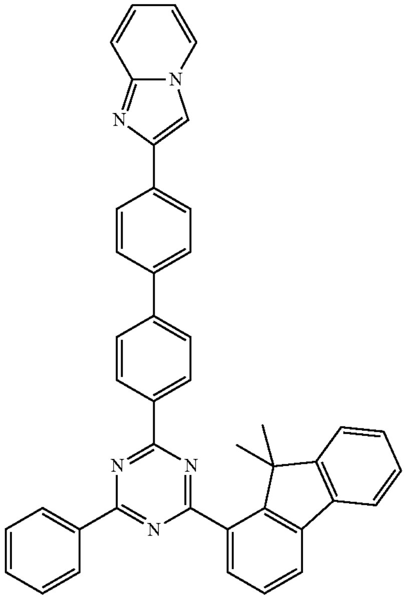
C-52
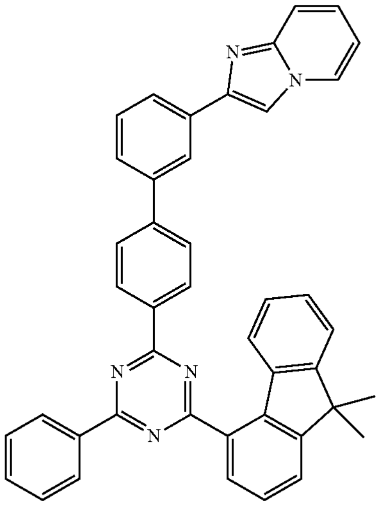

-continued
C-53
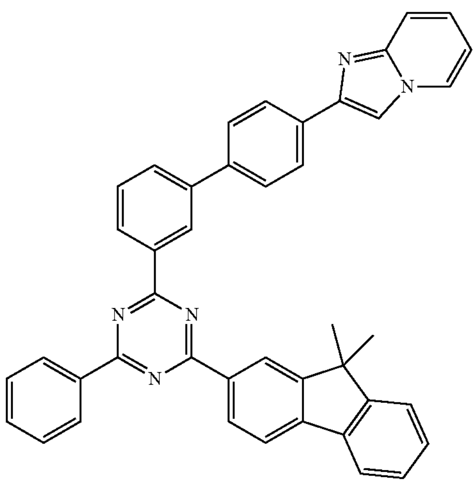
C-54
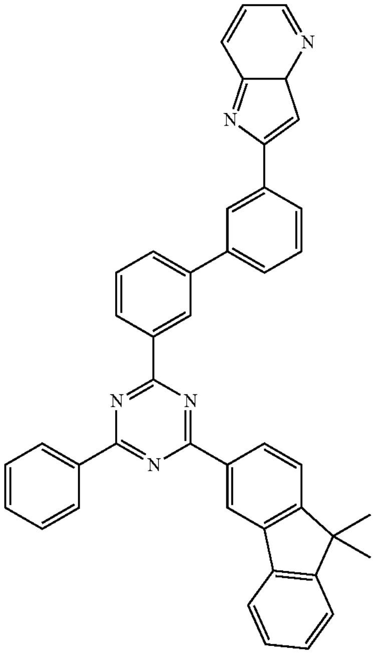
C-55
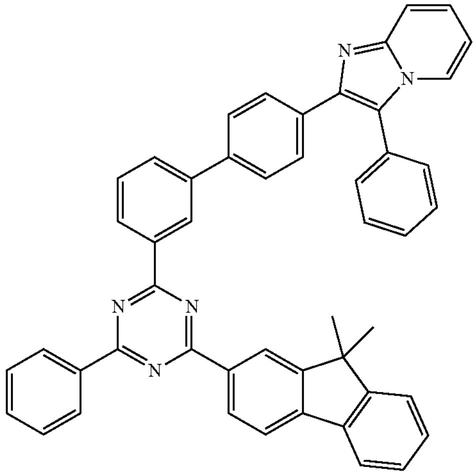
-continued
C-56
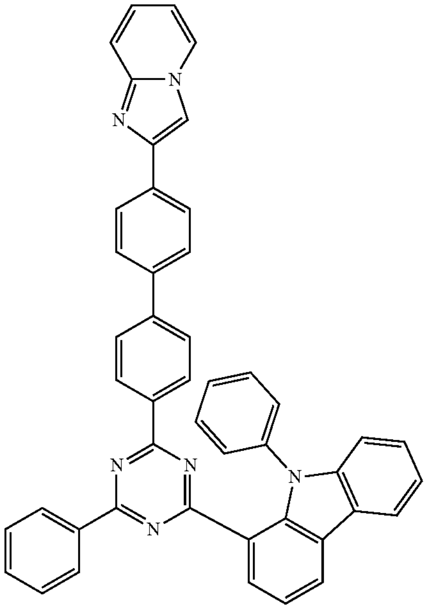
C-57
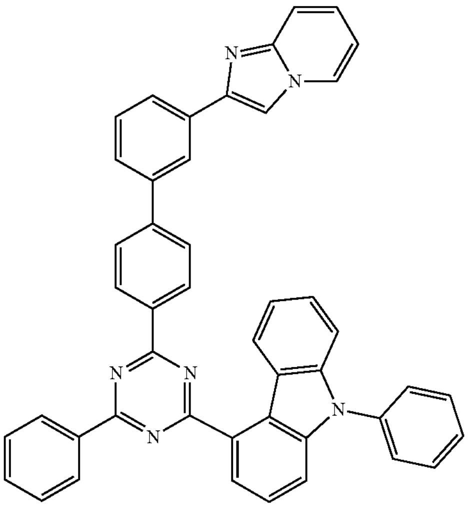
C-58
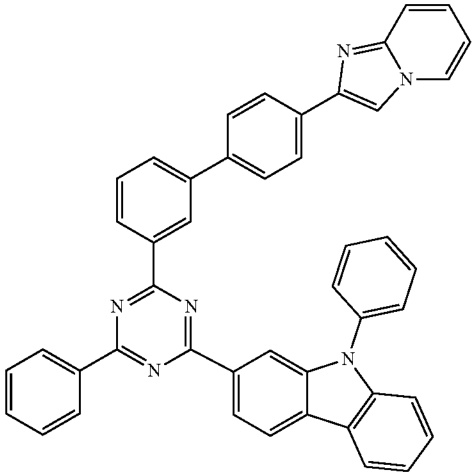

-continued
C-59
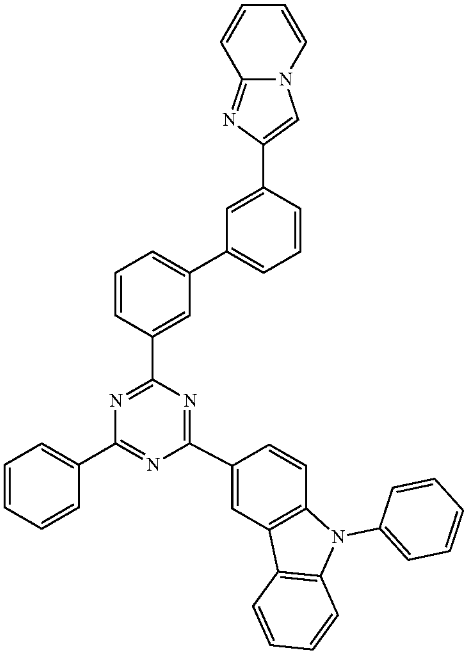
C-60
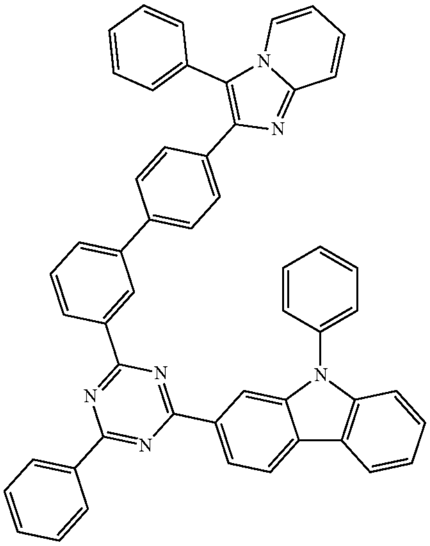
-continued
C-61
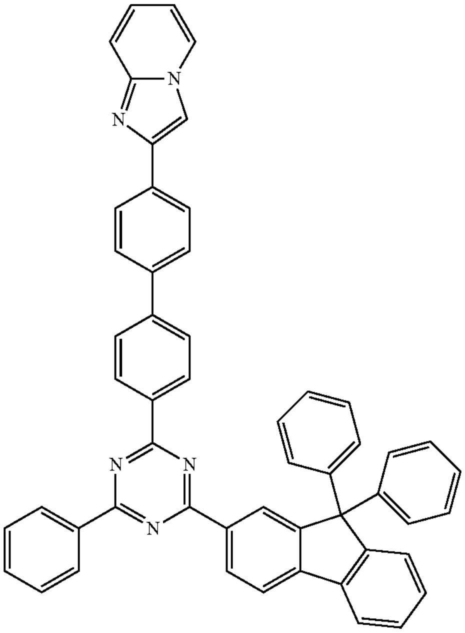
C-62
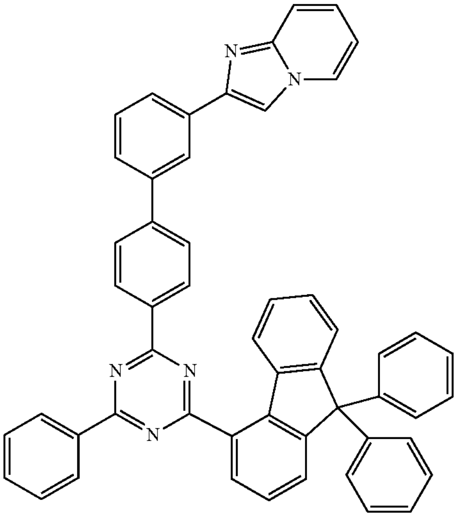
C-63
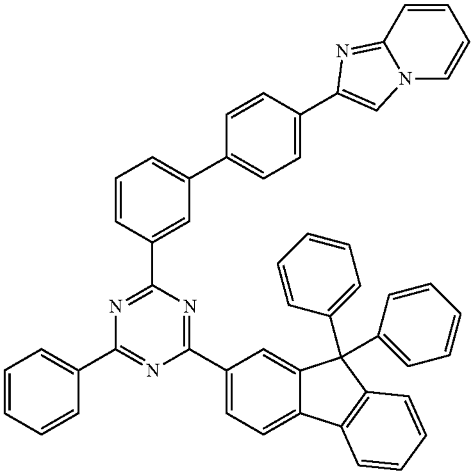

-continued
C-64
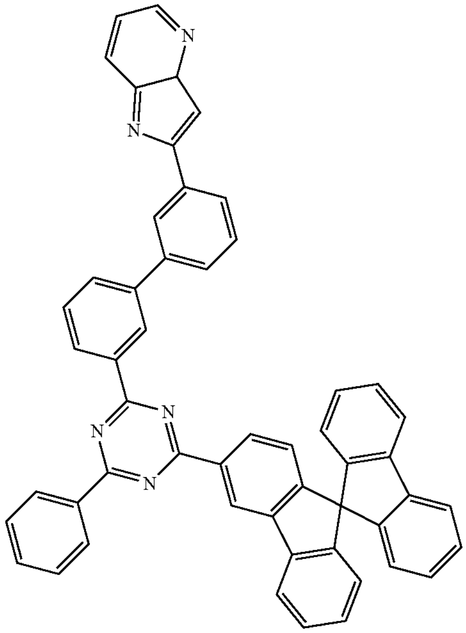
C-65
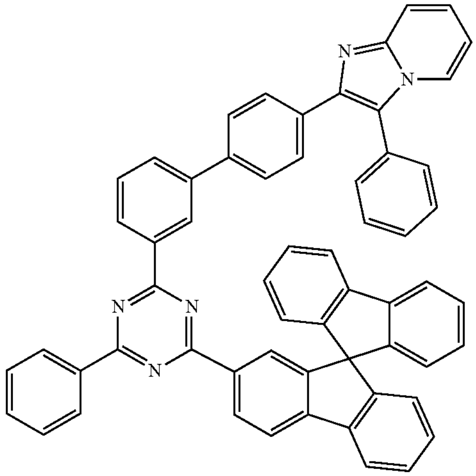
-continued
C-66
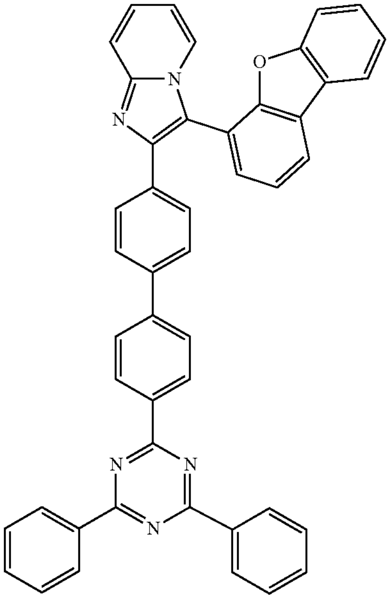
C-67
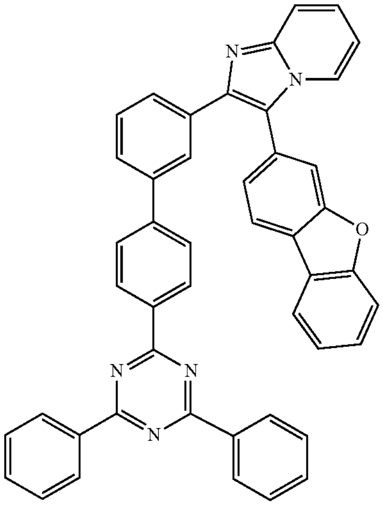
C-68
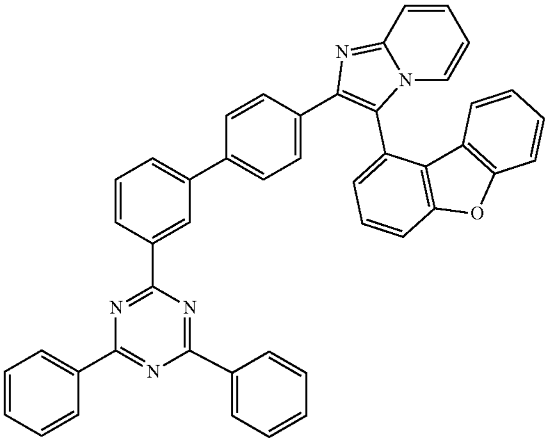

-continued
C-69
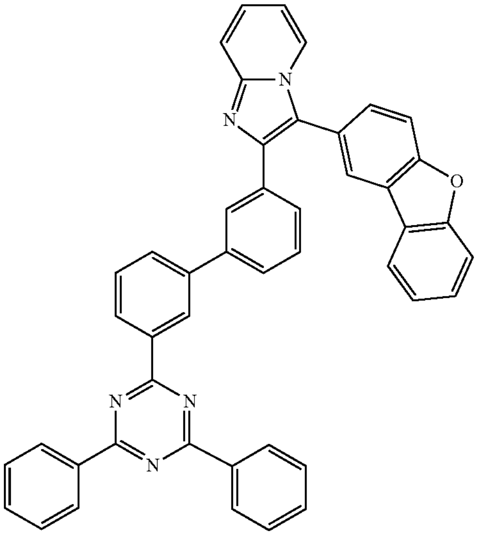
C-70
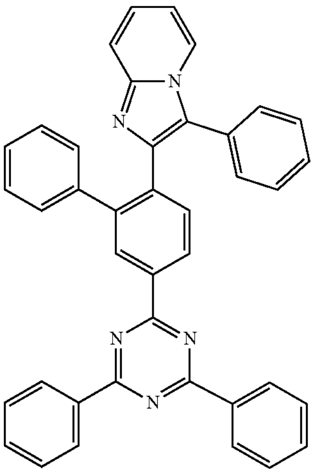
C-71
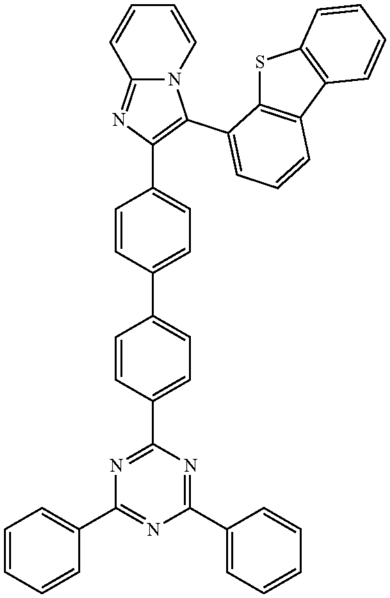
-continued
C-72
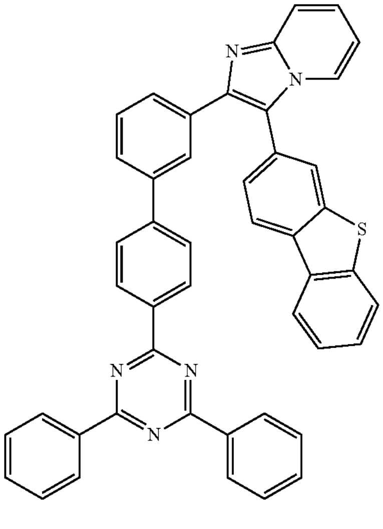
C-73
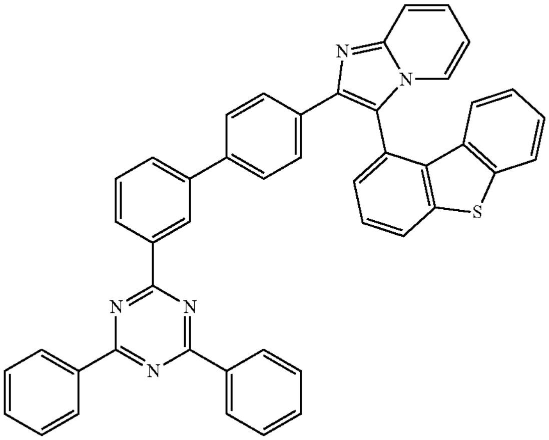
C-74
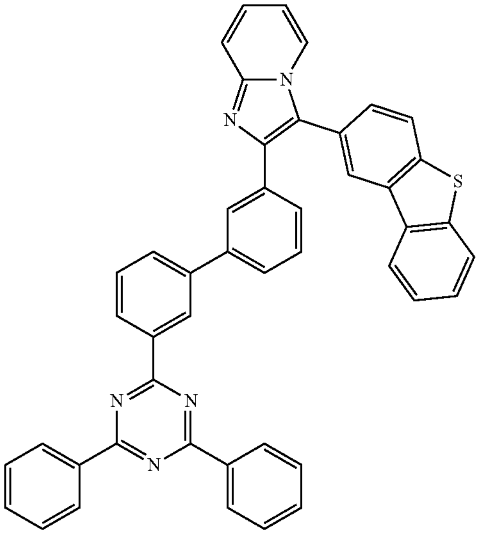

-continued
C-75
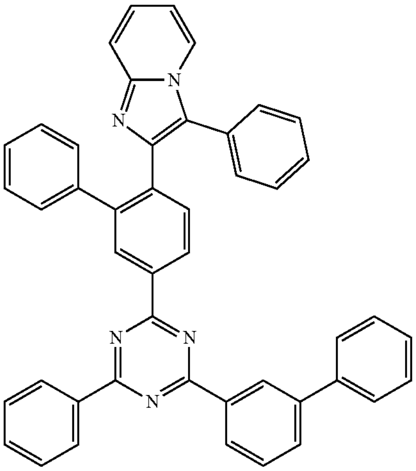
C-76
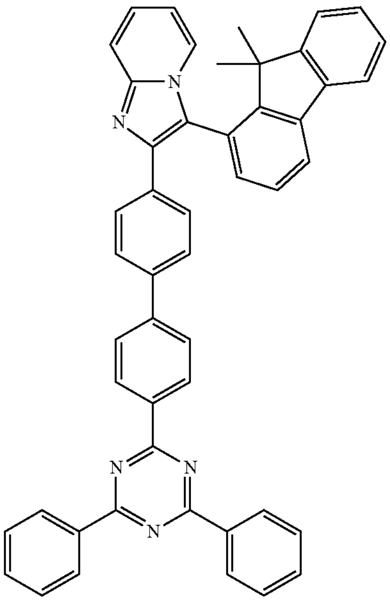
C-77
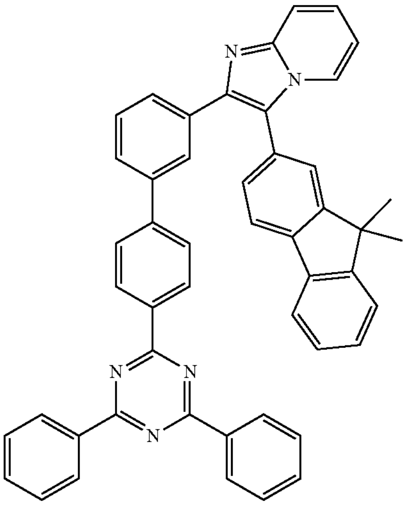
-continued
C-78
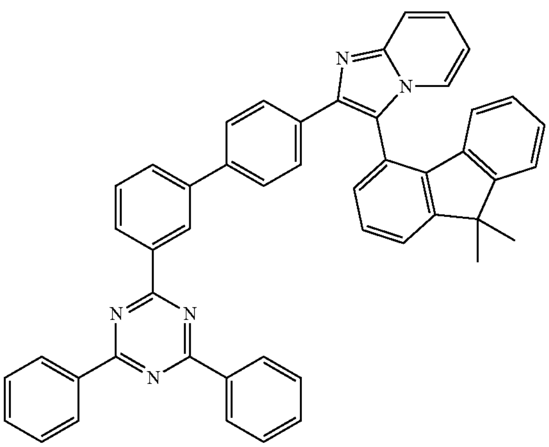
C-79
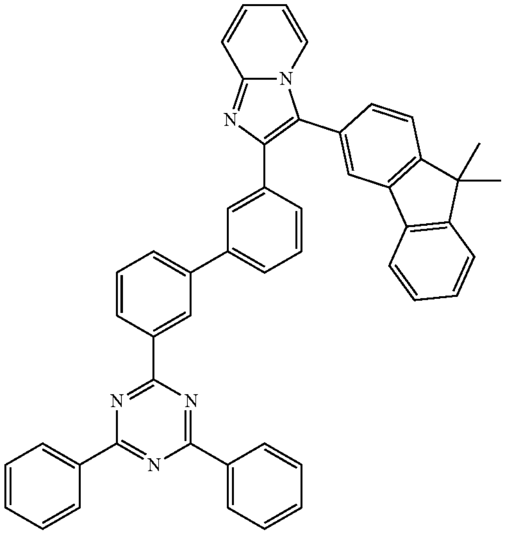
C-80
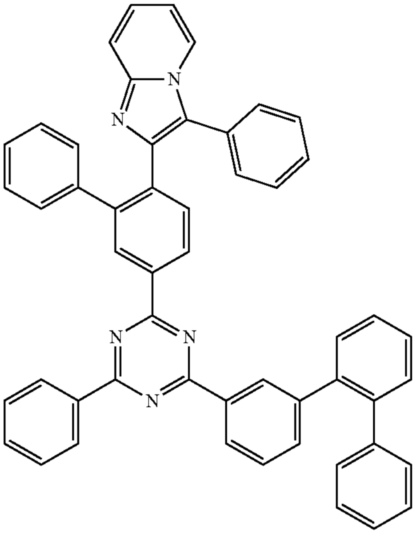

-continued
C-81
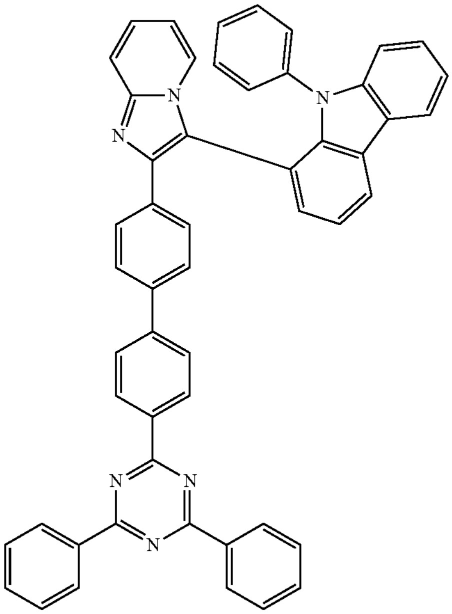
C-82
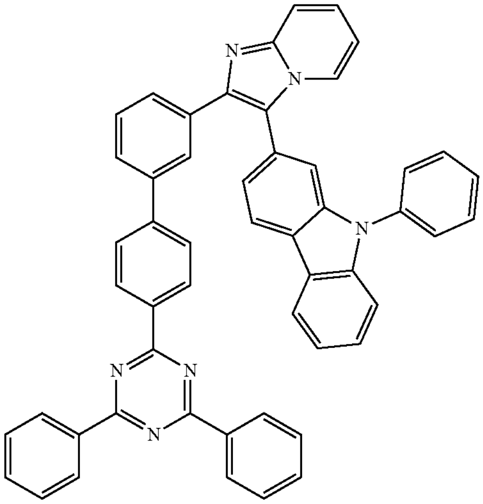
C-83
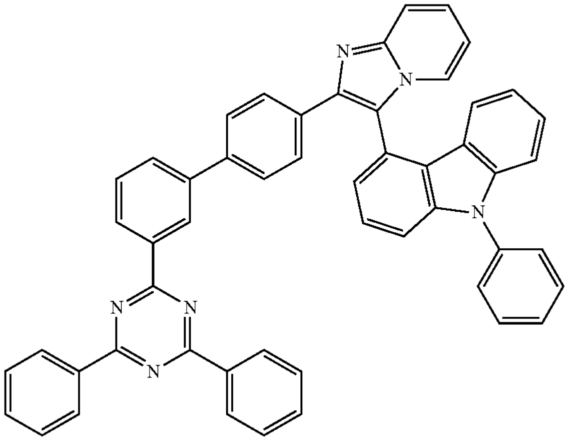
-continued
C-84
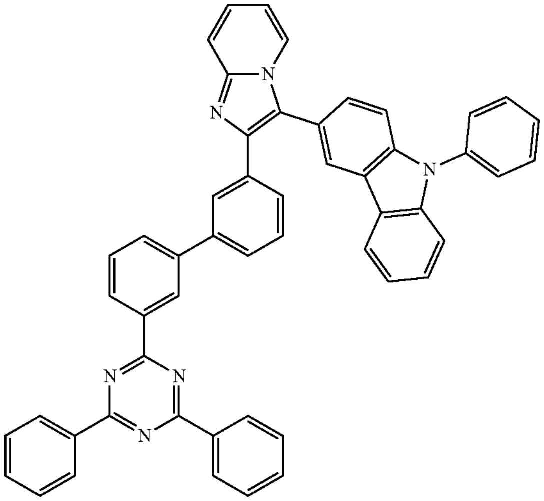
C-85
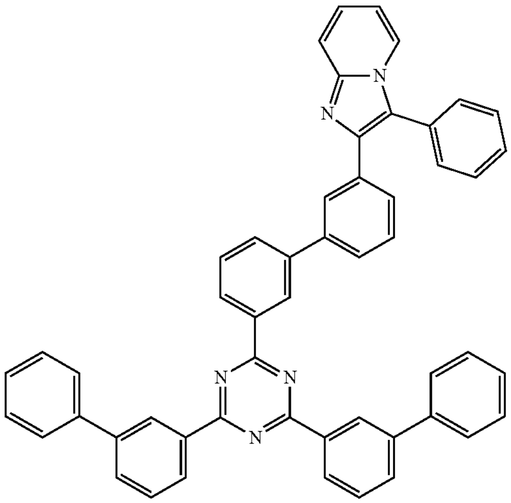

-continued
C-86
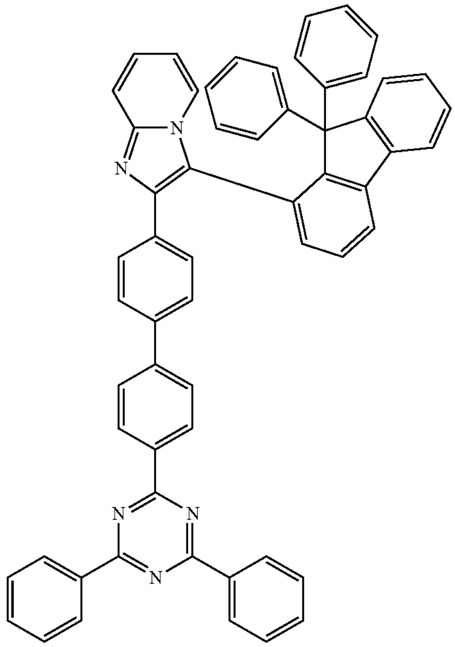
C-87
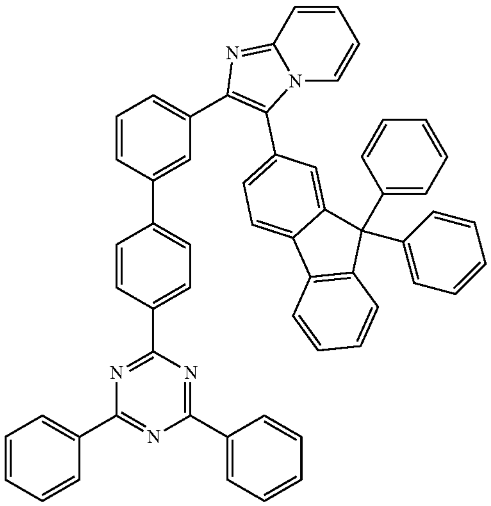
C-88
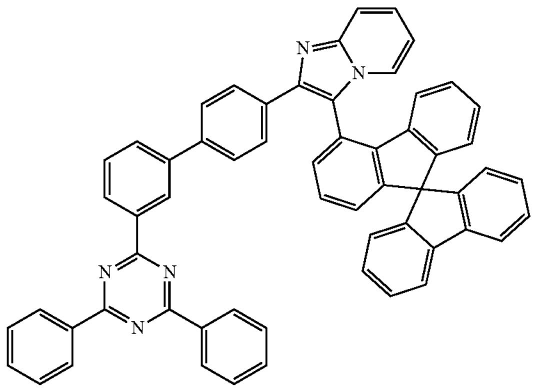
-continued
C-89
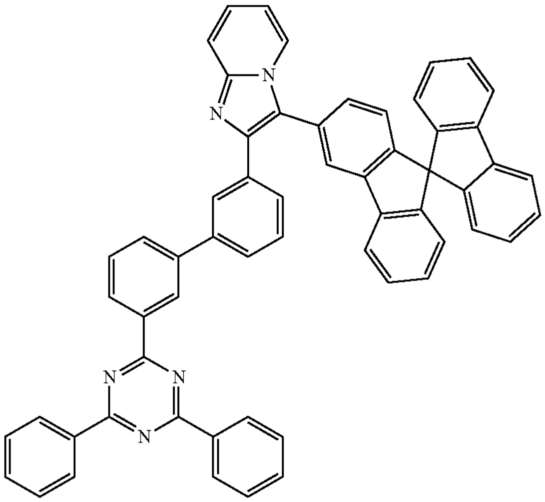
C-90
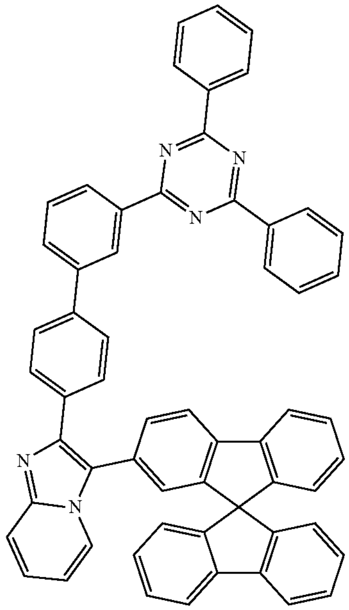
C-91
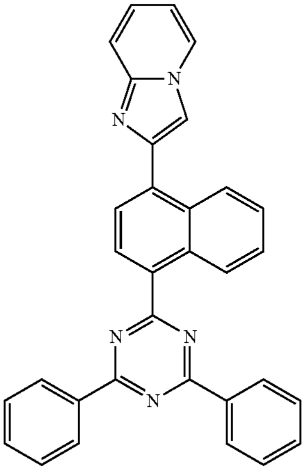

-continued
C-92
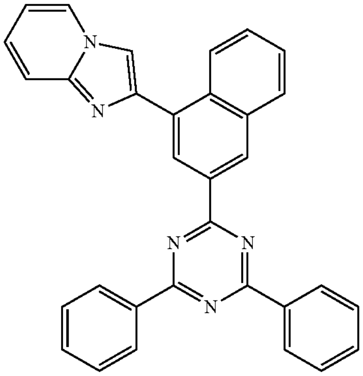
C-93
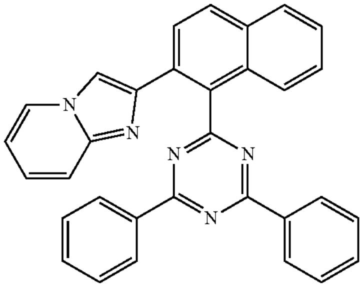
C-94
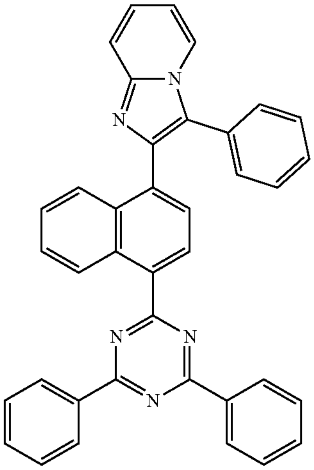
C-95
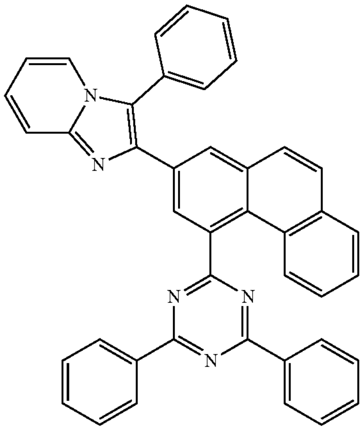
-continued
C-96
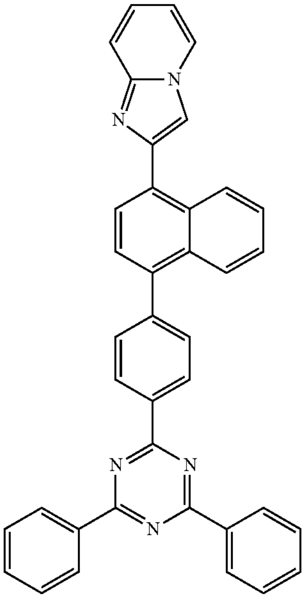
C-97
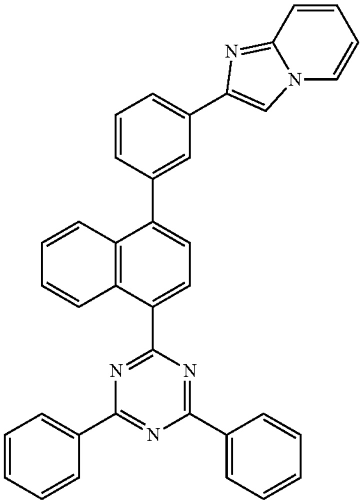
C-98
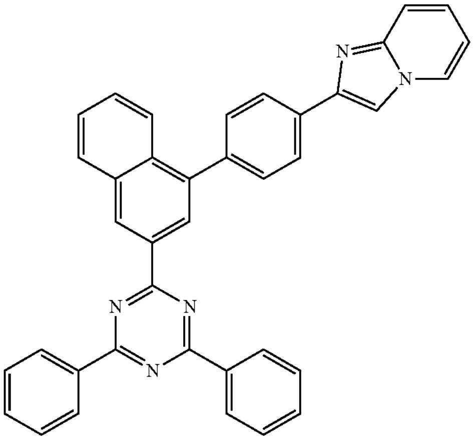

-continued
C-99
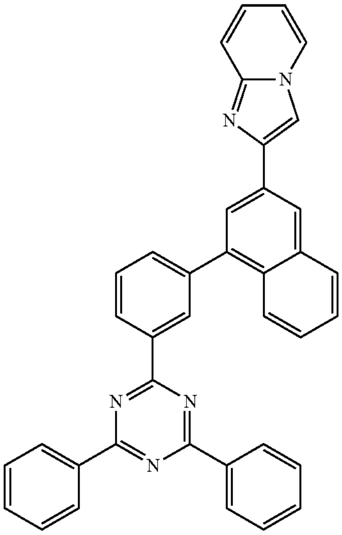
C-100
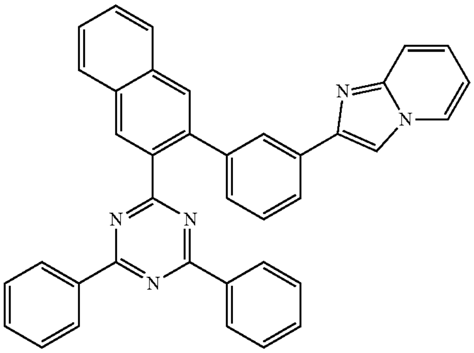
C-101
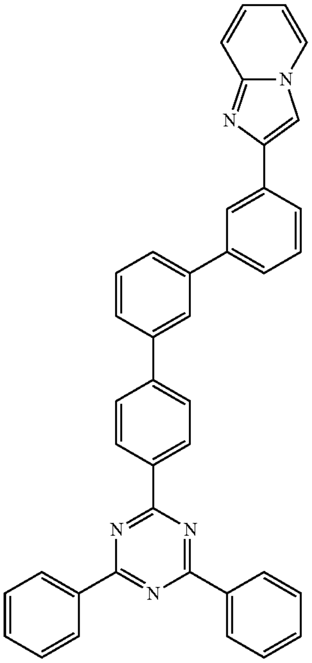
-continued
C-102
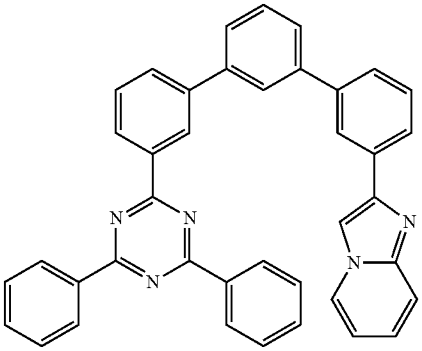
C-103
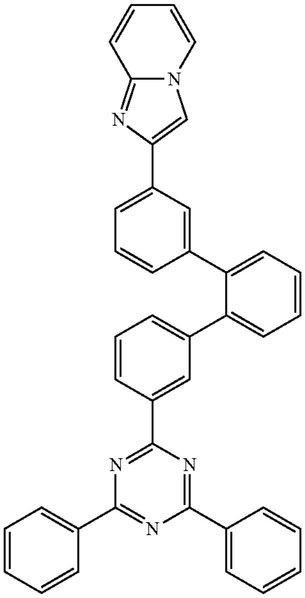
C-104
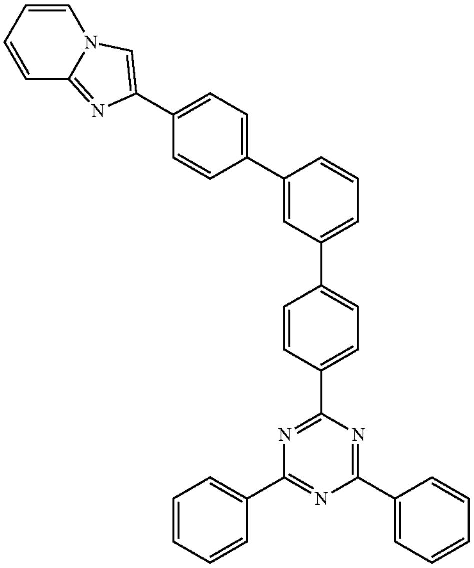

-continued
C-105
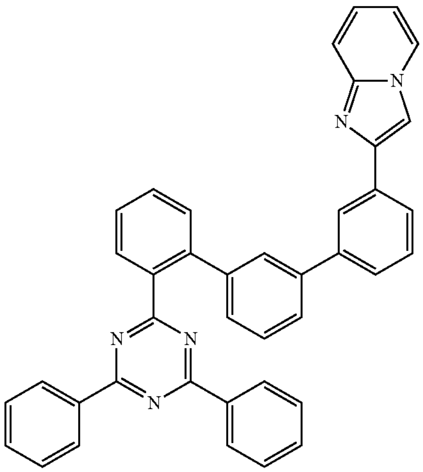
C-106
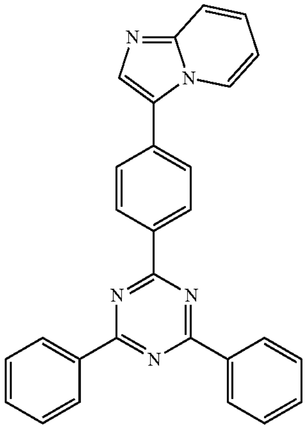
C-107
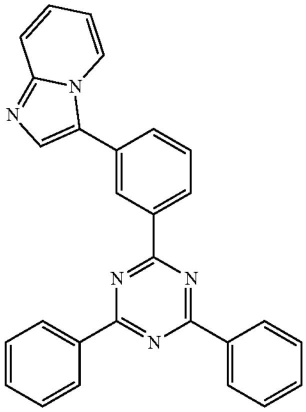
C-108
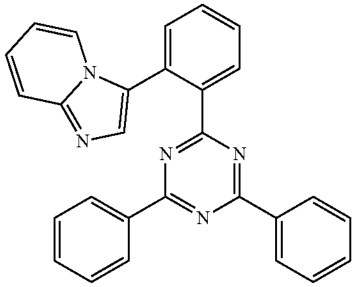
-continued
C-109
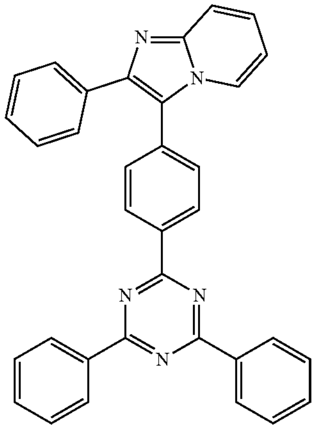
C-110
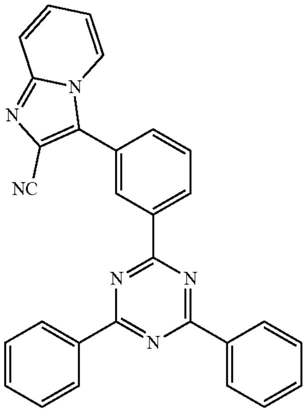
C-111
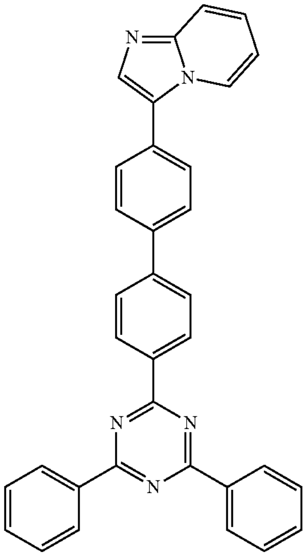

-continued
C-112
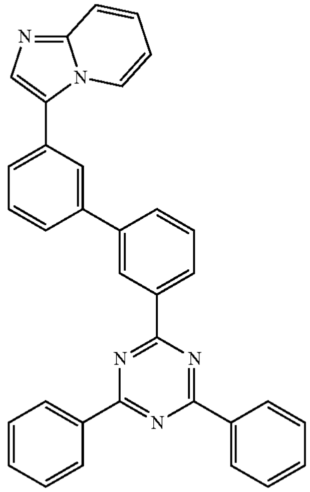
C-113
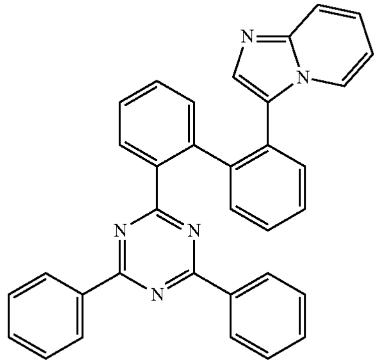
C-114
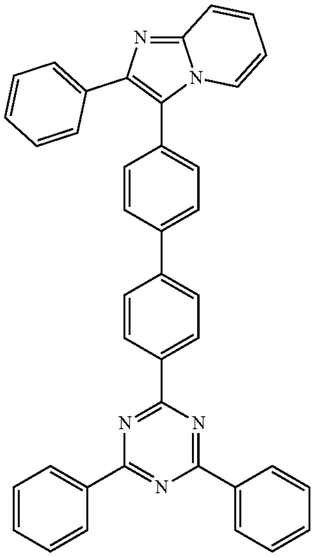
-continued
C-115
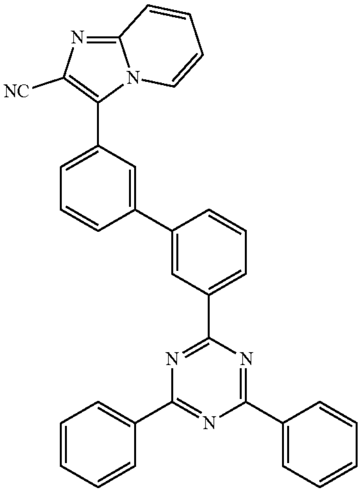
C-116
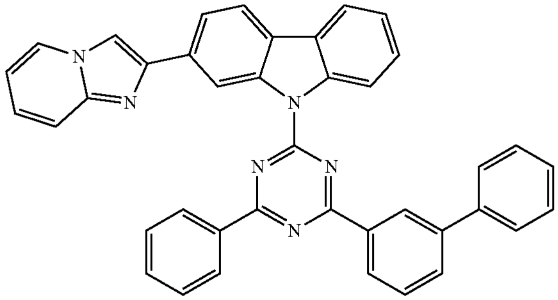
C-117
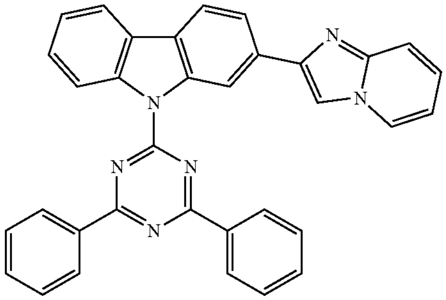
C-118
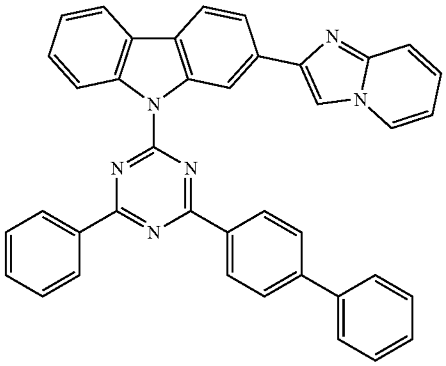

-continued
C-119
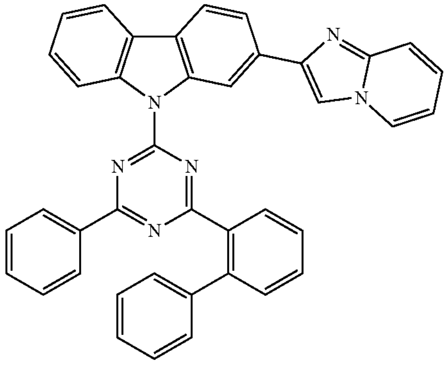
C-120
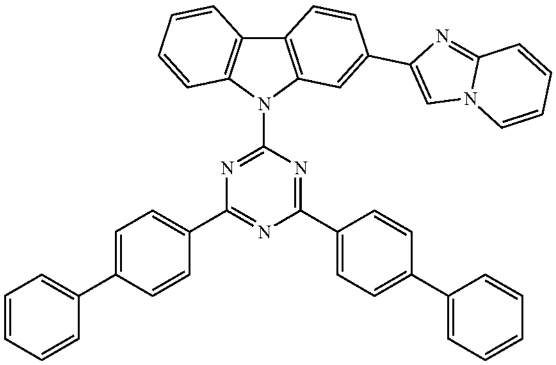
C-121
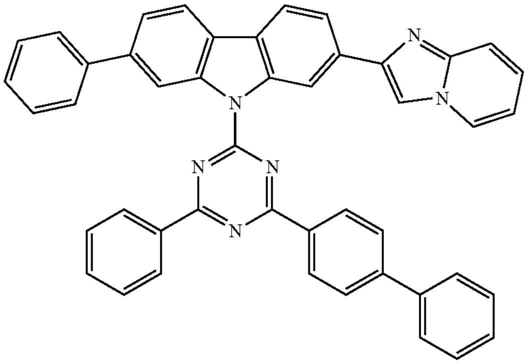
C-122
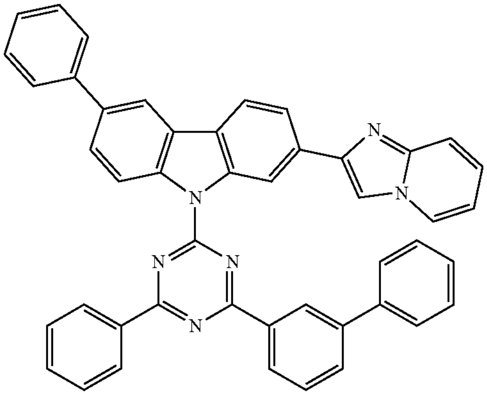
-continued
C-123
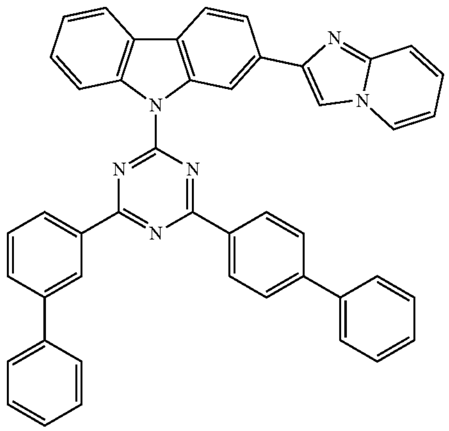
C-124
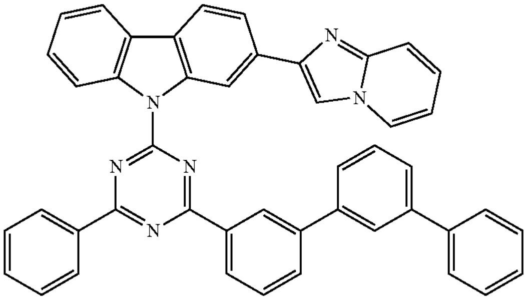
C-125
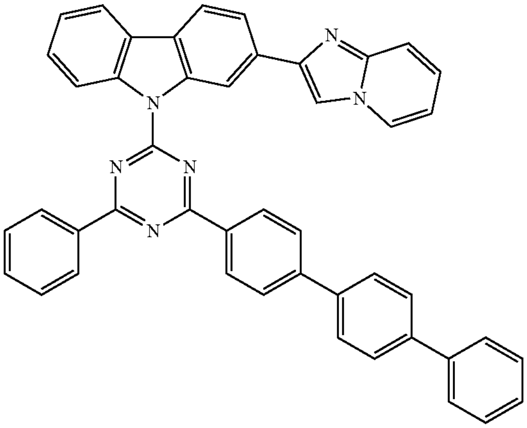
C-126
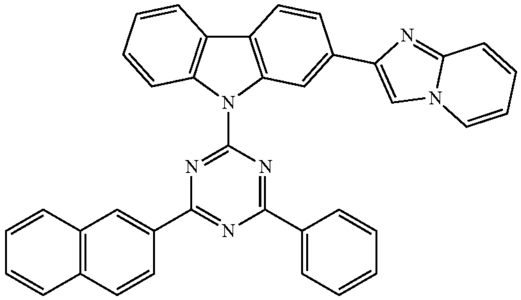

-continued
C-127
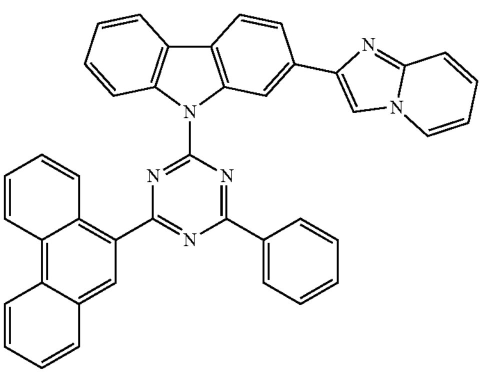
C-128
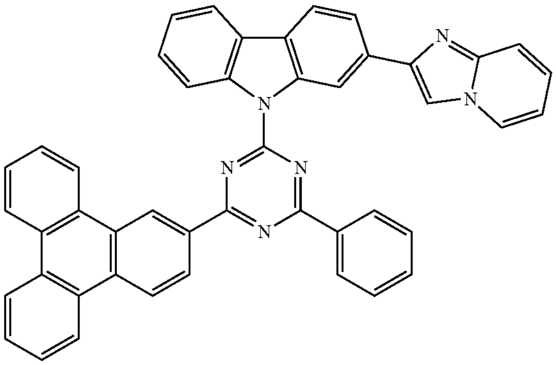
C-129
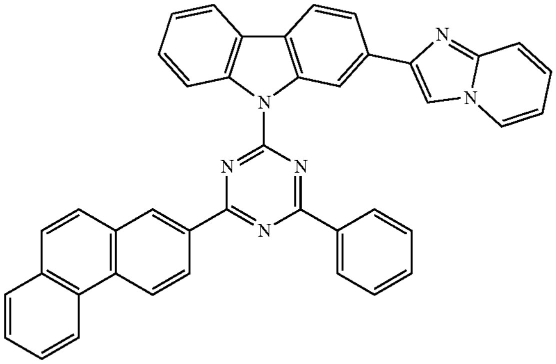
C-130
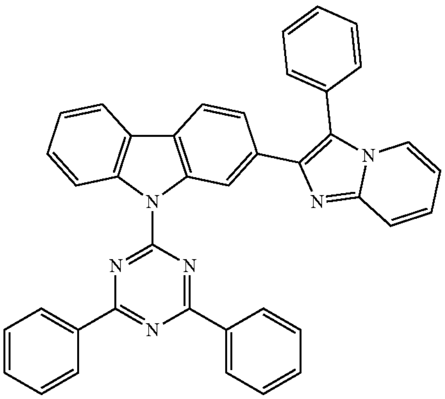
-continued
C-131
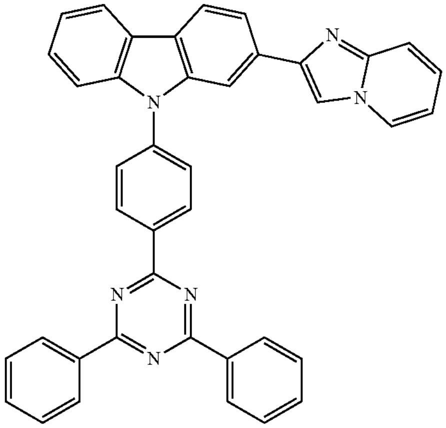
C-132
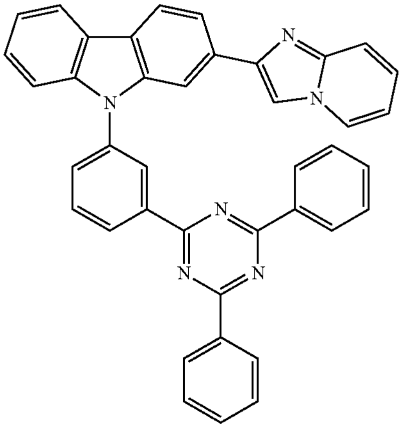
C-133
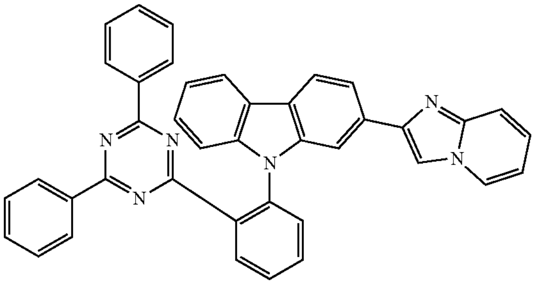

-continued
C-134
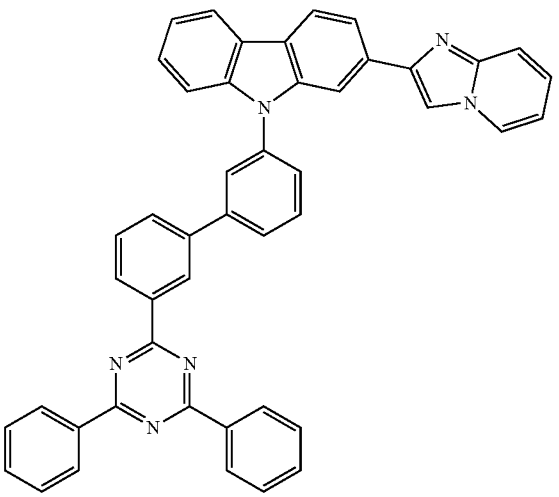
C-135
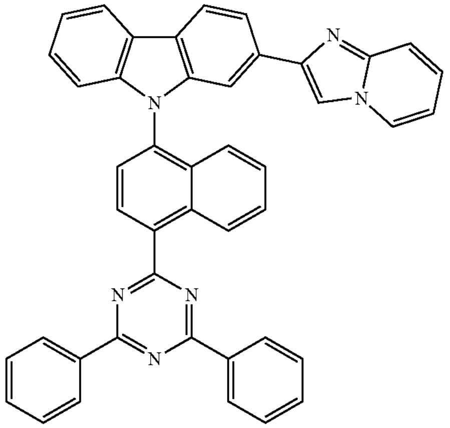
C-136
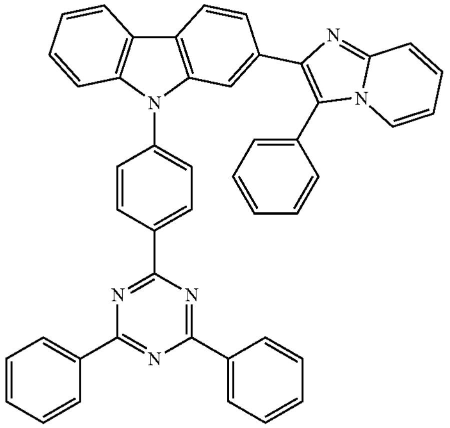
-continued
C-137
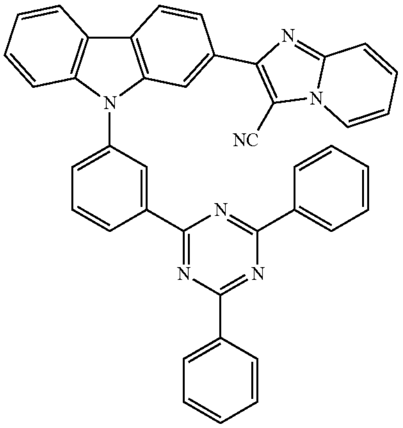
C-138
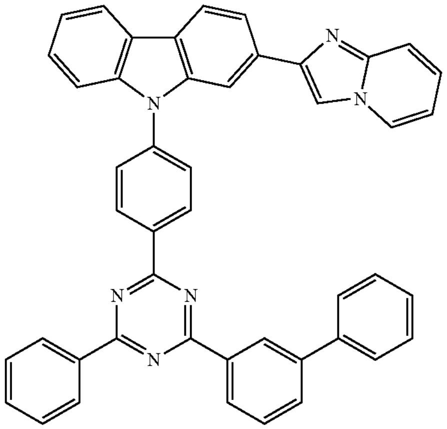
C-139
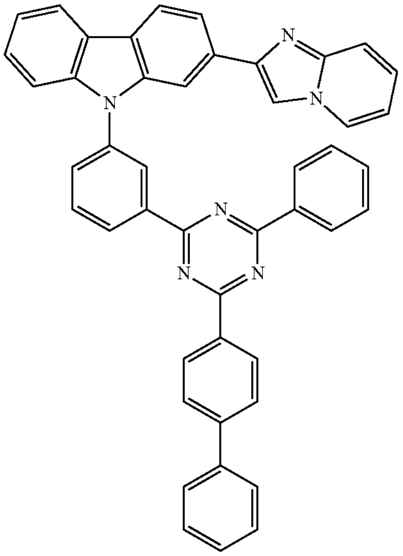

-continued
C-140
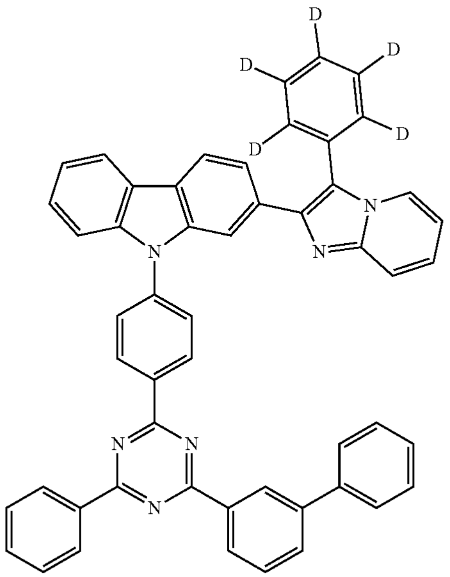
C-141
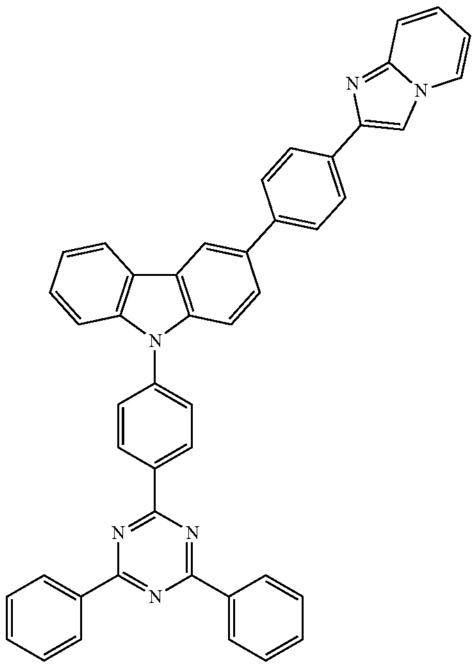
-continued
C-142
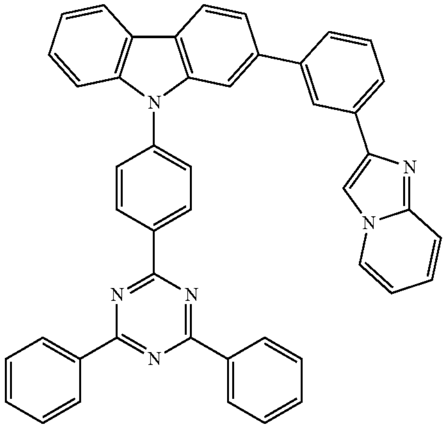
C-143
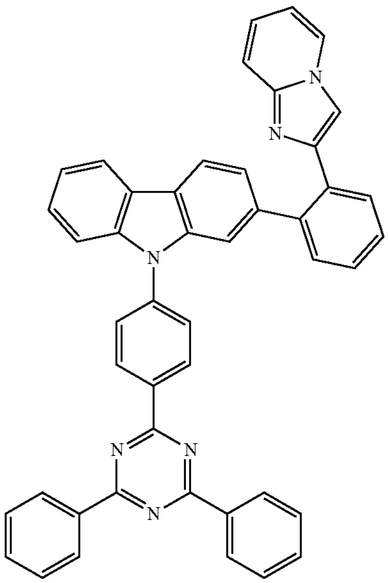
C-144
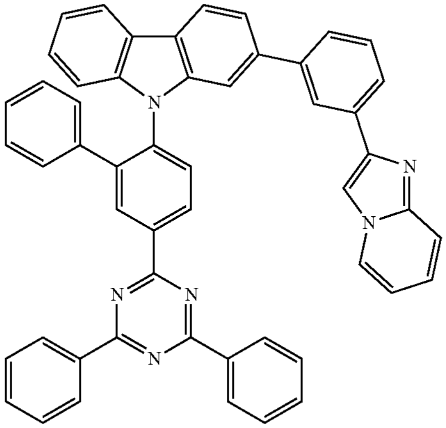

-continued
C-145
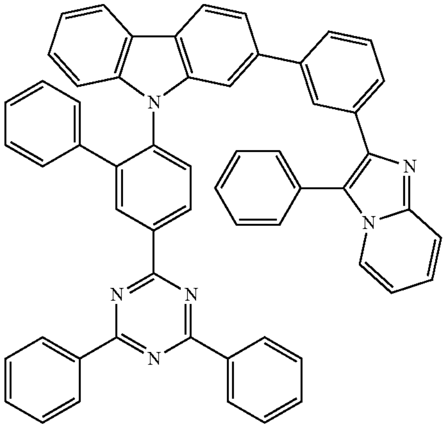
C-146
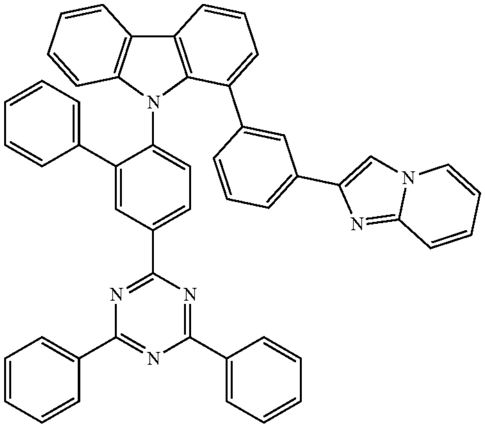
C-147
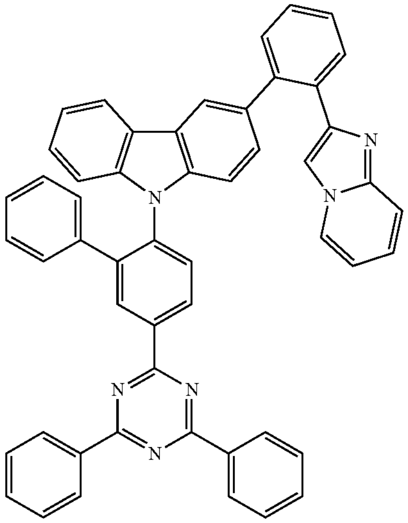
-continued
C-148
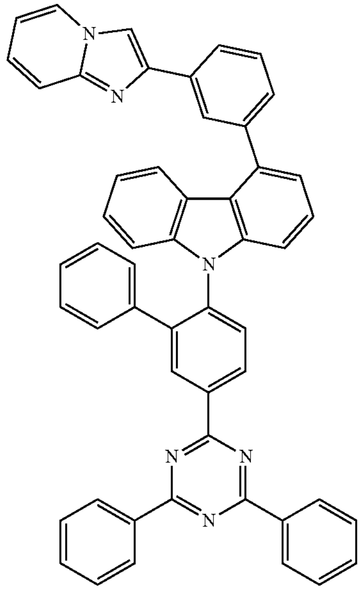
C-149
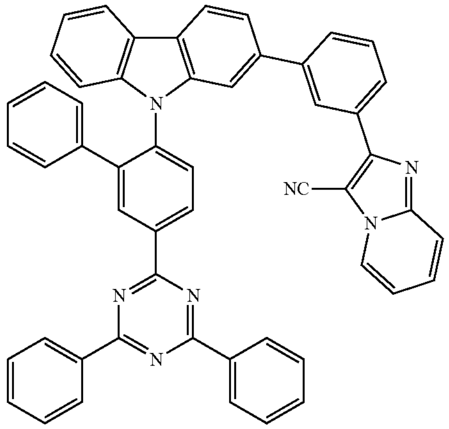
C-150
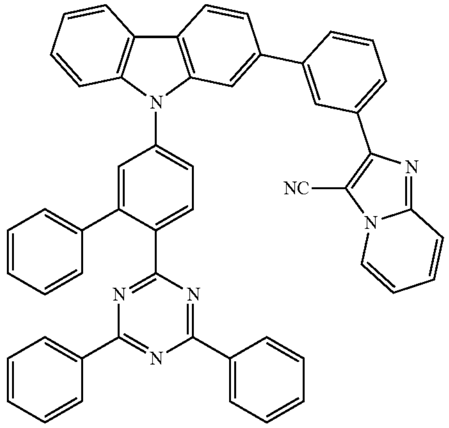

-continued
C-151
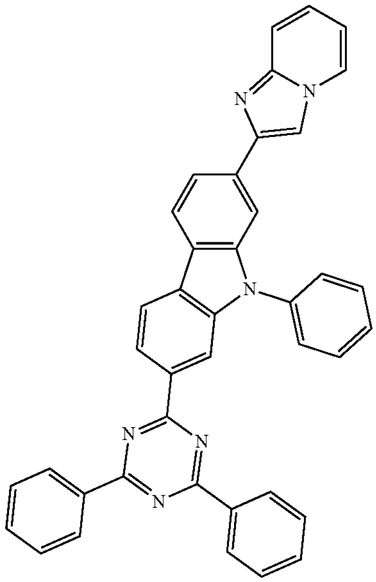
C-152
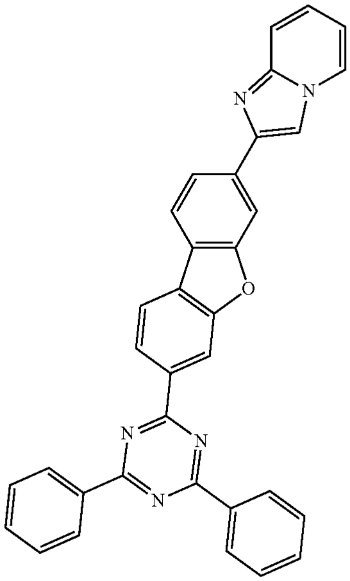
-continued
C-153
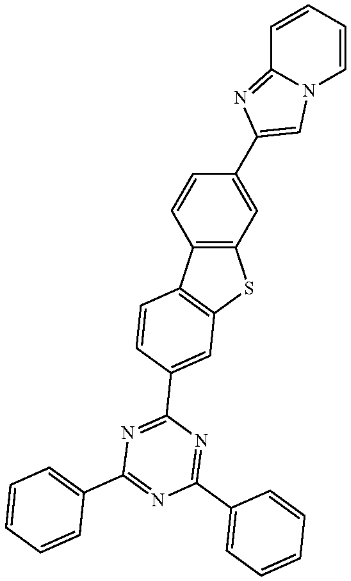
C-154
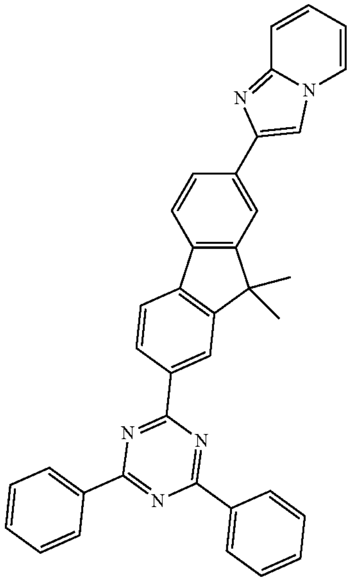

-continued
C-155
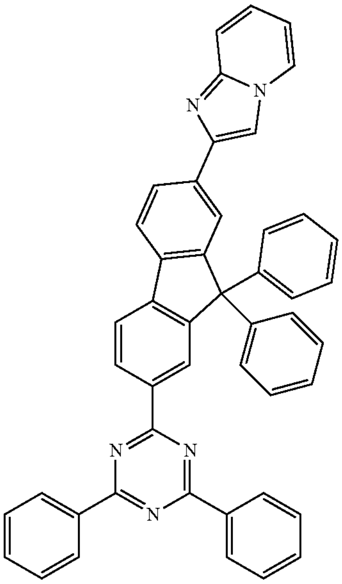
-continued
C-157
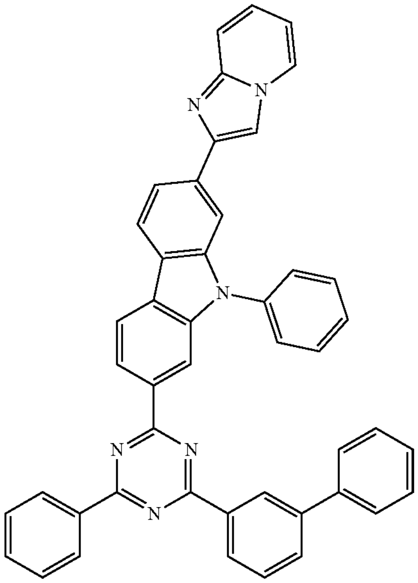
C-156
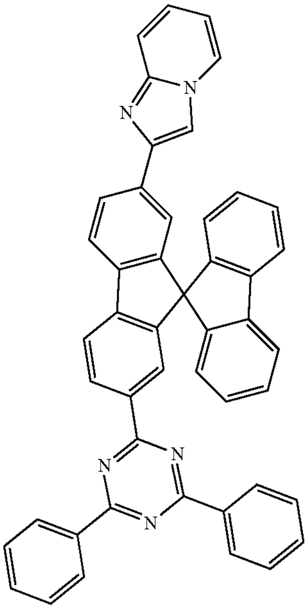
C-158
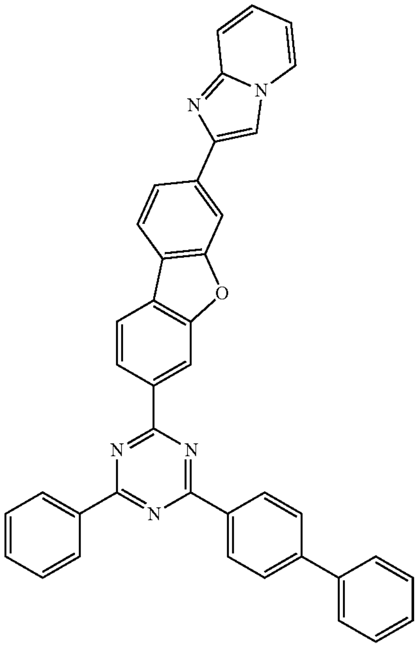

-continued
C-159
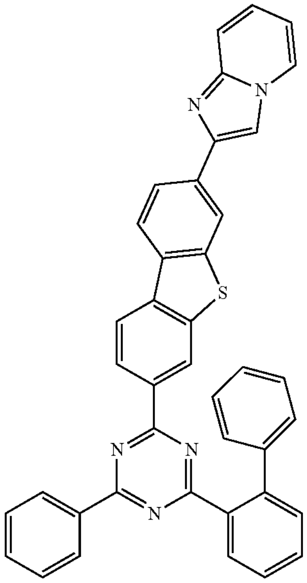
C-160
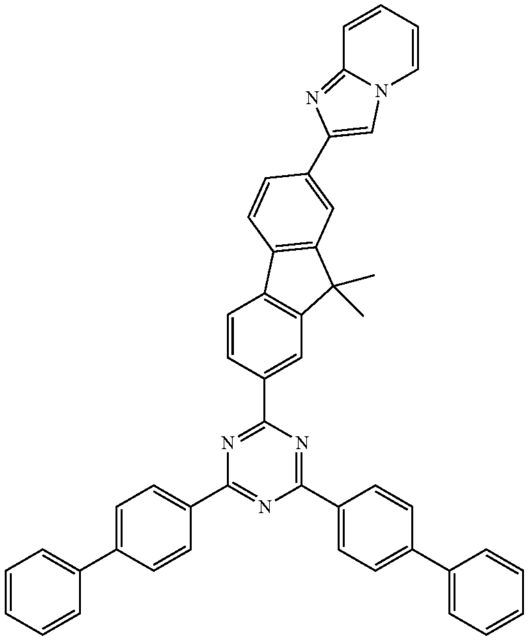
-continued
C-161
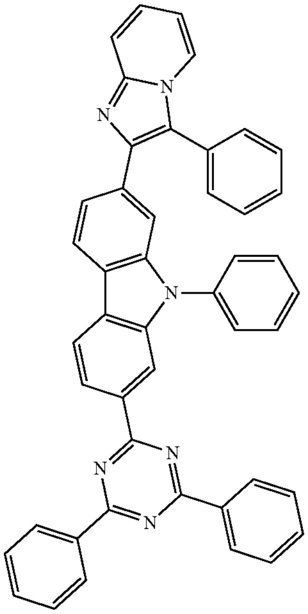
C-162
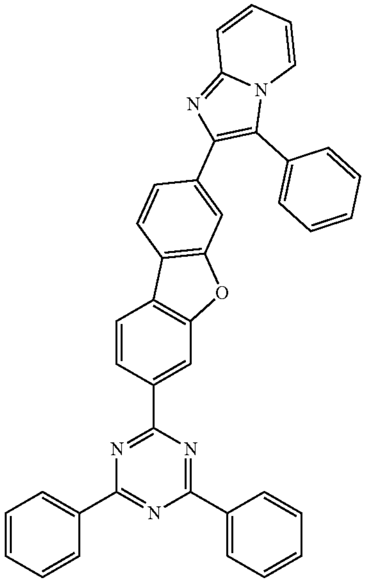

-continued
C-163
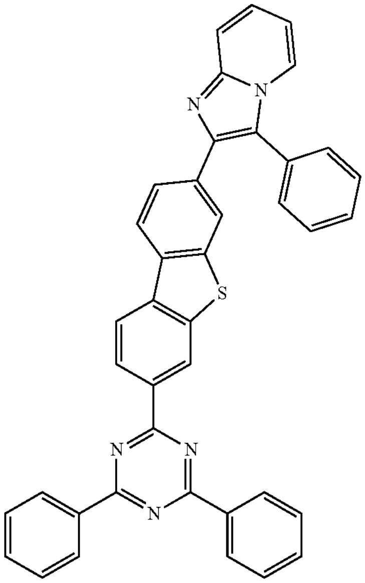
C-164
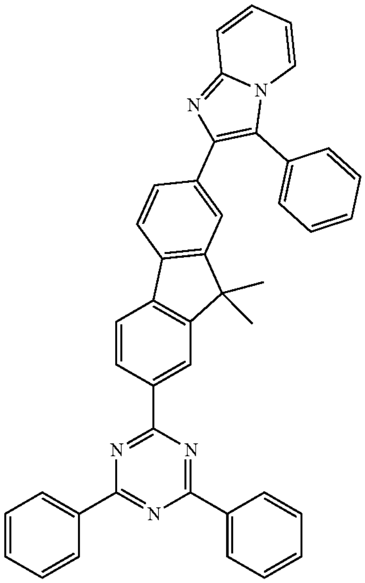
-continued
C-165
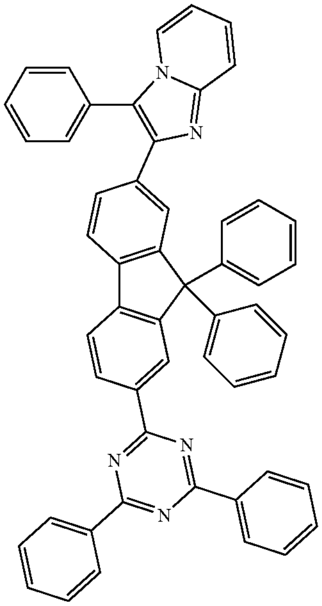
C-166
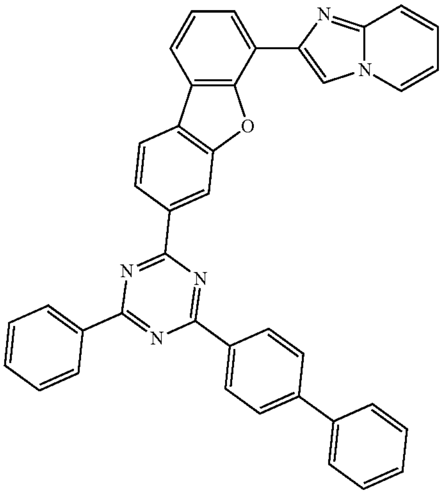

-continued
C-167
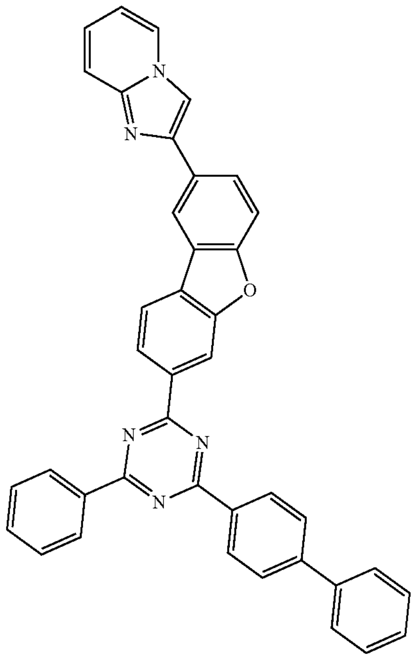
C-168
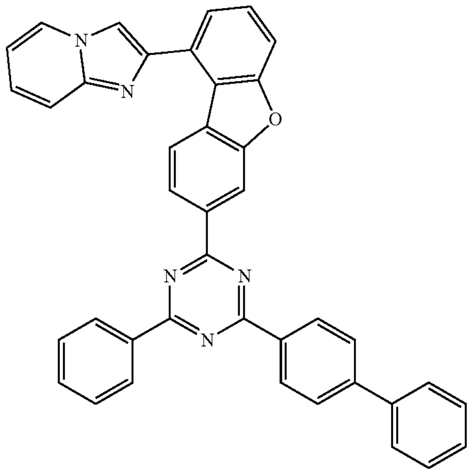
-continued
C-169
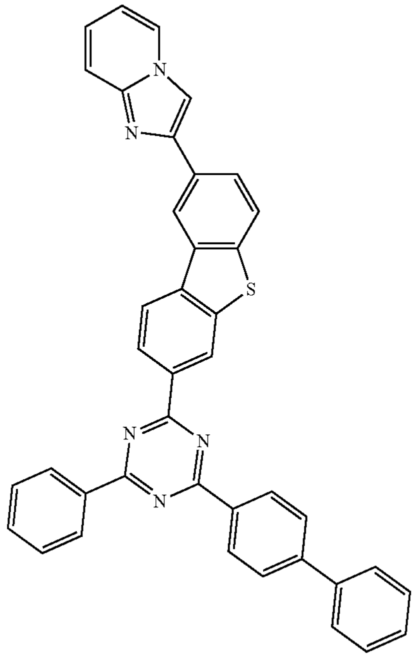
C-170
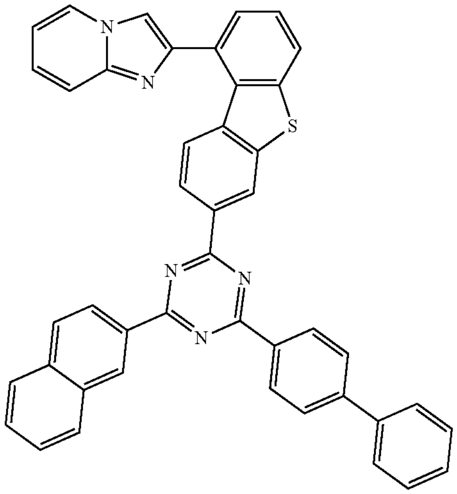
C-171
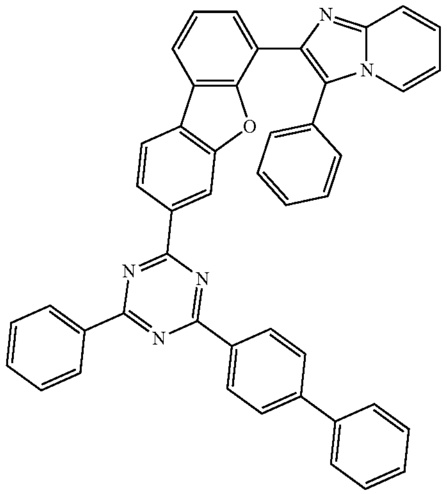

-continued
C-172
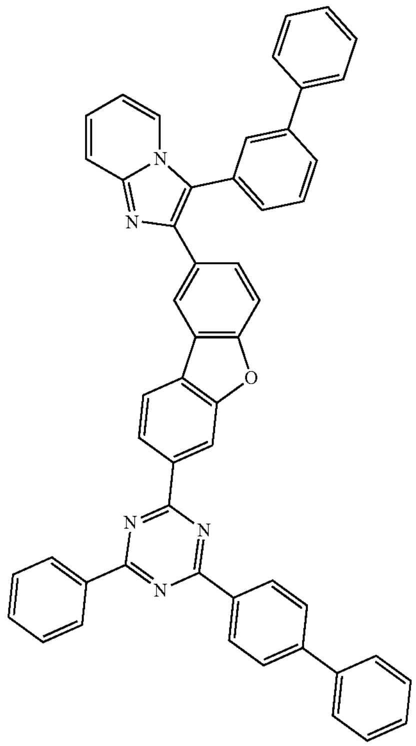
C-173
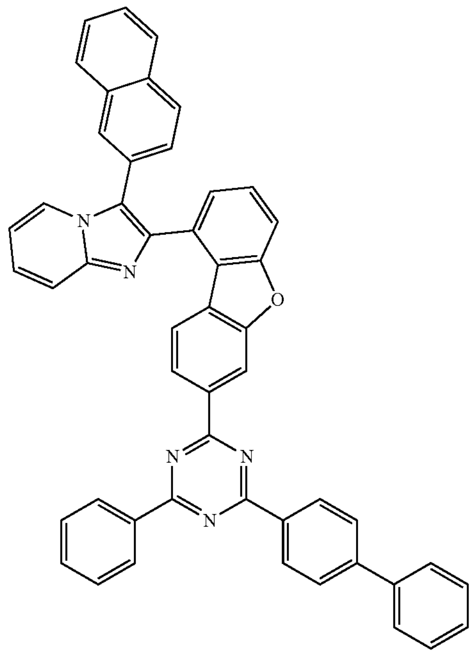
-continued
C-174
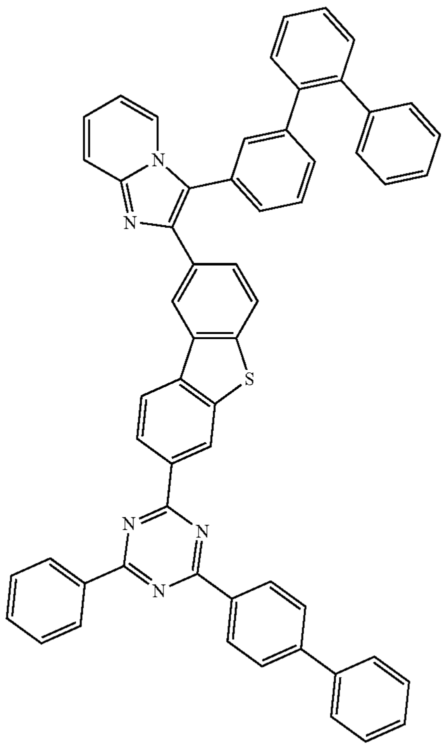
C-175
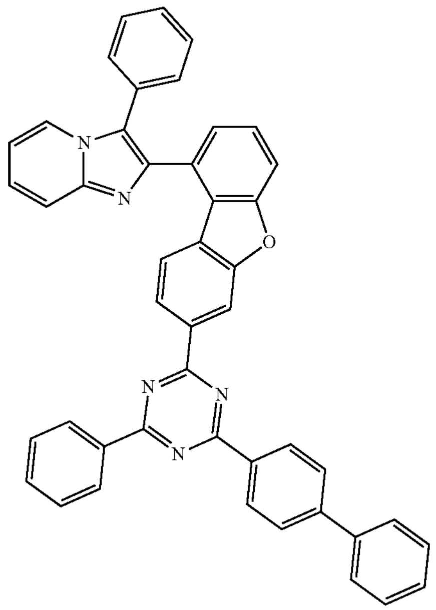

-continued
C-176
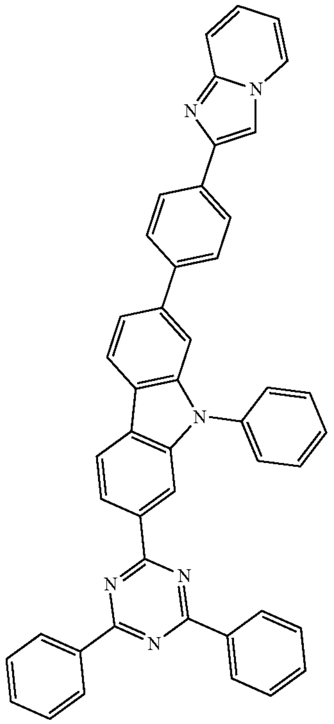
C-177
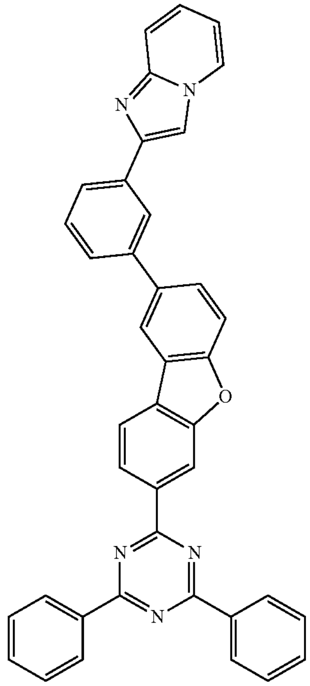
-continued
C-178
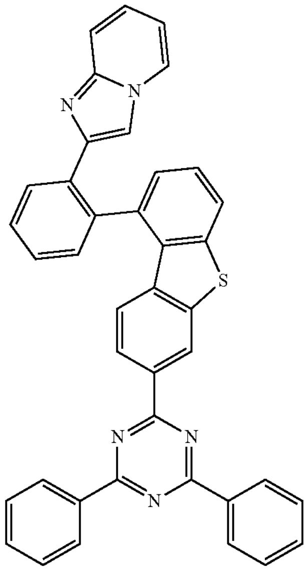
C-179
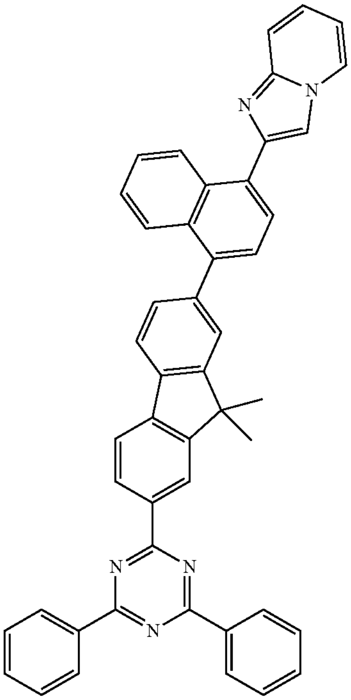

-continued
C-180
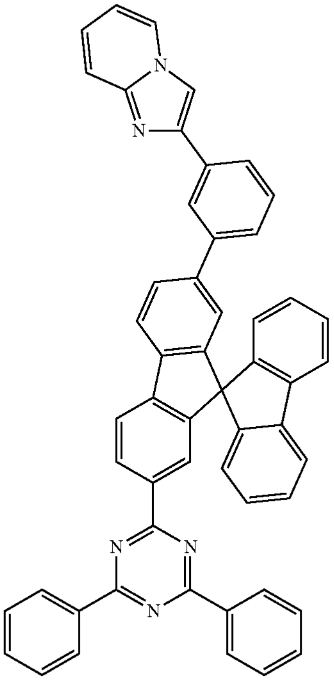
C-181
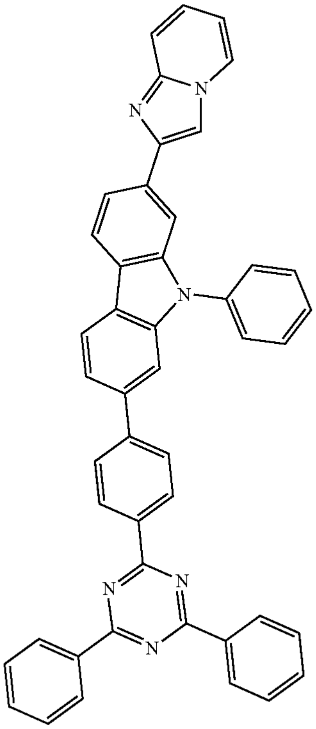
-continued
C-182
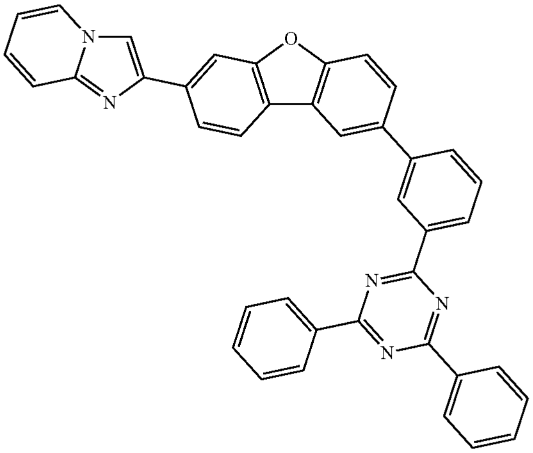
C-183
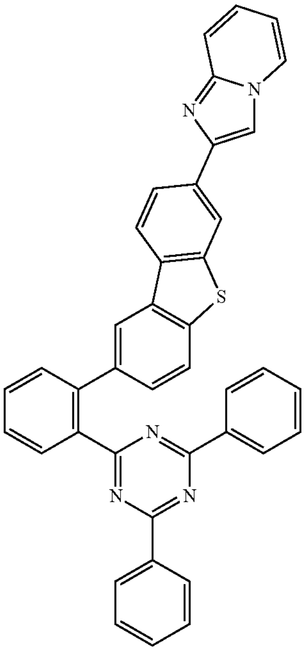

-continued
C-184
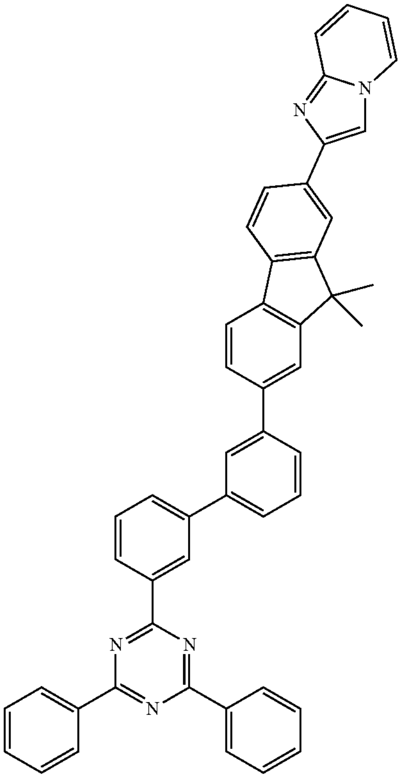
C-185
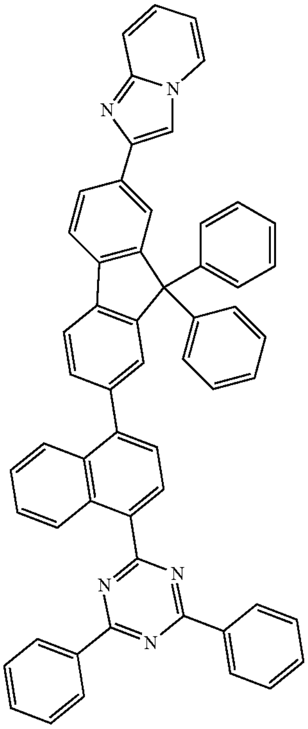
-continued
C-186
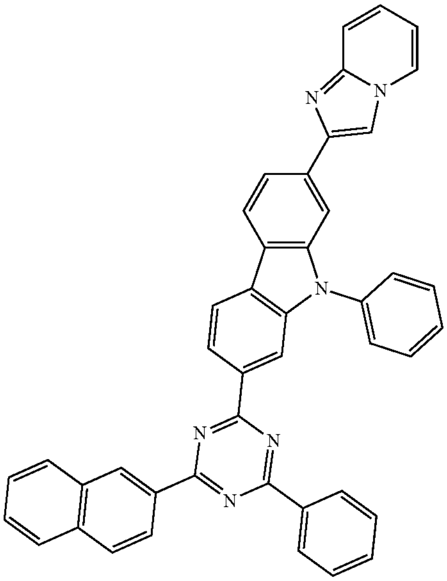
C-187
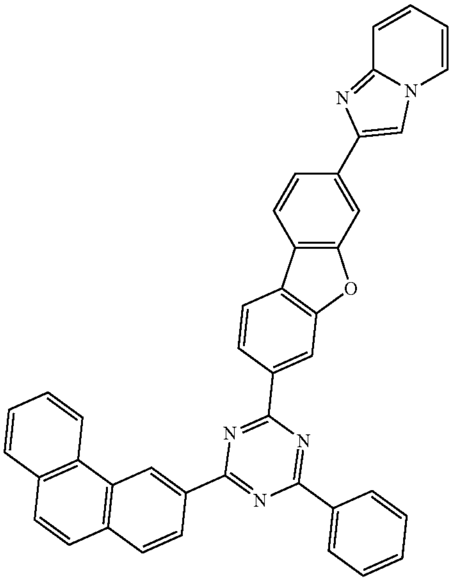

-continued
C-188
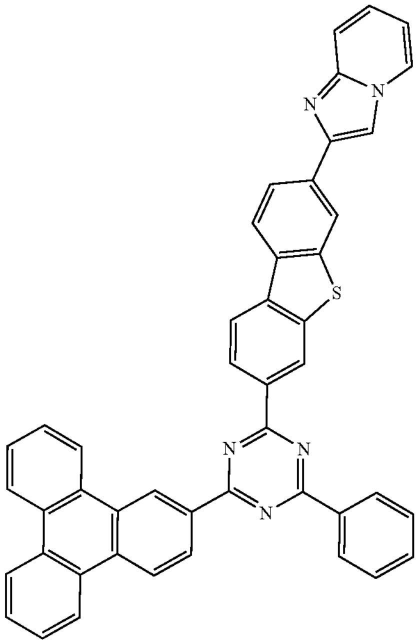
C-189
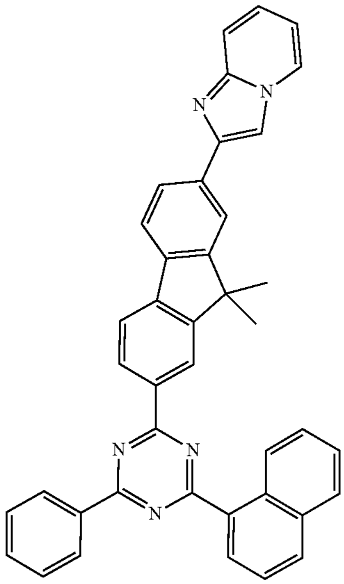
-continued
C-190
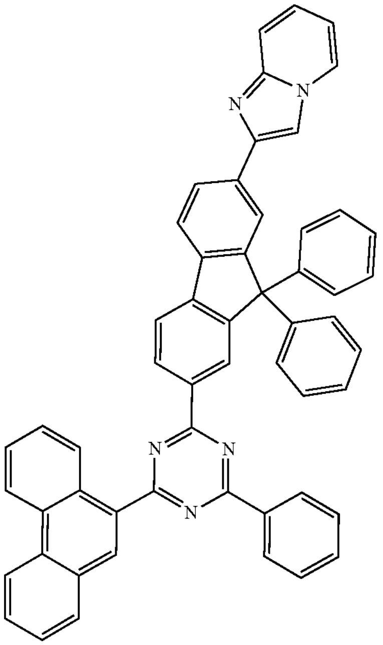
C-191
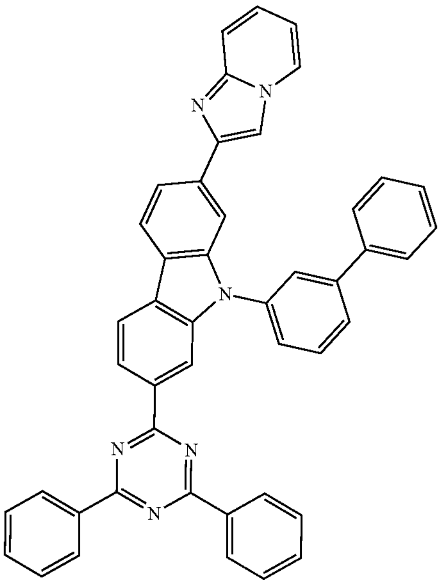

-continued
C-192
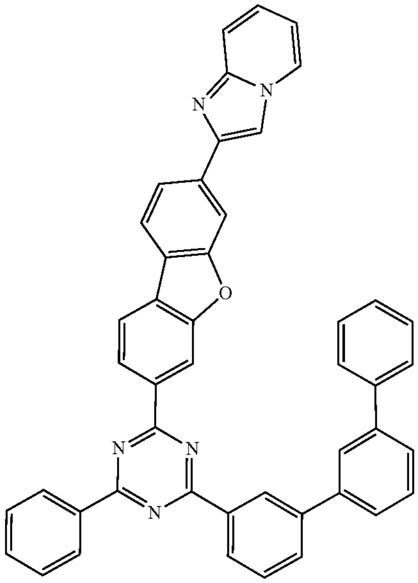
C-193
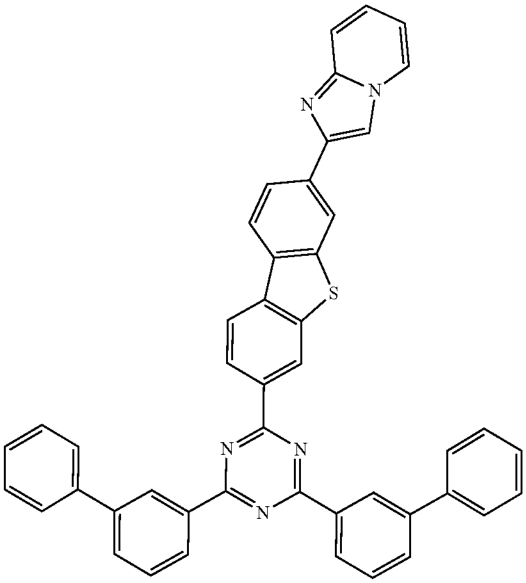
-continued
C-194
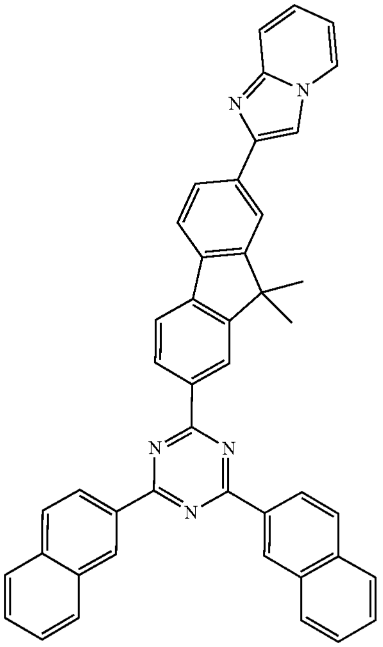
C-195
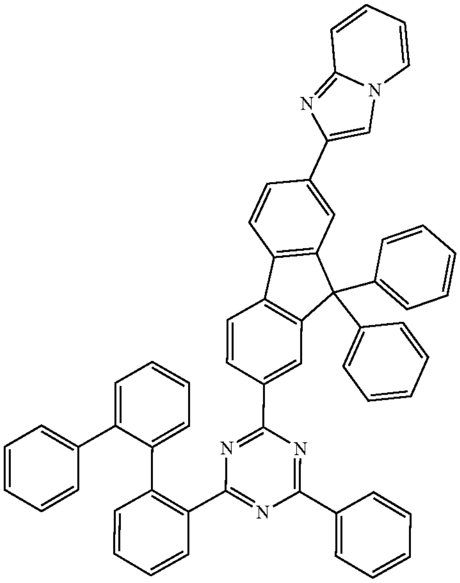
C-196
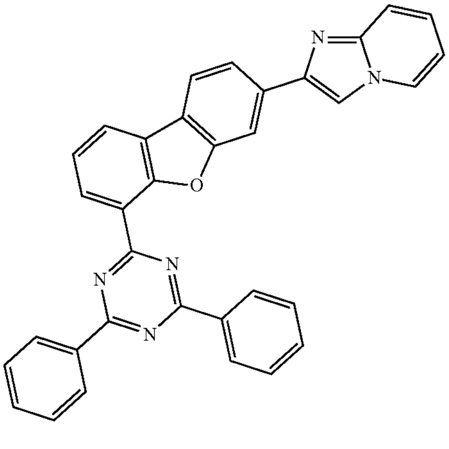

-continued
C-197
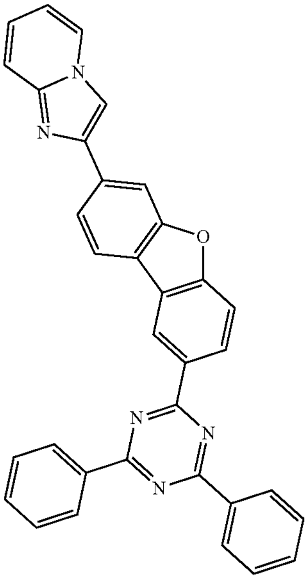
C-198
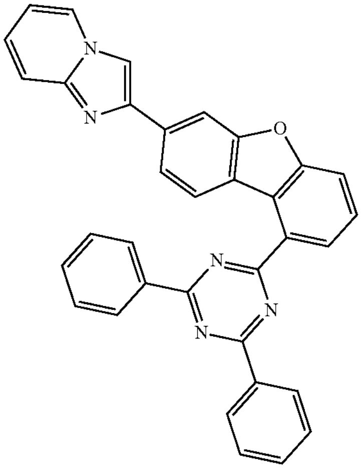
C-199
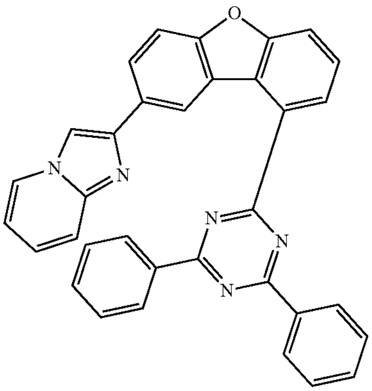
-continued
C-200
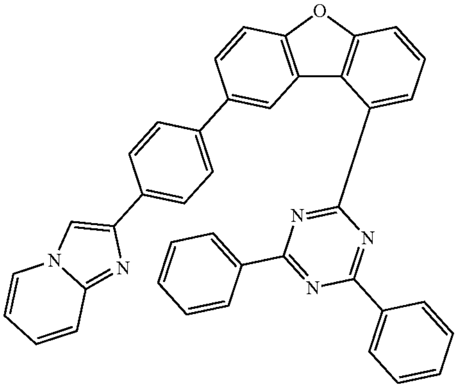
C-201
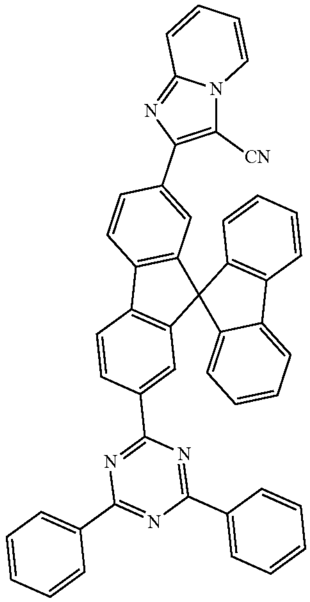
C-202
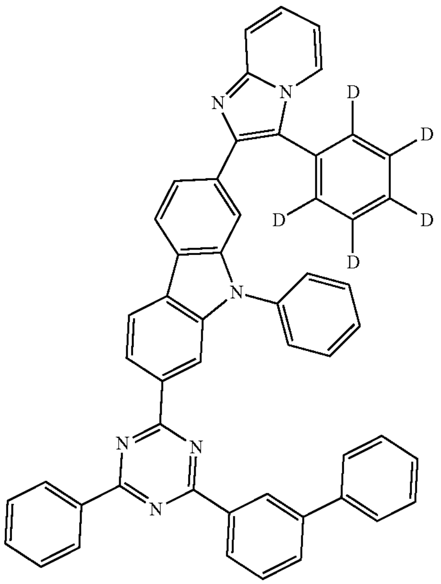

-continued
C-203
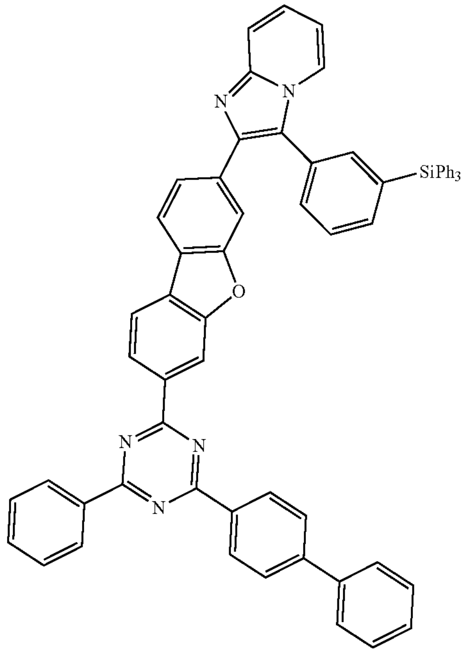
C-204
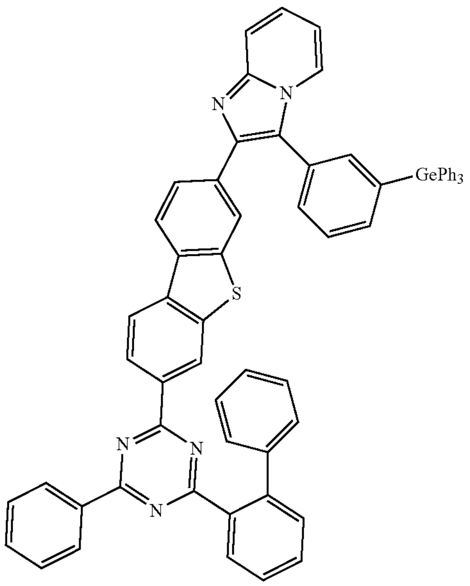
-continued
C-205
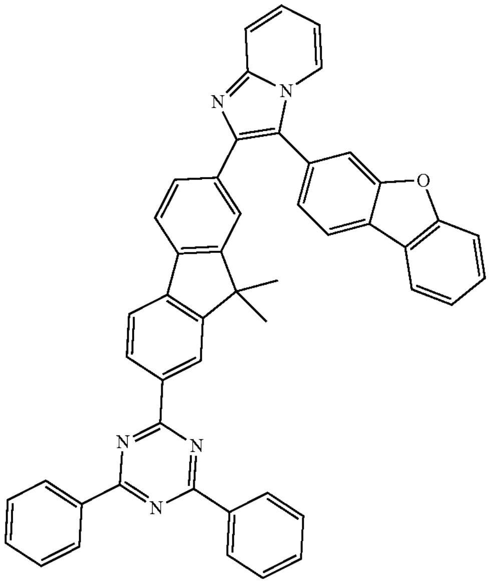
C-206
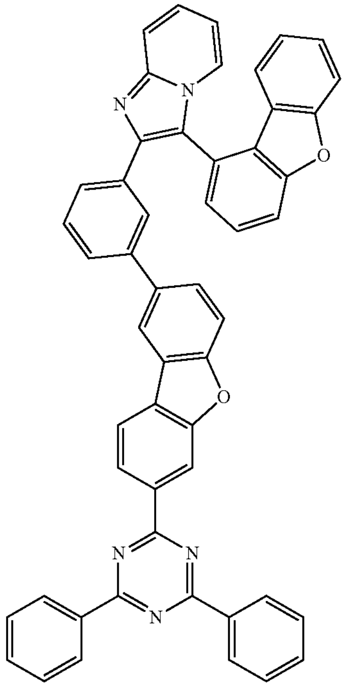

-continued
C-207
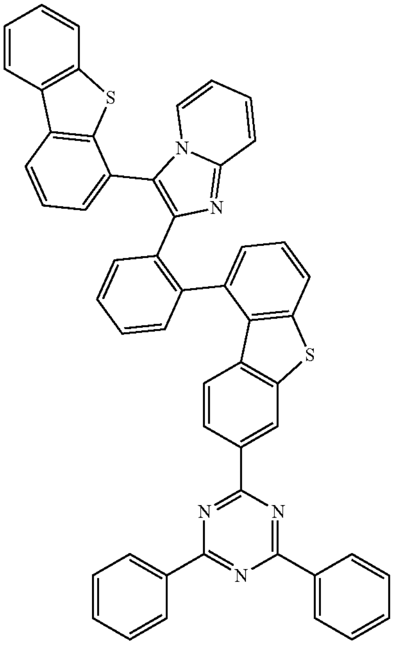
C-208
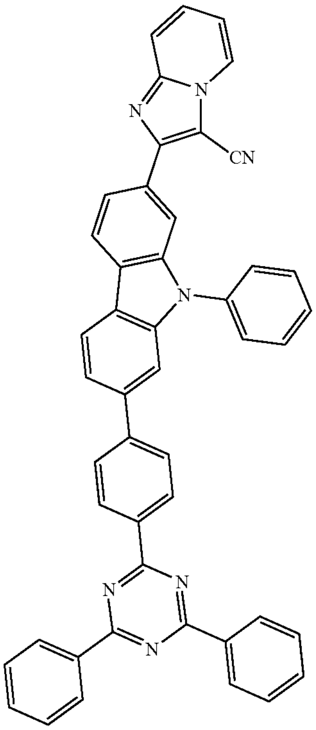
-continued
C-209
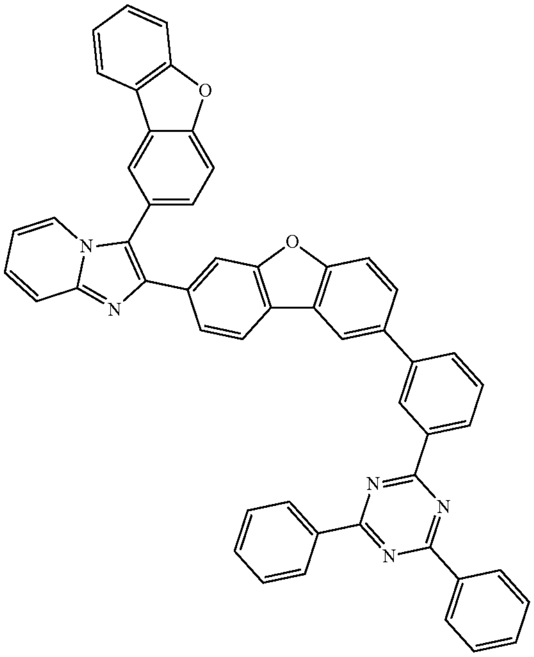
C-210
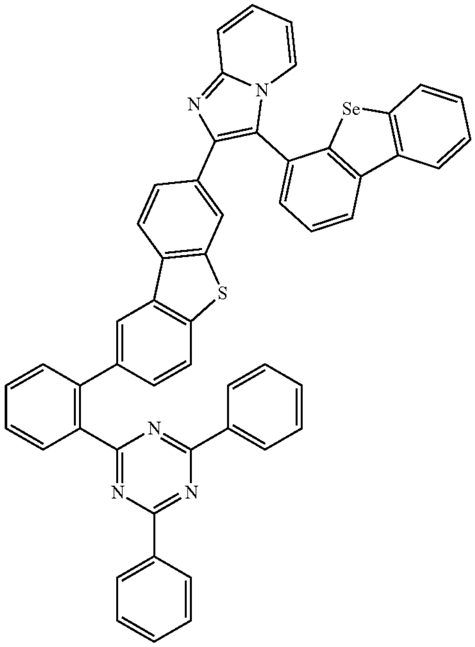

-continued
C-211
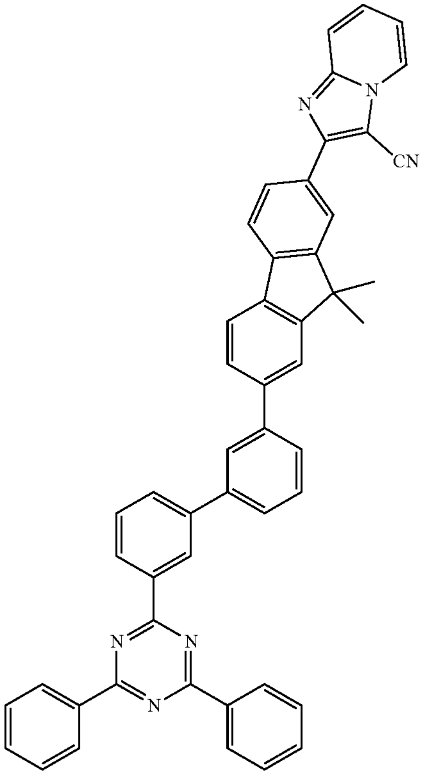
C-212
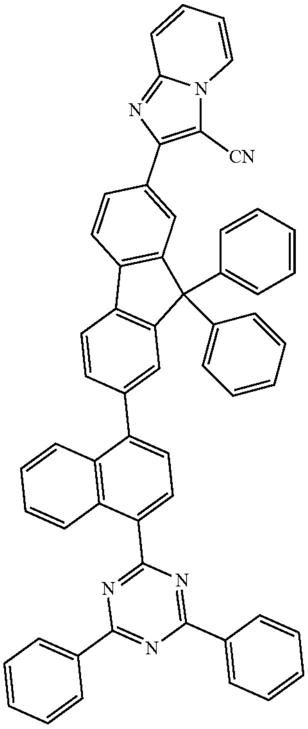
-continued
C-213
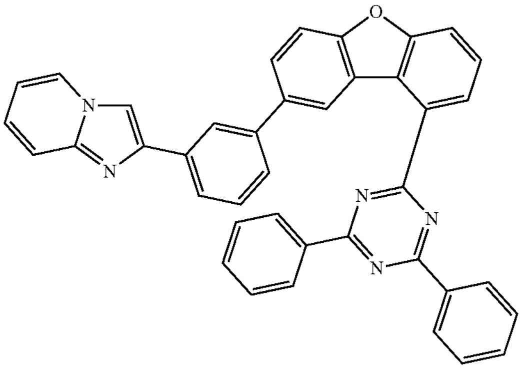
C-214
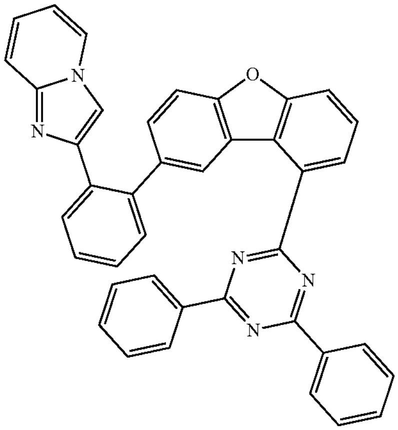
C-215
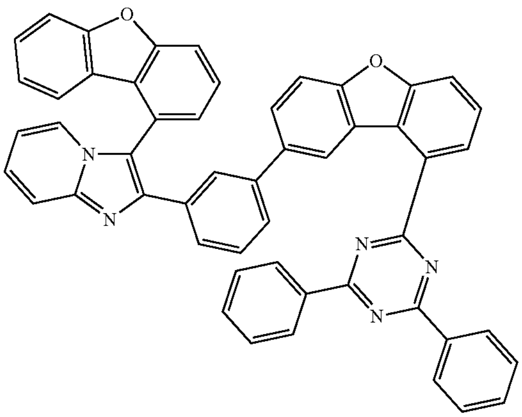

-continued
C-216
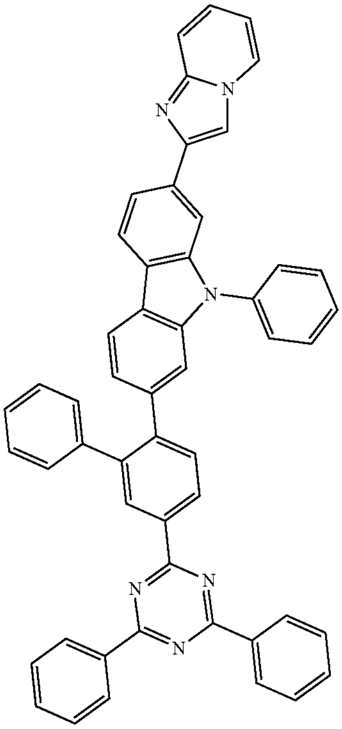
C-217
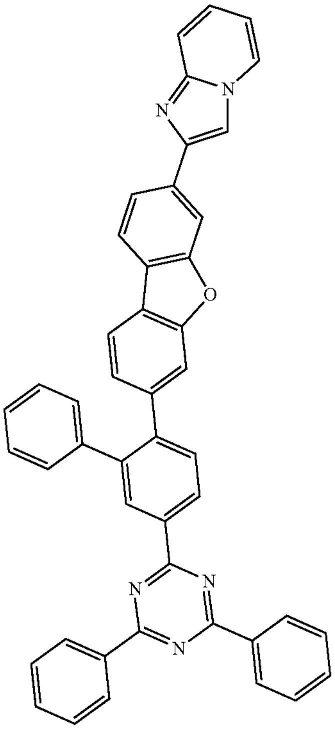
-continued
C-218
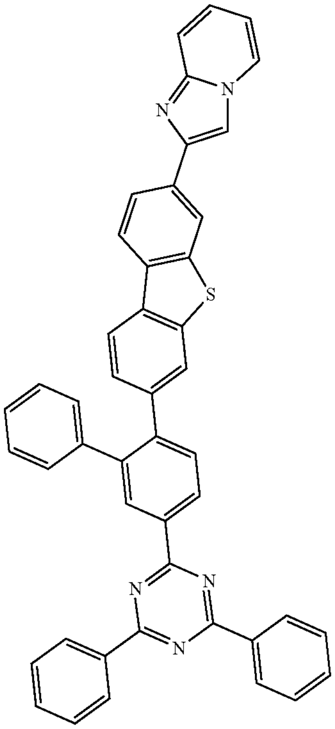
C-219
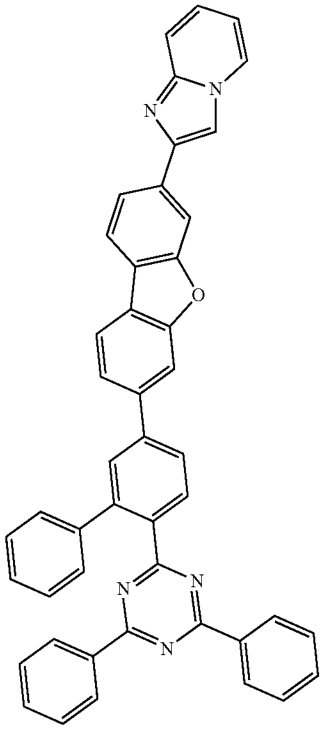
and -continued
C-220
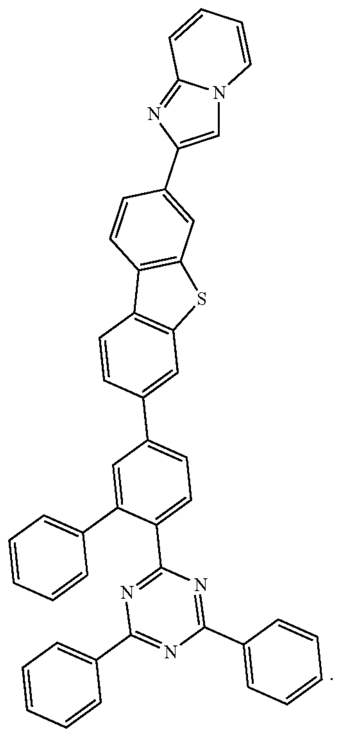
-continued
H2-2
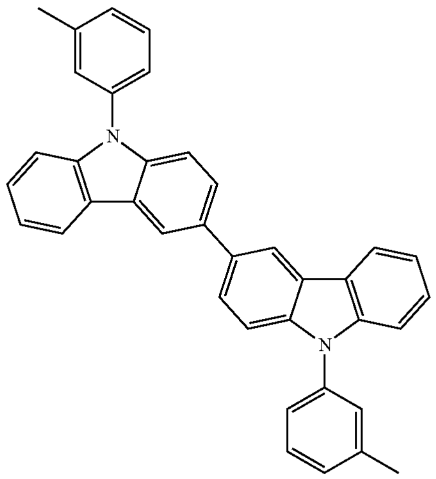
8. The plurality of host materials according to claim 1, wherein the compound represented by formula 2 is selected from the following compounds:
H2-1
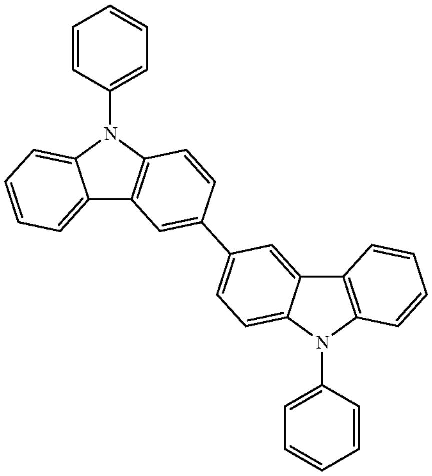
H2-3
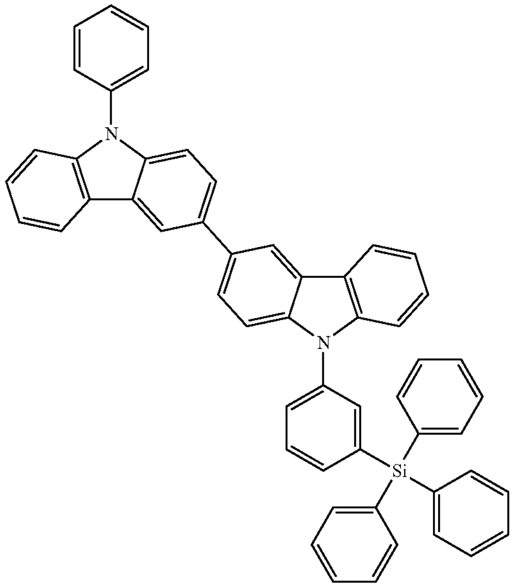

-continued
H2-4
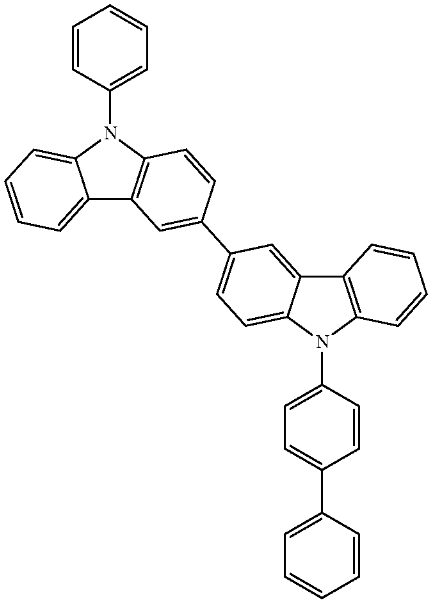
H2-5
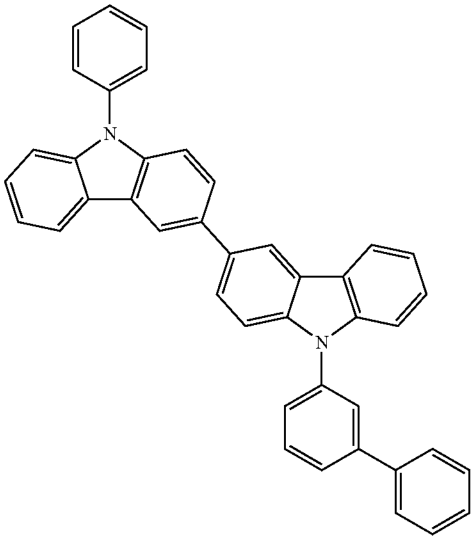
-continued
H2-6
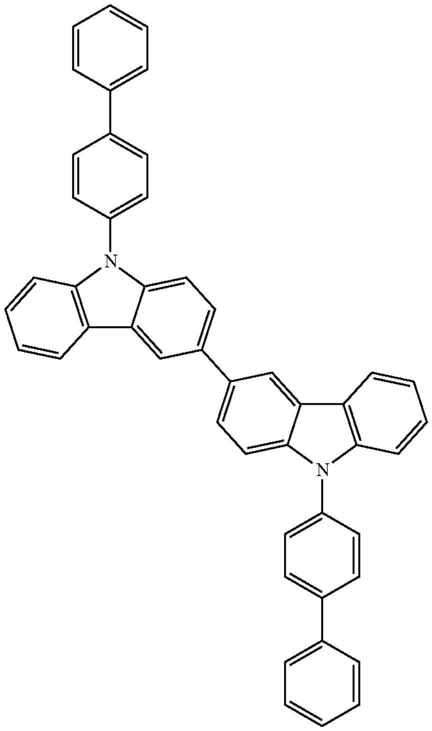
H2-7
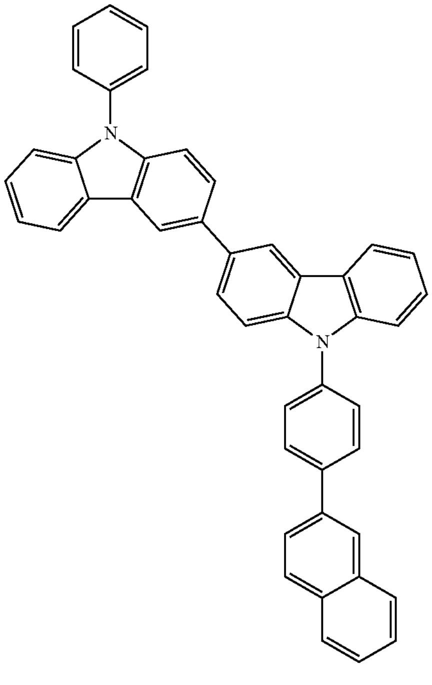

-continued
H2-8
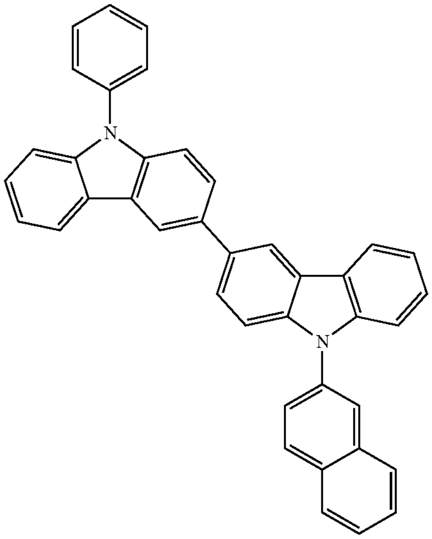
H2-9
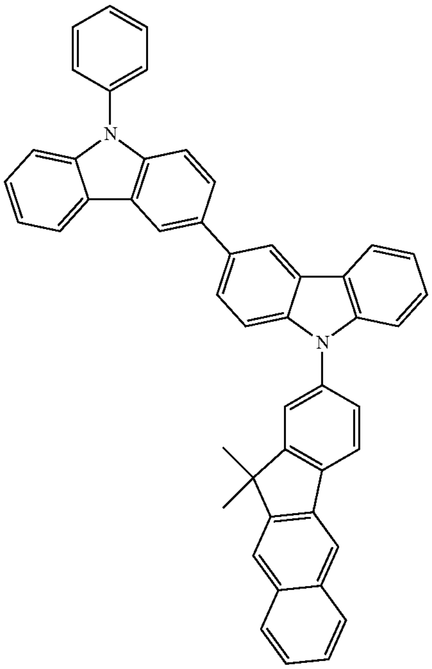
-continued
H2-10
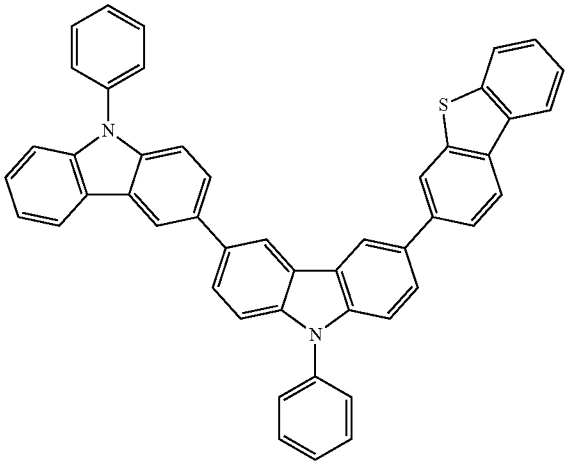
H2-11
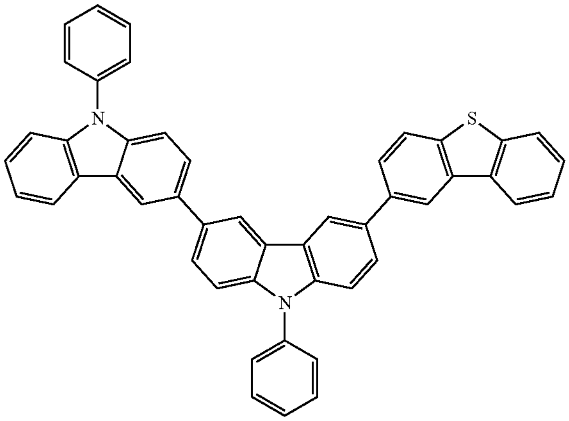
H2-12
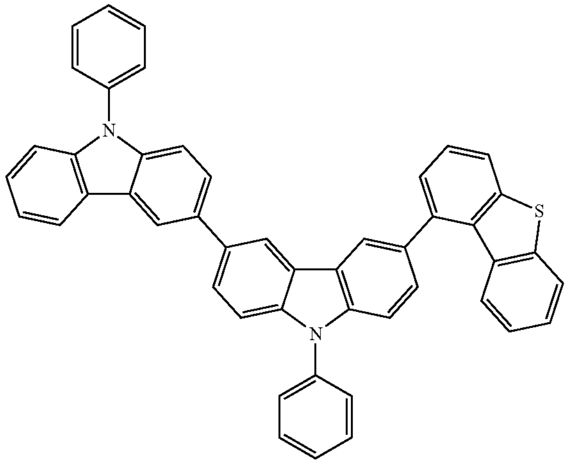

-continued
H2-13
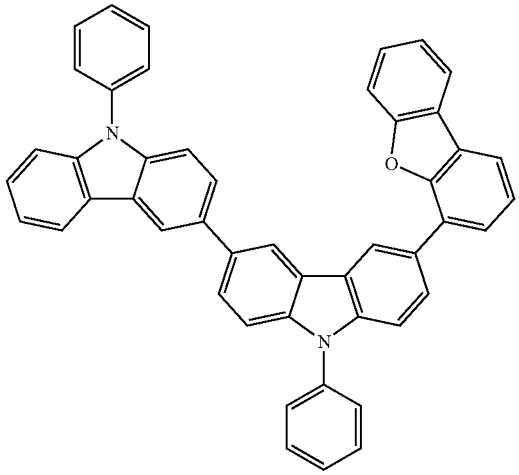
H2-14
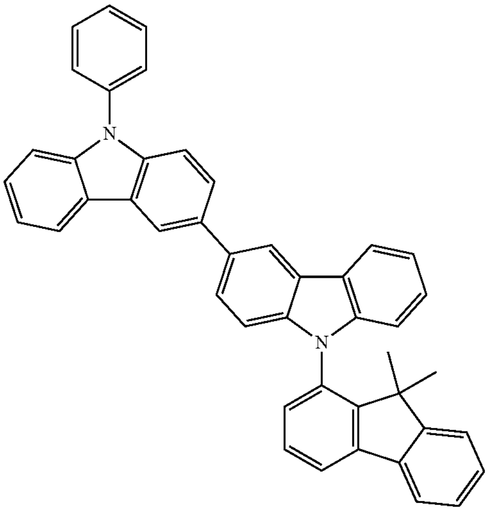
H2-15
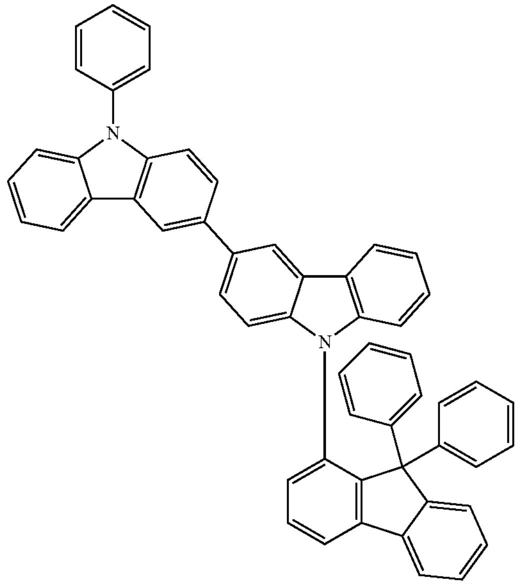
-continued
H2-16
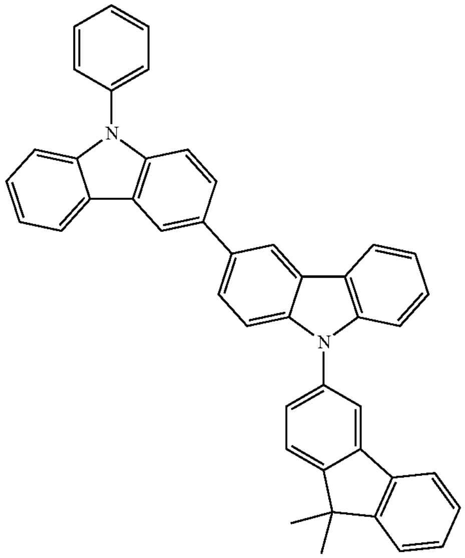
H2-17
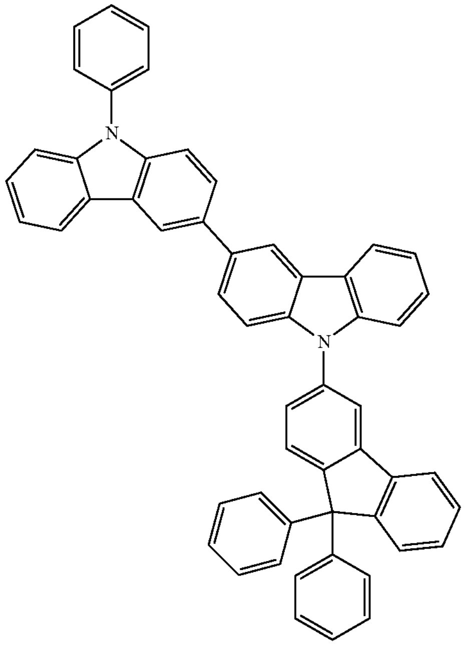

-continued
H2-18
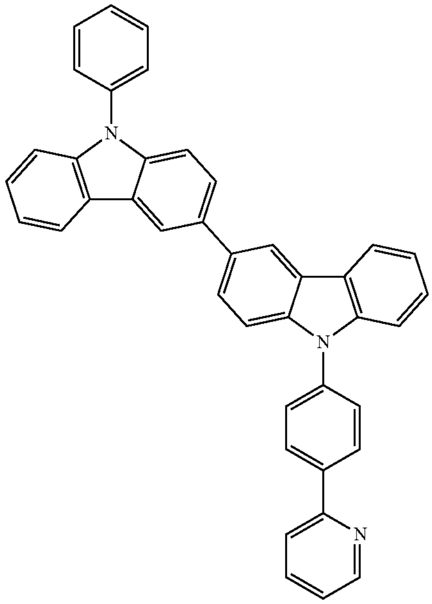
H2-19
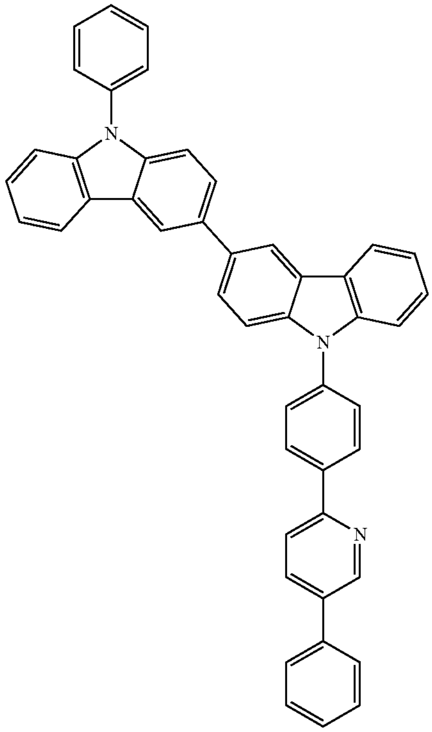
-continued
H2-20
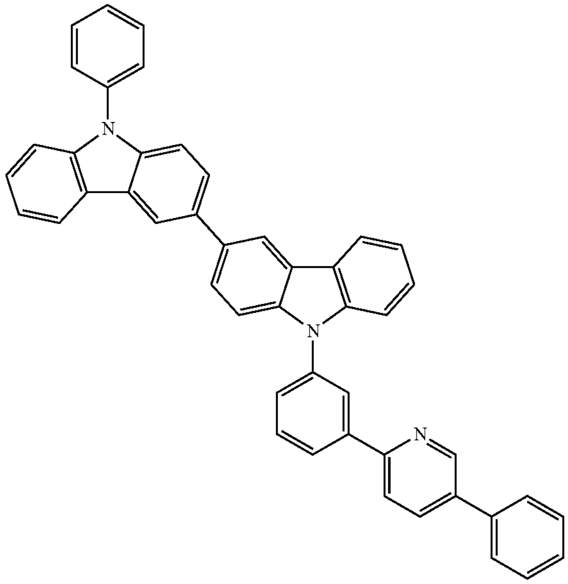
H2-21
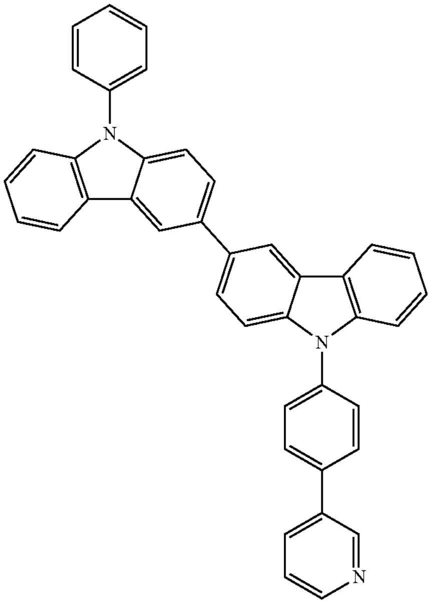

-continued
H2-22
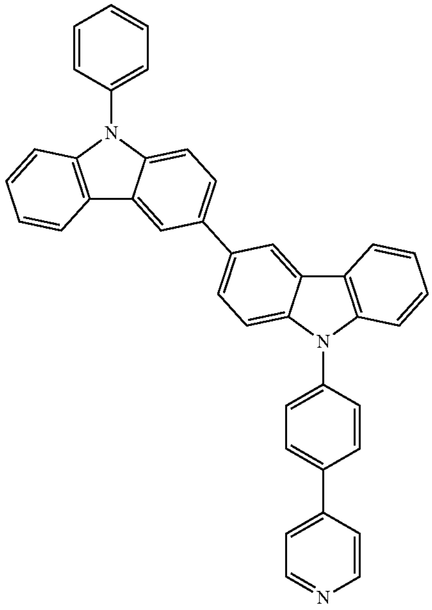
H2-23
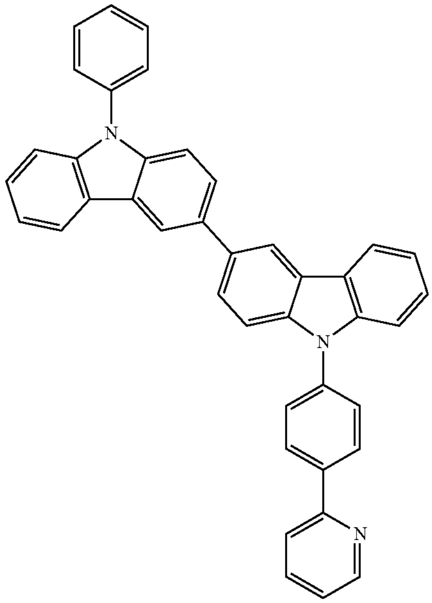
-continued
H2-24
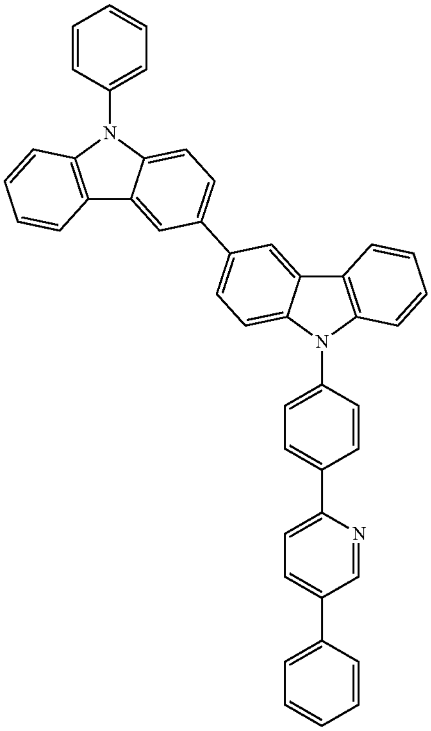
H2-25
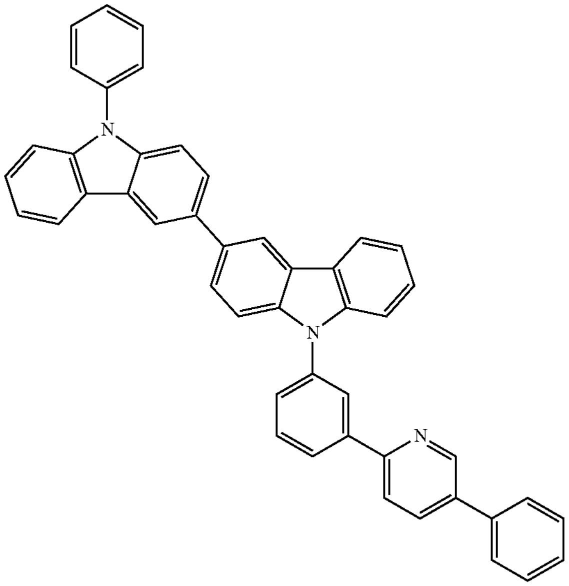

-continued
H2-26
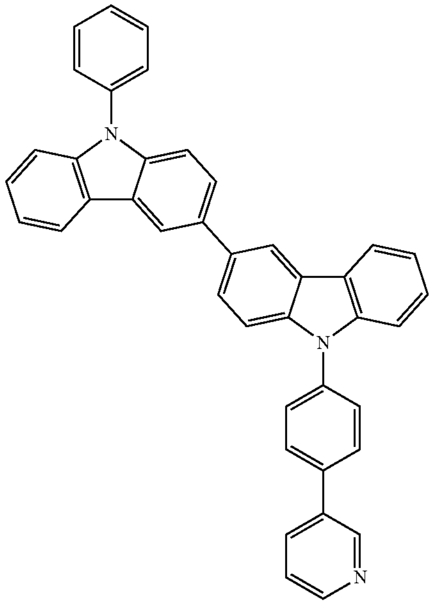
H2-27
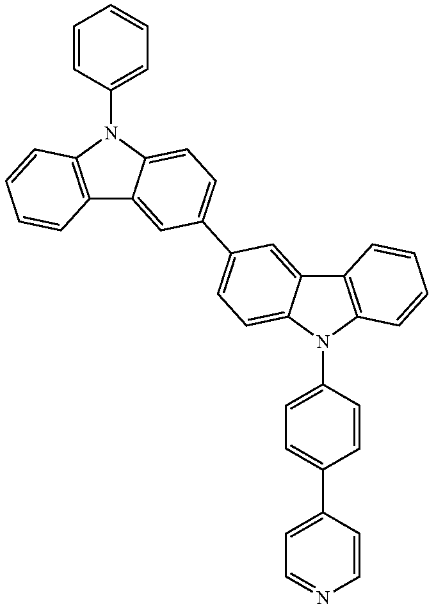
-continued
H2-28
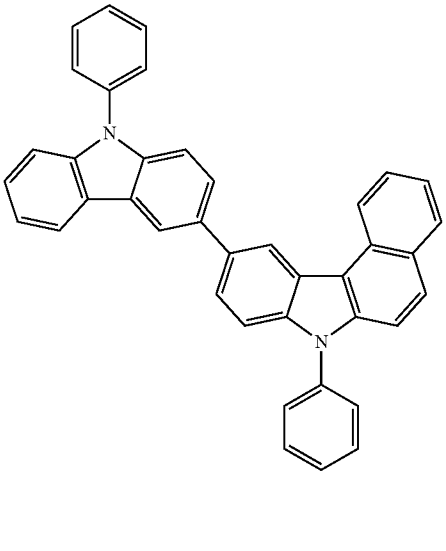
H2-29
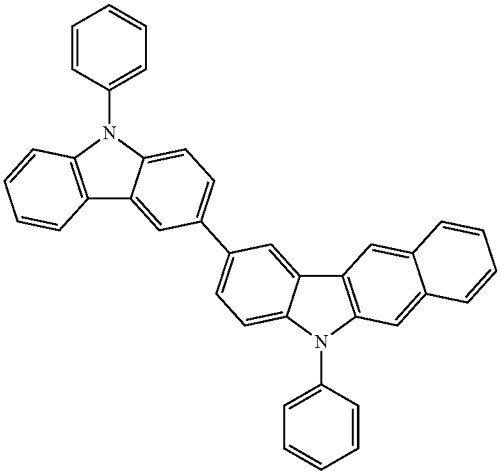
H2-30
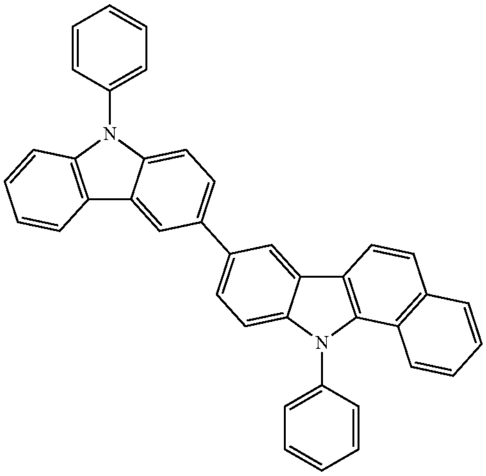

-continued
H2-31
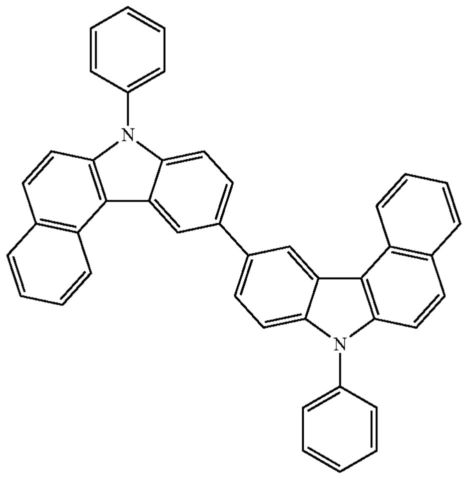
H2-32
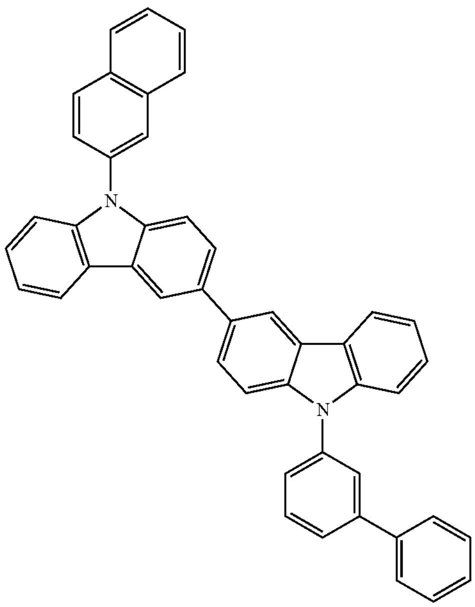
-continued
H2-33
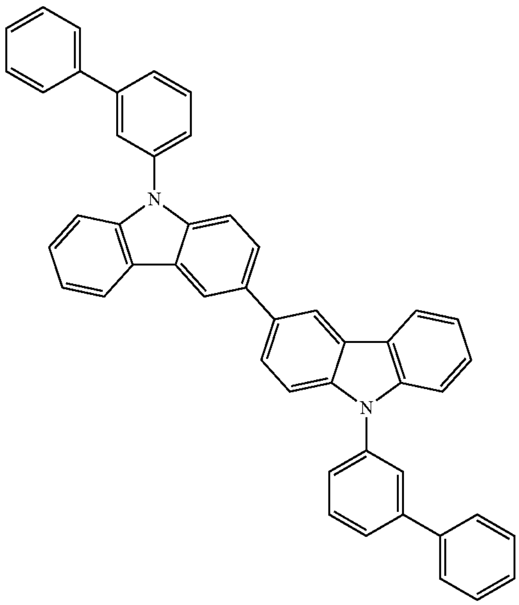
H2-34
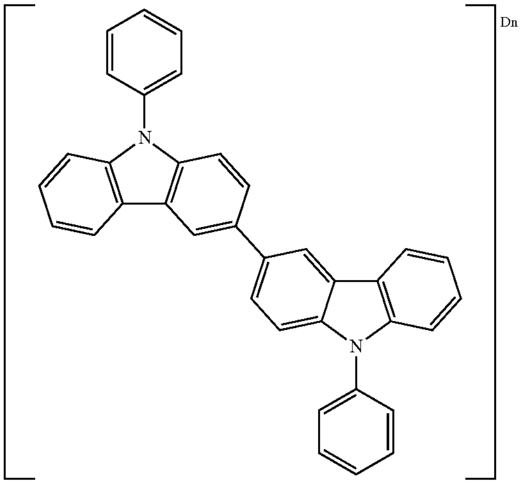

H2-35
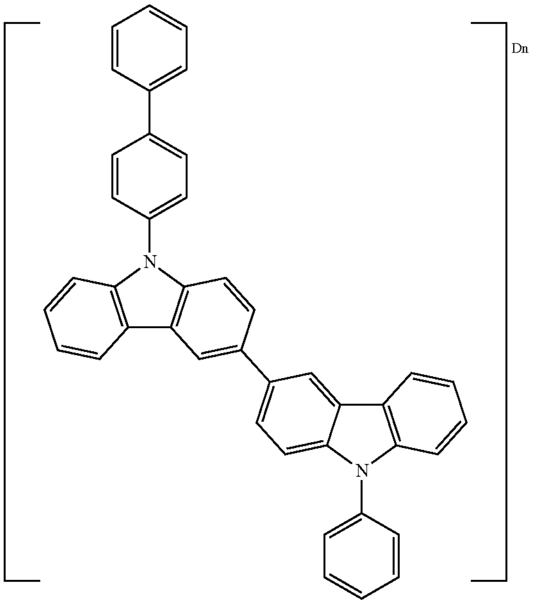
H2-36
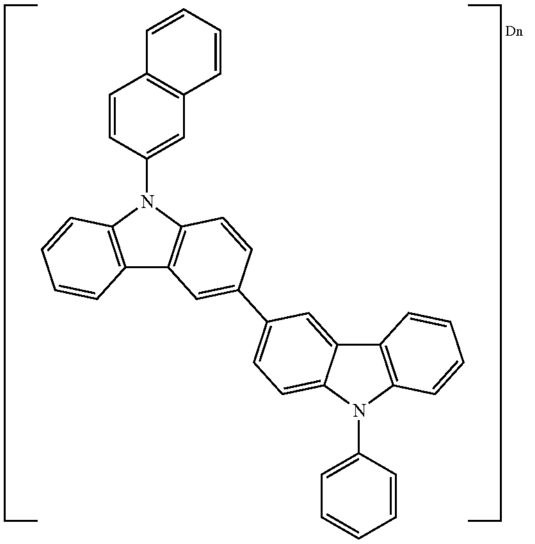
H2-37
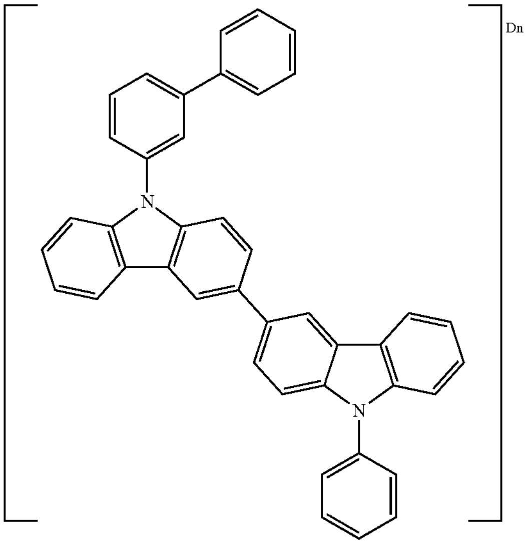
H2-38
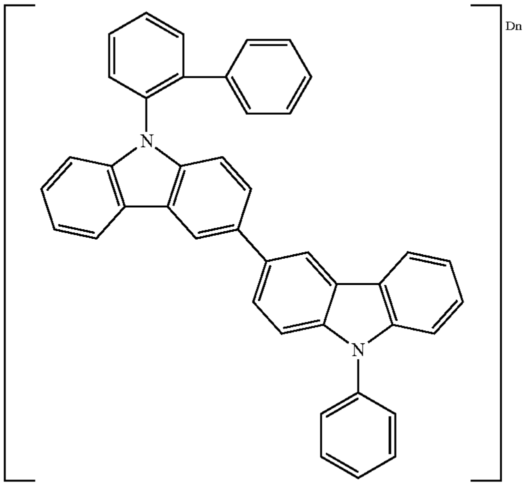
H2-39
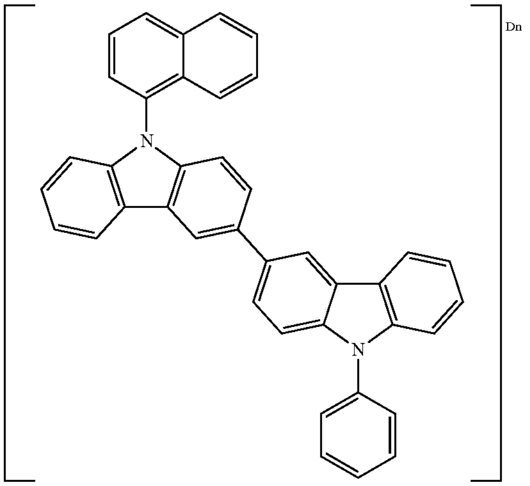

-continued
H2-40
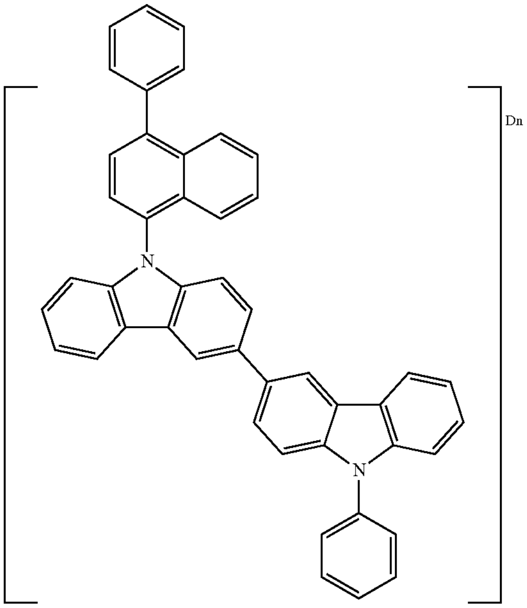
H2-41
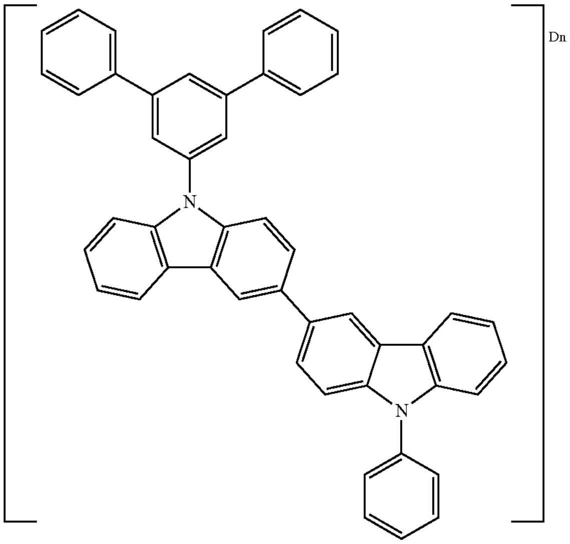
-continued
H2-42
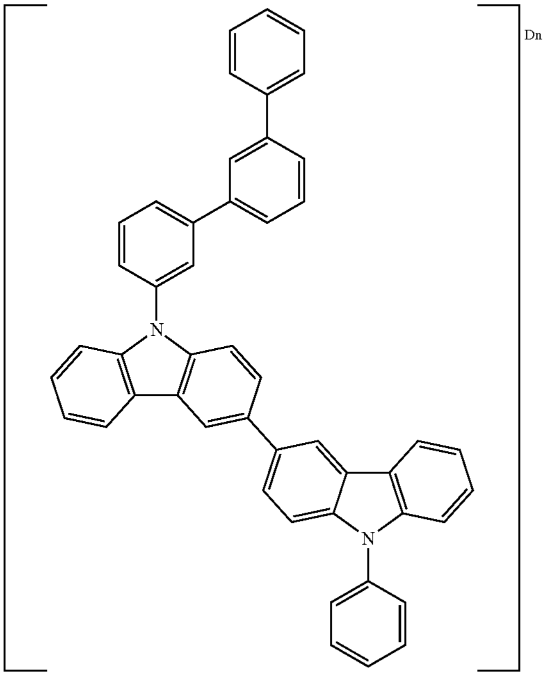
H2-43
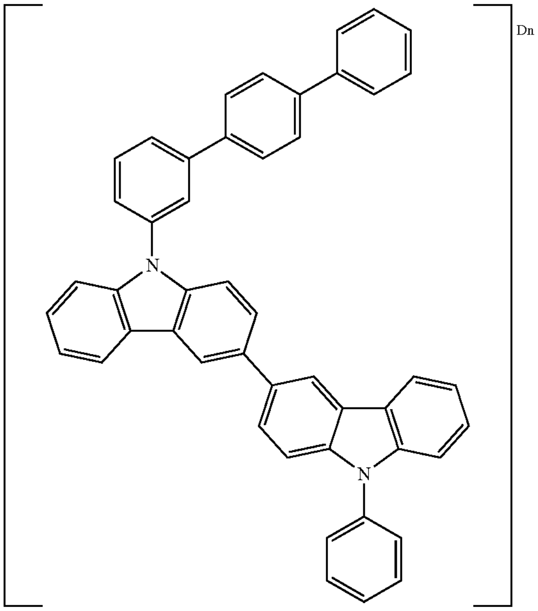

-continued
H2-44
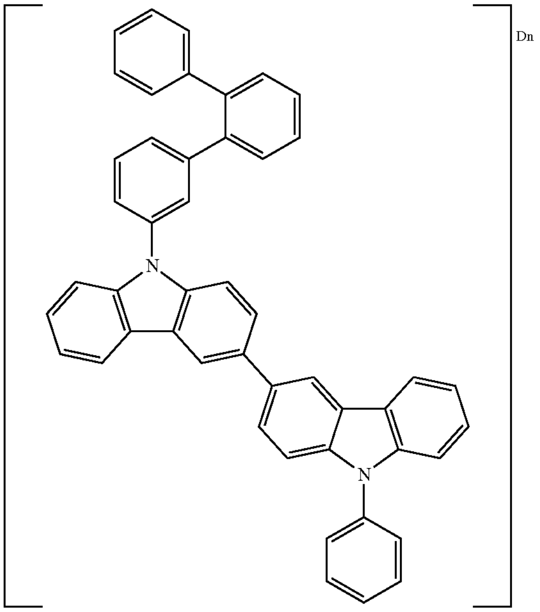
H2-45
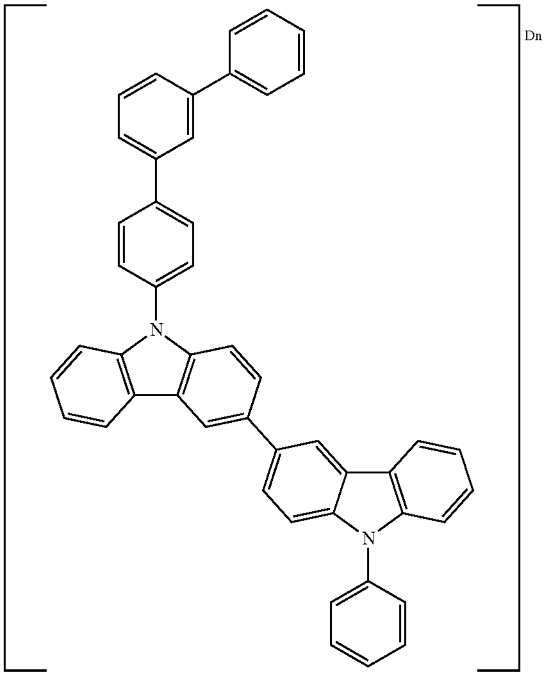
-continued
H2-46
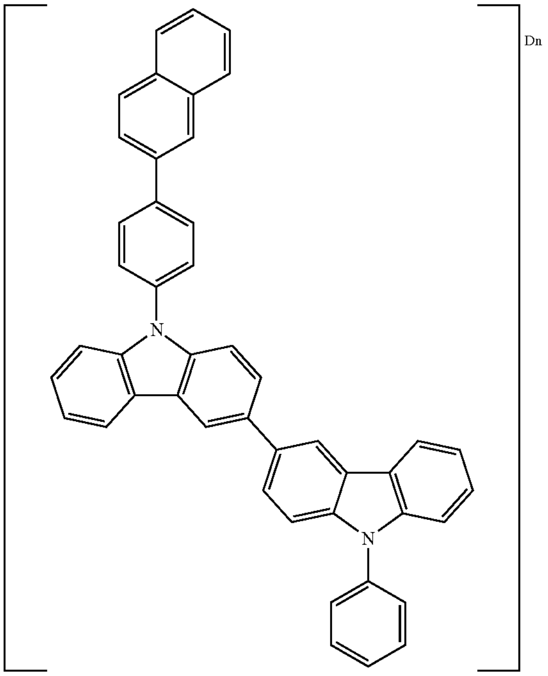
H2-47
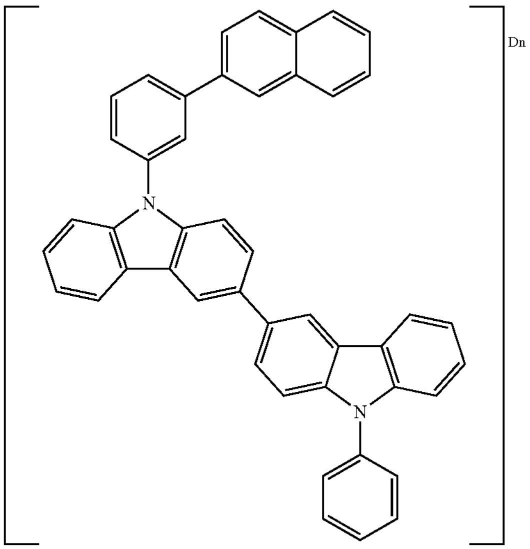

-continued
H2-48
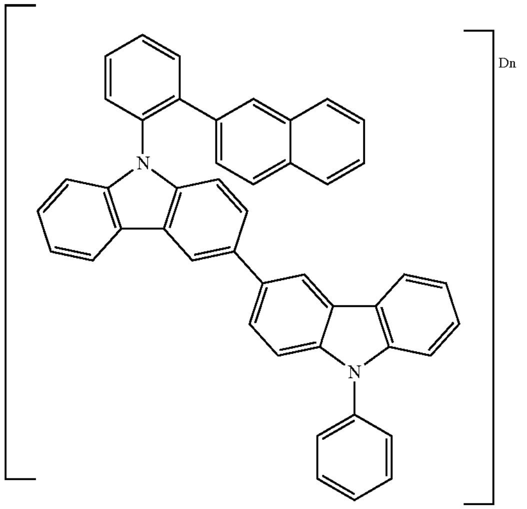
H2-49
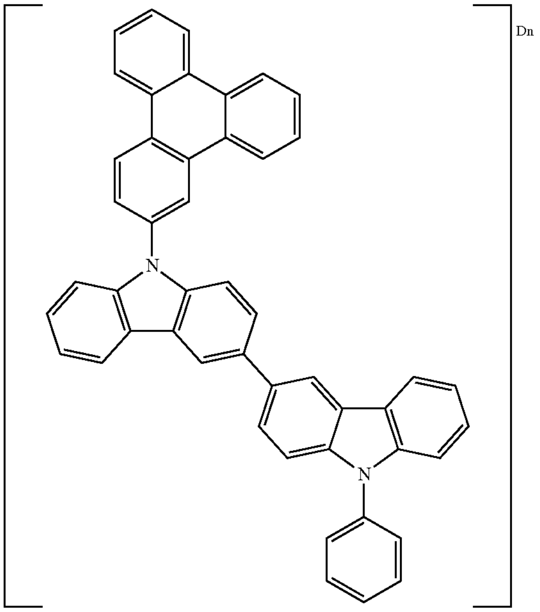
-continued
H2-50
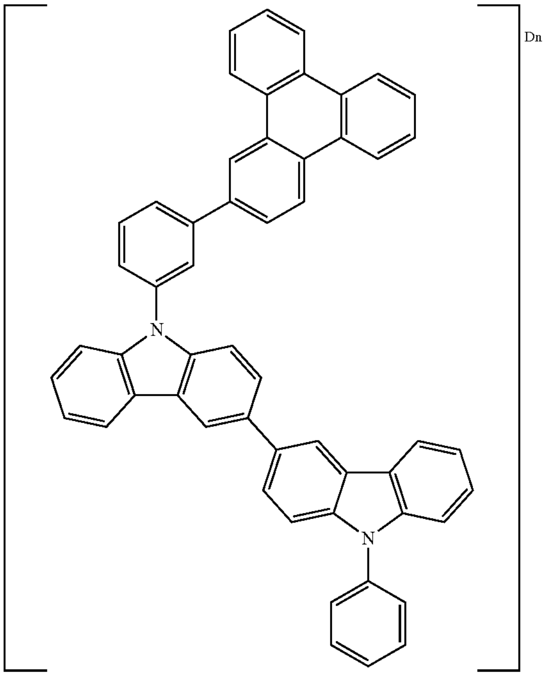
H2-51
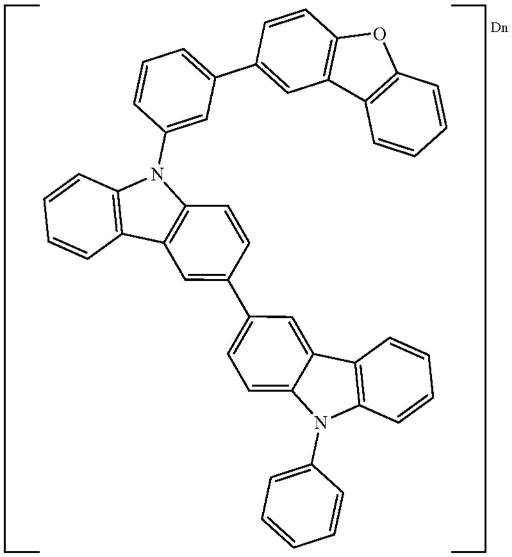

H2-52
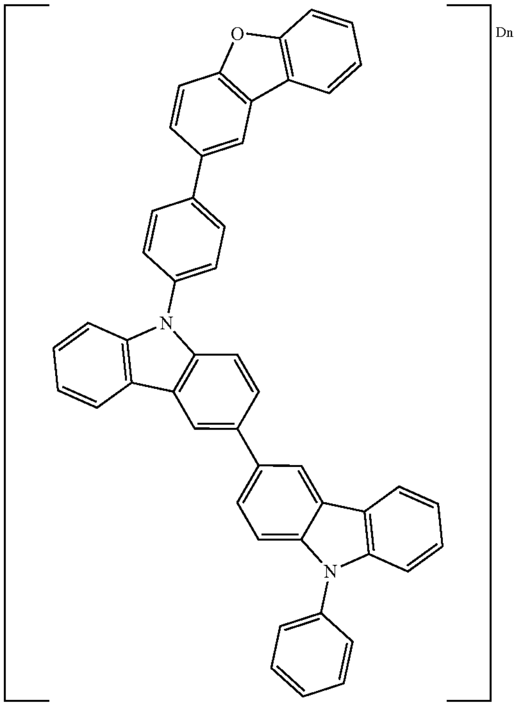
H2-53
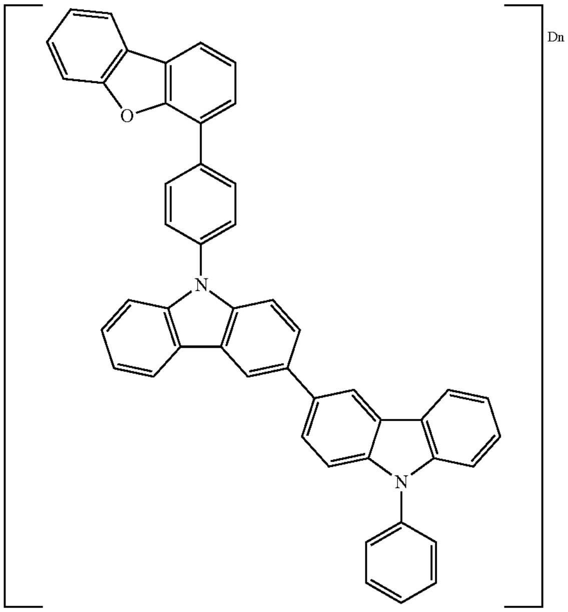
H2-54
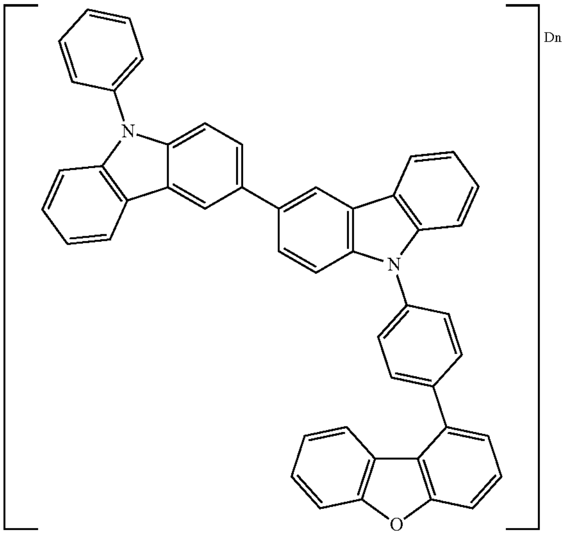
H2-55
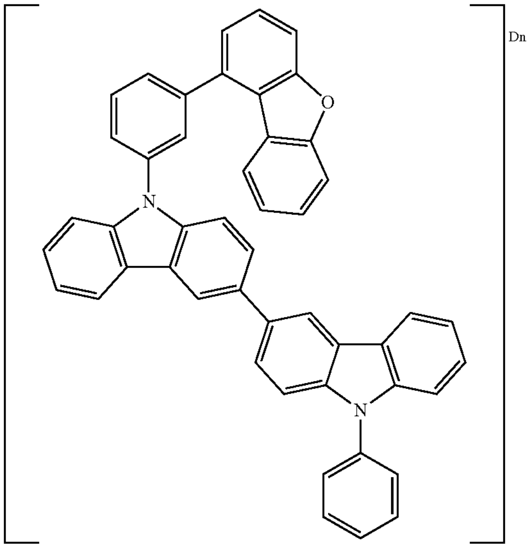

-continued
H2-56
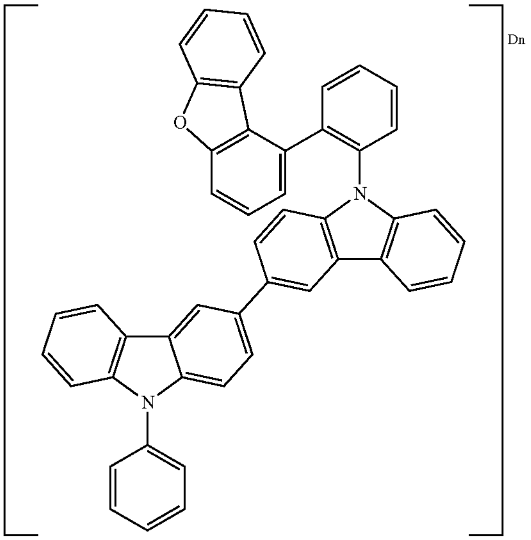
H2-57
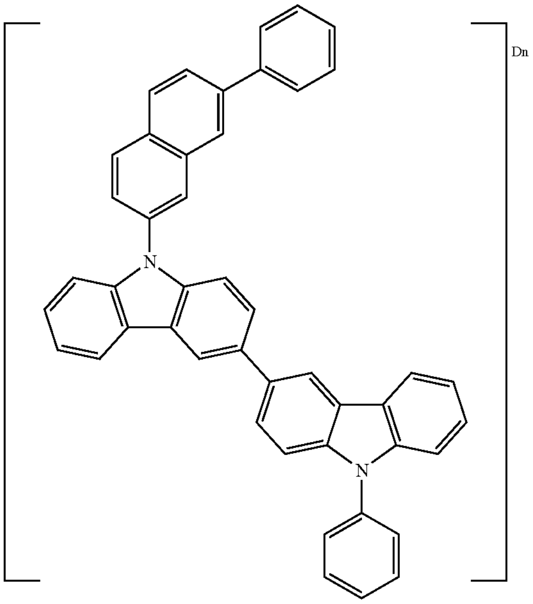
-continued
H2-58
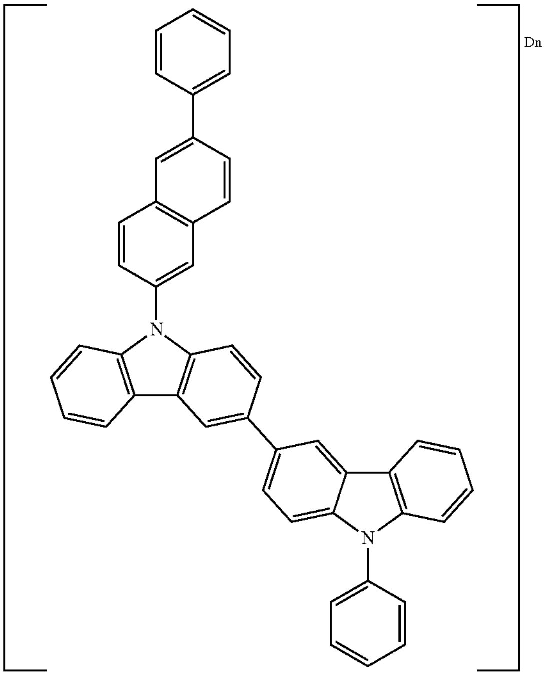
H2-59
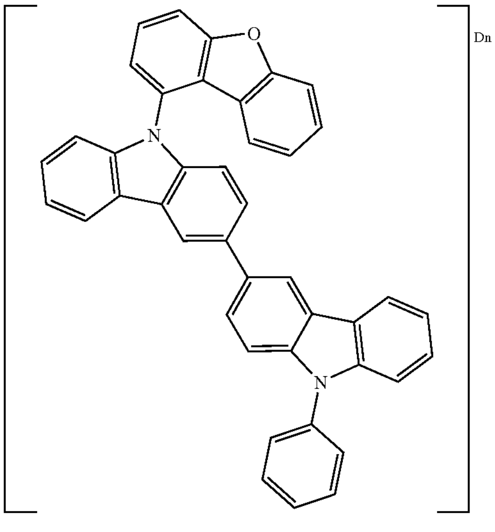

-continued
H2-60
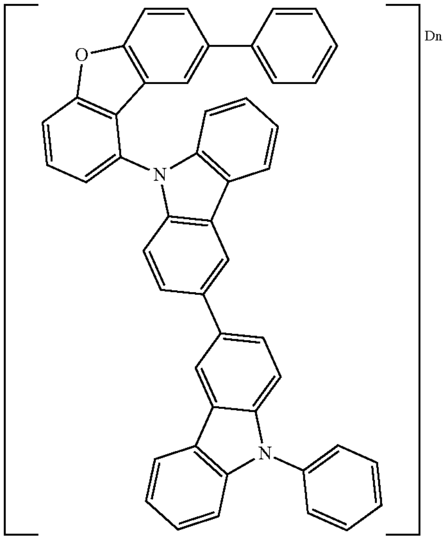
H2-61
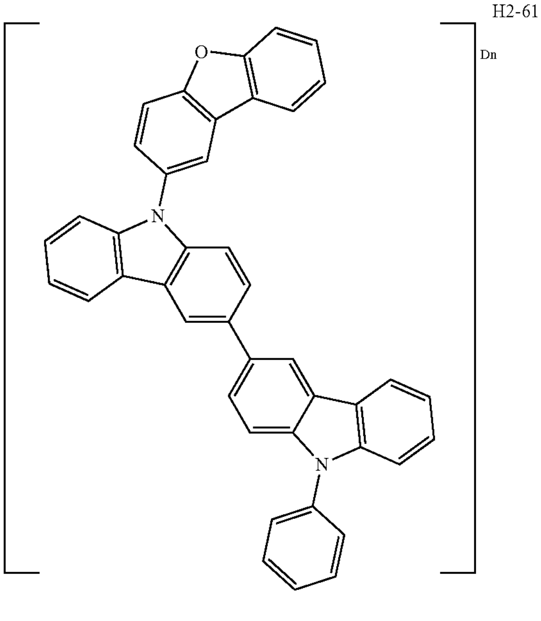
-continued
H2-62
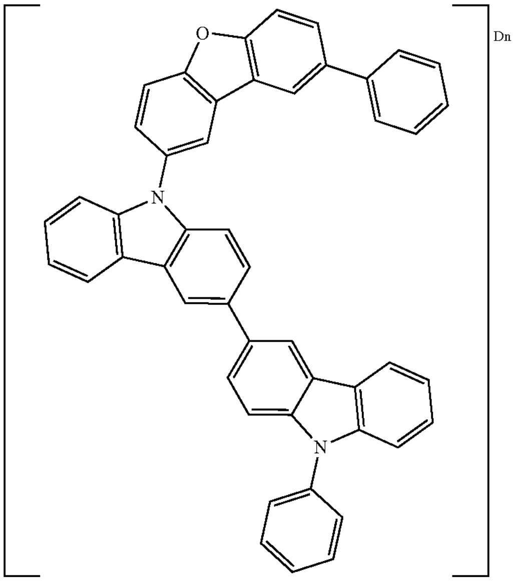
H2-63
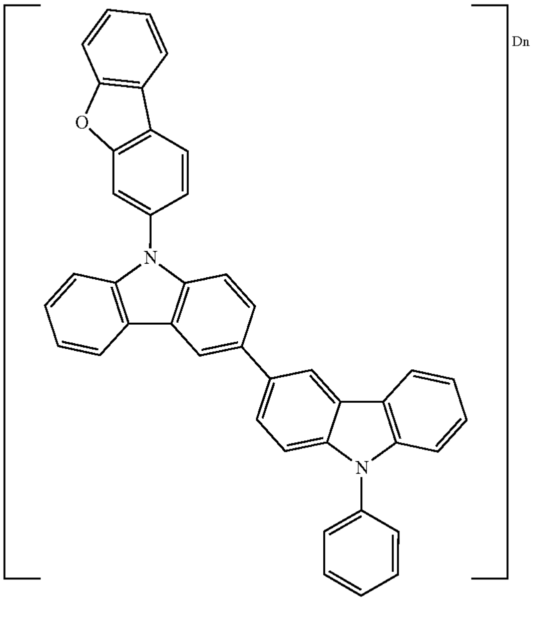

-continued
H2-64
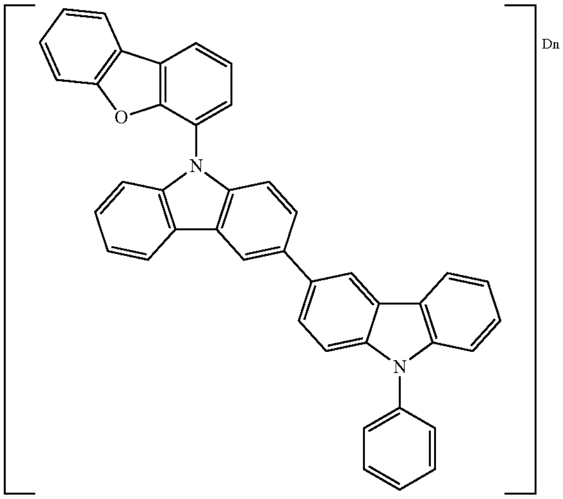
Dn
H2-65
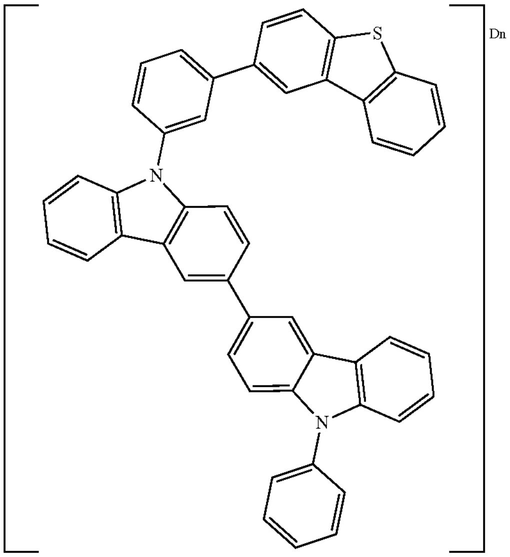
Dn
-continued
H2-66
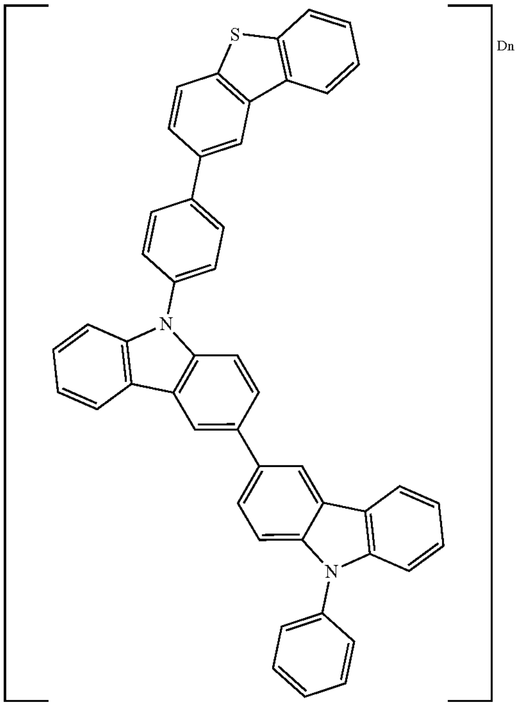
Dn
H2-67
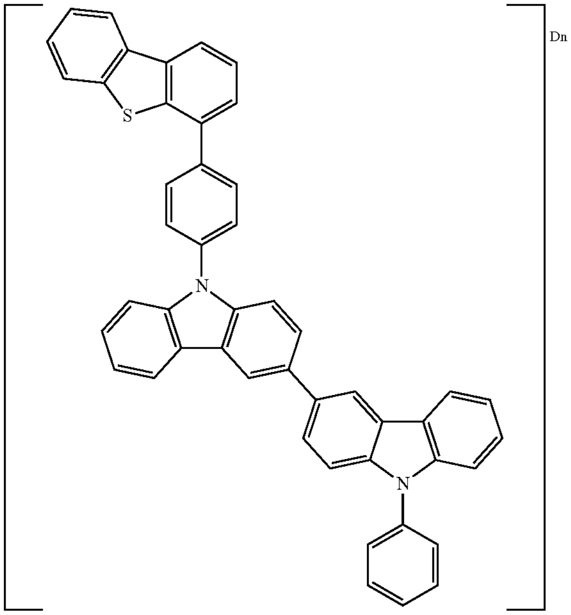
Dn -continued
H2-68
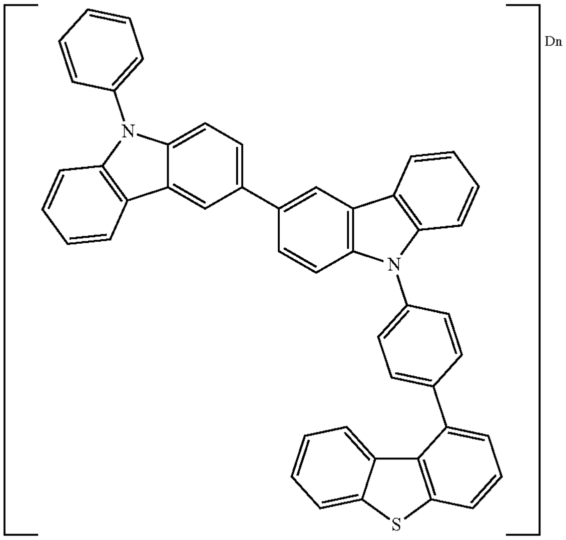
H2-69
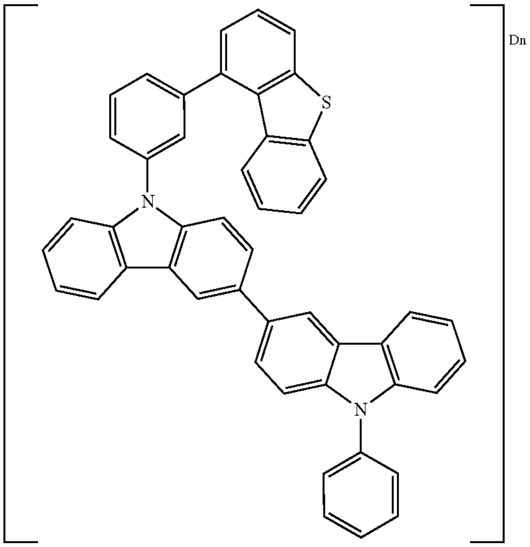
-continued
H2-70
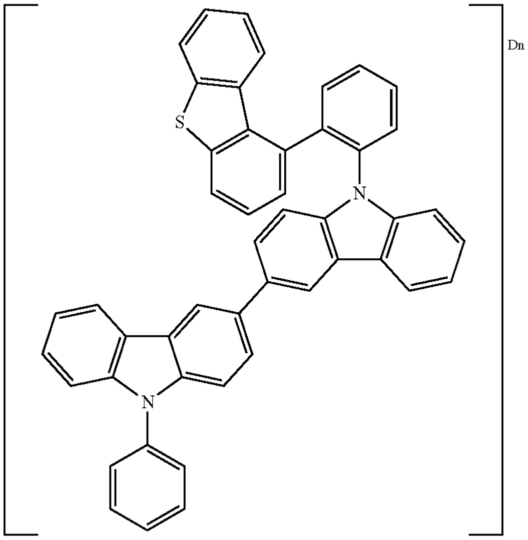
H2-71
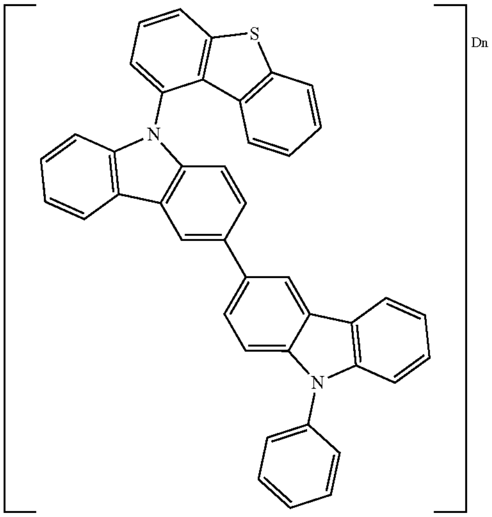
H2-72
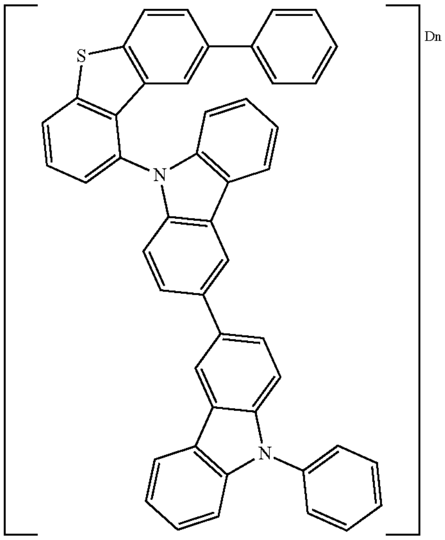

-continued
H2-73
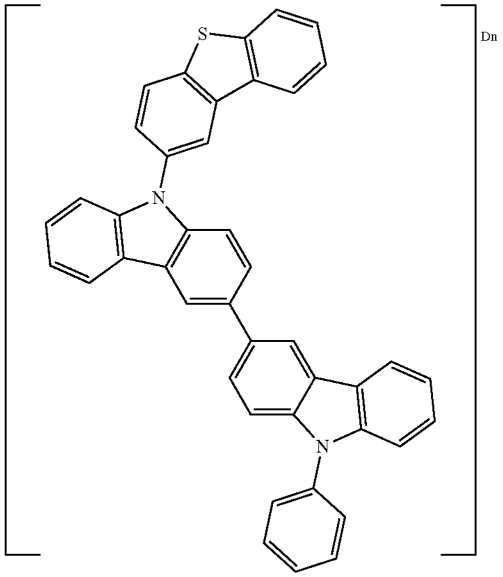
H2-74
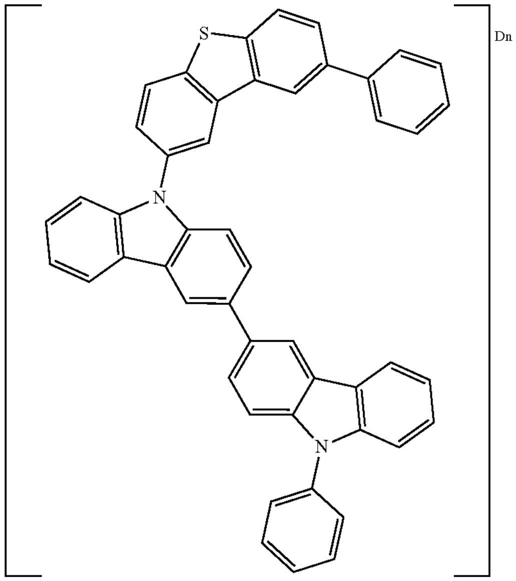
-continued
H2-75
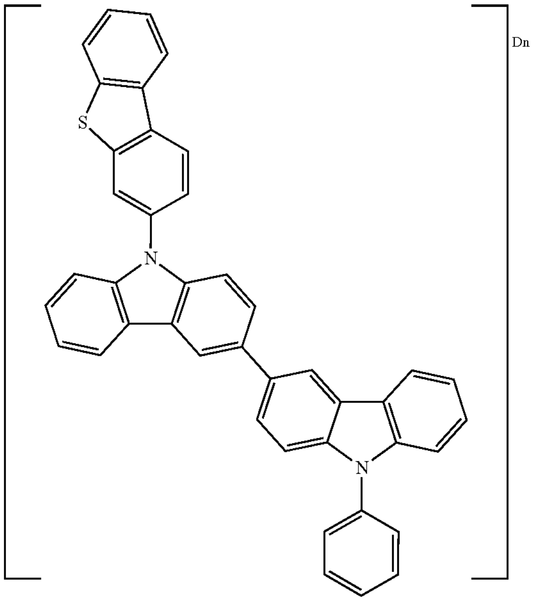
H2-76
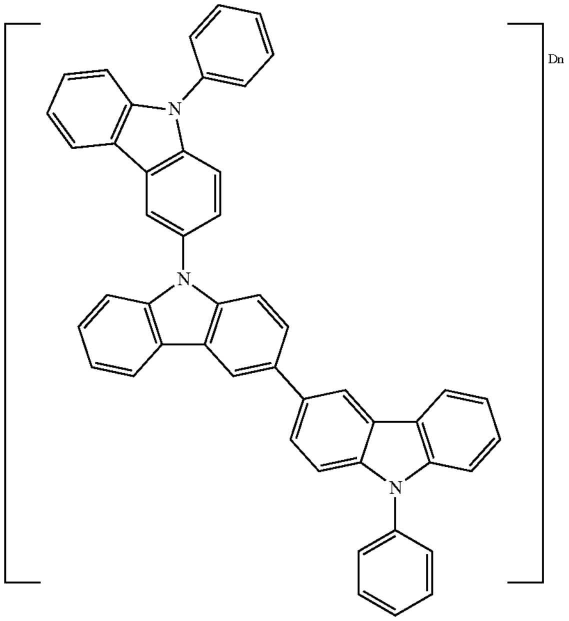

-continued
H2-77
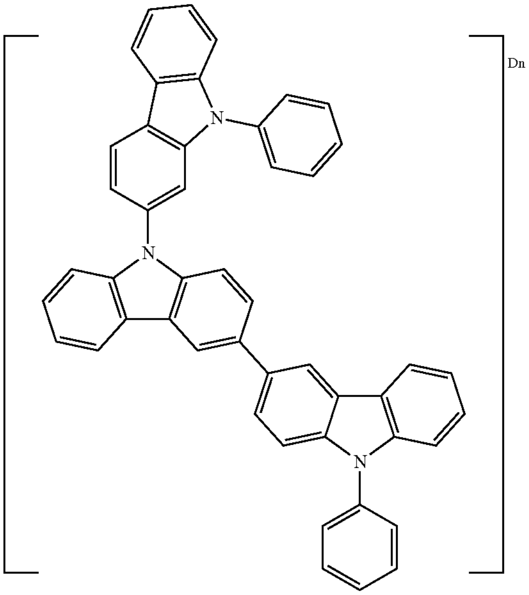
H2-78
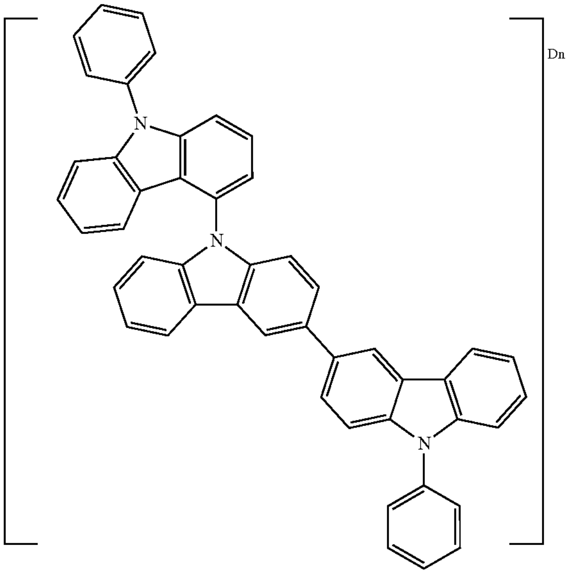
-continued
H2-79
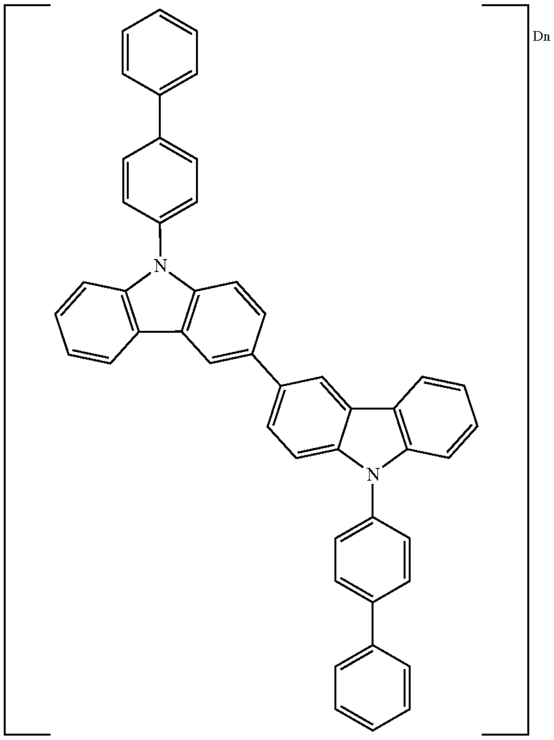
H2-80
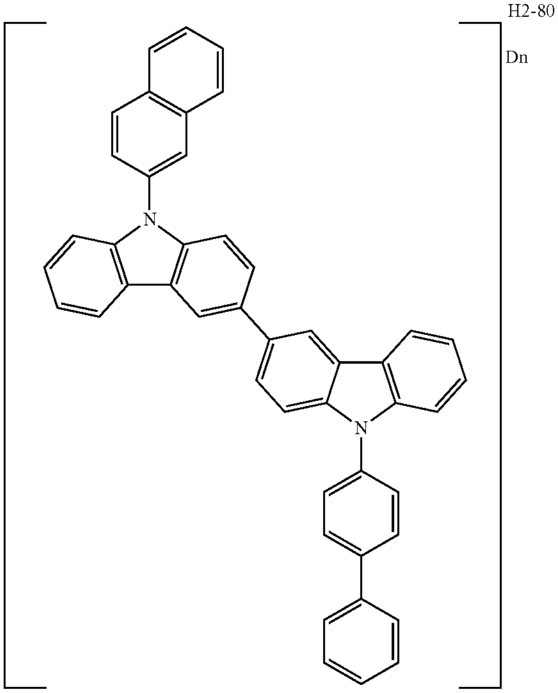

-continued
H2-81
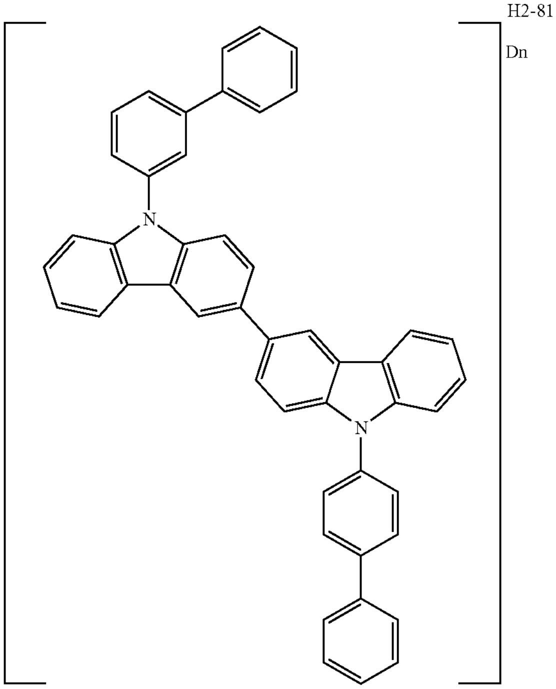
H2-82
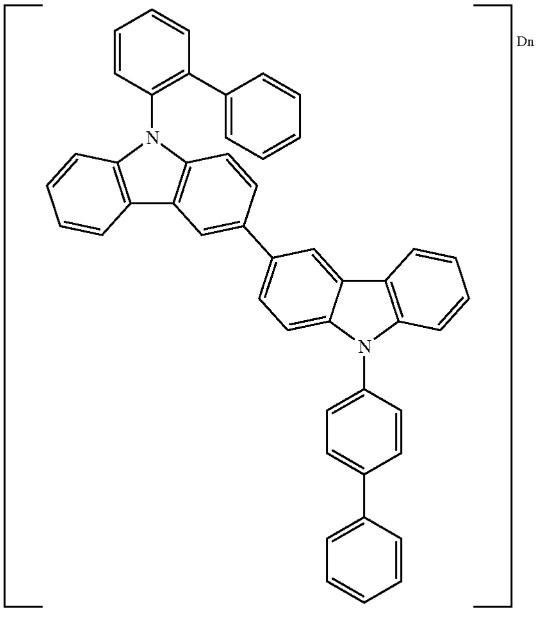
-continued
H2-83
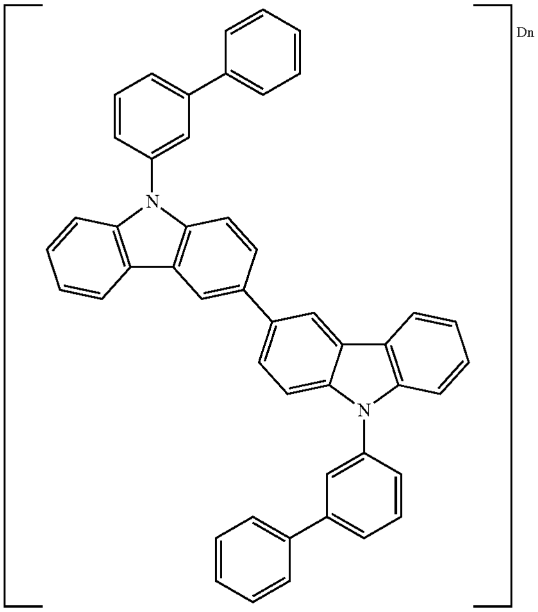
H2-84
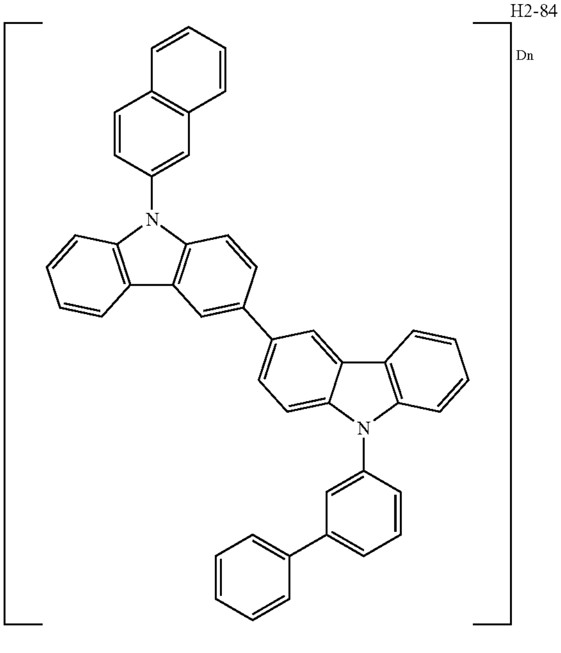

-continued
H2-85
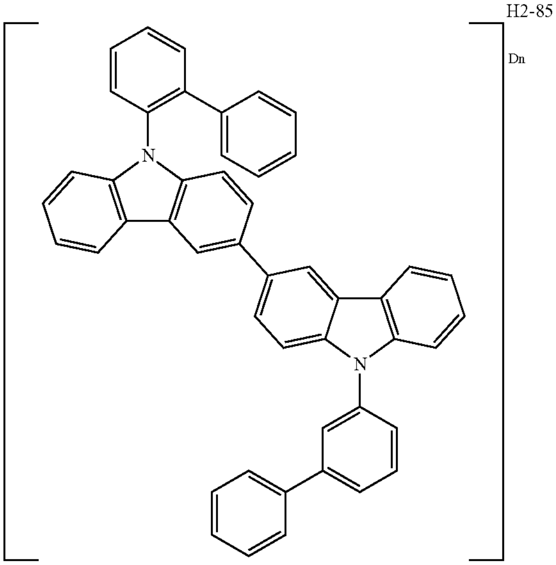
-continued
H2-87
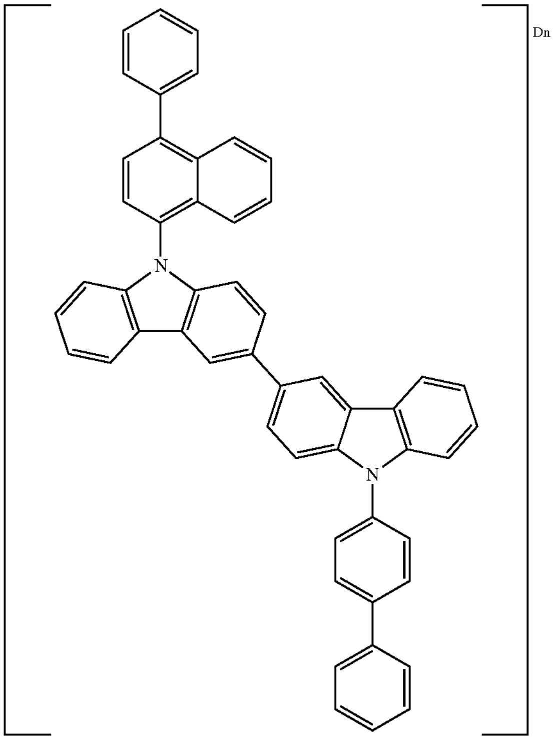
H2-86
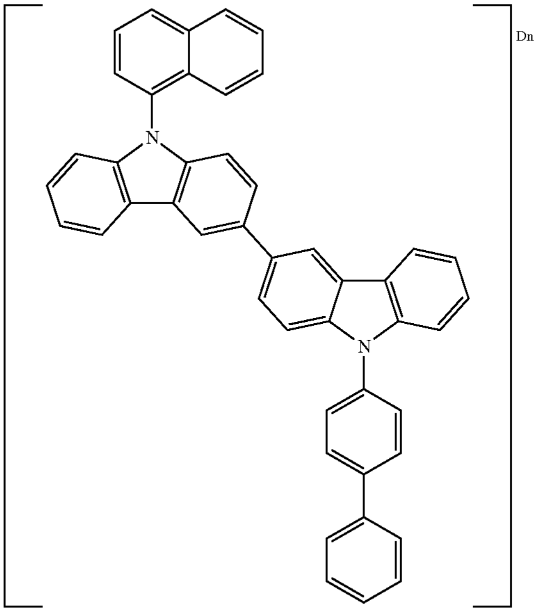
H2-88
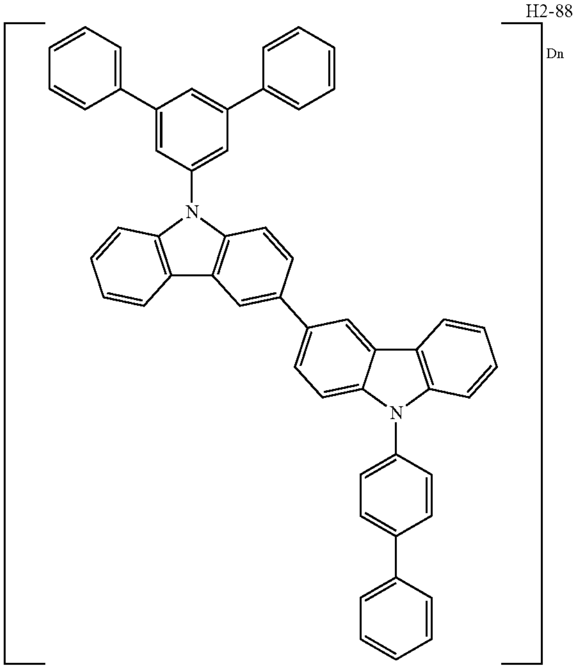

-continued
H2-89
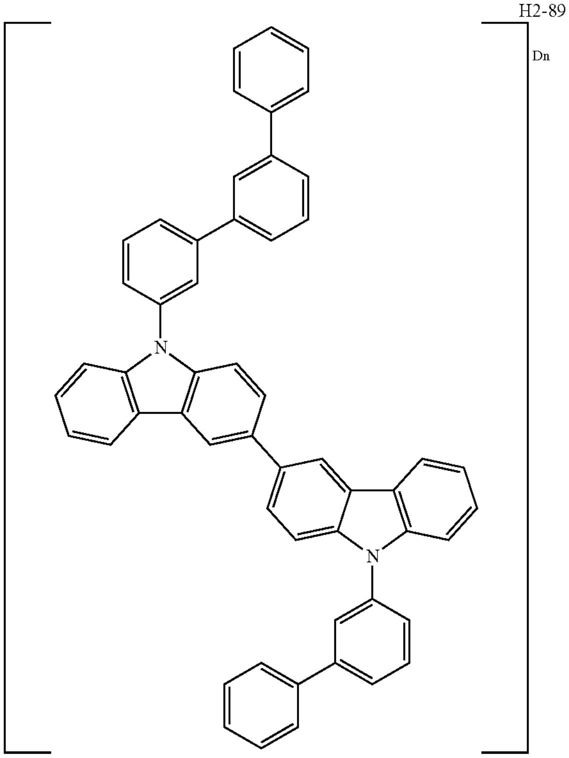
H2-90
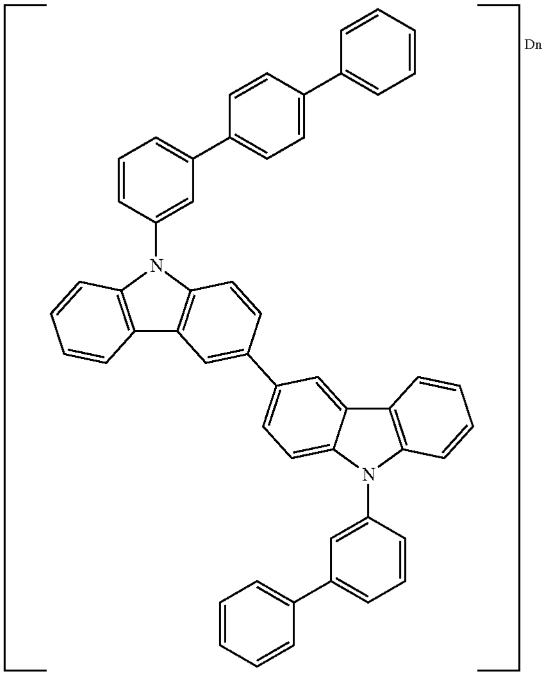
-continued
H2-91
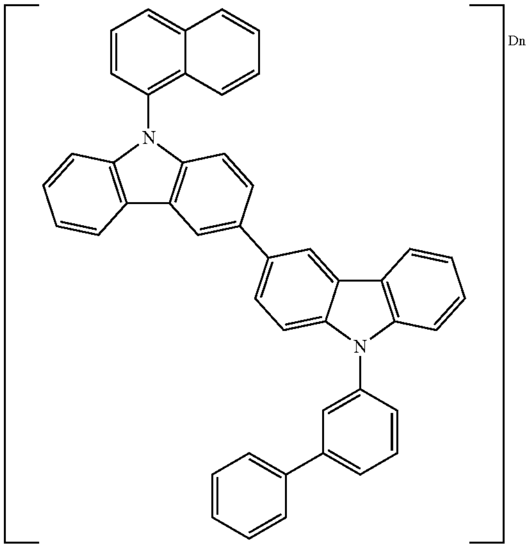
H2-92
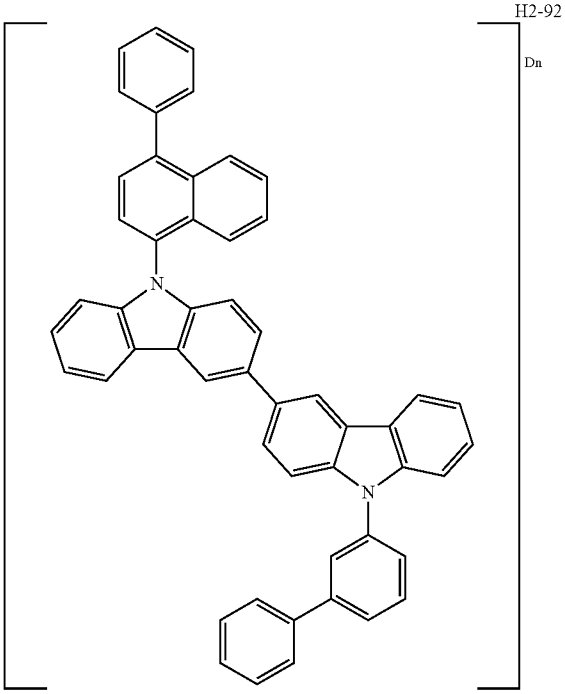

-continued
H2-93
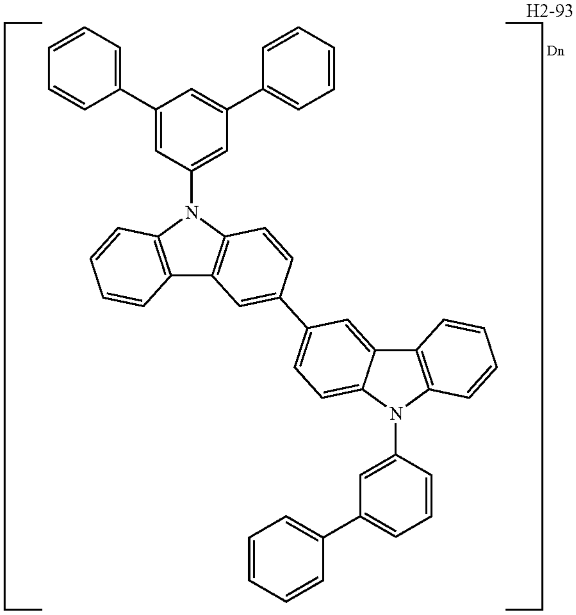
H2-94
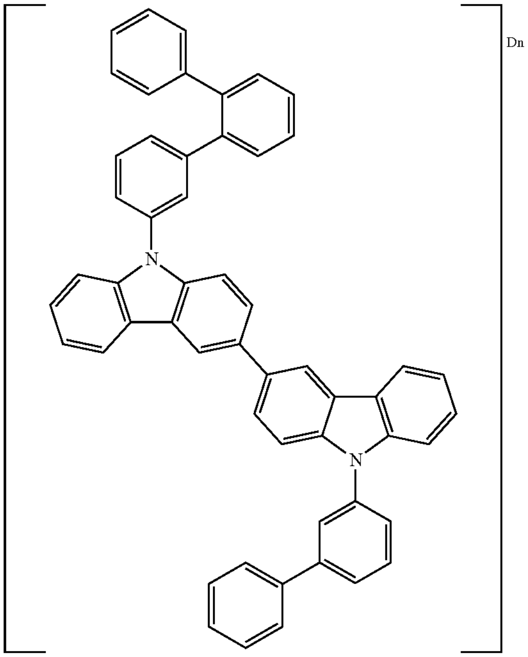
-continued
H2-95
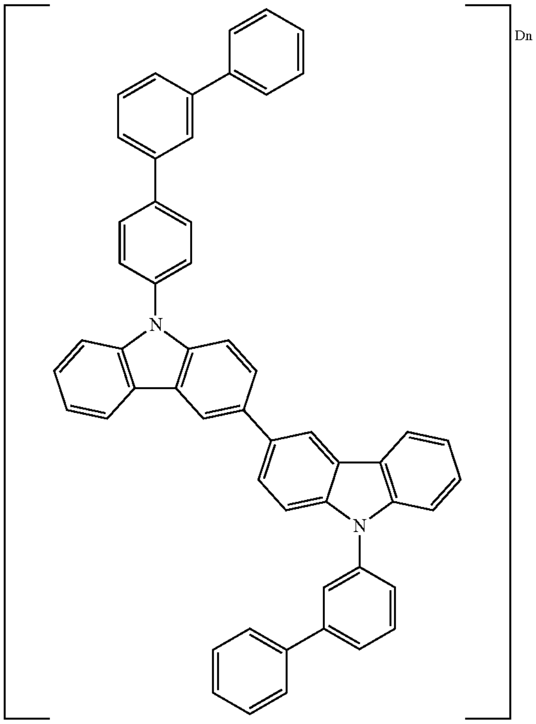
H2-96
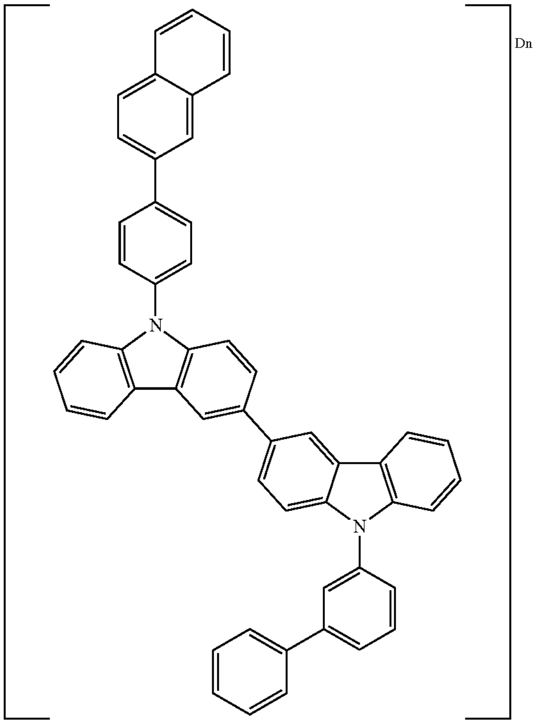

-continued
H2-97
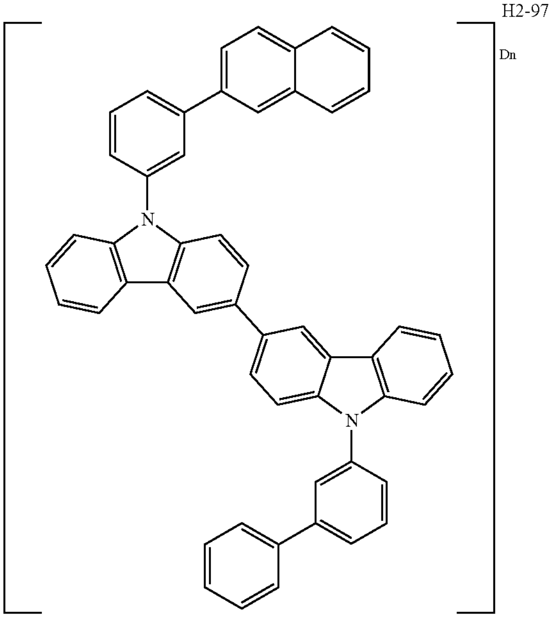
H2-98
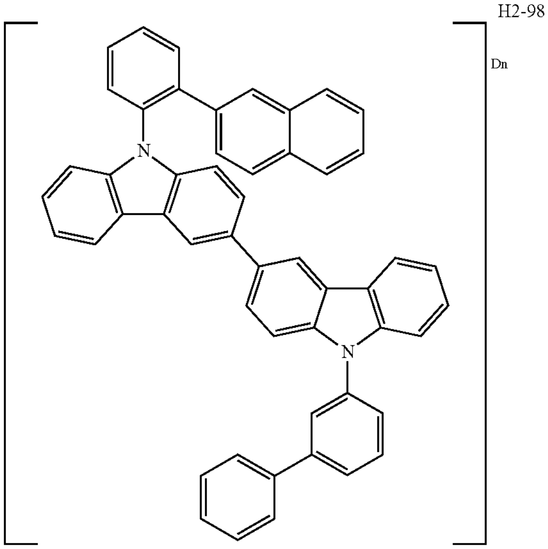
-continued
H2-99
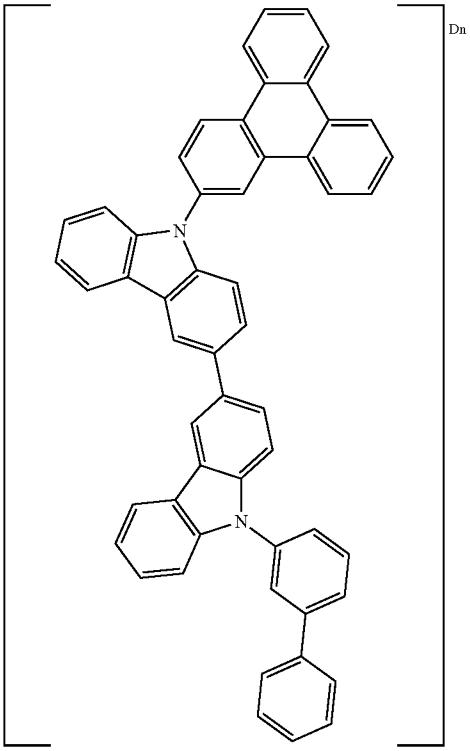
H2-100
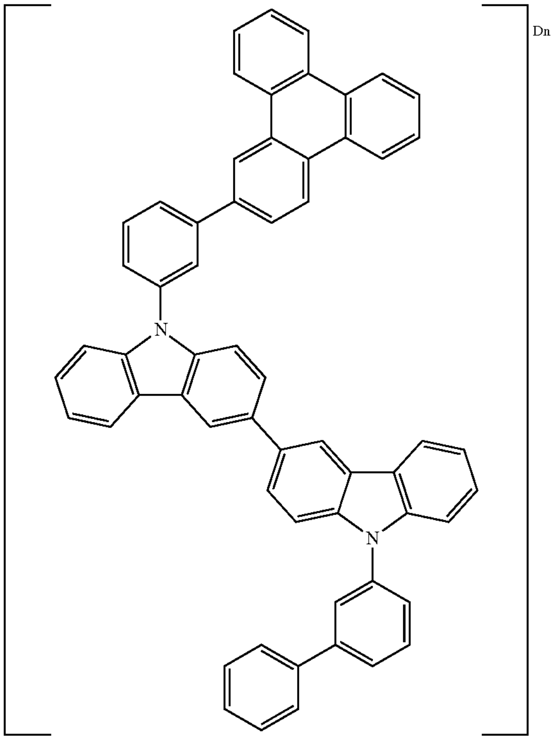

-continued
H2-101
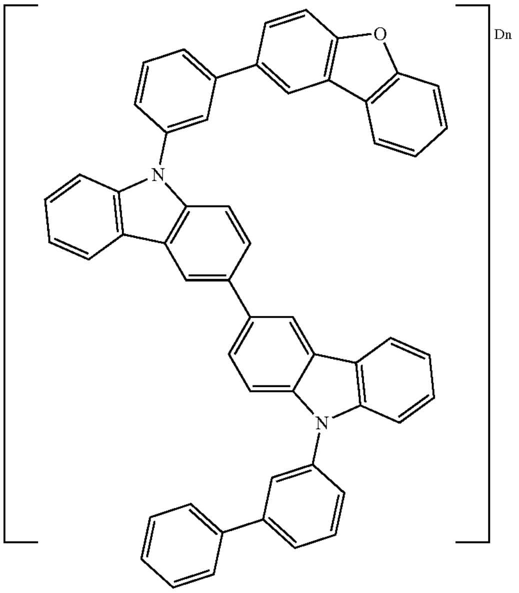
H2-102
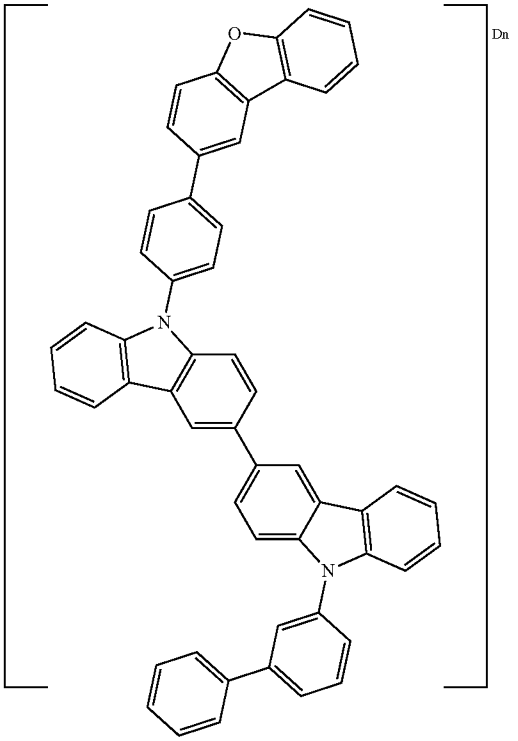
-continued
H2-103
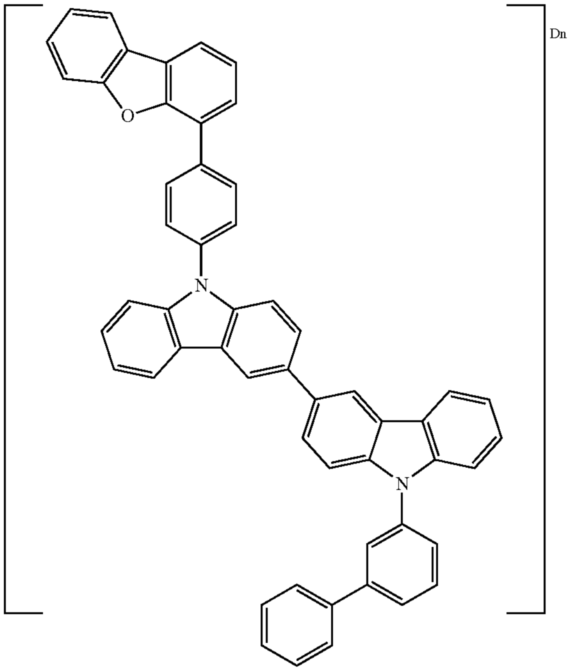
H2-104
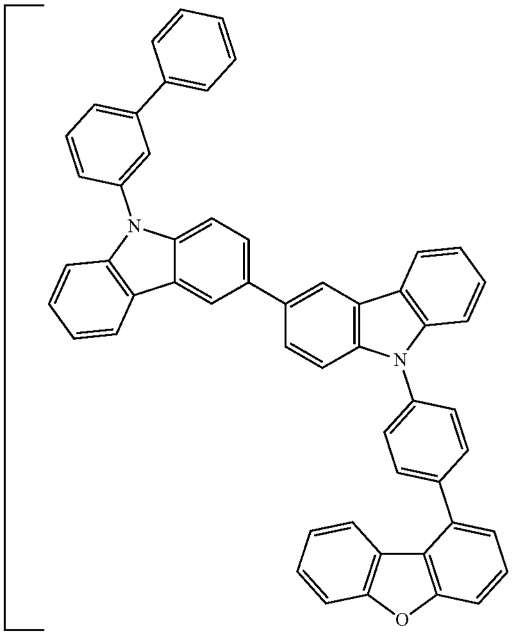

H2-105
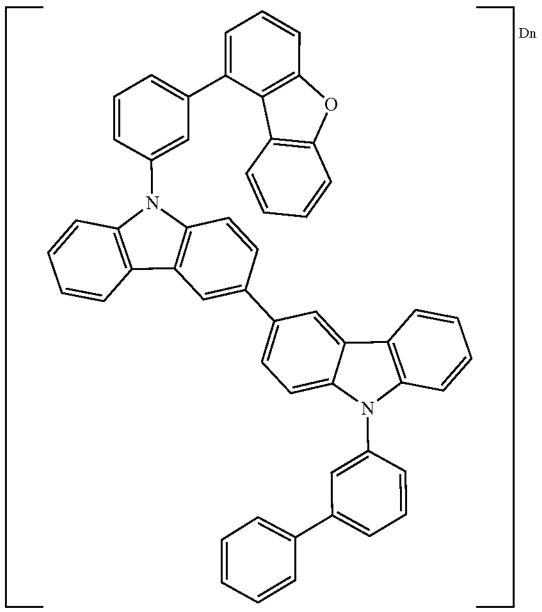
H2-107
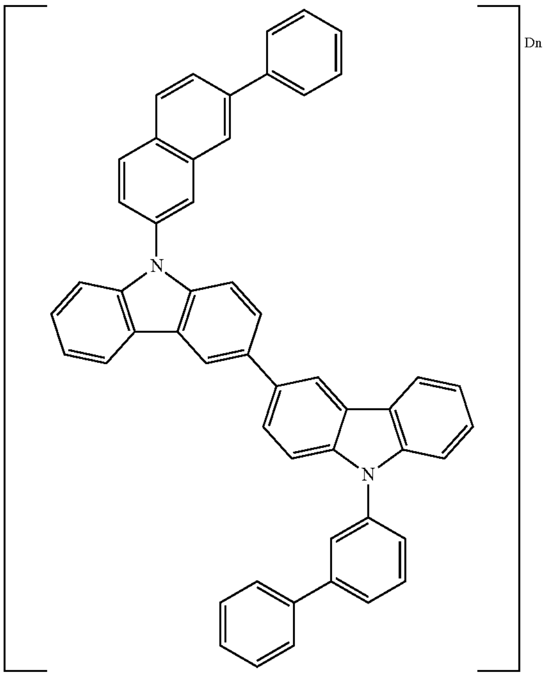
H2-106
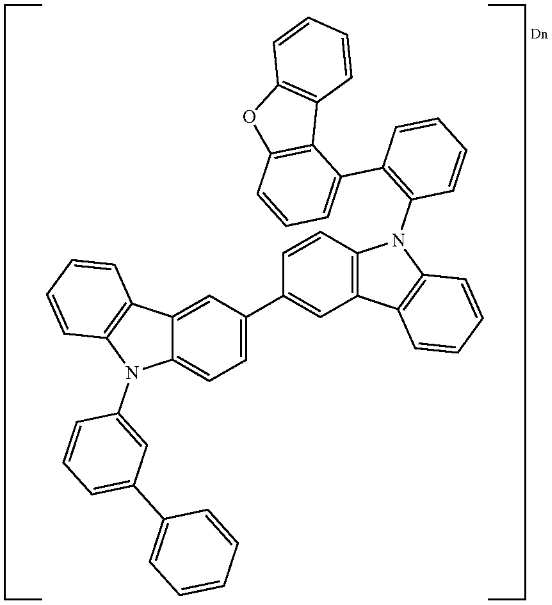
H2-108
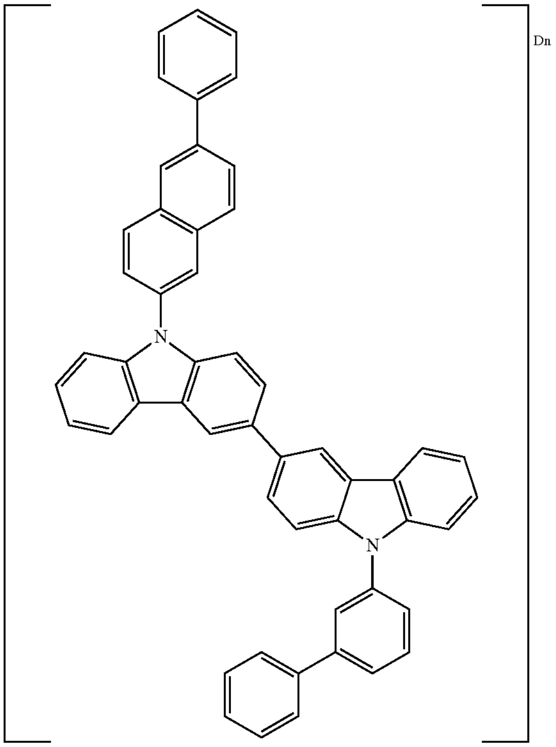

-continued
H2-109
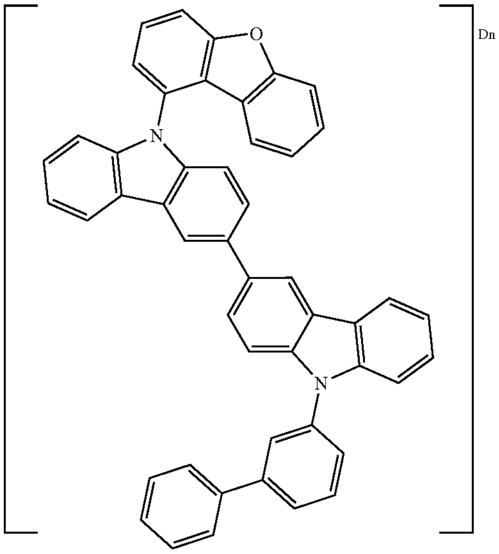
Dn
H2-110
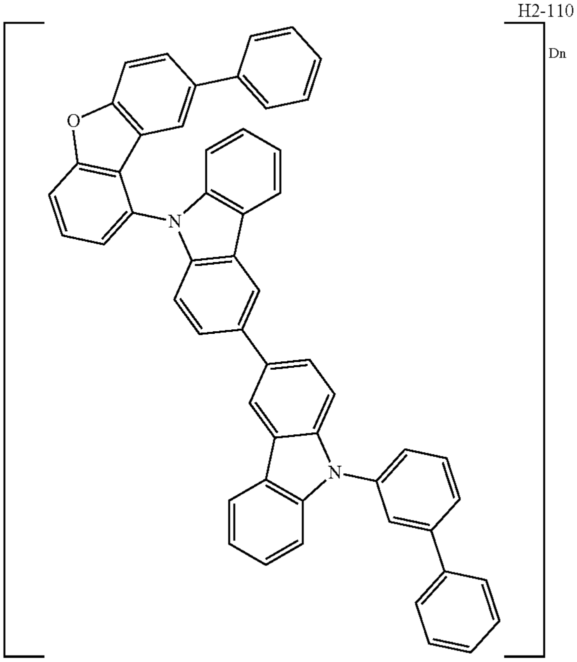
Dn
-continued
H2-111
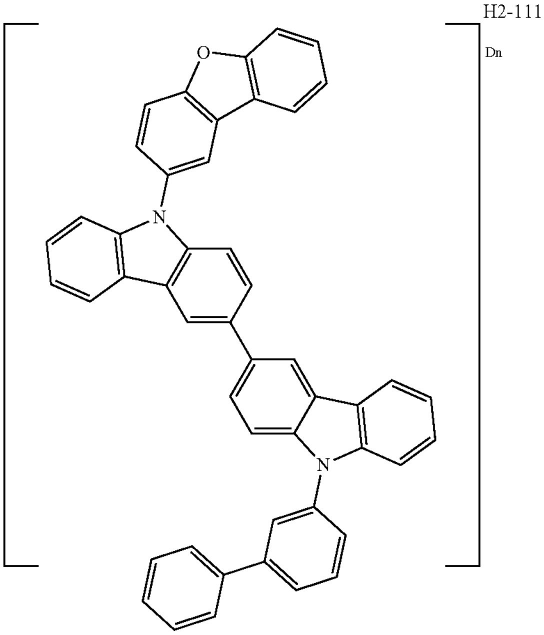
Dn
H2-112
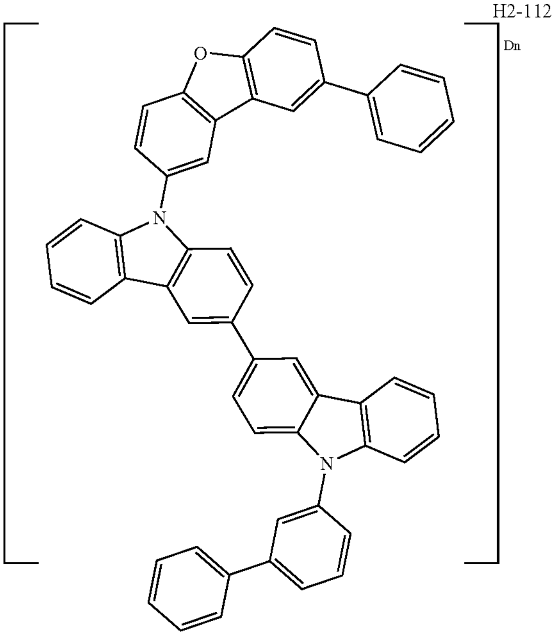
Dn -continued
H2-113
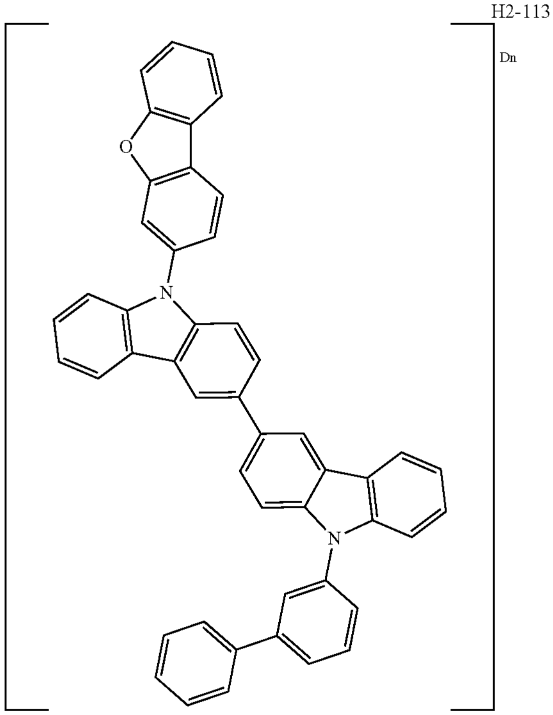
H2-114
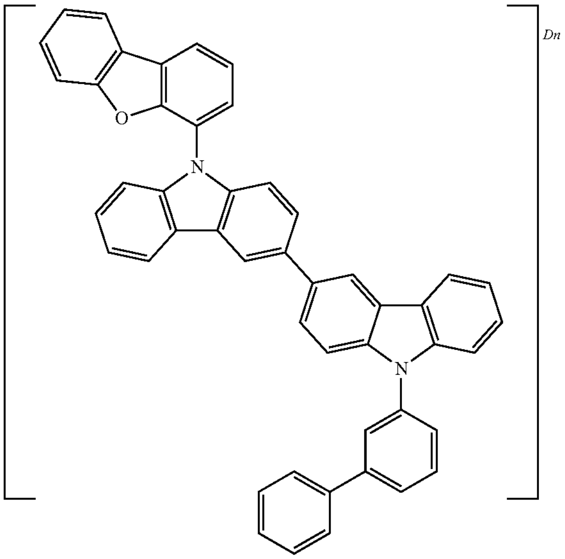
-continued
H2-115
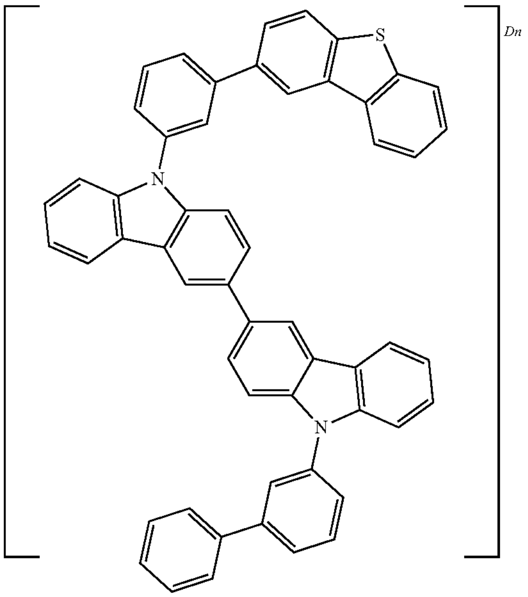
H2-116
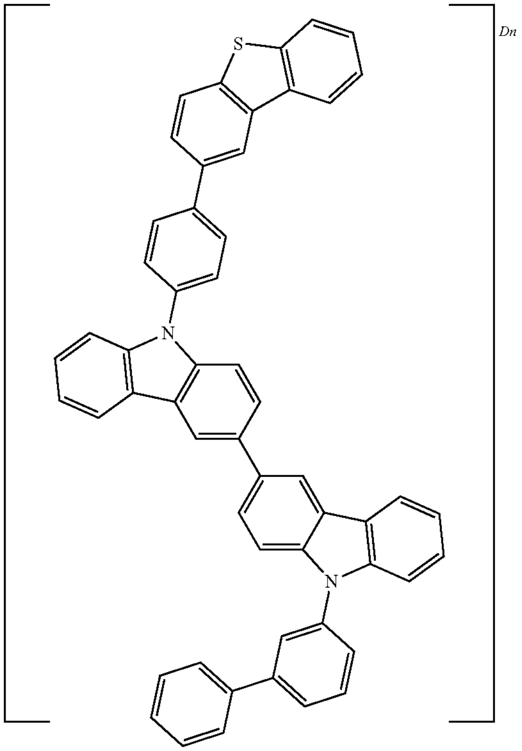

-continued
H2-117
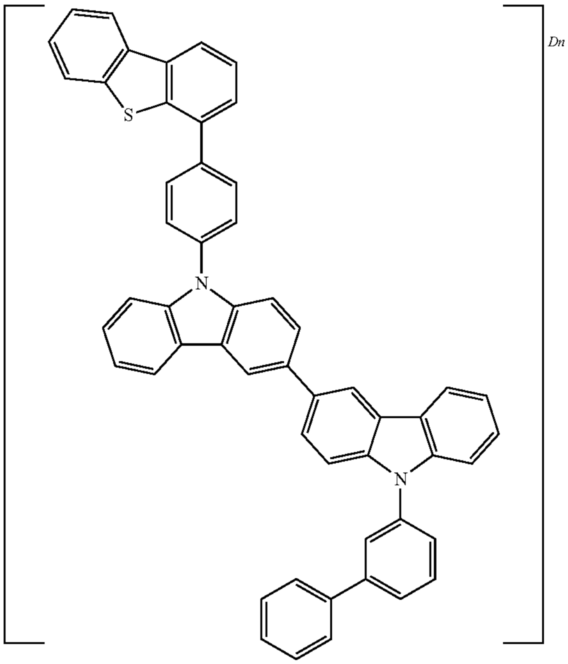
H2-118
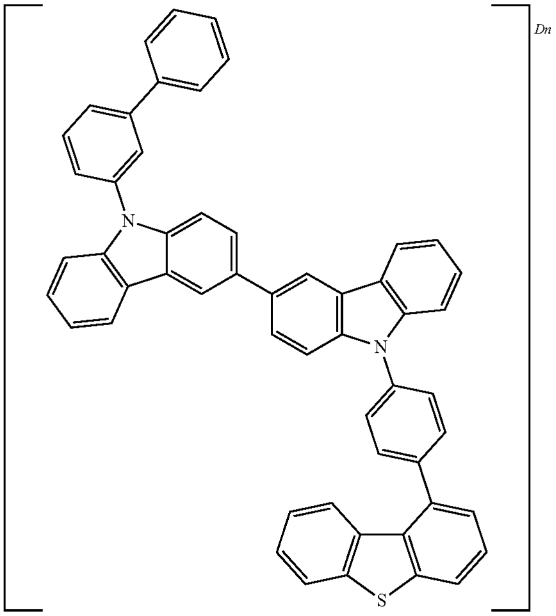
-continued
H2-119
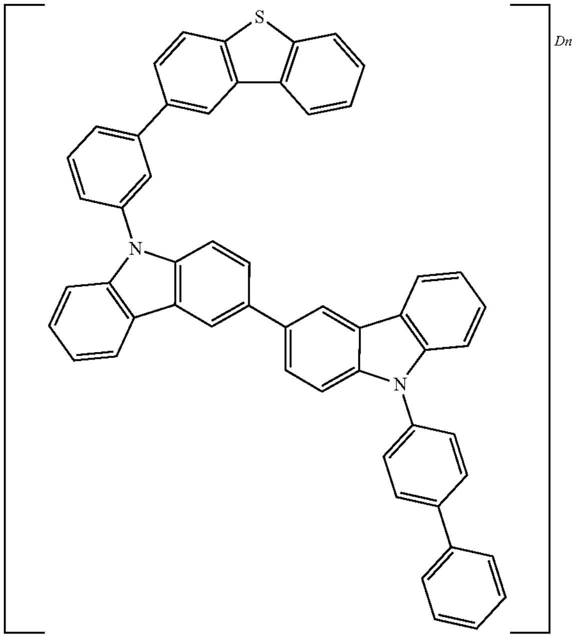
H2-120
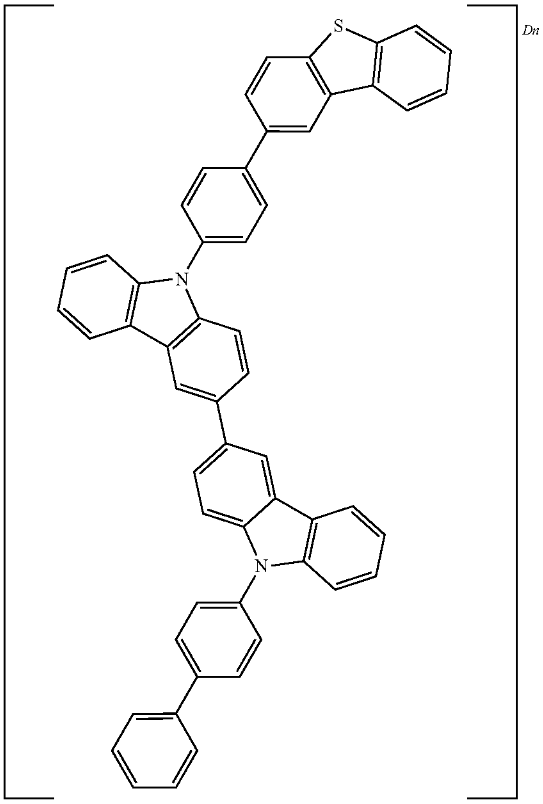

-continued
H2-121
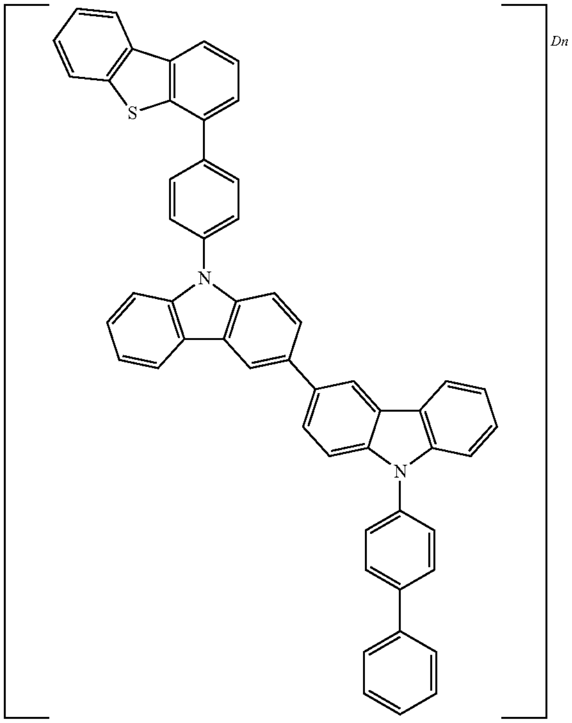
H2-122
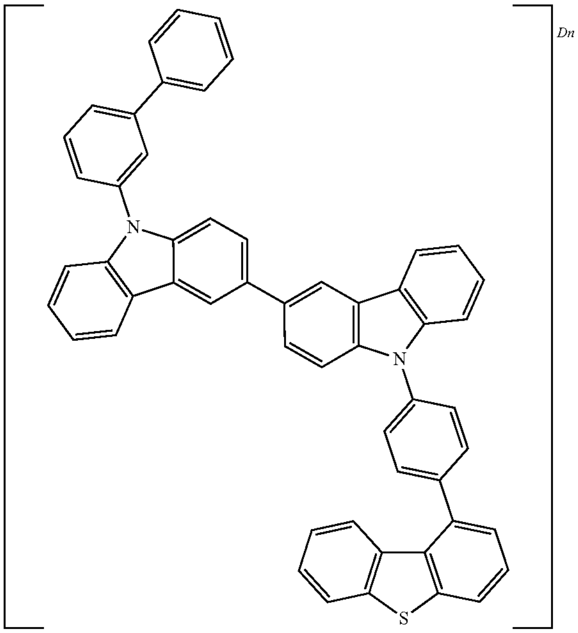
-continued
H2-123
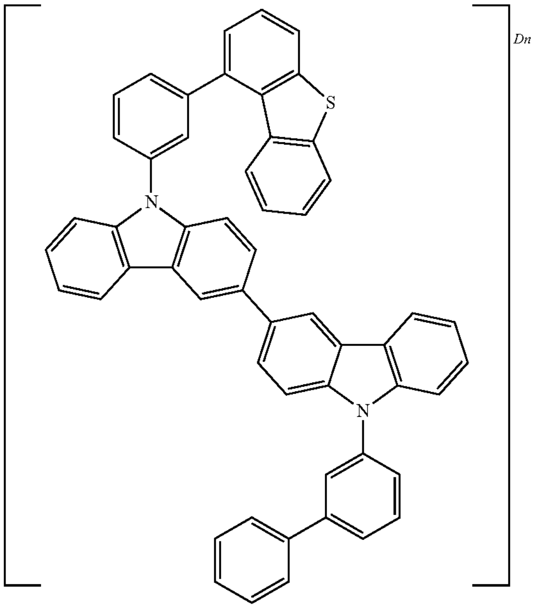
H2-124
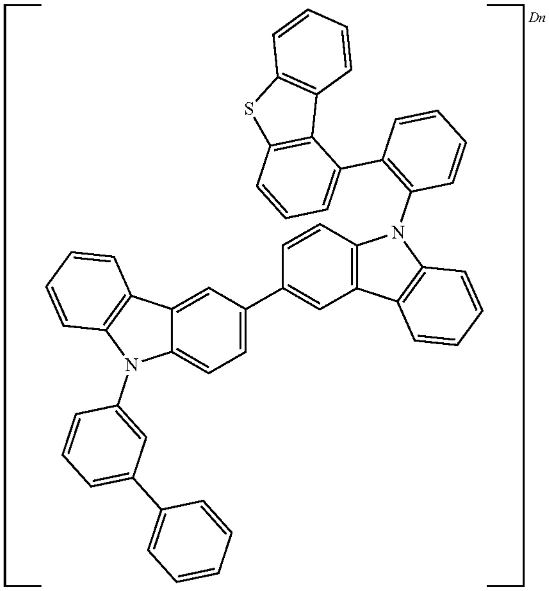

-continued
H2-125
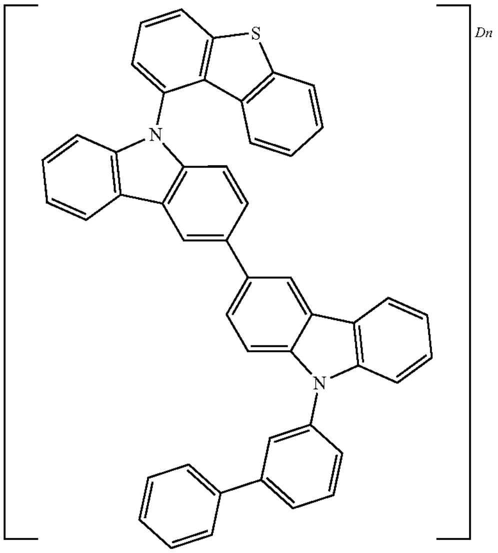
H2-127
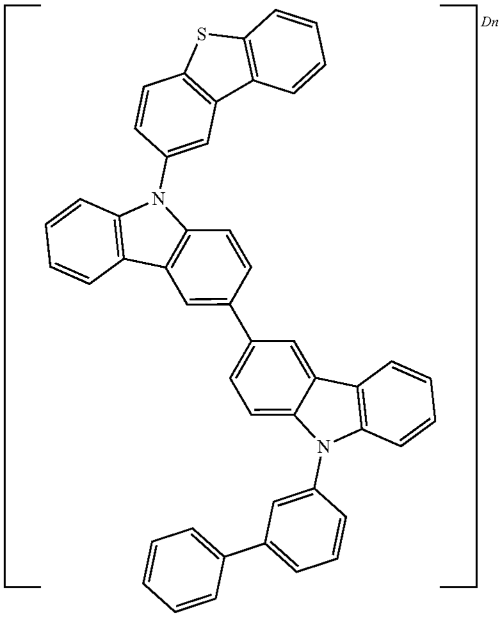
H2-126
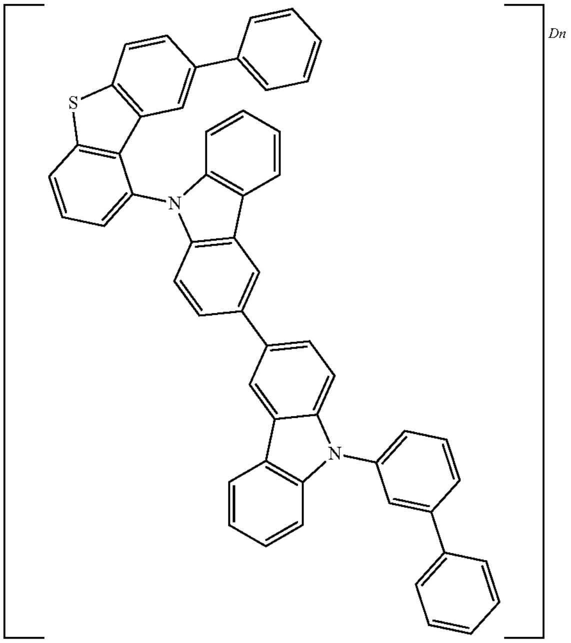
H2-128
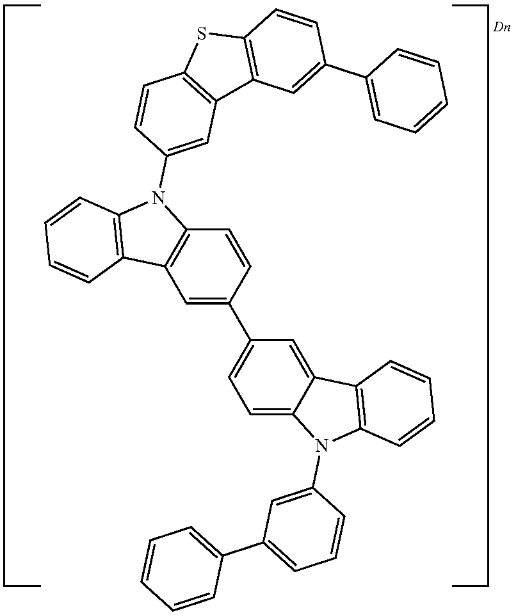

-continued
H2-129
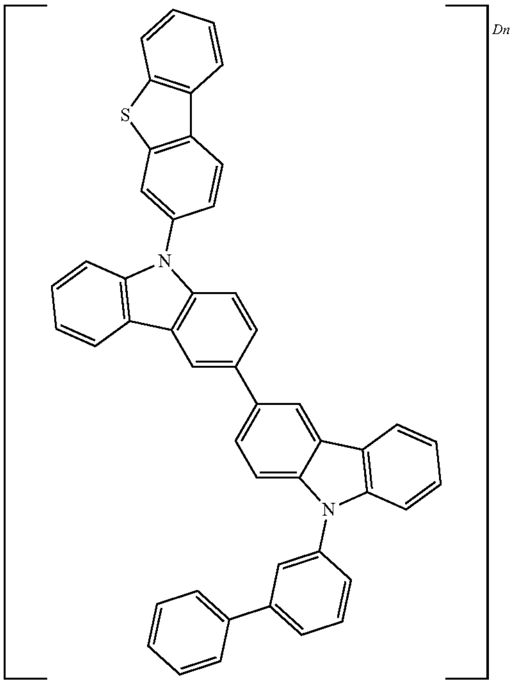
H2-130
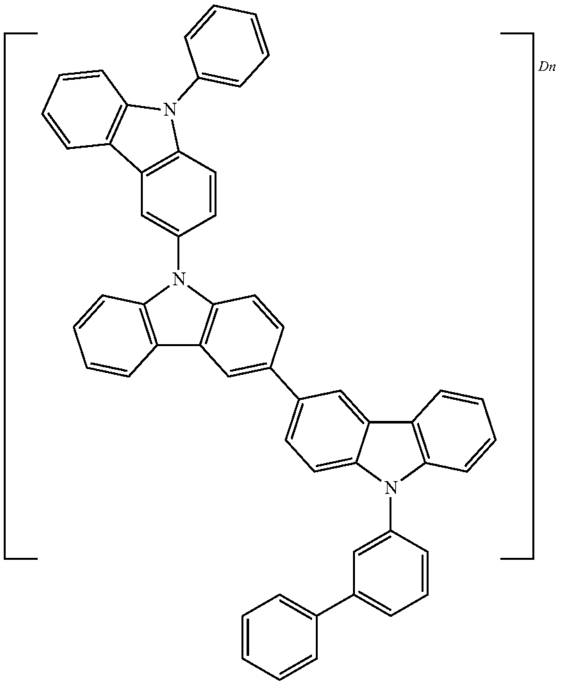
-continued
H2-131
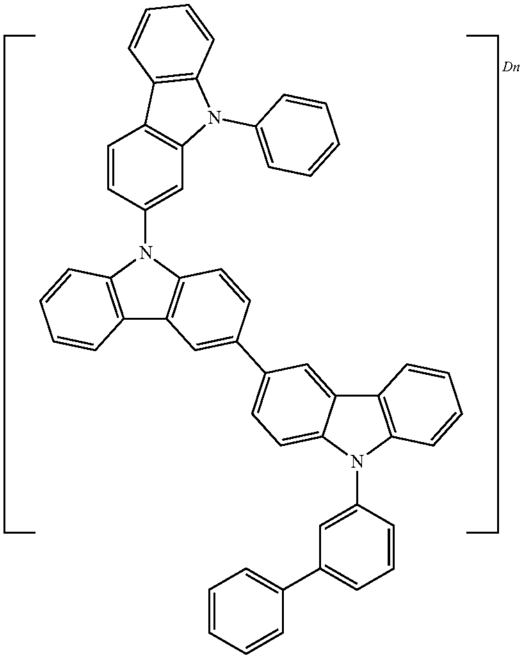
H2-132
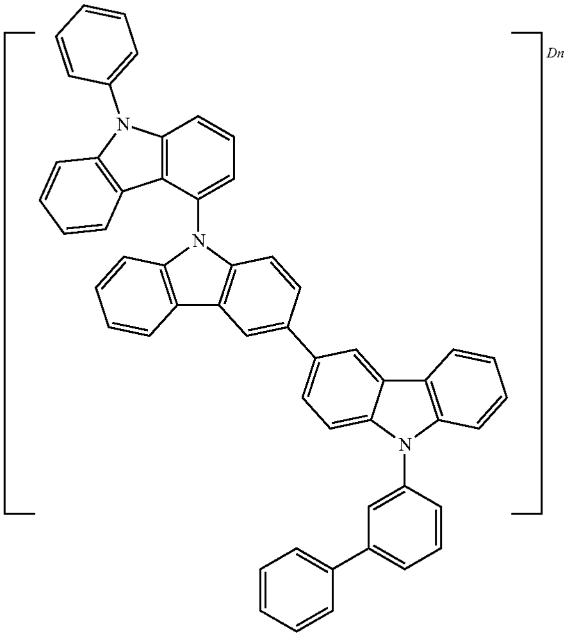

-continued
H2-133
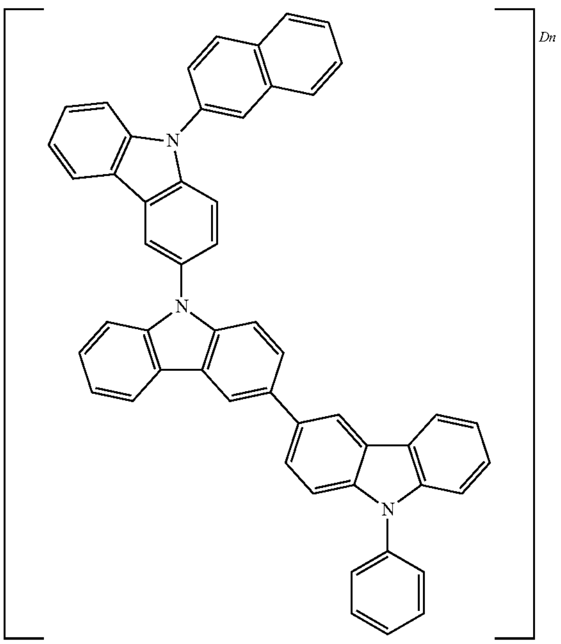
H2-134
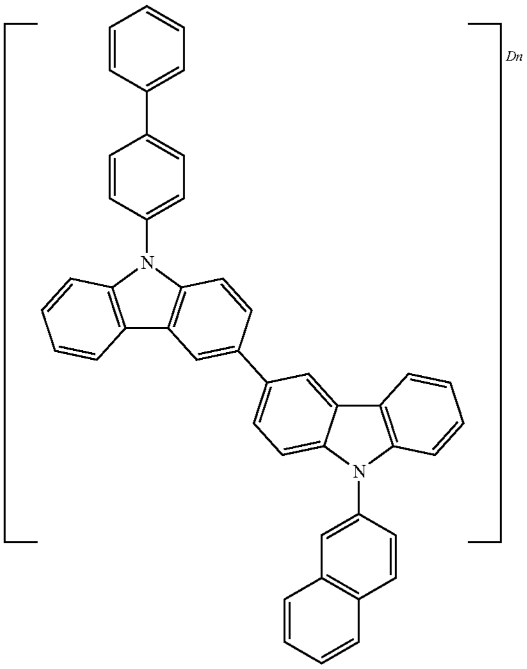
-continued
H2-135
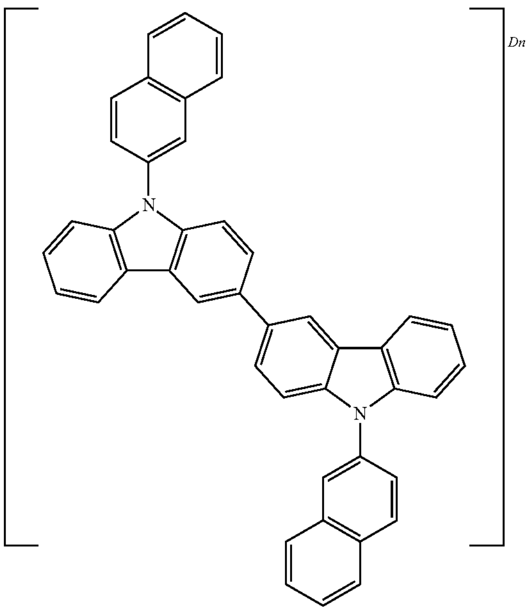
H2-136
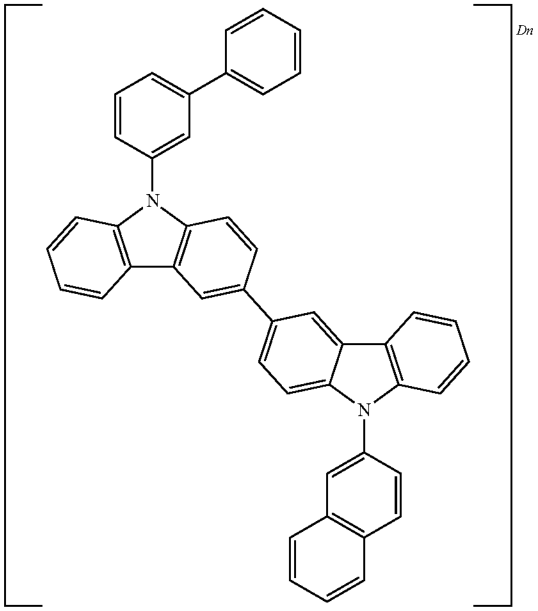

-continued
H2-137
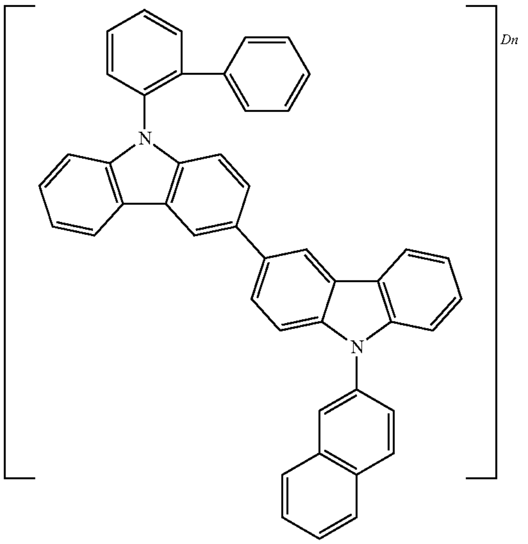
H2-138
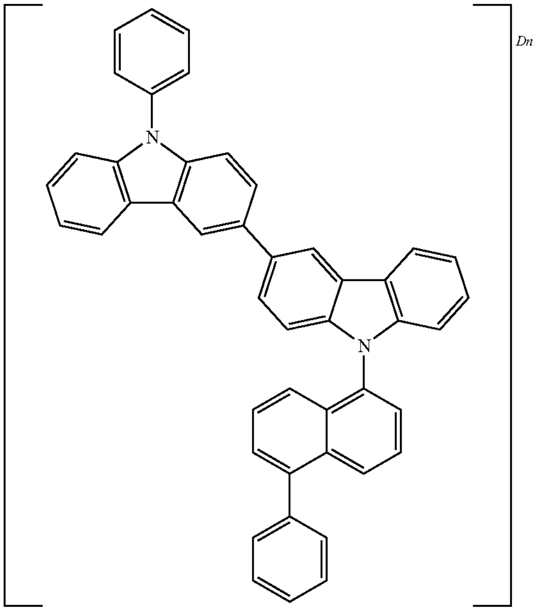
-continued
H2-139
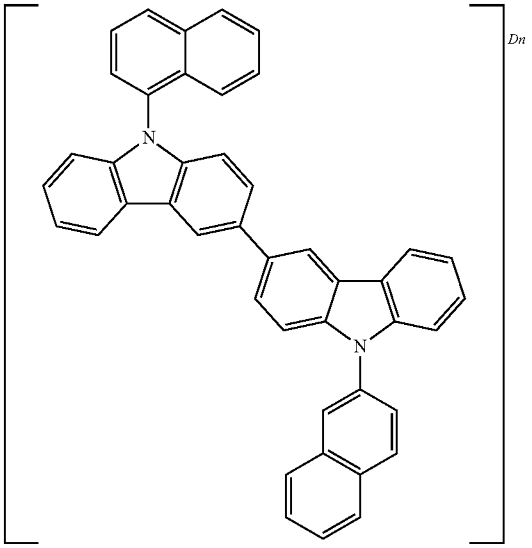
H2-140
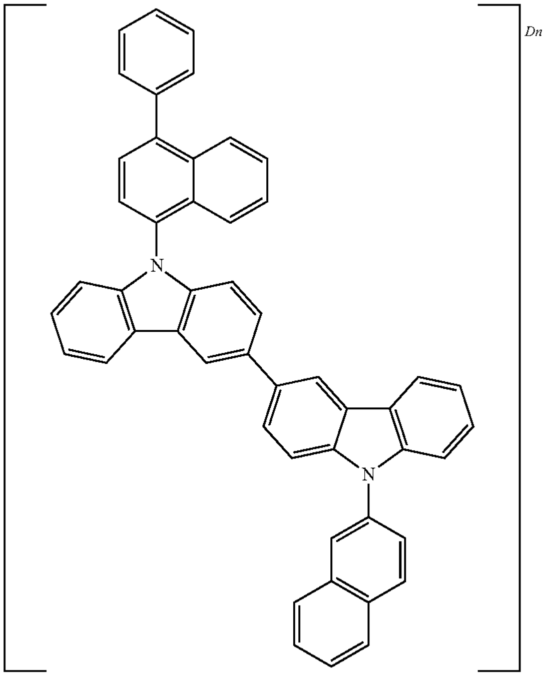

-continued
H2-141
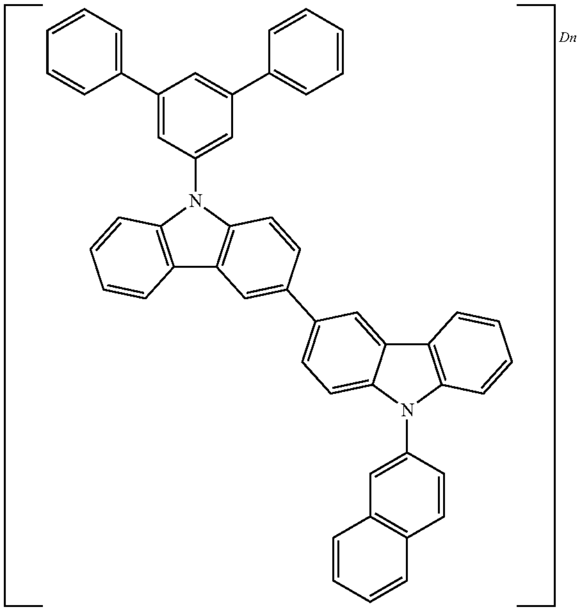
H2-142
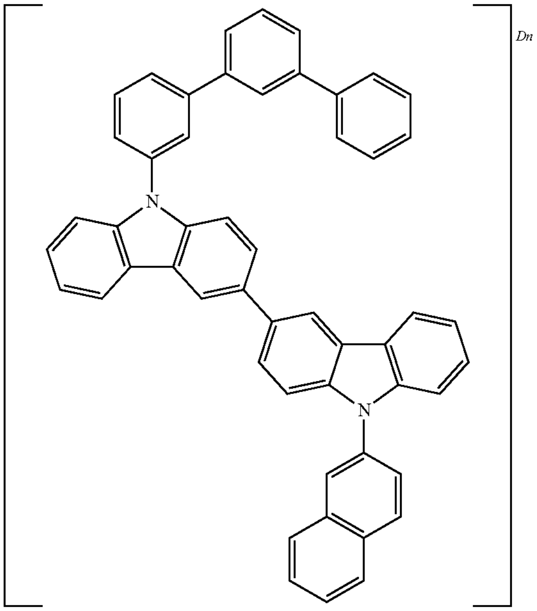
-continued
H2-143
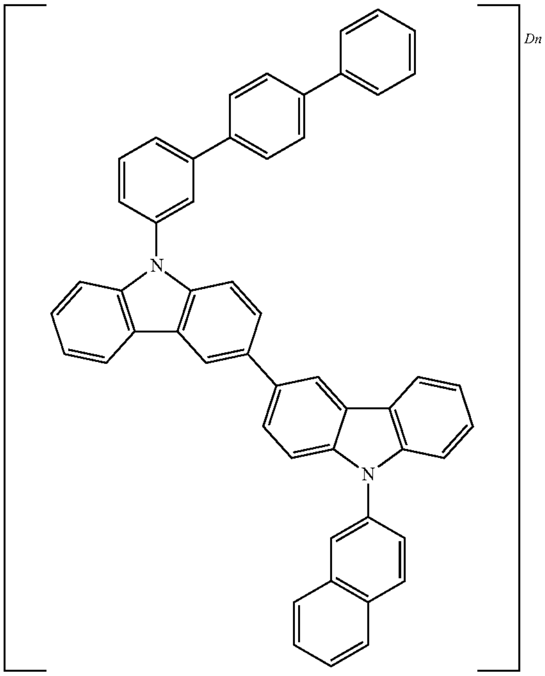
H2-144
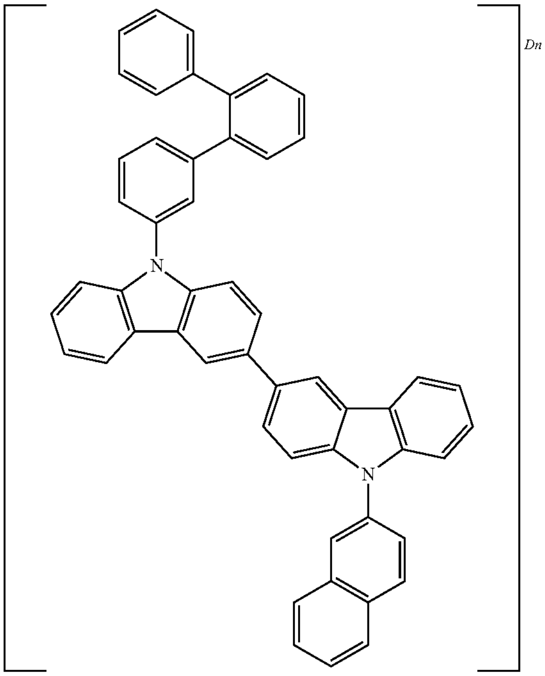

-continued
H2-145
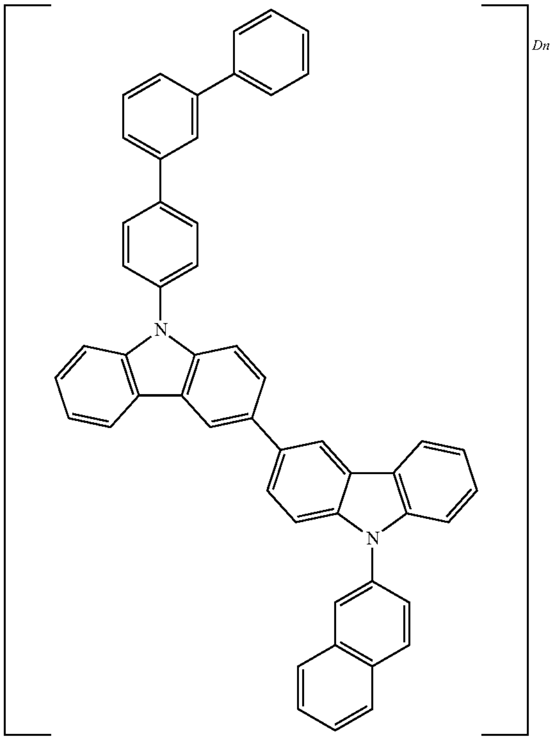
H2-146
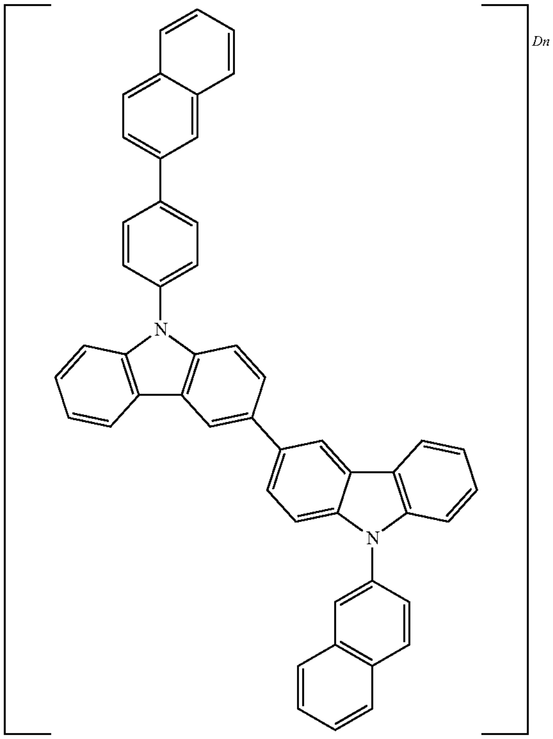
-continued
H2-147
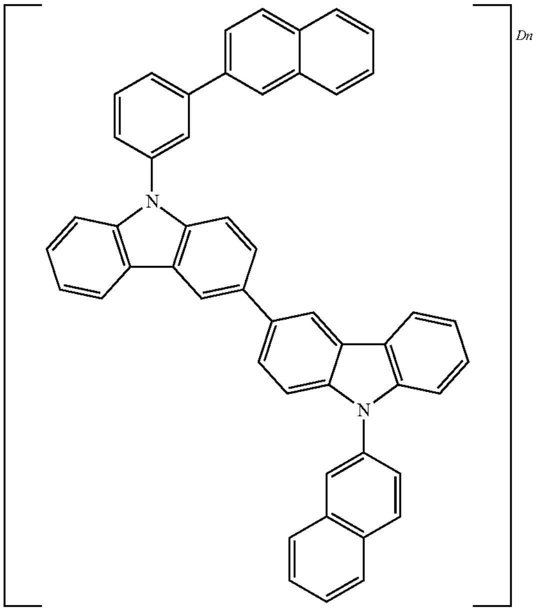
H2-148
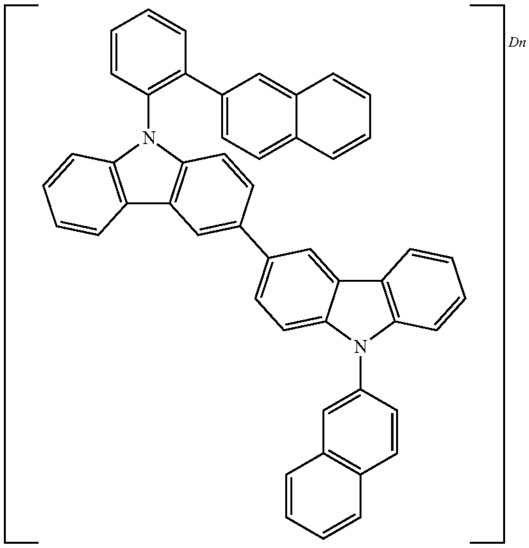

-continued
H2-149
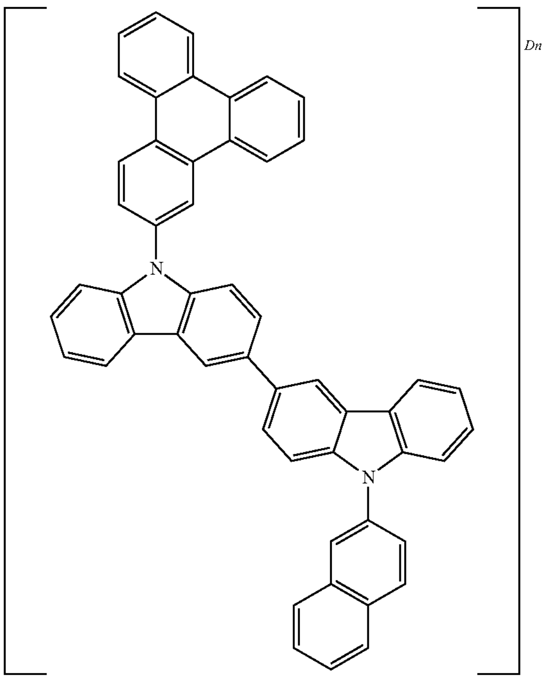
H2-150
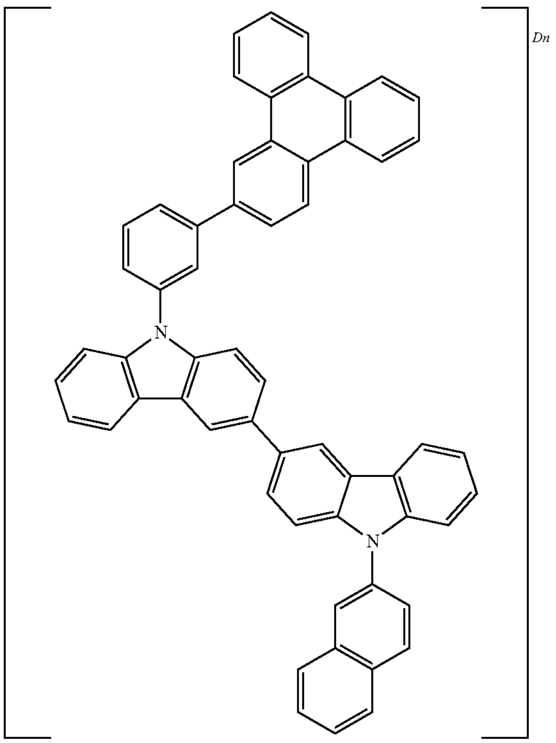
-continued
H2-151
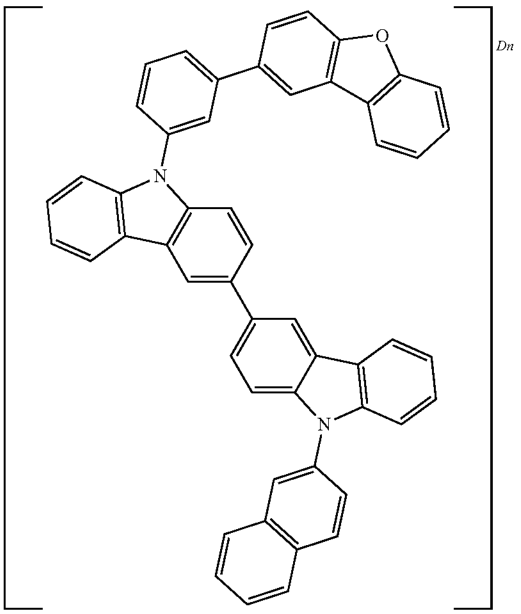
H2-152
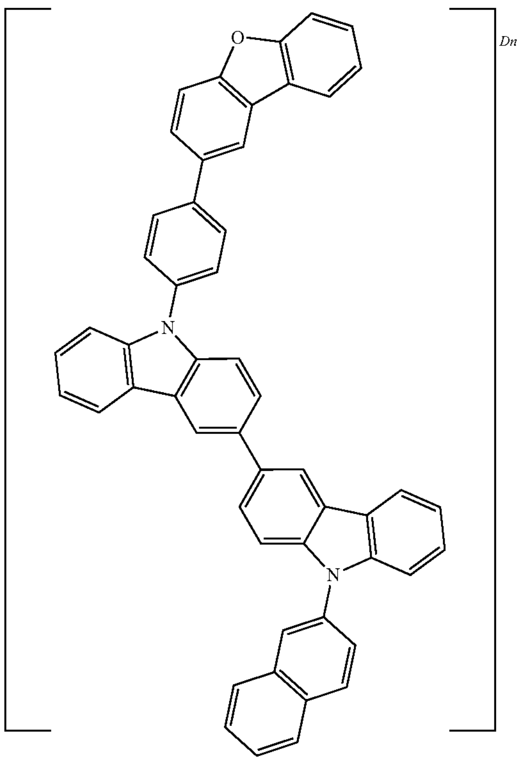

-continued
H2-153
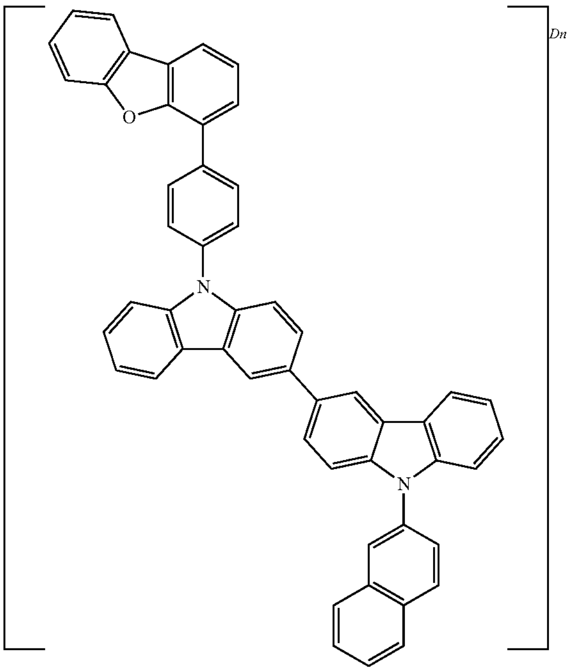
H2-154
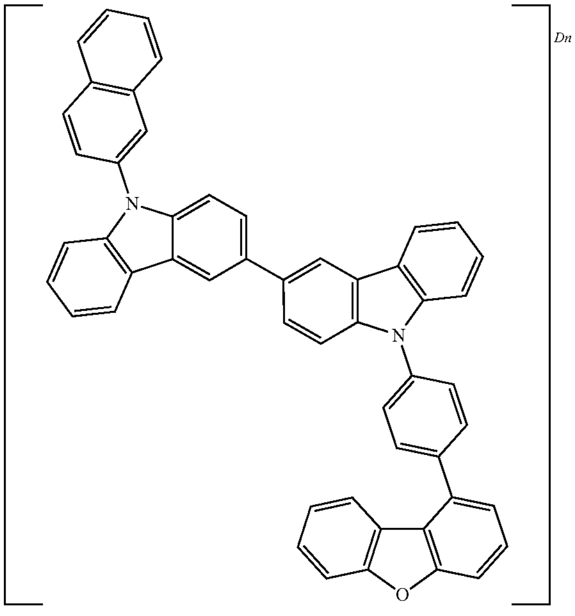
-continued
H2-155
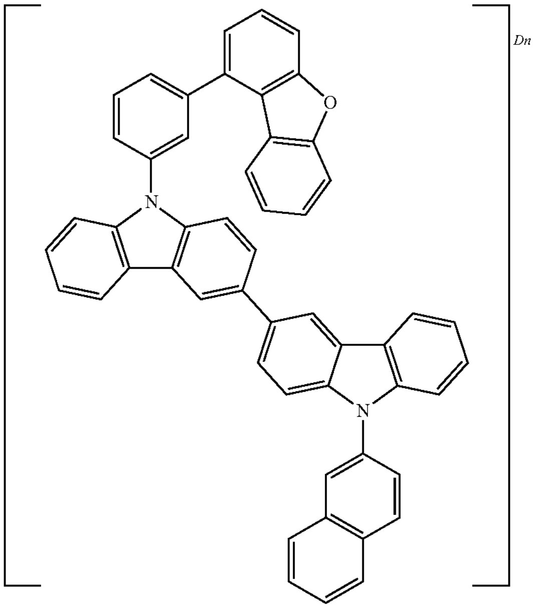
H2-156
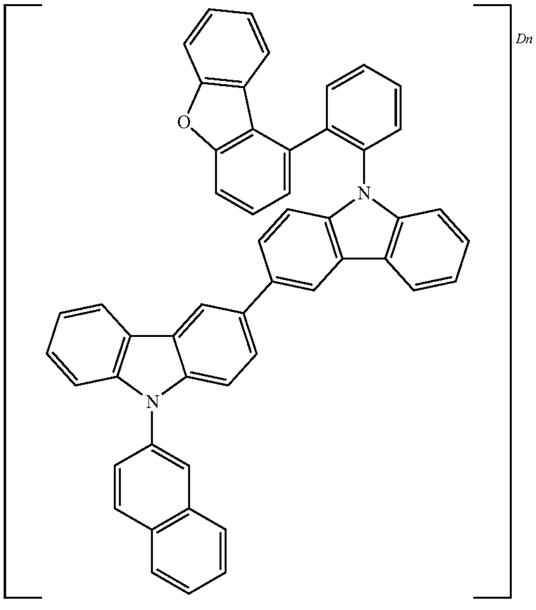

-continued
H2-157
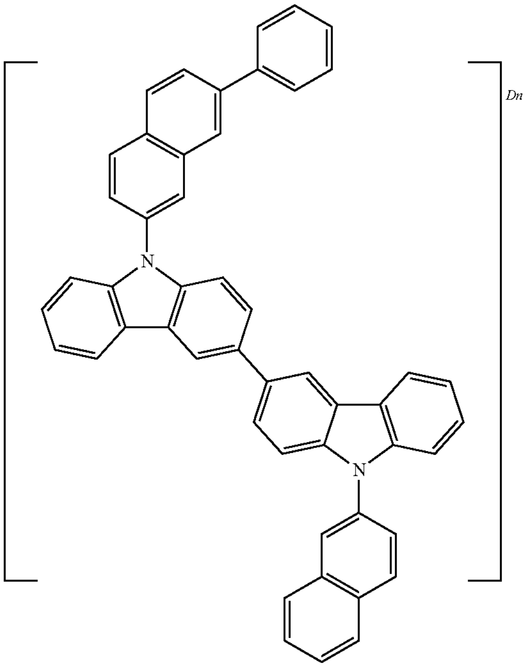
H2-158
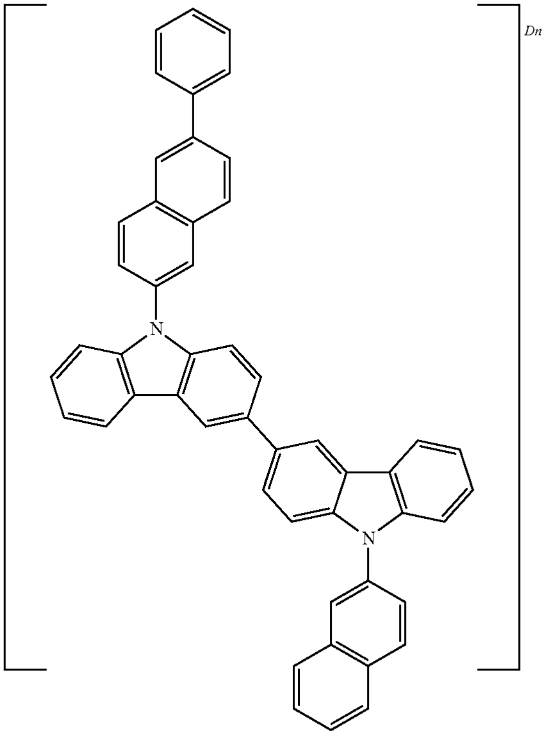
-continued
H2-159
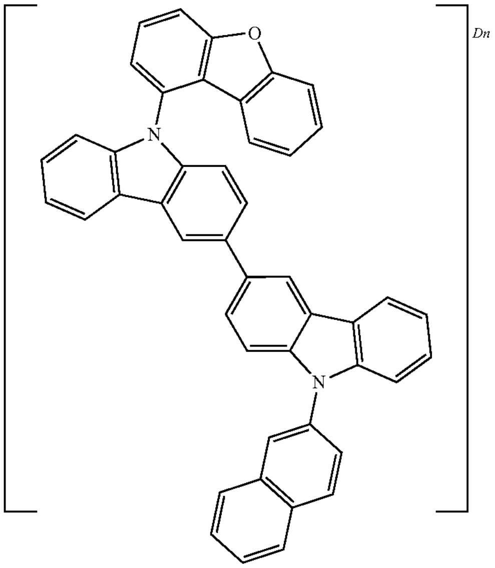
H2-160
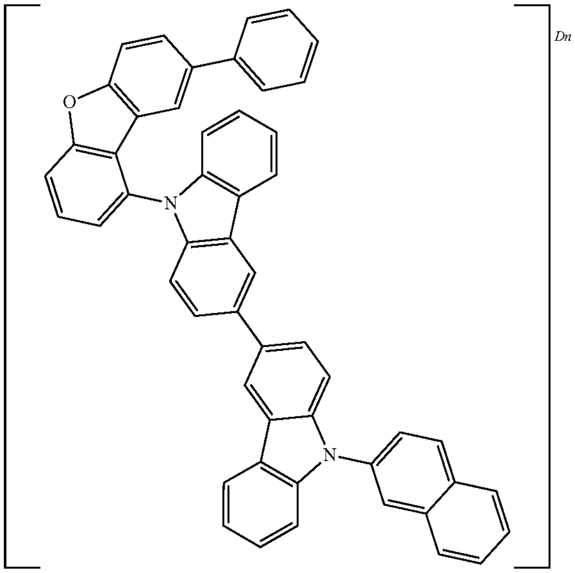

-continued
H2-161
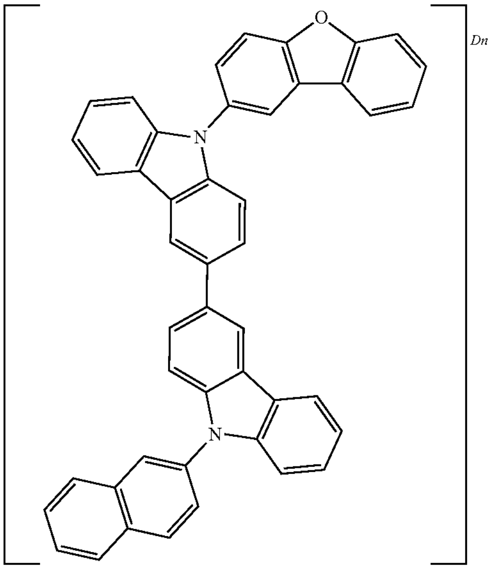
H2-162
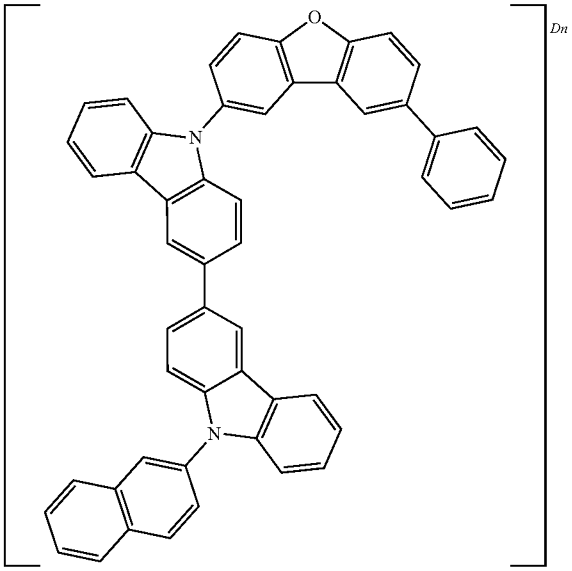
-continued
H2-163
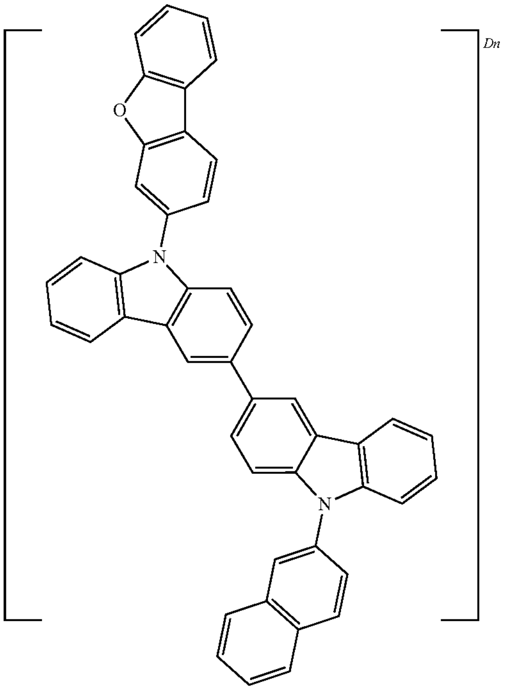
H2-164
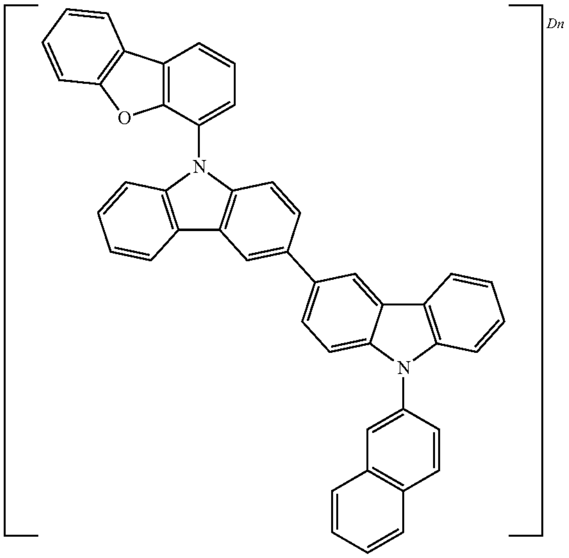

H2-165
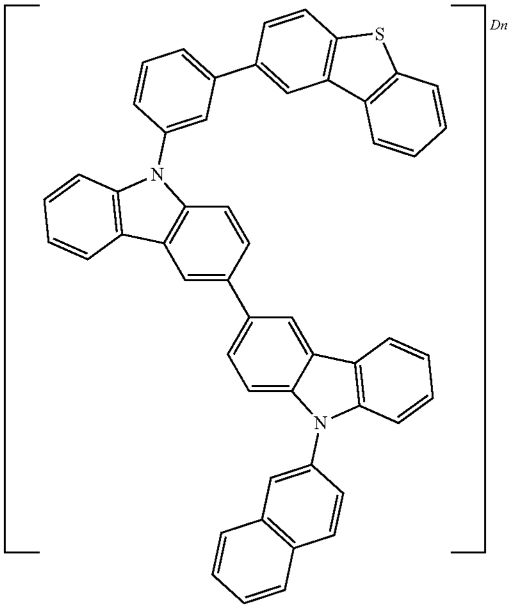
H2-166
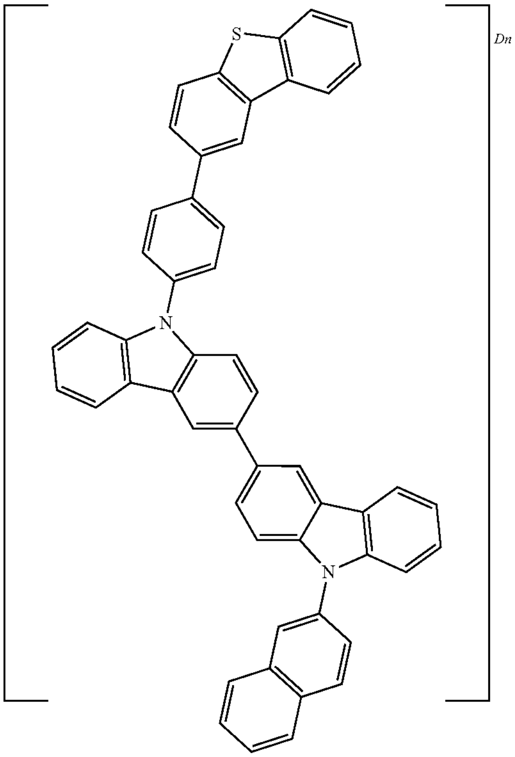
H2-167
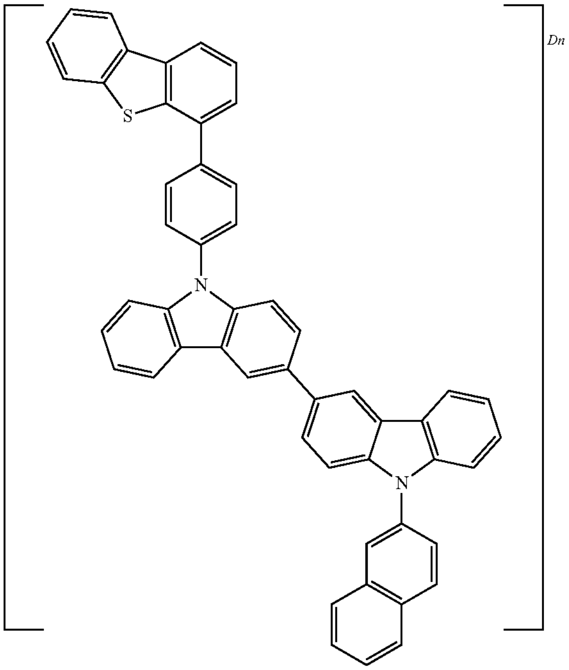
H2-168
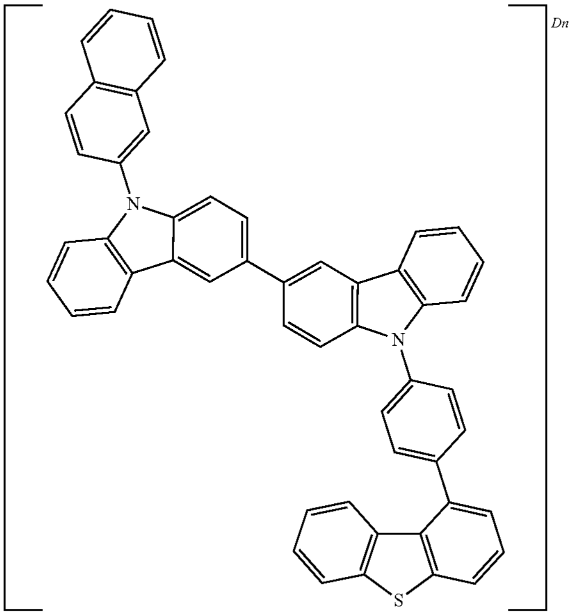

-continued
H2-169
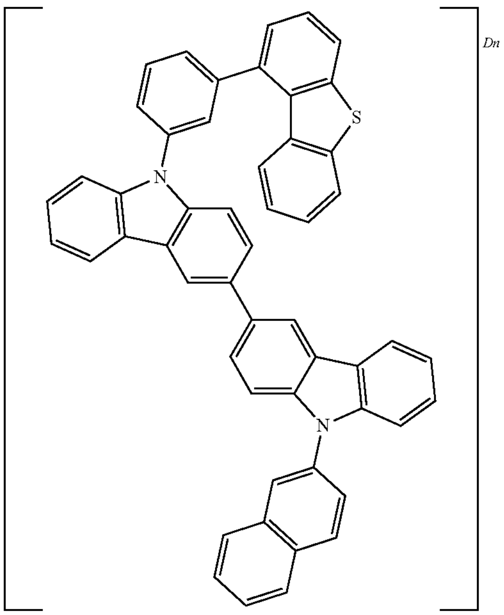
H2-170
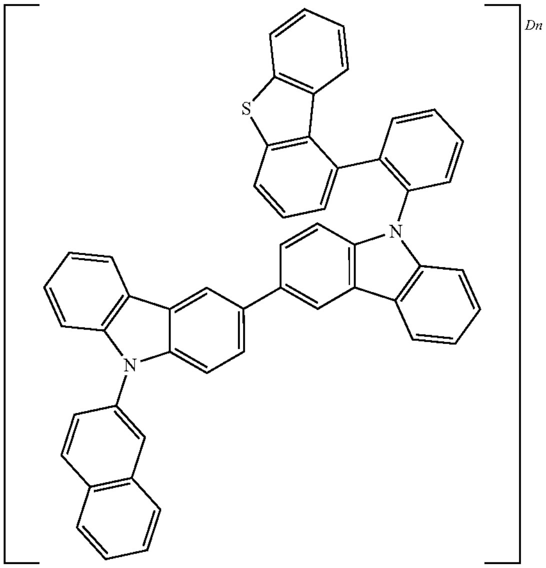
-continued
H2-171
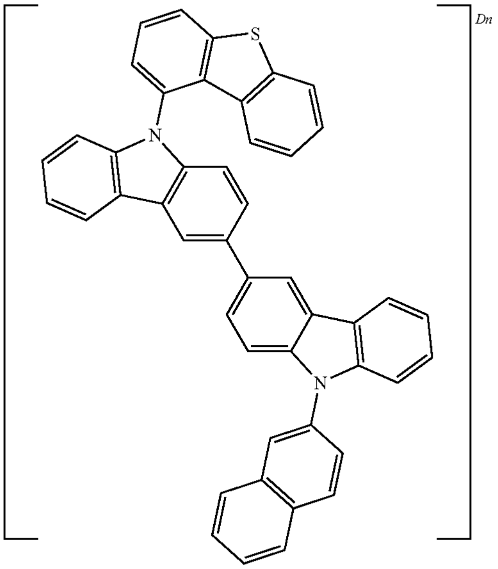
H2-172
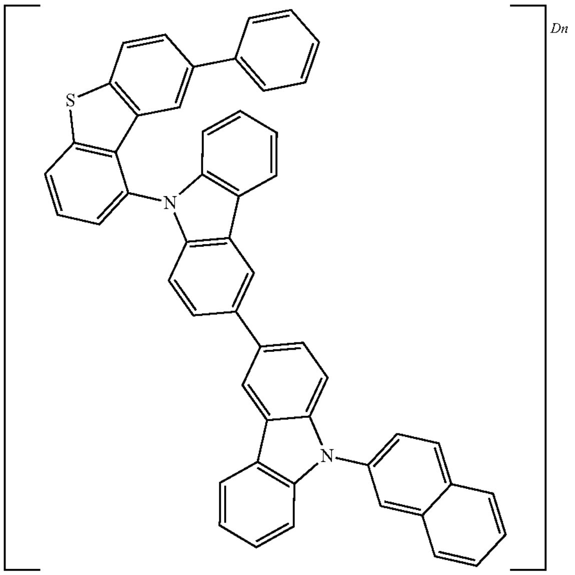

-continued
H2-173
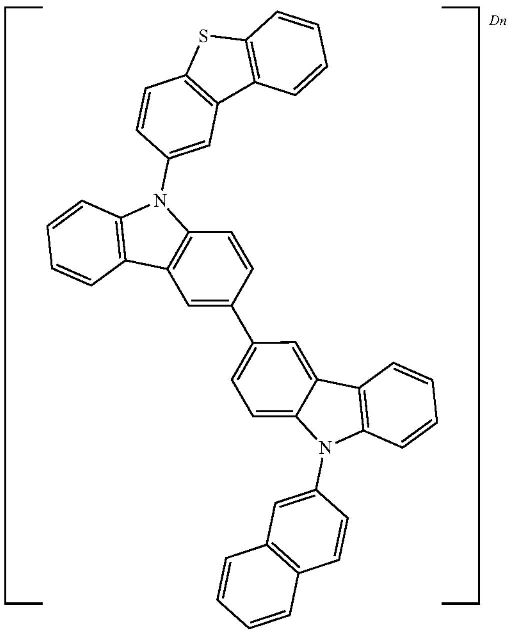
H2-174
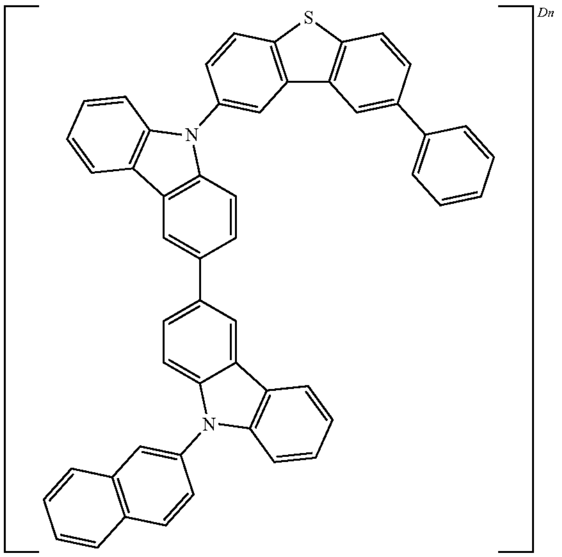
H2-175
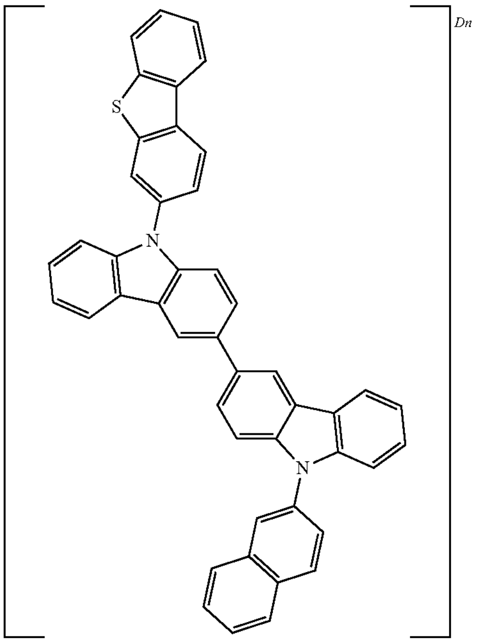

-continued
H2-176
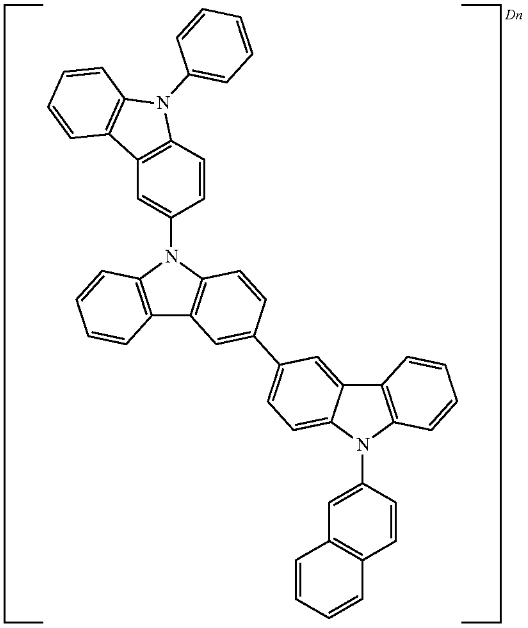
H2-177
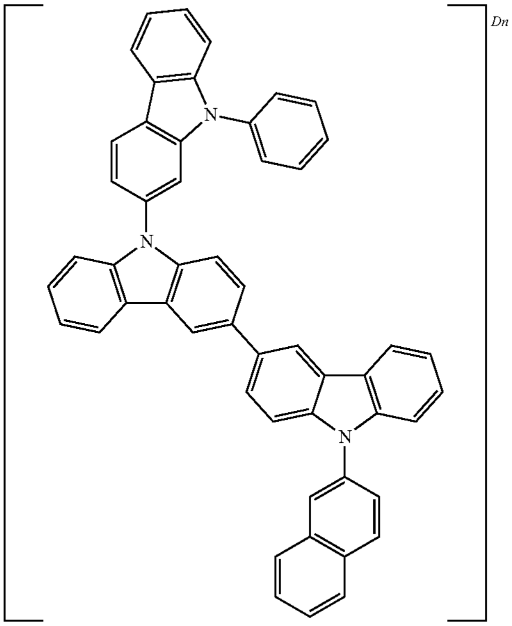
H2-178
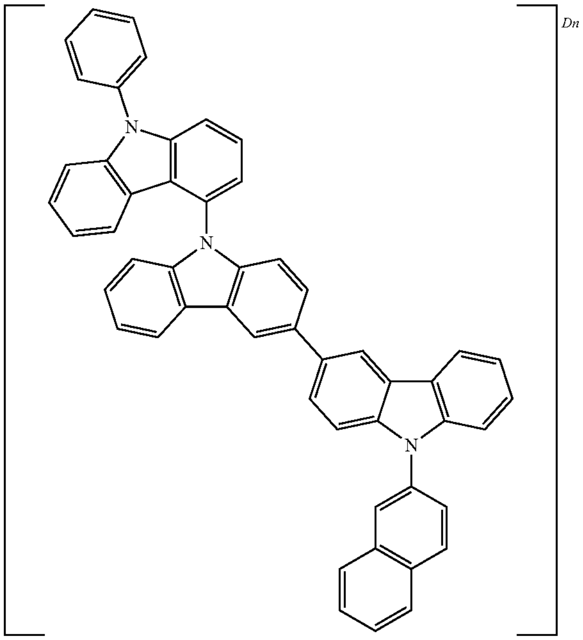
H2-179
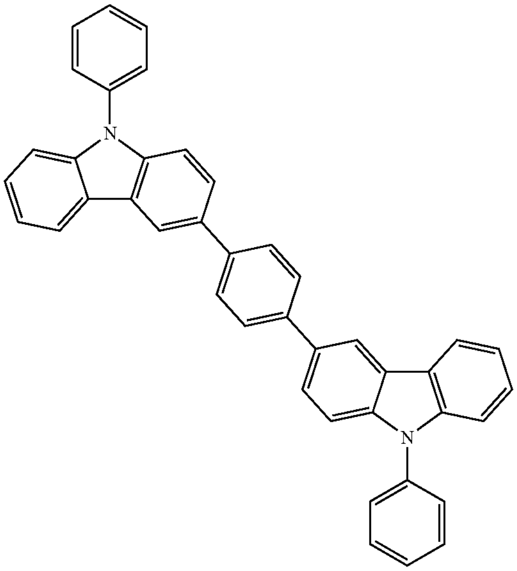

-continued
H2-180
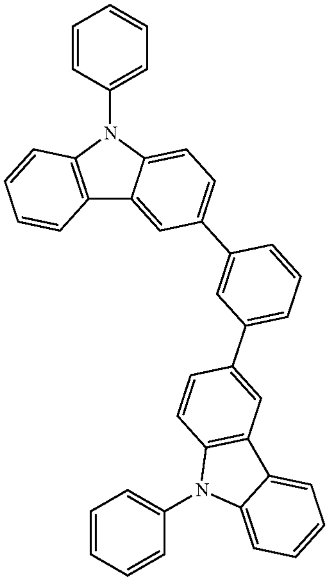
H2-181
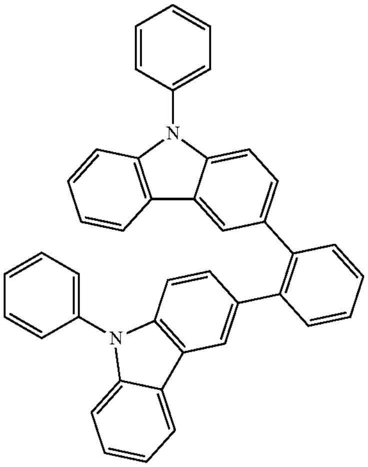
H2-182
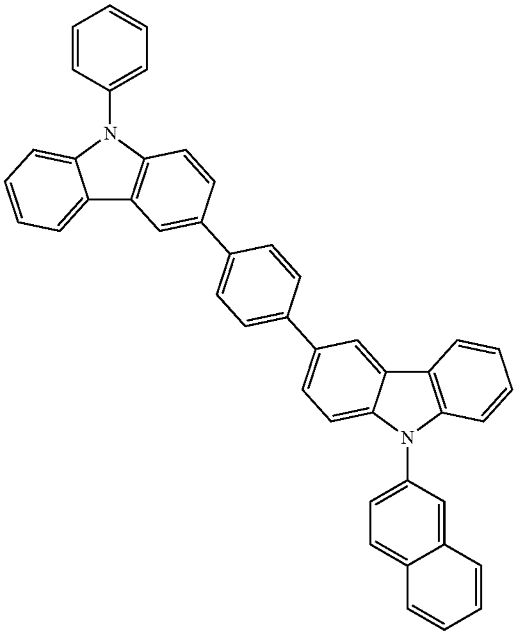
H2-183
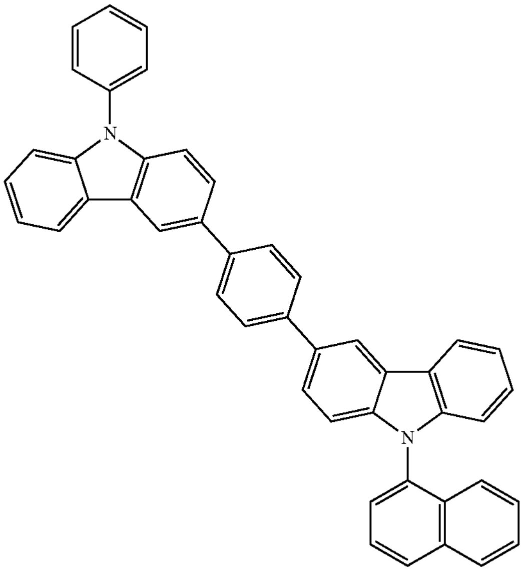

-continued
H2-184
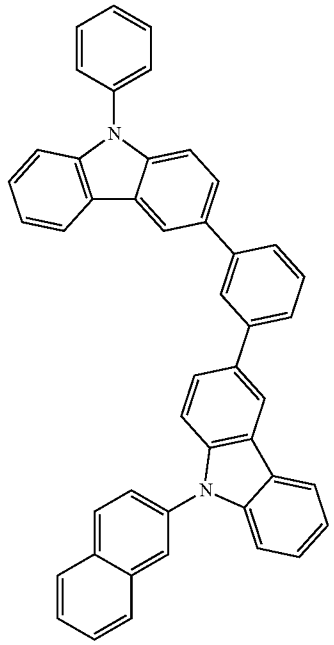
H2-185
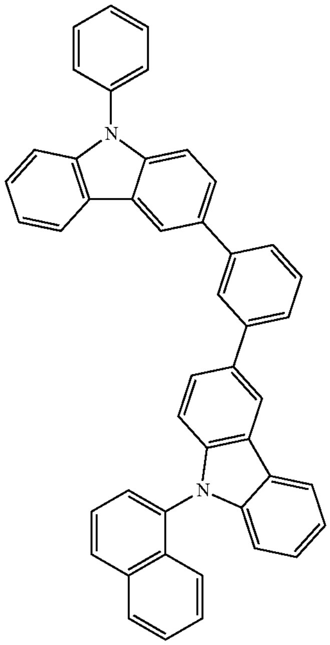
H2-186
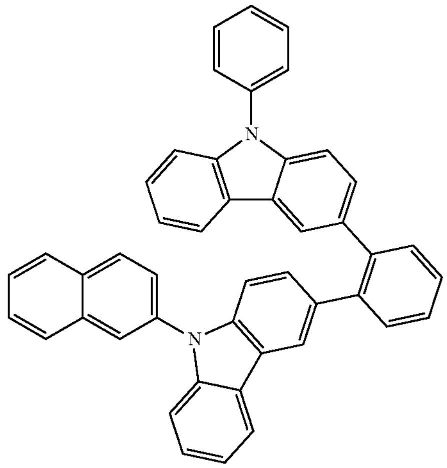
H2-187
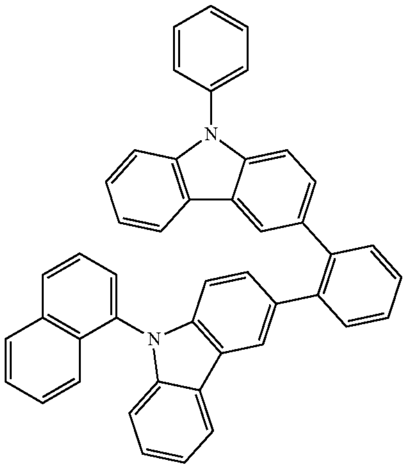

-continued
H2-188
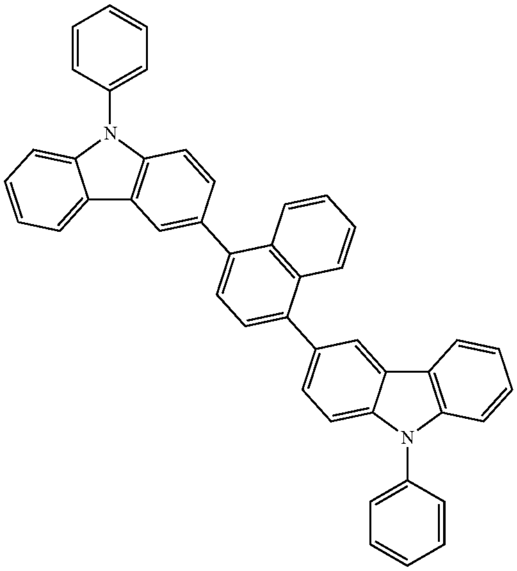
H2-189
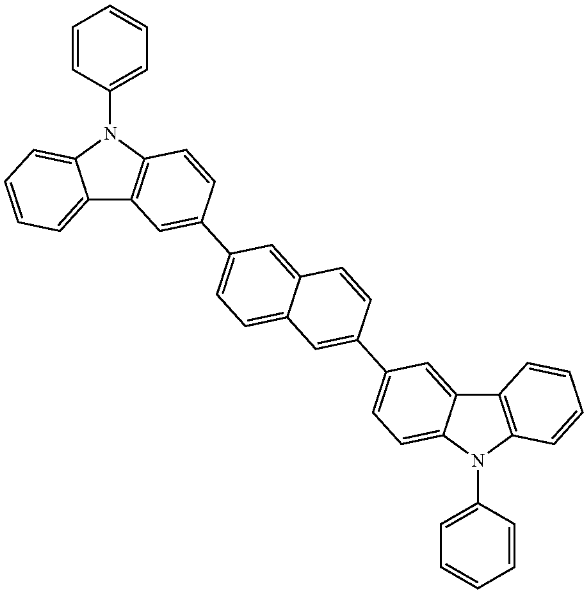
H2-190
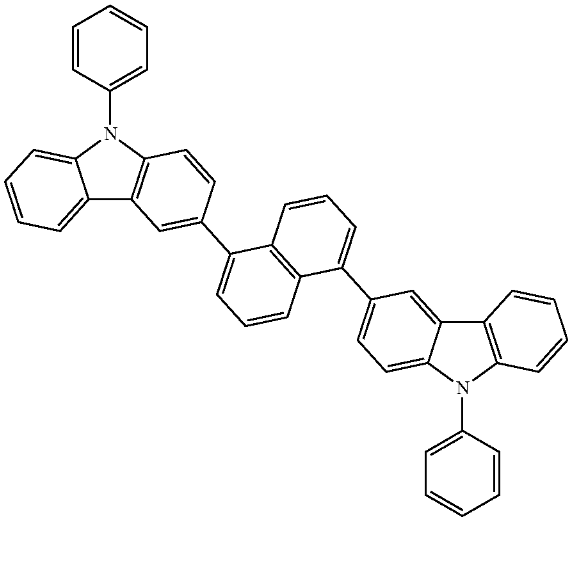
H2-191
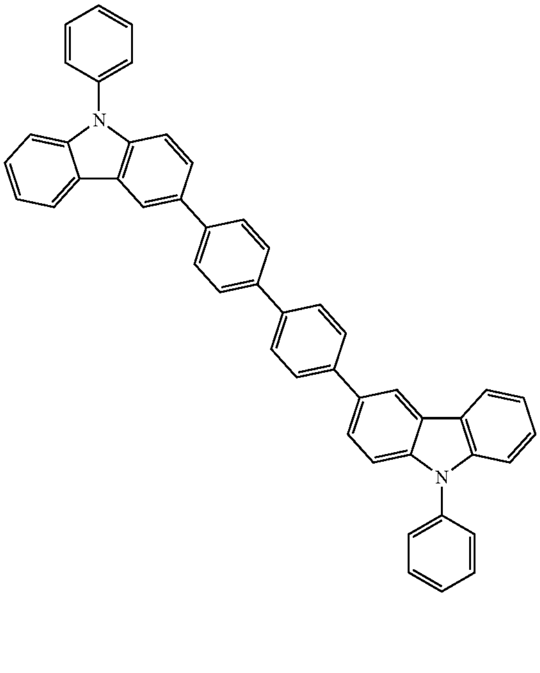

-continued
H2-192
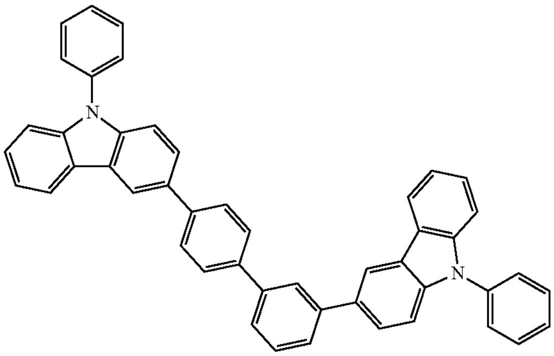
H2-193
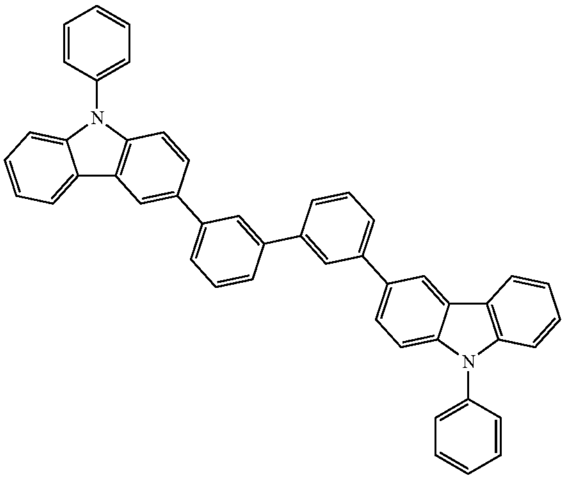
H2-194
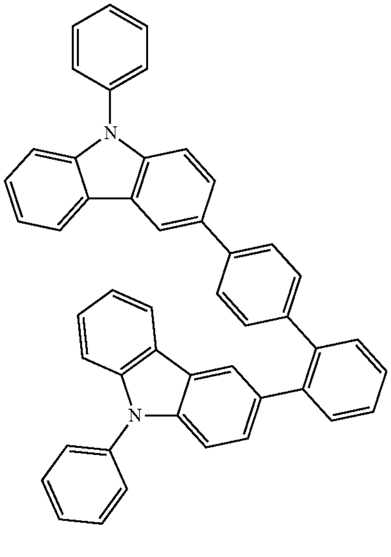
H2-195
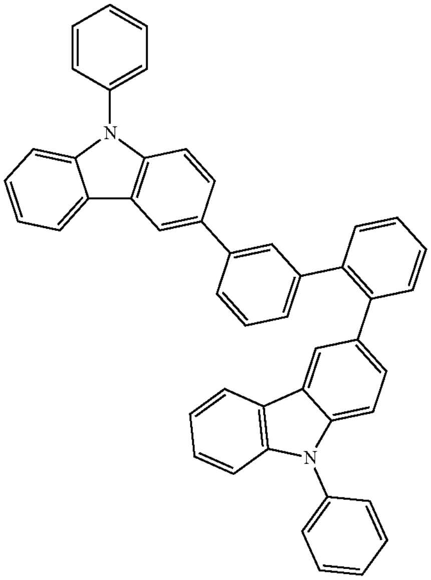

-continued
H2-196
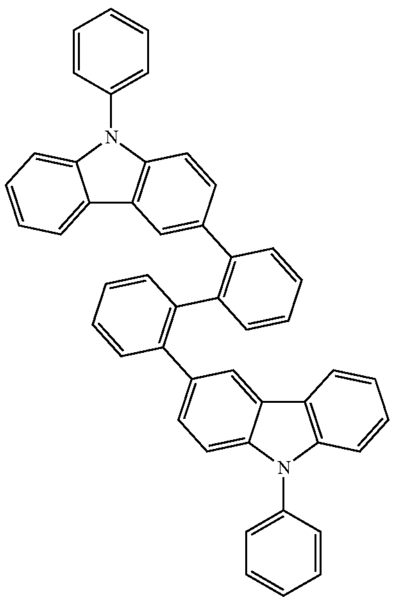
H2-197
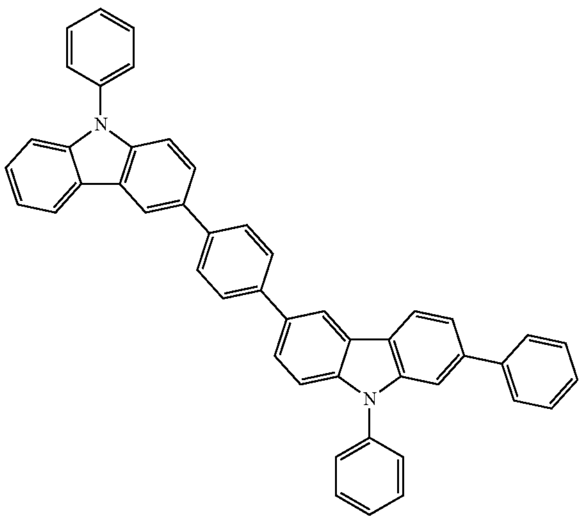
H2-198
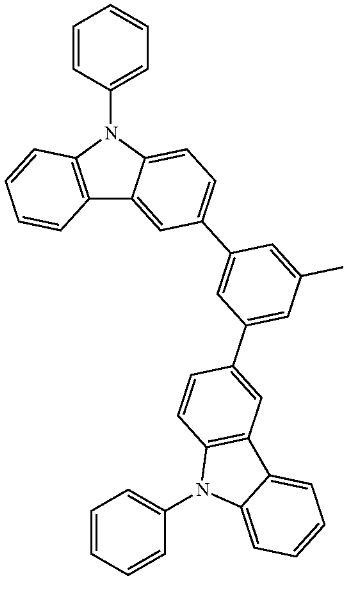

-continued
H2-199
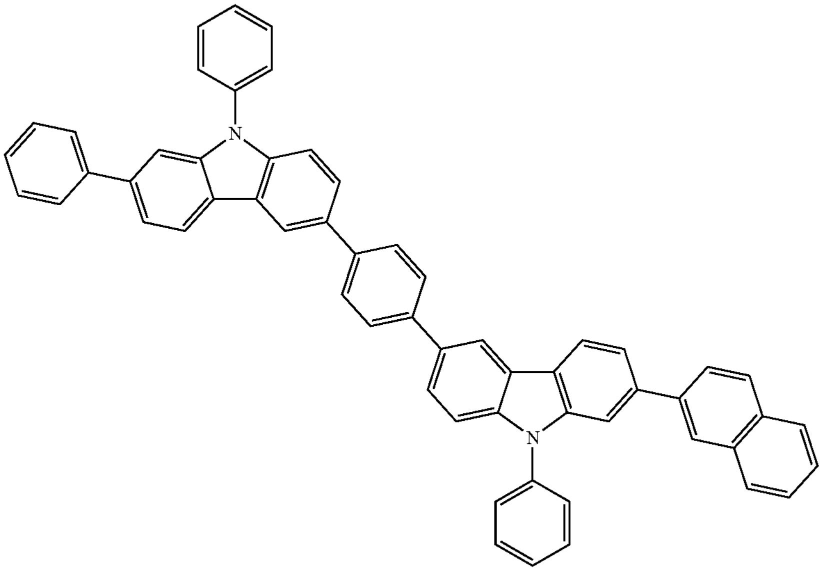
H2-200
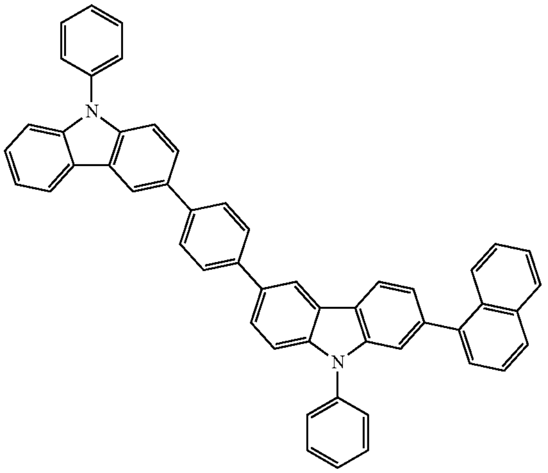
H2-201
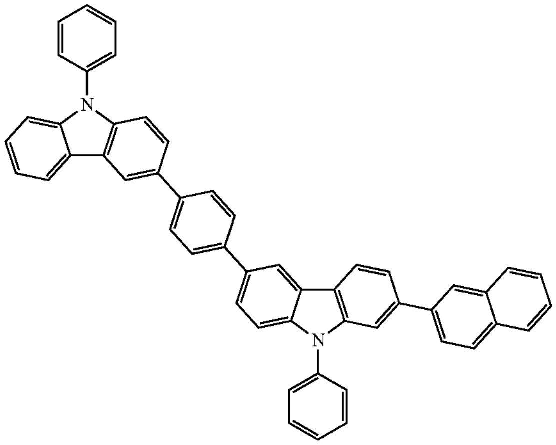

-continued
H2-202
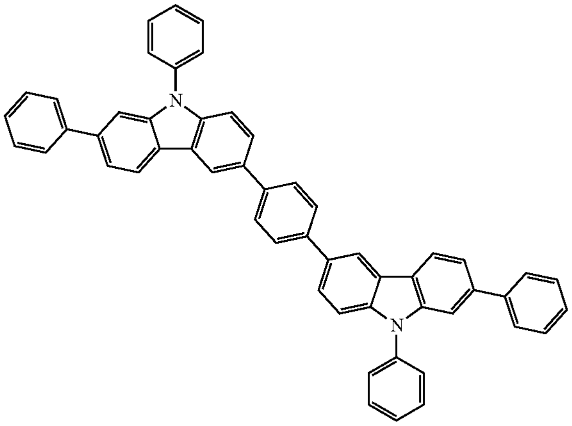
H2-203
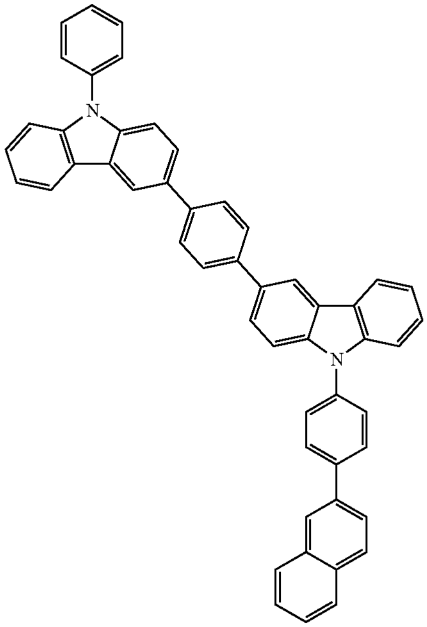
H2-204
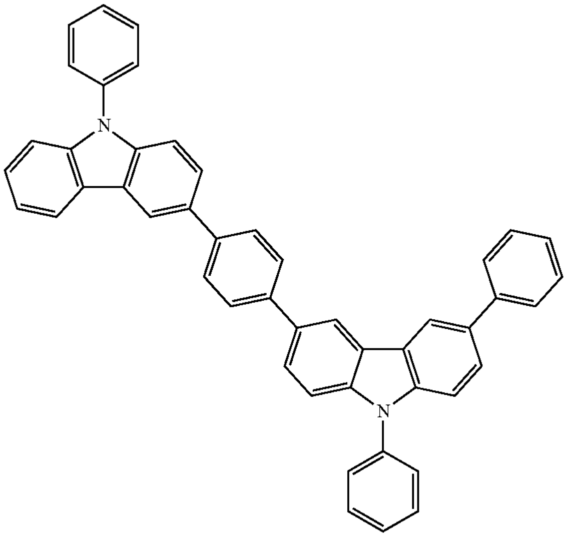
H2-205
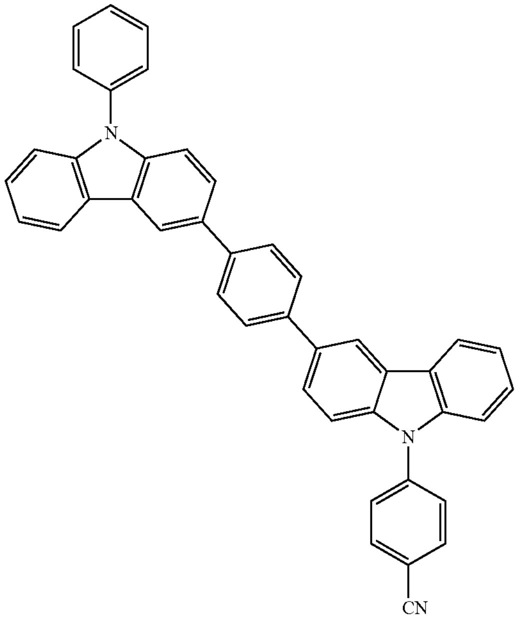

-continued
H2-206
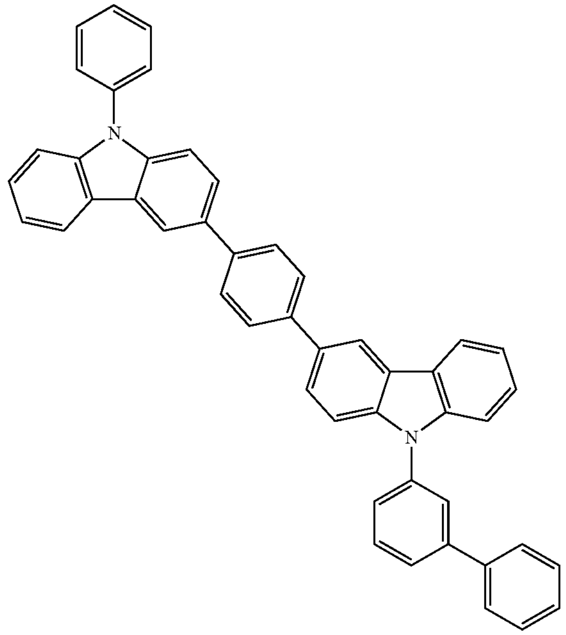
H2-207
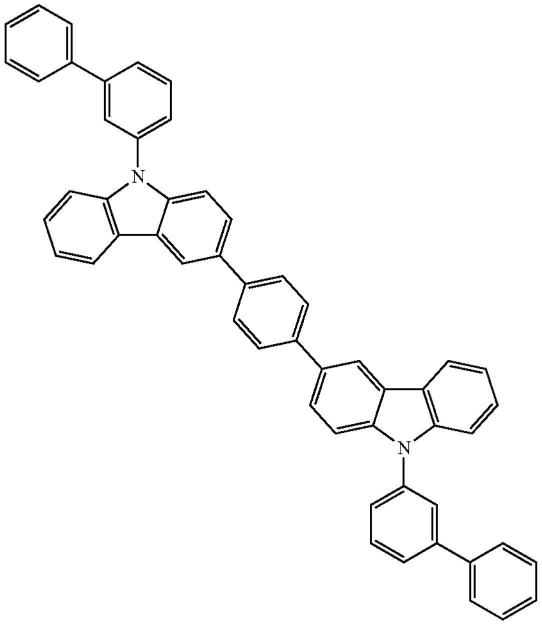
H2-208
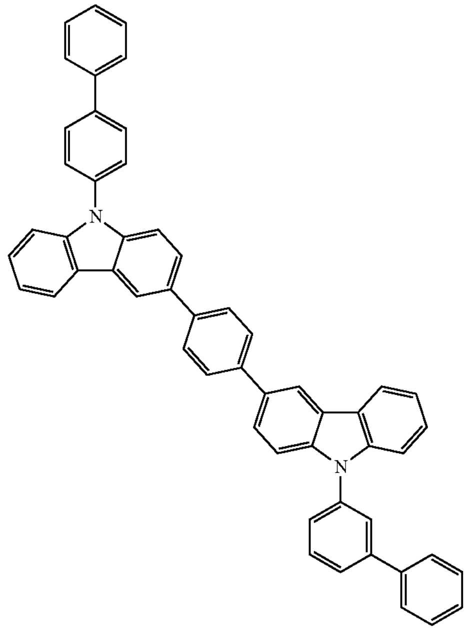
H2-209
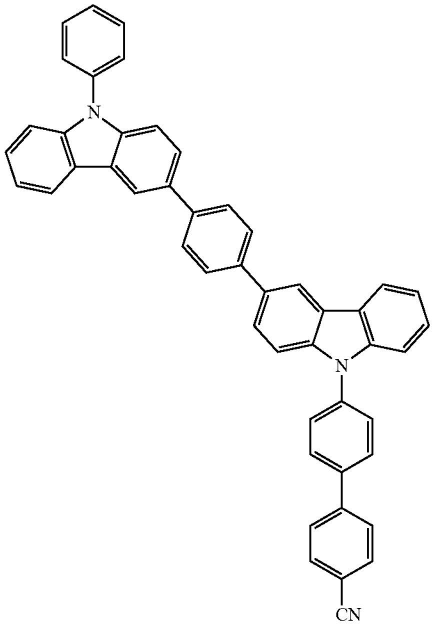
CN -continued
H2-210
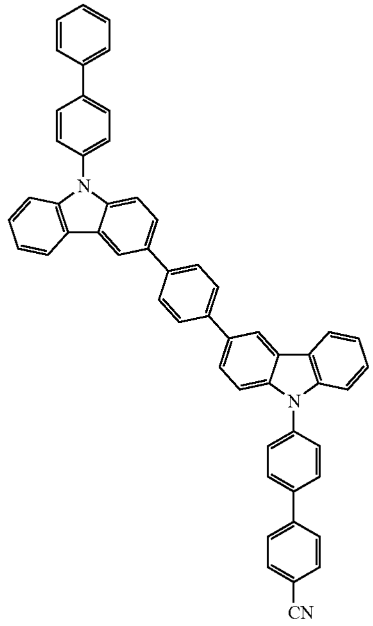
H2-211
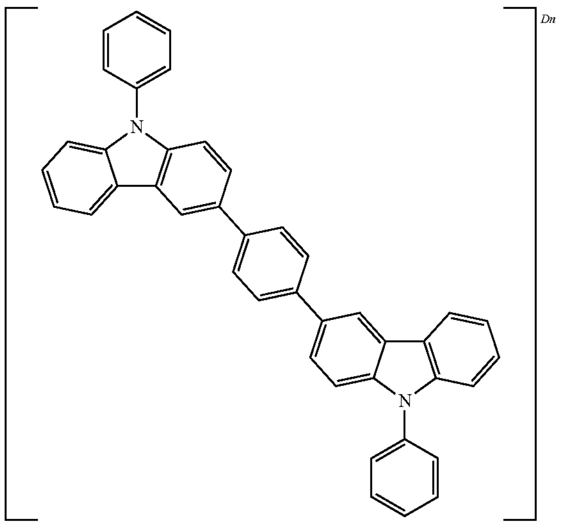
H2-212
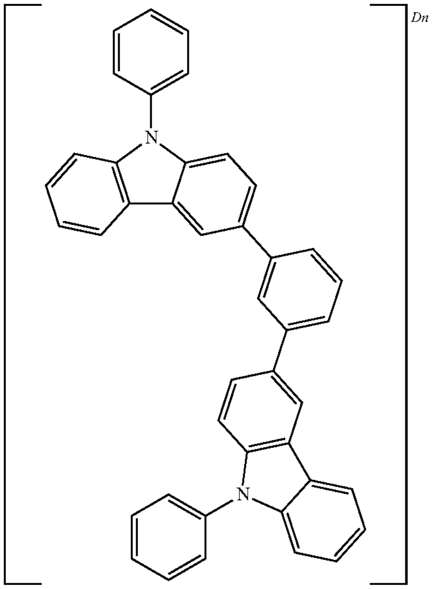
H2-213
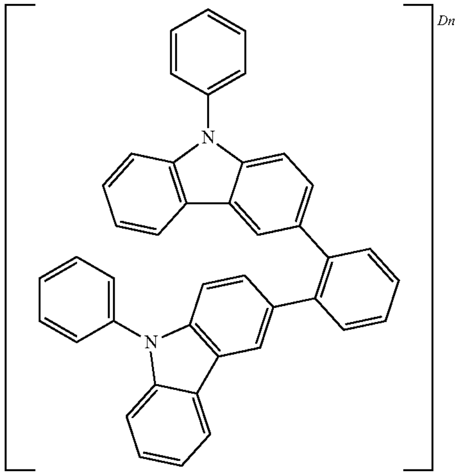

-continued
H2-214
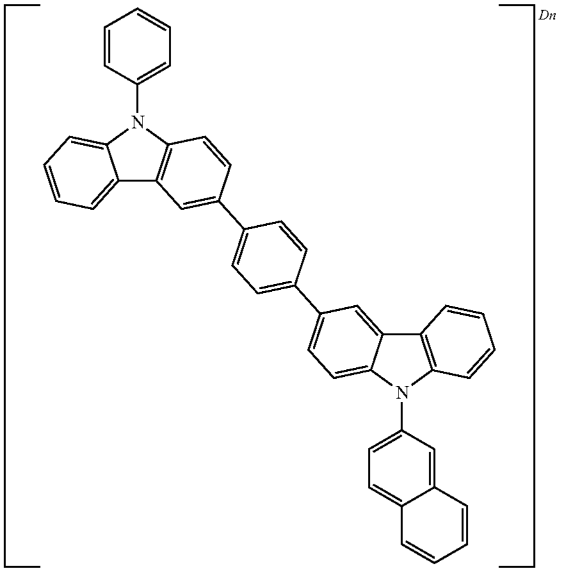
H2-215
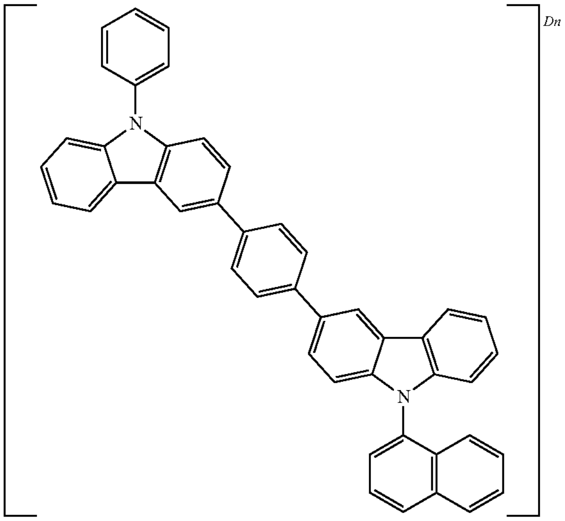
H2-216
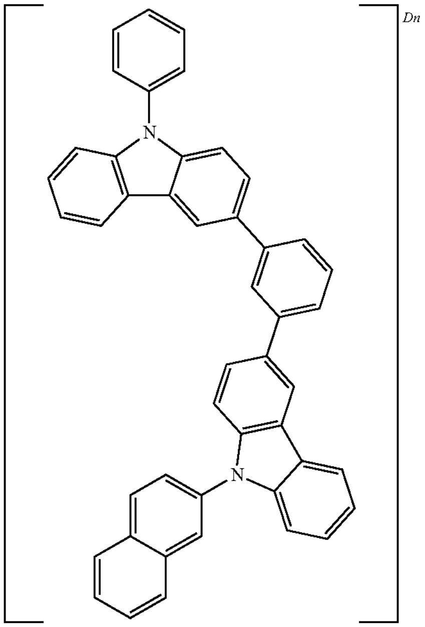
H2-217
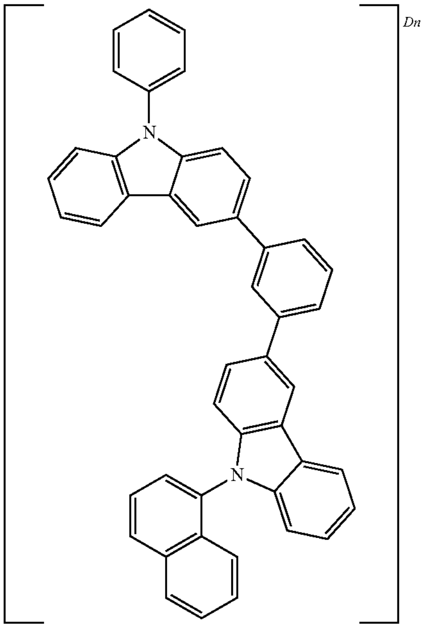

-continued
H2-218
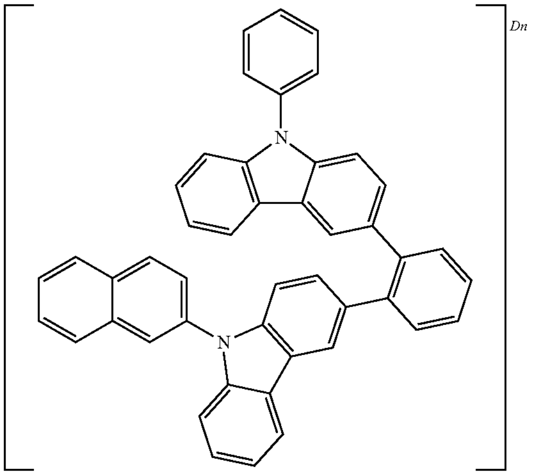
H2-219
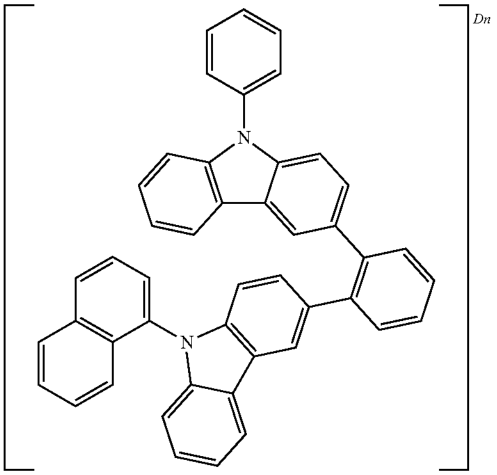
H2-220
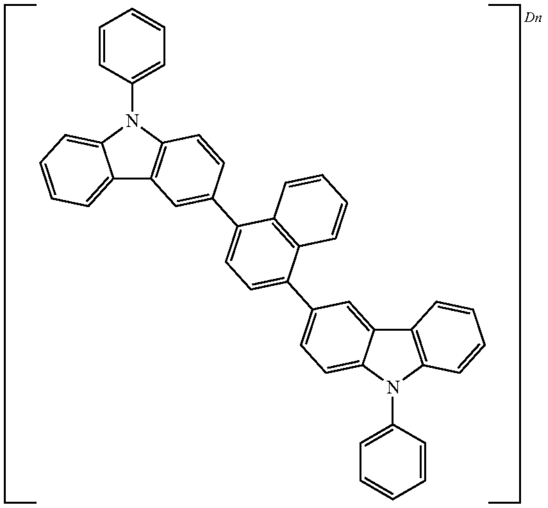
H2-221
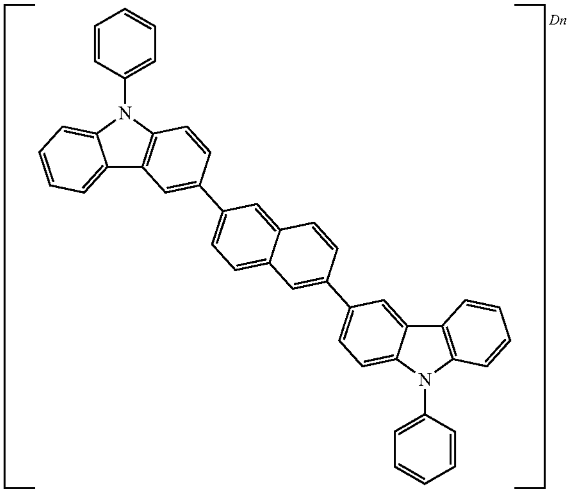
H2-222
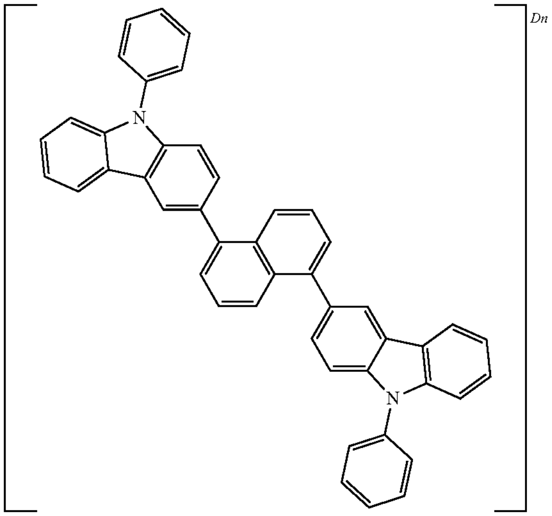
H2-223
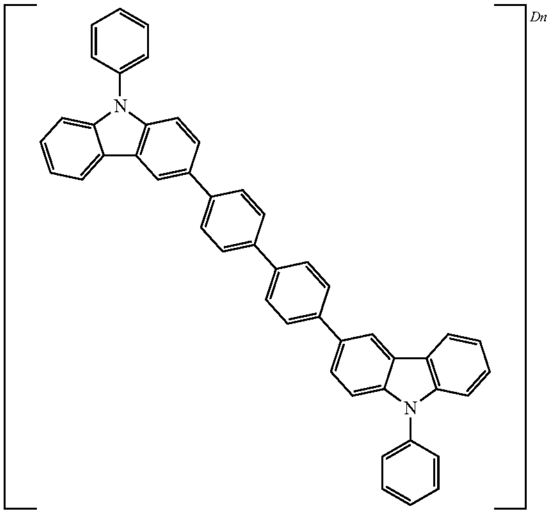

-continued
H2-224
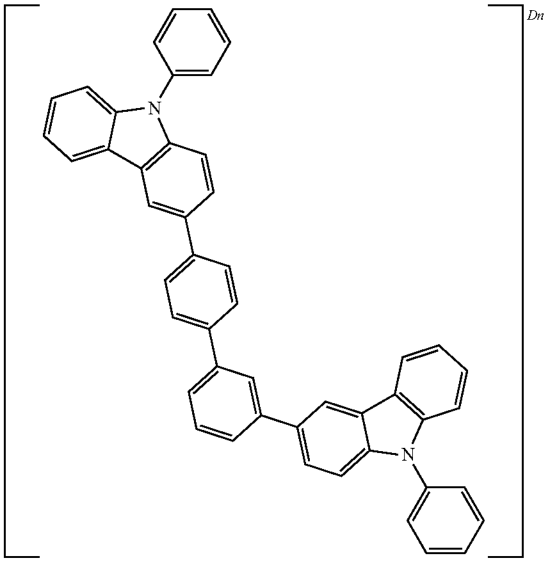
H2-225
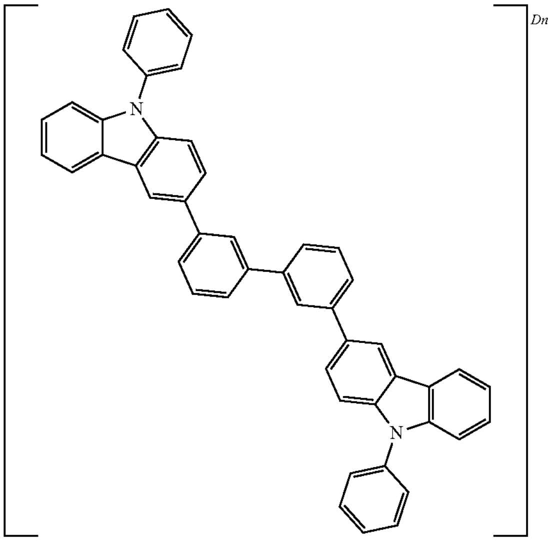
H2-226
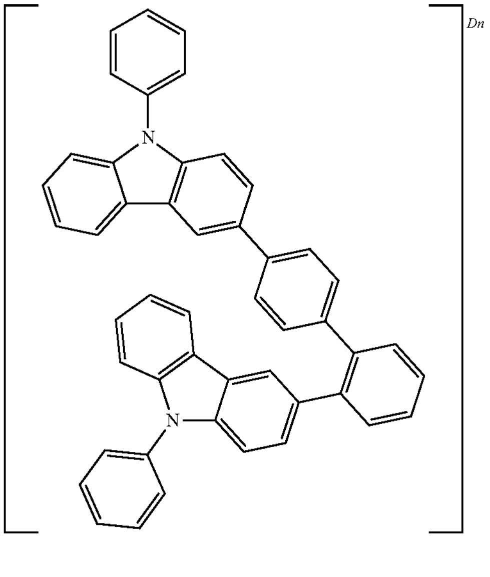
H2-227
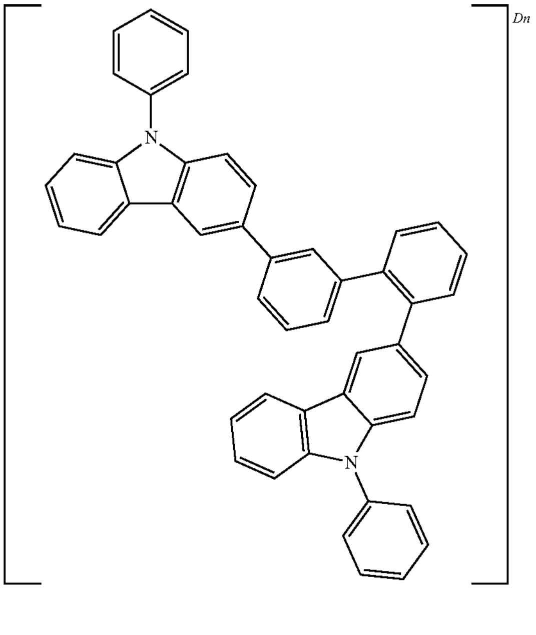

-continued

H2-228

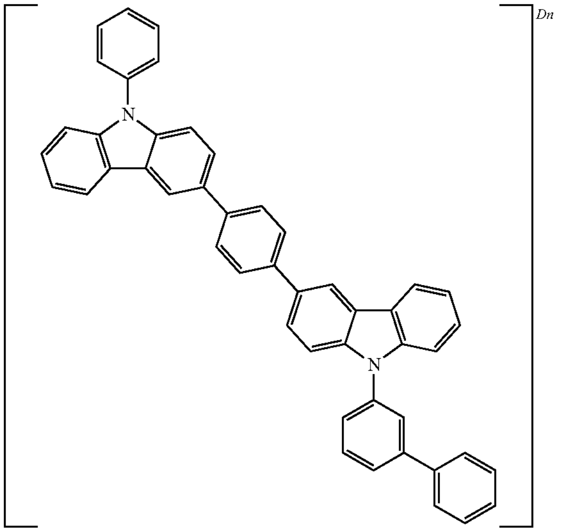

H2-229

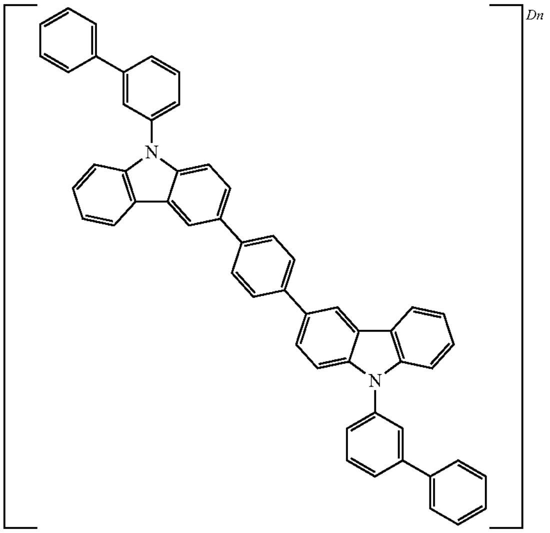

and

H2.230

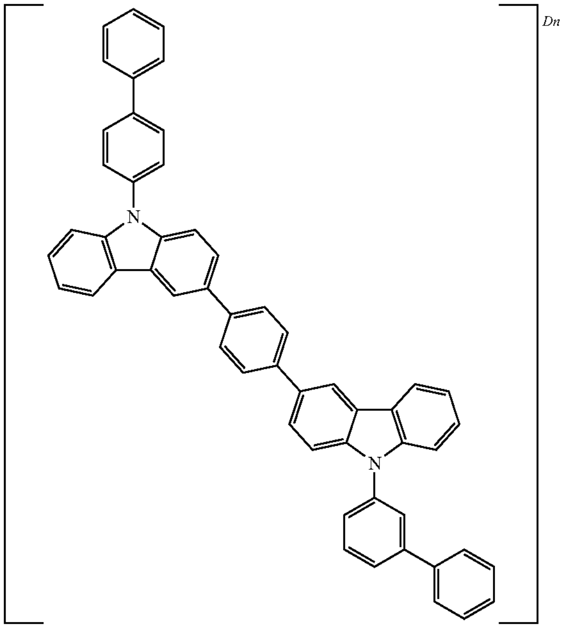

wherein,

Dn means that n of the hydrogens are replaced with deuterium, wherein the upper limit of n is determined according to the number of hydrogens that may be substituted for each compound.

9. An organic electroluminescent device comprising: a first electrode; a second electrode; and at least one light-emitting layer(s) between the first electrode and the second electrode, wherein the at least one light-emitting layer(s) comprises the plurality of host materials according to claim 1.

* * * * *